(12) United States Patent
Martini et al.

(10) Patent No.: US 10,519,455 B2
(45) Date of Patent: *Dec. 31, 2019

(54) POLYNUCLEOTIDES ENCODING ALPHA-GALACTOSIDASE A FOR THE TREATMENT OF FABRY DISEASE

(71) Applicant: ModernaTX, Inc., Cambridge, MA (US)

(72) Inventors: Paolo Martini, Cambridge, MA (US); Stephen G. Hoge, Brookline, MA (US); Kerry Benenato, Sudbury, MA (US); Vladimir Presnyak, Manchester, NH (US); Iain McFadyen, Arlington, MA (US); Ellalahewage Sathyajith Kumarasinghe, Harvard, MA (US); Xuling Zhu, Cambridge, MA (US); Lin Tung Guey, Cambridge, MA (US); Staci Sabnis, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/110,309

(22) Filed: Aug. 23, 2018

(65) Prior Publication Data

US 2019/0002890 A1 Jan. 3, 2019

Related U.S. Application Data

(63) Continuation of application No. PCT/US2017/033398, filed on May 18, 2017.

(60) Provisional application No. 62/338,354, filed on May 18, 2016.

(51) Int. Cl.
| | |
|---|---|
| *C12N 15/11* | (2006.01) |
| *C12N 15/67* | (2006.01) |
| *A61K 9/51* | (2006.01) |
| *C12N 9/40* | (2006.01) |
| *A61P 3/00* | (2006.01) |
| *A61K 38/47* | (2006.01) |
| *A61K 48/00* | (2006.01) |

(52) U.S. Cl.
CPC .......... *C12N 15/67* (2013.01); *A61K 9/5123* (2013.01); *A61K 38/47* (2013.01); *A61P 3/00* (2018.01); *C12N 9/2465* (2013.01); *C12Y 302/01022* (2013.01); *A61K 48/00* (2013.01)

(58) Field of Classification Search
None
See application file for complete search history.

(56) References Cited

U.S. PATENT DOCUMENTS

| 8,853,377 B2 | 10/2014 | Guild et al. |
|---|---|---|
| 9,061,021 B2 | 6/2015 | Guild et al. |
| 9,308,281 B2 | 4/2016 | Guild et al. |
| 9,447,431 B2 | 9/2016 | Thess et al. |
| 9,717,690 B2 | 8/2017 | Guild et al. |
| 9,821,114 B2 | 11/2017 | Cabrera Aquino et al. |
| 2009/0017533 A1 | 1/2009 | Selden et al. |
| 2009/0148906 A1 | 6/2009 | Selden et al. |
| 2013/0259924 A1 | 10/2013 | Bancel et al. |
| 2014/0010861 A1 | 1/2014 | Bancel et al. |
| 2014/0294938 A1 | 10/2014 | Guild et al. |
| 2015/0157565 A1 | 6/2015 | Heartlein et al. |
| 2015/0366997 A1 | 12/2015 | Guild et al. |
| 2016/0031928 A1 | 2/2016 | Derosa et al. |
| 2017/0240501 A1 | 8/2017 | DeRosa et al. |
| 2018/0008543 A1 | 1/2018 | Guild et al. |
| 2018/0086807 A1 | 3/2018 | Bancel et al. |
| 2018/0110878 A1 | 4/2018 | Nathwani et al. |
| 2018/0161454 A1 | 6/2018 | Fotin-Mleczek et al. |
| 2018/0169020 A1 | 6/2018 | Guild et al. |
| 2018/0169146 A1 | 6/2018 | Goldberg et al. |
| 2019/0000932 A1 | 1/2019 | Martini et al. |
| 2019/0000933 A1 | 1/2019 | Martini et al. |

FOREIGN PATENT DOCUMENTS

| EP | 1325138 B1 | 7/2013 |
|---|---|---|
| EP | 2717893 A1 | 4/2014 |
| EP | 2972360 B1 | 3/2018 |
| WO | 2012170930 A1 | 12/2012 |
| WO | 2014/164253 A1 | 10/2014 |
| WO | 2014172045 A1 | 10/2014 |
| WO | 2017049245 A2 | 3/2017 |
| WO | 2017/153936 A1 | 9/2017 |
| WO | 2017191274 A2 | 11/2017 |
| WO | 2018089846 A1 | 5/2018 |

OTHER PUBLICATIONS

Braam-Markson et al., Expression of a functional influenza viral cap-recognizing protein by using a bovine papilloma virus vector, PNAS, vol. 82, pp. 4326-4330. (Year: 1985).*

(Continued)

*Primary Examiner* — Dana H Shin

(74) *Attorney, Agent, or Firm* — Nelson Mullins Riley & Scarborough LLP; Amy E. Mandragouras, Esq.; Siew Y. Chong

(57) ABSTRACT

The invention relates to mRNA therapy for the treatment of Fabry disease. mRNAs for use in the invention, when administered in vivo, encode human the α-galactosidase A (GLA), isoforms thereof, functional fragments thereof, and fusion proteins comprising GLA. mRNAs of the invention are preferably encapsulated in lipid nanoparticles (LNPs) to effect efficient delivery to cells and/or tissues in subjects, when administered thereto. mRNA therapies of the invention increase and/or restore deficient levels of GLA expression and/or activity in subjects. mRNA therapies of the invention further decrease levels of toxic metabolites associated with deficient GLA activity in subjects, namely Gb3 and lyso-Gb3.

29 Claims, 30 Drawing Sheets

Specification includes a Sequence Listing.

(56) References Cited

OTHER PUBLICATIONS

Drew Weissman, mRNA transcript therapy, Expert Review of Vaccines, vol. 14, pp. 265-281. (Year: 2015).*
Asrani et al., Optimization of mRNA untranslated regions for improved expression of therapeutic mRNA, RNS Biology, vol. 15, pp. 756-762. (Year: 2018).*
U.S. Appl. No. 16/110,833, Nov. 26, 2018, D. Shin.
U.S. Appl. No. 16/110,788, Nov. 26, 2018, D. Shin.
U.S. Appl. No. 16/110,833, filed Aug. 23, 2018, Paolo Martini.
U.S. Appl. No. 16/110,788, filed Aug. 23, 2018, Paolo Martini.
International Preliminary Report on Patentability, PCT/US2017/033398, dated Nov. 29, 2018, 9 pages.
International Search Report and Written Opinion, PCT/US2017/033398, dated Aug. 22, 2017, 14 pages.
Ruiz De Garibay, A.P. et al., "Gene Therapy for Fabry Disease: A Review of the Literature," Biod, Adis International Ltd., vol. 27(3): 237-246 (2013).
U.S. Appl. No. 16/110,788, Feb. 11, 2019, D. Shin.
U.S. Appl. No. 16/110,833, Mar. 25, 2019, D. Shin.
Fan, T. et al., "Design and evaluation of solid lipid nanoparticles modified with peptide ligand for oral delivery of protein drugs," European Journal of Pharmaceutics and Biopharmaceutics, vol. 88: 518-528 (2014).
Wang, S. et al., "Determination of P-glycoprotein Inhibition by Excipients and Their Combinations Using an Integrated High-Throughput Process," Journal of Pharmaceutical Sciences, vol. 93(11): 2755-2767 (2004).

\* cited by examiner

FIG. 1A

SEQ ID NO: 1 (GLA, alpha-galactosidase A, wt)

MQLRNPELHLGCALALRFLALVSWDIPGARALDNGLARTPTMGWLHWERFMCNLDCQEE
PDSCISEKLFMEMAELMVSEGWKDAGYEYLCIDDCWMAPQRDSEGRLQADPQRFPHGIR
QLANYVHSKGLKLGIYADVGNKTCAGFPGSFGYYDIDAQTFADWGVDLLKFDGCYCDSL
ENLADGYKHMSLALNRTGRSIVYSCEWPLYMWPFQKPNYTEIRQYCNHWRNFADIDDSW
KSIKSILDWTSFNQERIVDVAGPGGWNDPDMLVIGNFGLSWNQQVTQMALWAIMAAPLF
MSNDLRHISPQAKALLQDKDVIAINQDPLGKQGYQLRQGDNFEVWERPLSGLAWAVAMI
NRQEIGGPRSYTIAVASLGKGVACNPACFITQLLPVKRKLGFYEWTSRLRSHINPTGTV
LLQLENTMQMSLKDLL

See alpha-galactosidase A, Uniprot Acc. No. P06280. This isoform has been chosen as the 'canonical' sequence. All positional information in this entry refers to it.

FIG. 1B

| Feature | Position | Length | Description |
|---|---|---|---|
| Active Site | 170-170 | 1 | Nucleophile |
| Active Site | 231-231 | 1 | Proton donor |
| Signal Peptide | 1-31 | 31 | Signal peptide |

FIG. 1C

SEQ ID NO: 2

```
ATGCAGCTGAGGAACCCAGAACTACATCTGGGCTGCGCGCTTGCGCTTCGCTTCCTGGCCCTCGTTT
CCTGGGACATCCCTGGGGCTAGAGCACTGGACAATGGATTGGCAAGGACGCCTACCATGGGCTGGCT
GCACTGGGAGCGCTTCATGTGCAACCTTGACTGCCAGGAAGAGCCAGATTCCTGCATCAGTGAGAAG
CTCTTCATGGAGATGGCAGAGCTCATGGTCTCAGAAGGCTGGAAGGATGCAGGTTATGAGTACCTCT
GCATTGATGACTGTTGGATGGCTCCCCAAAGAGATTCAGAAGGCAGACTTCAGGCAGACCCTCAGCG
CTTTCCTCATGGGATTCGCCAGCTAGCTAATTATGTTCACAGCAAAGGACTGAAGCTAGGGATTTAT
GCAGATGTTGGAAATAAAACCTGCGCAGGCTTCCCTGGGAGTTTTGGATACTACGACATTGATGCCC
AGACCTTTGCTGACTGGGGAGTAGATCTGCTAAAATTTGATGGTTGTTACTGTGACAGTTTGGAAAA
TTTGGCAGATGGTTATAAGCACATGTCCTTGGCCCTGAATAGGACTGGCAGAAGCATTGTGTACTCC
TGTGAGTGGCCTCTTTATATGTGGCCCTTTCAAAAGCCCAATTATACAGAAATCCGACAGTACTGCA
ATCACTGGCGAAATTTTGCTGACATTGATGATTCCTGGAAAAGTATAAAGAGTATCTTGGACTGGAC
ATCTTTTAACCAGGAGAGAATTGTTGATGTTGCTGGACCAGGGGGTTGGAATGACCCAGATATGTTA
GTGATTGGCAACTTTGGCCTCAGCTGGAATCAGCAAGTAACTCAGATGGCCCTCTGGGCTATCATGG
CTGCTCCTTTATTCATGTCTAATGACCTCCGACACATCAGCCCTCAAGCCAAAGCTCTCCTTCAGGA
TAAGGACGTAATTGCCATCAATCAGGACCCCTTGGGCAAGCAAGGGTACCAGCTTAGACAGGGAGAC
AACTTTGAAGTGTGGGAACGACCTCTCTCAGGCTTAGCCTGGGCTGTAGCTATGATAAACCGGCAGG
AGATTGGTGGACCTCGCTCTTATACCATCGCAGTTGCTTCCCTGGGTAAAGGAGTGGCCTGTAATCC
TGCCTGCTTCATCACACAGCTCCTCCCTGTGAAAAGGAAGCTAGGGTTCTATGAATGGACTTCAAGG
TTAAGAAGTCACATAAATCCCACAGGCACTGTTTTGCTTCAGCTAGAAAATACAATGCAGATGTCAT
TAAAAGACTTACTT
```

FIG. 2

| Protein | Length | Theoretical Minimum U (%) | Theoretical Minimum U (abs) | U Content (%) | U Content (abs) | U Content v Theoretical Minimum (%) | UU pairs | UU pairs v Theoretical Minimum (%) | UU pairs v WT (%) | UUU | UUUU | UUUUU |
|---|---|---|---|---|---|---|---|---|---|---|---|---|
| GLA-WT | 1287 | | | 25.64% | | | | | 100.00% | 12 | 4 | 0 |
| GLA-CO01 | 1287 | | | 17.09% | 220 | 66.67% | 131.74% | 20 | 47.06% | 5 | 0 | 0 |
| GLA-CO02 | 1287 | | | 16.32% | 210 | 63.64% | 125.75% | 24 | 47.06% | 1 | 0 | 0 |
| GLA-CO03 | 1287 | | | 16.55% | 213 | 64.55% | 127.54% | 13 | 25.49% | 5 | 1 | 0 |
| GLA-CO04 | 1287 | | | 17.48% | 225 | 68.18% | 134.73% | 17 | 33.33% | 4 | 0 | 0 |
| GLA-CO05 | 1287 | | | 16.08% | 207 | 62.73% | 123.95% | 16 | 31.37% | 6 | 0 | 0 |
| GLA-CO06 | 1287 | | | 16.94% | 218 | 66.06% | 130.54% | 21 | 41.18% | 2 | 0 | 0 |
| GLA-CO07 | 1287 | | | 17.02% | 219 | 66.36% | 131.14% | 11 | 21.57% | 9 | 0 | 0 |
| GLA-CO08 | 1287 | | | 17.25% | 222 | 67.27% | 132.93% | 20 | 39.22% | 4 | 0 | 0 |
| GLA-CO09 | 1287 | | | 16.86% | 217 | 65.76% | 129.94% | 19 | 37.25% | 2 | 1 | 0 |
| GLA-CO10 | 1287 | | | 16.39% | 211 | 63.94% | 126.35% | 16 | 31.37% | 3 | 0 | 0 |
| GLA-CO11 | 1287 | | | 16.71% | 215 | 65.15% | 128.74% | 17 | 33.33% | 3 | 0 | 0 |
| GLA-CO12 | 1287 | | | 17.25% | 222 | 67.27% | 132.93% | 23 | 45.10% | 2 | 1 | 0 |
| GLA-CO13 | 1287 | | | 16.24% | 209 | 63.33% | 125.15% | 16 | 31.37% | 5 | 0 | 0 |
| GLA-CO14 | 1287 | | | 16.55% | 213 | 64.55% | 127.54% | 22 | 43.14% | 3 | 0 | 0 |
| GLA-CO15 | 1287 | | | 17.25% | 222 | 67.27% | 132.93% | 27 | 52.94% | 1 | 0 | 0 |
| GLA-CO16 | 1287 | | | 17.87% | 230 | 69.70% | 137.72% | 19 | 37.25% | 7 | 0 | 0 |
| GLA-CO17 | 1287 | | | 17.48% | 225 | 68.18% | 134.73% | 17 | 33.33% | 4 | 0 | 0 |
| GLA-CO18 | 1287 | | | 17.09% | 220 | 66.67% | 131.74% | 21 | 41.18% | 3 | 1 | 0 |
| GLA-CO19 | 1287 | | | 17.25% | 222 | 67.27% | 132.93% | 18 | 35.29% | 4 | 1 | 0 |
| GLA-CO20 | 1287 | | | 16.86% | 217 | 65.76% | 129.94% | 17 | 33.33% | 3 | 0 | 0 |
| GLA-CO21 | 1287 | | | 16.94% | 218 | 66.06% | 130.54% | 18 | 35.29% | 6 | 0 | 0 |
| GLA-CO22 | 1287 | | | 16.08% | 207 | 62.73% | 123.95% | 18 | 35.29% | 3 | 0 | 0 |
| GLA-CO23 | 1287 | | | 17.25% | 222 | 67.27% | 132.93% | 22 | 43.14% | 4 | 1 | 0 |
| GLA-CO24 | 1287 | | | 17.17% | 221 | 66.97% | 132.34% | 19 | 37.25% | 3 | 0 | 0 |
| GLA-CO25 | 1287 | | | 17.79% | 229 | 69.39% | 137.13% | 27 | 31.37% | 6 | 1 | 0 |
| MAX | | | 230 | 17.87% | | 69.70% | 137.72% | 27 | | | | |
| MIN | | | 207 | 16.08% | | 62.73% | 123.95% | 11 | | | | |
| AVERAGE | | | 218.16 | 16.98% | | | | 18.68 | | 3.92 | | |
| MEDIAN | | | 219 | 17.02% | | 66.36% | 131.14% | 18 | | 4 | | |
| STD DEV | | | | 0.48% | | 1.78% | 3.45% | | | | 0.70 | |

FIG. 3

| Protein | Length | Theoretical Maximum G (%) | Theoretical Maximum G (abs) | | |
|---|---|---|---|---|---|
| GLA Protein | 429 | 40.48% | 521 | | |

| Nucleic Acid | Length | G Content (abs) | G Content (%) | G Content v WT (%) | G Content v Theoretical Maximum (%) |
|---|---|---|---|---|---|
| GLA-WT | 1287 | 333 | 25.87% | 100.00% | 63.92% |
| GLA-CO01 | 1287 | 393 | 30.54% | 118.02% | 75.43% |
| GLA-CO02 | 1287 | 413 | 32.09% | 124.02% | 79.27% |
| GLA-CO03 | 1287 | 394 | 30.61% | 118.32% | 75.62% |
| GLA-CO04 | 1287 | 400 | 31.08% | 120.12% | 76.78% |
| GLA-CO05 | 1287 | 408 | 31.70% | 122.52% | 78.31% |
| GLA-CO06 | 1287 | 408 | 31.70% | 122.52% | 78.31% |
| GLA-CO07 | 1287 | 394 | 30.61% | 118.32% | 75.62% |
| GLA-CO08 | 1287 | 398 | 30.92% | 119.52% | 76.39% |
| GLA-CO09 | 1287 | 391 | 30.38% | 117.42% | 75.05% |
| GLA-CO10 | 1287 | 400 | 31.08% | 120.12% | 76.78% |
| GLA-CO11 | 1287 | 392 | 30.46% | 117.72% | 75.24% |
| GLA-CO12 | 1287 | 391 | 30.38% | 117.42% | 75.05% |
| GLA-CO13 | 1287 | 395 | 30.69% | 118.62% | 75.82% |
| GLA-CO14 | 1287 | 398 | 30.92% | 119.52% | 76.39% |
| GLA-CO15 | 1287 | 398 | 30.92% | 119.52% | 76.39% |
| GLA-CO16 | 1287 | 380 | 29.53% | 114.11% | 72.94% |
| GLA-CO17 | 1287 | 406 | 31.55% | 121.92% | 77.93% |
| GLA-CO18 | 1287 | 391 | 30.38% | 117.42% | 75.05% |
| GLA-CO19 | 1287 | 399 | 31.00% | 119.82% | 76.58% |
| GLA-CO20 | 1287 | 408 | 31.70% | 122.52% | 78.31% |
| GLA-CO21 | 1287 | 402 | 31.24% | 120.72% | 77.16% |
| GLA-CO22 | 1287 | 401 | 31.16% | 120.42% | 76.97% |
| GLA-CO23 | 1287 | 397 | 30.85% | 119.22% | 76.20% |
| GLA-CO24 | 1287 | 384 | 29.84% | 115.32% | 73.70% |
| GLA-CO25 | 1287 | 392 | 30.46% | 117.72% | 75.24% |
| | MAX | 413 | 32.09% | 124.02% | 79.27% |
| | MIN | 380 | 29.53% | 114.11% | 72.94% |
| | MEAN | 397.32 | 30.87% | 119.33% | 76.26% |
| | MEDIAN | 398 | 30.92% | 119.52% | 76.39% |
| | STD DEV | 7.69 | 0.60% | 2.31% | 1.48% |

FIG. 4

| Protein | Length | Theoretical Maximum C | Theoretical Maximum C (abs) | | |
|---|---|---|---|---|---|
| GLA Protein | 429 | 42.91% | 552 | | |

| Nucleic Acid | Length | C Content(abs) | C Content(%) | C Content v WT (%) | C Content v Theoretical Maximum (%) |
|---|---|---|---|---|---|
| GLA-WT | 1287 | 294 | 22.84% | 100.00% | 53.26% |
| GLA-CO01 | 1287 | 407 | 31.62% | 138.44% | 73.87% |
| GLA-CO02 | 1287 | 386 | 29.99% | 131.29% | 70.05% |
| GLA-CO03 | 1287 | 409 | 31.78% | 139.12% | 74.23% |
| GLA-CO04 | 1287 | 391 | 30.38% | 132.99% | 70.96% |
| GLA-CO05 | 1287 | 402 | 31.24% | 136.73% | 72.96% |
| GLA-CO06 | 1287 | 398 | 30.92% | 135.37% | 72.23% |
| GLA-CO07 | 1287 | 401 | 31.16% | 136.39% | 72.78% |
| GLA-CO08 | 1287 | 390 | 30.30% | 132.65% | 70.78% |
| GLA-CO09 | 1287 | 401 | 31.16% | 136.39% | 72.78% |
| GLA-CO10 | 1287 | 405 | 31.47% | 137.76% | 73.50% |
| GLA-CO11 | 1287 | 405 | 31.47% | 137.76% | 73.50% |
| GLA-CO12 | 1287 | 412 | 32.01% | 140.14% | 74.77% |
| GLA-CO13 | 1287 | 400 | 31.08% | 136.05% | 72.60% |
| GLA-CO14 | 1287 | 408 | 31.70% | 138.78% | 74.05% |
| GLA-CO15 | 1287 | 392 | 30.46% | 133.33% | 71.14% |
| GLA-CO16 | 1287 | 415 | 32.25% | 141.16% | 75.32% |
| GLA-CO17 | 1287 | 386 | 29.99% | 131.29% | 70.05% |
| GLA-CO18 | 1287 | 402 | 31.24% | 136.73% | 72.96% |
| GLA-CO19 | 1287 | 400 | 31.08% | 136.05% | 72.60% |
| GLA-CO20 | 1287 | 389 | 30.23% | 132.31% | 70.60% |
| GLA-CO21 | 1287 | 394 | 30.61% | 134.01% | 71.51% |
| GLA-CO22 | 1287 | 408 | 31.70% | 138.78% | 74.05% |
| GLA-CO23 | 1287 | 393 | 30.54% | 133.67% | 71.32% |
| GLA-CO24 | 1287 | 412 | 32.01% | 140.14% | 74.77% |
| GLA-CO25 | 1287 | 396 | 30.77% | 134.69% | 71.87% |
| | MAX | 415 | 32.25% | 141.16% | 75.32% |
| | MIN | 386 | 29.99% | 131.29% | 70.05% |
| | AVERAGE | 400.08 | 31.09% | 136.08% | 72.61% |
| | MEDIAN | 401 | 31.16% | 136.39% | 72.78% |
| | STD DEV | 8.40 | 0.65% | 2.86% | 1.53% |

FIG. 5

| Protein | Length | Theoretical Maximum GC | Theoretical Maximum GC (abs) | | |
|---|---|---|---|---|---|
| GLA Protein | 429 | 66.82% | 860 | | |

| Nucleic Acid | Length | GC Content(abs) | GC Content(%) | GC Content v WT (%) | GC Content v Theoretical Maximum (%) |
|---|---|---|---|---|---|
| GLA-WT | 1287 | 627 | 48.72% | 100.00% | 72.91% |
| GLA-CO01 | 1287 | 800 | 62.16% | 127.59% | 93.02% |
| GLA-CO02 | 1287 | 799 | 62.08% | 127.43% | 92.91% |
| GLA-CO03 | 1287 | 803 | 62.39% | 128.07% | 93.37% |
| GLA-CO04 | 1287 | 791 | 61.46% | 126.16% | 91.98% |
| GLA-CO05 | 1287 | 810 | 62.94% | 129.19% | 94.19% |
| GLA-CO06 | 1287 | 806 | 62.63% | 128.55% | 93.72% |
| GLA-CO07 | 1287 | 795 | 61.77% | 126.79% | 92.44% |
| GLA-CO08 | 1287 | 788 | 61.23% | 125.68% | 91.63% |
| GLA-CO09 | 1287 | 792 | 61.54% | 126.32% | 92.09% |
| GLA-CO10 | 1287 | 805 | 62.55% | 128.39% | 93.60% |
| GLA-CO11 | 1287 | 797 | 61.93% | 127.11% | 92.67% |
| GLA-CO12 | 1287 | 803 | 62.39% | 128.07% | 93.37% |
| GLA-CO13 | 1287 | 795 | 61.77% | 126.79% | 92.44% |
| GLA-CO14 | 1287 | 806 | 62.63% | 128.55% | 93.72% |
| GLA-CO15 | 1287 | 790 | 61.38% | 126.00% | 91.86% |
| GLA-CO16 | 1287 | 795 | 61.77% | 126.79% | 92.44% |
| GLA-CO17 | 1287 | 792 | 61.54% | 126.32% | 92.09% |
| GLA-CO18 | 1287 | 793 | 61.62% | 126.48% | 92.21% |
| GLA-CO19 | 1287 | 799 | 62.08% | 127.43% | 92.91% |
| GLA-CO20 | 1287 | 797 | 61.93% | 127.11% | 92.67% |
| GLA-CO21 | 1287 | 796 | 61.85% | 126.95% | 92.56% |
| GLA-CO22 | 1287 | 809 | 62.86% | 129.03% | 94.07% |
| GLA-CO23 | 1287 | 790 | 61.38% | 126.00% | 91.86% |
| GLA-CO24 | 1287 | 796 | 61.85% | 126.95% | 92.56% |
| GLA-CO25 | 1287 | 788 | 61.23% | 125.68% | 91.63% |
| | MAX | 810 | 62.94% | 129.19% | 94.19% |
| | MIN | 788 | 61.23% | 125.68% | 91.63% |
| | AVERAGE | 797.4 | 61.96% | 127.18% | 92.72% |
| | MEDIAN | 796 | 61.85% | 126.95% | 92.56% |
| | STD DEV | 6.45 | 0.50% | 1.03% | 0.75% |

FIG. 6

| Sequence | GC | GC 1st | GC 2nd | GC 3rd |
|---|---|---|---|---|
| GLA-WT | 48.72 | 53.38 | 41.26 | 51.52 |
| GLA-CO25 | 61.23 | 57.11 | 41.26 | 85.31 |
| GLA-CO08 | 61.23 | 55.01 | 41.26 | 87.41 |
| GLA-CO23 | 61.38 | 55.48 | 41.26 | 87.41 |
| GLA-CO15 | 61.38 | 57.11 | 41.26 | 85.78 |
| GLA-CO04 | 61.46 | 56.18 | 41.26 | 86.95 |
| GLA-CO17 | 61.54 | 55.48 | 41.26 | 87.88 |
| GLA-CO09 | 61.54 | 55.94 | 41.26 | 87.41 |
| GLA-CO18 | 61.62 | 56.41 | 41.26 | 87.18 |
| GLA-CO16 | 61.77 | 57.34 | 41.26 | 86.71 |
| GLA-CO13 | 61.77 | 55.01 | 41.26 | 89.04 |
| GLA-CO07 | 61.77 | 57.11 | 41.26 | 86.95 |
| GLA-CO24 | 61.85 | 56.64 | 41.26 | 87.65 |
| GLA-CO21 | 61.85 | 56.18 | 41.26 | 88.11 |
| GLA-CO11 | 61.93 | 56.18 | 41.26 | 88.34 |
| GLA-CO20 | 61.93 | 56.18 | 41.26 | 88.34 |
| GLA-CO02 | 62.08 | 55.24 | 41.26 | 89.74 |
| GLA-CO19 | 62.08 | 56.64 | 41.26 | 88.34 |
| GLA-CO01 | 62.16 | 57.34 | 41.26 | 87.88 |
| GLA-CO03 | 62.39 | 56.41 | 41.26 | 89.51 |
| GLA-CO12 | 62.39 | 57.81 | 41.26 | 88.11 |
| GLA-CO10 | 62.55 | 56.18 | 41.26 | 90.21 |
| GLA-CO06 | 62.63 | 56.64 | 41.26 | 89.98 |
| GLA-CO14 | 62.63 | 56.18 | 41.26 | 90.44 |
| GLA-CO22 | 62.86 | 56.64 | 41.26 | 90.68 |
| GLA-CO05 | 62.94 | 56.41 | 41.26 | 91.14 |
| Overall | 61.45 | 56.24 | 41.26 | 86.85 |

FIG. 7

α-GLA IHC of Mouse Liver

α-GLA IHC of Mouse Liver

*Solid bar*: before mRNA administration
*Pattern bar*: 72 hr after mRNA administration

| Percent (%) Reduction of Lyso-Gb3 | | | |
|---|---|---|---|
|  | 0.5 mpk | 0.1 mpk | 0.05 mpk |
| Plasma | 72.9 | 37.5 | 19.5 |
| Heart | 50.0 | 6.1 | 3.1 |
| Kidney | 49.6 | 3.5 | -7.6 |

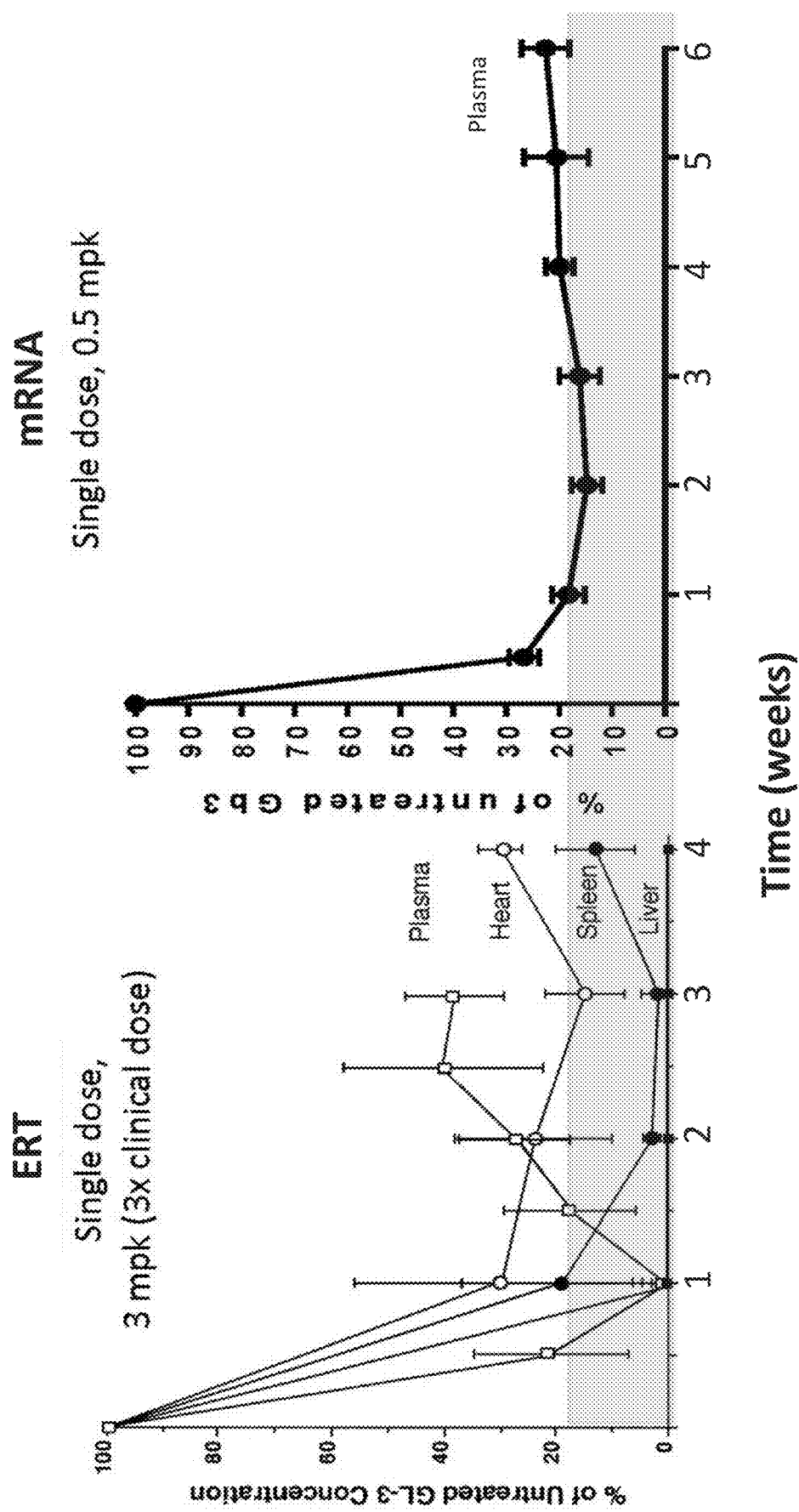

SEQUENCE LISTING

```
<160> NUMBER OF SEQ ID NOS: 170

<210> SEQ ID NO 1
<211> LENGTH: 429
<212> TYPE: PRT
<213> ORGANISM: Artificial Sequence
<220> FEATURE:
<223> OTHER INFORMATION: GLA, alpha-galactosidase A,

<400> SEQUENCE: 1

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60
```

Ser Glu Lys Leu Phe Met Glu Met Ala Glu Leu Met Val Ser Glu Gly
 65                  70                  75                  80

Trp Lys Asp Ala Gly Tyr Glu Tyr Leu Cys Ile Asp Asp Cys Trp Met
             85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425

<210> SEQ ID NO 2
<211> LENGTH: 1287
<212> TYPE: DNA
<213> ORGANISM: Artificial Sequence
<220> FEATURE:
<223> OTHER INFORMATION: wild type isoform

<400> SEQUENCE: 2

```
atgcagctga ggaacccaga actacatctg gctgcgcgc ttgcgcttcg cttcctggcc    60
ctcgtttcct gggacatccc tggggctaga gcactggaca atggattggc aaggacgcct   120
accatgggct ggctgcactg ggagcgcttc atgtgcaacc ttgactgcca ggaagagcca   180
gattcctgca tcagtgagaa gctcttcatg gagatggcag agctcatggt ctcagaaggc   240
tggaaggatg caggttatga gtacctctgc attgatgact gttggatggc tccccaaaga   300
gattcagaag gcagacttca ggcagaccct cagcgctttc ctcatgggat tcgccagcta   360
gctaattatg ttcacagcaa aggactgaag ctagggattt atgcagatgt tggaaataaa   420
acctgcgcag gcttccctgg gagttttgga tactacgaca ttgatgccca gaccttgct   480
gactggggag tagatctgct aaaatttgat ggttgttact gtgacagttt ggaaaatttg   540
gcagatggtt ataagcacat gtccttggcc ctgaatagga ctggcagaag cattgtgtac   600
tcctgtgagt ggcctctta tatgtggccc tttcaaaagc ccaattatac agaaatccga   660
cagtactgca atcactggcg aaatttgct gacattgatg attcctggaa agtataaag    720
agtatcttgg actggacatc ttttaaccag gagagaattg ttgatgttgc tggaccaggg   780
ggttggaatg acccagatat gttagtgatt ggcaactttg gcctcagctg aatcagcaa   840
gtaactcaga tggcccctctg gctatcatg gctgctcctt tattcatgtc taatgacctc   900
cgacacatca gccctcaagc caaagctctc cttcaggata aggacgtaat tgccatcaat   960
caggacccct tgggcaagca agggtaccag cttagacagg gagacaactt tgaagtgtgg  1020
gaacgacctc tctcaggctt agcctgggct gtagctatga taaaccggca ggagattggt  1080
ggacctcgct cttataccat cgcagttgct tccctgggta aaggagtggc ctgtaatcct  1140
gcctgcttca tcacacagct cctccctgtg aaaaggaagc tagggttcta tgaatggact  1200
tcaaggttaa gaagtcacat aaatcccaca ggcactgttt tgcttcagct agaaaataca  1260
atgcagatgt cattaaaaga cttactt                                      1287

<210> SEQ ID NO 3
<211> LENGTH: 1287
<212> TYPE: RNA
<213> ORGANISM: Artificial Sequence
<220> FEATURE:
<223> OTHER INFORMATION: GLA-CO01

<400> SEQUENCE: 3
augcagcuga ggaacccega gcugcaccug gguugcgccc uggcccugcg cuuccuggcg    60
cuggucagcu gggacauccc cggggcccgu gcccuugaua acggccuggc ccgaaccccc   120
acgaugggcu ggcugcacug ggagcguuuc augugcaacc ucgacuguca ggaggagcca   180
gacagcugua ucagcgaaaa gcuguucaug gaauggccg agcuuauggu gagcgagggc   240
uggaaggacg ccggguacga guaccugugc aucgacgacu gcuggauggc ccccagagg   300
gacuccgaag ccgccugca ggccgauccg cagcgcuucc cucacggcau caggcagcuc   360
gccaacuacg uacacagcaa gggccucaag cuggggaucu acgccgacgu gggcaacaag   420
accugcgccg gcuucccegg uagcuucggc uacuacgaca ucgaugccca gaccuucgcc   480
gacuggggcg ucgaucugcu gaaguuugac ggcugcuacu gcgauagccu ggagaaccug   540
gccgauggcu acaagcauau gagccuggcc cugaaccgga ccggccggag caucguguau   600
agcugcgagu ggcccucucua caugugggcc uuucaaaagc ccaacuacac cgagauccgc   660
caguacugca accacuggag gaauuucgcg gacaucgaug acagcuggaa guccaucaag   720
agcauccugg auuggacgag cuucaaccag gagcgcaucg ucgacguggc cggguccaggg   780
```

```
gguuggaacg aucccgacau gcucgugauc ggcaacuucg gccgagcug gaaucaacag    840 gugacucaga uggcgcugug gccaucaug gccgcccccc uguucaugag caaugaccuc    900
cgacacauca gcccgcaggc caaggcccug cuccaggaca aggauguuau cgcgaucaac    960
caggaccccc ugggcaagca gggcuaccag cuuaggcagg gagacaauuu cgaggugugg   1020
gagaggccgc uguccgggcu cgccugggcc guugccauga ucaauaggca agagaucggc   1080
ggccccagaa gcuacaccau agccguggcc agccugggca agggcguugc gugcaacccc   1140
gccugcuuca ucacgcagcu gcugcccguc aaacgcaagc ugggcuucua cgaguggacc   1200
agccgccugc gcucccauau caaccccacc gggaccgucc ugcugcagcu ggagaacacc   1260
augcagauga gccugaaaga ccugcug                                      1287
```

```
<210> SEQ ID NO 4
<211> LENGTH: 1287
<212> TYPE: RNA
<213> ORGANISM: Artificial Sequence
<220> FEATURE:
<223> OTHER INFORMATION: GLA-CO02

<400> SEQUENCE: 4
```

```
augcagcuca ggaacccuga gcuccaccuc ggguggcgccc uggcacuccg guuucuggcc     60
cuggugagcu gggacauccc cggcgcgcgu gcccuggaca acggucuggc caggaccccg    120
accauggggu ggcugcacug ggagcgguuc auguguaacc uggauugcca ggaagagccc    180
gacaguugca ucucggaaaa acguucaug gagauggccg agcugauggu gagcgagggu    240
uggaaagacg ccggauacga guaccugugc aucgacgacu gcuggauggc cccacagagg    300
gacuccgagg ggaggcugca ggccgacccc cagagguucc cccacggaau ccgacagcug    360
gccaacuacg uccacagcaa gggccugaaa cugggcaucu acgcagacgu uggcaauaag    420
accugcgccg gguucccggg gagcuucggc uacauugaca ucgacgccca gaccuucgcc    480 gacugggggcg uggaucuccu gaaguucgac ggcugcuacu gcgacucgcu ggagaacuug    540
gcagacggau acaagcauau gagccuggcc cugaaccgga ccggccgag caucguguac    600 agcugcgagu ggcccuguag uauguggccg uuccagaagc ccaauuacac ugagaucagg    660
caguauugca accacuggag gaacuucgcc gacaucgacg acagcuggaa aagcaucaag    720
agcauccugg acuggaccag cuucaaccag gagaggaucu cgacguggc cgggcccggg    780 ggcuggaacg accccgacau gcucgugauc ggcaacuucg gccuguccug gaaccagcag    840
gugacccaga uggcccugug ggcgauaaug gccgcccccc uguucaugag caacgaccug    900
aggcacauca gccccggcgc caaagcccug uugcaggaca aggacgugau cgcuaucaac    960
caggaucccc uggaaagcaa ggguaccag cugcggcagg cgacaacuu cgaggugugg   1020 gagaggccgc ugagcgggcu ggccugggcc guggccauga uaaauaggca ggagaucggc   1080 ggccccgagga guuacaccau cgccguggcg ucaucucggaa aaggcgucgc guguaacccc   1140
gccugcuuca ucacccagcu ccugcccgug aagaggaagc ugggcuucua cgaguggaca   1200
agcaggcuga gguccacau caacccgacc ggcaccgugc ugcugcagcu ggagaacacc   1260
augcagauga gccugaagga ccugcug                                      1287
```

```
<210> SEQ ID NO 5
<211> LENGTH: 1287
<212> TYPE: RNA
<213> ORGANISM: Artificial Sequence
<220> FEATURE:
```

<223> OTHER INFORMATION: GLA-CO03

<400> SEQUENCE: 5

| | | | | | |
|---|---|---|---|---|---|
| augcagcugc | ggaaccccga | gcugcaccug | gggugcgccc | ucgcccugag | guuccuggcc | 60 |
| cugguguccu | gggacauccc | ggggccagg | gcacucgaca | acggccucgc | aaggaccccc | 120 |
| accaugggcu | ggcugcacug | ggagcgcuuc | augugcaauc | uggacugca | ggaagaaccu | 180 |
| gacuccugca | cuccgagaa | gcuguucaug | gagauggccg | agcugauggu | ucccgagggg | 240 |
| uggaaggacg | ccggguacga | guaccugugc | aucgaugacu | gcuggauggc | ccccagaga | 300 |
| gacuccgagg | gccgccucca | ggccgaccca | cagcguuucc | cgcacggcau | caggcagcug | 360 |
| gccaacuacg | ugcacagcaa | gggccugaag | cuggcaucu | acgcagacgu | gggcaacaag | 420 |
| acgugcgcgg | gcuucccgg | cagcuucgga | uacaugaua | ucgacgccca | gaccuucgcc | 480 |
| gacugggggg | ucgaccugcu | gaaguucgau | ggcugcuacu | gcgauagccu | cgagaaccuc | 540 |
| gccgacggau | acaagcacau | gucgcucgcc | cugaaccgaa | ccggcaggag | cauagucuac | 600 |
| agcugcgagu | ggcccugua | caugugggccc | uccagaaac | ccaacuacac | ggagaucagg | 660 |
| caguauugca | ccacuggag | gaauuucgcc | gacaucgacg | acagcuggaa | gagcaucaaa | 720 |
| agcauccugg | auuggaccuc | cuucaaccag | gagaggaucg | uggacguggc | cggccccggga | 780 |
| ggcuggaacg | auccgacau | gcuggugauc | ggcaacuuug | gccugccug | gaaccagcag | 840 |
| gugacccaga | uggcccugug | ggccaucaug | gccgcccccc | uguuuaugag | caacgaccuc | 900 |
| cggcacauca | ucccccaggc | caaagcccuc | cugcaggaca | aggacgugau | cgccaucaac | 960 |
| caggaccccc | ugggcaagca | gggcuaccaa | cugaggcagg | gggacaauuu | ugaggugugg | 1020 |
| gagaggcccc | ugaguggucu | ggccugggcc | gucgcgauga | ucaaccgaca | ggagaucggc | 1080 |
| ggcccccgca | gcuauaccau | cgccgucgcc | agcugggga | agggcguggc | cugcaacccca | 1140 |
| gccugcuuua | ucacccagcu | acugcccgug | aaacgcaagc | uugggucua | cgaguggacc | 1200 |
| ucccggcuga | ggagccacau | caauccgacg | ggcaccgugc | ugcugcagcu | ggagaacacc | 1260 |
| augcaaauga | gccucaagga | ccuccuc | | | 1287 |

<210> SEQ ID NO 6
<211> LENGTH: 1287
<212> TYPE: RNA
<213> ORGANISM: Artificial Sequence
<220> FEATURE:
<223> OTHER INFORMATION: GLA-CO04

<400> SEQUENCE: 6

| | | | | | |
|---|---|---|---|---|---|
| augcagcugc | ggaaccccga | gcuccaccug | gggugcgccc | uggcccugcg | guuccuggcc | 60 |
| cucgugagcu | gggacauccc | gggagcccga | gcgcuggaua | acgggcuagc | caggaccccc | 120 |
| accaugggcu | ggcuccauug | ggagagguuc | augugcaauc | uggacugcca | ggaagagccc | 180 |
| gacagcugca | cuccgaaaa | gcuguucaug | gagauggccg | aacugauggu | uccgagggc | 240 |
| uggaaggacg | ccggauacga | guacucugc | auagacgacu | gcuggauggc | ccccagcgc | 300 |
| gacuccgagg | gccgacugca | ggccgacccc | cagcgcuuuc | ccauggcau | ccggcagcug | 360 |
| gccaacuaug | ugcacagcaa | gggccucaag | cucgggauau | acgcggacgu | ggggaauaag | 420 |
| acgugugcgg | gcuuccccgg | gucguucggu | uacaugaca | ucgacgcaca | gaccuucgcc | 480 |
| gauugggggg | ucgaccugcu | caaguuugac | ggcugcuauu | gugacagccu | ggagaaccuc | 540 |
| gccgacgggu | acaagcacau | gucccuggcc | cugaauagga | cgggcaggag | caucguauac | 600 |
| agcugcgagu | ggcccccugua | caugugggcca | uccagaagc | cgaacuauac | cgagauccgu | 660 |

| | |
|---|---|
| caguacugca accacuggag aacuucgcg acaucgacg acuccuggaa gagcaucaag | 720 |
| agcauccucg acuggacgag cuucaaccag gagaggauau uggacguggc cggcccggc | 780 |
| ggcuggaacg aucccgacau gcuggugauc ggcaacuucg ccugucgug aaucagcag | 840 |
| gugacccaga uggcccugug ggccaucaug gccgccccc uguuuaugag caaugaccug | 900 |
| aggcacaucu ccccacaagc caaggcccug cugcaagaca aggacgugau cgccauaaac | 960 |
| caggaucccc ucggcaagca ggggauaccag cucaggcagg gugauaacuu cgaggucugg | 1020 |
| gaacgaccc uguccgggcu ggccuggcc gugggccauga ucaaucgcca ggagaucggc | 1080 |
| gggcccaggu ccuacaccau cgccguggcc agccugggca agggcguggc cugcaacccu | 1140 |
| gccuguuca ucacacagcu ccugccggua aagaggaagc ugggcuucua cgaauggacc | 1200 |
| aguaggcuca gguccacau caaccccacc gguaccgugu ugcugcagcu ggagaauacg | 1260 |
| augcagaugu cgcugaaaga ucugcug | 1287 |

<210> SEQ ID NO 7
<211> LENGTH: 1287
<212> TYPE: RNA
<213> ORGANISM: Artificial Sequence
<220> FEATURE:
<223> OTHER INFORMATION: GLA-CO05

<400> SEQUENCE: 7

| | |
|---|---|
| augcagcugc ggaaccccga gcugcaccug ggugcgcac uggcccugag guuccuggcc | 60 |
| cuugugccu gggacauccc cggcgcccgg gcccuggaca acggucuggc caggacgccc | 120 |
| accaugggcu ggcugcacug ggagcgcuuu augugcaacc uggacugcca ggaggagccc | 180 |
| gacagcugca ucagcgagaa gcuguucaug gagauggcgg agcucauggu gagcgagggg | 240 |
| uggaaggacg ccggguacga guaccugugc aucgacgacu gcuggaguggc ccccagcgg | 300 |
| gacagcgagg gcaggcugca agccgacccc cagagguucc cccacgggau caggcagcuc | 360 |
| gccaacuacg ugcauucaaa ggggcugaaa cucggcaucu acgcggaugu gggaaacaag | 420 |
| accugcgccg gauucccgg gagcuucggg uacuacgaca ucgacgccca gaccuuugcc | 480 |
| gacuggggg ucgaccugcu gaaguuugac ggcugcuauu gcgacagccu ggagaaccua | 540 |
| gccgacgggu acaagcacau gagccuggc cugaaccgca ccgggcgcag caucgucuac | 600 |
| agcugcgagu ggcccuugua caugggccgu uccagaagc caacuacac ugagauccga | 660 |
| caguacugca accacuggag aaacuucgcc gacaucgacg acagcuggaa gagcaucaag | 720 |
| agcauccugg acuggaccuc cuucaaccag gagcggaucg uggacguggc cggcccgggc | 780 |
| gguuggaaug acccggacau gcuggugauc ggcaacuucg ccuguccug gaaccagcag | 840 |
| gugacgcaga uggcccugug ggcgaucaug gccgccccc uguucaugc caaugaccug | 900 |
| aggcacauuu cgccacaggc caaggcgcug cugcaggaua aggaugugau cgccaucaac | 960 |
| caggaccccc ugggcaagca aggcuaccag cuccgacaag gggauaauuu cgaggucugg | 1020 |
| gaacgccccc ucagcggccu ggccuggcc gugggccauga ucaacaggca ggagaucggu | 1080 |
| ggccccagga gcuacaccau cgccguggcc agccucggca agggcgucgc cugcaaccc | 1140 |
| gccugcuuca ucacccaauu acugcccgug aagaggaagc ugggguuucua cgaguggacc | 1200 |
| agcaggcugc gaagccacau caacccgacc ggcacaguc ugcugcagcu ggagaacacg | 1260 |
| augcagaugu cgcucaaaga ccugcug | 1287 |

<210> SEQ ID NO 8

<211> LENGTH: 1287
<212> TYPE: RNA
<213> ORGANISM: Artificial Sequence
<220> FEATURE:
<223> OTHER INFORMATION: GLA-C006

<400> SEQUENCE: 8

```
augcagcugc ggaaccccga gcugcaccug gggugcgccc uggcccugag guuccuggcc    60
cuggugagcu gggauauccc cggagcccgc gcccuggaua acgggcuggc caggaccccc   120
accaugggcu ggcugcacug ggagagguuc augugcaacc ucgacugcca ggaggagccg   180
gacuccugca ucagcgagaa gcucuuuaug gagauggccg agcugauggu uuccgagggc   240
uggaaggacg ccggauauga uaccugugc auugaugacu gcuggaugc gccccagcgu   300
gacuccgagg ccggcugca agccgacccc cagagguucc cccacgggau caggcagcug   360
gccaacuaug uccacucgaa ggggcugaag cuggcaucu acgccgacgu ggggaacaaa   420
accugcgccg gguucccagg cagcuucggc uacuaugaca uagacgccca gaccuucgcc   480
gacugggcg uggaccugcu gaaauucgau gguugcuacu cgacucccu ggaaaaccug   540
gccgauggcu acaagcacau gagccuggcc cugaauagga ccggccggag caucguauac   600
agcugugagu ggccgcugua caugggccc uuccagaaac ccaauuacac cgaauccgu   660
caguacugca ucacuggcg gaacuucgcg gacauugacg acagcuggaa gagcaucaaa   720
uccauacugg acuggaccag cuucaaccag gagaggauug uggacguggc cgggccgggg   780
ggguggaacg acccggacau gcuggugauc ggcaacuucg ccugagcug gaaucagcag   840
gugacccaga uggcgcugug gccaucaug gccgcccuc uguucauguc caacgaccug   900
cgccauauca gccccaggc caaggcgcuu cugcaggaca aggacgucau cgccaucaac   960
caggacccgc uggggaagca ggguaccag cugcgccagg ggacaacuu cgaggugugg  1020
gagaggccgc uguccggccu cgcguggcc gucgccauga ucaacaggca ggagaucggc  1080
ggccccagga gcuacaccau cgccguggcc uccugggca agggcguggc cugcaacccc  1140
gcgugcuuca ucacccagcu gcugccggug aaacgcaagc ugggcuucua cgaguggacc  1200
ucccgccuca gguccauau caaccccacc ggaaccgugc ugcugcagcu ggagaauacg  1260
augcaaaugu cccugaagga ccugcug                                     1287
```

<210> SEQ ID NO 9
<211> LENGTH: 1287
<212> TYPE: RNA
<213> ORGANISM: Artificial Sequence
<220> FEATURE:
<223> OTHER INFORMATION: GLA-C007

<400> SEQUENCE: 9

```
augcagcugc guaacccgga gcugcaccug ggcugcgccc uggcgcugag guuccuggcc    60
cuggugagcu gggacauccc cggcgcccgg gcccuggaca acggccuggc gaggaccccc   120
accauggggu ggcugcacug ggagcguuuc augugcaacc uggacugcca agaggagccc   180
gauagcugca ucuccgagaa acuauuuaug gagauggccg aacugauggu cagcgagggc   240
uggaaggacg ccgggguacga guaccugugc aucgaugacu gcuggaugc ccccaacgg   300
gacuccgagg gcaggcugca ggcggaccca gcgcguuuc cccacggcau aaggcagcua   360
gccaacuacg ugcacagcaa gggcugaag cuggcaucu acgccgacgu gggcaacaag   420
accugcgccg gcuucccgg auccuuggc uacuacgaca ucgacgccca gacguuugcc   480
gacugggggcg uggaccuccu caaguuugau gguugcuacu gcgacagccu cgagaaucug  540
```

-continued

```
gccgacggcu acaagcacau gucccuggcu cucaacagga ccgggcggag caucguguac    600
agcugcgagu ggccccucua cauguggccc uuccagaagc caaacuacac cgagauccgu    660
caguacugca accacuggcg gaacuucgcc gacauugaug acuccuggaa gagcaucaag    720
uccauacugg acuggaccuc auuuaaccag gagcgaaucg uggacguggc cggcccgggg    780
ggauggaacg accccgacau gcucgugauc ggaaacuucg gucugagcug gaaccagcag    840
gugacccaga uggcccucug ggcgaucaug gccgcgcccc uguucaugag caacgaucug    900
aggcacaucu cccccaggc caaggcccug cugcaggaca agacgugau cgccaucaau    960 caagacccc ugggcaagca aggauaccag cucaggcagg gcgacaacuu cgaggugugg    1020 gagcgcccc ucagcgggcu ggccugggcc gucgccauga uuaaucggca ggaaaucggc    1080 ggccccgga gcuauaccau cgccguggcc agccugggaa agggcgucgc augcaaucca    1140
gcgugcuuua ucacacagcu gcugcccgug aagcggaagc ugggcuucua ugaguggacc    1200
uccaggcuga ggagcacau aaaccccacc ggcaccguuc ugcuccagcu ggagaacacc    1260
augcagauga gucugaaaga ccugcuu                                      1287
```

<210> SEQ ID NO 10
<211> LENGTH: 1287
<212> TYPE: RNA
<213> ORGANISM: Artificial Sequence
<220> FEATURE:
<223> OTHER INFORMATION: GLA-CO08

<400> SEQUENCE: 10

```
augcagcuga ggaaccccga gcugcaccug ggugcgccc uggcccugag guuccuggcc    60
cuggucuccu gggacaucc cggggcgagg gcccuggaua acggccuggc gcggaccccc    120
accaugggcu ggcugcacug ggagcgcuuc augugcaacc uggacugcca ggaggaaccg    180
gacuccugca ucagcgagaa gcucuucaug gagauggccg agcugauggu ucccgagggg    240
uggaaggaug ccggcuacga guaccugugc aucgacgacu gcuggauggc cccccagagg    300
gauagcgagg gcaggcugca ggccgacccc cagcggguucc cccacggcau caggcaacug    360
gccaacuaug uucacagcaa aggccugaag cugggcaucu acgccgaugu ggggaauaag    420
accugugccg gauuucccgg cagcuuuggg uacuaugaua ucgaugccca gacguucgcc    480
gauuggggcg uggaccuccu gaaguucgac ggcugcuauu gcgauagccu ggagaaucug    540
gccgacggcu acaagcauau gagccucgcc cugaacagga ccggcagguc caucguguac    600
uccugcgaau ggccccugua cauguggccc uuccagaagc ccaacuacac ggagaucagg    660
caguacugca accacuggcg gaacuuugcc gacaucgacg acagcuggaa guccaucaag    720
agcauccugg acuggaccag cuucaaccaa gagaggaucg ucgaugugc cggcccagga    780 gguuggaacg acccugacau gcucgugaua ggcaauuucg gccugucug gaaccagcag    840 gugacccaga uggcccugug gccaucaug gccgcccccu auucaugag caacgaccug    900 cgucacauca gccccccaggc caaggcccuc cugcaggaca agacgugau cgcaaucaau    960 caggaucccc uaggcaagca gggguaucag cugcgucagg gcgacaacuu cgaggugugg    1020
gagaggccgu guccgggcu cgccugggca guggccauga ucaacaggca ggaaaucggc    1080
ggacccagga gcuacaccau cgccgucgcc agccugggca agggguggc gugcaauccc    1140 gccugcuuca ucacccagcu gcugcccgug aaaaggaagc uggggauucua cgagugggaca    1200 agccggcuca ggagucacau caaccccacc ggcaccgugu uacugcagcu ggagaacaca    1260
```

```
augcagauga gccugaaaga ccuguua                                      1287
```

<210> SEQ ID NO 11
<211> LENGTH: 1287
<212> TYPE: RNA
<213> ORGANISM: Artificial Sequence
<220> FEATURE:
<223> OTHER INFORMATION: GLA-CO09

<400> SEQUENCE: 11

```
augcagcuga ggaaccccga acugcaccug ggcugcgccc uggcccugcg uuuucucgca    60
cuggucuccu gggacauccc gggcgcaagg gcccuggaua acggccucgc ccggaccccc   120
accaugggcu ggcugcacug ggagcgguuc augugcaauc uggacugcca ggaggaaccc   180
gacagcugca ucuccgaaaa acuguucaug gagauggccg aacugauggu cagcgaaggc   240
uggaaggaug ccggcuacga guaccugugc aucgacgacu gcuggaupgc cccccagagg   300
gacagcgagg ggcgccucca ggccgacccc caaagguucc cccacggcau caggcagcug   360
gccaacuaug ugcacagcaa gggccucaag cuggggaucu augccgacgu cggaaacaaa   420
accugcgccg gcuuccccgg cagcuucggc uacuacgaca ucgacgccca gaccuucgcc   480
gacuggggcg uggaccugcu gaaguucgac ggcugcuacu gcgauucccu ggaaaaccug   540
gccgacgggu auaagcacau gagccucgcc cuuaaccgga ccgguaggag caucguguau   600
uccugugagu ggcccuugua caugggcccc uuucaaaagc ccaacuacac cgagauaagg   660
caguacugua accacuggag gaacuucgcc gacaucgacg acuccuggaa gucgaucaag   720
uccauucugg acuggaccuc cuucaaccag gaacggaucg uggacguggc cgguccggga   780
ggguggaacg aucccgacau gcuggugauu ggcaacuucg acugagcug gaaccagcag    840
gugacccaga uggcucugug ggccauuaug gccgcccccc uguucauguc caacgaccug   900
aggcacauca gcccucaagc caaggcccug cugcaggaca aggacgugau cgccaucaau   960
caggaccccc ugggcaagca gggcuaccaa cugaggcaag cgacaacuu cgaggugugg  1020
gagcgaccgc ugagcggccu ggccugggcc guggccauga ucaaccguca ggagaucggg  1080
ggcccaggga gcuacaccau agccgugggcg agccugggca agggagugcc cugcaauccc  1140
gccugcuuua uacccaacu gcugccagug aagaggaagc ugggcuucua cgaguggacc  1200
agcaggcuga ggucacacau caaccccacc gggacggugc cuccgcagcu cgagaauacc  1260
augcagauga gccugaagga ccugcug                                     1287
```

<210> SEQ ID NO 12
<211> LENGTH: 1287
<212> TYPE: RNA
<213> ORGANISM: Artificial Sequence
<220> FEATURE:
<223> OTHER INFORMATION: GLA-CO10

<400> SEQUENCE: 12

```
augcagcuga ggaauccaga gcugcaccug ggcugugccc uggcccugag guuccuggcc    60
cuggugagcu gggacauccc cggcgccagg gcccuugaca acggccuggc ccgcaccccc   120
acgaugggcu ggcugcacug ggagcgguuc augugcaacc uggacugcca agaagagccc   180
gacuccugca ucagcgaaaa gcucuucaug gagauggccg agcugauggu gagcgagggc   240
uggaaggacg ccggcuacga auaccugugc auagacgacu guuggaupgc cccgcagcgg   300
gacagcgaag acggcugca ggccgacccg cagagguuuc cccacggcau ccggcagcug   360
gccaacuacg uccauuccaa gggccugaag cugggaaucu acgcggacgu ggggaacaag   420
```

```
accugcgcgg gcuucccagg cuccuucggc uacuacgaca ucgacgccca aaccuucgcc    480
gacugggcg uggaccugcu gaaguucgac ggcugcuacu gugacucccu cgagaaucuc     540
gccgauggau acaagcauau gagccuggcc cuaaacagga ccggcagguc caucgugac     600
uccugcgagu ggcccuaua caugggccc uccagaagc ccaacuacac ggagauccgg       660
caguacugca accacuggag gaacuucgcc gacaucgacg acagcuggaa gagcaucaag    720
uccauccucg acuggacguc cuucaaccag gagaggaucg uggacguggc gggccccggg    780
ggauggaacg auccccgacau gcuggugauc ggcaacuucg gcugagcug gaaccaacag    840
gugacccaga uggccugug ggccaucaug gccgcccccc uguuuaugac gaaugaucug    900
cgucacauca gcccgcaggc caaggccug cuacaggaca aggacgugau cgccaucaac     960
caggaccccc uggaaaaca gggcuaccag cugaggcagg gcgauaauuu cgaggugugg   1020
gagcggcccc ugagcggacu ggccugggcc guggcgauga ucaacagaca ggagaucgga  1080
ggucccaggu ccuacaccau cgccguggcc uccuggggga agggcgugge cugcaacccc  1140
gccugcuuca ucaccagcu gcuccccguc aaaaggaagc uggggcuucua cgaguggacc  1200
ucccgccuga ggagccacau caaccccacc gggaccgugc ugcugcagcu ggagaauacc  1260
augcagauga gccugaagga ccugcug                                      1287

<210> SEQ ID NO 13
<211> LENGTH: 1287
<212> TYPE: RNA
<213> ORGANISM: Artificial Sequence
<220> FEATURE:
<223> OTHER INFORMATION: GLA-C011

<400> SEQUENCE: 13
augcagcugc gaaaucccga gcugcaccug ggcugcgcuc uggcccugcg cuuucuggcc     60
cugguguccu gggauauccc cggcgcucgc gcccuggaca cgggcucgc gagaaccccc    120
accauggggcu ggcuccacug gagagguuuc augugcaauc uggacugcca ggaggagccc   180
gauagcugua uaauccgagaa gcuguucaug gagauggccg agcugauggu gucagaggc    240
uggaaggacg ccggcuacga guaccugucc aucgacgacu gcuggauggc accccagcgg   300
gacuccgagg gccggcugca ggccgacccc cagagguuccc cucaugggau ccgccagcug   360
gcaaacuacg ugcacagcaa gggcgcugaag cuggaaaucu acgcggacgu ggggaauaag   420
accugugccg gcuucccgg gagcuucggc uacuacgaua ucgacgccca gaccuucgcc    480
gacugggggag uggaccugcu gaaguucgac ggaugcuacu gcgacagccu ggagaaccuc    540
gccgacggau auaaacauau gucccuggcc cugaacagga ccggaaggag caucgucuau   600
agcugcgagu ggcccuugua caugggccgu uccagaagc ccaacuacac cgagaucagg    660
caguacugca accacuggag gaacuucgcc gacaucgacg acagcuggaa gagcaucaag    720
agcauucugg acuggacaag cuuuaaccag gagaggaucg uggacguggc cggccccggc    780
ggcuggaacg accccgacau gcuggucauc ggcaacuucg gccugagcug gaaucagcag    840
gugacccaaa uggccugug ggccaucaug gccgcccccc uguucaugag caacgaucuc    900
cgacauauca gccccccaggc caaggcguug cugcaagaca aggacgugau cgccaucaau    960
caggaccccc uggcaagca ggguuaccaa cugaggcaag gcgacaacuu ugaggugugg    1020
gagcgacccc ucuccggccu cgccugggcc gucgccauga ucaaccgcca agagaucggc   1080
ggucccccgca gcuacaccau cgccguggcc agccugggca agggcgugc cugcaacccc   1140
```

| | |
|---|---|
| gccugcuuca ucacccagcu gcugccaguc aagcgcaagc ugggcuucua ugaauggacc | 1200 |
| agcaggcuga gaagccacau caaccccacc gggaccgugc uccugcagcu cgagaacacg | 1260 |
| augcagaugu cccugaaaga ccuguug | 1287 |

<210> SEQ ID NO 14
<211> LENGTH: 1287
<212> TYPE: RNA
<213> ORGANISM: Artificial Sequence
<220> FEATURE:
<223> OTHER INFORMATION: GLA-CO12

<400> SEQUENCE: 14

| | |
|---|---|
| augcagcugc gcaaccccga gcugcaccug ggcugcgccc uggcccugcg auuccuggcc | 60 |
| cucguauccu gggauauccc gggcgccagg gcccucgaua acggccuggc ccguaccccc | 120 |
| accauggggu ggcugcacug ggaacgcuuc augugcaacc uggauugcca agaggagccc | 180 |
| gacagcugca ucagcgagaa acuguucaug gagauggcug agcucauggu auccgagggg | 240 |
| uggaaggaug ccggcuacga guaucugugc aucgacgauu gcuggauggc ccccagcgc | 300 |
| gacagcgaag gcaggcugca ggccgauccc cagcgguuuc cgcacgggau ccggcagcug | 360 |
| gccaacuacu gcauagcaa gggccugaag cuggggauau augccgacgu ggggaacaag | 420 |
| accugcgccg gguuccccgg cagcuucggu uauuacgaua uugacgccca gaccuucgcc | 480 |
| gacugggcu uggaccuccu gaaguucgac ggcugcuacu gcgacagccu ggaaaaccug | 540 |
| gccgacggcu acaagcacau gagccuggcg cugaaucgaa ccggucgauc caucguguac | 600 |
| agcugcgagu ggcccuugua cauggggccc uuccagaagc cuaauuacac ugagauccgg | 660 |
| caguacugca aucacuggag gaacuucgcc gacaucgacg acuccuggaa guccaucaag | 720 |
| uccauccugg auuggaccag cuucaaccag gagaggaucg uggacgugc cggcccggc | 780 |
| ggcuggaaug accccgacau cugggugauc gggaacuucg gccugucgug gaaccagcaa | 840 |
| gugacccaaa uggcgcucug gccaucaug gccgcccccc ucuucaugc caaugaucuc | 900 |
| aggcacauca gcccccaggc caaggcccug cuacaggaca aggacgugau cgccaucaac | 960 |
| caggacccgc ucggcaagca gggcuaccaa cugaggcagg cgacaacuu ugaggugugg | 1020 |
| gaacggcccc ugagcggccu cgccugggcc guggccauga ucaaccggca ggagaucggc | 1080 |
| ggaccccguu cauacaccau cgccguugcc agccugggga aggggguggc cugcaacccc | 1140 |
| gccugcuuca uaacccagcu gcuucccguc aagcgaaagc ugggcuuuua cgaguggacg | 1200 |
| agccgccugc gcucgcacau caaccccacc ggcaccgugc uccugcagcu cgagaacacg | 1260 |
| augcagaugu cccugaagga ccugcug | 1287 |

<210> SEQ ID NO 15
<211> LENGTH: 1287
<212> TYPE: RNA
<213> ORGANISM: Artificial Sequence
<220> FEATURE:
<223> OTHER INFORMATION: GLA-CO13

<400> SEQUENCE: 15

| | |
|---|---|
| augcagcuca ggaaccccga gcuacaccug ggcugcgccc uggcauugag guuucuggcc | 60 |
| cuggugagcu gggacauccc gggagccagg gcccucgaca acggccucgc gaggaccccc | 120 |
| accauggggcu ggcugcacug ggagagguuu augugcaacc uagauugcca ggaggagccc | 180 |
| gacuccugca ucagcgagaa gcuguuuaug gagauggcgg agcugauggu guccgaaggg | 240 |
| uggaaggacg ccggauacga auaccugugc aucgacgacu gcuggauggc ccccagagg | 300 |

```
gacagcgagg gaaggcugca ggccgacccg cagagguucc cccaugggau caggcagcug        360
gcuaacuacg ugcacagcaa gggccugaag cugggcaucu acgccgacgu gggcaauaag        420
acgugcgccg gguucccggg cagcuucggc uacuacgaua ucgacgccca gaccuucgcc        480
gacugggggg uggaccugcu gaaguuugac ggcugcuacu gcgacucccu ggagaaccug        540
gccgacggau acaagcacau gagccucgcc cucaacagga ccgggcgcag caucgucuac        600
agcugcgagu ggccucucua cauggggccc uuccagaagc ccaacuacac agaaauccgc        660
caguacugca aucauuggcg caacuucgcc gacaucgacg acucguggaa guccaucaag        720
agcauccugc acuggaccag cuucaaccag gagcgcaucg ucgaugucgc cggcccggc        780 ggcuggaacg accccgacau gcuggugauc ggcaacuucg ccugagcug aaccaacag         840 gugacccaga uggccugug ggccaucaug gccgcgcccc uguucaugag caacgaccug        900
agacacauca gccccaggc caaggcccug cuccaggaca aggacgugau cgccaucaau        960
caagaccccc ugggcaagca gggcuaccag cugcgucagg gcgauaauuu cgaggugugg       1020
gagagacccc ucagcggcuu ggccugggcc gucgccauga uuaauaggca ggagaucggg       1080 ggcccccagaa gcuacacgau cgccguggcc agccugggaa aaggcguggc gugcaacccc       1140
gccugcuuca ucacccagcu gcuccccgug aaaagaaaac ugggcuucua cgaauggacc       1200
agcagacugc guagcacau caauccgacc gggacagugc ugcugcagcu ggagaacacc       1260
augcagauga gccucaaaga ucugcug                                          1287

<210> SEQ ID NO 16
<211> LENGTH: 1287
<212> TYPE: RNA
<213> ORGANISM: Artificial Sequence
<220> FEATURE:
<223> OTHER INFORMATION: GLA-CO14

<400> SEQUENCE: 16
augcagcugc ggaacccgga gcugcaccug ggcugcgcgc uggccuugcg auuccucgcc          60
cucgucucgu gggacauccc cggcgcccgc gcccuggaca acggccuugc caggacaccg         120
accaugggcu ggcugcacug ggagcgcuuc augugcaacc ucgacugcca ggaggagccc         180
gacagcugca ucuccgagaa gcuguucaug gagauggccg agcugauggu gucagagggg         240
uggaaggacg ccgggacga guacuugcg aucgacgacu gcuggauggc ccgcagaagg         300
gauuccgagg ggcggcugca ggccgacccc caacgguucc cacggcau caggcaacug         360 gcgaacuacg uacacuccaa gggccugaag cugggcaucu acgccgaugu cggcaacaag         420
accugcgcag gcuuucccgg cagcuuuggg uacuacgaca uugacgccca gaccuucgcc         480
gauugggugg uggaccugcu gaaauucgac ggcugcuacu gcgacucccu ggagaacuua         540
gcggacggcu acaagcauau gagccuggcc cugaaccgua ccgggcgcag caucgcuguac         600 agcugcgagu ggccccugua cauggggccu uccaaaagc ccaacuacac agagaucagg         660
caguacugca accacuggcg uaacuucgcc gacauugaug acagcggaa gagcaucaag         720 agcauccugg acuggaccag cuucaaccag gagaggaucg uggaugucgc cggcccggc          780 ggcuggaacg accccgacau gcuggugauc gggaacuucg gucugucgug aaucagcaa         840 gucacucaga uggcccugug ggccaucaug gccgcgccccc ucuuuaugag caacgaccug        900
cggcacauca gccccaggc caaggcccuc cugcaagaca aggacgugau cgccauuaac         960
caggacccuc ucggcaaaca gggcuaccag cugaggcagg gcgauaacuu cgaggugugg       1020
```

| | |
|---|---|
| gagaggcccc ugagcggccu ggccugggcc gucgcaauga ucaacaggca ggagauaggg | 1080 |
| gggccccgga gcuacaccau cgccgugcc agccugggca agggcguggc cugcaaccc | 1140 |
| gccugcuuca ucacccaacu ccugcccgug aagaggaagc ugggcuucua cgaguggacu | 1200 |
| agccggcuga gguccacau caaccccacc gggaccgucc ugcugcaacu ggagaacacc | 1260 |
| augcagauga gccugaagga ccugcug | 1287 |

<210> SEQ ID NO 17
<211> LENGTH: 1287
<212> TYPE: RNA
<213> ORGANISM: Artificial Sequence
<220> FEATURE:
<223> OTHER INFORMATION: GLA-CO15

<400> SEQUENCE: 17

| | |
|---|---|
| augcagcugc ggaacccgga gcugcaccuc gggugcgccc ucgcccucag guuccuggcc | 60 |
| cuggugagcu gggacauccc cggcgcccga gcccucgaca acggucuggc ccgcaccccc | 120 |
| accaugggcu ggcugcauug ggagcgauuc augugcaacc uggacuguca ggaggagccc | 180 |
| gauagcugca ucagcgagaa gcucuucaug gagauggccg agcugauggu gagcgagggg | 240 |
| uggaaggacg ccggguacga auaccugugu auagacgacu guuggauggc accgcagagg | 300 |
| gacagcgagg ccgccuuca ggccgauccc agcgguucc cccacggcau aaggcagcuc | 360 |
| gccaauuacg ugcacuccaa ggucugaaa cuggggaucu acgccgaugu gggcaacaag | 420 |
| acuugugccg gguuccccgg aucauucggc uauuacgaca ucgaugcgca gaccuucgcc | 480 |
| gacuggggug uggaccugcu gaaauucgau ggcugcuauu gcgaucccu ggagaaucug | 540 |
| gccgauggcu acaagcacau gucccuggcg cugaacagga ccggccgcag caucgcguac | 600 |
| agcugugagu ggccacugua cauggggccc uuccagaaac ccaacuauac cgagaucagg | 660 |
| caauacugca accacuggag gaacuucgcc gacaucgacg auagcuggaa aucaucaag | 720 |
| agcauccucg acuggacgag cuucaaccag gagcggaucg uggauguggc cggccccggc | 780 |
| ggcuggaacg accccgacau gcuggugauc ggcaauuucg gacugagcug gaaccagcag | 840 |
| gugacccaga uggcccucug ggccaucaug gccgccccac uguucaugc uaacgaccug | 900 |
| aggcacaucu cgccgcaggc caaggcccug uccaagaca aggacgugau ugccaucaac | 960 |
| caggacccc ugggcaagca ggggauaccag cuucgacagg gggauaacuu cgaggugugg | 1020 |
| gagcgaccgc ugagcggucu ggcgguggcc gucgccauga ucaacaggca ggagauaggc | 1080 |
| gggccccgaa gcuacacaau cgccgugcc agccugggca aggggguggc cugcaaccc | 1140 |
| gccugcuuca uaacccagcu gcugcccgug aaaaggaaac ugggcuucua cgaguggacc | 1200 |
| agccggcugc gauccacau uaaccccacc ggcaccgugc uucugcagcu ggaaaacacc | 1260 |
| augcagauga gccugaagga ccugcug | 1287 |

<210> SEQ ID NO 18
<211> LENGTH: 1287
<212> TYPE: RNA
<213> ORGANISM: Artificial Sequence
<220> FEATURE:
<223> OTHER INFORMATION: GLA-CO16

<400> SEQUENCE: 18

| | |
|---|---|
| augcagcugc gcaaucccga gcuccaccug ggguggccc uggcccgcg auuucucgcc | 60 |
| cucgugagcu gggacauccc cggcgcccga gcgcucgaca acggccuggc aaggaccccc | 120 |
| accaugggcu ggcugcacug ggagcgcuuu augugcaacc ucgacugcca ggaggagccc | 180 |

| | |
|---|---|
| gacuccugca ucucggaaaa gcucuuuaug gagauggccg agcugauggu guccgagggg | 240 |
| uggaaggacg ccggcuacga guaccucugu aucgaugauu gcuggauggc cccccagcgg | 300 |
| gacuccgagg ggaggcucca ggccgacccc caacgcuucc cccauggcau ccggcagcug | 360 |
| gccaacuaug ugcacagcaa gggccugaag cuuggcaucu acgccgacgu uggcaacaag | 420 |
| accugcgcgg gcuuccccgg cagcuucggc uacuacgaua uagacgccca gacguucgcc | 480 |
| gacugggcg uggacuuacu uaaauuugac ggaugcuacu gugacccccu ggagaaccug | 540 |
| gccgacggcu acaagcacau gagccuggcc cucaaccgga ccggcaggag caucguguac | 600 |
| uccugcgagu ggcccucucua caugggccc uuccagaagc ccaacuacac cgagauccgg | 660 |
| caauacugua accacuggag gaacuuugcc gacaucgaug acuccuggaa auccaucaag | 720 |
| aguauccugg auuggaccag cuucaaccag gagcguaucg uggacguggc cggcccggc | 780 |
| ggguggaacg accccgacau gcuggucauc ggcaacuucg ccuuccug gaaucagcag | 840 |
| guuacccaga uggcacugug ggccaucaug gccgcccccc uguucaugag caacgaccug | 900 |
| cgacacauca gccccaggc gaaggcacug cuacaggaua aggacgugau cgcgaucaac | 960 |
| cagaccccccc ugggcaagca gggcuaccag cuacgccaag gggacaacuu ugagugugug | 1020 |
| gagcggccuc uguccggccu ggccugggcc guggccauga ucaacaggca ggagaucggc | 1080 |
| gggccccgcu cuuacaccau cgccguggcc agccucggga aaggcguggc cugcaacccg | 1140 |
| gccugcuuca ucacccagcu ucugcccgug aaacgcaagc ugggcuucua ugagguggacc | 1200 |
| uccaggcuga ggagccacau caacccaacc gguaccgugc ugcugcagcu ggaaaauacc | 1260 |
| augcagaugu cccugaagga ucugcuu | 1287 |

<210> SEQ ID NO 19
<211> LENGTH: 1287
<212> TYPE: RNA
<213> ORGANISM: Artificial Sequence
<220> FEATURE:
<223> OTHER INFORMATION: GLA-CO17

<400> SEQUENCE: 19

| | |
|---|---|
| augcagcuga ggaaccccga gcuccaccug ggcugcgccc ucgcccugag auuccuggcc | 60 |
| cugguguccu gggacauucc cggagcgagg gcgcuggaca acggacuggc ccgcacaccg | 120 |
| accaugggcu ggcugcacug ggagcgauuc augugcaacc uggacugcca ggaggagccc | 180 |
| gacucaugca ucuccgagaa gcuguucaug gagauggccg agcugauggu guccgagggc | 240 |
| uggaaggaug caggguauga guaucugugc aucgacgacu gcuggauggc cccccagagg | 300 |
| gacagcgagg gcaggcugca ggccgacccg cagcgguuuc cgcacgggau caggcagcug | 360 |
| gccaacuaug ugcacuccaa gggccugaag cuggaaaucu acgcggacgu gggcaacaag | 420 |
| accugcgccg gguuccccgg gagcuuuggg uacuacgaca ucgacgccca gaccuucgcc | 480 |
| gauugggggg uggaccugcu gaaguucgac ggaugcuacu gugacagucu ggagaaccug | 540 |
| gccgacggcu auaagcauau gagccuggcc cugaaucgca ccggcaggag caucguguac | 600 |
| uccugcgagu ggccccugua uauggggccc uuccagaagc ccaacuacac cgagaucagg | 660 |
| caguacugua ucacuggag gaacuucgcg acauagacg acagcuggaa auccaucaaa | 720 |
| agcauacugg acuggaccuc cuucaaccag gagaggaucg uggacguggc cggcccgggc | 780 |
| ggguggaacg accccgacau gcuggucauc gguaacuucg acuguccug gaaucagcag | 840 |
| gugacccaga uggcccugug ggccaucaug gccgcgccuc uguuuaugag caacgaccug | 900 |

| | |
|---|---|
| cgccacaucu cgccccaggc caaagccuua cugcaggaca aggacgugau cgccaucaac | 960 |
| caggacccuc uggguaaaca ggggua ccag cugcggcagg gcgauaacuu ugaggucugg | 1020 |
| gagcgccccc uguccggccu cgccugggcc guggccauga ucaauaggca ggaaauaggc | 1080 |
| ggccccaggu ccuacaccau cgccguggcc agccugggca aaggcguggc cuguaacccg | 1140 |
| gccugcuuca ucacccagcu guugcccgug aagcguaagc uggggu ucua cgaguggacu | 1200 |
| uccagacuga ggagccauau caaccccacc ggcaccgugc ugcugcagcu ggagaacacc | 1260 |
| augcagauga gccugaaaga ucugcug | 1287 |

<210> SEQ ID NO 20
<211> LENGTH: 1287
<212> TYPE: RNA
<213> ORGANISM: Artificial Sequence
<220> FEATURE:
<223> OTHER INFORMATION: GLA-CO18

<400> SEQUENCE: 20

| | |
|---|---|
| augcagcuca ggaacccuga acugcaccug gcugugccc uggcccugcg cuuccucgcc | 60 |
| cucgugagcu gggacauccc cggcgccaga gcccucgaua acggccuggc caggaccccc | 120 |
| accaugggcu ggcuccacug ggagcgcuuc auguguaauc uggauugcca ggaggagccg | 180 |
| gacagcugca ucagcgagaa gcucuucaug gagauggcgg agcugauggu guccgaaggg | 240 |
| uggaaggacg ccggcuauga guaccugugc aucgaugacu guuggauggc cccccagcga | 300 |
| gacagcgagg gacgccugca ggccgacccc cagcgcuucc cccacgggau caggcagcug | 360 |
| gccaauuacg uccacagcaa gggccucaag cugggcaucu acgccgacgu ggggaacaaa | 420 |
| acgugcgccg guuuuccggg caguuucggc uauuacgaua ucgacgccca gaccuucgcc | 480 |
| gauugggggag uggaucugcu caaauuugac ggcugcuacu gcgauucgcu ggagaaccug | 540 |
| gccgacggcu acaagcacau guccugg gcc cucaacagga ccggccgcuc caucguguac | 600 |
| agcugcgaau ggccucucua caugggg ccc uuccagaaac ccaacuauac cgagaucagg | 660 |
| caauacugca aucacuggcg gaacuucgcc gacaucgacg auuccuggaa gagcaucaaa | 720 |
| agcauccugg acuggacauc guucaaucag gagcggauug uggacguggc cggcccggga | 780 |
| ggcuggaacg accccgacau gcuggugauc gggaacuucg gccugagcug gaaccagcag | 840 |
| gugacccaga uggccuugug ggccaucaug gcggccccc ucuucaugag caacgaccug | 900 |
| cggcacauca gccccaggc caaggcccua cugcaggaua aggaugugau cgcgaucaac | 960 |
| caggauccc ugggcaagca gggcuaccag uccgacagg gcgacaacuu cgaggugugg | 1020 |
| gaaaggcccc ugucaggccu ggccugggcc guggcgauga ucaacaggca ggaaauaggc | 1080 |
| ggacccagga gcuacaccau cgcuguggcc agccugggca aaggcguggc gugcaacccg | 1140 |
| gccuguuuca ucacacaacu gcugccgggu aagaggaagc ucggcuucua cgaguggacg | 1200 |
| uccaggcugc gccccacau caaccccacg ggaccgugc ugcuccaacu ggagaacacc | 1260 |
| augcagauga gccgaaagga ccugcuc | 1287 |

<210> SEQ ID NO 21
<211> LENGTH: 1287
<212> TYPE: RNA
<213> ORGANISM: Artificial Sequence
<220> FEATURE:
<223> OTHER INFORMATION: GLA-CO19

<400> SEQUENCE: 21

| | |
|---|---|
| augcagcucc ggaacccgga gcuccaccug gcugugccc uggcccucag guuccuggcc | 60 |

| | |
|---|---|
| cuggucuccu gggacauccc cggcgcccgg gcacucgaca acggccuggc gcgaacgccc | 120 |
| acgaugggcu ggcugcacug ggagagauuc augugcaacc uggacugcca ggaggagccg | 180 |
| gacuccugca ucagcgagaa gcuguuuaug gagauggccg agcugauggu cagcgaaggc | 240 |
| uggaaggaug ccggcuauga guaccugugc aucgacgauu gcuggauggc ccccagagg | 300 |
| gacagcgagg gccgacugca ggccgacccc cagcgguucc cccauggcau caggcagcug | 360 |
| gcgaacuacg ugcacuccaa gggccugaaa ucggcaucu acgccgacgu aggcaacaag | 420 |
| accugcgccg gcuucccggg gagcuuuggc uacuacgaca ucgacgcaca gaccuucgca | 480 |
| gacuggggcg uggaccugcu gaaguucgau gguuguuauu cgacucccu ggagaaccua | 540 |
| gccgacggau acaaacauau gagccuggcg cugaacagga ccggccgcuc cauaguguau | 600 |
| uccugcgagu ggccccucua caugggccc uuccaaaagc cgaacuacac ggagauacgc | 660 |
| caguacugca ucacuggag gaacuuugcc gacaucgacg auuccuggaa guccaucaag | 720 |
| ucgauccugg acuggaccag cuucaaccag gagaggaucg uggacgucgc cggcccggu | 780 |
| ggauggaaug aucccgacau gcuggugauc ggcaacuucg gccugagcug gaaccagcag | 840 |
| gugacccaga uggcccugug ggccaucaug gccgcccccc uguucaugag caacgaccug | 900 |
| aggcauauca gcccgcaggc caaggcccuc cugcaggaca aggacgugau cgccaucaac | 960 |
| caggaccccc uggggaagca aggguaucag cugaggcagg gcgauaauuu cgaggugugg | 1020 |
| gagcggcccc ucuccggccu ggcgugggcc guggccauga ucaacaggca ggagaucggc | 1080 |
| gggcccaggu ccuauacaau cgccguggcc agcucgggga agggcguggc cuguaacccc | 1140 |
| gccugcuuca ucacccagcu gcugcccgug aagcggaagc ugggauuuua cgaauggaca | 1200 |
| agccgucugc gguccacau caaucccacg ggcaccgugc ugcugcagcu cgagaacacg | 1260 |
| augcagaugu cccuuaagga ccugcug | 1287 |

<210> SEQ ID NO 22
<211> LENGTH: 1287
<212> TYPE: RNA
<213> ORGANISM: Artificial Sequence
<220> FEATURE:
<223> OTHER INFORMATION: GLA-CO20

<400> SEQUENCE: 22

| | |
|---|---|
| augcaacuga gaaccccga acugcaccug ggcugcgccc uggcccugag guuccuggca | 60 |
| cuagugagcu gggacauccc gggcgcgagg gcccuggaua cgggcuggc caggacccc | 120 |
| accaugggcu ggcuccacug ggagcgguuc augugcaauc uggauugcca agaggagccc | 180 |
| gacagcugca ucuccgagaa acuguucaug gagauggcgg agcugauggu guccgaaggg | 240 |
| uggaaggacg ccggcuacga guaccugugc aucgacgauu gcuggauggc ccccagcgg | 300 |
| gacuccgaag gcaggcucca ggccgacccc cagcguuucc cgcacggcau ccgccagcuc | 360 |
| gccaauuaug ugcacagcaa ggggcugaag ucggcaucu acgccgaugu gggcaacaag | 420 |
| acgugugccg gcuucccggg gagcuucggg uacuacgaca ucgaugccca gaccuucgcc | 480 |
| gacuggggg uggaccugcu gaaguucgac ggaugcuacu cgauagccu ggagaaccug | 540 |
| gccgacggcu acaagcacau gagccuggcc cugaaccgaa ccggcagguc caucguguac | 600 |
| uccugugagu ggccccugua caugguggccg uuccagaagc ccaacuacac ugagaucagg | 660 |
| caguauugua accacuggag gaauuuugcc gauaucgacg auagcggaa gagcaucaag | 720 |
| ucaauccugg acuggaccuc cuucaaccag gagcggaucg uggacguggc cggaccgggc | 780 |

| | |
|---|---|
| ggcuggaacg accccgacau gcucgugauc ggcaacuuug ccugagcug gaaccagcag | 840 |
| gugacccaga uggcgcugug ggcaauaaug ccgccccc uguucaugag caacgaccug | 900 |
| aggcacauca gcccccaggc caaggcgcug cugcaggaua aagacgugau cgccaucaau | 960 |
| caggacccc uggggaagca aggcuaccag cucaggcagg gggauaacuu cgaggugugg | 1020 |
| gaacggccgc uuagcggccu ggccugggcc guggccauga ucaaucgcca ggaaucggc | 1080 |
| gggccgagga gcuauaccau cgccguggcc ucccugggga agggcgugc cugcaacccc | 1140 |
| gccugcuuua uacccagcu gcucccugug aagaggaagc ugggcuucua cgaauggacg | 1200 |
| agccgccuga ggagccacau caaccccacc ggcaccgugc ugcugcagcu cgagaacaca | 1260 |
| augcagauga gccugaagga ucugcuc | 1287 |

<210> SEQ ID NO 23
<211> LENGTH: 1287
<212> TYPE: RNA
<213> ORGANISM: Artificial Sequence
<220> FEATURE:
<223> OTHER INFORMATION: GLA-CO21

<400> SEQUENCE: 23

| | |
|---|---|
| augcagcucc ggaaccccga gcugcaccug ggugcgccc uggcccugag guuccucgcc | 60 |
| cucgugagcu gggauauccc cggcgccagg gcgcuggaua acggccucgc gcgcaccccg | 120 |
| accaugggcu ggcuccacug ggagagguuc augugcaauc uggacugcca agaggagccc | 180 |
| gacagcugca ucagcgagaa gcuguucaug gagauggccg agcugauggu gucggagggc | 240 |
| uggaaagacg ccggcuacga guaccugugc auagacgauu gcuggauggc cccccagagg | 300 |
| gacagcgagg gccgccugca ggccgacccc cagagguucc cccacgggau caggcagcuc | 360 |
| gcaaauuacg ugcacagcaa gggacugaaa cucgguaucu acgccgaugu gggcaacaag | 420 |
| accugcgccg gauucccugg cagcuuuggc uauuacgaca uagacgccca gaccuucgcc | 480 |
| gauuggggcg uugaccugcu caaguucgac ggguguuacu gcgacagccu ggagaaccug | 540 |
| gccgacgggu acaaacacau gucccuggcg cugaacagga ccggaagguc caucguguac | 600 |
| uccugcgagu ggcccugua uaugugggcc uuucagaagc cgaacuacac cgagaucagg | 660 |
| caguacugca accauuggcg gaacuuugcg gacauagacg acagcuggaa gagcauaaag | 720 |
| agcauccuug acuggacgag cuucaaccag gaacggaucg uggaugugc cggcccggc | 780 |
| ggcuggaaug accccgacau gcuggugauc ggcaacuucg gucugucaug gaaccagcag | 840 |
| gugacccaga uggccugug ggcgaucaug ccgccccc ucuucaugag caacgaucug | 900 |
| cgccauauca gcccccaggc caaggcccuc cugcaggaua aggacgucau cgcuaucaac | 960 |
| caggacccc ucggcaagca gggguaccag cugcgccagg gcgacaacuu ugagguggg | 1020 |
| gagaggccgc ugagcggccu ggccugggcc guagcgauga ucaaucggca agagaucggc | 1080 |
| ggccccggu ccuacaccau cgccguggcc agccugggca aggggguggc cuguaacccc | 1140 |
| gccuguuuca ucacccagcu gcugcccgug aaaaggaagc uggguuucua cgaguggacu | 1200 |
| agcaggcuca ggagccacau caacccgacc ggcaccgugc ugcugcaacu ggagaacacc | 1260 |
| augcagaugu cacugaaaga ccugcug | 1287 |

<210> SEQ ID NO 24
<211> LENGTH: 1287
<212> TYPE: RNA
<213> ORGANISM: Artificial Sequence
<220> FEATURE:
<223> OTHER INFORMATION: GLA-CO22

```
<400> SEQUENCE: 24
augcagcucc ggaacccgga gcuccaccug ggcugugccc ucgcccugcg cuuccuagcc    60
cuggugaccu gggauauccc cggcgccagg gcccucgaca acggacuggc ccggaccccc   120
accaugggau ggcuccauug ggagaggauu augugcaacc uggacugcca ggaggagccc   180
gauagcugua ucagcgagaa gcuguucaug gagauggccg agcugauggu gagcgaaggu   240
uggaaggacg ccggcuacga guaccucugc aucgacgacu gcuggaaugc ccccagcgg    300 gacagcgagg ggaggcugca ggcggauccc cagagguucc ccacggcau ccggcagcug    360 gccaauuacg uccacuccaa gggacugaag cuggcacucu acgccgacgu ggguaacaag   420
accugcgcgg gguuccccgg cagcuucggc uacuacgaca ucgacgcgca gaccuucgca   480
gacuggggcg uggaccugcu gaaauucgac ggcugcuacu gcgacucacu ggaaaaccuc   540
gccgacggcu acaagcacau gagccuggcc cugaacagga ccggccggag caucgucuac   600
uccugugagu ggcccucucua caugggccc uuccagaagc ccaacuacac ggagauccga   660
caauacugca accacuggcg gaacuuugcc gacaucgacg acagcuggaa guccaucaaa   720
ucgauccugg acuggaccag cuucaaccag gagaggaucg uggacguggc cggcccgggg   780
ggcuggaaug accccgacau gcuggugauc ggcaacuucg gcugucaug gaaccaacag   840 gugacccaga uggccugugug ggccauaaug gccgcccccc uguucaugag caauugaccug   900 aggcacauca cccccaggc gaaggcccug cugcaggaca aggacgaugau cgccaucaac   960 caggaccccc ugggcaaaca gggcuaccag cccggcgcggg ggacaauuu cgaggugugg  1020 gagaggcccc uguccggacu ggccugggcg gucgccauga ucaacaggca agagauaggg  1080
ggccccagga gcuacacgau cgcgguggcc agccucggga agggggguggc cugcaacccc  1140 gccugcuuca uaacccaacu acuccccgua aagaggaagc ugggcuucua cgaguggacc  1200
agccgcucug ggagccauau caacccgacc ggcaccgugc ugcuccagcu ggagaacacc  1260
augcagauga gucugaagga ccuccug                                     1287

<210> SEQ ID NO 25
<211> LENGTH: 1287
<212> TYPE: RNA
<213> ORGANISM: Artificial Sequence
<220> FEATURE:
<223> OTHER INFORMATION: GLA-CO23

<400> SEQUENCE: 25
augcagcugc gaaaucccga gcugcaccug ggcugugccc uggcucucag guuccuggcg    60
cuggugagcu gggauauccc cggcgccaga gcgcuggaca acggccucgc ccgaaccccg   120
accaugggcu ggcugcacug ggagcgguuu augugcaacc ucgacugcca ggaggaaccg   180
gacagcugca ucuccgagaa gcuguucaug gagauggccg aacugauggu gagcgagggc   240
uggaaggaug ccggcuacga guaccugugc aucgacgauu gcuggauggc ccccagagg    300 gauuccgagg gcaggcugca ggccgacccc cagagguucc cgcacggcau acgccaacuc   360
gccaacuacg ugcacuccaa gggcuugaaa cuggggaucu acgccgacgu gggcauuaag   420
accugugccg gcuucccccgg cucuucggg uacuacgaca ucgacgccca gacguucgcc   480
gacuggggcg uggaccugcu gaaguucgau gggugcuauu gcgacagccu ggaaaaccug   540
gccgacggcu acaaacacau gagccuggcc cugaaccgua ccggcaggag caucguguac   600
uccugcgagu ggccccuua caugggccgu uucagaagc ccaauuacac cgagauacgg    660
```

| | |
|---|---|
| caguauugua accacuggag gaauuucgcc gacauagaug acuccuggaa aagcaucaag | 720 |
| agcauucugg acuggaccag cuucaaccag gagaggaucg uggaugucgc cgggcccgga | 780 |
| ggcuggaaug accccgacau gcuggugauc ggcaacuucg gcugaguug gaaucagcag | 840 |
| gucacucaga uggcccugug gccaucaug gccgccccc uuucauguc caacgaccug | 900 |
| cgacacauca gcccccaggc gaaggcccuc cuucaggaca aggaugugau cgccaucaac | 960 |
| caggaccccc uggggaagca aggcuaucag cucaggcagg gcgauaacuu cgaggugugg | 1020 |
| gagaggcccc ugagcggccu ggccugggcc guggccauga ucaacaggca agaaauaggc | 1080 |
| ggcccccagga gcuacaccau cgccguggcc agccugggga agggcguggc cugcaacccc | 1140 |
| gccugcuuca ucacccagcu gcugcccgug aagcggaagc ugggcuucua cgaguggacg | 1200 |
| uccaggcuca ggagccacau caaccccacc gggaccgugc ugcugcaacu ggaaaacacc | 1260 |
| augcagauga gcuugaaaga ccuccug | 1287 |

<210> SEQ ID NO 26
<211> LENGTH: 1287
<212> TYPE: RNA
<213> ORGANISM: Artificial Sequence
<220> FEATURE:
<223> OTHER INFORMATION: GLA-CO24

<400> SEQUENCE: 26

| | |
|---|---|
| augcagcugc gcaaccccga gcugcaccug ggcugugccc uggcccugcg uuuccuggcc | 60 |
| cuggucagcu gggacauccc cggcgcccgg gcccuggaca cgggcuggc caggacuccc | 120 |
| accaugggcu ggcugcacug ggagagguuc augugcaacc uggacuguca agaagagccg | 180 |
| gacagcugca ucuccgagaa gcuguucaug gagaugcgg agcugauggu auccgaggga | 240 |
| uggaaggacg ccggcuauga guaucugugu aucgacgacu gcuggaugc cccccagagg | 300 |
| gacagcgagg gccgccucca agccgaccc caacgguucc cgcacggcau caggcagcug | 360 |
| gccaacuacg ugcacuccaa gggccugaag cuggcauau acgccgacgu gggcaacaag | 420 |
| accugcgccg gauuccccgg cuccuucggu acuacgaua uagacgccca gaccuucgcc | 480 |
| gacuggggug uggaccugcu gaaguucgau gggugcuacu gcgauucccu ggagaaccuc | 540 |
| gccgacgggu auaagcacau guccuggcc cugaacagga ccgggaggag cauugucuac | 600 |
| agcugcgagu ggcccugua caugugggcca uuccagaagc ccaacuacac cgagauccgu | 660 |
| caguacugca accacuggag gaacuucgcc gauaucgacg acuccuggaa auccaucaag | 720 |
| uccauccugg auggaccag cuucaaccag gaacgcauug uggaugugc cggacccggc | 780 |
| ggcuggaacg accccgauau gcucgucauc ggcaacuucg gccugccug gaaucaacag | 840 |
| guuacccaga uggcccuaug ggcgaucaug gccgccccc uguuuaugag caacgaccug | 900 |
| aggcacauca gcccucaggc aaaggcccug cugcaggaca aagacgucau agccaucaac | 960 |
| caagaccccc ucggcaagca gggcuaccaa cugcgacagg gcgacaacuu cgaggugugg | 1020 |
| gagaggcccc ugagcggucu ggccugggcc guggccauga ucaacaggca ggagaucggc | 1080 |
| ggcccccggu ccuauaccau cgccguggcc ucccuggca aggggguggc augcaacccc | 1140 |
| gccuguuuca ucacccaacu gcugcccgug aaaaggaagc ugggcuucua ugaguggacc | 1200 |
| agccggcugc gcucccacau caaccccacc ggcaccgugc ugcugcagcu cgaaaacacg | 1260 |
| augcagauga gccucaagga ccugcug | 1287 |

<210> SEQ ID NO 27
<211> LENGTH: 1287

```
<212> TYPE: RNA
<213> ORGANISM: Artificial Sequence
<220> FEATURE:
<223> OTHER INFORMATION: GLA-CO25

<400> SEQUENCE: 27
augcagcuca ggaaucccga gcugcaccug ggcugcgccc uggcgcucag guuccuggcc      60
cuggugagcu gggacauccc cggcgccagg gcccucgaua acggccuggc ccggacccccc    120
accaugggcu ggcugcauug ggagcgcuuc augugcaauc ucgacugcca ggaggagccg    180
gacucaugua ucagcgaaaa gcuguucaug gagauggccg agcugauggu guccgaaggg    240
uggaaggacg ccggguacga guaccugugc aucgaugacu guuggauggc cccccagcgc    300
gauagcgagg gccggcugca ggccgauccc cagcguuucc cccacgggau ccgucagcug    360
gccaacuaug ugcauagcaa agggcugaaa ucggcaucu acgccgacgu agggaacaag    420
accugugcag gcuuccccgg guccuucggc uacuacgaua ucgaugccca gaccuuugcc    480
gacuggggcg ucgaccugcu gaaguucgac ggcugcuacu gugaucccu ggagaaccuc    540
gccgacggcu acaagcacau gagccuggcc cugaaccgga ccggcaggag cauuguguac    600
agcugcgaau ggccccugua caugggcc uuccagaaac ccaacuacac cgagauccgg    660
caguacugca aucauuggag gaacuuugcc gauaucgacg auagcuggaa aaguaucaag    720
agcauccuug acuggaccag cuuuaaccag gagcgcaucg uugacguggc cggacccgga    780
ggcuggaacg acccggauau gcuggugauc ggcaauuucg gccugagcug gaaccagcag    840
gugacgcaga uggcccugug ggccaucaug gccgccccc ucuucaugag caacgaccug    900
aggcauauau caccccaggc caaggcccuc cugcaggaca aagacgugau cgccauaaau    960
caggaccccc uggcaagca aggcuaccaa cugcggcagg gcgacaacuu cgaggugugg  1020
gagcgaccgc uguccggccu ggcguggcg guggccauga ucaaucggca ggagaucggc  1080
ggccccaggu ccuacacaau cgccgucgcc agccugggca agggggucgc cugcaauccg  1140
gccugcuuua ucacccagcu gcugcccgug aagaggaagc ugggauuuua ugaguggacc  1200
agccggcuca ggucccauau caaccccacc gguaccgugc ugcugcagcu cgaaaacacc  1260
augcagaugu cccugaagga ccuucug                                       1287

<210> SEQ ID NO 28
<211> LENGTH: 87
<212> TYPE: RNA
<213> ORGANISM: Artificial Sequence
<220> FEATURE:
<223> OTHER INFORMATION: Synthetic: miR-142

<400> SEQUENCE: 28
gacagugcag ucacccauaa aguagaaagc acuacuaaca gcacuggagg guguaguguu     60
uccuacuuua uggaugagug uacugug                                         87

<210> SEQ ID NO 29
<211> LENGTH: 23
<212> TYPE: RNA
<213> ORGANISM: Artificial Sequence
<220> FEATURE:
<223> OTHER INFORMATION: Synthetic: miR-142-3p

<400> SEQUENCE: 29
uguaguguuu ccuacuuuau gga                                              23

<210> SEQ ID NO 30
```

```
<211> LENGTH: 23
<212> TYPE: RNA
<213> ORGANISM: Artificial Sequence
<220> FEATURE:
<223> OTHER INFORMATION: Synthetic: miR-142-3p binding site

<400> SEQUENCE: 30
uccauaaagu aggaaacacu aca                                           23

<210> SEQ ID NO 31
<211> LENGTH: 21
<212> TYPE: RNA
<213> ORGANISM: Artificial Sequence
<220> FEATURE:
<223> OTHER INFORMATION: Synthetic: miR-142-5p

<400> SEQUENCE: 31
cauaaaguag aaagcacuac u                                             21

<210> SEQ ID NO 32
<211> LENGTH: 21
<212> TYPE: RNA
<213> ORGANISM: Artificial Sequence
<220> FEATURE:
<223> OTHER INFORMATION: Synthetic: miR-142-5p binding site

<400> SEQUENCE: 32
aguagugcuu ucuacuuuau g                                             21

<210> SEQ ID NO 33
<211> LENGTH: 47
<212> TYPE: RNA
<213> ORGANISM: Artificial Sequence
<220> FEATURE:
<223> OTHER INFORMATION: Synthetic: 5'UTR-001, Upstream UTR

<400> SEQUENCE: 33
gggaaauaag agagaaaaga agaguaagaa gaaauauaag agccacc                 47

<210> SEQ ID NO 34
<211> LENGTH: 47
<212> TYPE: RNA
<213> ORGANISM: Artificial Sequence
<220> FEATURE:
<223> OTHER INFORMATION: Synthetic: 5'UTR-002, Upstream UTR

<400> SEQUENCE: 34
gggagaucag agagaaaaga agaguaagaa gaaauauaag agccacc                 47

<210> SEQ ID NO 35
<211> LENGTH: 145
<212> TYPE: RNA
<213> ORGANISM: Artificial Sequence
<220> FEATURE:
<223> OTHER INFORMATION: 5'UTR-003 (Upstream UTR)

<400> SEQUENCE: 35
ggaauaaaag ucucaacaca acauauacaa aacaaacgaa ucucaagcaa ucaagcauuc   60
uacuucuauu gcagcaauuu aaaucauuuc uuuuaaagca aaagcaauuu ucugaaaauu  120
uucaccauuu acgaacgaua gcaac                                        145

<210> SEQ ID NO 36
<211> LENGTH: 42
<212> TYPE: RNA
<213> ORGANISM: Artificial Sequence
```

```
<220> FEATURE:
<223> OTHER INFORMATION: Synthetic: 5'UTR-004, Upstream UTR

<400> SEQUENCE: 36
gggagacaag cuuggcauuc cgguacuguu gguaaagcca cc                           42

<210> SEQ ID NO 37
<211> LENGTH: 47
<212> TYPE: RNA
<213> ORGANISM: Artificial Sequence
<220> FEATURE:
<223> OTHER INFORMATION: Synthetic: 5'UTR-005, Upstream UTR

<400> SEQUENCE: 37
gggagaucag agagaaaaga agaguaagaa gaaauauaag agccacc                      47

<210> SEQ ID NO 38
<211> LENGTH: 145
<212> TYPE: RNA
<213> ORGANISM: Artificial Sequence
<220> FEATURE:
<223> OTHER INFORMATION: Synthetic: 5'UTR-006, Upstream UTR

<400> SEQUENCE: 38
ggaauaaaag ucucaacaca acauauacaa acaaacgaa ucucaagcaa ucaagcauuc          60
uacuucuauu gcagcaauuu aaaucauuuc uuuuaaagca aaagcaauuu ucugaaaauu        120
uucaccauuu acgaacgaua gcaac                                             145

<210> SEQ ID NO 39
<211> LENGTH: 42
<212> TYPE: RNA
<213> ORGANISM: Artificial Sequence
<220> FEATURE:
<223> OTHER INFORMATION: Synthetic: 5'UTR-007, Upstream UTR

<400> SEQUENCE: 39
gggagacaag cuuggcauuc cgguacuguu gguaaagcca cc                           42

<210> SEQ ID NO 40
<211> LENGTH: 47
<212> TYPE: RNA
<213> ORGANISM: Artificial Sequence
<220> FEATURE:
<223> OTHER INFORMATION: Synthetic: 5'UTR-008, Upstream UTR

<400> SEQUENCE: 40
gggaauuaac agagaaaaga agaguaagaa gaaauauaag agccacc                      47

<210> SEQ ID NO 41
<211> LENGTH: 47
<212> TYPE: RNA
<213> ORGANISM: Artificial Sequence
<220> FEATURE:
<223> OTHER INFORMATION: Synthetic: 5'UTR-009, Upstream UTR

<400> SEQUENCE: 41
gggaaauuag acagaaaaga agaguaagaa gaaauauaag agccacc                      47

<210> SEQ ID NO 42
<211> LENGTH: 47
<212> TYPE: RNA
<213> ORGANISM: Artificial Sequence
<220> FEATURE:
<223> OTHER INFORMATION: Synthetic: 5'UTR-010, Upstream,
```

<400> SEQUENCE: 42
gggaaauaag agaguaaaga acaguaagaa gaaauauaag agccacc        47

<210> SEQ ID NO 43
<211> LENGTH: 47
<212> TYPE: RNA
<213> ORGANISM: Artificial Sequence
<220> FEATURE:
<223> OTHER INFORMATION: Synthetic: 5'UTR-011, Upstream UTR

<400> SEQUENCE: 43
gggaaaaaag agagaaaaga agacuaagaa gaaauauaag agccacc        47

<210> SEQ ID NO 44
<211> LENGTH: 47
<212> TYPE: RNA
<213> ORGANISM: Artificial Sequence
<220> FEATURE:
<223> OTHER INFORMATION: Synthetic: 5'UTR-012, Upstream UTR

<400> SEQUENCE: 44
gggaaauaag agagaaaaga agaguaagaa gauauauaag agccacc        47

<210> SEQ ID NO 45
<211> LENGTH: 47
<212> TYPE: RNA
<213> ORGANISM: Artificial Sequence
<220> FEATURE:
<223> OTHER INFORMATION: Synthetic: 5'UTR-013, Upstream UTR

<400> SEQUENCE: 45
gggaaauaag agacaaaaca agaguaagaa gaaauauaag agccacc        47

<210> SEQ ID NO 46
<211> LENGTH: 47
<212> TYPE: RNA
<213> ORGANISM: Artificial Sequence
<220> FEATURE:
<223> OTHER INFORMATION: Synthetic: 5'UTR-014, Upstream UTR

<400> SEQUENCE: 46
gggaaauuag agaguaaaga acaguaagua gaauuaaaag agccacc        47

<210> SEQ ID NO 47
<211> LENGTH: 47
<212> TYPE: RNA
<213> ORGANISM: Artificial Sequence
<220> FEATURE:
<223> OTHER INFORMATION: Synthetic: 5'UTR-15, Upstream UTR

<400> SEQUENCE: 47
gggaaauaag agagaauaga agaguaagaa gaaauauaag agccacc        47

<210> SEQ ID NO 48
<211> LENGTH: 47
<212> TYPE: RNA
<213> ORGANISM: Artificial Sequence
<220> FEATURE:
<223> OTHER INFORMATION: Synthetic: 5'UTR-016, Upstream UTR

<400> SEQUENCE: 48
gggaaauaag agagaaaaga agaguaagaa gaaauuaaag agccacc        47

<210> SEQ ID NO 49
<211> LENGTH: 47

```
<212> TYPE: RNA
<213> ORGANISM: Artificial Sequence
<220> FEATURE:
<223> OTHER INFORMATION: Synthetic: 5'UTR-017, Upstream UTR

<400> SEQUENCE: 49
gggaauuaag agagaaaaga agaguaagaa gaaauuuaag agccacc                47

<210> SEQ ID NO 50
<211> LENGTH: 92
<212> TYPE: RNA
<213> ORGANISM: Artificial Sequence
<220> FEATURE:
<223> OTHER INFORMATION: Synthetic: 5'UTR-018, Upstream UTR

<400> SEQUENCE: 50
ucaagcuuuu ggacccucgu acagaagcua auacgacuca cuauagggaa auaagagaga   60
aaagaagagu aagaagaaau auaagagcca cc                                92

<210> SEQ ID NO 51
<211> LENGTH: 142
<212> TYPE: RNA
<213> ORGANISM: Artificial Sequence
<220> FEATURE:
<223> OTHER INFORMATION: Synthetic: 3'UTR with miR 142-3p binding site,
      P1 insertion

<400> SEQUENCE: 51
ugauaauagu ccauaaagua ggaaacacua cagcuggagc cucgguggcc augcuucuug   60
ccccuugggc cucccccag ccccuccucc ccuccugca cccguacccc cguggucuuu    120
gaauaaaguc ugagugggcg gc                                          142

<210> SEQ ID NO 52
<211> LENGTH: 142
<212> TYPE: RNA
<213> ORGANISM: Artificial Sequence
<220> FEATURE:
<223> OTHER INFORMATION: Synthetic: 3'UTR with miR 142-3p binding site,
      P2 insertion

<400> SEQUENCE: 52
ugauaauagg cuggagccuc gguggcucca uaaaguagga aacacuacac augcuucuug   60
ccccuugggc cucccccag ccccuccucc ccuccugca cccguacccc cguggucuuu    120
gaauaaaguc ugagugggcg gc                                          142

<210> SEQ ID NO 53
<211> LENGTH: 142
<212> TYPE: RNA
<213> ORGANISM: Artificial Sequence
<220> FEATURE:
<223> OTHER INFORMATION: Synthetic: 3'UTR including miR142-3p binding
      site

<400> SEQUENCE: 53
ugauaauagg cuggagccuc gguggccaug cuucuugccc cuuccauaaa guaggaaaca   60
cuacaugggc cucccccag ccccuccucc ccuccugca cccguacccc cguggucuuu    120
gaauaaaguc ugagugggcg gc                                          142

<210> SEQ ID NO 54
<211> LENGTH: 142
<212> TYPE: RNA
<213> ORGANISM: Artificial Sequence
```

```
<220> FEATURE:
<223> OTHER INFORMATION: Synthetic: 3'UTR including miR142-3p binding
      site

<400> SEQUENCE: 54
ugauaauagg cuggagccuc ggguggccaug cuucuugccc cuugggccuc ccccagucc      60 auaaaguagg aaacacuaca ccccuccucc ccuuccugca cccguacccc cguggucuuu    120
gaauaaaguc ugaguggggcg gc                                             142

<210> SEQ ID NO 55
<211> LENGTH: 142
<212> TYPE: RNA
<213> ORGANISM: Artificial Sequence
<220> FEATURE:
<223> OTHER INFORMATION: Synthetic: 3'UTR including miR142-3p binding
      site

<400> SEQUENCE: 55
ugauaauagg cuggagccuc ggguggccaug cuucuugccc cuugggccuc ccccagccc      60 cuccuccccu ucuccauaaa guaggaaaca cuacacugca cccguacccc cguggucuuu    120
gaauaaaguc ugaguggggcg gc                                             142

<210> SEQ ID NO 56
<211> LENGTH: 142
<212> TYPE: RNA
<213> ORGANISM: Artificial Sequence
<220> FEATURE:
<223> OTHER INFORMATION: Synthetic: 3 UTR with miR 142-3p binding site

<400> SEQUENCE: 56
ugauaauagg cuggagccuc ggguggccaug cuucuugccc cuugggccuc ccccagccc      60 cuccuccccu uccugcaccc guaccccuc cauaaaguag gaaacacuac aguggucuuu    120
gaauaaaguc ugaguggggcg gc                                             142

<210> SEQ ID NO 57
<211> LENGTH: 142
<212> TYPE: RNA
<213> ORGANISM: Artificial Sequence
<220> FEATURE:
<223> OTHER INFORMATION: Synthetic: 3'UTR including miR142-3p binding
      site

<400> SEQUENCE: 57
ugauaauagg cuggagccuc ggguggccaug cuucuugccc cuugggccuc ccccagccc      60 cuccuccccu uccugcaccc guaccccgu ggucuuugaa uaaaguucca uaaaguagga     120
aacacuacac ugaguggggcg gc                                             142

<210> SEQ ID NO 58
<211> LENGTH: 371
<212> TYPE: RNA
<213> ORGANISM: Artificial Sequence
<220> FEATURE:
<223> OTHER INFORMATION: 3'UTR-001 (Creatine Kinase UTR)

<400> SEQUENCE: 58
gcgccugccc accugccacc gacugcugga acccagccag ugggagggcc uggcccacca      60
gaguccugcu cccucacucc ucgccccgcc cccuguccca gaucccaccu uggggggcucu   120 cuccacccuu cucagaguuc caguuucaac cagaguucca accaaugggc uccauccucu    180
ggauucuggc caaugaaaua ucuccccuggc agggucccucu ucuuuccca gagcuccacc    240
```
ccaaccagga gcucuaguua auggagagcu cccagcacac ucggagcuug ugcuuugucu    300
ccacgcaaag cgauaaauaa aagcauuggu ggccuuuggu cuuugaauaa agccgaguua    360
ggaagucuag a    371

<210> SEQ ID NO 59
<211> LENGTH: 568
<212> TYPE: RNA
<213> ORGANISM: Artificial Sequence
<220> FEATURE:
<223> OTHER INFORMATION: 3'UTR-002 (Myoglobin UTR)

<400> SEQUENCE: 59
gccccugccg cucccacccc cacccaucug gccccggggu ucaagagaga gcggggucug     60
aucucgugua gccauauaga guuugcuucu gagugucugc uuuguuuagu agaggugggc    120
aggaggagcu gaggggcugg ggcugggugu uugaaguugg cuuugcaugc ccagcgaugc    180
gccucccugu gggaugucau cacccuggga accgggagug gcccuuggcu cacuguguuc    240
ugcaugguuu ggaucugaau uaauugugccu ucuucuaaa ucccaaccga acuucuucca    300
accuccaaac uggcuguaac cccaaauccca agccauuaac uacaccugac aguagcaauu    360
gucugauuaa ucacuggccc cuugaagaca gcagaaugau ccuuugcaau gaggaggaga    420
ucugggcugg gcgggccagc uggggaagca uuugacuauc uggaacuugu gugugccucc    480
ucagguaugg cagugacuca ccugguuuua auaaaacaac cugcaacauc caugguucu    540 ugaauaaagc cugaguagga agucuaga    568

<210> SEQ ID NO 60
<211> LENGTH: 289
<212> TYPE: RNA
<213> ORGANISM: Artificial Sequence
<220> FEATURE:
<223> OTHER INFORMATION: 3'UTR-003 alpha-actin UTR)

<400> SEQUENCE: 60
acacacucca ccuccagcac gcgacuucuc aggacgacga aucuucucaa ugggggggcg     60
gcugagcucc agccaccccg cagucacuuu cuuuguaaca acuuccguug cugccaucgu    120
aaacugacac aguguuuaua acguguacau acauuaaucu auuaccauu uuuguuauuu    180 uucgaaacaa agcccuguggg aagaaaaugg aaaacuugaa gaagcauuaa agucauucug    240
uuaagcugcg uaaauggucu uugaauaaag ccgaguagg aagucuaga    289

<210> SEQ ID NO 61
<211> LENGTH: 379
<212> TYPE: RNA
<213> ORGANISM: Artificial Sequence
<220> FEATURE:
<223> OTHER INFORMATION: 3'UTR-004 (Albumin UTR)

<400> SEQUENCE: 61
caucacauuu aaaagcaucu cagccuacca ugagaauaag agaaagaaaa ugaagaucaa     60
aagcuuauuc aucguuuuu cuuuuucguu ggguguaaagc caacacccug ucuaaaaaac    120
auaaauuucu uuaaucauuu ugccucuuuu cucugugcuu caauuaauaa aaauggaaa    180 gaaucuaaua gagugguaca gcacuguuu uuucaaaga ugaguugcua ccugaaaau    240 ucuguagguu cuguggaagu uccagugauuc ucucuuauuc cacuucgua gaggauuucu    300 aguuucuugu gggcuaauua aauaaaucau uaauacucuu cuaauggucu uugaauaaag    360

-continued

```
ccugaguagg aagucuaga                                               379

<210> SEQ ID NO 62
<211> LENGTH: 118
<212> TYPE: RNA
<213> ORGANISM: Artificial Sequence
<220> FEATURE:
<223> OTHER INFORMATION: 3'UTR-005 (?-globin UTR)

<400> SEQUENCE: 62
gcugccuucu gcggggcuug ccuucuggcc augcccuucu ucucucccuu gcaccuguac    60
cucuuggucu uugaauaaag ccugaguagg aaggcggccg cucgagcaug caucuaga    118

<210> SEQ ID NO 63
<211> LENGTH: 908
<212> TYPE: RNA
<213> ORGANISM: Artificial Sequence
<220> FEATURE:
<223> OTHER INFORMATION: 3'UTR-006 (G-CSF UTR)

<400> SEQUENCE: 63
gccaagcccu ccccaucccca uguauuuauc ucuauuuaau auuuaugucu auuuaagccu    60
cauauuuaaa gacagggaag agcagaacgg agccccaggc cucuguguccc uucccugcau   120 uucugaguuu cauucuccug ccuguagcag ugagaaaaag cuccuguccu cccaucccu    180 ggacugggag guagauaggu aaauaccaag uauuuauuac uaugacugcu ccccagcccu    240
ggcucugcaa ugggcacugg gaugagccgc ugugagcccc uguccugag ggucccacc    300 ugggacccuu gagaguauca ggucucccac gugggagaca agaaauacccu guuuaauauu    360 uaaacagcag uguuccccau cugggguccu u gcaccccuca cucuggccuc agccgacugc    420
acagcggccc cugcauccccc uuggcuguga ggccccugga caagcagagg uggccagagc    480
ugggaggcau ggcccugggg ucccacgaau ugcugggga aucucguuuu ucuucuuaag    540
acuuuuggga caugguuuga cucccgaaca ucaccgacgc gucuccuguu uuucggggug    600
gccucgggac accugcccug cccccacgag ggucaggacu ugacucuuu uuaggggccag    660 gcaggugccu ggacauuugc cuugcuggac ggggacugggg gaugugggag ggagcagaca    720
ggaggaauca ugucaggccu gugugugaaa ggaagcucca cugucacccu ccaccucuuc    780
accccccacu caccagugue ccuccacug ucacauugua acugaacuuc aggauaauaa    840
aguguuugcc uccaugguc uugaauaaag ccugaguagg aaggcggccg cucgagcaug    900
caucuaga                                                            908

<210> SEQ ID NO 64
<211> LENGTH: 835
<212> TYPE: RNA
<213> ORGANISM: Artificial Sequence
<220> FEATURE:
<223> OTHER INFORMATION: 3'UTR-007 (Col1a2; collagen, type I, alpha 2
      UTR)

<400> SEQUENCE: 64
acucaaucua aauuaaaaaa gaaagaaauu ugaaaaaacu uucucuuugc cauucuuucu    60
ucuucuuuuu uaacugaaag cugaauccuu ccauuucuuc ugcacaucua cuugcuuaaa   120 uuguggggcaa aagagaaaaa gaaggauuga ucagagcauu gugcaauaca guucauuaa   180 cuccuucccc cgcucccccca aaauuugaa uuuuuuuuc aacacucuua caccuguuau   240
ggaaaauguc aaccuuugua agaaaaccaa aauaaaaauu gaaaaauaaa aaccauaaac   300
```

| | |
|---|---|
| auuugcacca cuuguggcuu uugaauaucu uccacagagg gaaguuuaaa acccaaacuu | 360 |
| ccaaagguuu aaacuaccuc aaaacacuuu cccaugagug ugauccacau uguuaggugc | 420 |
| ugaccuagac agagaugaac ugagguccuu guuuguuuu guucauaaua caaaggugcu | 480 |
| aauuaauagu auucagaua cuugaagaau guugauggug cuagaagaau uugagaagaa | 540 |
| auacuccugu auugaguugu aucguguggu guauuuuuua aaaauuuga uuuagcauuc | 600 |
| auauuuucca ucuuauuccc aauuaaaagu augcagauua uuugcccaaa ucuucuucag | 660 |
| auucagcauu uguucuuugc cagcucucauu uucaucuucu uccaugguuc cacagaagcu | 720 |
| uuguuucuug ggcaagcaga aaaauuaaau uguaccuauu uuguauaugu gagauguuua | 780 |
| aauaaauugu gaaaaaaug aaauaaagca uguuugguuu uccaaaagaa cauau | 835 |

<210> SEQ ID NO 65
<211> LENGTH: 297
<212> TYPE: RNA
<213> ORGANISM: Artificial Sequence
<220> FEATURE:
<223> OTHER INFORMATION: 3'UTR-008 (Col6a2; collagen, type VI, alpha 2 UTR)

<400> SEQUENCE: 65

| | |
|---|---|
| cgccgccgcc cgggccccgc agucgagggu cgugagccca ccccguccau ggugcuaagc | 60 |
| gggcccgggu cccacacggc cagcaccgcu gcucacucgg acgacgcccu gggccugcac | 120 |
| cucuccagcu ccucccacgg gguccccgua gccccggccc ccgcccagcc ccaggucucc | 180 |
| ccaggcccuc cgcaggcugc ccggccuccc uccccucgca gccaucccaa ggcuccugac | 240 |
| cuaccuggcc ccugagcucu ggagcaagcc cugacccaau aaaggcuuug aacccau | 297 |

<210> SEQ ID NO 66
<211> LENGTH: 602
<212> TYPE: RNA
<213> ORGANISM: Artificial Sequence
<220> FEATURE:
<223> OTHER INFORMATION: 3'UTR-009 (RPN1; ribophorin I UTR)

<400> SEQUENCE: 66

| | |
|---|---|
| ggggcuagag cccucuccgc acagcgugga gacggggcaa ggagggggu uauuaggauu | 60 |
| ggugguuuug uuuugcuuug uuuaaagccg ugggaaaaug gcacaacuuu accucugugg | 120 |
| gagaugcaac acugagagcc aaggggguggg aguugggaua auuuuauau aaaagaaguu | 180 |
| uuuccacuuu gaauugcuaa aaguggcauu uuuccuaugu gcagucacuc cucucauuuc | 240 |
| uaaaauaggg acgguggccag gcacggugg ucaugccugu aaucccagca cuuugggagg | 300 |
| ccgaggcagg cggcucacga ggucaggaga ucgagacuau ccuggcuaac acgguaaaac | 360 |
| ccugucucua cuaaaaguac aaaaaauuag cugggcgugg uggugggcac cuguaguccc | 420 |
| agcuacucgg gaggcugagg caggagaaag gcaugaaucc aagaggcaga gcuugcagug | 480 |
| agcugagauc acgccauugc acuccagccu gggcaacagu guuaagacuc ugucucaaau | 540 |
| auaaauaaau aaauaaauaa auaaauaaau aaauaaaau aaagcgagau guugcccuca | 600 |
| aa | 602 |

<210> SEQ ID NO 67
<211> LENGTH: 785
<212> TYPE: RNA
<213> ORGANISM: Artificial Sequence
<220> FEATURE:
<223> OTHER INFORMATION: 3'UTR-010 (LRP1; low density lipoprotein receptor-related protein 1 UTR)

<400> SEQUENCE: 67

```
ggcccugccc cgucggacug cccccagaaa gccuccugcc cccugccagu gaaguccuuc      60
agugagcccc uccccagcca gcccuuccccu ggcccgccg gauguauaaa uguaaaaaug     120
aaggaauuac auuuuauaug ugagcgagca agccggcaag cgagcacagu auuauuucuc     180
cauccccucc cugccugcuc cuuggcaccc ccaugcugcc uucagggaga caggcaggga     240
gggcuugggg cugcaccucc uaccuccca ccagaacgca cccacuggg agagcuggug       300
gugcagccuu ccccucccug uauaagacac uuugccaagg cucucccucc ucgcccauc      360
ccugcuugcc cgcucccaca gcuuccugag ggcuaauucu gggaagggag aguucuuugc     420
ugccccuguc uggaagacgu ggcucugggu gagguaggcg ggaaggaug gaguguuuua      480
guucuugggg gaggccaccc caaaccccag ccccaacucc aggggcaccu augagauggc     540
caugcucaac cccccucccca gacaggcccu cccugucucc agggccccca ccgagguucc    600
cagggcugga gacuuccucu gguaaacauu ccuccagccu ccccuccccu ggggacgcca     660
aggaggugg ccacacccag gaagggaaag cgggcagccc cguuugggg acgugaacgu       720
uuuaauaauu uuugcugaau uccuuuacaa cuaaauaaca cagauauugu uauaauaaa      780
auugu                                                                 785
```

<210> SEQ ID NO 68
<211> LENGTH: 3001
<212> TYPE: RNA
<213> ORGANISM: Artificial Sequence
<220> FEATURE:
<223> OTHER INFORMATION: 3'UTR-011 (Nnt1; cardiotrophin-like cytokine factor 1 UTR)

<400> SEQUENCE: 68

```
auauuaagga ucaagcuguu agcuaauaau gccaccucug caguuugggg aacaggcaaa     60
uaaaguauca guauacaugg ugauguacau cuguagcaaa gcucuggag aaaaugaaga     120
cugaagaaag caaagcaaaa acuguauaga gagauuuuuc aaaagcagua auccccucaau   180
uuuaaaaaag gauugaaaau ucuaaauguc uuucugugca uauuuuugu guuaggaauc     240
aaaaguauuu uauaaaagga gaaagaacag ccucauuuua gaugugaucc uguuggauuu    300
uuuauugccuc cucaguaacc agaaauguuu uaaaaaacua aguguuuagg auuucaagac    360
aacauuauac auggcucuga aauaucugac acaauguaaa cauugcaggc accugcauuu     420
uauguuuuuu uuucaacaa auguagcaaa uuugaaacuu uugaacuu cugagcuguc        480
cccuugcaau ucaaccgcag uuugaauuaa ucauaucaaa ucaguuuuaa uuuuuaaau      540
uguacuucag agucuauauu ucaagggcac auuuucucac uacuauuua auacauuaaa     600
ggacuaaua aucuuucaga gaugcuggaa acaaaucauu ugcuuuauau guuucauuag     660
aauaccaaug aaacauacaa cuugaaaauu aguaauagua uuuuugaaga uccauuucu     720
aauuggagau ucuuuuaauu ucgaucaacu uauaauguugu aguacuauau uaagugcacu    780
ugaguggaau ucaacauuug acuaauaaaa ugagucauc auguuggcaa gugaugugc      840
aauuaucucu ggugacaaaa gaguaaaauc aaauauuucu gccuguuaca aaucaagg      900
aagaccugcu acuaugaaau agaugacauu aaucugucuu cacuguuuau aauacggaug    960
gauuuuuuu caaaucagug ugugguuuga ggucuauugu aauugaugac auuugagaga    1020
aauggguggcu uuuuuuagcu accucuuugu ucauuuaagc accaguaaag aucaugucuu   1080
uuuauagaag uguagauuuu cuuugugacu uugcuaucgu gccuaaagcu cuaaauauag    1140
```

```
gugaaugugu gaugaauacu cagauuauuu gucucucuau auaauuaguu ugguacuaag    1200
uuucucaaaa aauuauuaac acaugaaaga caaucucuaa accagaaaaa gaaguaguac    1260
aaauuuuguu acuguaaugc ucgcguuuag ugaguuaaaa acacacagua ucuuuugguu    1320
uuauaaucag uuucuauuuu gcugugccug agauuaagau cuguguaugu gugugugugu    1380
gugugugcgu uuguguguua aagcagaaaa gacuuuuuua aaaguuuuaa gugauaaaug    1440
caauuuguua auugaucuua gaucacuagu aaacucaggg cugaauuaua ccauguauau    1500
ucuauuagaa gaaaguaaac accaucuuua uuccugcccu uuuucuucuc ucaaaguagu    1560
uguaguuaua ucuagaaaga agcaauuuug auuucuugaa aagguaguuc cugcacucag    1620
uuuaaacuaa aaauaaucau acuuggauuu uauuuauuuu ugucauagua aaaauuuuaa    1680
uuuauauaua uuuuuauuua guauuaucuu auucuuugcu auuugccaau ccuuugucau    1740 caauugueguu aaaugaauug aaaauucaug cccuguucau uuuauuuuac uuuauugguu    1800
aggauauuua aaggauuuuu guauauauaa uuucuuaaau uaauauucca aaagguuagu    1860
ggacuuagau uauaaauuau ggcaaaaauc uaaaaacaac aaaaaugauu uuuauacauu    1920
cuauuucauu auuccucuuu uuccaauaag ucauacaauu gguagauaug acuuauuuua    1980
uuuuuguauu auucacuaua ucuuuaugau auuuaaguau aaauaauuaa aaaaauuuau    2040
uguaccuuau agucugucac caaaaaaaaa aaauuaucug uagguaguga aaugcuaaug    2100
uugauuuguc uuuaagggcu uguuaacuau ccuuuauuuu cucauuuguc uuaaauuagg    2160 aguuugugu u uaaauuacuc aucuaagcaa aaaauguaua uaaaucccau uacuggguau    2220
auacccaaag gauuauaaau caugcugcua uaaagacaca ugcacacgua uguuuauugc    2280
agcacuauuc acaauagcaa agacuuggaa ccaacccaaa uguccaucaa ugauagacuu    2340
gauuaagaaa augugcacau auacaccaug gaauacuaug cagccauaaa aaaggaugag    2400
uucauguccu uuguagggac auggauaaag cuggaaacca ucauucgag caaacuauug    2460 caaggacaga aaaccaaaca cugcauguuc ucacucauag gugggaauug aacaaugaga    2520
acacuuggac acaagguggg gaacaccaca caccagggcc ugucaugggg uggggggagu    2580
ggggagggau agcauuagga gauauaccua auguaaauga ugaguuaaug ggucagcac    2640 accaacaugg cacauguaua cauauguagc aaaccugcac guuguguaca uguacccuag    2700
aacuuaaagu auaauuaaaa aaaaaagaa acagaagcu auuuauaaag aaguauuug    2760 cugaaauaaa ugugaucuuu cccauuaaaa aaauaaagaa auuuugggu aaaaaaacac    2820 aauauauugu auucuugaaa aauucuaaga gagugggaugu gaaguuucu caccacaaaa    2880 gugauaacua auugagguaa ugcacauauu aauuagaaag auuuugucau uccacaaugu    2940
auauauacuu aaaauaugu uauacacaau aaauacauac auuaaaaaau aaguaaagu    3000 a                                                                   3001
```

<210> SEQ ID NO 69
<211> LENGTH: 1037
<212> TYPE: RNA
<213> ORGANISM: Artificial Sequence
<220> FEATURE:
<223> OTHER INFORMATION: 3'UTR-012 (Col6a1; collagen, type VI, alpha 1 UTR)

<400> SEQUENCE: 69

```
cccacccugc acgccggcac caaacccugu ccucccaccc cucccacuc aucacuaaac     60 agaguaaaau gugaugcgaa uuuucccgac caaccugauu cgcuagauuu uuuuuaagga   120
```

```
aaagcuugga aagccaggac acaacgcugc ugccugcuuu gugcaggguc cuccggggcu    180
cagcccugag uuggcaucac cugcgcaggg cccucugggg cucagcccug agcuagaguc    240
accugcacag ggcccucuga ggcucagccc ugagcuggcg ucaccugugc agggcccucu    300
ggggcucagc ccugagcugg ccucaccugg guuccccacc ccgggcucuc cugcccugcc    360
cuccugcccg cccucccucc ugccugcgca gccuucccc uaggcaccuc ugugcugcau    420
cccaccagcc ugagcaagac gcccucucgg ggccugugcc gcacuagccu cccucuccuc    480
uguccccaua gcuggutttu cccaccaauc cucaccuaac aguuacuuua caauuaaacu    540
caaagcaagc ucuucccuc agcuggggc agccauggc cucugucgu uuuggaaa          600 ccaaggucag gaggccguug cagacauaaa ucucggcgac ucggccccgu cuccugaggg    660
uccugcuggu gaccggccug gaccuuggcc cuacagcccu ggaggccgcu gcugaccagc    720
acugaccccg accucagaga guacucgcag gggcgcuggc ugcacucaag cccucgaga     780 uuaacggugc uaaccccguc ugcucccucc cccgcagag acuggggccu ggacuggaca    840
ugagagcccc uuggugccac agagggcugu gucuuacuag aaacaacgca aaccucuccu    900
uccucagaau agugaugugu ucgacguuuu aucaaaggcc cccuuucuau guucauguua    960 guuugcucc uucuguguuu uuuucugaac cauauccaug uugcugacuu uccaaauaa     1020 agguuucac uccucuc                                                    1037

<210> SEQ ID NO 70
<211> LENGTH: 577
<212> TYPE: RNA
<213> ORGANISM: Artificial Sequence
<220> FEATURE:
<223> OTHER INFORMATION: 3'UTR-013 (Calr; calreticulin UTR)

<400> SEQUENCE: 70
agaggccugc cuccagggcu ggacugaggc cugagcgcuc cugccgcaga gcuggccgcg    60
ccaaauaaug ucucugugag acucgagaac uuucauuuuu uuccaggcug guucggauuu    120 ggggugauu uugguuuugu uccccuccuc cacucccccc cacccccucc ccgcccuuuu    180 uuuuuuuuu uuuuaaacug guauuuuauc uuugauucuc cuucagcccu cacccccuggu    240 ucucaucuuu cuugaucaac aucuuuucuu gccucugucc ccuucucuca ucucuuagcu    300
ccccuccaac cugggggggca ggugugugga aagccacag gccugagauu ucaucugcuc    360
uccuuccugg agcccagagg agggcagcag aaggggugg ugucccaac ccccagcac      420 ugaggaagaa cggggcucuu ucauuucac cccucccuuu uccccugcc cccaggacug     480 ggccacuucu gggugggggca gugggucca gauuggcuca cacugagaau guaagaacua    540
caaacaaaau uucauuaaaa uuaaauuuug ugucucc                             577

<210> SEQ ID NO 71
<211> LENGTH: 2212
<212> TYPE: RNA
<213> ORGANISM: Artificial Sequence
<220> FEATURE:
<223> OTHER INFORMATION: 3'UTR-014 (Col1a1; collagen, type I, alpha 1
      UTR

<400> SEQUENCE: 71
cucccuccau cccaaccugg cucccuccca cccaaccaac uuccccccca acccggaaac    60
agacaagcaa cccaaacuga accccccucaa aagccaaaaa augggagaca auucacaug    120 gacuuuggaa aauauuuuuu uccuuugcau ucaucucuca aacuuaguuu uuaucuugga    180
```

```
ccaaccgaac augaccaaaa accaaaagug cauucaaccu uaccaaaaaa aaaaaaaaaa    240
aaagaauaaa uaaauaacuu uuuaaaaaag gaagcuuggu ccacuugcuu gaagacccau    300
gcggggguaa gucccuuucu gcccguuggg cuuaugaaac cccaaugcug cccuuucugc    360
uccuuucucc acacccccu uggggccucc ccuccacucc uucccaaauc uguccccca      420 gaagacacag gaaacaaugu auugucugcc cagcaaucaa aggcaaugcu caaacaccca    480
aguggccccc acccucagcc cgcuccugcc cgcccagcac cccaggccc uggggaccu      540 ggguucuca gacugccaaa gaagccuugc caucggcgc ucccauggcu cuugcaacau      600
cucccuuucg uuuuugaggg ggucaugccg ggggagccac cagccccuca cuggguucgg    660
aggagaguca ggaagggcca cgacaaagca gaaacaucgg auuggggaa cgcgugucaa     720 ucccuugugc cgcagggcug ggcgggagag acuguucugu ccuugugua acuguuugc      780 ugaaagacua ccucguucuu gucuugaugu gucaccgggg caacugccug ggggcgggga    840 uggggggcagg guggaagcgg cuccccauuu uauaccaaag gugcuacauc uaugugaugg   900
gugggguggg gagggaauca cuggugcuau agaaauugag augccccccc aggccagcaa    960
auguuccuuu uuguucaaag ucuauuuuua uccuugaua uuuucuuuu uuuuuuuu        1020 uuuuugugga uggggacuug ugaauuuuuc uaaaggugcu auuuaacaug ggaggagagc    1080
gugugcggcu ccagcccagc ccgcugcuca cuuccaccc ucuccacc ugccucuggc       1140 uucucaggcc ucugcucucc gaccucucuc cucugaaacc cuccuccaca gcugcagccc    1200 auccuccccgg cucccuccua gucuguccug cguccucugu cccgggguu cagagacaac    1260 ucccaaagc acaaagcagu uuuucccccu agggguggga ggaagcaaaa gacucuguac    1320
cuauuuugua uguguauaau aauuugagau guuuuaauu auuugauug cuggaauaaa     1380 gcaugugga augacccaaa cauaauccgc aguggccucc uaauuccuu cuuggaguu      1440 ggggagggg uagacaugg gaaggggcuu uggggugaug ggcuugccuu ccauccugc      1500 ccuuucccuc cccacuauuc ucuucuagau cccccauaa ccccacuccc cuuucucuca    1560
cccuucuuau accgcaaacc uuucuacuuc cucuuucauu uucuauucuu gcaauuuccu    1620
ugcaccuuuu ccaaauccuc uucuccccug caauaccaua caggcaaucc acgugcacaa   1680
cacacacaca cacucuucac aucugggguu guccaaaccu caucccacu ccccuucaag    1740 cccauccacu cuccaccccc uggaugcccu gcacuuggug gcggugggau gcucauggau   1800
acugggaggg ugaggggagu ggaacccgug aggaggaccu ggggccucu ccuugaacug    1860 acaugaaggg ucaucggcc ucugcucccu ucucacccac gcugaccucc ugccgaagga    1920
gcaacgcaac aggagagggg ucugcugagc cuggcgaggg ucgggaggg accaggagga    1980 aggcgugcuc ccugcucgcu guccuggccc uggggagug agggagacag acaccuggga   2040
gagcuguggg gaaggcacuc gcaccgugcu cuugggaagg aaggagaccu ggcccugcuc   2100
accacggacu ggguugccucg accuccugaa uccccagaac acaacccccc ugggcugggg   2160
uggucugggg aaccaucgug cccccgccuc ccgccuacuc cuuuuuaagc uu            2212
```

<210> SEQ ID NO 72
<211> LENGTH: 729
<212> TYPE: RNA
<213> ORGANISM: Artificial Sequence
<220> FEATURE:
<223> OTHER INFORMATION: 3'UTR-015 (Plod1; procollagen-lysine,
    2-oxoglutarate 5-dioxygenase 1 UTR)

<400> SEQUENCE: 72

-continued

| | |
|---|---|
| uuggccaggc cugacccucu uggaccuuuc uucuuugccg acaaccacug cccagcagcc | 60 |
| ucugggaccu cggggucccca gggaacccag uccagccucc uggcuguuga cuucccauug | 120 |
| cucuuggagc caccaaucaa agagauucaa agagauuccu gcaggccaga ggcggaacac | 180 |
| accuuuaugg cugggggcucu ccguggguguu cuggacccag ccccuggaga caccauucac | 240 |
| uuuuacugcu uguagugac cgugcucuc caaccugucu uccugaaaaa ccaaggcccc | 300 |
| cuuccccac cucuuccaug gggugagacu ugagcagaac aggggcuucc ccaaguugcc | 360 |
| cagaaagacu gucugggguga aagccaugg ccagagcuuc ucccaggcac aggguguugca | 420 |
| ccagggacuu cugcuucaag uuuuggggua aagacaccug gaucagacuc caagggcugc | 480 |
| ccugagucug ggacuucugc cuccauggcu ggucaugaga gcaaaccgua guccccugga | 540 |
| gacagcgacu ccagagaacc ucuugggaga cagaagaggc aucugugcac agcucgaucu | 600 |
| ucuacuugcc uguggggagg ggagugacag guccacacac cacacuggu cacccuguccc | 660 |
| uggaugccuc ugaagagagg gacagaccgu cagaaacugg agaguuucua uuaaaggguca | 720 |
| uuuaaaacca | 729 |

<210> SEQ ID NO 73
<211> LENGTH: 847
<212> TYPE: RNA
<213> ORGANISM: Artificial Sequence
<220> FEATURE:
<223> OTHER INFORMATION: 3'UTR-016 (Nucb1; nucleobindin 1 UTR)

<400> SEQUENCE: 73

| | |
|---|---|
| uccuccggga ccccagcccu caggauuccu gaugcuccaa ggcgacugau gggcgcugga | 60 |
| ugaaguggca cagucagcuu cccuggggggc uggugucaug uugggcuccu ggggcggggg | 120 |
| cacggccugg cauuucacgc auugcugcca ccccaggucc accugucucc acuuucacag | 180 |
| ccuccaaguc uguggcucuu cccuucgucu cuccgagggg cuugccuucu cucgguccca | 240 |
| gugaggugcu cagugaucgg cuuaacuuag agaagcccgc ccccuccccu ucccgucug | 300 |
| ucccaagagg gucugcucug agccugcguu ccuaggugcc ucggccucag cugccugggu | 360 |
| uguggccgcc cuagcauccu guaugcccac agcuacugga auccccgcug cugcuccggg | 420 |
| ccaagcuucu gguugauuaa ugagggcaug ggguggucccc ucaagaccuu ccccuaccuu | 480 |
| uuguggaaccc agugaugccu caaagacagu guccccucca cagcggggug ccaggggcag | 540 |
| gggauccuca guauagccgg ugaaccccuga uaccaggagc cugggccucc cugaaccccu | 600 |
| ggcuuccagc caucucaucg ccagccuccu ccuggaccuc uuggccccca gcccuucccc | 660 |
| cacacagccc cagaagggguc ccagagcuga cccacaccca ggaccuaggc ccagcccuc | 720 |
| agccucaucu ggagccccug aagaccaguc ccacccaccu uucuggccuc aucugacacu | 780 |
| gcuccgcauc cugcugugug uccuguucca guuccgguu ccauccaaau acacuuucug | 840 |
| gaacaaa | 847 |

<210> SEQ ID NO 74
<211> LENGTH: 110
<212> TYPE: RNA
<213> ORGANISM: Artificial Sequence
<220> FEATURE:
<223> OTHER INFORMATION: 3'UTR-017 (a-globin)

<400> SEQUENCE: 74

| | |
|---|---|
| gcuggagccu cgguggccau gcuucuugcc ccuugggccu cccccagcc ccuccucccc | 60 | uuccugcacc cguacccccg uggucuuuga auaaagucug aguggcggc         110

<210> SEQ ID NO 75
<211> LENGTH: 119
<212> TYPE: RNA
<213> ORGANISM: Artificial Sequence
<220> FEATURE:
<223> OTHER INFORMATION: Synthetic: 3 UTR, no miR binding sites

<400> SEQUENCE: 75
ugauaauagg cuggagccuc gguggccaug cuucuugccc cuugggccuc ccccagccc         60 cuccucccu uccugcaccc guaccccgu ggucuuugaa uaaagucuga gugggcggc          119

<210> SEQ ID NO 76
<211> LENGTH: 18
<212> TYPE: DNA
<213> ORGANISM: Artificial Sequence
<220> FEATURE:
<223> OTHER INFORMATION: Synthetic: Syn5 promoter

<400> SEQUENCE: 76
attgggcacc cgtaagg                                                     18

<210> SEQ ID NO 77
<211> LENGTH: 92
<212> TYPE: RNA
<213> ORGANISM: Artificial Sequence
<220> FEATURE:
<223> OTHER INFORMATION: 5' UTR

<400> SEQUENCE: 77
ucaagcuuuu ggacccucgu acagaagcua auacgacuca cuauagggaa auaagagaga       60
aaagaagagu aagaagaaau auaagagcca cc                                    92

<210> SEQ ID NO 78
<211> LENGTH: 51
<212> TYPE: RNA
<213> ORGANISM: Artificial Sequence
<220> FEATURE:
<223> OTHER INFORMATION: 3' UTR

<400> SEQUENCE: 78
ugauaauagg cuggagccuc gguggccaug cuucuugccc cuugggccuc c                51

<210> SEQ ID NO 79
<211> LENGTH: 1287
<212> TYPE: RNA
<213> ORGANISM: Artificial Sequence
<220> FEATURE:
<223> OTHER INFORMATION: Synthetic: GLA-CO26

<400> SEQUENCE: 79
augcagcucc ggaaccccga gcuccaccuu ggcugcgccc ucgccuugcg guuccucgca       60
cuugugagcu gggacauacc aggcgcccgg gcccucgaca cggcucugc ccgcaccca       120 accaugggcu ggcuccacug ggagcgcuuc augugcaacc ucgacugcca ggaggagccc      180
gacuccugca ucuccgagaa gcuuuucaug gagauggccg agcucauggu guccgagggc      240
uggaaggacg ccggcuacga guaccucugc aucgacgacu gcuggauggc cccgcagcgc      300
gacagcgagg gucgccucca ggccgacccc cagcgguucc cucacggcau ccgccagcuc      360
gccaacuacg uccacuccaa gggccucaag cucggcaucu acgccgacgu cggcaacaag      420
accugcgccg gcuucccgg cuccuucggc uacuacgaca ucgacgccca gaccuucgcc      480

```
gacuggggcg ucgaccuccu caaguucgac ggcugcuacu gcgacucccu cgagaaccuc    540
gccgacggcu acaagcacau gucccucgcc cucaaccgca ccggccgcuc caucgucuac    600
uccugcgagu ggcccucuca caugggccc uuccagaagc ccaacuacac cgagauaagg    660
caguacugca accacuggcg caauuucgcc gauaucgaug acuccuggaa guccaucaag    720
agcauccugg acuggaccuc cuucaaccag gagcgcaucg ucgacgucgc cggccccggc    780
ggcuggaacg accccgacau gcucgucauc ggaaacuucg gccugcccug aaccagcag    840 gucacccaga uggcccucug gccaucaug gccgccccac uguucauguc caacgaccuc    900
cgccacauca gcccgcaggc caaggcccuc uccaggaca aggacgucau cgccaucaac    960
caagacccgc ucggcaagca gggcuaccag cuccgccagg gcgacaacuu cgaggugugg   1020
gaacgucccc ucagcggccu ggcgugggcc gucgccauga ucaaccgcca ggagaucggc   1080
ggcccgcgcu ccuacaccau cgccguggcc agccugggca agggcgucgc cugcaaccc    1140 gccugcuuca ucacccagcu ccucccoguc aagagaaagc ugggcuucua cgaguggacc   1200
agccgccucc gcucccacau caaccccacc ggcaccgucc ugcuccagcu ggagaacacc   1260
augcagauga gccucaagga ccugcuc                                       1287

<210> SEQ ID NO 80
<211> LENGTH: 1287
<212> TYPE: RNA
<213> ORGANISM: Artificial Sequence
<220> FEATURE:
<223> OTHER INFORMATION: Synthetic: GLA-CO27

<400> SEQUENCE: 80
augcagcugc ggaaccccga gcugcaccug ggcugcgccc uggcccugcg guuccuggcc     60
cuggugagcu gggacauccc cggcgcccgg gcccuggaca acggccuggc ccggacgccc    120
accaugggcu ggcugcacug ggagcgguuc augugcaacc uggacugcca ggaggagccc    180
gacagcugca ucagcgagaa gcuguucaug gagauggccg agcugauggu gagcgagggc    240
uggaaggacg ccggcuacga guaccugugc aucgacgacu gcuggauggc ccccagcgg    300 gacagcgagg gccggcugca ggccgacccg cagcgguucc cucacggcau ccggcagcug    360
gccaacuacg ugcacagcaa gggccugaag cugggcaucu acgccgacgu gggcaacaag    420
accugcgccg gcuuccccgg cagcuucggc uacuacgaca ucgacgccca gaccuucgcc    480
gacuggggcg uggaccugcu gaaguucgac ggcugcuacu gcgacagccu ggagaaccug    540
gccgacggcu acaagcacau gagccuggcc cugaaccgga ccggccggag caucguguac    600
agcugcgagu ggcccuguca cauggcccc uuccagaagc ccaacuacac cgagauccgg    660
caguacugca accacuggcg caacuucgcc gacaucgacg acagcuggaa gagcaucaag    720
agcauccugg acuggaccag cuucaaccag gagcggaucg uggacgugc cggccccggc    780 ggcuggaacg accccgacau gcuggugauc ggcaacuucg gccugagcug aaccagcag    840 gugacccaga uggcccugug gccaucaug gccgcgcccc uguucaugag caacgaccug    900
cggcacauca gcccucaggc caaggcccug cugcaggaca aggacgugau cgccaucaac    960
caggacccac uggcaagca gggcuaccag cugcggcagg gcgacaacuu cgaggugugg   1020 gagcggccc ugagcggccu ggcgugggc gucgccauga ucaaccgcca ggagaucggc    1080
ggcccgcgga gcuacaccau cgccguggcc agccugggca agggcguggc cugcaaccc    1140 gccugcuuca ucacccagcu gcugcccgug aagcggaagc ugggcuucua cgaguggacc   1200
```

```
agccggcugc ggagccacau caaccccacc ggcaccgugc ugcugcagcu ggagaacacc    1260
augcagauga gccugaagga ccugcug                                        1287

<210> SEQ ID NO 81
<211> LENGTH: 164
<212> TYPE: RNA
<213> ORGANISM: Artificial Sequence
<220> FEATURE:
<223> OTHER INFORMATION: Synthetic: 3 UTR with miR 142-3p and miR 126-3p
      binding sites

<400> SEQUENCE: 81
ugauaauagu ccauaaagua ggaaacacua cagcuggagc cucggugcc augcuucuug       60 ccccuugggc uccccccag ccccuccucc cuuccugca cccguacccc cgcauuauu       120 acucacggua cgaguggucu uugaauaaag ucgaguggg cggc                      164

<210> SEQ ID NO 82
<211> LENGTH: 164
<212> TYPE: RNA
<213> ORGANISM: Artificial Sequence
<220> FEATURE:
<223> OTHER INFORMATION: Synthetic: 3 UTR with miR 142-3p and miR 126-3p
      binding sites variant 2

<400> SEQUENCE: 82
ugauaauagu ccauaaagua ggaaacacua cagcuggagc cucggugcc uagcuucuug       60 ccccuugggc uccccccag ccccuccucc cuuccugca cccguacccc cgcauuauu       120 acucacggua cgaguggucu uugaauaaag ucgaguggg cggc                      164

<210> SEQ ID NO 83
<211> LENGTH: 85
<212> TYPE: RNA
<213> ORGANISM: Artificial Sequence
<220> FEATURE:
<223> OTHER INFORMATION: Synthetic: miR-126

<400> SEQUENCE: 83
cgcuggcgac gggacauuau uacuuuuggu acgcgcugug acacuucaaa cucguaccgu       60
gaguaauaau gcgccgucca cggca                                            85

<210> SEQ ID NO 84
<211> LENGTH: 22
<212> TYPE: RNA
<213> ORGANISM: Artificial Sequence
<220> FEATURE:
<223> OTHER INFORMATION: Synthetic: miR-126-3p

<400> SEQUENCE: 84
ucguaccgug aguaauaaug cg                                               22

<210> SEQ ID NO 85
<211> LENGTH: 22
<212> TYPE: RNA
<213> ORGANISM: Artificial Sequence
<220> FEATURE:
<223> OTHER INFORMATION: Synthetic: miR-126-3p binding site

<400> SEQUENCE: 85
cgcauuauua cucacgguac ga                                               22

<210> SEQ ID NO 86
<211> LENGTH: 21
```

```
<212> TYPE: RNA
<213> ORGANISM: Artificial Sequence
<220> FEATURE:
<223> OTHER INFORMATION: Synthetic: miR-126-5p

<400> SEQUENCE: 86
cauuauuacu uuggguacgc g                                              21

<210> SEQ ID NO 87
<211> LENGTH: 21
<212> TYPE: RNA
<213> ORGANISM: Artificial Sequence
<220> FEATURE:
<223> OTHER INFORMATION: Synthetic: miR-126-5p binding site

<400> SEQUENCE: 87
cgcguaccaa aaguaauaau g                                              21

<210> SEQ ID NO 88
<211> LENGTH: 133
<212> TYPE: RNA
<213> ORGANISM: Artificial Sequence
<220> FEATURE:
<223> OTHER INFORMATION: Synthetic: 3'UTR with miR 142-3p binding site

<400> SEQUENCE: 88
gcuggagccu cgguggccau gcuucuugcc ccuugggccu ccccccagcc ccuccuccec    60 uuccugcacc cguaccccu ccauaaagua ggaaacacua caguggucuu ugaauaaagu   120 cugaguggge ggc                                                     133

<210> SEQ ID NO 89
<211> LENGTH: 22
<212> TYPE: RNA
<213> ORGANISM: Artificial Sequence
<220> FEATURE:
<223> OTHER INFORMATION: Synthetic: miR 146-3p sequence

<400> SEQUENCE: 89
ccucugaaau ucaguucuuc ag                                             22

<210> SEQ ID NO 90
<211> LENGTH: 22
<212> TYPE: RNA
<213> ORGANISM: Artificial Sequence
<220> FEATURE:
<223> OTHER INFORMATION: Synthetic: miR 146-5p sequence

<400> SEQUENCE: 90
ugagaacuga auuccauggg uu                                             22

<210> SEQ ID NO 91
<211> LENGTH: 22
<212> TYPE: RNA
<213> ORGANISM: Artificial Sequence
<220> FEATURE:
<223> OTHER INFORMATION: Synthetic: miR 155-3p sequence

<400> SEQUENCE: 91
cuccuacaua uuagcauuaa ca                                             22

<210> SEQ ID NO 92
<211> LENGTH: 23
<212> TYPE: RNA
<213> ORGANISM: Artificial Sequence
<220> FEATURE:
```

<223> OTHER INFORMATION: Synthetic: miR 155-5p sequence

<400> SEQUENCE: 92
uuaaugcuaa ucgugauagg ggu                                          23

<210> SEQ ID NO 93
<211> LENGTH: 22
<212> TYPE: RNA
<213> ORGANISM: Artificial Sequence
<220> FEATURE:
<223> OTHER INFORMATION: Synthetic: miR 16-3p sequence

<400> SEQUENCE: 93
ccaguauuaa cugugcugcu ga                                           22

<210> SEQ ID NO 94
<211> LENGTH: 22
<212> TYPE: RNA
<213> ORGANISM: Artificial Sequence
<220> FEATURE:
<223> OTHER INFORMATION: Synthetic: miR 16-5p sequence

<400> SEQUENCE: 94
uagcagcacg uaaauauugg cg                                           22

<210> SEQ ID NO 95
<211> LENGTH: 21
<212> TYPE: RNA
<213> ORGANISM: Artificial Sequence
<220> FEATURE:
<223> OTHER INFORMATION: Synthetic: miR 21-3p sequence

<400> SEQUENCE: 95
caacaccagu cgaugggcug u                                            21

<210> SEQ ID NO 96
<211> LENGTH: 22
<212> TYPE: RNA
<213> ORGANISM: Artificial Sequence
<220> FEATURE:
<223> OTHER INFORMATION: Synthetic: miR 21-5p sequence

<400> SEQUENCE: 96
uagcuuauca gacugauguu ga                                           22

<210> SEQ ID NO 97
<211> LENGTH: 22
<212> TYPE: RNA
<213> ORGANISM: Artificial Sequence
<220> FEATURE:
<223> OTHER INFORMATION: Synthetic: miR 223-3p sequence

<400> SEQUENCE: 97
ugucaguuug ucaaauaccc ca                                           22

<210> SEQ ID NO 98
<211> LENGTH: 22
<212> TYPE: RNA
<213> ORGANISM: Artificial Sequence
<220> FEATURE:
<223> OTHER INFORMATION: Synthetic: miR 223-5p sequence

<400> SEQUENCE: 98
cguguauuug acaagcugag uu                                           22

```
<210> SEQ ID NO 99
<211> LENGTH: 22
<212> TYPE: RNA
<213> ORGANISM: Artificial Sequence
<220> FEATURE:
<223> OTHER INFORMATION: Synthetic: miR 24-3p sequence

<400> SEQUENCE: 99
uggcucaguu cagcaggaac ag                                              22

<210> SEQ ID NO 100
<211> LENGTH: 22
<212> TYPE: RNA
<213> ORGANISM: Artificial Sequence
<220> FEATURE:
<223> OTHER INFORMATION: Synthetic: miR 24-5p sequence

<400> SEQUENCE: 100
ugccuacuga gcugauauca gu                                              22

<210> SEQ ID NO 101
<211> LENGTH: 21
<212> TYPE: RNA
<213> ORGANISM: Artificial Sequence
<220> FEATURE:
<223> OTHER INFORMATION: Synthetic: miR 27-3p sequence

<400> SEQUENCE: 101
uucacagugg cuaaguuccg c                                               21

<210> SEQ ID NO 102
<211> LENGTH: 22
<212> TYPE: RNA
<213> ORGANISM: Artificial Sequence
<220> FEATURE:
<223> OTHER INFORMATION: Synthetic: miR 27-5p sequence

<400> SEQUENCE: 102
agggcuuagc ugcuugugag ca                                              22

<210> SEQ ID NO 103
<211> LENGTH: 141
<212> TYPE: RNA
<213> ORGANISM: Artificial Sequence
<220> FEATURE:
<223> OTHER INFORMATION: Synthetic: 3'UTR with miR 126-3p binding site

<400> SEQUENCE: 103
ugauaauagg cuggagccuc gguggccaug cuucuugccc cuugggccuc ccccagccc      60 cuccuccccu uccugcaccc guaccccccg cauuauuacu cacgguacga guggucuuug    120
aauaaagucu gaguggggcgg c                                             141

<210> SEQ ID NO 104
<211> LENGTH: 23
<212> TYPE: RNA
<213> ORGANISM: Artificial Sequence
<220> FEATURE:
<223> OTHER INFORMATION: Synthetic: miR 155-5p sequence

<400> SEQUENCE: 104
uuaaugcuaa uugugauagg ggu                                             23

<210> SEQ ID NO 105
<211> LENGTH: 23
<212> TYPE: RNA
```

```
<213> ORGANISM: Artificial Sequence
<220> FEATURE:
<223> OTHER INFORMATION: Synthetic: miR 155-5p binding site

<400> SEQUENCE: 105
accccuauca caauuagcau uaa                                              23

<210> SEQ ID NO 106
<211> LENGTH: 188
<212> TYPE: RNA
<213> ORGANISM: Artificial Sequence
<220> FEATURE:
<223> OTHER INFORMATION: Synthetic: 3 UTR with 3 miR 142-3p binding
      sites

<400> SEQUENCE: 106
ugauaauagu ccauaaagua ggaaacacua cagcuggagc cucggguggcc augcuucuug     60 ccccuugggc cuccauaaag uaggaaacac uacaucccccc cagccccucc ucccuuccu    120 gcacccguac ccccuccaua aaguaggaaa cacuacagug gucuuugaau aaagucugag    180
ugggcggc                                                             188

<210> SEQ ID NO 107
<211> LENGTH: 140
<212> TYPE: RNA
<213> ORGANISM: Artificial Sequence
<220> FEATURE:
<223> OTHER INFORMATION: Synthetic: 3UTR with miR 142-5p binding site

<400> SEQUENCE: 107
ugauaauagg cuggagccuc gguggccaug cuucuugccc cuugggccuc ccccagccc      60 cucccccccu uccugcaccc guaccccccag uagugcuuuc uacuuuaugg uggucuuuga   120
auaaagucug agugggcggc                                                140

<210> SEQ ID NO 108
<211> LENGTH: 182
<212> TYPE: RNA
<213> ORGANISM: Artificial Sequence
<220> FEATURE:
<223> OTHER INFORMATION: Synthetic: 3UTR with 3 miR 142-5p binding sites

<400> SEQUENCE: 108
ugauaauaga guagugcuuu cuacuuuaug gcuggagccu cgguggccau gcuucuugcc     60
ccuugggcca guagugcuuu cuacuuuaug uccccccagc cccuccuccc cuuccugcac   120
ccguaccccc aguagugcuu ucuacuuuau gguggucuuu gaauaaaguc ugaguggcg    180 gc                                                                   182

<210> SEQ ID NO 109
<211> LENGTH: 184
<212> TYPE: RNA
<213> ORGANISM: Artificial Sequence
<220> FEATURE:
<223> OTHER INFORMATION: Synthetic: 3UTR with 2 miR 142-5p binding sites
      and 1 miR 142-3p binding site

<400> SEQUENCE: 109
ugauaauaga guagugcuuu cuacuuuaug gcuggagccu cgguggccau gcuucuugcc     60
ccuugggccu ccauaaagua ggaaacacua caucccccca gccccuccuc ccuuccugc    120 acccguaccc ccaguagugc uuucuacuuu auggugguucu uugaauaaag ucgaguggg   180 cggc                                                                 184
```

-continued

```
<210> SEQ ID NO 110
<211> LENGTH: 142
<212> TYPE: RNA
<213> ORGANISM: Artificial Sequence
<220> FEATURE:
<223> OTHER INFORMATION: Synthetic: 3UTR with miR 155-5p binding site

<400> SEQUENCE: 110
ugauaauagg cuggagccuc gguggccaug cuucuugccc cuugggccuc cccccagccc      60
cuccuccccu uccugcaccc guaccccac cccuaucaca auuagcauua aguggucuuu     120
gaauaaaguc ugagugggcg gc                                             142

<210> SEQ ID NO 111
<211> LENGTH: 188
<212> TYPE: RNA
<213> ORGANISM: Artificial Sequence
<220> FEATURE:
<223> OTHER INFORMATION: Synthetic: 3 UTR with 3 miR 155-5p binding
      sites

<400> SEQUENCE: 111
ugauaauaga ccccuaucac aauuagcauu aagcuggagc cucgguggcc augcuucuug      60
ccccuugggc caccccuauc acaauuagca uuaauccccc cagccccucc ucccuuccu     120 gcacccguac ccccaccccu aucacaauua gcauuaagug gucuuugaau aaagucugag    180
ugggcggc                                                             188

<210> SEQ ID NO 112
<211> LENGTH: 188
<212> TYPE: RNA
<213> ORGANISM: Artificial Sequence
<220> FEATURE:
<223> OTHER INFORMATION: Synthetic: 3UTR with 2 miR 155-5p binding sites
      and 1 miR 142-3p binding site

<400> SEQUENCE: 112
ugauaauaga ccccuaucac aauuagcauu aagcuggagc cucgguggcc augcuucuug      60
ccccuugggc cuccauaaag uaggaaacac uacaucccc cagccccucc ucccuuccu      120 gcacccguac ccccaccccu aucacaauua gcauuaagug gucuuugaau aaagucugag    180
ugggcggc                                                             188

<210> SEQ ID NO 113
<211> LENGTH: 142
<212> TYPE: RNA
<213> ORGANISM: Artificial Sequence
<220> FEATURE:
<223> OTHER INFORMATION: Synthetic: 3'UTR with miR 142-3p binding site,
      P3 insertion

<400> SEQUENCE: 113
ugauaauagg cuggagccuc gguggccaug cuucuugccc cuugggccuc cauaaaguag      60
gaaacacuac auccccccag ccccuccucc ccuuccugca cccguacccc cguggucuuu    120
gaauaaaguc ugagugggcg gc                                             142

<210> SEQ ID NO 114
<211> LENGTH: 21
<212> TYPE: RNA
<213> ORGANISM: Artificial Sequence
<220> FEATURE:
<223> OTHER INFORMATION: Synthetic: miR-142-5p binding site
```

<400> SEQUENCE: 114
aguagugcuu ucuacuuuau g                                           21

<210> SEQ ID NO 115
<211> LENGTH: 70
<212> TYPE: RNA
<213> ORGANISM: Artificial Sequence
<220> FEATURE:
<223> OTHER INFORMATION: Synthetic: 5' UTR with miR142-3p binding site
      at position p1

<400> SEQUENCE: 115
gggaaauaag aguccauaaa guaggaaaca cuacaagaaa agaagaguaa gaagaaauau     60
aagagccacc                                                           70

<210> SEQ ID NO 116
<211> LENGTH: 70
<212> TYPE: RNA
<213> ORGANISM: Artificial Sequence
<220> FEATURE:
<223> OTHER INFORMATION: Synthetic: 5' UTR with miR142-3p binding site
      at position p2

<400> SEQUENCE: 116
gggaaauaag agagaaaaga agaguaaucc auaaaguagg aaacacuaca gaagaaauau     60
aagagccacc                                                           70

<210> SEQ ID NO 117
<211> LENGTH: 70
<212> TYPE: RNA
<213> ORGANISM: Artificial Sequence
<220> FEATURE:
<223> OTHER INFORMATION: Synthetic: 5' UTR with miR142-3p binding site
      at position p3

<400> SEQUENCE: 117
gggaaauaag agagaaaaga agaguaagaa gaaauauaau ccauaaagua ggaaacacua     60
cagagccacc                                                           70

<210> SEQ ID NO 118
<211> LENGTH: 181
<212> TYPE: RNA
<213> ORGANISM: Artificial Sequence
<220> FEATURE:
<223> OTHER INFORMATION: Synthetic: 3UTR with 3 miR 142-5p binding sites

<400> SEQUENCE: 118
ugauaauaga guagugcuuu cuacuuuaug gcuggagccu cgguggccau gcuucuugcc     60
ccuugggcca guagugcuuu cuacuuuaug uccccccagc cccucucccc uuccugcacc    120
cguaccccca guagugcuuu cuacuuuaug guggucuuug aauaaagucu gaguggcgg    180 c                                                                   181

<210> SEQ ID NO 119
<211> LENGTH: 1498
<212> TYPE: RNA
<213> ORGANISM: Artificial Sequence
<220> FEATURE:
<223> OTHER INFORMATION: Synthetic: GLA-mRNA #1

<400> SEQUENCE: 119
gggaaauaag agagaaaaga agaguaagaa gaaauauaag agccaccaug cagcuccgga     60

```
accccgagcu ccaccuuggc ugcgcccucg ccuugcgguu ccucgcacuu gugagcuggg      120
acauaccagg cgcccgggcc cucgacaacg gccucgcccg cacccaacc augggcuggc      180 uccacuggga gcgcuucaug ugcaaccucg acugccagga ggagcccgac uccugcaucu     240
ccgagaagcu uuucauggag auggccgagc ucaugguguc cgagggcugg aaggacgccg     300
gcuacgagua ccucugcauc gacgacugcu ggauggcccc gcagcgcgac agcgagggug     360
gccuccaggc cgaccgcag cgguucccuc acggcauccg ccagcucgcc aacuacgucc      420
acuccaaggg ccucaagcuc ggcaucuacg ccgacgucgg caacaagacc ugcgccggcu     480
uccccggcuc cuucggcuac uacgacaucg acgcccagac cuucgccgac uggggcgucg    540
accuccucaa guucgacggc ugcuacugcg acccccucga gaaccucgcc gacggcuaca    600
agcacauguc ccucgcccuc aaccgcaccg gccgcuccau cgucuacucc ugcgagugc     660 cccucuacau guggcccuuc cagaagccca acuacaccga gauaaggcag uacugcaacc    720
acuggcgcaa uucgccgau aucgaugacu ccuggaaguc caucaagagc auccuggacu     780
ggaccuccuu caaccaggag cgcaucgucg acgucgccgg ccccggcggc uggaacgacc    840
ccgacaugcu cgucaucgga aacuucggcc uguccuggaa ccagcagguc acccagaugg    900
cccucugggc caucaugccc gccccacugu ucauguccaa cgaccucgc cacaucagcc     960 cgcaggccaa ggccuccuc caggacaagg acgucaucgc caucaaccaa gacccgcucg    1020
gcaagcaggg cuaccagcuc cgccagggcg acaacuucga ggugugggaa cgucccuca    1080 gcggccuggc gugggccguc gccaugauca accgccagga gaucggcggc ccgcgcuccu    1140
acaccaucgc cguggccagc cugggcaagg gcgucgccug caaccccgcc ugcuucauca    1200
cccagcuccu ccccgucaag agaaaagcugg gcuucuacga guggaccagc cgccuccgcu    1260
cccacaucaa ccccaccggc accgucugc uccagcugga gaacaccaug cagaugagcc    1320
ucaaggaccu gcucugauaa uaguccauaa aguaggaaac acuacagcug gagccucggu    1380
ggccaugcuu cuugccccuu gggccucccc ccagcccuc cuccccuucc ugcacccgua    1440 cccccccgcau uauuacucac gguacgagug gucuuugaau aaagucugag ugggcggc      1498
```

<210> SEQ ID NO 120
<211> LENGTH: 1498
<212> TYPE: RNA
<213> ORGANISM: Artificial Sequence
<220> FEATURE:
<223> OTHER INFORMATION: Synthetic: GLA-mRNA #2

<400> SEQUENCE: 120

```
gggaauaaag agagaaaaga agaguaagaa gaaauauaag agccaccaug cagcugcgga      60
accccgagcu gcaccugggc ugcgcccugg cccugcgguu ccuggcccug gugagcuggg     120
acauccccgg cgcccgggcc cuggacaacg gccuggcccg gacgcccacc augggcuggc    180
ugcacuggga gcgguucaug ugcaaccugg acugccagga ggagcccgac agcugcauca    240
gcgagaagcu guucauggag auggccgagc ugauggugag cgagggcugg aaggacgccg     300
gcuacgagua ccugugcauc gacgacugcu ggauggcgcc ccagcgggac agcgagggcc     360
ggcugcaggc cgacccgcag cgguucccuc acggcaaccg gcagcuggcc aacuacguge    420 acagcaaggg ccugaagcug ggcaucuacg ccgacguggg caacaagacc ugcgccggcu     480
uccccggcag cuucggcuac uacgacaucg acgcccagac cuucgccgac uggggcgugg    540
accugcugaa guucgacggc ugcuacugcg acagccugga gaaccuggcc gacggcuaca    600
```

| | |
|---|---|
| agcacaugag ccuggcccug aaccggaccg gccggagcau cguguacagc ugcgaguggc | 660 |
| cccuguacau guggcccuuc cagaagccca acuacaccga gauccggcag uacugcaacc | 720 |
| acuggcggaa cuucgccgac aucgacgaca gcuggaagag caucaagagc auccuggacu | 780 |
| ggaccagcuu caaccaggag cggaucgugg acguggccgg ccccggcggc uggaacgacc | 840 |
| ccgacaugcu ggugaucggc aacuucggcc ugagcuggaa ccagcaggug acccagaugg | 900 |
| cccguggggc caucauggcc gcgcccugu ucaugagcaa cgaccugcgg cacaucagcc | 960 |
| cucaggccaa ggcccugcug caggacaagg acgugaucgc caucaaccag gacccacugg | 1020 |
| gcaagcaggg cuaccagcug cggcagggcg acaacuucga ggugugggag cggcccuga | 1080 |
| gcggccuggc cugggccgug gccaugauca accggcagga gaucggcggc ccgcggagcu | 1140 |
| acaccaucgc cguggccagc cuggcaagg gcguggccug caaccccgcc ugcuucauca | 1200 |
| cccagcugcu gcccgugaag cggaagcugg gcuucuacga guggaccagc cggcugcgga | 1260 |
| gccacaucaa ccccaccggc accgugcugc ugcagcugga gaacaccaug cagaugagcc | 1320 |
| ugaaggaccu gcugugauaa uaguccauaa aguaggaaac acuacagcug gagccucggu | 1380 |
| ggccaugcuu cuugccccuu gggccucccc ccagccccuc uccccuuucc ugcacccgua | 1440 |
| ccccccgcau uauuacucac gguacgagug gucuuugaau aaagucugag ugggcggc | 1498 |

<210> SEQ ID NO 121
<211> LENGTH: 1498
<212> TYPE: RNA
<213> ORGANISM: Artificial Sequence
<220> FEATURE:
<223> OTHER INFORMATION: Synthetic: GLA-mRNA #3

<400> SEQUENCE: 121

| | |
|---|---|
| gggaauaag agagaaaaga agaguaagaa gaaauauaag agccaccaug cagcugagga | 60 |
| acccagaacu acaucugggc ugcgcgcuug cgcuucgcuu ccuggcccuc guuuccuggg | 120 |
| acaucccugg ggcugagca cuggacaaug gauuggcaag gacgccuacc augggcuggc | 180 |
| ugcacuggga gcgcuucaug ugcaaccuug acugccagga agagccagau ccugcauca | 240 |
| gugagaagcu cuucauggag auggcagagc ucauggucuc agaaggcugg aaggaugcag | 300 |
| guuaugagua cccucugcauu gaugacuguu ggauggcucc ccaaagagau ucagaaggca | 360 |
| gacuucaggc agaccucag cgcuuuccuc augggauucg ccagcuagcu aauuauguuc | 420 |
| acagcaaagg acugaagcua gggauuuaug cagauguugg aaauaaaacc ugcgcaggcu | 480 |
| ucccuggag uuuuggauac uacgacauug augcccagac cuuugcugac uggggaguag | 540 |
| aucugcuaaa auuugauggu guuacugug acaguuugga aaauuggca gaugguuaua | 600 |
| agcacauguc cuggcccug aauaggacug gcagaagcau uguguacucc ugugaguggc | 660 |
| cucuuuauau guggcccuuu caaaagccca auuauacaga aauccgacag uacugcaauc | 720 |
| acuggcgaaa uuugcugac auugaugauu ccuggaaaag uauaagagu auccuggacu | 780 |
| ggacaucuuu uaaccaggag agaauuguug auguugcugg accaggggu uggaaugacc | 840 |
| cagauauguu agugauuggc aacuuuggcc ucagcuggaa ucagcaagua acucagaugg | 900 |
| cccucugggu uaucauggcu gucccuuaau caugucuaa ugaccuccga cacaucagcc | 960 |
| cucaagccaa agcucucccuu caggauaagg acguaauugc caucaaucag daccccuugg | 1020 |
| gcaagcaagg guaccagcuu agacaggag acaacuuuga agugugggaa cgaccucucu | 1080 |
| caggcuuagc cugggcugua gcauagauaa accggcagga gauugguga ccucgcucuu | 1140 |
| auaccaucgc aguugcuucc cuggguaaag gaguggccug uaauccugcc ugcuucauca | 1200 |

| | |
|---|---|
| cacagcuccu cccugugaaa aggaagcuag gguucuauga auggacuuca agguuaagaa | 1260 |
| gucacauaaa ucccacaggc acuguuuugc uucagcuaga aaauacaaug cagaugucau | 1320 |
| uaaaagacuu acuuugauaa uaguccauaa aguaggaaac acuacagcug gagccucggu | 1380 |
| ggccaugcuu cuugccccuu gggcucuccc ccagccccuc cuccccuucc ugcacccgua | 1440 |
| cccccccgcau uauuacucac gguacgagug gucuuugaau aaagucugag ugggcggc | 1498 |

<210> SEQ ID NO 122
<211> LENGTH: 1498
<212> TYPE: RNA
<213> ORGANISM: Artificial Sequence
<220> FEATURE:
<223> OTHER INFORMATION: Synthetic: GLA-mRNA #4

<400> SEQUENCE: 122

| | |
|---|---|
| gggaaauaag agagaaaaga agaguaagaa gaaauauaag agccaccaug cagcucagga | 60 |
| acccggagcu ccaccucggc ugcgcccucg cccucagguu ccucgcucuu gugagcuggg | 120 |
| acaucccggg cgccagggcc cucgacaacg gccucgccag aaccccgacc augggcuggc | 180 |
| uccacuggga gagguucaug uguaaucugg acugccagga ggagccggau agcugcauca | 240 |
| gcgagaagcu guucauggag auggccgagc ugauggucuc cgagggcugg aaggacgccg | 300 |
| gcuaugagua ccuuugcauc gaugacugcu ggauggcccc gcagcgggac agcgagggca | 360 |
| ggcugcaagc ugacccucag cguuucccgc acggcauccg gcagcuggcc aacuacgugc | 420 |
| acagcaaggg ccugaagcug ggcaucuacg cggacgucgg caacaagacc ugcgccggcu | 480 |
| ucccgggaag cuucggcuac uacgacaucg acgcccagac cuucgccgac uggggcgugg | 540 |
| accugcugaa guucgacggc ugcuacugug acagccugga gaaccuggcc gacggcuaca | 600 |
| agcacauguc ccuggcucug aauagaaccg gcaggagcau aguguacagc ugcgagugcc | 660 |
| cacuguacau guggccguuc cagaagccga acuacaccga aaucagacaa uacugcaacc | 720 |
| acuggcggaa uuucgccgau aucgacgacu ccuggaaguc caucaagucc auccuggacu | 780 |
| ggaccucccu uccaaccagga gagaaucgug acguggccgg cccuggugga uggaacgauc | 840 |
| cagacaugcu gguuaucggc aauuucgccc ugagcuggaa ccagcaggug acgcagaugg | 900 |
| cccugugggc caucauggcc gccccacugu caugccaa cgaccuccgc cacaucagcc | 960 |
| cgcaggccaa ggccuccuc caagacaagg acgugaucgc caucaaccaa gacccgcucg | 1020 |
| gcaagcaggg cuaccagcug cgccagggcg acaauuucga ggucggggag cgcccgcugu | 1080 |
| cuggucuggc gugggccgug gccaugauca auagacagga gaucggcggc ccgcggagcu | 1140 |
| acaccaucgc cguagccagc cugggcaagg gcguggccug caacccggcu uguuucauca | 1200 |
| cccagcugcu cccgguuaag agaaagcugg gcuucuacga guggaccagc gguugcgca | 1260 |
| gccauaucaa cccgacuggc accgugcugc ugcagcugga aacacaaug cagaugucc | 1320 |
| ugaaggaccu gcucugauaa uaguccauaa aguaggaaac acuacagcug gagccucggu | 1380 |
| ggccaugcuu cuugccccuu gggcucuccc ccagccccuc cuccccuucc ugcacccgua | 1440 |
| cccccccgcau uauuacucac gguacgagug gucuuugaau aaagucugag ugggcggc | 1498 |

<210> SEQ ID NO 123
<211> LENGTH: 1498
<212> TYPE: RNA
<213> ORGANISM: Artificial Sequence
<220> FEATURE:
<223> OTHER INFORMATION: Synthetic: GLA-mRNA #5

<400> SEQUENCE: 123

```
gggaaauaag agagaaaaga agaguaagaa gaaauauaag agccaccaug cagcuccgca    60
auccggagcu ccaccucggc ugcgcccucg cccucagguu ccucgcccuu gugagcuggg   120
auaucccggg cgccagggcc cucgacaacg gcuuagccag aaccccaacg augggcuggc   180
uccacuggga gagguucaug ugcaaccugg acugccagga ggaaccggac agcugcaucu   240
ccgagaagcu guucauggag auggccagcu cauggugag cgagggcugg aaggacgccg    300
gcuacgagua ucucugcauc gacgacugcu ggaguggcccc acagagggac uccgagggca   360
ggcugcaggc cgacccgcag agauucccuc acggcauccg gcaacuggcc aacuacgugc   420
acagcaaggg ccugaagcug ggaaucuacg ccgacguggg caacaagacc ugugcuggcu   480
ucccgggcag cuucggcuac uaugacaucu augcccagac cuucgccgac uggggcgucg   540
accugcucaa guucgacggc uguuacugcg acagccugga gaaccuggca gacggcuaua   600
agcacaugag ccuggcacuc aacaggaccg gcaggucaau agugacacagc ugcgagugggc  660
cgcuguacau guggccauuc cagaagccga auuacaccga gauaaggcag uauugcaacc   720
acuggcgaaa cuucgcggau aucgaugaca gcuggaaguc gauaaagagc auccuggacu   780
ggaccagcuu caaccaggag aggaucgugg acgucgccgg cccgggcggc uggaacgacc   840
cggacaugcu ggugaucgga aacuucggcu cagcuggaa ccaacaggug acccagaugg   900
cccugugggc caucauggcg gcaccucugu caugagcaa ugaccugcgg cauaucagcc    960
cgcaggccaa ggcccugcuc caggacaagg acgucauagc caucaaucag gacccgcugg  1020
gcaagcaggg cuaccaacug cggcagggag acaacuucga gguguggag cggccgcuga  1080
gcggccuggc auggccgug gccaugauca auagacagga gaucggcggc ccgcggagcu  1140
acaccaucgc cguggcgagu cuuggcaagg guguggccug caauccggcc ugcuucauca  1200
cccagcugcu gccagucaag cgcaagcucg gauucuacga guggaccagc cgucugcgca  1260
gccacaucaa uccuaccggc acggugcccc ugcagcugga gaacaccaug caaaugucuc  1320
ucaaggaccu gcugugauaa uaguccauaa aguaggaaac acuacagcug gagccucggu  1380
ggccaugcuu cuugcccuu gggccucccc ccagcccuc cucccuucc ugcacccgua    1440
cccccccgcau uauuacucac gguacgagug gucuuugaau aaagucugag ugggcggc    1498
```

<210> SEQ ID NO 124
<211> LENGTH: 1498
<212> TYPE: RNA
<213> ORGANISM: Artificial Sequence
<220> FEATURE:
<223> OTHER INFORMATION: Synthetic: GLA-mRNA #6

<400> SEQUENCE: 124

```
gggaaauaag agagaaaaga agaguaagaa gaaauauaag agccaccaug cagcuccgga    60
acccagaacu ccaccucggc ugcgcccucg cccuccgguu ccuugcccuc guguccuggg   120
acauuccagg cgcccgggcc cucgacaacg gcccgcccg accccaacc augggcuggc    180
uccauuggga gagguucaug ugcaaccugg acugccaaga ggagccggac uccugcaucu   240
ccgagaagcu guucauggag auggccagcu cauggugag cgagggcugg aaggacgccg    300
gcuacgaaua ucugugcauc gacgauugcu ggauggcccc ucaaagagac agcgagggca   360
gacugcaggc cgacccgcag cgcuucccuc augcauccg gcaacucgcg aauuaugugc    420
acagcaaggg ccugaagcug ggcaucuacg ccgacgucgu uaacaagacc ugcgccggcu   480
ucccaggcag cuucggcuac uacgacaucg acgcccagac cuucgccgac uggggcguag   540
```

```
accuccugaa guucgacggu ugcuacugcg acucccugga gaaccuagcc gacggcuaca      600
agcacauguc ccucgcccug aacagaaccg gccgguccau cgucuauucc ugcgagugcc      660
cgcuguacau guggccguuc cagaagccua acuacacaga gauccgccag uacugcaacc      720
acuggcggaa uuucgccgau aucgacgaca guuggaaguc caucaagagc auacuggauu      780
ggaccuccuu caaccaggag aggaucgugg acguggccgg cccgggcggu uggaacgacc      840
cagacaugcu ggugaucgga aacuucgccc ugagcuggaa ccagcaggug acccagaugg      900
cccucugggc caucauggcc gccccucugu ucaugccaa ugaccucagg cauaucuccc       960
cgcaggccaa ggcucuccuc caggacaagg acgugaucgc caucaaucag gauccgcugg      1020
gaaagcaggg auaccagcug aggcagggcg acaacuucga ggugugggag cgcccacuga      1080
gcggccugcu uugggccgug gccaugauca accggcaaga gaucggcggc cgcggagcu       1140 acaccauugc cguggcuagc cugggcaagg gcguggccug caacccggcc ugcuucauca      1200
cccagcuucu gccgguaaag cguaagcugg gcuucuacga guggaccagc agacugagga      1260
gccacaucaa cccgaccggc accgugcugc uccagcugga gaacaccaug cagaugagcc      1320
ugaaggaucu gcucugauaa uaguccauaa aguaggaaac acuacagcug gagccucggu      1380
ggccaugcuu cuugccccuu gggccucccc ccagccccuc ucccccuucc ugcacccgua      1440 cccccccgcau uauuacucac gguacgagug gucuuugaau aaagucugag ugggcggc      1498

<210> SEQ ID NO 125
<211> LENGTH: 1498
<212> TYPE: RNA
<213> ORGANISM: Artificial Sequence
<220> FEATURE:
<223> OTHER INFORMATION: Synthetic: GLA-mRNA #7

<400> SEQUENCE: 125 gggaauaag agagaaaaga agaguaagaa gaaauauaag agccaccaug caacuccgca       60
auccggagcu ccaccucggc ugugcgcucg cccuuagauu ccucgcccuc ugagcugggg      120
acaucccagg cgcccgggcc cucgacaacg gccuagccg cacuccuaca augggcuggu       180
ugcacuggga acgcuucaug uguaaccugg acugccagga ggaaccggac agcuguaucu      240
ccgagaagcu guucauggag augggccagc ugauggugag cgagggcugg aaggaugccg      300
gcuacgagua ccugugguauc gaugacugcu ggauggcccc cagcgagau agcgagggac      360 gccugcaggc cgacccgcag agauucccgc acggcauccg ccagcuggcc aauuauguuc      420
acagcaaggg ccugaagcug ggcaucuacg ccgacguggg caacaagacc ugcgccggau      480
uccggggcag cuucggcuac uacgauauag augcccaaac auucgccgac uggggcgucg      540
accugcuuaa guucgacggc ugcuacugcg auagccugga gaaucuggcc gacggcuaca      600
agcacaugag ccuggcccuc aacaggaccg gaaggcucau cguacagc ugcgaauggc        660 cucuguacau guggccuuuc cagaagccga acuacaccga gauccggcag uacuguaauc      720
acuggaggaa cuucgccgac aucgacgauu cuuggaaguc uaucaagucc auccuggacu      780
ggaccuccuu caaucaggag agaauugucg acguggccgg cccgggugcc uggaacgacc      840
cggacaugcu ggugaucggc aacuucgccc ugagcuggaa ccagcaggug acccagaugg      900
cccugugggc cauaauggcc gccccacucu ucaugccaa cgaccugcgg cacaucagcc      960
cacaggccaa ggcacugcuc caggacaagg acgugaucgc caucaaccaa gacccucugg     1020
gcaagcaggg uuaccagcuu agacagggcg acaacuucga ggugugggag cgcccgcuuu     1080
```

```
ccggccucgc cugggccgug gccaugauca acaggcagga aaucggaggc ccgcgcuccu    1140
auacuaucgc cguggcgagc cuggcaagg gcguggccug caacccggcc ugcuucauca    1200
cccagcugcu gccagucaag agaaagcugg gcuucuacga guggaccucc agacugagau    1260
cccacaucaa uccuaccggc accgucugc ugcagcugga aacacgaug cagaugucgc    1320 ugaaggaccu ccugugauaa uaguccauaa aguaggaaac acuacagcug gagccucggu    1380
ggccaugcuu cuugcccuu gggcucuccc ccagccccuc ucccccuucc ugcacccgua    1440
ccccccgcau uauuacucac gguacgagug gucuuugaau aaagucugag ugggcggc    1498
```

<210> SEQ ID NO 126
<211> LENGTH: 1498
<212> TYPE: RNA
<213> ORGANISM: Artificial Sequence
<220> FEATURE:
<223> OTHER INFORMATION: Synthetic: GLA-mRNA #8

<400> SEQUENCE: 126

```
gggaauaag agagaaaaga agaguaagaa gaaauauaag agccaccaug cagcuccgga     60
acccagagcu ucaccuuggc ugcgcccucg cccucagguu ccuagcccuc gugccuggg    120 acaucccagg cgcccgggcc cuugacaacg gccucgccag aaccccgacc augggcuggc    180
uccacuggga gcgcuucaug ugcaaccugg acugucagga ggagccggac ucauguauca    240
gcgagaagcu guucauggaa augccgaauu uaaggugu cgaggcugg aaggacgccg    300 gcuaugagua ccugugcauc gacgauugcu ggaugcccc gcagagagac agcgagggca    360
gacugcaggc cgaccacag agguucccac acggcaucag gcagcuggcc aacuacgugc    420
acuccaaggg ccugaagcug ggcaucuacg ccgauguggg caauaagacc ugcgccggcu    480
ucccgggcag cuucggcuau uacgauaucg acgcccagac guucgccgac uggggcgugg    540
aucugcugaa guucgacggc uguuacugug acagccugga gaaucuggcc gauggcuaca    600
agcauaugag ucucgcccuc aacaggaccg gccgcucaau cguguacagc ucgcgagugc    660
cgcuguacau guggccguuc cagaagccaa acuacaccga gaucaggcaa uacugcaacc    720
auuggcgcaa cuucgccgau auagaugaca gcuggaaguc caucaagucc auccuggacu    780
ggaccagcuu caaucaggag cguauagugg acguggccgg cccgggcggu uggaacgacc    840
cagacaugcu ggugaucggc aacuucggcc ugagcuggaa ccagcaggug acccagaugg    900
cccugugggc caucauggcc gccccacugu caugccaa cgaccugcgg cacaucagcc    960
cgcaggccaa ggcgcugcug caggauaagg acgugauagc uaucaaccaa gacccacugg   1020
gcaagcaggg auaucagcug aggcaaggcg acaacuucga ggugugggag aggccgcuca   1080
gcggccuggc cugggccgug gccaugauca acaggcaaga gaucggaggc ccgagaagcu   1140
acaccaucgc ggucgccagc cugggcaagg guguggcgug caacccagca ugcuucauca   1200
cccagcugcu gccggugaag aggaagcugg gauucuacga guggacuagc agacugagga   1260
gccacaucaa cccgaccggc accgucugc ugcagcucga aacaccaug cagaugucccc   1320 ugaaggaucu gcugugauaa uaguccauaa aguaggaaac acuacagcug gagccucggu   1380
ggccaugcuu cuugcccuu gggcucuccc ccagccccuc ucccccuucc ugcacccgua   1440
ccccccgcau uauuacucac gguacgagug gucuuugaau aaagucugag ugggcggc    1498
```

<210> SEQ ID NO 127
<211> LENGTH: 1498
<212> TYPE: RNA
<213> ORGANISM: Artificial Sequence
<220> FEATURE:
<223> OTHER INFORMATION: Synthetic: GLA-mRNA #9

<400> SEQUENCE: 127

```
gggaaauaag agagaaaaga agaguaagaa gaaauauaag agccaccaug cagcuccgga      60
acccagaguu gcaucucggu ugcgccuuag cucuccgguu ccucgcccuc gugagcuggg     120
acaucccagg cgccagggcu cucgacaacg gacuugccag gaccccgaca augggcuggc    180
uccacuggga gcgguucaug ugcaaccugg auugucagga ggagccagac uccugcaucu    240
ccgagaagcu guucauggag auggccgaac ucauggugag cgagggaugg aaggacgccg    300
gcuaugagua ucugugcauc gacgauugcu ggauggcccc gcagagggau agcgagggcc    360
gccuccaggc cgacccgcag cgauucccgc acggcauccg acagcuggcc aacuacgugc    420
acuccaaggg ccucaagcug ggcauauacg ccgacgucgg aaacaagacg ugcgccggcu    480
ucccgggcag cuucggcuac uaugacaucg acgcccagac guucgcggau uggggcgugg    540
accugcugaa guucgacggc ugcuacgcgc auagccucga gaaucuggcc gacggauaca    600
agcauaugag ccucgcccug aacaggaccg gccguuccau cgucuacuca ugcgagugc      660
cgcucuacau guggccauuc cagaagccua auuacaccga gauccggcag uacugcaacc    720
acuggcgaaa uuucgcagau auagacgaua gcuggaaguc caucaagucu auccuggacu    780
ggacuuccuu caaccaggaa aggaucgucg acguggcggg cccgggcggc uggaacgacc    840
cggacaugcu ggugaucggc aacuucggcc ugagcuggaa ccagcaggug acccagaugg    900
cccugugggc caucauggcc gccccucugu caugccaa ugaccugcgg cacaucagcc        960
cgcaggccaa ggcccugcug caagacaagg augugauugc caucaaucag gacccucucg   1020
gcaagcaggg cuaccagcuc cgacagggag auaacuucga agugugggag cggccgcuga   1080
gcggccuggc cugggccguc gccaugauca accggcagga gaucggcggc ccacgcuccu   1140
acaccaucgc cguggccucc cugggcaagg gcguggccug caauccggca ugcuucauca   1200
cccagcugcu gccagucaag aggaagcugg gcuucuauga auggaccagc agacugcgau   1260
cccacaucaa cccaaccggc accgugcgc ugcagcugga gaacacuaug cagaugagcc     1320
ugaaggaccu gcugugauaa uaguccauaa aguaggaaac acuacagcug gagccucggu   1380
ggccaugcuu cuugcccuu gggcucccc ccagccccuc cuccccuucc ugcacccgua      1440
cccccccgcau uauuacucac gguacgagug gucuuugaau aaagucugag ugggcggc     1498
```

<210> SEQ ID NO 128
<211> LENGTH: 1498
<212> TYPE: RNA
<213> ORGANISM: Artificial Sequence
<220> FEATURE:
<223> OTHER INFORMATION: Synthetic: GLA-mRNA #10

<400> SEQUENCE: 128

```
gggaaauaag agagaaaaga agaguaagaa gaaauauaag agccaccaug cagcucagaa      60
acccagagcu ccauuugggc ugcgcccucg cccuccgguu ccucgcccuc gugagcuggg     120
acaucccggg cgccagagcc cucgacaacg gacucgcccg aacaccaacc augggcuggc    180
uccauuggga gagguucaug ugcaaccugg acugccagga ggagccggau agcugcauca    240
gcgagaagcu guucauggag auggccgagc ugaugguguc cgagggcugg aaggacgccg    300
gcuaugagua ucugugcauc gacgacgcu ggauggcccc acagggggac uccgagggaa      360
ggcugcaggc cgacccgcag agguucccuc acggcauccg ucagcucgcc aacuacgugc    420
```

| | |
|---|---|
| acuccaaggg ccugaagcug gcaucuacg ccgacguggg caacaagacc ugcgccggcu | 480 |
| ucccaggcag cuucggauac uaugacaucg acgcccagac cuucgccgac ugggcgugg | 540 |
| aucugcugaa guucgacggc ugcuacugcg acagcuugga gaaucuggcc gacgguuaca | 600 |
| agcacaugag ccuagcccug aaccggaccg aaggagcau cguguacagc ugcgaguggc | 660 |
| cgcuguacau guggccauuc cagaagccga acuacaccga gauuaggcag uacugcaacc | 720 |
| acuggagaaa cuucgcagau aucgacgaca gcuggaaguc caucaagagc auccuggauu | 780 |
| ggaccagcuu caaccaggag cggaucgugg acguggccgg uccgggaggc uggaacgacc | 840 |
| cggacaugcu ggugaucggc aacuucggac ugagcuggaa ccagcaagug acccagaugg | 900 |
| cccugugggc caucauggcc gccccucuau ucaugucuaa cgaccugcgg cacauuuccc | 960 |
| cgcaggccaa ggcccugcug caggacaagg acgucaucgc gaucaaucag gacccacugg | 1020 |
| gcaagcaggg cuaucagcug cgucagggcg acaauuucga ggugugggag cggccgcuga | 1080 |
| gcggccuggc cugggccgug gccaugauca ccggcagga gaucggaggc ccagaaagcu | 1140 |
| acaccaucgc aguugccagc cugggcaagg gcguggccug caacccggcc ugcuucauca | 1200 |
| cccagcugcu accggugaag cguaagcugg gcuucuacga guggaccagc aggcucagga | 1260 |
| gccacaucaa cccgaccggc accgugcgc uccagcugga gaacaccaug cagaugucccc | 1320 |
| ugaaggaucu gcugugauaa uaguccauaa aguaggaaac acuacagcug gagccucggu | 1380 |
| ggccaugcuu cuugccccuu gggcucuccc ccagccccuc cuccccuucc ugcacccgua | 1440 |
| ccccccgcau auuacucac gguacgagug gucuuugaau aaagucgag ugggcggc | 1498 |

<210> SEQ ID NO 129
<211> LENGTH: 1498
<212> TYPE: RNA
<213> ORGANISM: Artificial Sequence
<220> FEATURE:
<223> OTHER INFORMATION: Synthetic: GLA-mRNA #11

<400> SEQUENCE: 129

| | |
|---|---|
| gggaaauaag agagaaaaga agaguaagaa gaaauauaag agccaccaug caacucagga | 60 |
| acccggagcu ccaccuaggc ugcgcccucg cccuccgcuu ccucgcacuc gugagcuggg | 120 |
| acaucccagg ugccagagcg cucgacaacg gacucgcccg gaccccuacc augggcuggc | 180 |
| uccacuggga gcgcuucaug ugcaaccugg acugccagga ggaaccggac agcugcaucu | 240 |
| ccgagaagcu guucauggag augggccgagc ugaugguggag cgagggcugg aaggacgccg | 300 |
| gcuacgagua ccgugcauc gacgacgcu ggauggcccc ucagggggac agcgagggca | 360 |
| ggcugcaggc cgaccgcag cgcuuccggc acggcauccg gcagcuggcu aacuacgugc | 420 |
| acagcaaggg ccugaagcuc ggcaucuacg ccgacguggg aaacaagacc ugcgcgggcu | 480 |
| ucccaggauc cuucggcuau uacgacaucg acgcccagac cuucgccgac uggggcgugg | 540 |
| accugcugaa guucgacgga ugcuacgugu acucccucga gaaccuggcu gacggcuaca | 600 |
| agcacaugag ccuggcccug aaccgcaccg gcaggagcau cguguauagc ugugaauggc | 660 |
| cgcuguacau guggccguuc cagaagccua acuacaccga gaucagacag uauugcaacc | 720 |
| auuggcggaa uucgccgac aucgaugacu ccuggaaguc cauaaagagc auccuggauu | 780 |
| ggaccagcuu caaucaagag aggauagugg acguggccgg uccgggcgga uggaacgacc | 840 |
| cggacaugcu ggugaucggc aacuucggcu ugagcuggaa ccagcaggug acucagaugg | 900 |
| cccugugggc caucauggcc gccccacugu ucauagcaa cgaccugaga cacaucagcc | 960 |
| cgcaggccaa ggcccugcug caggauaagg acgucaucgc caucaaccaa gauccgcugg | 1020 |

| | |
|---|---|
| gcaagcaggg cuaccagcug cgccagggcg acaacuucga ggugugggag cggccgcuga | 1080 |
| gcggccuggc cugggccguu gcaaugauca accgucagga gaucggcggc ccgagguccu | 1140 |
| acacgaucgc cguggccucu cucggcaagg gcguggccug uaacccggcc ugcuucauca | 1200 |
| cccagcugcu gccggugaag cgcaaguugg gcuucuacga guggaccagc cggcugcggu | 1260 |
| cccacaucaa uccaaccggc accgugcugc ugcagcugga aacaccaug caaaugagcc | 1320 |
| ucaaggauuu gcugugauaa uaguccauaa aguaggaaac acuacagcug gagccucggu | 1380 |
| ggccaugcuu cuugcccuu gggccucccc ccagccccuc ucccccuucc ugcacccgua | 1440 |
| cccccccgcau uauuacucac gguacgagug gucuuugaau aaagucugag ugggcggc | 1498 |

<210> SEQ ID NO 130
<211> LENGTH: 1498
<212> TYPE: RNA
<213> ORGANISM: Artificial Sequence
<220> FEATURE:
<223> OTHER INFORMATION: Synthetic: GLA-mRNA #12

<400> SEQUENCE: 130

| | |
|---|---|
| gggaauaag agagaaaaga agaguaagaa gaaauauaag agccaccaug cagcuccgga | 60 |
| accccgagcu ccaccucggc ugcgcccuug ccuugcgguu ccucgcgcuc gugagcuggg | 120 |
| acaucccagg cgccagggcc cucgacaacg gccucgcccg gaccccgacc augggcuggc | 180 |
| uccacuggga gcgguucaug ugcaaccugg acugccagga ggagcccgac agcugcauca | 240 |
| gcgagaagcu guucauggag augggccagc ugauggugag cgagggcugg aaggacgccg | 300 |
| gcuacgagua ccugugcauc gacgacugcu ggauggcccc gcagcgggac agcgaaggcc | 360 |
| ggcugcaggc cgacccgcaa agauucccac acggcauccg gcagcuggcc aacuacgugc | 420 |
| acagcaaggg ccugaagcug ggcaucuacg ccgacguggg caacaagacc ugcgccggcu | 480 |
| ucccgggcag cuucggcuac uacgacaucg acgcccagac cuucgccgac uggggcgugg | 540 |
| accugcugaa guucgacggc ugcuacugcg acagccugga gaaccuggcc gacggcuaca | 600 |
| agcacaugag ccucgcccug aaccggaccg gccggagcau cguguacagc ugcgaguggc | 660 |
| cccuguacau guggcccuuc cagaagccca acuacaccga aucagacag uacugcaacc | 720 |
| acuggcggaa cuucgcugac aucgaugaca gcuggaaguc aaucaagagc auacuggacu | 780 |
| ggaccagcuu caaccaggag cggaucgugg acguggccgg ccccggcggc uggaacgacc | 840 |
| ccgacaugcu ggugaucggc aacuucggcc ugagcuggaa ccagcaggug acccagaugg | 900 |
| cccugugggc caucauggcc gccccacucu caugagcaa cgaccugcgg cacaucagcc | 960 |
| cgcaggccaa ggcccugcug caggacaagg acgugaucgc caucaaucag gacccucugg | 1020 |
| gcaagcaggg cuaccagcug aggcagggcg acaacuucga ggugugggag aggccccuga | 1080 |
| gcggccuggc cugggccgug gccaugauca accggcagga gaucggcggc ccucggagcu | 1140 |
| acaccaucgc cguagccagc cugggugaagg gcguggccug caaccccgcc ugcuucauca | 1200 |
| cccagcugcu gcccgugaag cggaagcucg gauucuacga guggaccucc agacugcgga | 1260 |
| gccacaucaa ccccaccggc accgugcucc ugcagcuuga aacaccaug cagaugucac | 1320 |
| ugaaggaucu gcugugauaa uaguccauaa aguaggaaac acuacagcug gagccucggu | 1380 |
| ggccaugcuu cuugcccuu gggccucccc ccagccccuc ucccccuucc ugcacccgua | 1440 |
| cccccccgcau uauuacucac gguacgagug gucuuugaau aaagucugag ugggcggc | 1498 |

<210> SEQ ID NO 131

```
<211> LENGTH: 1498
<212> TYPE: RNA
<213> ORGANISM: Artificial Sequence
<220> FEATURE:
<223> OTHER INFORMATION: Synthetic: GLA-mRNA #13

<400> SEQUENCE: 131
```

| | | | | | |
|---|---|---|---|---|---|
| gggaauuaag | agagaaaaga | agaguaagaa | gaaauauaag | agccaccaug | cagcuccgga | 60 |
| accccgagcu | ccaccucggc | ugcgcccuug | cccuccgguu | ccucgcccuu | gugagcuggg | 120 |
| acauccccgg | cgcccgggcc | cuugacaacg | gccucgcccg | accccgacc | augggcuggc | 180 |
| uccacuggga | gcgguucaug | ugcaaccugg | acugccagga | ggagcccgac | agcugcauca | 240 |
| gcgagaagcu | guucauggag | auggccgagc | ugauggugag | cgagggcugg | aaggacgccg | 300 |
| gcuacgagua | ccugugcauc | gacgacugcu | ggauggcccc | gcagcgggac | agcgaggguc | 360 |
| ggcugcaggc | cgacccacag | cgcuucccuc | acggcauccg | gcagcuggcc | aacuacgugc | 420 |
| acagcaaggg | ccugaagcug | ggcaucuacg | ccgacguggg | caacaagacc | ugcgccggcu | 480 |
| ucccgggcag | cuucggcuac | uacgacaucg | acgcccagac | cuucgccgac | ggggcgugg | 540 |
| accugcugaa | guucgacggc | ugcuacugcg | acagccugga | gaaccuggcc | gacggcuaca | 600 |
| agcacaugag | ccugcgcug | aaccggaccg | gccggagcau | cguguacagc | ugcgagugg c | 660 |
| cccuguacau | guggcccuuc | cagaagccca | acuacaccga | gaucagacag | uacugcaacc | 720 |
| acuggcggaa | uuucgccgau | aucgaugaca | gcuggaaguc | caucaagucc | auccuggauu | 780 |
| ggaccagcuu | caaccaggag | cggaucgugg | acguggccgg | ccccggcggc | uggaacgacc | 840 |
| ccgacaugcu | ggugaucggc | aacuucggcc | ugagcuggaa | ccagcaggug | acccagaugg | 900 |
| cccuguggg | caucauggcc | gccccacucu | ucaugagcaa | cgaccugcgg | cacaucagcc | 960 |
| cgcaggccaa | ggcccugcug | caggacaagg | acgugaucgc | caucaaucag | gacccacugg | 1020 |
| gcaagcaggg | cuaccagcuc | cggcagggcg | acaacuucga | ggugugggag | aggccgcuga | 1080 |
| gcggccuugc | gugggccgug | gccaugauca | accggcagga | gaucggcggc | cgcggagcu | 1140 |
| acaccaucgc | cguggcaagc | cugggaaagg | gcguggccug | caaccccgcc | ugcuucauca | 1200 |
| cccagcugcu | gcccgugaag | cggaaguuag | gcuucuacga | guggaccucc | aggcugcgga | 1260 |
| gccacaucaa | ccccaccggc | accgugcugc | ugcaacugga | gaauaccaug | cagaugagcc | 1320 |
| ugaaggaucu | gcgugauaa | uaguccauaa | aguaggaaac | acuacagcug | gagcucgggu | 1380 |
| ggccaugcuu | cuugcccuu | gggccucccc | ccagccccuc | cuccccuucc | ugcacccgua | 1440 |
| ccccccgcau | uauuacucac | gguacgagug | gucuuugaau | aaagucugag | ugggcggc | 1498 |

```
<210> SEQ ID NO 132
<211> LENGTH: 1498
<212> TYPE: RNA
<213> ORGANISM: Artificial Sequence
<220> FEATURE:
<223> OTHER INFORMATION: Synthetic: GLA-mRNA #14

<400> SEQUENCE: 132
```

| | | | | | |
|---|---|---|---|---|---|
| gggaauuaag | agagaaaaga | agaguaagaa | gaaauauaag | agccaccaug | cagcuccgga | 60 |
| accccgagcu | ccaccucggc | ugcgcccucg | cccuccgguu | ccuagcccuc | gugagcuggg | 120 |
| acauaccggg | cgccagggcg | cucgacaacg | gccucgcccg | accccgacc | augggcuggc | 180 |
| uccacuggga | gcgguucaug | ugcaaccugg | acugccagga | ggagcccgac | agcugcauca | 240 |
| gcgagaagcu | guucauggag | auggccgagc | ugauggugag | cgagggcugg | aaggacgccg | 300 |
| gcuacgagua | ccugugcauc | gacgacugcu | ggauggcacc | ucagcgggac | uccgagggcc | 360 |

```
ggcugcaggc cgacccucag agauucccgc acggcauccg gcagcuggcc aacuacgugc    420
acagcaaggg ccugaagcug ggcaucuacg ccgacguggg caacaagacc ugcgccggcu    480
ucccgggcag cuucggcuac uacgacaucg acgcccagac cuucgccgac uggggcgugg    540
accugcugaa guucgacggc ugcuacgcg acagccugga gaaccuggcc gacggcuaca    600
agcacauguc ucucgccuug aaccggaccg gccggagcau cguguacagc ugcgagugc    660 cccuguacau guggcccuuc cagaagccca acuacaccga uccgccag uacugcaacc    720 acuggcggaa uucgccgau auugacgaua gcuggaaguc caucaagucc auccuggauu    780
ggaccagcuu caaccaggag cggaucgugg acguggccgg ccccggcggc uggaacgacc    840
ccgacaugcu ggugaucggc aacuucggcc ugagcuggaa ccagcaggug acccagaugg    900 cccuguggc caucauggcc gccccacucu caugagcaa cgaccugcgg cacaucagcc    960
cgcaggccaa ggcccugcug caggacaagg acgugaucgc cauuaaucag gacccgcugg    1020
gcaagcaggg cuaccagcuc aggcaggcg acaacuucga ggugugggag aggccucuga    1080
gcggucuggc cugggccgug gccaugauca accggcagga gaucggcgga ccgcggagcu    1140
acaccaucgc ggguggccagc cuggaaaggg gcguggccug caaccccgcc ugcuucauca    1200
cccagcugcu gcccgugaag agaaagcucg gcuucuacga guggacguca agacugcgga    1260
gccacaucaa ccccaccggc accgugcucc ugcagcugga gaauaccaug cagaugcccc    1320
ugaaggaccu ccugugauaa uaguccauaa aguaggaaac acuacagcug gagccucggu    1380
ggccaugcuu cuugcccuu gggcucuccc ccagccccuc cuccccuucc ugcacccgua    1440 cccccccgcau uauuacucac gguacgagug gucuuugaau aaagucugag ugggcggc    1498
```

<210> SEQ ID NO 133
<211> LENGTH: 1498
<212> TYPE: RNA
<213> ORGANISM: Artificial Sequence
<220> FEATURE:
<223> OTHER INFORMATION: Synthetic: GLA-mRNA #15

<400> SEQUENCE: 133

```
gggaaauaag agagaaaaga agaguaagaa gaaauauaag agccaccaug cagcuccgga     60
accccgagcu ucaccuaggc ugcgcccucg cccuccgguu ccuugcccua gugagcuggg    120
acaucccagg cgcccgcgcc cucgacaacg gccucgcccg gaccccuacc augggcuggc    180
uccacuggga gcgguucaug ugcaaccugg acugccagga ggagcccgac agcugcauca    240
gcgagaagcu guucauggag auggccgagc ugauggugga cgagggcugg aaggacgccg    300
gcuacgagua ccgugcauc gacgacugcu ggauggcgcc gcagcgggac ucugagggcc    360
ggcugcaggc cgacccgcag agguucccgc acggcauccg gcagcuggcc aacuacgugc    420
acagcaaggg ccugaagcug ggcaucuacg ccgacguggg caacaagacc ugcgccggcu    480
ucccuggcag cuucggcuac uacgacaucg acgcccagac cuucgccgac uggggcgugg    540
accugcugaa guucgacggc ugcuacgcg acagccugga gaaccuggcc gacggcuaca    600
agcacaugag cuuggcgcuc aaccggaccg gccggagcau cguguacagc ugcgagugc    660 cccuguacau guggcccuuc cagaagccca acuacaccga uccgccag uacugcaacc    720 acuggcggaa uucgccgau aucgaugauu ccuggaaguc caucaagucc auccucgacu    780
ggaccagcuu caaccaggag cggaucgugg acguggccgg ccccggcggc uggaacgacc    840
ccgacaugcu ggugaucggc aacuucggcc ugagcuggaa ccagcaggug acccagaugg    900
```

| | |
|---|---:|
| cccugugggc caucauggcc gcgccacucu ucaugagcaa cgaccugcgg cacaucagcc | 960 |
| cgcaggccaa ggcccugcug caggacaagg acgugaucgc cauuaaccaa gacccgcugg | 1020 |
| gcaagcaggg cuaccagcug cgccagggcg acaacuucga ggugugggag aggccucugu | 1080 |
| ccggacuggu uugggccgug gccaugauca accggcagga gaucggcgga ccacggagcu | 1140 |
| acaccaucgc cguggcgagc cuggguaagg gcguggccug caaccccgcc ugcuucauca | 1200 |
| cccagcugcu gcccgugaag agaaagcugg guuucuacga guggaccucg agacugcgga | 1260 |
| gccacaucaa ccccaccggc accgugcucc ugcagcucga gaacaccaug cagaugucec | 1320 |
| ucaaggaccu ccugugauaa uaguccauaa aguaggaaac acuacagcug gagccucggu | 1380 |
| ggccaugcuu cuugccccuu gggccucccc ccagcccuc cucccuucc ugcacccgua | 1440 |
| cccccccgcau uauuacucac gguacgagug gucuuugaau aaagucugag ugggcggc | 1498 |

<210> SEQ ID NO 134
<211> LENGTH: 1498
<212> TYPE: RNA
<213> ORGANISM: Artificial Sequence
<220> FEATURE:
<223> OTHER INFORMATION: Synthetic: GLA-mRNA #16

<400> SEQUENCE: 134

| | |
|---|---:|
| gggaauuaag agagaaaaga agaguaagaa gaaauauaag agccaccaug cagcuccgga | 60 |
| accccgagcu ccaccucggc ucgcccucg cccuccgguu ccucgcgcuc gugagcuggg | 120 |
| acaucccagg cgcccgggcu cucgacaacg gccuagcccg gaccccgacc augggcuggc | 180 |
| uccacuggga gcguucaug ugcaaccugg acugccagga ggagcccgac agcugcauca | 240 |
| gcgagaagcu guucauggag auggccgagc ugauggugag cgagggcugg aaggacgccg | 300 |
| gcuacgagua ccugugcauc gacgacugcu ggauggcccc acagcgggac agcgagggac | 360 |
| ggcugcaggc cgauccgcag cguuucccgc acggcauccg gcagcuggcc aacuacgugc | 420 |
| acagcaaggg ccugaagcug ggcaucuacg ccgacguggg caacaagacc ugcgccggcu | 480 |
| ucccaggcag cuucggcuac uacgacaucg acgcccagac cuucgccgac uggggcgugg | 540 |
| accugcugaa guucgacggc uguuacgcg acagccugga gaaccuggcc gacggcuaca | 600 |
| agcacauguc ccuggcacug aaccggaccg gccggagcau cguguacagc ugcgaguggc | 660 |
| cccuguacau guggcccuuc cagaagccca acuacaccga gaucagcaa uacugcaacc | 720 |
| acuggcggaa uuucgccgau auagacgaua gcuggaaguc caucaaguce auccuggauu | 780 |
| ggaccagcuu caaccaggag cggaucgugg acguggccgg ccccggcggc uggaacgacc | 840 |
| ccgacaugcu gguigaucggc aacuucggcc ugagcuggaa ccagcaggug acccagaugg | 900 |
| cccugugggc caucauggcc gcccucucu ucaugagcaa cgaccugcgg cacaucagcc | 960 |
| cgcaggccaa ggcccugcug caggacaagg acgugaucgc caucaaucaa gacccgcugg | 1020 |
| gcaagcaggg cuaccagcug agacagggcg acaacuucga ggugugggag aggccgcugu | 1080 |
| cgggacuggc cuggggccgug gccaugauca accggcagga gaucggcggc ccgcggagcu | 1140 |
| acaccaucgc gguggccucg cugggaaagg gcguggccug caaccccgcc ugcuucauca | 1200 |
| cccagcugcu gcccgugaag cguaagcugg gauucuacga guggaccucc agacugcgga | 1260 |
| gccacaucaa ccccaccggc accgugcuuc ugcagcugga gaauaccaug cagaugucec | 1320 |
| ucaaggaccu ccugugauaa uaguccauaa aguaggaaac acuacagcug gagccucggu | 1380 |
| ggccaugcuu cuugccccuu gggccucccc ccagccccuc cucccuucc ugcacccgua | 1440 |
| cccccccgcau uauuacucac gguacgagug gucuuugaau aaagucugag ugggcggc | 1498 |

<210> SEQ ID NO 135
<211> LENGTH: 1498
<212> TYPE: RNA
<213> ORGANISM: Artificial Sequence
<220> FEATURE:
<223> OTHER INFORMATION: Synthetic: GLA-mRNA #17

<400> SEQUENCE: 135

| | |
|---|---|
| gggaaauaag agagaaaaga agaguaagaa gaaauauaag agccaccaug cagcuccgga | 60 |
| accccgagcu ccaccuuggc ugcgcccuug ccuugcgguu cuuagcccuc gugagcuggg | 120 |
| acaucccagg cgcccgcgcc cucgacaacg gccucgcccg caccccuacc augggcuggc | 180 |
| uccacuggga gcgcuucaug ugcaaccucg acugccagga ggagcccgac uccugcaucu | 240 |
| ccgagaagcu guucauggag auggccgagc ucauggucuc cgagggcugg aaggacgccg | 300 |
| gcuacgagua ccucugcauc gacgacugcu ggauggcccc gcagcgcgac agcgagggca | 360 |
| ggcuccaggc cgacccacag agguucccac acggcauccg ccagcucgcc aacuacgucc | 420 |
| acuccaaggg ccucaagcuc ggcaucuacg ccgacgucgg caacaagacc ugcgccggcu | 480 |
| uccccggcuc cuucggcuac uacgacaucg acgcccagac cuucgccgac uggggcgucg | 540 |
| accuccucaa guucgacggc ugcuacugcg acucccucga gaaccucgcc gacggcuaca | 600 |
| agcacauguc ccucgcccuc aaccgcaccg gccgcuccau cgucuacucc ugcgagugge | 660 |
| cccucuacau guggcccuuc cagaagccca acuacaccga gaucaggcag uacugcaacc | 720 |
| acuggcgcaa uuucgccgau aucgaugaca gcuggaaguc caucaagagc auccuggacu | 780 |
| ggaccuccuu caaccaggag cgcaucgucg acgucgccgg ccccggcggc uggaacgacc | 840 |
| ccgacaugcu cgucaucggu aacuucggcc ugucuuggaa ccagcagguc acccagaugg | 900 |
| cccucugggc caucauggcc gccccacugu ucauguccaa cgaccccgc cacaucuccc | 960 |
| cucaggccaa ggcccuccuc caggacaagg acgucaucgc caucaaucag gacccgcucg | 1020 |
| gcaagcaggg cuaccagcuc cgccagggcg acaacuucga ggugugggag aggcccucu | 1080 |
| ccggacucgc cugggccguc gccaugauca ccgccagga gaucggcggc ccacgcuccu | 1140 |
| acaccaucgc cguggccucc cugggcaagg gcgucgccug caaccccgcc ugcuucauca | 1200 |
| cccagcuccu ccccgucaag aggaagcugg gcuucuacga guggacaagc cgccuccgcu | 1260 |
| cccacaucaa ccccaccggc accgugcgc ugcagcugga aacaccaug cagaugucccc | 1320 |
| ugaaggaccu gcucugauaa uaguccauaa aguaggaaac acuacagcug gagccucggu | 1380 |
| ggccaugcuu cuugcccuu gggcucuccc ccagccccuc cuccccuucc ugcacccgua | 1440 |
| ccccccgcau uauuacucac gguacgagug gucuuugaau aaagucugag ugggcggc | 1498 |

<210> SEQ ID NO 136
<211> LENGTH: 1498
<212> TYPE: RNA
<213> ORGANISM: Artificial Sequence
<220> FEATURE:
<223> OTHER INFORMATION: Synthetic: GLA-mRNA #18

<400> SEQUENCE: 136

| | |
|---|---|
| gggaaauaag agagaaaaga agaguaagaa gaaauauaag agccaccaug cagcuccgga | 60 |
| accccgagcu ccaccuuggc ugcgcccuug ccucccgguu ccucgcccuc gugagcuggg | 120 |
| acauaccggg cgccagggcc cucgacaacg gccucgcccg cacccccgacc augggcuggc | 180 |
| uccacuggga gcgcuucaug ugcaaccucg acugccagga ggagcccgac uccugcaucu | 240 |

| | |
|---|---|
| ccgagaagcu guucauggag auggccgagc ucauggoguc cgagggcugg aaggacgccg | 300 |
| gcuacgagua ccucugcauc gacgacugcu ggauggcccc gcagcgcgac agcgaggguc | 360 |
| gccuccaggc cgacccacag agauucccgc acggcauccg ccagcucgcc aacuacgucc | 420 |
| acuccaaggg ccucaagcuc ggcaucuacg ccgacgucgg caacaagacc ugcgccggcu | 480 |
| uccccggcuc cuucggcuac uacgacaucg acgcccagac cuucgccgac uggggcgucg | 540 |
| accuccucaa guucgacggc ugcuacgcgc acucccucga gaaccucgcc gacgcuaca | 600 |
| agcacaugag ccucgcucuc aaccgcaccg gccgcuccau cgucuacucc ugcgagugcc | 660 |
| cccucuacau guggcccuuc cagaagccca acuacaccga gauucgccag uacugcaacc | 720 |
| acuggcgcaa uuucgccgau aucgaugacu ccuggaaguc caucaagagc auccuggacu | 780 |
| ggaccuccuu caaccaggag cgcaucgucg acgucgccgg ccccggcggc uggaacgacc | 840 |
| ccgacaugcu cgucaucgga aacuucggcc ugagcuggaa ccagcagguc acccagaugg | 900 |
| cccucugggc caucauggcc gccccauugu caugccaa cgaccucgc cacaucuccc | 960 |
| cgcaggccaa ggccuccuc caggacaagg acgucaucgc caucaaucag gacccgcucg | 1020 |
| gcaagcaggg cuaccagcuc cgccagggcg acaacuucga ggugugggag cggccucucu | 1080 |
| ccggacuggc cugggccguc gccaugauca accgccagga gaucggcggc ccacgccccu | 1140 |
| acaccaucgc cguggccagc cugggcaagg gcgucgccug caaccccgcc ugcuucauca | 1200 |
| cccagcuccu ccccgucaag aggaagcugg gcuucuacga guggaccagc cgccuccgcu | 1260 |
| cccacaucaa ccccaccggc accgugcugc ugcagcugga gaacaccaug cagaugagcc | 1320 |
| ugaaggaccu gcucugauaa uaguccauaa aguaggaaac acuacagcug gagccucggu | 1380 |
| ggccaugcuu cuugccccuu gggccucccc ccagccccuc uccccuucc ugcacccgua | 1440 |
| ccccccgcau uauuacucac gguacgagug gucuuugaau aaagucugag ugggcggc | 1498 |

<210> SEQ ID NO 137
<211> LENGTH: 1498
<212> TYPE: RNA
<213> ORGANISM: Artificial Sequence
<220> FEATURE:
<223> OTHER INFORMATION: Synthetic: GLA-mRNA #19

<400> SEQUENCE: 137

| | |
|---|---|
| gggaaauaag agagaaaaga agaguaagaa gaaauauaag agccaccaug cagcuccgga | 60 |
| accccgagcu ccaccucggc ugcgcccucg cccuccgguu ccucgcccua gugagcuggg | 120 |
| acaucccggg cgccagggcc cucgacaacg gccucgcccg caccccaacc augggcuggc | 180 |
| uccacuggga gcgcuucaug ugcaaccucg acugccagga ggagcccgac uccugcaucu | 240 |
| ccgagaagcu guucauggag auggccgagc ucauggoguc cgagggcugg aaggacgccg | 300 |
| gcuacgagua ccucugcauc gacgacugcu ggauggcccc acagcgcgac agcgagggcc | 360 |
| gccuccaggc cgacccacag agguucccgc acggcauccg ccagcucgcc aacuacgucc | 420 |
| acuccaaggg ccucaagcuc ggcaucuacg ccgacgucgg caacaagacc ugcgccggcu | 480 |
| uccccggcuc cuucggcuac uacgacaucg acgcccagac cuucgccgac uggggcgucg | 540 |
| accuccucaa guucgacggc ugcuacgcgc acucccucga gaaccucgcc gacgcuaca | 600 |
| agcacaugag ccuggcgcuc aaccgcaccg gccgcuccau cgucuacucc ugcgagugcc | 660 |
| cccucuacau guggcccuuc cagaagccca acuacaccga gauccgacag uacugcaacc | 720 |
| acuggcgcaa uuucgccgau aucgaugauu ccuggaaguc caucaagagc auccucgauu | 780 |
| ggaccuccuu caaccaggag cgcaucgucg acgucgccgg ccccggcggc uggaacgacc | 840 |

```
ccgacaugcu cgucaucggu aacuucggcc ugagcuggaa ccagcagguc acccagaugg      900
cccucugggc caucauggcc gccccgcuuu ucauguccaa cgaccuccgc cacaucucgc      960
cgcaggccaa ggcccuccuc caggacaagg acgucaucgc caucaaucag gacccgcucg     1020
gcaagcaggg cuaccagcuc cgccaggcg acaacuucga ggugugggag cggcccucga      1080
gcggccuggc gugggccguc gccaugauca accgccagga gaucggcggu ccacgcuccu     1140
acaccaucgc cguggccagc cugggcaagg gcgucgccug caaccccgcc ugcuucauca     1200
cccagcuccu ccccgucaag aggaagcugg gauucuacga guggacuagc aggcugcgcu     1260
cccacaucaa ccccaccggc accgugcucc ugcagcugga gaauaccaug cagaugcccc     1320
ugaaggaccu gcucugauaa uaguccauaa aguaggaaac acuacagcug gagccucggu     1380
ggccaugcuu cuugcccccuu gggcucuccc ccagccccuc cuccccuucc ugcacccgua    1440
ccccccgcau uauuacucac gguacgagug gucuuugaau aaagucugag ugggcggc      1498
```

<210> SEQ ID NO 138
<211> LENGTH: 1498
<212> TYPE: RNA
<213> ORGANISM: Artificial Sequence
<220> FEATURE:
<223> OTHER INFORMATION: Synthetic: GLA-mRNA #20

<400> SEQUENCE: 138

```
gggaaauaag agagaaaaga agaguaagaa gaaauauaag agccaccaug cagcugcgga       60
accccgagcu gcaccugggc ugcgcccugg cccugcgguu ccuggcccug gugagcuggg      120
acauccccgg cgcccgggcg cuggacaacg ggcuggcgag gacgccgacg auggggguggc     180 ugcacuggga gagguucaug ugcaaccugg acugccagga ggagccggac agcugcauca     240
gcgagaagcu guucauggag augcgggagc ugauggugac cgaggggugg aaggacgcgg     300
gguacgagua ccugugcauc gacgacugcu ggaugcgcc gcagagggac agcgagggga     360
ggcugcaggc ggacccgcag agguucccgc acgggaucag gcagcuggcg aacuacgugc     420
acagcaaggg gcugaagcug gggaucuacg cggacgugggg gaacaagacg ugcgcggggu     480
ucccggggag cuucggguac uacgacaucg acgcgcagac guucgcggac uggggugugg     540
accugcugaa guucgacggg ugcuacugcg acagccugga gaaccuggcg acggguaca      600 agcacaugag ccuggcgcug aacaggacgg ggaggagcau cgugcuacagc ugcgagugc     660 cgcuguacau guggccguuc cagaagccga cuacacgga gaucaggcag uacugcaacc      720
acuggaggaa cuucgcggac aucgacgaca gcuggaagag caucaagagc auccuggacu     780
ggacgagcuu caaccaggag aggaucgugg acguggcggg gccgggaggg uggaacgacc     840
cggacaugcu ggugaucggg aacuucggcc ugagcuggaa ccagcaggug acgcagaugg     900
cgcugugggc gaucauggcg gcgccgcugu ucaugagcaa cgaccugagg cacaucagcc     960
cgcaggcgaa ggcgcugcug caggacaagg acgucaucgc gaucaaccag gacccgcugg     1020
ggaagcaggg guaccagcug aggcagggug acaacuucga ggugugggag aggccgcuga     1080 gcggcucgc gugggcggug gcgaugauca acaggcagga gaucggaggg ccgaggagcu      1140
acacgaucgc ggugcgagc cugggaaggg gcguggcgug caaccggcg ugcuucauca     1200 cgcagcugcu gccggugaag aggaagcugg gguucuacga guggacgagc aggcugagga     1260
gccacaucaa cccgacgggg acggugcugc ugcagcugga gaacacgaug cagaugagcc     1320
ugaaggaccu gcugugauaa uaguccauaa aguaggaaac acuacagcug gagccucggu     1380
```

| | |
|---|---|
| ggccaugcuu cuugccccuu gggccucccc ccagccccuc cuccccuucc ugcacccgua | 1440 |
| cccccccgcau uauuacucac gguacgagug gucuuugaau aaagucugag ugggcggc | 1498 |

<210> SEQ ID NO 139
<211> LENGTH: 1498
<212> TYPE: RNA
<213> ORGANISM: Artificial Sequence
<220> FEATURE:
<223> OTHER INFORMATION: Synthetic: GLA-mRNA #21

<400> SEQUENCE: 139

| | |
|---|---|
| gggaauaag agagaaaaga agaguaagaa gaaauauaag agccaccaug cagcugcgga | 60 |
| accccgagcu gcaccugggc ugcgcccugg cccugcgguu ccuggcccug gugagcuggg | 120 |
| acaucccgg cgcccgggcc cucgacaacg gccucgcccg cacgcccacc augggcuggc | 180 |
| uccacuggga gcgcuucaug ugcaaccucg acugccagga ggagcccgac uccugcaucu | 240 |
| ccgagaagcu cuucauggag auggccgagc ucauggucuc cgagggcugg aaggacgccg | 300 |
| gcuacgagua ccucugcauc gacgacugcu ggauggcgcc ccagcgcgac uccgagggcc | 360 |
| gccuccaggc cgacccucag cgcuucccgc acggcauccg ccagcucgcc aacuacgucc | 420 |
| acuccaaggg ccucaagcuc ggcaucuacg ccgacgucgg caacaagacc ugcgccggcu | 480 |
| uccccggcuc cuucggcuac uacgacaucg acgcccagac cuucgccgac uggggcgucg | 540 |
| accuccucaa guucgacggc ugcuacugcg acuccccucg aaccucgcc gacggcuaca | 600 |
| agcacaugu ccucgcccuc aaccgcaccg gccgcuccau cgucuacucc ugcgagugc | 660 |
| cccucuacau guggccuuc cagaagccca acuacaccga gauccgccag uacugcaacc | 720 |
| acugggcaa cuucgccgac aucgacgacu ccuggaaguc caucaagucc auccucgacu | 780 |
| ggaccuccuu caaccaggag cgcaucgucg acgucgccgg ccccggcggc uggaacgacc | 840 |
| ccgacaugcu cgucaucggc aacuucggcc ucuccuggaa ccagcaagguc acccagaugg | 900 |
| cccucugggc caucauggcc gcgcccucu ucauguccaa cgaccuccgc cacaucucgc | 960 |
| cccaggccaa ggcccuccuc caggacaagg acgucaucgc caucaaccag gacccgcucg | 1020 |
| gcaagcaggg cuaccagcuc cgccaggcg acaacuucga ggucugggag cgcccgcucu | 1080 |
| ccggccucgc cuggggccguc gccaugauca accgccagga gaucggcggc ccacgcuccu | 1140 |
| acaccaucgc cgucgccucc cucggcaagg gcgucgccug caaccccgcc ugcuucauca | 1200 |
| cccagcuccu ccccgucaag cgcaagcucg gcuucuacga guggaccucc cgccuccgcu | 1260 |
| cccacaucaa ccccaccggc accguccucc uccagcucga gaacaccaug cagaugcccc | 1320 |
| ucaaggaccu ccucugauaa uaguccauaa aguaggaaac acuacagcug gagccucggu | 1380 |
| ggccaugcuu cuugccccuu gggccucccc ccagccccuc cuccccuucc ugcacccgua | 1440 |
| cccccccgcau uauuacucac gguacgagug gucuuugaau aaagucugag ugggcggc | 1498 |

<210> SEQ ID NO 140
<211> LENGTH: 1498
<212> TYPE: RNA
<213> ORGANISM: Artificial Sequence
<220> FEATURE:
<223> OTHER INFORMATION: Synthetic: GLA-mRNA #22

<400> SEQUENCE: 140

| | |
|---|---|
| gggaauaag agagaaaaga agaguaagaa gaaauauaag agccaccaug cagcugagga | 60 |
| acccagaacu acaucugggc ugcgcgcuug cgcuucgcuu ccuggcccuc guuuccuggg | 120 |
| acaucccugg ggcuagagca cuggacaaug gauuggcaag gacgccuacc augggcuggc | 180 |

```
ugcacuggga gcgcuucaug ugcaaccuug acugccagga agagccagau uccugcauca    240
gugagaagcu cuucauggag auggcagagc ucauggucuc agaaggcugg aaggaugcag    300
guuaugagua ccucugcauu gaugacuguu ggauggcucc ccaaagagau ucagaaggca    360
gacuucaggc agacccucag cgcuuuccuc augggauucg ccagcuagcu aauuauguuc    420
acagcaaagg acugaagcua gggauuuaug cagauguugg aaauaagacc ugcgcaggcu    480
ucccugggag uuuuggauac uacgacauug augcccagac cuuugcugac uggggaguag    540
aucugcuaaa guugauggu uguuacugug acaguuugga gaauuuggca gaugguuaua    600
agcacauguc cuuggcccug aauaggacgu gcagaagcau uguguacucc ugugaguggc    660
cucuuuauau uggcccuuu cagaagccca auuauacaga aauccgacag uacugcaauc    720
acuggcgaaa uuuugcugac auugaugauu ccuggaagau auaaagagu aucuuggacu    780 ggacaucuuu uaaccaggag agaauuguug auguugcugg accaggcggu uggaaugacc    840
cagauauguu agugauuggc aacuuuggcc ucagcuggaa ucagcaagua acucagaugg    900
cccucugggc uaucauggcu gcuccuuuau ucaugucuaa ugaccuccga cacaucagcc    960
cucaagccaa agcucuccuu caggauaagg acguaauugc caucaaucag acccccuugg   1020
gcaagcaagg guaccagcuu agacagggag acaacuuuga agugggaa cgaccucucu    1080 caggcuuagc cugggcugua gcuaugauaa accggcagga gauuguugga ccucgcucuu   1140
auaccaucgc aguugcuucc cuggguaaag gaguggccug uaauccugcc ugcuucauca   1200
cacagcuccu cccugugaag aggaagcuag gguucuauga auggacuuca agguuaagaa   1260
gucacauaaa ucccacaggc acguuuugc uucagcuaga gaauacaaug cagaugucau   1320
uaaaggacuu acuuugauaa uagccauaa aguaggaaac acuacagcug gagccucggu   1380
ggccaugcuu cuugcccccuu gggccucccc ccagccccuc cuccccuucc ugcacccgua   1440 cccccccgcau uauuacucac gguacgagug gucuuugaau aaagucugag ugggcggc    1498
```

<210> SEQ ID NO 141
<211> LENGTH: 1287
<212> TYPE: RNA
<213> ORGANISM: Artificial Sequence
<220> FEATURE:
<223> OTHER INFORMATION: Synthetic: GLA-CO28

<400> SEQUENCE: 141

```
augcagcuca ggaacccgga gcuccaccuc ggcugcgccc ucgcccucag guuccucgcu     60
cuugugagcu gggacauccc gggcgccagg gcccucgaca acggccucgc cagaaccccg    120
accaugggcu ggcuccacug ggagagguuc auguguaauc uggacugcca ggaggagccg    180
gauagcugca ucagcgagaa gcuguucaug gagauggccg agcugauggu guccgagggc    240
uggaaggacg ccggcuauga guaccuuugc aucgaugacu gcuggauggc cccgcagcgg    300
gacagcgagg gcaggcugca agcugacccu cagcguuucc cgcacggcau ccggcagcug    360
gccaacuacg ugcacagcaa gggccugaag cugggcaucu acgcggacgu cggcaacaag    420
accugcgccg gcuucccggg aagcuucggc uacuacgaca ucgacgccca gaccuucgcc    480 gacugggcg uggaccugcu gaaguucgac ggcugcuacu gugacagccu ggagaaccug    540
gccgacggcu acaagcacau gucccggcu cugaauagaa ccggcaggag cauaguguac    600
agcugcgagu ggccacugua caugguggcg uuccagaagc cgaacuacac cgaaaucaga    660
caauacugca accacuggcg gaauuucgcc gauaucgacg acuccuggaa guccaucaag    720
```

| | |
|---|---|
| uccauccugg acuggaccuc cuucaaccag agagaaucg uggacgugge cggcccuggu | 780 |
| ggauggaacg auccagacau gcugguuauc ggcaauuucg gccugagcug aaccagcag | 840 |
| gugacgcaga uggcccugug gccaucaug ccgccccac uguucauguc caacgaccuc | 900 |
| cgccacauca gcccgcaggc caaggcccuc cuccaagaca aggacgugau cgccaucaac | 960 |
| caagacccgc ucggcaagca gggcuaccag cugcgccagg cgacaauuu cgaggucugg | 1020 |
| gagcgcccgc ugucuggucu ggcguggcc guggccauga ucaauagaca ggagaucggc | 1080 |
| ggcccgcgga gcuacaccau cgccguagcc agccugggca agggcguggc cugcaacccg | 1140 |
| gcuuguuuca ucacccagcu gcucccgguu aagagaaagc ugggcuucua cgaguggacc | 1200 |
| agccgguugc gcagccauau caacccgacu ggcaccgugc ugcugcagcu ggagaacaca | 1260 |
| augcagaugu cccugaagga ccugcuc | 1287 |

```
<210> SEQ ID NO 142
<211> LENGTH: 1287
<212> TYPE: RNA
<213> ORGANISM: Artificial Sequence
<220> FEATURE:
<223> OTHER INFORMATION: Synthetic: GLA-CO29

<400> SEQUENCE: 142
```

| | |
|---|---|
| augcagcucc gcaauccgga gcuccaccuc ggcugcgccc ucgcccucag guuccucgcc | 60 |
| cuugugagcu gggauauccc gggcgccagg gcccucgaca acggcuuagc cagaaccoca | 120 |
| acgauggcu ggcuccacug ggagagguuc augugcaacc uggacugcca ggaggaaccg | 180 |
| gacagcugca ucuccgagaa gcuguucaug gagauggccg agcucauggu gagcgagggc | 240 |
| uggaaggacg ccggcuacga guaucucugc aucgacgacu gcuggauggc cccacagagg | 300 |
| gacuccgagg caggcugca ggccgacccg cagagauucc cucacggcau ccggcaacug | 360 |
| gccaacuacg ugcacagcaa gggccugaag cugggaaucu acgccgacgu gggcaacaag | 420 |
| accugugcug gcuucccggg cagcuucggc uacauagaca ucgaugccca gaccuucgcc | 480 |
| gacuggggcg ucgaccugcu caaguucgac ggcuguuacu gcgacagccu ggagaaccug | 540 |
| gcagacggcu auaagcacau gagccuggca cucaacagga ccggcaagguc aauaguguac | 600 |
| agcugcgagu ggccgcugua caugugggcca uccagaaagc cgaauuacac cgagauaagg | 660 |
| caguauugca accacuggcg aaacuucgcg gauaucgaug acagcuggaa gucgauaaag | 720 |
| agcauccugg acuggaccag cuucaaccag gagaggaucg uggacgucgc cggcccgggc | 780 |
| ggcuggaacg acccggacau gcuggugauc ggaaacuucg gccucagcug gaaccaacag | 840 |
| gugacccaga uggcccugug gccaucaug gcggcaccuc guucaugag caaugaccug | 900 |
| cggcauauca gcccgcaggc caaggcccug cuccaggaca aggacgucau agccaucaau | 960 |
| caggacccgc uggcaagca gggcuaccaa cugcggcagg gagacaacuu cgaggugugg | 1020 |
| gagcggccgc ugagcggccu ggcaugggcc guggccauga ucaauagaca ggagaucggc | 1080 |
| ggcccgcgga gcuacaccau cgccguggcg agucuuggca agggugggc cugcaauccg | 1140 |
| gccugcuuca ucacccagcu gcugccaguc aagcgcaagc ucggauucua cgaguggacc | 1200 |
| agccgucugc gcagccacau caauccuacc ggcacggugc uccugcagcu ggagaacacc | 1260 |
| augcaaaugu cucucaagga ccugcug | 1287 |

```
<210> SEQ ID NO 143
<211> LENGTH: 1287
<212> TYPE: RNA
<213> ORGANISM: Artificial Sequence
```

<220> FEATURE:
<223> OTHER INFORMATION: Synthetic: GLA-CO30

<400> SEQUENCE: 143

```
augcagcucc ggaacccaga acuccaccuc ggcugcgccc ucgcccuccg guuccuugcc      60
cucguguccu gggacauucc aggcgcccgg gcccucgaca acggcucugc ccggaccccu     120
accaugggcu ggcuccauug ggagagguuc augugcaacc uggacugcca agaggagccg     180
gacuccugca ucuccgagaa gcuguucaug gagauggccg agcucauggu gagcgagggc     240
uggaaggacg ccggcuacga auaucugugc aucgacgauu gcuggauggc cccucaaaga     300
gacagcgagg gcagacugca ggccgacccg cagcgcuucc cucauggcau ccggcaacuc     360
gcgaauuaug ugcacagcaa gggccugaag cugggcaucu acgccgacgu cgguaacaag     420
accugcgccg gcuucccagg cagcuucggc uacuacgaca ucgacgccca gaccuucgcc     480
gacuggggcg uagaccuccu gaaguucgac gguugcuacu gcgacucccu ggagaaccua     540
gccgacggcu acaagcacau gucccucgcc cugaacagaa ccggccgguc caucgucuau     600
uccugcgagu ggccgcugua cauguggccg uuccagaagc cuaacuacac agagauccgc     660
caguacugca accacuggcg gaauuucgcc gauaucgacg acaguuggaa guccaucaag     720
agcauacugg auuggaccuc cuucaaccag gagaggaucg uggacgugcc cggcccgggc     780
gguuggaacg acccagacau gcuggugauc ggaaacuucg gccugagcug gaaccagcag     840
gugacccaga uggcccucug gccaucaug gccgccccuc uguucauguc caaugaccuc     900
aggcauaucu ccccgcaggc caaggcucuc cuccaggaca aggacgugau cgccaucaau     960
caggauccgc ugggaaagca gggauaccag cugaggcagg gcgacaacuu cgaggugugg    1020
gagcgcccac ugagcggccu ggcuugggcu guggccauga ucaaccggca agagaucggc    1080
ggcccgcgga gcuacaccau ugccguggcu agccugggca agggcguggc cugcaacccg    1140
gccugcuuca ucacccagcu ucugccggua aagcguaagc ugggcuucua cgaguggacc    1200
agcagacuga ggagccacau caacccgacc ggcaccgugc ugcuccagcu ggagaacacc    1260
augcagauga gccugaagga ucugcuc                                        1287
```

<210> SEQ ID NO 144
<211> LENGTH: 1287
<212> TYPE: RNA
<213> ORGANISM: Artificial Sequence
<220> FEATURE:
<223> OTHER INFORMATION: Synthetic: GLA-CO31

<400> SEQUENCE: 144

```
augcaacucc gcaauccgga gcuccaccuc ggcugugcgc ucgcccuuag auuccucgcc      60
cucgugagcu gggacauccc aggcgcccgg gcccucgaca acggcucuagc ccgcacuccu    120
acaaugggcu gguugcacug ggaacgcuuc augugcuaacc uggacugcca ggaggaaccg    180
gacagcugua ucuccgagaa gcuguucaug gagauggccg agcugauggu gagcgagggc    240
uggaaggaug ccggcuacga guaccugugu aucgaugacu gcuggauggc cccgcagcga    300
gauagcgagg gacgcugcaa ggccgacccg cagagauucc cgcacggcau ccgcagcug    360
gccaauuaug uucacagcaa gggccugaag cugggcaucu acgccgacgu gggcaacaag    420
accugcgccg gauucccggg cagcuucggc uacuacgaua uagaugccca aacauucgcc    480
gacuggggcg ucgaccugcu uaaguucgac ggcugcuacu gcgauagccu ggagaaucug    540
gccgacggcu acaagcacau gagccuggcc cucaacagga ccggaagguc caucgcguac    600
```

| | |
|---|---:|
| agcugcgaau ggccucugua cauguggccu uuccagaagc cgaacuacac cgagauccgg | 660 |
| caguacugua aucacuggag gaacuucgcc gacaucgacg auucuuggaa gucuaucaag | 720 |
| uccauccugg acuggaccuc cuucaaucag gagagaauug ucgacguggc cggcccgggu | 780 |
| ggcuggaacg acccggacau gcuggugauc ggcaacuucg ccugagcug gaaccagcag | 840 |
| gugacccaga uggcccugug ggccauaaug gccgcccac ucuucauguc caacgaccug | 900 |
| cggcacauca gcccacaggc caaggcacug uccaggaca aggacgugau cgccaucaac | 960 |
| caagacccuc ugggcaagca ggguuaccag cuuagacagg gcgacaacuu cgaggugugg | 1020 |
| gagcgcccgc uuuccggccu cgccuggggcc guggccauga ucaacaggca ggaaaucgga | 1080 |
| ggcccgcgcu ccuauacuau cgccguggcg agccugggca agggcguggc cugcaacccg | 1140 |
| gccugcuuca ucacccagcu gcugccaguc aagagaaagc ugggcuucua cgaguggacc | 1200 |
| uccagacuga gaucccacau caauccuacc ggcaccgugc ugcugcagcu ggagaacacg | 1260 |
| augcagaugu cgcugaagga ccuccug | 1287 |

<210> SEQ ID NO 145
<211> LENGTH: 1287
<212> TYPE: RNA
<213> ORGANISM: Artificial Sequence
<220> FEATURE:
<223> OTHER INFORMATION: Synthetic: GLA-CO32

<400> SEQUENCE: 145

| | |
|---|---:|
| augcagcucc ggaacccaga gcuucaccuu ggcugcgccc ucgcccucag guuccuagcc | 60 |
| cucguguccu gggacauccc aggcgcccgg gcccuugaca acggcucgc cagaaccccg | 120 |
| accaugggcu ggcuccacug ggagcgcuuc augugcaacc uggacuguca ggaggagccg | 180 |
| gacucaugua ucagcgagaa gcuguucaug gaaauggccg aauuaauggu guccgagggc | 240 |
| uggaaggacg ccggcuauga guaccugugc aucgacgauu gcuggauggc cccgcagaga | 300 |
| gacagcgagg gcagacugca ggccgaccca cagaggguucc cacacggcau caggcagcug | 360 |
| gccaacuacg ugcacuccaa gggccugaag cugggcaucu acgccgaugu gggcaauaag | 420 |
| accugcgccg gcuucccggg cagcuucggc uauuacgaua ucgacgccca gacguucgcc | 480 |
| gacuggggcg uggaucugcu gaaguucgac ggcuguuacu gugacagccu ggagaaucug | 540 |
| gccgauggcu acaagcauau gagucucgcc cucaacagga ccggccgcuc aaucguguac | 600 |
| agcugcgagu ggccgcugua cauguggccg uuccagaagc caaacuacac cgagaucagg | 660 |
| caauacugca accauuggcg caacuucgcc gauauagaug acagcuggaa guccaucaag | 720 |
| uccauccugg acuggaccag cuucaaucag gagcguauag uggacguggc cggcccgggc | 780 |
| gguuggaacg acccagacau gcuggugauc ggcaacuucg ccugagcug gaaccagcag | 840 |
| gugacccaga uggcccugug ggccaucaug gccgcccac uguucauguc caacgaccug | 900 |
| cggcacauca gcccgcaggc caaggcgcug cugcaggaua aggacgugau agcuaucaac | 960 |
| caagacccac ugggcaagca ggguauacag cugaggcaag gcgacaacuu cgaggugugg | 1020 |
| gagaggccgc ucagcggccu ggccuggggcc guggccauga ucaacaggca agagaucgga | 1080 |
| ggcccgagaa gcuacaccau cgcggucgcc agccugggca aggguguggc gugcaaccca | 1140 |
| gcaugcuuca ucacccagcu gcugccggug aagaggaagc ugggauucua cgaguggacu | 1200 |
| agcagacuga ggagccacau caacccgacc ggcaccgucc ugcugcagcu cgagaacacc | 1260 |
| augcagaugu cccugaagga ucugcug | 1287 |

<210> SEQ ID NO 146
<211> LENGTH: 1287
<212> TYPE: RNA
<213> ORGANISM: Artificial Sequence
<220> FEATURE:
<223> OTHER INFORMATION: Synthetic: GLA-CO33

<400> SEQUENCE: 146

| | | | | | |
|---|---|---|---|---|---|
| augcagcucc | ggaacccaga | guugcaucuc | gguugcgccu | uagcucuccg | guuccucgcc | 60 |
| cucgugagcu | gggacauccc | aggcgccagg | gcucucgaca | acggacuugc | caggaccccg | 120 |
| acaaugggcu | ggcuccacug | ggagcgguuc | augugcaacc | uggauugucca | ggaggagcca | 180 |
| gacuccugca | ucuccgagaa | gcuguucaug | gagauggccg | aacucauggu | gagcgaggga | 240 |
| uggaaggacg | ccggcuauga | guaucugugc | aucgacgauu | gcuggauggc | cccgcagagg | 300 |
| gauagcgagg | gccgccucca | ggccgacccg | cagcgauucc | cgcacggcau | ccgacagcug | 360 |
| gccaacuacg | ugcacuccaa | gggccucaag | cugggcauau | acgccgacgu | cggaaacaag | 420 |
| acgugcgccg | gcuucccggg | cagcuucggc | uacuaugaca | ucgacgccca | gacguucgcg | 480 |
| gauuggggcg | uggaccugcu | gaaguucgac | ggcugcuacu | gcgauagccu | cgagaaucug | 540 |
| gccgacggau | acaagcauau | gagccucgcc | cugaacagga | ccggccguuc | caucguguac | 600 |
| ucaugcgagu | ggccgcucua | cauguggcca | uuccagaagc | cuaauuacac | cgagauccgg | 660 |
| caguacugca | ccacuggcg | aaauuucgca | gauauagacg | auagcuggaa | guccaucaag | 720 |
| ucuauccugg | acuggacuuc | cuucaaccag | gaaaggaucg | ucgacguggc | gggcccgggc | 780 |
| ggcuggaacg | acccggacau | gcuggugauc | ggcaacuucg | gccugagcug | gaaccagcag | 840 |
| gugacccaga | uggcccugug | ggccaucaug | gccgccccuc | uguucauguc | caaugaccug | 900 |
| cggcacauca | gcccgcaggc | caaggcccug | cugcaagaca | aggaugugau | ugccaucaau | 960 |
| caggacccuc | ucggcaagca | gggcuaccag | cuccgacagg | gagauaacuu | cgaagugugg | 1020 |
| gagcggccgc | ugagcggccu | ggccuggggc | gucgccauga | ucaaccggca | ggagaucggc | 1080 |
| ggcccacgcu | ccuacaccau | cgccguggcc | ucccugggca | agggcguggc | cugcaauccg | 1140 |
| gcaugcuuca | ucacccagcu | gcugccaguc | aagaggaagc | ugggcuucua | ugaauggacc | 1200 |
| agcagacugc | gaucccacau | caacccaacc | ggcaccgugc | ugcugcagcu | ggagaacacu | 1260 |
| augcagauga | gccugaagga | ccugcug | | | | 1287 |

<210> SEQ ID NO 147
<211> LENGTH: 1287
<212> TYPE: RNA
<213> ORGANISM: Artificial Sequence
<220> FEATURE:
<223> OTHER INFORMATION: Synthetic: GLA-CO34

<400> SEQUENCE: 147

| | | | | | |
|---|---|---|---|---|---|
| augcagcuca | gaaacccaga | gcuccauuug | ggcugcgccc | ucgcccuccg | guuccucgcc | 60 |
| cucgugagcu | gggacauccc | gggcgccaga | gcccucgaca | acggacucgc | ccgaacacca | 120 |
| accaugggcu | ggcuccauug | ggagagguuc | augugcaacc | uggacugcca | ggaggagccg | 180 |
| gauagcugca | ucagcgagaa | gcuguucaug | gagauggccg | agcugauggu | guccgagggc | 240 |
| uggaaggacg | ccggcuauga | guaucugugc | aucgacgacu | gcuggauggc | cccacagcgg | 300 |
| gacuccgagg | gaaggcugca | ggccgacccg | cagagguucc | cucacggcau | ccgucagcuc | 360 |
| gccaacuacg | ugcacuccaa | gggccugaag | cugggcaucu | acgccgacgu | gggcaacaag | 420 |
| accugcgccg | gcuucccagg | cagcuucgga | uacuaugaca | ucgacgccca | gaccuucgcc | 480 |

| | |
|---|---|
| gacuggggcg uggaucugcu gaaguucgac ggcugcuacu cgacagcuu ggagaaucug | 540 |
| gccgacgguu acaagcacau gagccuagcc cugaaccgga ccggaaggag caucguguac | 600 |
| agcugcgagu ggccgcugua caugugccca uuccagaagc cgaacuacac cgagauuagg | 660 |
| caguacugca accacuggag aaacuucgca gauaucgacg acagcuggaa guccaucaag | 720 |
| agcauccugg auuggaccag cuucaaccag gagcggaucg uggacguggc cgguccggga | 780 |
| ggcuggaacg accggacau gcuggugauc ggcaacuucg acugagcug gaaccagcaa | 840 |
| gugacccaga uggcccugug gccaucaug gccgccccuc uauucaguc uaacgaccug | 900 |
| cggcacauuu ccccgcaggc caaggcccug cugcaggaca aggacgucau cgcgaucaau | 960 |
| caggacccac ugggcaagca gggcuaucag cugcgucagg gcgacaauuu cgaggugugg | 1020 |
| gagcggccgc ugagcggccu ggccugggcc guggccauga ucaaccggca ggagaucgga | 1080 |
| ggcccgagaa gcuacaccau cgcaguugcc agccugggca agggcguggc cugcaacccg | 1140 |
| gccugcuuca ucacccagcu gcuaccggug aagcguaagc ugggcuucua cgaguggacc | 1200 |
| agcaggcuca ggagccacau caacccgacc ggcaccgugc ugcuccagcu ggagaacacc | 1260 |
| augcagaugu cccugaagga ucugcug | 1287 |

<210> SEQ ID NO 148
<211> LENGTH: 1287
<212> TYPE: RNA
<213> ORGANISM: Artificial Sequence
<220> FEATURE:
<223> OTHER INFORMATION: Synthetic: GLA-CO35

<400> SEQUENCE: 148

| | |
|---|---|
| augcaacuca ggaacccgga gcuccaccua ggcugcgccc ucgcccuccg cuuccucgca | 60 |
| cucgugagcu gggacauccc aggugccaga gcgcucgaca acggacucgc ccggaccccu | 120 |
| accaugggcu ggcuccacug ggagcgcuuc augugcaacc uggacugcca ggaggaaccg | 180 |
| gacagcugca ucuccgagaa gcuguucaug gagaugggccg agcugauggu gagcgagggc | 240 |
| uggaaggacg ccggcuacga guaccugugc aucgacgacu gcuggauggc cccucagagg | 300 |
| gacagcgagg gcaggcugca ggccgacccg cagcgcuucc cgcacggcau ccggcagcug | 360 |
| gcuaacuacg ugcacagcaa gggccugaag cucggcaucu acgccgacgu gggaaacaag | 420 |
| accugcgcgg gcuucccagg auccuucggc uauuacgaca ucgacgccca gaccuucgcc | 480 |
| gacuggggcg uggaccugcu gaaguucgac ggaugcuacu gugacucccu cgagaaccug | 540 |
| gcugacggcu acaagcacau gagccuggcc cugaaccgca ccggcaggag caucguguau | 600 |
| agcugugaau ggccgcugua caugggccg uccagaagc cuaacuacac cgagaucaga | 660 |
| caguauugca accauggcg gaauuucgcc gacaucgaug acuccuggaa guccauaaag | 720 |
| agcauccugg auuggaccag cuucaaucaa gagaggauag uggacguggc cgguccgggc | 780 |
| ggauggaacg accggacau gcuggugauc ggcaacuucg gucugagcug gaaccagcag | 840 |
| gugacucaga uggcccugug gccaucaug gccgcuccac guucaugag caacgaccug | 900 |
| agacacauca gcccgcaggc caaggcccug cugcaggaua aggacgucau cgccaucaac | 960 |
| caagauccgc ugggcaagca gggcuaccag cugcgccagg gcgacaacuu cgaggugugg | 1020 |
| gagcggccgc ugagcggccu ggccugggcc guugcaauga ucaaccguca ggagaucggc | 1080 |
| ggcccgaggu ccuacacgau cgccguggcc ucucucggca agggcguggc cuguaacccg | 1140 |
| gccugcuuca ucacccagcu gcugccggug aagcgcaagu gggcuucua cgaguggacc | 1200 |
| agccggcugc gguccacau caauccaacc ggcaccgugc ugcugcagcu ggagaacacc | 1260 |

-continued augcaaauga gccucaagga uuugcug 1287

<210> SEQ ID NO 149
<211> LENGTH: 1287
<212> TYPE: RNA
<213> ORGANISM: Artificial Sequence
<220> FEATURE:
<223> OTHER INFORMATION: Synthetic: GLA-CO36

<400> SEQUENCE: 149

| | | | | | |
|---|---|---|---|---|---|
| augcagcucc | ggaaccccga | gcuccaccuc | ggcugcgccc | uugccuugcg | guuccucgcg | 60 |
| cucgugagcu | gggacauccc | aggcgccagg | gcccucgaca | acggcccugc | ccggaccccg | 120 |
| accaugggcu | ggcuccacug | ggagcgguuc | augugcaacc | uggacugcca | ggaggagccc | 180 |
| gacagcugca | ucagcgagaa | gcuguucaug | gagauggccg | agcugauggu | gagcgagggc | 240 |
| uggaaggacg | ccggcuacga | guaccugugc | aucgacgacu | gcuggauggc | cccgcagcgg | 300 |
| gacagcgaag | gccggcugca | ggccgacccg | caaagauucc | cacacggcau | ccggcagcug | 360 |
| gccaacuacg | ugcacagcaa | gggccugaag | cugggcaucu | acgccgacgu | gggcaacaag | 420 |
| accugcgccg | gcuucccggg | cagcuucggc | uacuacgaca | ucgacgccca | gaccuucgcc | 480 |
| gacugggggcg | uggaccugcu | gaaguucgac | ggcugcuacu | gcgacagccu | ggagaaccug | 540 |
| gccgacggcu | acaagcacau | gagccucgcc | cugaaccgga | ccggccggag | caucguguac | 600 |
| agcugcgagu | ggcccccugua | caugggcccc | uuccagaagc | ccaacuacac | cgagaucaga | 660 |
| caguacugca | ccacuggcg | gaacuucgcu | gacaucgaug | acagcuggaa | gucaaucaag | 720 |
| agcauacugg | acuggaccag | cuucaaccag | gagcggaucg | uggacguggc | cggccccggc | 780 |
| ggcuggaacg | accccgacau | gcuggugauc | ggcaacuucg | gccugagcug | gaaccagcag | 840 |
| gugacccaga | uggcccugug | ggccaucaug | gccgccccac | ucuucaugag | caacgaccug | 900 |
| cggcacauca | gcccgcaggc | caaggcccug | cugcaggaca | aggacgugau | cgccaucaau | 960 |
| caggacccuc | ugggcaagca | gggcuaccag | cugaggcagg | gcgacaacuu | cgaggugugg | 1020 |
| gagaggcccc | ugagcggccu | ggccugggcc | guggccauga | ucaaccggca | ggagaucggc | 1080 |
| ggccccucgga | gcuacaccau | cgccguagcc | agccuggggua | agggcguggc | cugcaaccc | 1140 |
| gccugcuuca | ucacccagcu | gcugcccgug | aagcggaagc | ucggauucua | cgaguggacc | 1200 |
| uccagacugc | ggagccacau | caaccccacc | ggcaccgugc | uccugcagcu | ugagaacacc | 1260 |
| augcagaugu | cacugaagga | ucugcug | | | | 1287 |

<210> SEQ ID NO 150
<211> LENGTH: 1287
<212> TYPE: RNA
<213> ORGANISM: Artificial Sequence
<220> FEATURE:
<223> OTHER INFORMATION: Synthetic: GLA-CO37

<400> SEQUENCE: 150

| | | | | | |
|---|---|---|---|---|---|
| augcagcucc | ggaaccccga | gcuccaccuc | ggcugcgccc | uugcccuccg | guuccucgcc | 60 |
| cuugugagcu | gggacauccc | cggcgcccgg | gcccuugaca | acggcccugc | ccggaccccg | 120 |
| accaugggcu | ggcuccacug | ggagcgguuc | augugcaacc | uggacugcca | ggaggagccc | 180 |
| gacagcugca | ucagcgagaa | gcuguucaug | gagauggccg | agcugauggu | gagcgagggc | 240 |
| uggaaggacg | ccggcuacga | guaccugugc | aucgacgacu | gcuggauggc | cccgcagcgg | 300 |
| gacagcgagg | gucggcugca | ggccgacccca | cagcgcuucc | cucacggcau | ccggcagcug | 360 |

| | |
|---|---|
| gccaacuacg ugcacagcaa gggccugaag cugggcaucu acgccgacgu gggcaacaag | 420 |
| accugcgccg gcuucccggg cagcuucggc uacuacgaca ucgacgccca gaccuucgcc | 480 |
| gacuggggcg uggaccugcu gaaguucgac ggcugcuacu gcgacagccu ggagaaccug | 540 |
| gccgacggcu acaagcacau gagccucgcg cugaaccgga ccggccggag caucguguac | 600 |
| agcugcgagu ggcccugua cauguggccc uuccagaagc ccaacuacac cgagaucaga | 660 |
| caguacugca accacggcg gaauuucgcc gauaucgaug acagcuggaa guccaucaag | 720 |
| uccauccugg auuggaccag cuucaaccag gagcggaucg uggacguggc cggccccggc | 780 |
| ggcuggaacg accccgacau gcuggugauc ggcaacuucg gccugagcug gaaccagcag | 840 |
| gugacccaga uggcccugug ggccaucaug gccgccccac ucuucaugag caacgaccug | 900 |
| cggcacauca gcccgcaggc caaggcccug cugcaggaca aggacgugau cgccaucaau | 960 |
| caggacccac ugggcaagca gggcuaccag cuccggcagg gcgacaacuu cgaggugugg | 1020 |
| gagaggccgc ugagcggccu ugcgugggcc guggccauga ucaaccggca ggagaucggc | 1080 |
| ggcccgcgga gcuacaccau cgccguggca agccugggaa agggcguggc cugcaacccc | 1140 |
| gccugcuuca ucaccagcu gcugcccgug aagcggaagu uaggcuucua cgaguggacc | 1200 |
| uccaggcugc ggagccacau caaccccacc ggcaccgugc ugcugcaacu ggagaauacc | 1260 |
| augcagauga gccugaagga ucugcug | 1287 |

<210> SEQ ID NO 151
<211> LENGTH: 1287
<212> TYPE: RNA
<213> ORGANISM: Artificial Sequence
<220> FEATURE:
<223> OTHER INFORMATION: Synthetic: GLA-CO38

<400> SEQUENCE: 151

| | |
|---|---|
| augcagcucc ggaaccccga gcuccaccuc ggcugcgccc ucgccuuccg guuccuagcc | 60 |
| cucgugagcu gggacauacc gggcgccagg gcgcucgaca acggccucgc ccggaccccg | 120 |
| accaugggcu ggcuccacug ggagcgguuc augugcaacc uggacugcca ggaggagccc | 180 |
| gacagcugca ucagcgagaa gcuguucaug gagauggccg agcugauggu gagcgagggc | 240 |
| uggaaggacg ccggcuacga guaccugugc aucgacgacu gcuggauggc accucagcgg | 300 |
| gacuccgagg gccggcugca ggccgacccu cagagauucc cgcacggcau ccggcagcug | 360 |
| gccaacuacg ugcacagcaa gggccugaag cugggcaucu acgccgacgu gggcaacaag | 420 |
| accugcgccg gcuucccggg cagcuucggc uacuacgaca ucgacgccca gaccuucgcc | 480 |
| gacuggggcg uggaccugcu gaaguucgac ggcugcuacu gcgacagccu ggagaaccug | 540 |
| gccgacggcu acaagcacau gucucucgcc uugaaccgga ccggccggag caucguguac | 600 |
| agcugcgagu ggcccugua cauguggccc uuccagaagc ccaacuacac cgagaucgc | 660 |
| caguacugca accacggcg gaauuucgcc gauauugacg auagcuggaa guccaucaag | 720 |
| uccauccugg auuggaccag cuucaaccag gagcggaucg uggacguggc cggccccggc | 780 |
| ggcuggaacg accccgacau gcuggugauc ggcaacuucg gccugagcug gaaccagcag | 840 |
| gugacccaga uggcccugug ggccaucaug gccgccccac ucuucaugag caacgaccug | 900 |
| cggcacauca gcccgcaggc caaggcccug cugcaggaca aggacgugau cgccauuaau | 960 |
| caggacccgc ugggcaagca gggcuaccag cucaggcagg gcgacaacuu cgaggugugg | 1020 |
| gagaggccuc ugagcggucu ggccugggcc guggccauga ucaaccggca ggagaucggc | 1080 |
| ggaccgcgga gcuacaccau cgcgguggcc agccugggaa agggcguggc cugcaacccc | 1140 |

-continued

| | |
|---|---|
| gccugcuuca ucacccagcu gcugcccgug aagagaaagc ucggcuucua cgaguggacg | 1200 |
| ucaagacugc ggagccacau caaccccacc ggcaccgugc uccugcagcu ggagaauacc | 1260 |
| augcagaugu cccugaagga ccuccug | 1287 |

<210> SEQ ID NO 152
<211> LENGTH: 1287
<212> TYPE: RNA
<213> ORGANISM: Artificial Sequence
<220> FEATURE:
<223> OTHER INFORMATION: Synthetic: GLA-CO39

<400> SEQUENCE: 152

| | |
|---|---|
| augcagcucc ggaaccccga gcuucaccua ggcugcgccc ucgcccuccg guuccuugcc | 60 |
| cuagugagcu gggacauccc aggcgcccgc gcccucgaca acggccucgc ccggaccccu | 120 |
| accaugggcu ggcuccacug ggagcgguuc augugcaacc uggacugcca ggaggagccc | 180 |
| gacagcugca ucagcgagaa gcuguucaug gagauggccg agcugauggu gagcgagggc | 240 |
| uggaaggacg ccggcuacga guaccugugc aucgacgacu gcuggauggc ccgcagcgg | 300 |
| gacucugagg gccggcugca ggccgacccg cagagguucc cgcacggcau ccggcagcug | 360 |
| gccaacuacg ugcacagcaa gggccugaag cugggcaucu acgccgacgu gggcaacaag | 420 |
| accugcgccg gcuucccugg cagcuucggc uacuacgaca ucgacgccca gaccuucgcc | 480 |
| gacuggggcg uggaccugcu gaaguucgac ggcugcuacu gcgacagccu ggagaaccug | 540 |
| gccgacggcu acaagcacau gagcuuggcg cucaaccgga ccggccggag caucguguac | 600 |
| agcugcgagu ggcccugua caugggccc uuccagaagc ccaacuacac cgagauccgc | 660 |
| caguacugca ccacuggcg gaauuucgcc gauaucgaug auuccuggaa guccaucaag | 720 |
| uccauccucg acuggaccag cuucaaccag gagcggaucg uggacgugc cggccccggc | 780 |
| ggcuggaacg accccgacau gcuggugauc ggcaacuucg ccugagcug gaaccagcag | 840 |
| gugacccaga uggcccugug ggccaucaug gccgcgccac ucuucaugag caacgaccug | 900 |
| cggcacauca gcccgcaggc caaggcccug cugcaggaca aggacgugau cgccauuaac | 960 |
| caagacccgc ugggcaagca gggcuaccag cugcgccagg cgacaacuu cgaggugugg | 1020 |
| gagaggccuc uguccggacu gguugggcc guggccauga ucaaccggca ggagaucggc | 1080 |
| ggaccacgga gcuacaccau cgccguggcg agcugggua agggcgugc cugcaacccc | 1140 |
| gccugcuuca ucacccagcu gcugcccgug aagagaaagc ugggguucua cgaguggacc | 1200 |
| ucgagacugc ggagccacau caaccccacc ggcaccgugc uccugcagcu cgagaacacc | 1260 |
| augcagaugu ccccaagga ccuccug | 1287 |

<210> SEQ ID NO 153
<211> LENGTH: 1287
<212> TYPE: RNA
<213> ORGANISM: Artificial Sequence
<220> FEATURE:
<223> OTHER INFORMATION: Synthetic: GLA-CO40

<400> SEQUENCE: 153

| | |
|---|---|
| augcagcucc ggaaccccga gcuccaccuc ggcugcgccc ucgcccuccg guuccucgcg | 60 |
| cucgugagcu gggacauccc aggcgcccgg gcucucgaca acggccuagc ccggaccccg | 120 |
| accaugggcu ggcuccacug ggagcgguuc augugcaacc uggacugcca ggaggagccc | 180 |
| gacagcugca ucagcgagaa gcuguucaug gagauggccg agcugauggu gagcgagggc | 240 |

| | |
|---|---|
| uggaaggacg ccggcuacga guaccugugc aucgacgacu gcuggauggc cccacagcgg | 300 |
| gacagcgagg gacggcugca ggccgauccg cagcguuucc cgcacggcau ccggcagcug | 360 |
| gccaacuacg ugcacagcaa gggccugaag cugggcaucu acgccgacgu gggcaacaag | 420 |
| accugcgccg gcuucccagg cagcuucggc uacuacgaca ucgacgccca gaccuucgcc | 480 |
| gacuggggcg uggaccugcu gaaguucgac ggcuguuacu gcgacagccu ggagaaccug | 540 |
| gccgacggcu acaagcacau gucccuggca cugaaccgga ccggccggag caucguguac | 600 |
| agcugcgagu ggccccugua cauguggccc uuccagaagc ccaacuacac cgagaucaga | 660 |
| caauacugca accacuggcg gaauuucgcc gauauagacg auagcuggaa guccaucaag | 720 |
| uccauccugg auuggaccag cuucaaccag gagcggaucu ggacgugggc cggccccggc | 780 |
| ggcuggaacg accccgacau gcuggugauc ggcaacuucg ccugagcug gaaccagcag | 840 |
| gugacccaga uggcccugug ggccaucaug gccgccccuc ucuucaugag caacgaccug | 900 |
| cggcacauca gcccgcaggc caaggcccug cugcaggaca aggacgugau cgccaucaau | 960 |
| caagacccgc ugggcaagca gggcuaccag cugagacagg gcgacaacuu cgaggugugg | 1020 |
| gagaggccgc ugucgggacu ggccugggcc guggccauga ucaaccggca ggagaucggc | 1080 |
| ggcccgcgga gcuacaccau cgcgguggcc ucgcugggaa agggcguggc cugcaacccc | 1140 |
| gccugcuuca ucacccagcu gcugcccgug aagcguaagc ugggauucua cgaguggacc | 1200 |
| uccagacugc ggagcacau caaccccacc ggcaccgugc uucugcagcu ggagaauacc | 1260 |
| augcagaugu cccucaagga ccuccug | 1287 |

<210> SEQ ID NO 154
<211> LENGTH: 1287
<212> TYPE: RNA
<213> ORGANISM: Artificial Sequence
<220> FEATURE:
<223> OTHER INFORMATION: Synthetic: GLA-CO41

<400> SEQUENCE: 154

| | |
|---|---|
| augcagcucc ggaaccccga gcuccaccuu ggcugcgccc uugccuugcg guucuuagcc | 60 |
| cucgugagcu gggacauccc aggcgcccgc gcccucgaca acggcccucgc ccgcaccccu | 120 |
| accaugggcu ggcuccacug ggagcgcuuc augugcaacc ucgacugcca ggaggagccc | 180 |
| gacuccugca ucuccgagaa gcuguucaug gagauggccg agcucauggu guccgagggc | 240 |
| uggaaggacg ccggcuacga guaccucugc aucgacgacu gcuggauggc cccgcagcgc | 300 |
| gacagcgagg gcaggcucca ggccgaccca cagagguucc cacacggcau ccgccagcuc | 360 |
| gccaacuacg uccacuccaa gggccucaag cucggcaucu acgccgacgu cggcaacaag | 420 |
| accugcgccg gcuucccagg cucccuucggc uacuacgaca ucgacgccca gaccuucgcc | 480 |
| gacuggggcg ucgaccuccu caaguucgac ggcugcuacu gcgacucccu cgagaaccuc | 540 |
| gccgacggcu acaagcacau gucccucgcc cucaaccgca ccggccgcuc caucgucuac | 600 |
| uccugcgagu ggccccucua cauguggccc uuccagaagc ccaacuacac cgagaucagg | 660 |
| caguacugca accacuggcg caauuucgcc gauaucgaug acagcuggaa guccaucaag | 720 |
| agcauccugg acuggaccuc cuucaaccag gagcgcaucg ucgacgucgc cggccccggc | 780 |
| ggcuggaacg accccgacau gcucgucauc ggcaacuucg ccugucuug gaaccagcag | 840 |
| gucacccaga uggcccucug ggccaucaug gccgccccac uguucaugug caacgaccuc | 900 |
| cgccacaucu cccucaggc caaggcccuc uccaggaca aggacgucau cgccaucaau | 960 |
| caggacccgc ucggcaagca gggcuaccag cuccgccagg gcgacaacuu cgaggugugg | 1020 |

-continued

| | |
|---|---|
| gagaggcccc ucuccggacu cgccugggcc gucgccauga ucaaccgcca ggagaucggc | 1080 |
| ggcccacgcu ccuacaccau cgccguggcc uccugggca agggcgucgc cugcaacccc | 1140 |
| gccugcuuca ucaccagcu ccuccccguc aagaggaagc ugggcuucua cgaguggaca | 1200 |
| agccgccucc gcucccacau caaccccacc ggcaccgugc ugcugcagcu ggagaacacc | 1260 |
| augcagaugu cccugaagga ccugcuc | 1287 |

<210> SEQ ID NO 155
<211> LENGTH: 1287
<212> TYPE: RNA
<213> ORGANISM: Artificial Sequence
<220> FEATURE:
<223> OTHER INFORMATION: Synthetic: GLA-CO42

<400> SEQUENCE: 155

| | |
|---|---|
| augcagcuuc ggaaccccga gcuccaccuu ggcugcgccc uugcccuccg guuccucgcc | 60 |
| cucgugagcu gggacauacc gggcgccagg gcccucgaca acggcccucgc ccgcaccccg | 120 |
| accaugggcu ggcuccacug ggagcgcuuc augugcaacc ucgacugcca ggaggagccc | 180 |
| gacuccugca ucuccgagaa gcuguucaug gagauggccg agcucauggu guccgagggc | 240 |
| uggaaggacg ccggcuacga guaccucugc aucgacgacu gcuggauggc cccgcagcgc | 300 |
| gacagcgagg gucgccucca ggccgaccca cagagauucc cgcacggcau ccgccagcuc | 360 |
| gccaacuacg uccacuccaa gggccucaag cucggcaucu acgccgacgu cggcaacaag | 420 |
| accugcgccg gcuuccccgg ucccuucggc uacuacgaca ucgacgccca gaccuucgcc | 480 |
| gacuggggcg ucgaccuccu caaguucgac ggcugcuacu gcgacucccu cgagaaccuc | 540 |
| gccgacggcu acaagcacau gagccucgcu cucaaccgca ccggccgcuc caucgucuac | 600 |
| uccugcgagu ggcccucua caugggccc uuccagaagc ccaacuacac cgagauucgc | 660 |
| caguacugca ccacuggcg caauuucgcc gauaucgaug accuccuggaa guccaucaag | 720 |
| agcauccugg acuggaccuc cuucaaccag gagcgcaucg ucgacgucgc cggccccggc | 780 |
| ggcuggaacg accccgacau gcucgucauc ggaaacuucg gccugagcug gaaccagcag | 840 |
| gucacccaga uggcccucug gccaucaug gccgcccau uguucaugc caacgaccuc | 900 |
| cgccacaucu ccccgcaggc caaggcccuc cuccaggaca aggacgucau cgccaucaau | 960 |
| caggacccgc ucggcaagca gggcuaccag uccgccaggg cgacaacuu cgaggugugg | 1020 |
| gagcggccuc ucuccggacu ggccugggcc gucgccauga ucaaccgcca ggagaucggc | 1080 |
| ggcccacgcu ccuacaccau cgccguggcc agcugggca agggcgucgc cugcaacccc | 1140 |
| gccugcuuca ucaccagcu ccuccccguc aagaggaagc ugggcuucua cgaguggacc | 1200 |
| agccgccucc gcucccacau caaccccacc ggcaccgugc ugcugcagcu ggagaacacc | 1260 |
| augcagauga gccugaagga ccugcuc | 1287 |

<210> SEQ ID NO 156
<211> LENGTH: 1287
<212> TYPE: RNA
<213> ORGANISM: Artificial Sequence
<220> FEATURE:
<223> OTHER INFORMATION: Synthetic: GLA-CO43

<400> SEQUENCE: 156

| | |
|---|---|
| augcagcucc ggaaccccga gcuccaccuc ggcugcgccc ucgcccuccg guuccucgcc | 60 |
| cuagugagcu gggacauccc gggcgccagg gcccucgaca acggcucgc ccgcaccccca | 120 |

| | |
|---|---|
| accaugggcu ggcuccacug ggagcgcuuc augugcaacc ucgacugcca ggaggagccc | 180 |
| gacuccugca ucuccgagaa gcuguucaug gagauggccg agcucauggu guccgagggc | 240 |
| uggaaggacg ccggcuacga guaccucugc aucgacgacu gcuggauggc cccacagcgc | 300 |
| gacagcgagg gccgccucca ggccgaccca cagagguucc cgcacggcau ccgccagcuc | 360 |
| gccaacuacg uccacuccaa gggccucaag cucggcaucu acgccgacgu cggcaacaag | 420 |
| accugcgccg gcuucccggg ucccuucggc uacuacgaca ucgacgccca gaccuucgcc | 480 |
| gacuggggcg ucgaccuccu caaguucgac ggcugcuacu gcgacucccu cgagaaccuc | 540 |
| gccgacggcu acaagcacau gagccuggcg cucaaccgca ccggccgcuc caucgucuac | 600 |
| uccugcgagu ggccccucua cauguggccc uuccagaagc ccaacuacac cgagauccga | 660 |
| caguacugca accacuggcg caauuucgcc gauaucgaug auuccuggaa guccaucaag | 720 |
| agcauccucg auuggaccuc cuucaaccag gagcgcaucu cgacgucgc cggccccggc | 780 |
| ggcuggaacg accccgacau gcucgucauc gguaacuucg ccugagcug gaaccagcag | 840 |
| gucacccaga uggcccucug ggccaucaug gccgccccgc uuucaugguc caacgaccuc | 900 |
| cgccacaucu cgccgcaggc caaggcccuc cuccaggaca aggacgucau cgccaucaau | 960 |
| caggacccgc ucggcaagca gggcuaccag cuccgccagg gcgacaacuu cgaggugugg | 1020 |
| gagcggcccc ucagcggccu ggcguggggcc gucgccauga ucaaccgcca ggagaucggc | 1080 |
| gguccacgcu ccuacaccau cgccguggcc agccugggca agggcucgc cugcaacccc | 1140 |
| gccugcuuca ucacccagcu ccuccccguc aagaggaagc ugggauucua cgaguggacu | 1200 |
| agcaggcugc gcucccacau caaccccacc ggcaccgugc ccugcagcu ggagaauacc | 1260 |
| augcagaugu cccugaagga ccugcuc | 1287 |

<210> SEQ ID NO 157
<211> LENGTH: 1287
<212> TYPE: RNA
<213> ORGANISM: Artificial Sequence
<220> FEATURE:
<223> OTHER INFORMATION: Synthetic: GLA-CO44

<400> SEQUENCE: 157

| | |
|---|---|
| augcagcugc ggaaccccga gcugcaccug ggcugcgccc uggcccugcg guuccuggcc | 60 |
| cuggugagcu gggacauccc cggcgcccgg gcgcuggaca cgggcuggc gaggacgccg | 120 |
| acgauggggu ggcugcacug ggagagguuc augugcaacc uggacugcca ggaggagccg | 180 |
| gacagcugca ucagcgagaa gcuguucaug gagauggcgg agcugauggu gagcgagggg | 240 |
| uggaaggacg cggguacga guaccugugc aucgacgacu gcuggauggc ccgcagagg | 300 |
| gacagcgagg ggaggcugca ggcggacccg cagagguucc cgcacgggau caggcagcug | 360 |
| gcgaacuacg ugcacagcaa ggggcugaag cuggggaucu acgcggacgu ggggaacaag | 420 |
| acgugcgcgg gguucccggg gagcuucggg uacuacgaca ucgacgcgca gacguucgcg | 480 |
| gacuggggug uggaccugcu gaaguucgac ggugcuacu gcgacagccu ggagaaccug | 540 |
| gcggacgggu acaagcacau gagccuggcg cugaacagga cggggaggag caucgucuac | 600 |
| agcugcgagu ggccgcugua cauguggccg uuccagaagc cgaacuacac ggagaucagg | 660 |
| caguacugca accacuggag gaacuucgcg gacaucgacg acagcuggaa gagcaucaag | 720 |
| agcauccugg acuggaccgag cuucaaccag gagaggaucg uggacguggc ggggccggga | 780 |
| ggguggaacg acccggacau gcuggugauc gggaacuucg gcugagcug gaaccagcag | 840 |
| gugacgcaga uggcgcugug ggcgaucaug gcggcgccgc uguucaugag caacgaccug | 900 |

-continued

| | |
|---|---|
| aggcacauca gcccgcaggc gaaggcgcug cugcaggaca aggacgugau cgcgaucaac | 960 |
| caggacccgc uggggaagca gggguaccag cugaggcagg gugacaacuu cgaggugugg | 1020 |
| gagaggccgc ugagcgggcu ggcguggcg guggcgauga ucaacaggca ggagaucgga | 1080 |
| gggccgagga gcuacacgau cgcgguggcg agccugggga agggcguggc gugcaacccg | 1140 |
| gcgugcuuca ucacgcagcu gcugccggug aagaggaagc uggggurcua cgaguggacg | 1200 |
| agcaggcuga ggagccacau caacccgacg gggacggugc ugcugcagcu ggagaacacg | 1260 |
| augcagauga gccugaagga ccugcug | 1287 |

<210> SEQ ID NO 158
<211> LENGTH: 1287
<212> TYPE: RNA
<213> ORGANISM: Artificial Sequence
<220> FEATURE:
<223> OTHER INFORMATION: Synthetic: GLA-CO45

<400> SEQUENCE: 158

| | |
|---|---|
| augcagcugc ggaaccccga gcugcaccug ggcugcgccc uggcccugcg guuccuggcc | 60 |
| cugugagcu gggacaucc cggcgcccgg gcccucgaca cggccucgc ccgcacgccc | 120 |
| accaugggcu ggcuccacug ggagcgcuuc augugcaacc ucgacugcca ggaggagccc | 180 |
| gacuccugca ucuccgagaa gcucuucaug gagauggccg agcucauggu cuccgagggc | 240 |
| uggaaggacg ccggcuacga guaccucugc aucgacgacu gcuggauggc ccccagcgc | 300 |
| gacuccgagg gccgccucca ggccgacccu cagcgcuucc gcacggcau ccgccagcuc | 360 |
| gccaacuacg uccacuccaa gggccucaag ucggcaucu acgccgacgu cggcaacaag | 420 |
| accugcgccg gcuuccccgg cuccuucggc uacuacgaca ucgacgccca gaccuucgcc | 480 |
| gacuggggcg ucgaccuccu caaguucgac ggcugcuacu gcgacucccu cgagaaccuc | 540 |
| gccgacggcu acaagcacau guccucgcc cucaaccgca ccggccgcuc caucgucuac | 600 |
| uccugcgagu ggcccucua cauggggccc uccagaagc caacuacac cgagauccgc | 660 |
| caguacugca ccacuggcg caacuucgcc gacaucgacg acuccuggaa guccaucaag | 720 |
| uccauccucg acuggaccuc cuucaaccag gagcgcaucg ucgacgucgc cggcccggc | 780 |
| ggcuggaacg accccgacau gcucgucauc ggcaacuucg ccucuccug gaaccagcag | 840 |
| gucacccaga uggcccucug gccaucaug gccgcgcccc ucuucauguc caacgaccuc | 900 |
| cgccacaucu cgcccaggc caaggcccuc uccaggaca aggacgucau cgccaucaac | 960 |
| caggacccgc ucggcaagca gggcuaccag cuccgccagg cgacaacuu cgaggucugg | 1020 |
| gagcgccgc ucuccggccu cgccugggcc gucgccauga ucaaccgcca ggagaucggc | 1080 |
| ggccacgcu ccuacaccau cgccgucgcc ccucuggca agggcgucgc cugcaacccc | 1140 |
| gccugcuuca ucacccagcu ccuccccguc aagcgcaagc ucggcuucua cgaguggacc | 1200 |
| uccgcucuc gcucccacau caaccccacc ggcaccgucc uccucagcu cgagaacacc | 1260 |
| augcagaugu cccucaagga ccuccuc | 1287 |

<210> SEQ ID NO 159
<211> LENGTH: 1287
<212> TYPE: RNA
<213> ORGANISM: Artificial Sequence
<220> FEATURE:
<223> OTHER INFORMATION: Synthetic: GLA-CO46

<400> SEQUENCE: 159

| | |
|---|---|
| augcagcuga ggaacccaga acuacaucug ggcugcgcgc uugcgcuucg cuuccuggcc | 60 |

```
cucguuuccu gggacauccc uggggcuaga gcacuggaca auggauuggc aaggacgccu    120
accaugggcu ggcugcacug ggagcgcuuc augugcaacc uugacugcca ggaagagcca    180
gauuccugca ucagugagaa gcucuucaug gagauggcag agcucauggu ucagaaggc     240 uggaaggaug cagguuauga guaccucugc auugaugacu guuggauggc ucccaaaga     300 gauucagaag gcagacuuca ggcagacccu cagcgcuuuc ucaugggau cgccagcua      360 gcuaauuaug uucacagcaa aggacugaag cuagggauuu augcagaugu ggaaauaag     420 accugcgcag gcuucccugg gaguuuugga uacuacgaca uugaugccca gaccuuugcu    480
gacuggggag uagaucugcu aaaguuugau gguuguuacu gugacaguuu ggagaauuug    540
gcagaugguu auaagcacau guccuuggcc cugaauagga cuggcagaag cauuguguac    600
uccugugagu ggccucuuua uaugggccc uuucagaagc ccaauuauac agaaauccga     660
caguacugca ucacuggcg aaauuuugcu gacauugaug auuccuggaa gaguauaaag     720
aguaucuugg acuggacauc uuuuaaccag gagagaauug uugauguugc uggaccaggc    780
gguuggaaug acccagauau guuagugauu ggcaacuuug ccucagcug aaucagcaa      840 guaacucaga uggcccucug ggcuaucaug gcugccccu uauucaugc uaaugaccuc      900 cgacacauca gcccucaagc caaagcucuc cucaggaua aggacguaau ugccaucaau     960
caggaccccu uggcaagca agggauccag cuagacagg agacaacuu ugaagugugg      1020 gaacgaccuc ucucaggcuu agccugggcu guagcuauga uaaaccggca ggagauuggu   1080
ggaccucgcu cuuauaccau cgcaguugcu ucccgggua aggagguggc cguaauccu     1140 gccugcuuca ucacacagcu ccucccugug aagaggaagc uagggcuucua ugaauggacu   1200 ucaagguaa gaagucacau aaaucccaca ggcacuguuu ugcuucagcu agagaauaca    1260
augcagaugu cauuaaagga cuacuu                                        1287
```

<210> SEQ ID NO 160
<211> LENGTH: 1475
<212> TYPE: RNA
<213> ORGANISM: Artificial Sequence
<220> FEATURE:
<223> OTHER INFORMATION: Synthetic: GLA-mRNA #23

<400> SEQUENCE: 160

```
gggaaauaag agagaaaaga agaguaagaa gaaauauaag agccaccaug cagcuccgga    60
accccgagcu ccaccuuggc ugcgcccucg ccuugcgguu ccucgcacuu gugagcuggg   120
acauaccagg cgccccgggcc cucgacaacg gccucgcccg caccccaacc augggcuggc   180
uccacuggga gcgcuucaug ugcaaccucg acugcaggca ggagcccgac uccugcaucu   240
ccgagaagcu uuucauggag auggccgagc ucaugguguc cgagggcugg aaggacgccg   300
gcuacgagua ccucugcauc gacgacugcu ggauggcccc gcagcgcgac agcgagggu   360 gccuccaggc cgaccgcag cgguucccuc acggcaucg ccagcucgcc aacuacgucc     420
acuccaaggg ccucaagcuc ggcaucuacg ccgacgucgg caacaagacc ugcgccggcu   480
uccccggcuc cuucggcuac uacgacaucg cgcccagac cuucgccgac uggggcgucg   540
accuccucaa guucgacggc ugcuacgcgc acucccucga gaaccucgcc gacggcuaca   600
agcacauguc ccucgcccuc aaccgcaccg gccgcuccau cgucuacucc ugcgaguggc   660
cccucuacau gggcccuuc cagaagccca acuacaccga auaaggcag uacugcaacc    720 acuggcgcaa uuucgccgau aucgaugacu ccuggaaguc caucaagagc auccuggacu   780
ggaccuccuu caaccaggag cgcaucgucg acgucgccgg cccggcggc uggaacgacc    840
```

| ccgacaugcu cgucaucgga aacuucggcc uguccuggaa ccagcagguc acccagaugg | 900 |
| cccucugggc caucauggcc gccccacugu caugcccaa cgaccuccgc cacaucagcc | 960 |
| cgcaggccaa ggcccuccuc caggacaagg acgucaucgc caucaaccaa gacccgcucg | 1020 |
| gcaagcaggg cuaccagcuc cgccaggcg acaacuucga ggugugggaa cgucccuca | 1080 |
| gcggccuggc gugggccguc gccaugauca accgccagga gaucggcggc ccgcgcuccu | 1140 |
| acaccaucgc cguggccagc cugggcaagg gcgucgccug caaccccgcc ugcuucauca | 1200 |
| cccagcuccu ccccgucaag agaaagcugg gcuucuacga guggaccagc cgccuccgcu | 1260 |
| cccacaucaa ccccaccggc accguccugc uccagcugga gaacaccaug cagaugagcc | 1320 |
| ucaaggaccu gcucugauaa uaggcuggag ccucggugcc caugcuucuu gccccuuggg | 1380 |
| ccucccccca gccccuccuc cccuuccugc acccguaccc ccgcauuau uacucacggu | 1440 |
| acgagugguc uuugaauaaa gucugagugg gcggc | 1475 |

<210> SEQ ID NO 161
<211> LENGTH: 142
<212> TYPE: RNA
<213> ORGANISM: Artificial Sequence
<220> FEATURE:
<223> OTHER INFORMATION: Synthetic: 3 UTR with miR 142-3p binding site
      variant 2

<400> SEQUENCE: 161

| ugauaauagg cuggagccuc gguggccuag cuucuugccc cuugggccuc ccccagccc | 60 |
| cuccucccu uccugcaccc guaccccuc cauaaaguag gaaacacuac aguggucuuu | 120 |
| gaauaaaguc ugaguggggcg gc | 142 |

<210> SEQ ID NO 162
<211> LENGTH: 119
<212> TYPE: RNA
<213> ORGANISM: Artificial Sequence
<220> FEATURE:
<223> OTHER INFORMATION: Synthetic: 3 UTR, no miR binding sites
      variant 2

<400> SEQUENCE: 162

| ugauaauagg cuggagccuc gguggccuag cuucuugccc cuugggccuc ccccagccc | 60 |
| cuccucccu uccugcaccc guaccccgu ggucuuugaa uaaagucuga gugggcggc | 119 |

<210> SEQ ID NO 163
<211> LENGTH: 141
<212> TYPE: RNA
<213> ORGANISM: Artificial Sequence
<220> FEATURE:
<223> OTHER INFORMATION: Synthetic: 3 UTR with miR 126-3p binding site
      variant 3

<400> SEQUENCE: 163

| ugauaauagg cuggagccuc gguggccuag cuucuugccc cuugggccuc ccccagccc | 60 |
| cuccucccu uccugcaccc guaccccccg cauuauuacu cacgguacga guggucuuug | 120 |
| aauaaagucu gaguggcgg c | 141 |

<210> SEQ ID NO 164
<211> LENGTH: 188
<212> TYPE: RNA
<213> ORGANISM: Artificial Sequence
<220> FEATURE:
<223> OTHER INFORMATION: Synthetic: 3 UTR with 3 miR 142-3p binding
      sites variant 2

```
<400> SEQUENCE: 164
ugauaauagu ccauaaagua ggaaacacua cagcuggagc cucgguggcc uagcuucuug    60
ccccuugggc cuccauaaag uaggaaacac uacaucccccc cagccccucc ucccuuccu    120 gcacccguac ccccuccaua aaguaggaaa cacuacagug gucuuugaau aaagucugag    180
ugggcggc                                                              188

<210> SEQ ID NO 165
<211> LENGTH: 142
<212> TYPE: RNA
<213> ORGANISM: Artificial Sequence
<220> FEATURE:
<223> OTHER INFORMATION: Synthetic: 3'UTR with miR 142-3p binding site,
      P1 insertion variant 2

<400> SEQUENCE: 165
ugauaauagu ccauaaagua ggaaacacua cagcuggagc cucgguggcc uagcuucuug    60
ccccuugggc cucccccag ccccuccucc ccuuccugca cccguacccc cguggucuuu     120
gaauaaaguc ugaguggggcg gc                                             142

<210> SEQ ID NO 166
<211> LENGTH: 142
<212> TYPE: RNA
<213> ORGANISM: Artificial Sequence
<220> FEATURE:
<223> OTHER INFORMATION: Synthetic: 3'UTR with miR 142-3p binding site,
      P2 insertion variant 2

<400> SEQUENCE: 166
ugauaauagg cuggagccuc gguggcucca uaaaguagga aacacuacac uagcuucuug    60
ccccuugggc cucccccag ccccuccucc ccuuccugca cccguacccc cguggucuuu     120
gaauaaaguc ugaguggggcg gc                                             142

<210> SEQ ID NO 167
<211> LENGTH: 142
<212> TYPE: RNA
<213> ORGANISM: Artificial Sequence
<220> FEATURE:
<223> OTHER INFORMATION: Synthetic: 3'UTR with miR 142-3p binding site,
      P3 insertion variant 2

<400> SEQUENCE: 167
ugauaauagg cuggagccuc gguggccuag cuucuugccc cuugggccuc cauaaaguag    60
gaaacacuac aucccccag ccccuccucc ccuuccugca cccguacccc cguggucuuu     120
gaauaaaguc ugaguggggcg gc                                             142

<210> SEQ ID NO 168
<211> LENGTH: 142
<212> TYPE: RNA
<213> ORGANISM: Artificial Sequence
<220> FEATURE:
<223> OTHER INFORMATION: Synthetic: 3UTR with miR 155-5p binding site
      variant 2

<400> SEQUENCE: 168
ugauaauagg cuggagccuc gguggccuag cuucuugccc cuugggccuc ccccagccc     60 cucccccccu uccugcaccc guaccccac cccuaucaca auuagcauua aguggucuuu     120
gaauaaaguc ugaguggggcg gc                                             142
```

```
<210> SEQ ID NO 169
<211> LENGTH: 188
<212> TYPE: RNA
<213> ORGANISM: Artificial Sequence
<220> FEATURE:
<223> OTHER INFORMATION: Synthetic: 3 UTR with 3 miR 155-5p binding
      sites variant 2

<400> SEQUENCE: 169
ugauaauaga ccccuaucac aauuagcauu aagcuggagc cucggguggcc uagcuucuug         60 ccccuugggc caccccuauc acaauuagca uuaauccccc cagccccucc uccccuuccu        120
gcacccguac ccccacccu aucacaauua gcauuaagug gucuuugaau aaagucugag         180
ugggcggc                                                                 188

<210> SEQ ID NO 170
<211> LENGTH: 188
<212> TYPE: RNA
<213> ORGANISM: Artificial Sequence
<220> FEATURE:
<223> OTHER INFORMATION: Synthetic: 3UTR with 2 miR 155-5p binding sites
      and 1 miR 142-3p binding site variant 2

<400> SEQUENCE: 170
ugauaauaga ccccuaucac aauuagcauu aagcuggagc cucggguggcc uagcuucuug         60 ccccuugggc cuccauaaag uaggaaacac uacauccccc cagccccucc uccccuuccu        120
gcacccguac ccccacccu aucacaauua gcauuaagug gucuuugaau aaagucugag         180
ugggcggc                                                                 188
```

POLYNUCLEOTIDES ENCODING ALPHA-GALACTOSIDASE A FOR THE TREATMENT OF FABRY DISEASE

CROSS-REFERENCE TO RELATED APPLICATIONS

This application is a Continuation of Application PCT/US2017/033398 filed on May 18, 2017. Application PCT/US2017/033398 claims the benefit of U.S. Provisional Application No. 62/338,354 filed on May 18, 2016. The entire contents of the above-referenced patent applications are incorporated herein by this reference.

REFERENCE TO A SEQUENCE LISTING SUBMITTED ELECTRONICALLY

The instant application contains a Sequence Listing which has been submitted in ASCII format via EFS-Web and is hereby incorporated by reference in its entirety. Said ASCII copy, created on Nov. 16, 2018, is named SeqListing_MDN_740PCCN-2 and is 182343 bytes in size. The Sequence Listing is being submitted by EFS Web and is hereby incorporated by reference into the specification.

BACKGROUND

Fabry disease is an X-linked inherited disorder that is caused by mutations in the α-galactosidase A (GLA) gene, which encodes an enzyme that is involved in recycling fats within the lysosomal compartments of cells. Fabry disease is also referred to as α-galactosidase A deficiency, Anderson-Fabry disease, angiokeratoma corporis diffusum, angiokeratoma diffuse, ceramide trihexosidase deficiency, Fabry's disease, GLA deficiency, and hereditary dystopic lipidosis. It has an estimated incidence of 1 in 40,000 to 400,000 males. Deegan et al., 2006 *J Med. Genet.* 43(4):347-352.

GLA, which is also referred to as GALA, is a homodimeric glycoprotein that hydrolyzes the terminal α-galactosyl moieties from glycolipids and glycoproteins. See, e.g., GenBank Accession Numbers NM_000169 for the GLA mRNA sequence and NP_000160 for the GLA amino acid sequence. The GLA precursor protein is 429 amino acids in length and contains a signal peptide of 31 amino acids that is cleaved during protein processing. Mutations in GLA lead to an accumulation of globotriaosylceramide (Gb3), globotriaosylsphingosine (lyso-Gb3), galabiosylceramide (Ga2), and neutral glycosphingolipids in lysosomes of several tissues, including the endothelium of the vascular tree. Gervas-Arruga et al., 2015 *BMC Genet.* 16:109. While normal individuals have very low levels of Gb3, patients with Fabry disease progressively accumulate Gb3 in both plasma and a range of tissues.

The classic form of Fabry disease usually manifests in childhood or adolescence with periodic crises of severe pain in the extremities (acroparesthesias), the appearance of vascular cutaneous lesions (angiokeratomas), sweating abnormalities (anhydrosis, hypohydosis, and rarely hyperhidrosis), characteristic corneal and lenticular opacities, and proteinuria. End-stage renal disease usually occurs in the third to fifth decade, and even those individuals successfully treated for renal disease usually suffer from cardiac or cerebrovascular disease. Mehta et al. *GeneReviews: Fabry Disease*, University of Washington, Seattle (2013).

Currently, treatment for Fabry disease typically consists of diphenylhydantoin, carbamazepine, or gabapentin to reduce pain; ACE inhibitors or angiotensin receptor blockers to reduce proteinuria; and chronic hemodialysis and/or renal transplantation to treat renal disease. Enzyme replacement therapy is also often recommended, but its effectiveness is unproven. Mehta et al. *GeneReviews: Fabry Disease*, University of Washington, Seattle (2013). Improved therapeutics and therapies are thus needed to treat Fabry disease.

BRIEF SUMMARY

The present invention provides mRNA therapeutics for the treatment of Fabry disease. The mRNA therapeutics of the invention are particularly well-suited for the treatment of Fabry disease as the technology provides for the intracellular delivery of mRNA encoding GLA followed by de novo synthesis of functional GLA protein within target cells. The instant invention features the incorporation of modified nucleotides within therapeutic mRNAs to (1) minimize unwanted immune activation (e.g., the innate immune response associated with the in vivo introduction of foreign nucleic acids) and (2) optimize the translation efficiency of mRNA to protein. Exemplary aspects of the invention feature a combination of nucleotide modifications to reduce the innate immune response and sequence optimization, in particular, within the open reading frame (ORF) of therapeutic mRNAs encoding GLA to enhance protein expression.

In further embodiments, the mRNA therapeutic technology of the instant invention also features delivery of mRNA encoding GLA via a lipid nanoparticle (LNP) delivery system. The instant invention features novel ionizable lipid-based LNPs which have improved properties when combined with mRNA encoding GLA and administered in vivo, for example, cellular uptake, intracellular transport and/or endosomal release or endosomal escape. The LNP formulations of the invention also demonstrate reduced immunogenicity associated with the in vivo administration of LNPs.

In certain aspects, the invention relates to compositions and delivery formulations comprising a polynucleotide, e.g., a ribonucleic acid (RNA), e.g., a messenger RNA (mRNA), encoding α-galactosidase A (GLA) and methods for treating Fabry disease in a subject in need thereof by administering the same.

The present disclosure provides a pharmaceutical composition comprising a lipid nanoparticle encapsulated mRNA that comprises an open reading frame (ORF) encoding an α-galactosidase A (GLA) polypeptide, wherein the composition is suitable for administration to a human subject in need of treatment for Fabry disease.

The present disclosure further provides a pharmaceutical composition comprising: (a) a mRNA that comprises (i) an open reading frame (ORF) encoding an α-galactosidase A (GLA) polypeptide, wherein the ORF comprises at least one chemically modified nucleobase, sugar, backbone, or any combination thereof, (ii) an untranslated region (UTR) comprising a microRNA (miRNA) binding site; and (b) a delivery agent, wherein the pharmaceutical composition is suitable for administration to a human subject in need of treatment for Fabry disease.

The present disclosure further provides a pharmaceutical composition comprising an mRNA that comprises an open reading frame (ORF) encoding a human α-galactosidase A (GLA) polypeptide, wherein the composition, when administered as a single intravenous dose to a human subject suffering from Fabry disease, is sufficient to increase plasma GLA activity level to or above a reference physiologic level for at least 12 hours, at least 18 hours, at least 24 hours, at least 36 hours, at least 48 hours, or at least 72 hours. In some embodiments, the pharmaceutical composition, when administered as a single intravenous dose to the human subject suffering from Fabry disease, is sufficient to maintain at least 10%, at least 20%, at least 30%, at least 40%, or at least 50%, at least 60%, at least 70%, at least 80%, at least 90%, or more than 100% of a reference plasma GLA activity 24 hours, 48 hours, 72 hours, 96 hours, 120 hours, 144 hours, or 168 hours post-administration. In some embodiments, the pharmaceutical composition, when administered as a single intravenous dose to the human subject suffering from Fabry disease, is sufficient to increase plasma GLA activity for at least 24 hours, for at least 48 hours, for at least 72 hours, for at least 96 hours, for at least 120 hours, for at least 144 hours, or for at least 168 hours post-administration, wherein the increased plasma GLA activity level is at least 10%, at least 20%, at least 30%, at least 40%, at least 50%, at least 60%, at least 70%, at least 80%, at least 90%, or more than 100% compared to the subject's baseline GLA activity level or a reference GLA activity level.

The present disclosure further provides a pharmaceutical composition comprising an mRNA that comprises an open reading frame (ORF) encoding a human α-galactosidase A (GLA) polypeptide, wherein the composition, when administered as a single intravenous dose to a human subject suffering from Fabry disease, is sufficient to increase one or more of plasma, liver, heart, kidney, or spleen GLA activity level to or above one or more corresponding reference levels for at least 12 hours, at least 18 hours, at least 24 hours, at least 36 hours, at least 48 hours, or at least 72 hours. In some embodiments, the pharmaceutical composition, when administered as a single intravenous dose to the human subject suffering from Fabry disease, is sufficient to maintain at least 10%, at least 20%, at least 30%, at least 40%, at least 50%, at least 60%, at least 70%, at least 80%, at least 90%, or more than 100% GLA activity in one or more of plasma, liver, heart, kidney, or spleen of the subject for 24 hours, 48 hours, 72 hours, 96 hours, 120 hours, 144 hours, or 168 hours post-administration. In some embodiments, the pharmaceutical composition, when administered as a single intravenous dose to the human subject suffering from Fabry disease, is sufficient to increase one or more of plasma, liver, heart, kidney, or spleen GLA activity for at least 24 hours, for at least 48 hours, for at least 72 hours, for at least 96 hours, for at least 120 hours, for at least 144 hours, or for at least 168 hours post-administration, wherein the increased one or more plasma, liver, heart, kidney, or spleen GLA activity level is at least 10%, at least 20%, at least 30%, at least 40%, at least 50%, at least 60%, at least 70%, at least 80%, at least 90%, or more than 100% compared to the subject's corresponding baseline GLA activity level or a corresponding reference GLA activity level.

The present disclosure further provides a pharmaceutical composition comprising an mRNA comprising an open reading frame (ORF) encoding a human α-galactosidase A (GLA) polypeptide, wherein the composition when administered to a subject in need thereof as a single intravenous dose is sufficient to reduce plasma levels of (i) Gb3 by at least 20%, at least 30%, at least 40%, at least 50%, at least, 60%, at least 70%, at least 80%, at least 90%, at least 95%, at least 100%, at least 2-fold, at least 3-fold, at least 4-fold, at least 5-fold, at least 10-fold, at least 20-fold, or at least 50-fold as compared to the subject's baseline Gb3 plasma level or a reference Gb3 plasma level, for at least 7 days, at least 14 days, at least 21 days, at least 28 days, at least 35 days, or at least 42 days post-administration, and/or (ii) Lyso-Gb3 by at least 20%, at least 30%, at least 40%, at least 50%, at least, 60%, at least 70%, at least 80%, at least 90%, at least 95%, at least 100%, at least 2-fold, at least 3-fold, at least 4-fold, at least 5-fold, at least 10-fold, at least 20-fold, or at least 50-fold as compared to the subject's baseline Gb3 plasma level or a reference Lyso-Gb3 plasma level, for at least 7 days, at least 14 days, at least 21 days, at least 28 days, at least 35 days, or at least 42 days post-administration. In some embodiments, the administration reduces the plasma Gb3 levels or the plasma lyso-Gb3 between 40% and 100%, between 50% and 100%, between 60% and 100%, between 70% and 100%, between 80% and 100%, or between 90% and 100% as compared to the subject's baseline Gb3 plasma level or a reference Lyso-Gb3 plasma level, for at least 7 days, at least 14 days, at least 21 days, at least 28 days, at least 35 days, or at least 42 days post-administration.

The present disclosure further provides a pharmaceutical composition comprising an mRNA comprising an open reading frame (ORF) encoding a human α-galactosidase A (GLA) polypeptide, wherein the composition when administered to a subject in need thereof as a single intravenous dose is sufficient to reduce tissue levels of (i) Gb3 in one or more of heart, kidney, liver, or spleen tissue by at least 20%, at least 30%, at least 40%, at least 50%, at least, 60%, at least 70%, at least 80%, at least 90%, at least 95%, at least 100%, at least 2-fold, at least 3-fold, at least 4-fold, at least 5-fold, at least 10-fold, at least 20-fold, or at least 50-fold as compared to the subject's baseline levels in one or more of the tissues or a reference Gb3 level in one or more of the tissues, for at least 7 days, at least 14 days, at least 21 days, at least 28 days, at least 35 days, or at least 42 days post-administration, and/or (ii) Lyso-Gb3 in one or more of heart, kidney, liver, or spleen tissue by at least 20%, at least 30%, at least 40%, at least 50%, at least, 60%, at least 70%, at least 80%, at least 90%, at least 95%, at least 100%, at least 2-fold, at least 3-fold, at least 4-fold, at least 5-fold, at least 10-fold, at least 20-fold, or at least 50-fold as compared to the subject's baseline level in one or more of the tissues or a reference Lyso-Gb3 level in one or more of the tissues, for at least 7 days, at least 14 days, at least 21 days, at least 28 days, at least 35 days, or at least 42 days post-administration. In some embodiments, the administration reduces the level of Gb3 or the level of lyso-Gb3 in one or more of heart, kidney, liver, or spleen tissue between 40% and 100%, between 50% and 100%, between 60% and 100%, between 70% and 100%, between 80% and 100%, or between 90% and 100% as compared to the subject's baseline level or a reference level in that tissue, for at least 7 days, at least 14 days, at least 21 days, at least 28 days, at least 35 days, or at least 42 days post-administration.

In some embodiments, the pharmaceutical compositions disclosed herein further comprise a delivery agent.

In certain aspects, the invention relates to a polynucleotide comprising an open reading frame (ORF) encoding α-galactosidase A (GLA) polypeptide, wherein the uracil or thymine content of the ORF relative to the theoretical minimum uracil or thymine content of a nucleotide sequence encoding the GLA polypeptide (% $U_{TM}$ or % $T_{TM}$) is between about 100% and about 150%.

In certain embodiments, the % $U_{TM}$ or % $T_{TM}$ is between about 110% and about 150%, about 115% and about 150%, about 120% and about 150%, about 110% and about 145%, about 115% and about 145%, about 120% and about 145%, about 110% and about 140%, about 115% and about 140%, or about 120% and about 140%. In certain embodiments, the % $U_{TM}$ or % $T_{TM}$ is between (i) 115%, 116%, 117%, 118%, 119%, 120%, 121%, 122%, or 123% and (ii) 138%, 139%, 140%, 141%, 142%, 143%, 144%, or 145%. In certain embodiments, the uracil or thymine content of the ORF relative to the uracil or thymine content of the corresponding wild-type ORF (% $U_{WT}$ or % $T_{WT}$) is less than 100%. In certain embodiments, the % $U_{TM}$ or % $T_{TM}$ is less than about 95%, less than about 90%, less than about 85%, less than 80%, less than 75%, less than 74%, less than 73%, less than 72%, less than 71%, or less than 70%. In certain embodiments, the % $U_{WT}$ or % $T_{WT}$ is between 62% and 70%.

In certain embodiments, the uracil or thymine content in the ORF relative to the total nucleotide content in the ORF (% $U_{TL}$ or % $T_{TL}$) is less than about 50%, less than about 40%, less than about 30%, or less than about 20%. In certain embodiments, the % $U_{TL}$ or % $T_{TL}$ is less than about 20%. In certain embodiments, the % $U_{TL}$ or % $T_{TL}$, is between about 16% and about 18%.

In certain embodiments, the guanine content of the ORF with respect to the theoretical maximum guanine content of a nucleotide sequence encoding the GLA polypeptide (% $G_{TMX}$) is at least 64%, at least 65%, at least 70%, at least 75%, at least 75%, at least about 80%, at least about 85%, at least about 90%, at least about 95%, or about 100%. In certain embodiments, the % $G_{TMX}$ is between about 70% and about 85%, between about 70% and about 80%, between about 71% and about 80%, or between about 72% and about 80%.

In certain embodiments, the cytosine content of the ORF relative to the theoretical maximum cytosine content of a nucleotide sequence encoding the GLA polypeptide (% $C_{TMX}$) is at least 54%, at least 55%, at least 60%, at least 65%, at least 70%, at least 75%, at least about 80%, at least about 85%, at least about 90%, at least about 95%, or about 100%. In certain embodiments, % $C_{TMX}$ is between about 60% and about 80%, between about 65% and about 80%, between about 70% and about 80%, or between about 70% and about 76%.

In certain embodiments, the guanine and cytosine content (G/C) of the ORF relative to the theoretical maximum G/C content in a nucleotide sequence encoding the GLA polypeptide (% $G/C_{TMX}$) is at least about 73%, at least about 75%, at least about 80%, at least about 85%, at least about 90%, at least about 95%, or about 100%. In certain embodiments, % $G/C_{TMX}$ is between about 80% and about 100%, between about 85% and about 99%, between about 90% and about 97%, or between about 91% and about 95%. In certain embodiments, the G/C content in the ORF relative to the G/C content in the corresponding wild-type ORF (% $G/C_{WT}$) is at least 102%, at least 103%, at least 104%, at least 105%, at least 106%, at least 107%, at least about 110%, at least about 115%, at least about 120%, or at least about 125%. In certain embodiments, the average G/C content in the $3^{rd}$ codon position in the ORF is at least 30%, at least 31%, at least 32%, at least 33%, at least 34%, at least 35%, at least 36%, at least 37%, at least 38%, at least 39%, or at least 40% higher than the average G/C content in the $3^{rd}$ codon position in the corresponding wild-type ORF.

In certain embodiments, the ORF further comprises at least one low-frequency codon.

In some embodiments, the ORF has at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from the group consisting of SEQ ID NOs: 3 to 27, 79 to 80, and 141 to 159. In some embodiments, the ORF has at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOs: 3 to 27, 79 to 80, and 141 to 159. In some embodiments, the ORF has at least 85%, at least 90%, at least 91%, at least 92%, at least 93%, at least 94%, at least 95%, at least 96%, at least 97%, at least 98%, at least 99%, or 100% sequence identity to the nucleic acid sequence of SEQ ID NO: 79 or 80. In some embodiments, the ORF has at least 95%, at least 96%, at least 97%, at least 98%, at least 99%, or 100% sequence identity to the nucleic acid sequence of SEQ ID NO: 79 or 80. In some embodiments, the ORF comprises the nucleic acid sequence of SEQ ID NO: 79 or 80.

In certain embodiments, the GLA polypeptide comprises an amino acid sequence at least about 95%, at least about 96%, at least about 97%, at least about 98%, at least about 99%, or about 100% identical to the polypeptide sequence of wild type GLA (SEQ ID NO: 1), and wherein the GLA polypeptide has α-galactosidase activity.

In certain embodiments, the GLA polypeptide is a variant, derivative, or mutant having a α-galactosidase activity.

In certain embodiments, the polynucleotide sequence further comprises a nucleotide sequence encoding a transit peptide.

In some embodiments, the polynucleotide is single stranded. In some embodiments, the polynucleotide is double stranded. In some embodiments, the polynucleotide is DNA. In some embodiments, the polynucleotide is RNA. In some embodiments, the polynucleotide is mRNA.

In some embodiments, the polynucleotide comprises at least one chemically modified nucleobase, sugar, backbone, or any combination thereof. In some embodiments, the at least one chemically modified nucleobase is selected from the group consisting of pseudouracil (ψ), N1-methylpseudouracil (m1ψ), 2-thiouracil (s2U), 4'-thiouracil, 5-methylcytosine, 5-methyluracil, and any combination thereof. In some embodiments, the at least one chemically modified nucleobase is selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof. In some embodiments, the at least one chemically modified nucleobase is 5-methoxyuracil. In some embodiments, at least about 25%, at least about 30%, at least about 40%, at least about 50%, at least about 60%, at least about 70%, at least about 80%, at least about 90%, at least about 95%, at least about 99%, or 100% of the uracils are 5-methoxyuracils. In some embodiments, at least about 25%, at least about 30%, at least about 40%, at least about 50%, at least about 60%, at least about 70%, at least about 80%, at least about 90%, at least about 95%, at least about 99%, or 100% of the uracils or thymines are chemically modified. In some embodiments, at least about 25%, at least about 30%, at least about 40%, at least about 50%, at least about 60%, at least about 70%, at least about 80%, at least about 90%, at least about 95%, at least about 99%, or 100% of the guanines are chemically modified. In some embodiments, at least about 25%, at least about 30%, at least about 40%, at least about 50%, at least about 60%, at least about 70%, at least about 80%, at least about 90%, at least about 95%, at least about 99%, or 100% of the cytosines are chemically modified. In some embodiments, at least about 25%, at least about 30%, at least about 40%, at least about 50%, at least about 60%, at least about 70%, at least about 80%, at least about 90%, at least about 95%, at least about 99%, or 100% of the adenines are chemically modified.

In certain embodiments, the polynucleotide further comprises a microRNA binding site.

In certain embodiments, the microRNA binding site comprises one or more nucleotide sequences selected from Table 3 or Table 4.

In some embodiments, the polynucleotide comprises at least two different microRNA (miR) binding sites.

In some embodiments, the microRNA is expressed in an immune cell of hematopoietic lineage or a cell that expresses TLR7 and/or TLR8 and secretes pro-inflammatory cytokines and/or chemokines, and wherein the polynucleotide (e.g., mRNA) comprises one or more modified nucleobases.

In some embodiments, the mRNA comprises at least one first microRNA binding site of a microRNA abundant in an immune cell of hematopoietic lineage and at least one second microRNA binding site is of a microRNA abundant in endothelial cells.

In some embodiments, the mRNA comprises multiple copies of a first microRNA binding site and at least one copy of a second microRNA binding site.

In some embodiments, the mRNA comprises first and second microRNA binding sites of the same microRNA.

In some embodiments, the microRNA binding sites are of the 3p and 5p arms of the same microRNA.

In some embodiments, the microRNA binding site binds to miR-126, miR-142, miR-144, miR-146, miR-150, miR-155, miR-16, miR-21, miR-223, miR-24, miR-27, miR-26a, or any combination thereof.

In some embodiments, the microRNA binding site binds to miR126-3p, miR-142-3p, miR-142-5p, miR-155, or any combination thereof.

In some embodiments, the microRNA binding site is a miR-126 binding site. In some embodiments, at least one microRNA binding site is a miR-142 binding site. In some embodiments, one microRNA binding site is a miR-126 binding site and the second microRNA binding site is for a microRNA selected from the group consisting of miR-142-3p, miR-142-5p, miR-146-3p, miR-146-5p, miR-155, miR-16, miR-21, miR-223, miR-24 and miR-27.

In some embodiments, the mRNA comprises at least one miR-126-3p binding site and at least one miR-142-3p binding site. In some embodiments, the mRNA comprises at least one miR-142-3p binding site and at least one 142-5p binding site.

In some embodiments, the microRNA binding sites are located in the 5' UTR, 3' UTR, or both the 5' UTR and 3' UTR of the mRNA. In some embodiments, the microRNA binding sites are located in the 3' UTR of the mRNA. In some embodiments, the microRNA binding sites are located in the 5' UTR of the mRNA. In some embodiments, the microRNA binding sites are located in both the 5' UTR and 3' UTR of the mRNA. In some embodiments, at least one microRNA binding site is located in the 3' UTR immediately adjacent to the stop codon of the coding region of the mRNA. In some embodiments, at least one microRNA binding site is located in the 3' UTR 70-80 bases downstream of the stop codon of the coding region of the mRNA. In some embodiments, at least one microRNA binding site is located in the 5' UTR immediately preceding the start codon of the coding region of the mRNA. In some embodiments, at least one microRNA binding site is located in the 5' UTR 15-20 nucleotides preceding the start codon of the coding region of the mRNA. In some embodiments, at least one microRNA binding site is located in the 5' UTR 70-80 nucleotides preceding the start codon of the coding region of the mRNA.

In some embodiments, the mRNA comprises multiple copies of the same microRNA binding site positioned immediately adjacent to each other or with a spacer of less than 5, 5-10, 10-15, or 15-20 nucleotides.

In some embodiments, the mRNA comprises multiple copies of the same microRNA binding site located in the 3' UTR, wherein the first microRNA binding site is positioned immediately adjacent to the stop codon and the second and third microRNA binding sites are positioned 30-40 bases downstream of the 3' most residue of the first microRNA binding site.

In some embodiments, the microRNA binding site comprises one or more nucleotide sequences selected from SEQ ID NO:30 and SEQ ID NO:32. In some embodiments, the miRNA binding site binds to miR-142. In some embodiments, the miRNA binding site binds to miR-142-3p or miR-142-5p. In certain embodiments, the miR-142 comprises SEQ ID NO: 28.

In some embodiments, the microRNA binding site comprises one or more nucleotide sequences selected from SEQ ID NO:85 and SEQ ID NO:87. In some embodiments, the miRNA binding site binds to miR-126. In some embodiments, the miRNA binding site binds to miR-126-3p or miR-126-5p. In some embodiments, the miR-126 comprises SEQ ID NO: 83.

In some embodiments, the mRNA comprises a 3' UTR comprising a microRNA binding site that binds to miR-142, miR-126, or a combination thereof.

In some embodiments, the mRNA comprises a 3' UTR comprising a nucleic acid sequence at least about 90%, at least about 95%, at least about 96%, at least about 97%, at least about 98%, at least about 99%, or 100% identical to a 3' UTR sequence selected from the group consisting of SEQ ID NOs: 51 to 75, 81 to 82, 88, 103, 106 to 113, 118, and 161 to 170, or any combination thereof. In some embodiments, the 3' UTR comprises a nucleic acid sequence selected from the group consisting of SEQ ID NOs: 51 to 75, 81 to 82, 88, 103, 106 to 113, 118, and 161 to 170, and any combination thereof.

In certain embodiments, the polynucleotide, e.g., mRNA, further comprises a 5' UTR. In certain embodiments, the 5' UTR comprises a nucleic acid sequence at least 90%, at least about 95%, at least about 96%, at least about 97%, at least about 98%, at least about 99%, or about 100% identical to a 5' UTR sequence selected from the group consisting of SEQ ID NO: 33 to 50, 77, and 115 to 117, or any combination thereof. In some embodiments, the 5' UTR comprises a sequence selected from the group consisting of SEQ ID NO: 33 to 50, 77, and 115 to 117, and any combination thereof. In some embodiments, the mRNA comprises a 5' UTR comprising the nucleic acid sequence of SEQ ID NO: 33.

In certain embodiments, the polynucleotide, e.g., mRNA, further comprises a 5' terminal cap. In certain embodiments, the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof. In some embodiments, the 5' terminal cap comprises a Cap1.

In certain embodiments, the polynucleotide, e.g., mRNA, further comprises a poly-A region. In certain embodiments, the poly-A region is at least about 10, at least about 20, at least about 30, at least about 40, at least about 50, at least about 60, at least about 70, at least about 80, or at least about 90 nucleotides in length. In certain embodiments, the poly-A region has about 10 to about 200, about 20 to about 180, about 50 to about 160, about 70 to about 140, or about 80 to about 120 nucleotides in length.

In certain embodiments, the polynucleotide, e.g., mRNA, encodes a GLA polypeptide that is fused to one or more heterologous polypeptides. In certain embodiments, the one or more heterologous polypeptides increase a pharmacokinetic property of the GLA polypeptide. In certain embodiments, upon administration to a subject, the polynucleotide has: (i) a longer plasma half-life; (ii) increased expression of a GLA polypeptide encoded by the ORF; (iii) greater structural stability; or (iv) any combination thereof, relative to a corresponding polynucleotide comprising SEQ ID NO: 2.

In certain embodiments, the polynucleotide, e.g., mRNA, comprises: (i) a 5'-terminal cap; (ii) a 5'-UTR; (iii) an ORF encoding a GLA polypeptide; (iv) a 3'-UTR; and (v) a poly-A region. In certain embodiments, the 3'-UTR comprises a miRNA binding site. In some embodiments, the polynucleotide comprises a nucleic acid sequence selected from the group consisting of SEQ ID NO: 119 to 120, 122 to 140, and 160 for example, SEQ ID NO: 119 or 120. In some embodiments the polynucleotide further comprises a 5'-terminal cap (e.g., Cap1) and a poly-A-tail region (e.g., about 100 nucleotides in length).

In certain aspects, the invention relates to a method of producing the polynucleotide, e.g., mRNA, of the present invention, the method comprising modifying an ORF encoding a GLA polypeptide by substituting at least one uracil nucleobase with an adenine, guanine, or cytosine nucleobase, or by substituting at least one adenine, guanine, or cytosine nucleobase with a uracil nucleobase, wherein all the substitutions are synonymous substitutions. In certain embodiments, the method further comprises replacing at least about 90%, at least about 95%, at least about 99%, or about 100% of uracils with 5-methoxyuracils.

In certain aspects, the invention relates to a composition comprising (a) the polynucleotide, e.g., mRNA, of the invention, and (b) a delivery agent. In certain embodiments, the delivery agent comprises a lipidoid, a liposome, a lipoplex, a lipid nanoparticle, a polymeric compound, a peptide, a protein, a cell, a nanoparticle mimic, a nanotube, or a conjugate. In certain embodiments, the delivery agent comprises a lipid nanoparticle. In certain embodiments, the lipid nanoparticle comprises a lipid selected from the group consisting of 3-(didodecylamino)-N1,N1,4-tridodecyl-1-piperazineethanamine (KL10), N1-[2-(didodecylamino) ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)[1,3]-dioxolane (DLin-KC2-DMA), 1,2-dioleyloxy-N,N-dimethylaminopropane (DODMA), (13Z,16Z)—N,N-dimethyl-3-nonydocosa-13-16-dien-1-amine (L608), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy] octyl}oxy)-N,N-dimethyl-3-[(9Z,12Z)-octadeca-9,12-dien-1-yloxy]propan-1-amine (Octyl-CLinDMA (2R)), (2 S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)), and any combination thereof. In some embodiments, the lipid nanoparticle comprises DLin-MC3-DMA.

In certain embodiments, the delivery agent comprises a compound having the Formula (I)

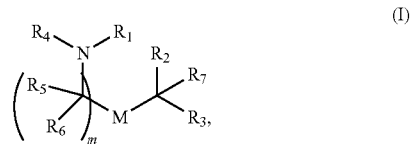

or a salt or stereoisomer thereof, wherein
$R_1$ is selected from the group consisting of $C_{5-30}$ alkyl, $C_{5-20}$ alkenyl, —R*YR", —YR", and —R"M'R';
$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O) R, —N(R)S(O)$_2$R, —N(R)C(O)N(R)$_2$, —N(R)C(S)N (R)$_2$, —N(R)R$_8$, —O(CH$_2$)$_n$OR, —N(R)C(=NR$_9$)N (R)$_2$, —N(R)C(=CHR$_9$)N(R)$_2$, —OC(O)N(R)$_2$, —N(R)C(O)OR, N(OR)C(O)R, —N(OR)S(O)$_2$R, —N(OR)C(O)OR, —N(OR)C(O)N(R)$_2$, —N(OR) C(S)N(R)$_2$, —N(OR)C(=NR$_9$)N(R)$_2$, —N(OR)C (=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH (OH)—, —P(O)(OR')O—, —S(O)$_2$—, —S—S—, an aryl group, and a heteroaryl group;
$R_7$ is selected from the group consisting of $C_{1-3}$ alkyl, $C_{2-3}$ alkenyl, and H;
$R_8$ is selected from the group consisting of $C_{3-6}$ carbocycle and heterocycle;
$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;
each R is independently selected from the group consisting of $C_{1-3}$ alkyl, $C_{2-3}$ alkenyl, and H;
each R' is independently selected from the group consisting of $C_{1-18}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{2-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13; and provided when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In certain aspects, the invention relates to a composition comprising a nucleotide sequence encoding a GLA polypeptide and a delivery agent, wherein the delivery agent comprises a compound having the Formula (I)

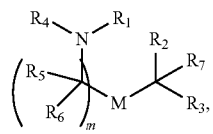

or a salt or stereoisomer thereof, wherein
$R_1$ is selected from the group consisting of $C_{5-30}$ alkyl, $C_{5-20}$ alkenyl, —R*YR", —YR", and —R"M'R';
$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of a $C_{3-6}$ carbocycle, —$(CH_2)_nQ$, —$(CH_2)_n$CHQR, —CHQR, —CQ$(R)_2$, and unsubstituted $C_{1-6}$ alkyl, where Q is selected from a carbocycle, heterocycle, —OR, —O$(CH_2)_n$N$(R)_2$, —C(O)OR, —OC(O)R, —CX$_3$, —CX$_2$H, —CXH$_2$, —CN, —N$(R)_2$, —C(O)N$(R)_2$, —N(R)C(O)R, —N(R)S(O)$_2$R, —N(R)C(O)N$(R)_2$, —N(R)C(S)N$(R)_2$, —N(R)R$_8$, —O$(CH_2)_n$OR, —N(R)C(=NR$_9$)N$(R)_2$, —N(R)C(=CHR$_9$)N$(R)_2$, —OC(O)N$(R)_2$, —N(R)C(O)OR, —N(OR)C(O)R, —N(OR)S(O)$_2$R, —N(OR)C(O)OR, —N(OR)C(O)N$(R)_2$, —N(OR)C(S)N$(R)_2$, —N(OR)C(=NR$_9$)N$(R)_2$, —N(OR)C(=CHR$_9$)N$(R)_2$, —C(=NR$_9$)N$(R)_2$, —C(=NR$_9$)R, —C(O)N(R)OR, and —C(R)N$(R)_2$C(O)OR, and each n is independently selected from 1, 2, 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;
$R_7$ is selected from the group consisting of $C_{1-3}$ alkyl, $C_{2-3}$ alkenyl, and H;
$R_8$ is selected from the group consisting of $C_{3-6}$ carbocycle and heterocycle;
$R_9$ is selected from the group consisting of H, CN, NO$_2$, $C_{1-6}$ alkyl, —OR, —S(O)$_2$R, —S(O)$_2$N$(R)_2$, $C_{2-6}$ alkenyl, $C_{3-6}$ carbocycle and heterocycle;
each R is independently selected from the group consisting of $C_{1-3}$ alkyl, $C_{2-3}$ alkenyl, and H;
each R' is independently selected from the group consisting of $C_{1-18}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{2-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13; and provided when $R_4$ is —$(CH_2)_nQ$, —$(CH_2)_n$CHQR, —CHQR, or —CQ$(R)_2$, then (i) Q is not —N$(R)_2$ when n is 1, 2, 3, 4 or 5, or (ii) Q is not 5, 6, or 7-membered heterocycloalkyl when n is 1 or 2.

In some embodiments, the delivery agent comprises a compound having the Formula (I), or a salt or stereoisomer thereof, wherein
$R_1$ is selected from the group consisting of $C_{5-20}$ alkyl, $C_{5-20}$ alkenyl, —R*YR", —YR", and —R"M'R';
$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of a $C_{3-6}$ carbocycle, —$(CH_2)_nQ$, —$(CH_2)_n$CHQR, —CHQR, —CQ$(R)_2$, and unsubstituted $C_{1-6}$ alkyl, where Q is selected from a carbocycle, heterocycle, —OR, —O$(CH_2)_n$N$(R)_2$, —C(O)OR, —OC(O)R, —CX$_3$, —CX$_2$H, —CXH$_2$, —CN, —N$(R)_2$, —C(O)N$(R)_2$, —N(R)C(O)R, —N(R)S(O)$_2$R, —N(R)C(O)N$(R)_2$, —N(R)C(S)N$(R)_2$, and —C(R)N$(R)_2$C(O)OR, and each n is independently selected from 1, 2, 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;
$R_7$ is selected from the group consisting of $C_{1-3}$ alkyl, $C_{2-3}$ alkenyl, and H;
each R is independently selected from the group consisting of $C_{1-3}$ alkyl, $C_{2-3}$ alkenyl, and H;
each R' is independently selected from the group consisting of $C_{1-18}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{2-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13; and provided when $R_4$ is —$(CH_2)_nQ$, —$(CH_2)_n$CHQR, —CHQR, or —CQ$(R)_2$, then (i) Q is not —N$(R)_2$ when n is 1, 2, 3, 4 or 5, or (ii) Q is not 5, 6, or 7-membered heterocycloalkyl when n is 1 or 2.

In certain embodiments, the compound is of Formula (IA):

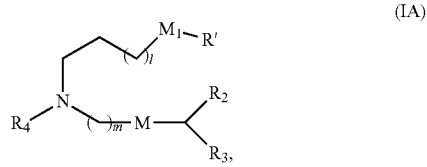

or a salt or stereoisomer thereof, wherein
l is selected from 1, 2, 3, 4, and 5;
m is selected from 5, 6, 7, 8, and 9;
$M_1$ is a bond or M';
$R_4$ is unsubstituted $C_{1-3}$ alkyl, or —$(CH_2)_n$Q, in which n is 1, 2, 3, 4, or 5 and Q is OH, —NHC(S)N$(R)_2$, —NHC(O)N$(R)_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl, or heterocycloalkyl;

M and M' are independently selected from —C(O)O—, —OC(O)—, —C(O)N(R')—, —P(O)(OR')O—, —S—S—, an aryl group, and a heteroaryl group; and R$_2$ and R$_3$ are independently selected from the group consisting of H, C$_{1-14}$ alkyl, and C$_{2-14}$ alkenyl.

In certain embodiments, m is 5, 7, or 9.

In some embodiments, the compound is of Formula (IA), or a salt or stereoisomer thereof, wherein l is selected from 1, 2, 3, 4, and 5;
m is selected from 5, 6, 7, 8, and 9;
M$_1$ is a bond or M';
R$_4$ is unsubstituted C$_{1-3}$ alkyl, or —(CH$_2$)$_n$Q, in which n is 1, 2, 3, 4, or 5 and Q is OH, —NHC(S)N(R)$_2$, or —NHC(O)N(R)$_2$;

M and M' are independently selected from —C(O)O—, —OC(O)—, —C(O)N(R')—, —P(O)(OR')O—, an aryl group, and a heteroaryl group; and R$_2$ and R$_3$ are independently selected from the group consisting of H, C$_{1-14}$ alkyl, and C$_{2-14}$ alkenyl.

In some embodiments, m is 5, 7, or 9.

In certain embodiments, the compound is of Formula (II):

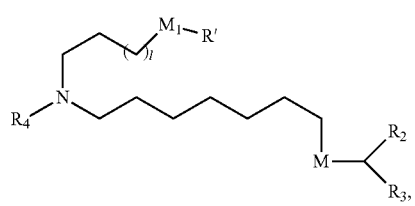

(II)

or a salt or stereoisomer thereof, wherein
l is selected from 1, 2, 3, 4, and 5;
M$_1$ is a bond or M';
R$_4$ is unsubstituted C$_{1-3}$ alkyl, or —(CH$_2$)$_n$Q, in which n is 2, 3, or 4 and Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl, or heterocycloalkyl; M and M' are independently selected from —C(O)O—, —OC(O)—, —C(O)N(R')—, —P(O)(OR')O—, —S—S—, an aryl group, and a heteroaryl group; and R$_2$ and R$_3$ are independently selected from the group consisting of H, C$_{1-14}$ alkyl, and C$_{2-14}$ alkenyl.

In some embodiments, the compound is of Formula (II), or a salt or stereoisomer thereof, wherein
l is selected from 1, 2, 3, 4, and 5;
M$_1$ is a bond or M';
R$_4$ is unsubstituted C$_{1-3}$ alkyl, or —(CH$_2$)$_n$Q, in which n is 2, 3, or 4 and Q is OH, —NHC(S)N(R)$_2$, or —NHC(O)N(R)$_2$;

M and M' are independently selected from —C(O)O—, —OC(O)—, —C(O)N(R')—, —P(O)(OR')O—, an aryl group, and a heteroaryl group; and R$_2$ and R$_3$ are independently selected from the group consisting of H, C$_{1-14}$ alkyl, and C$_{2-14}$ alkenyl.

In some embodiments, M$_1$ is M'.
In some embodiments, M and M' are independently —C(O)O— or —OC(O)—.

In some embodiments, l is 1, 3, or 5.

In some embodiments, the compound is selected from the group consisting of Compound 1 to Compound 232, salts and stereoisomers thereof, and any combination thereof.

In some embodiments, the compound is selected from the group consisting of Compound 1 to Compound 147, salts and stereoisomers thereof, and any combination thereof.

In certain embodiments, the compound is of the Formula (IIa),

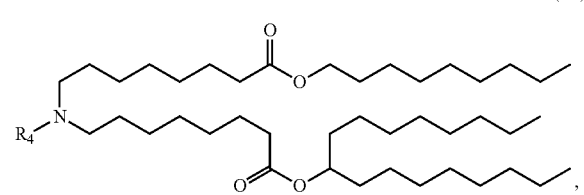

(IIa)

or a salt or stereoisomer thereof.

In certain embodiments, the compound is of the Formula (IIb),

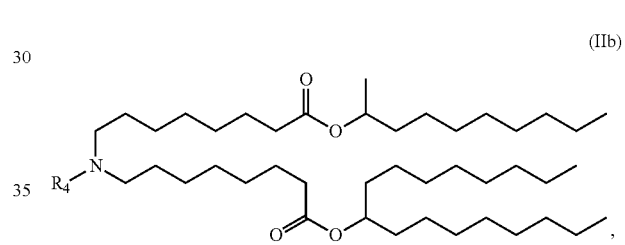

(IIb)

or a salt or stereoisomer thereof.

In certain embodiments, the compound is of the Formula (IIc) or (IIe),

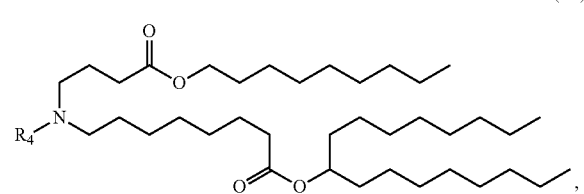

(IIc)

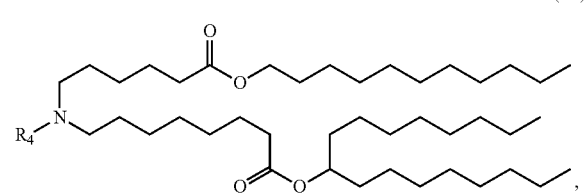

(IIe)

or a salt or stereoisomer thereof.

In certain embodiments, R$_4$ is as described herein. In some embodiments, R$_4$ is selected from —(CH$_2$)$_n$Q and —(CH$_2$)$_n$CHQR.

In certain embodiments, the compound is of the Formula (IId),

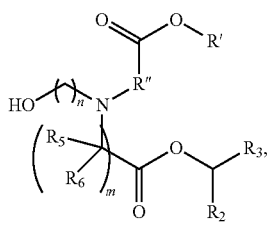
(IId)

or a salt or stereoisomer thereof,
wherein n is selected from 2, 3, and 4, and m, R', R", and R$_2$ through R$_6$ are as described herein. For example, each of R$_2$ and R$_3$ may be independently selected from the group consisting of C$_{5-14}$ alkyl and C$_{5-14}$ alkenyl.

In some embodiments, the compound is of the Formula (IId), or a salt or stereoisomer thereof,
wherein R$_2$ and R$_3$ are independently selected from the group consisting of C$_{5-14}$ alkyl and C$_{5-14}$ alkenyl, n is selected from 2, 3, and 4, and R', R", R$_5$, R$_6$ and m are as defined herein.

In some embodiments, R$_2$ is C$_8$ alkyl.
In some embodiments, R$_3$ is C$_5$ alkyl, C$_6$ alkyl, C$_7$ alkyl, C$_8$ alkyl, or C$_9$ alkyl.
In some embodiments, m is 5, 7, or 9.
In some embodiments, each R$_5$ is H.
In some embodiments, each R$_6$ is H. In some embodiments, the delivery agent comprises a compound having the Formula (III)

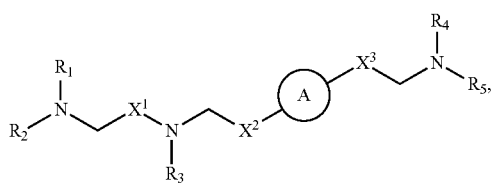
(III)

or salts or stereoisomers thereof, wherein
ring A is

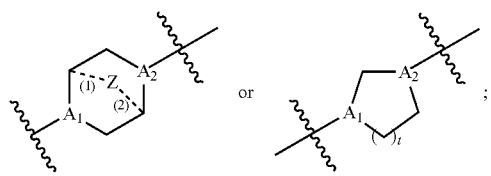

t is 1 or 2;
A$_1$ and A$_2$ are each independently selected from CH or N;
Z is CH$_2$ or absent wherein when Z is CH$_2$, the dashed lines (1) and (2) each represent a single bond; and when Z is absent, the dashed lines (1) and (2) are both absent;
R$_1$, R$_2$, R$_3$, R$_4$, and R$_5$ are independently selected from the group consisting of C$_{5-20}$ alkyl, C$_{5-20}$ alkenyl, —R"MR', —R*YR", —YR", and —R*OR";
each M is independently selected from the group consisting of —C(O)O—, —OC(O)—, —OC(O)O—, —C(O)N(R')—, —N(R')C(O)—, —C(O)—, —C(S)—, —C(S)S—, —S C(S)—, —CH(OH)—, —P(O)(OR')O—, —S(O)$_2$—, an aryl group, and a heteroaryl group;
X$^1$, X$^2$, and X$^3$ are independently selected from the group consisting of a bond, —CH$_2$—, —(CH$_2$)$_2$—, —CHR—, —CHY—, —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, —CH$_2$—OC(O)—, —CH(OH)—, —C(S)—, and —CH(SH)—;
each Y is independently a C$_{3-6}$ carbocycle;
each R* is independently selected from the group consisting of C$_{1-12}$ alkyl and C$_{2-12}$ alkenyl;
each R is independently selected from the group consisting of C$_{1-3}$ alkyl and a C$_{3-6}$ carbocycle;
each R' is independently selected from the group consisting of C$_{1-12}$ alkyl, C$_{2-12}$ alkenyl, and H; and
each R" is independently selected from the group consisting of C$_{3-12}$ alkyl and C$_{3-12}$ alkenyl,
wherein when ring A is

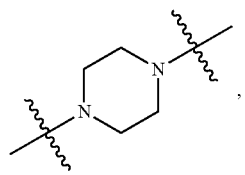 [SMILES: *N1CCN(*)CC1]

then
i) at least one of X$^1$, X$^2$, and X$^3$ is not —CH$_2$—; and/or
ii) at least one of R$_1$, R$_2$, R$_3$, R$_4$, and R$_5$ is —R"MR'.

In some embodiments, the compound is of any of Formulae (IIIa1)-(IIIa6):

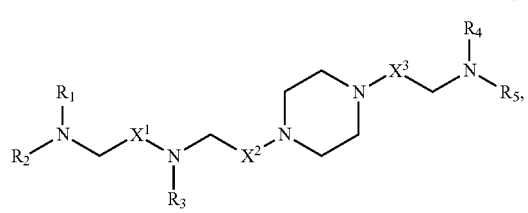
(IIIa1)

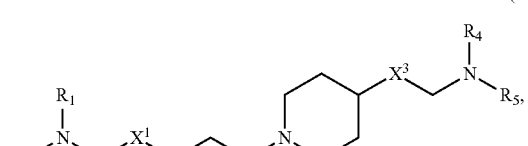
(IIIa2)

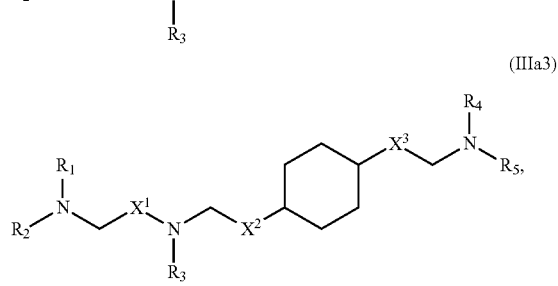
(IIIa3)

-continued (IIIa4)

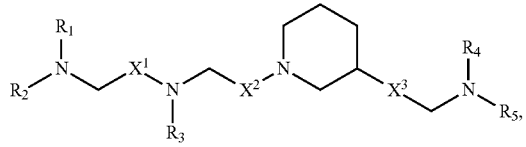

(IIIa5)

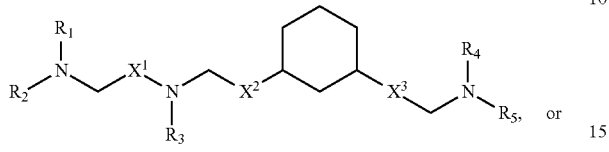

(IIIa6)

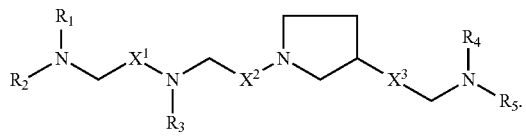

The compounds of Formula (III) or any of (IIIa1)-(IIIa6) include one or more of the following features when applicable.

In some embodiments, ring A is

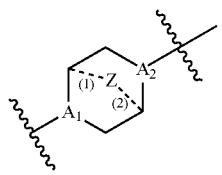

In some embodiments, ring A is

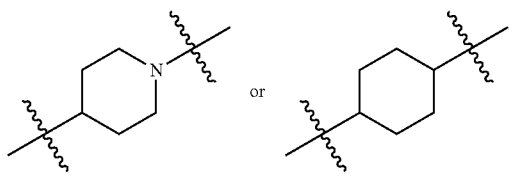

In some embodiments, ring A is

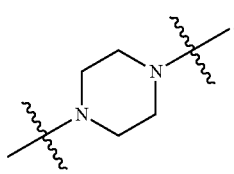

In some embodiments, ring A is

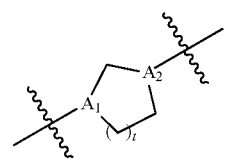

In some embodiments, ring A is

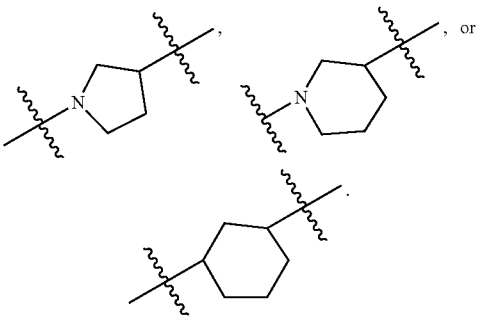

In some embodiments, ring A is

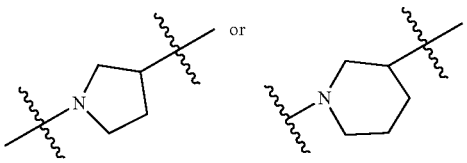 [SMILES: *C1CCN(*)C1 ; *C1CCCN(*)C1]

wherein ring, in which the N atom is connected with $X^2$.

In some embodiments, Z is $CH_2$.

In some embodiments, Z is absent.

In some embodiments, at least one of $A_1$ and $A_2$ is N.

In some embodiments, each of $A_1$ and $A_2$ is N.

In some embodiments, each of $A_1$ and $A_2$ is CH.

In some embodiments, $A_1$ is N and $A_2$ is CH.

In some embodiments, $A_1$ is CH and $A_2$ is N.

In some embodiments, at least one of $X^1$, $X^2$, and $X^3$ is not —$CH_2$—. For example, in certain embodiments, $X^1$ is not —$CH_2$—. In some embodiments, at least one of $X^1$, $X^2$, and $X^3$ is —C(O)—.

In some embodiments, $X^2$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—.

In some embodiments, $X^3$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—. In other embodiments, $X^3$ is —$CH_2$—.

In some embodiments, $X^3$ is a bond or —$(CH_2)_2$—.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is —R"MR'. In some embodiments, at most one of $R_1$, $R_2$, $R_3$, $R_4$, and $R_5$ is —R"MR'. For example, at least one of $R_1$, $R_2$, and $R_3$ may be —R"MR', and/or at least one of $R_4$ and $R_5$ is —R"MR'. In certain embodiments, at least one M is —C(O)O—. In some embodiments, each M is —C(O)O—. In some embodiments, at least one M is —OC(O)—. In some embodiments, each M is —OC(O)—. In some embodiments, at least one M is —OC(O)O—. In some embodiments, each M is —OC(O)O—. In some embodiments, at least one R" is $C_3$ alkyl. In certain embodiments, each R" is $C_3$ alkyl. In some embodiments, each R" is $C_5$ alkyl. In certain embodiments, each R" is $C_5$ alkyl. In some embodiments, at least one R" is $C_6$ alkyl. In certain embodiments, each R" is $C_6$ alkyl. In some embodiments, at least one R" is $C_7$ alkyl. In certain embodiments, each R" is $C_7$ alkyl. In some embodiments, at least one R' is $C_5$ alkyl. In certain embodiments, each R' is $C_5$ alkyl. In other embodiments, at least one R' is $C_1$ alkyl. In certain embodiments, each R' is $C_1$ alkyl. In some embodiments, at least one R' is $C_2$ alkyl. In certain embodiments, each R' is $C_2$ alkyl.

In some embodiments, at least one of $R_1$, $R_2$, $R_3$, $R_4$, and $R_5$ is $C_{12}$ alkyl. In certain embodiments, each of $R_1$, $R_2$, $R_3$, $R_4$, and $R_5$ are $C_{12}$ alkyl.

In some embodiments, the delivery agent comprises a compound having the Formula (IV)

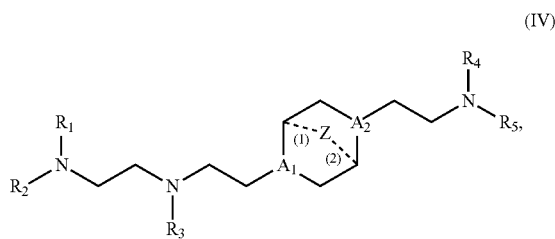

(IV)

or salts or stereoisomer thereof, wherein $A_1$ and $A_2$ are each independently selected from CH or N and at least one of $A_1$ and $A_2$ is N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{6-20}$ alkyl and $C_{6-20}$ alkenyl;

wherein when ring A is

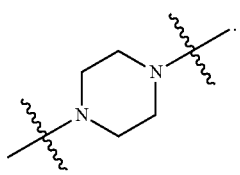 [SMILES: *N1CCN(*)CC1]

then i) $R_1$, $R_2$, $R_3$, $R_4$, and $R_5$ are the same, wherein $R_1$ is not $C_{12}$ alkyl, $C_{18}$ alkyl, or $C_{18}$ alkenyl;

ii) only one of $R_1$, $R_2$, $R_3$, $R_4$, and $R_5$ is selected from $C_{6-20}$ alkenyl;

iii) at least one of $R_1$, $R_2$, $R_3$, $R_4$, and $R_5$ have a different number of carbon atoms than at least one other of $R_1$, $R_2$, $R_3$, $R_4$, and $R_5$;

iv) $R_1$, $R_2$, and $R_3$ are selected from $C_{6-20}$ alkenyl, and $R_4$ and $R_5$ are selected from $C_{6-20}$ alkyl; or v) $R_1$, $R_2$, and $R_3$ are selected from $C_{6-20}$ alkyl, and $R_4$ and $R_5$ are selected from $C_{6-20}$ alkenyl.

In some embodiments, the compound is of Formula (IVa):

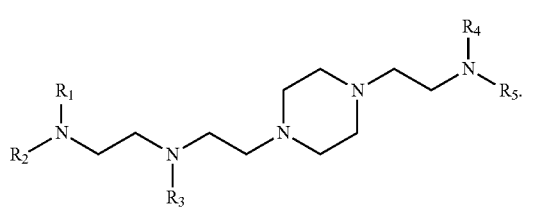

(IVa)

The compounds of Formula (IV) or (IVa) include one or more of the following features when applicable.

In some embodiments, Z is $CH_2$.
In some embodiments, Z is absent.
In some embodiments, at least one of $A_1$ and $A_2$ is N.
In some embodiments, each of $A_1$ and $A_2$ is N.
In some embodiments, each of $A_1$ and $A_2$ is CH.
In some embodiments, $A_1$ is N and $A_2$ is CH.
In some embodiments, $A_1$ is CH and $A_2$ is N.
In some embodiments, $R_1$, $R_2$, $R_3$, $R_4$, and $R_5$ are the same, and are not $C_{12}$ alkyl, $C_{18}$ alkyl, or $C_{18}$ alkenyl. In some embodiments, $R_1$, $R_2$, $R_3$, $R_4$, and $R_5$ are the same and are $C_9$ alkyl or $C_{14}$ alkyl.

In some embodiments, only one of $R_1$, $R_2$, $R_3$, $R_4$, and $R_5$ is selected from $C_{6-20}$ alkenyl. In certain such embodiments, $R_1$, $R_2$, $R_3$, $R_4$, and $R_5$ have the same number of carbon atoms. In some embodiments, $R_4$ is selected from $C_{5-20}$ alkenyl. For example, $R_4$ may be $C_{12}$ alkenyl or $C_{18}$ alkenyl.

In some embodiments, at least one of $R_1$, $R_2$, $R_3$, $R_4$, and $R_5$ have a different number of carbon atoms than at least one other of $R_1$, $R_2$, $R_3$, $R_4$, and $R_5$.

In certain embodiments, $R_1$, $R_2$, and $R_3$ are selected from $C_{6-20}$ alkenyl, and $R_4$ and $R_5$ are selected from $C_{6-20}$ alkyl. In other embodiments, $R_1$, $R_2$, and $R_3$ are selected from $C_{6-20}$ alkyl, and $R_4$ and $R_5$ are selected from $C_{6-20}$ alkenyl. In some embodiments, $R_1$, $R_2$, and $R_3$ have the same number of carbon atoms, and/or $R_4$ and $R_5$ have the same number of carbon atoms. For example, $R_1$, $R_2$, and $R_3$, or $R_4$ and $R_5$, may have 6, 8, 9, 12, 14, or 18 carbon atoms. In some embodiments, $R_1$, $R_2$, and $R_3$, or $R_4$ and $R_5$, are $C_{18}$ alkenyl (e.g., linoleyl). In some embodiments, $R_1$, $R_2$, and $R_3$, or $R_4$ and $R_5$, are alkyl groups including 6, 8, 9, 12, or 14 carbon atoms.

In some embodiments, $R_1$ has a different number of carbon atoms than $R_2$, $R_3$, $R_4$, and $R_5$. In other embodiments, $R_3$ has a different number of carbon atoms than $R_1$, $R_2$, $R_4$, and $R_5$. In further embodiments, $R_4$ has a different number of carbon atoms than $R_1$, $R_2$, $R_3$, and $R_5$.

In other embodiments, the delivery agent comprises a compound having the Formula (V)

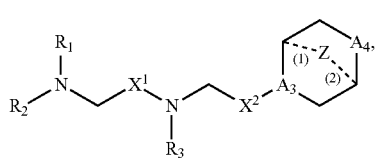

(V)

or salts or stereoisomers thereof, in which $A_3$ is CH or N;

$A_4$ is $CH_2$ or NH; and at least one of $A_3$ and $A_4$ is N or NH;

Z is $CH_2$ or absent wherein when Z is $CH_2$, the dashed lines (1) and (2) each represent a single bond; and when Z is absent, the dashed lines (1) and (2) are both absent;

$R_1$, $R_2$, and $R_3$ are independently selected from the group consisting of $C_{5-20}$ alkyl, $C_{5-20}$ alkenyl, —R"MR', —R*YR", —YR", and —R*OR";

each M is independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$X^1$ and $X^2$ are independently selected from the group consisting of —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—

—CH$_2$—, —OC(O)—CH$_2$—, —CH$_2$—C(O)O—, —CH$_2$—OC(O)—, —CH(OH)—, —C(S)—, and —CH(SH)—;

each Y is independently a C$_{3-6}$ carbocycle;
each R* is independently selected from the group consisting of C$_{1-12}$ alkyl and C$_{2-12}$ alkenyl;
each R is independently selected from the group consisting of C$_{1-3}$ alkyl and a C$_{3-6}$ carbocycle;
each R' is independently selected from the group consisting of C$_{1-12}$ alkyl, C$_{2-12}$ alkenyl, and H; and
each R" is independently selected from the group consisting of C$_{3-12}$ alkyl and C$_{3-12}$ alkenyl.

In some embodiments, the compound is of Formula (Va):

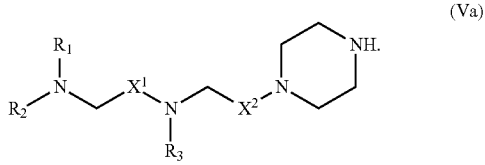

(Va)

The compounds of Formula (V) or (Va) include one or more of the following features when applicable.

In some embodiments, Z is CH$_2$.
In some embodiments, Z is absent.
In some embodiments, at least one of A$_3$ and A$_4$ is N or NH.
In some embodiments, A$_3$ is N and A$_4$ is NH.
In some embodiments, A$_3$ is N and A$_4$ is CH$_2$.
In some embodiments, A$_3$ is CH and A$_4$ is NH.
In some embodiments, at least one of X$^1$ and X$^2$ is not —CH$_2$—. For example, in certain embodiments, X$^1$ is not —CH$_2$—. In some embodiments, at least one of X$^1$ and X$^2$ is —C(O)—.
In some embodiments, X$^2$ is —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, or —CH$_2$—OC(O)—.
In some embodiments, R$^1$, R$_2$, and R$_3$ are independently selected from the group consisting of C$_{5-20}$ alkyl and C$_{5-20}$ alkenyl. In some embodiments, R$_1$, R$_2$, and R$_3$ are the same. In certain embodiments, R$_1$, R$_2$, and R$_3$ are C$_6$, C$_9$, C$_{12}$, or C$_{14}$ alkyl. In other embodiments, R$_1$, R$_2$, and R$_3$ are C$_{18}$ alkenyl. For example, R$_1$, R$_2$, and R$_3$ may be linoleyl.

In other embodiments, the delivery agent comprises a compound having the Formula (VI):

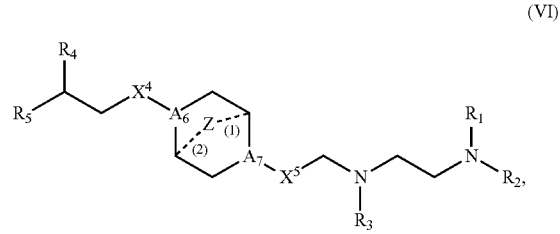

(VI)

or salts or stereoisomers thereof, in which
A$_6$ and A$_7$ are each independently selected from CH or N, wherein at least one of A$_6$ and A$_7$ is N;
Z is CH$_2$ or absent wherein when Z is CH$_2$, the dashed lines (1) and (2) each represent a single bond; and when Z is absent, the dashed lines (1) and (2) are both absent;

X$^4$ and X$^5$ are independently selected from the group consisting of —CH$_2$—, —(CH$_2$)$_2$—, —CHR—, —CHY—, —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, —CH$_2$—OC(O)—, —CH(OH)—, —C(S)—, and —CH(SH)—;

R$_1$, R$_2$, R$_3$, R$_4$, and R$_5$ each are independently selected from the group consisting of C$_{5-20}$ alkyl, C$_{5-20}$ alkenyl, —R"MR', —R*YR", —YR", and —R*OR";

each M is independently selected from the group consisting of —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;
each Y is independently a C$_{3-6}$ carbocycle;
each R* is independently selected from the group consisting of C$_{1-12}$ alkyl and C$_{2-12}$ alkenyl;
each R is independently selected from the group consisting of C$_{1-3}$ alkyl and a C$_{3-6}$ carbocycle;
each R' is independently selected from the group consisting of C$_{1-12}$ alkyl, C$_{2-12}$ alkenyl, and H; and
each R" is independently selected from the group consisting of C$_{3-12}$ alkyl and C$_{3-12}$ alkenyl.

In some embodiments, R$_1$, R$_2$, R$_3$, R$_4$, and R$_5$ each are independently selected from the group consisting of C$_{6-20}$ alkyl and C$_{6-20}$ alkenyl.

In some embodiments, R$_1$ and R$_2$ are the same. In certain embodiments, R$_1$, R$_2$, and R$_3$ are the same. In some embodiments, R$_4$ and R$_5$ are the same. In certain embodiments, R$_1$, R$_2$, R$_3$, R$_4$, and R$_5$ are the same.

In some embodiments, at least one of R$_1$, R$_2$, R$_3$, R$_4$, and R$_5$ is C$_{9-12}$ alkyl. In certain embodiments, each of R$_1$, R$_2$, R$_3$, R$_4$, and R$_5$ independently is C$_9$, C$_{12}$ or C$_{14}$ alkyl. In certain embodiments, each of R$_1$, R$_2$, R$_3$, R$_4$, and R$_5$ is C$_9$ alkyl.

In some embodiments, A$_6$ is N and A$_7$ is N. In some embodiments, A$_6$ is CH and A$_7$ is N.

In some embodiments, X$^4$ is —CH$_2$— and X$^5$ is —C(O)—. In some embodiments, X$^4$ and X$^5$ are —C(O)—.

In some embodiments, when A$_6$ is N and A$_7$ is N, at least one of X$^4$ and X$^5$ is not —CH$_2$—, e.g., at least one of X$^4$ and X$^5$ is —C(O)—. In some embodiments, when A$_6$ is N and A$_7$ is N, at least one of R$_1$, R$_2$, R$_3$, R$_4$, and R$_5$ is —R"MR'.

In some embodiments, at least one of R$_1$, R$_2$, R$_3$, R$_4$, and R$_5$ is not —R"MR'.

In certain embodiments, the composition is a nanoparticle composition.

In certain embodiments, the delivery agent further comprises a phospholipid.

In certain embodiments, the phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16:0 PE), 1,2-distearoyl-sn-glycero-3-phosphoethanolamine, 1,2- dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and any mixtures thereof.

In certain embodiments, the delivery agent further comprises a structural lipid.

In certain embodiments, the structural lipid is selected from the group consisting of cholesterol, fecosterol, sitosterol, ergosterol, campesterol, stigmasterol, brassicasterol, tomatidine, ursolic acid, alpha-tocopherol, and any mixtures thereof.

In certain embodiments, the delivery agent further comprises a PEG lipid.

In certain embodiments, the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and any mixtures thereof. In some embodiments, the PEG lipid has the formula:

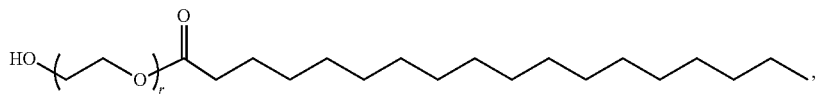

wherein r is an integer between 1 and 100. In some embodiments, the PEG lipid is Compound 428.

In certain embodiments, the delivery agent further comprises an ionizable lipid selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)).

In certain embodiments, the delivery agent further comprises a phospholipid, a structural lipid, a PEG lipid, or any combination thereof. In some embodiments, the delivery agent comprises Compound 18, DSPC, Cholesterol, and Compound 428, e.g., with a mole ratio of about 50:10:38.5:1.5.

In certain embodiments, the composition is formulated for in vivo delivery.

In certain embodiments, the composition is formulated for intramuscular, subcutaneous, or intradermal delivery.

The present disclosure further provides a polynucleotide comprising an mRNA comprising: (i) a 5' UTR, (ii) an open reading frame (ORF) encoding a human α-galactosidase A (GLA) polypeptide, wherein the ORF comprises a nucleic acid sequence selected from the group consisting of SEQ ID NOs: 3 to 27, 79 to 80, and 141 to 159, and (iii) a 3' UTR comprising a microRNA binding site selected from miR-142, miR-126, or a combination thereof, wherein the mRNA comprises at least one chemically modified nucleobase.

The present disclosure further provides a polynucleotide comprising an mRNA comprising: (i) a 5'-terminal cap; (ii) a 5' UTR comprising a sequence selected from the group consisting of SEQ ID NO: 33 to 50, 77, and 115 to 117, and any combination thereof; (iii) an open reading frame (ORF) encoding a human α-galactosidase A (GLA) polypeptide, wherein the ORF comprises a sequence selected from the group consisting of SEQ ID NOs: 3 to 27, 79 to 80, and 141 to 159, wherein the mRNA comprises at least one chemically modified nucleobase selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof; and (iv) a 3' UTR comprising a nucleic acid sequence selected from the group consisting of SEQ ID NOs: 51 to 75, 81 to 82, 88, 103, 106 to 113, 118, and 161 to 170, and any combination thereof and (v) a poly-A-region.

In some embodiments, the polynucleotide comprises a nucleic acid sequence selected from the group consisting of SEQ ID NOs: 119-120, 122-140, and 160, e.g., SEQ ID NO: 119 or 120.

The present disclosure further provides a pharmaceutical composition comprising the polynucleotide, e.g., an mRNA, and a delivery agent. In some embodiments, the delivery agent is a lipid nanoparticle comprising Compound 18, Compound 236, a salt or a stereoisomer thereof, or any combination thereof. In some embodiments, the polynucleotide comprising a nucleotide sequence encoding a GLA polypeptide disclosed herein is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

In one aspect of the embodiments disclosed herein, the subject is a human subject in need of treatment or prophylaxis for Fabry disease.

In one aspect of the embodiments disclosed herein, upon administration to the subject, the mRNA has: (i) a longer plasma half-life; (ii) increased expression of a GLA polypeptide encoded by the ORF; (iii) a lower frequency of arrested translation resulting in an expression fragment; (iv) greater structural stability; or (v) any combination thereof, relative to a corresponding mRNA having the nucleic acid sequence of SEQ ID NO: 2 and/or administered as naked mRNA.

In some embodiments, a pharmaceutical composition or polynucleotide, e.g., an mRNA, disclosed herein is suitable for administration as a single unit dose or a plurality of single unit doses.

In some embodiments, a pharmaceutical composition or polynucleotide, e.g., an mRNA, disclosed herein is suitable for reducing the level of one or more biomarkers of Fabry disease in the subject.

In some embodiments, a pharmaceutical composition or polynucleotide, e.g., an mRNA, disclosed herein is for use in treating, preventing or delaying the onset of Fabry disease signs or symptoms in the subject. In some embodiments, the signs or symptoms include pain, gastrointestinal disturbances, skin lesions such as angiokeratomata, renal impairment, cardiomyopathy, stroke, or a combination thereof.

In certain aspects, the invention relates to a host cell comprising the polynucleotide, e.g., an mRNA. In certain embodiments, the host cell is a eukaryotic cell. In certain aspects, the invention relates to a vector comprising the polynucleotide. In certain aspects, the invention relates to a method of making a polynucleotide comprising enzymatically or chemically synthesizing the polynucleotide. In certain aspects, the invention relates to a polypeptide which is encoded by a polynucleotide of the invention, a composition comprising a polynucleotide of the invention, a host cell comprising a polynucleotide of the invention, a vector comprising a polynucleotide of the invention, or a polynucleotide produced by a disclosed method of making the polynucleotide. In certain aspects, the invention relates to a method of expressing in vivo an active GLA polypeptide in a subject in need thereof comprising administering to the subject an effective amount of the polynucleotide, the composition, the host cell, or the vector. In certain aspects, the invention relates to a method of treating Fabry disease or preventing the signs and/or symptoms of Fabry disease in a subject in need thereof comprising administering to the subject a therapeutically effective amount of the polynucleotide, the composition, the host cell, or the vector, wherein the administration alleviates the signs or symptoms of Fabry disease in the subject.

In certain aspects, the invention relates to a method to prevent or delay the onset of Fabry disease signs or symptoms in a subject in need thereof comprising administering to the subject a prophylactically effective amount of the polynucleotide (e.g., an mRNA), the composition, the host cell, or the vector before Fabry disease signs or symptoms manifest, wherein the administration prevents or delays the onset of Fabry disease signs or symptoms in the subject. In certain aspects, the invention relates to a method to ameliorate the signs or symptoms of Fabry disease in a subject in need thereof comprising administering to the subject a therapeutically effective amount of the polynucleotide, the composition, the host cell, or the vector before Fabry disease signs or symptoms manifest, wherein the administration ameliorates Fabry disease signs or symptoms in the subject.

The present disclosure further provides a method of expressing an α-galactosidase A (GLA) polypeptide in a human subject in need thereof comprising administering to the subject an effective amount of a pharmaceutical composition or a polynucleotide, e.g., an mRNA, described herein, wherein the pharmaceutical composition or polynucleotide is suitable for administrating as a single dose or as a plurality of single unit doses to the subject.

The present disclosure further provides a method of treating, preventing or delaying the onset of Fabry disease signs or symptoms in a human subject in need thereof comprising administering to the subject an effective amount of a pharmaceutical composition or a polynucleotide, e.g., an mRNA, described herein, wherein the administration treats, prevents or delays the onset of one or more of the signs or symptoms of Fabry disease in the subject. In some embodiments, the administration slows, stops, or reverses the progressive accumulation of Gb3 or lyso-Gb3 in the plasma or tissues of the subject.

The present disclosure further provides a method for the treatment of Fabry disease, comprising administering to a human subject suffering from Fabry disease a single intravenous dose of a pharmaceutical composition or a polynucleotide, e.g., an mRNA, described herein.

The present disclosure further provides a method of reducing the Gb3 plasma level or lyso-Gb3 plasma level in a human subject comprising administering to the subject an effective amount of a pharmaceutical composition or a polynucleotide, e.g., an mRNA, described herein, wherein the administration reduces the Gb3 or lyso-Gb3 level in the subject. In some embodiments, (i) Gb3 plasma level is reduced by at least 20%, at least 30%, at least 40%, at least 50%, at least, 60%, at least 70%, at least 80%, at least 90%, at least 95%, at least 100%, at least 2-fold, at least 3-fold, at least 4-fold, at least 5-fold, at least 10-fold, or at least 20-fold as compared to the subject's baseline Gb3 plasma level or a reference Gb3 plasma level, for at least 7 days, at least 14 days, at least 21 days, at least 28 days, at least 35 days, or at least 42 days post-administration, and/or (ii) Lyso-Gb3 plasma level is reduced by at least 20%, at least 30%, at least 40%, at least 50%, at least, 60%, at least 70%, at least 80%, at least 90%, at least 95%, at least 100%, at least 2-fold, at least 3-fold, at least 4-fold, at least 5-fold, at least 10-fold, or at least 20-fold as compared to the subject's baseline Lyso-Gb3 plasma level or a reference Lyso-Gb3 plasma levels, for at least 7 days, at least 14 days, at least 21 days, at least 28 days, at least 35 days, or at least 42 days post-administration.

In some embodiments, the Gb3 plasma level is reduced to less than 10 nmol/mL, less than 9 nmol/mL, less than 8 nmol/mL, less than 7 nmol/mL, less than 6 nmol/mL, less than 5 nmol/mL, less than 4 nmol/mL, less than 3 nmol/mL, or less than 2 nmol/mL in the subject.

In some embodiments, 24 hours after the pharmaceutical composition or polynucleotide, e.g., an mRNA, is administered to the subject, the GLA activity in the subject is increased at least 20%, at least 30%, at least 40%, at least 50%, at least 60%, at least 70%, at least 80%, at least 90%, at least 100%, at least 150%, at least 200%, at least 300%, at least 400%, at least 500%, or at least 600% compared to the subject's baseline GLA activity or a reference GLA activity level.

In some embodiments, the GLA activity is increased in the heart, kidney, liver, or spleen of the subject.

In some embodiments, the increased GLA activity persists for greater than 24, 36, 48, 60, 72, 96, 120, 144, or 168 hours. In some embodiments, the increased GLA activity persists for greater than one week, greater than two weeks, greater than three weeks, greater than four weeks, greater than five weeks, or greater than six weeks.

In some embodiments, the pharmaceutical composition or polynucleotide, e.g., an mRNA, is administered to the subject the level of Gb3 in the subject is reduced by at least about 20%, at least about 30%, at least about 40%, at least about 50%, at least about 60%, at least about 70%, at least about 80%, at least about 90%, or 100% compared to the subject's baseline Gb3 level or a reference Gb3 level.

In some embodiments, the level of Gb3 is reduced in one or more of the plasma, heart, kidney, liver, and/or spleen of the subject.

In some embodiments, the administration reduces the level of Gb3 or the level of lyso-Gb3 in one or more of plasma, heart, kidney, liver, or spleen to between 40% and 100%, between 50% and 100%, between 60% and 100%, between 70% and 100%, between 80% and 100%, or between 90% and 100% as compared to the subject's baseline level or a reference level in that tissue, for at least 7 days, at least 14 days, at least 21 days, at least 28 days, at least 35 days, or at least 42 days post-administration.

In some embodiments, after administration to the subject the level of Gb3 in the subject is reduced compared to the subject's baseline Gb3 level or a reference Gb3 level for at least one day, at least two days, at least three days, at least four days, at least five days, at least one week, at least two weeks, at least three weeks, at least four weeks, or at least six weeks.

In some embodiments, 24 hours after the pharmaceutical composition or polynucleotide, e.g., an mRNA, is administered to the subject the level of lyso-Gb3 in the subject is reduced by at least about 20%, at least about 30%, at least about 40%, at least about 50%, at least about 60%, at least about 70%, at least about 80%, at least about 90%, or 100% compared to the subject's baseline lyso-Gb3 level or a reference lyso-Gb3 level.

In some embodiments, the level of lyso-Gb3 is reduced in one or more of the plasma, heart, kidney, liver, and/or spleen of the subject.

In some embodiments, after administration to the subject the level of lyso-Gb3 in the subject is reduced compared to the subject's baseline lyso-Gb3 level or a reference lyso-Gb3 level for at least one day, at least two days, at least three days, at least four days, at least five days, at least one week, at least two weeks, at least three weeks, at least four weeks, or at least six weeks.

In some embodiments, the pharmaceutical composition or polynucleotide, e.g., an mRNA, is administered as a single dose of less than 1.5 mg/kg, less than 1.25 mg/kg, less than 1 mg/kg, less than 0.75 mg/kg, or less than 0.5 mg/kg.

In some embodiments, the administration to the subject is about once a week, about once every two weeks, or about once a month.

In some embodiments, the pharmaceutical composition or polynucleotide, e.g., an mRNA, is administered intravenously.

BRIEF DESCRIPTION OF THE DRAWINGS/FIGURES

FIGS. 1A, 1B and 1C show the protein sequence (FIG. 1A), table with domain features (FIG. 1B), and graphic representation of domain structure (FIG. 1C) of wild type GLA.

FIG. 2 shows the nucleic acid sequence of wild type GLA.

FIG. 3 shows uracil (U) metrics corresponding to wild type GLA and 25 sequence optimized GLA polynucleotides. The column labeled "U content (%)" corresponds to the % $U_{TL}$ parameter. The column labeled "U Content v. WT (%)" corresponds to % $U_{WT}$. The column labeled "U Content v. Theoretical Minimum (%)" corresponds to % $U_{TM}$. The column labeled "UU pairs v. WT (%)" corresponds to % $U_{WT}$.

FIG. 4 shows guanine (G) metrics corresponding to wild type GLA and 25 sequence optimized GLA polynucleotides. The column labeled "G Content (%)" corresponds to % $G_{TL}$. The column labeled "G Content v. WT (%)" corresponds to % $G_{WT}$. The column labeled "G Content v. Theoretical Maximum (%)" corresponds to % $G_{TMX}$.

FIG. 5 shows cytosine (C) metrics corresponding to wild type GLA and 25 sequence optimized GLA polynucleotides. The column labeled "C Content (%)" corresponds to % $C_{TL}$. The column labeled "C Content v. WT (%)" corresponds to % $C_{WT}$. The column labeled "C Content v. Theoretical Maximum (%)" corresponds to % $C_{TMX}$.

FIG. 6 shows guanine plus cytosine (G/C) metrics corresponding to wild type GLA and 25 sequence optimized GLA polynucleotides. The column labeled "G/C Content (%)" corresponds to % $G/C_{TL}$. The column labeled "G/C Content v. WT (%)" corresponds to % $G/C_{WT}$. The column labeled "G/C Content v. Theoretical Maximum (%)" corresponds to % $G/C_{TMX}$.

FIG. 7 shows a comparison between the G/C compositional bias for codon positions 1, 2, 3 corresponding to the wild type GLA and 25 sequence optimized GLA polynucleotides.

Figure 8:
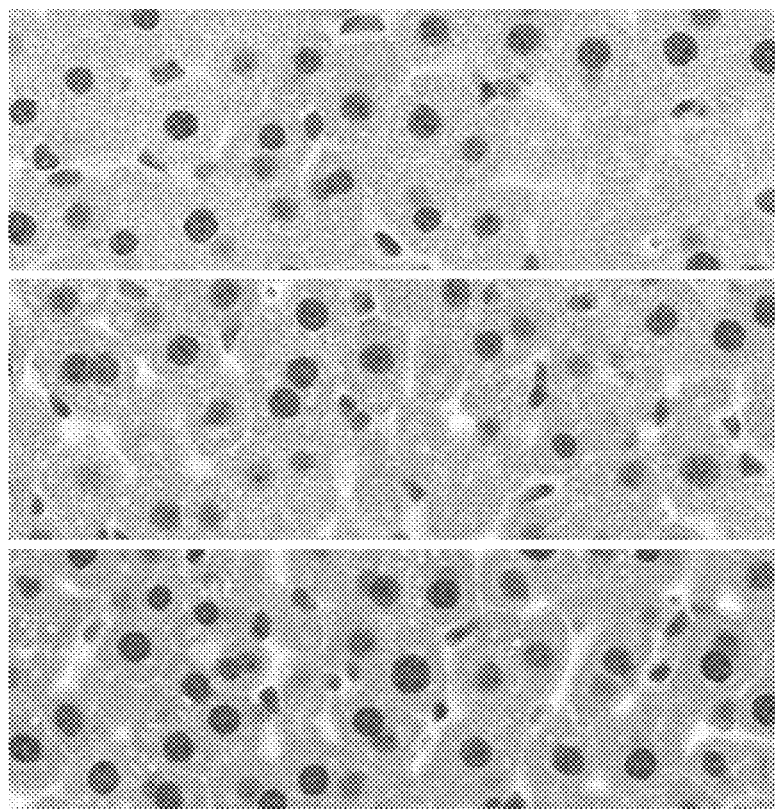

FIG. 8 shows anti-GLA immunohistochemical staining of the livers of wild-type CD1 mice treated with mRNA encoding GFP, counterstained with hematoxylin. The mice were sacrificed 48 hours after injection of mRNA. FIG. 8 shows only low levels of anti-GLA staining in these liver sections.

Figure 9:
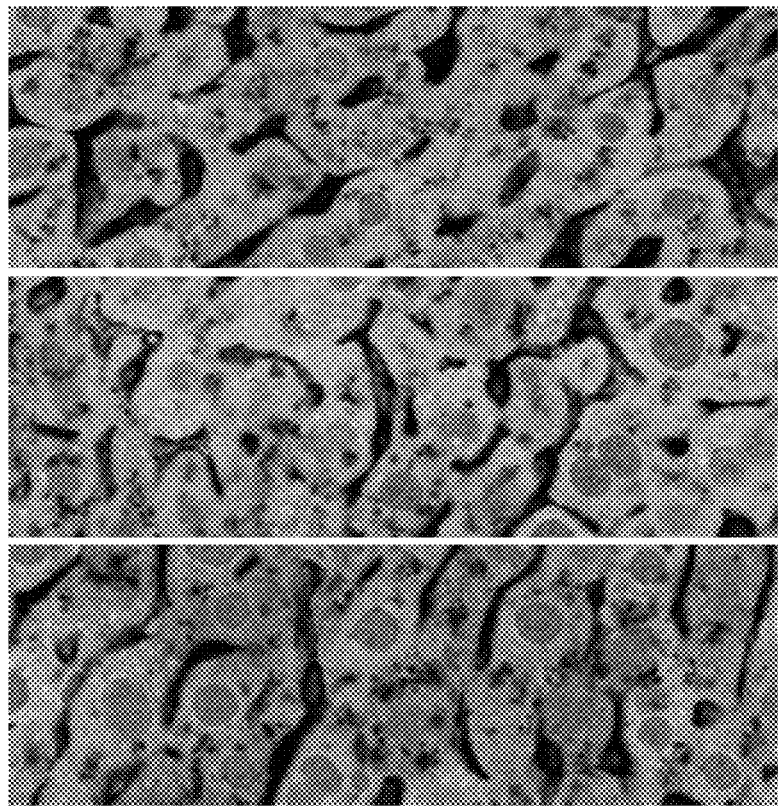

FIG. 9 shows anti-GLA immunohistochemical staining of the livers of wild-type CD1 mice treated with mRNA encoding GLA, counterstained with hematoxylin. The mice were sacrificed 48 hours after injection of mRNA. FIG. 9 shows high levels of anti-GLA staining in both the hepatocytes and the sinusoids of the livers in GLA mRNA treated animals.

Figure 10A:
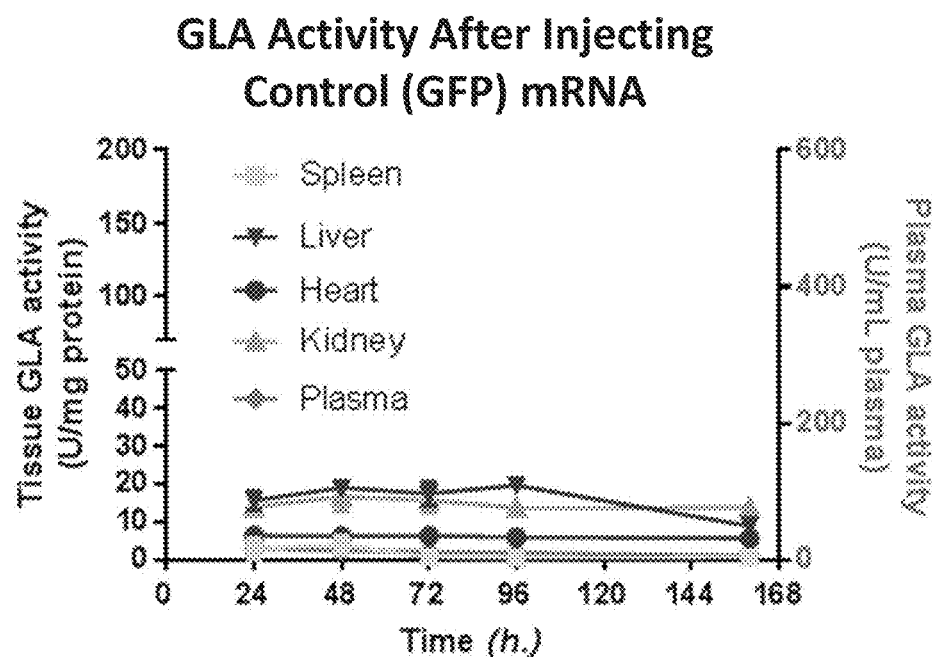
Figure 10B:
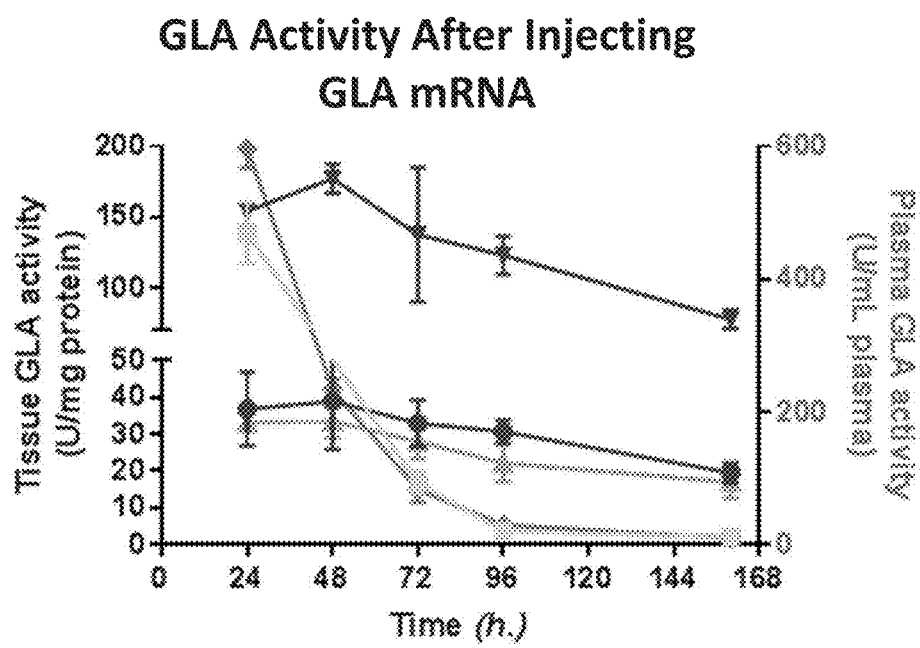
Figure 10C:
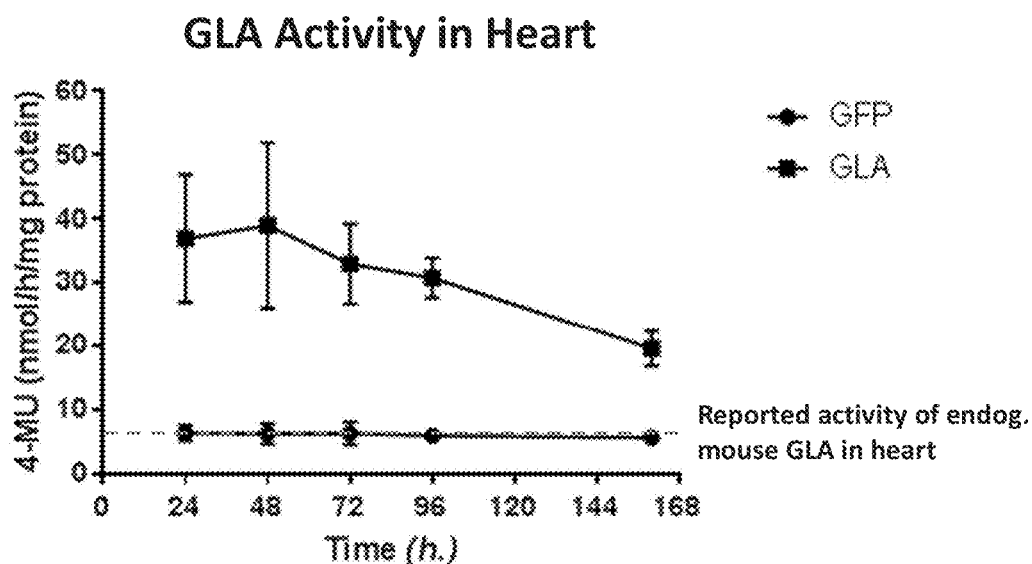
Figure 10D:
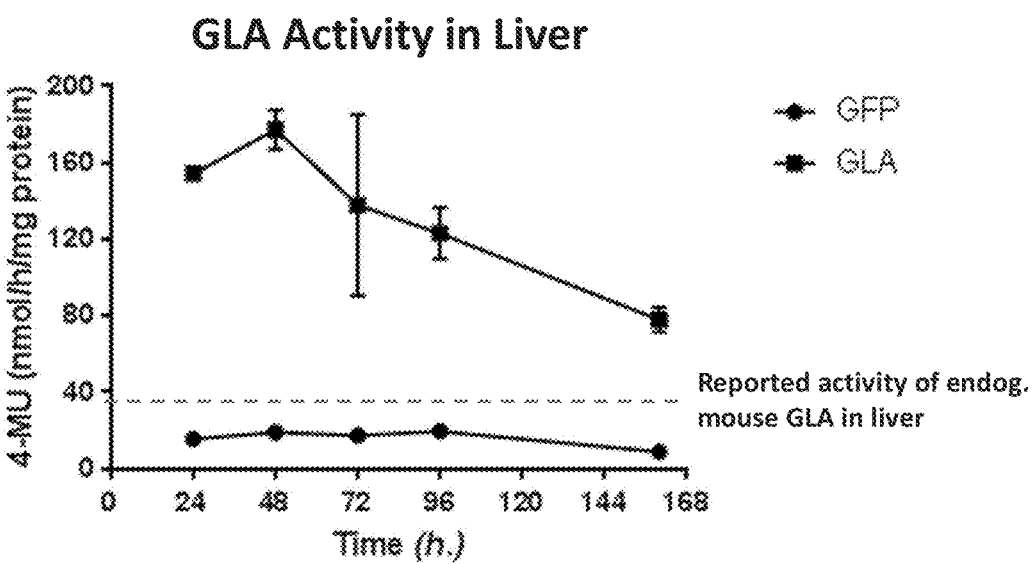
Figure 10E:
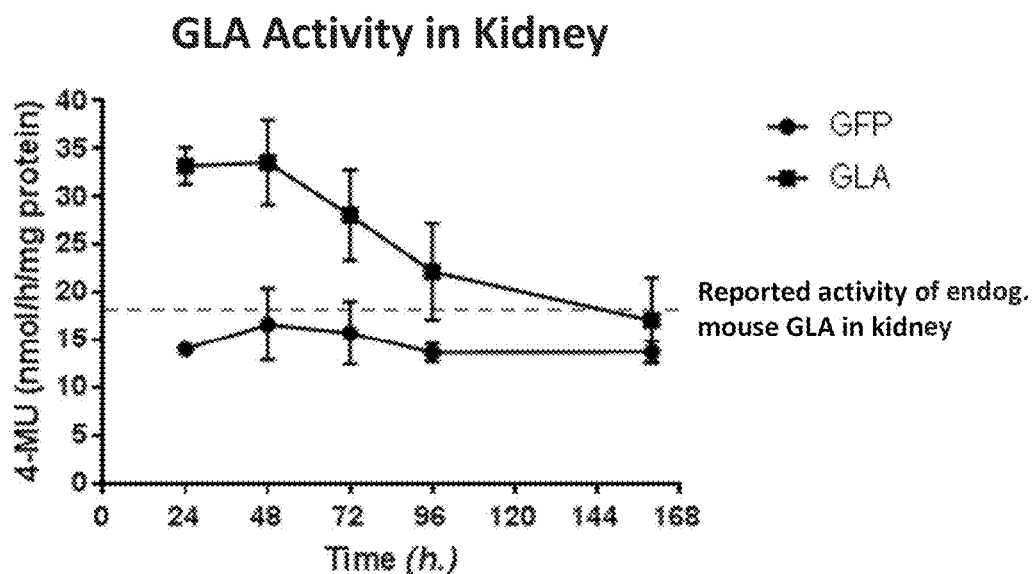
Figure 10F:
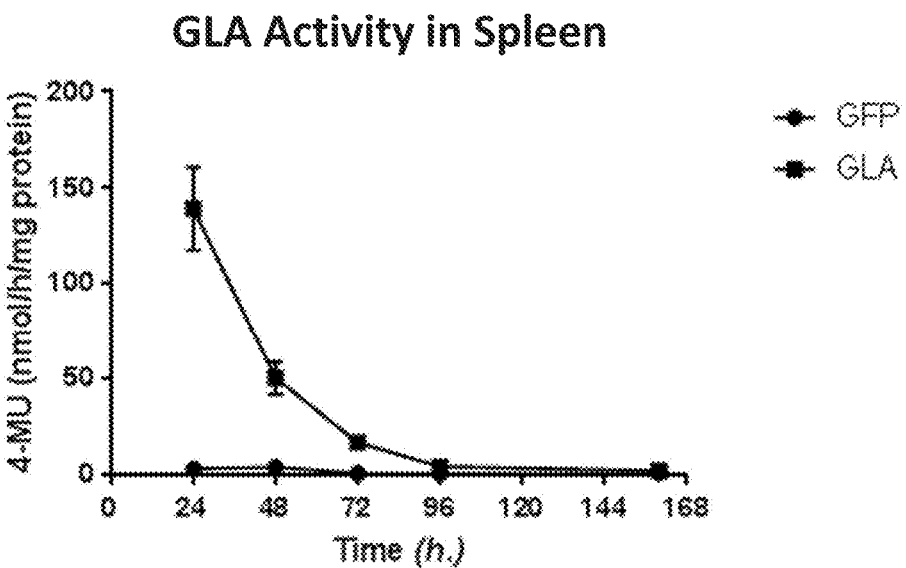
Figure 10G:
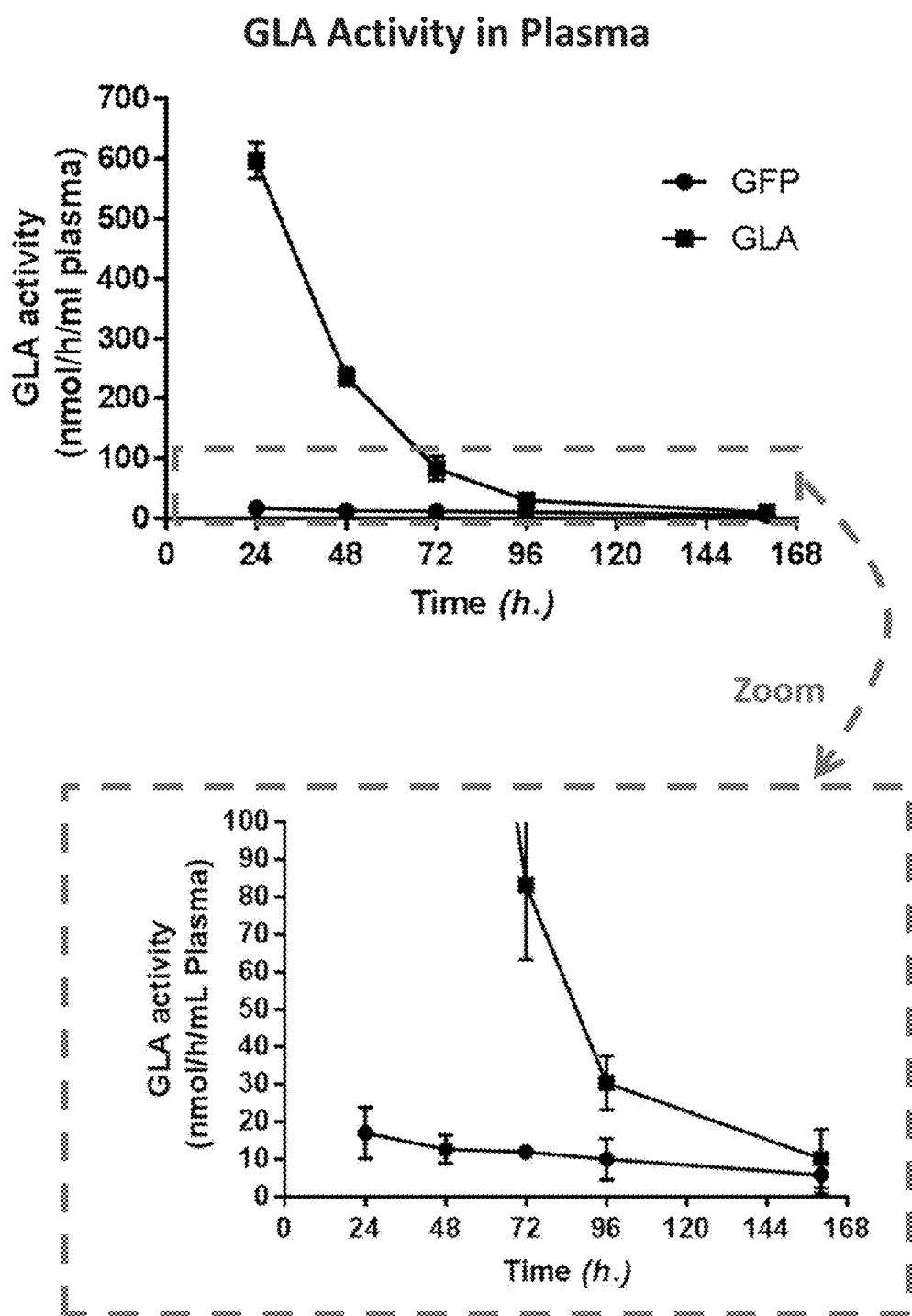

FIGS. 10A to 10G show the GLA protein levels in plasma, liver, spleen, kidney, and heart from the control GFP mRNA and GLA mRNA injected wild-type CD1 mice. As a baseline, FIG. 10A shows GLA activity levels over time in spleen, liver, heart, kidney, and plasma of wild-type mice administered control GFP mRNA. FIG. 10B shows the increased GLA activity levels over time in spleen, liver, heart, kidney, and plasma of wild-type mice treated with GLA mRNA. FIGS. 10C, 10D, 10E, 10F, and 10G show the GLA activity for wild-type mice administered GFP mRNA compared to GLA mRNA in the heart, liver, kidney, spleen, and plasma, respectively. The approximate endogenous mouse GLA activities for the heart (FIG. 10C), liver (FIG. 10D), and kidney (FIG. 10E) are shown as a dotted line in each figure for reference. After treatment with GLA mRNA, increased GLA activity levels were observed 24 hours after treatment in all tissues examined.

Figure 11A:
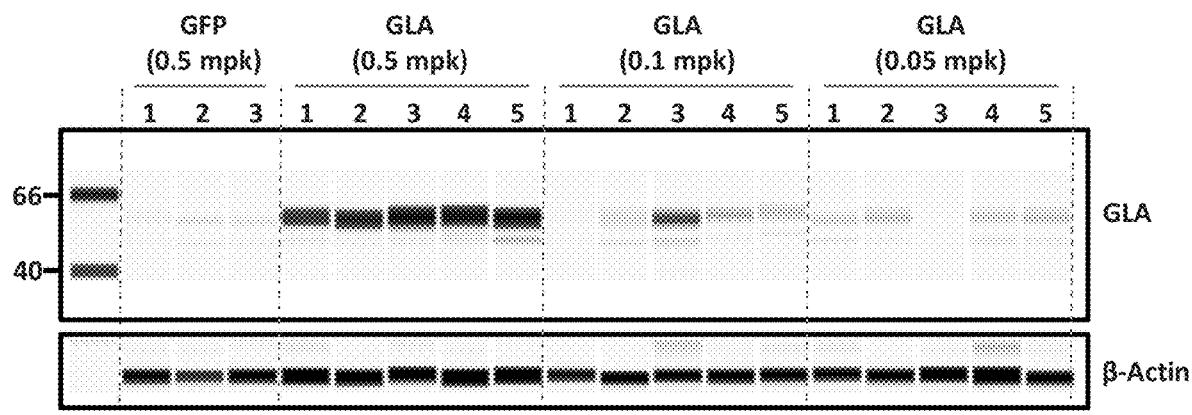
Figure 11B:
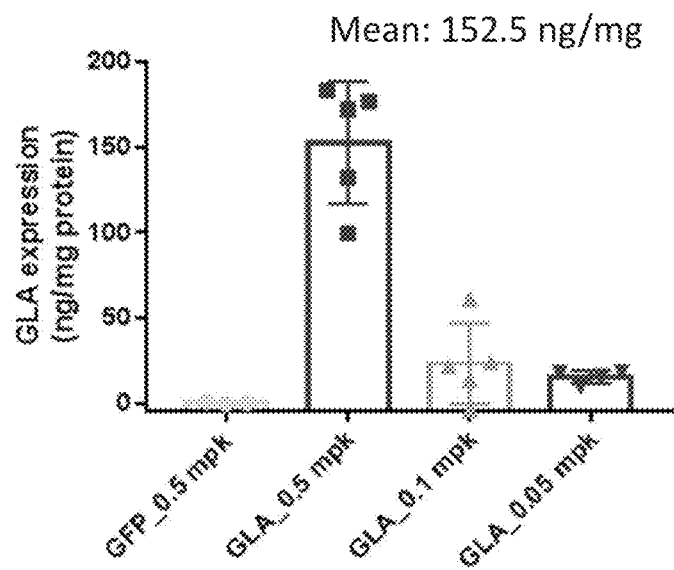

FIGS. 11A and 11B show GLA protein levels in GLA knockout mouse livers at 72 hours post-IV dosing as analyzed by capillary electrophoresis (CE). FIG. 11A shows a dose-response of GLA expression in the liver 72 hours after administration of mRNA encoding GLA, with significant GLA expression relative to GFP control observed at each concentration of GLA mRNA administered. Quantification of the protein expression at 72 hours is plotted in FIG. 11B.

Figure 12A:
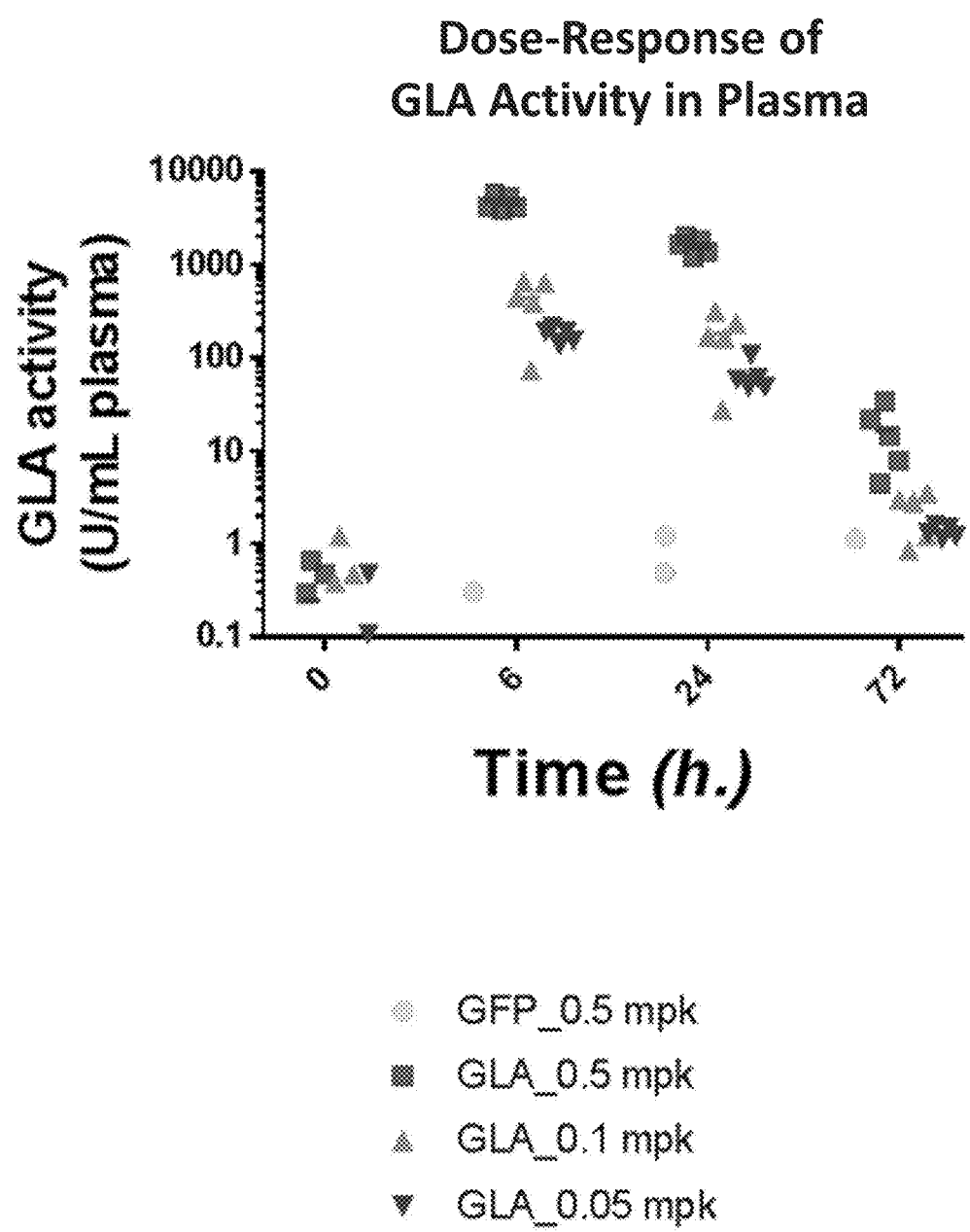
Figure 12B:
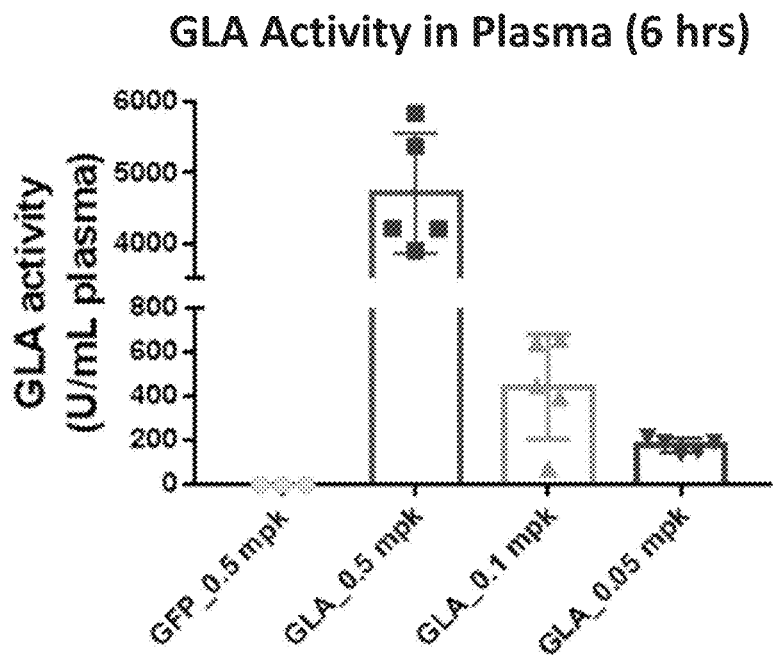
Figure 12C:
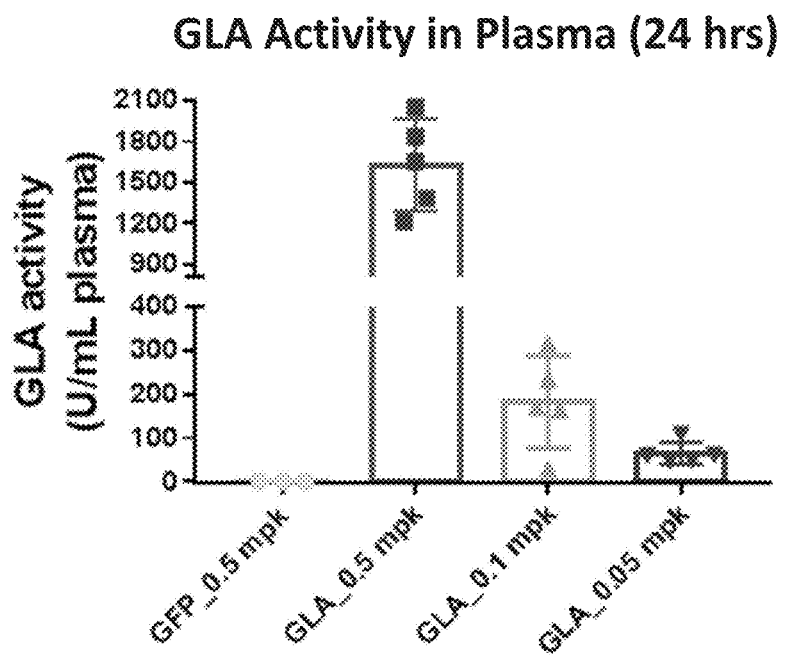
Figure 12D:
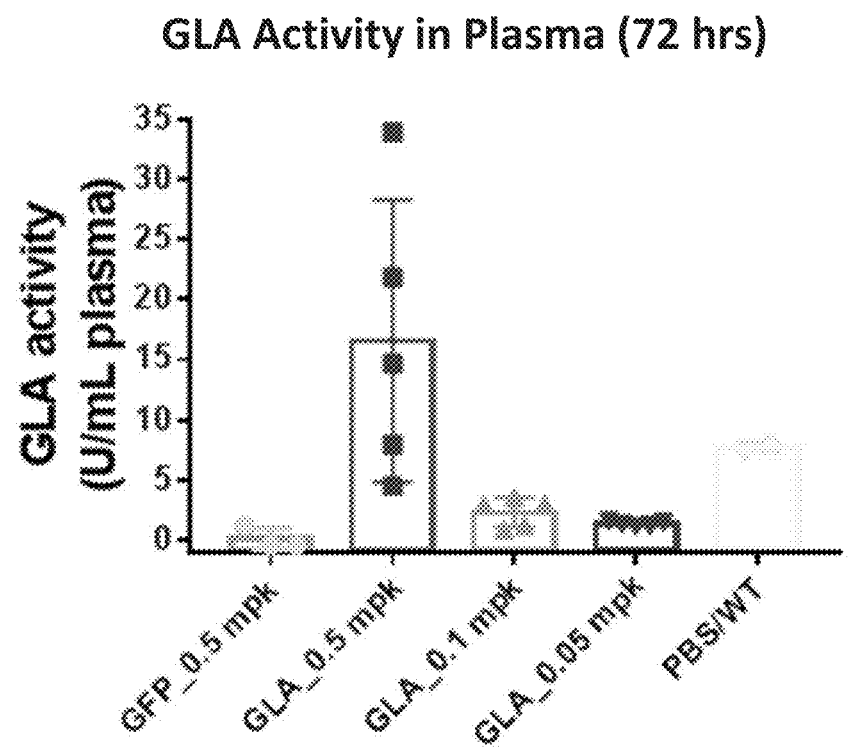

FIGS. 12A to 12D show a dose-response analysis of GLA activity in in plasma after treatment with mRNA encoding GLA or GFP. FIG. 12A shows a logarithmic plot of GLA activity in plasma of GLA knockout mice over time for each dose of GLA mRNA compared to the GLA activity in plasma for mice administered control GFP mRNA. FIGS. 12B, 12C, and 12D show the GLA activity in plasma for each dose at 6 hours, 24 hours, and 72 hours after treatment, respectively. The mice treated with mRNA encoding GLA showed increased GLA activity in a dose-dependent manner at each time point.

Figure 13:
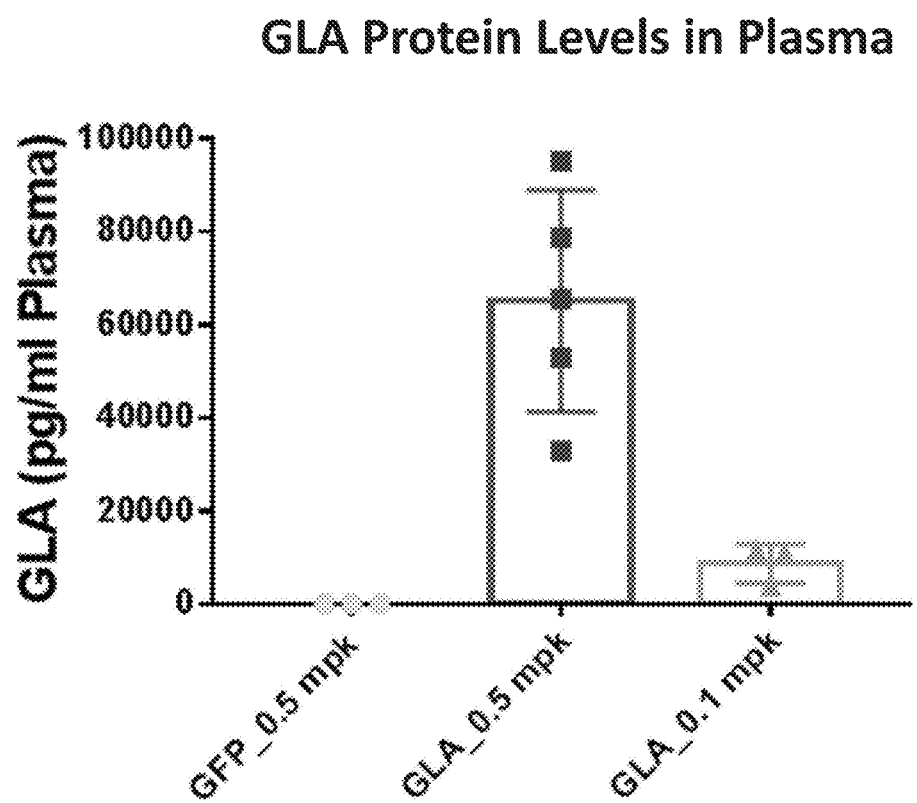
Figure 14A:
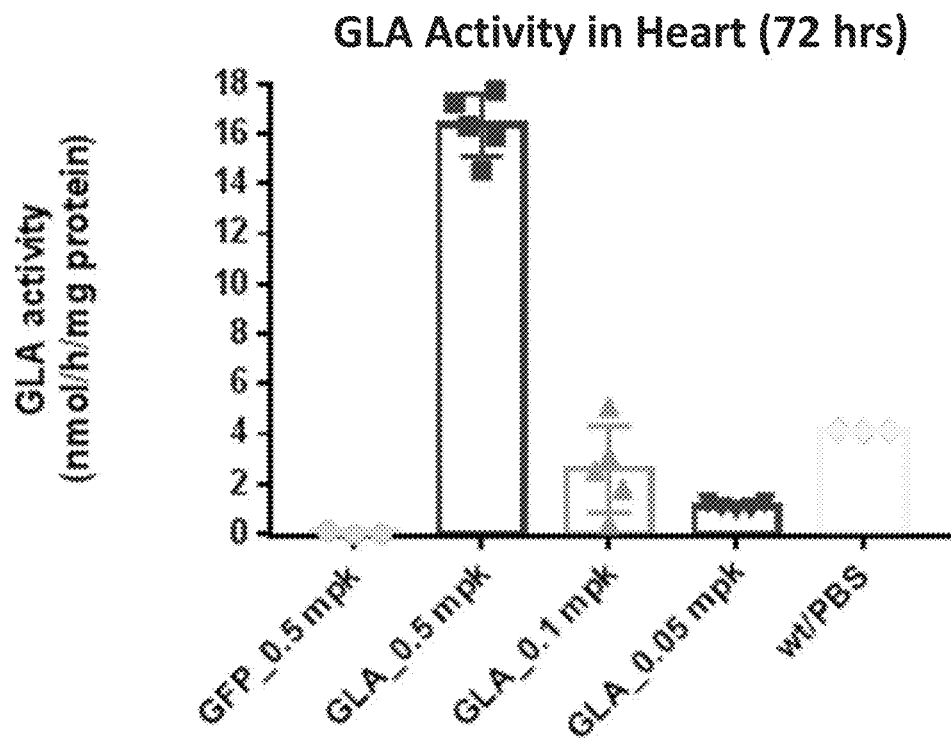
Figure 14B:
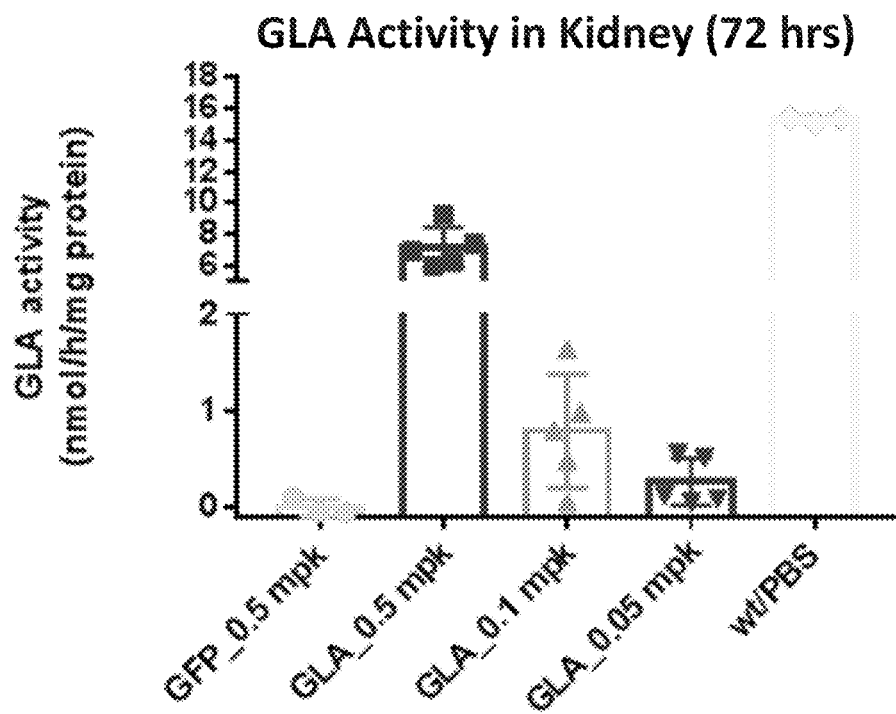
Figure 14C:
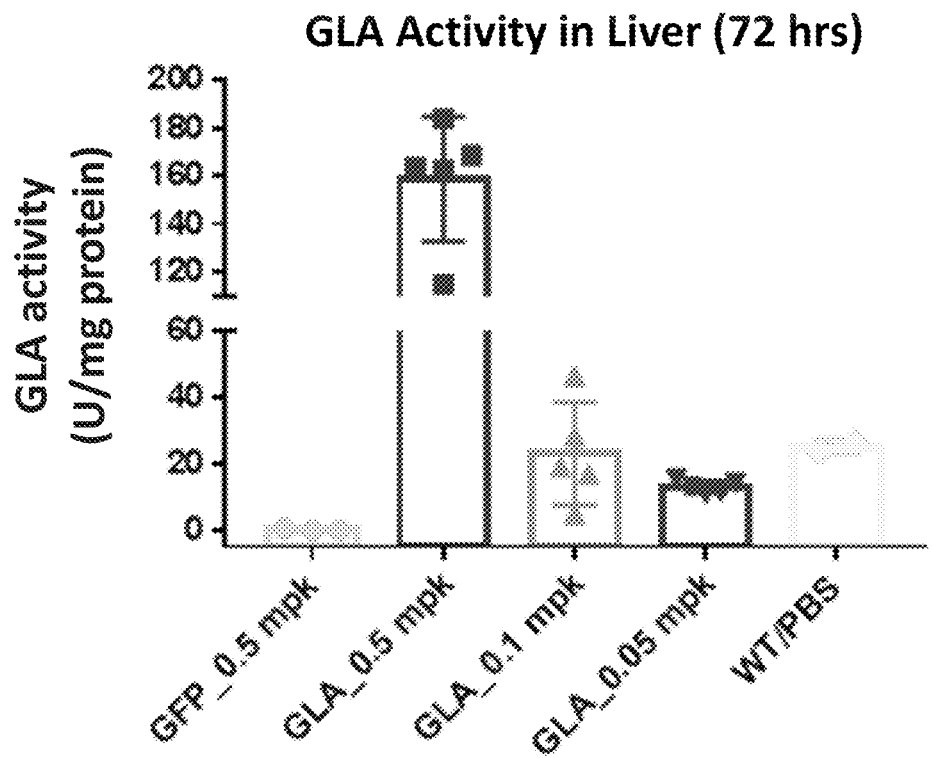
Figure 14D:
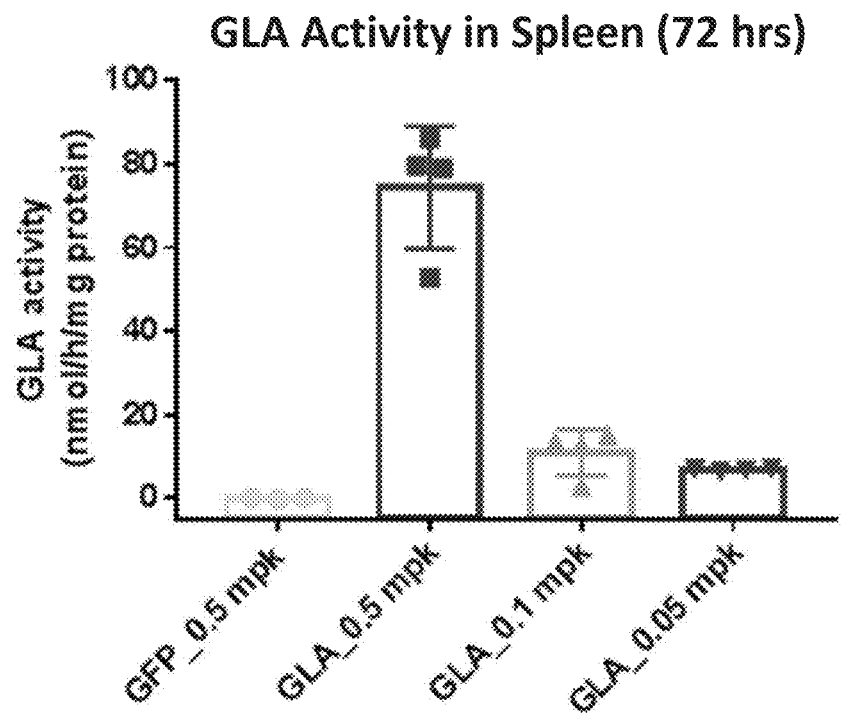

FIG. 13 shows an ELISA assay performed to quantitate GLA expression in plasma 6 hours after administering mRNA encoding GLA or GFP. While no GLA protein was detected in the plasma of control GFP mice, significant levels of GLA protein were detected in the plasma of mice administered 0.1 mg/kg or 0.5 mg/kg GLA mRNA.

FIGS. 14A to 14D show GLA activity in heart, kidney, liver, and spleen tissues, respectively, harvested from the GLA knockout mice 72 hours after administration of GLA mRNA. In each tissue, the GLA activity was elevated for GLA mRNA treated mice in a dose dependent manner.

Figure 15A:
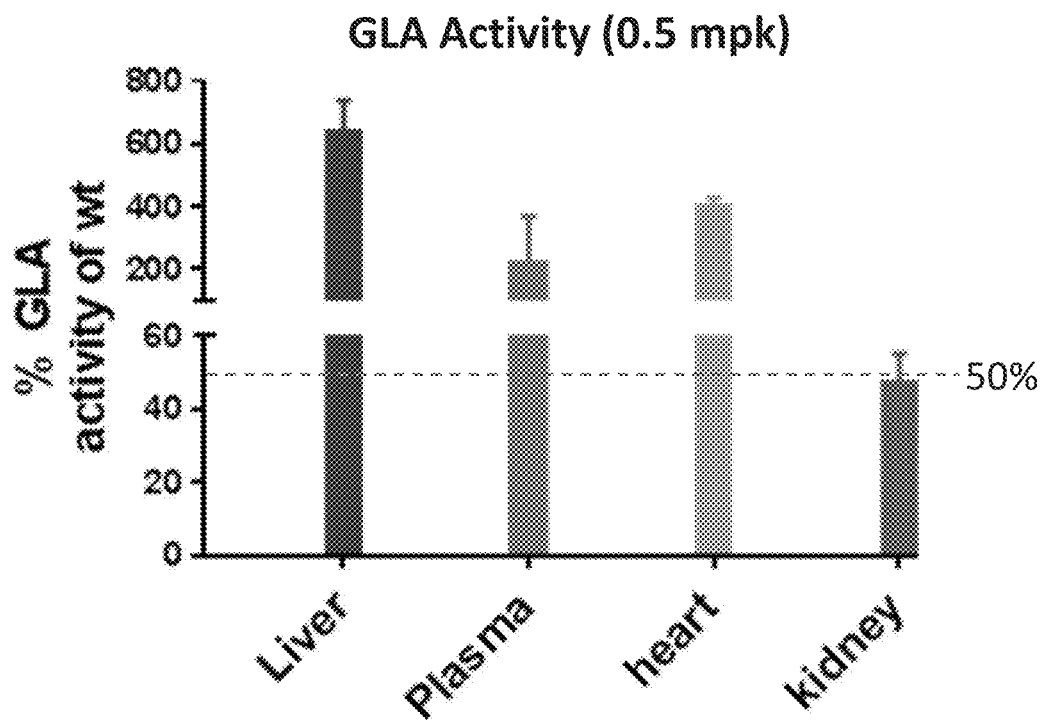
Figure 15B:
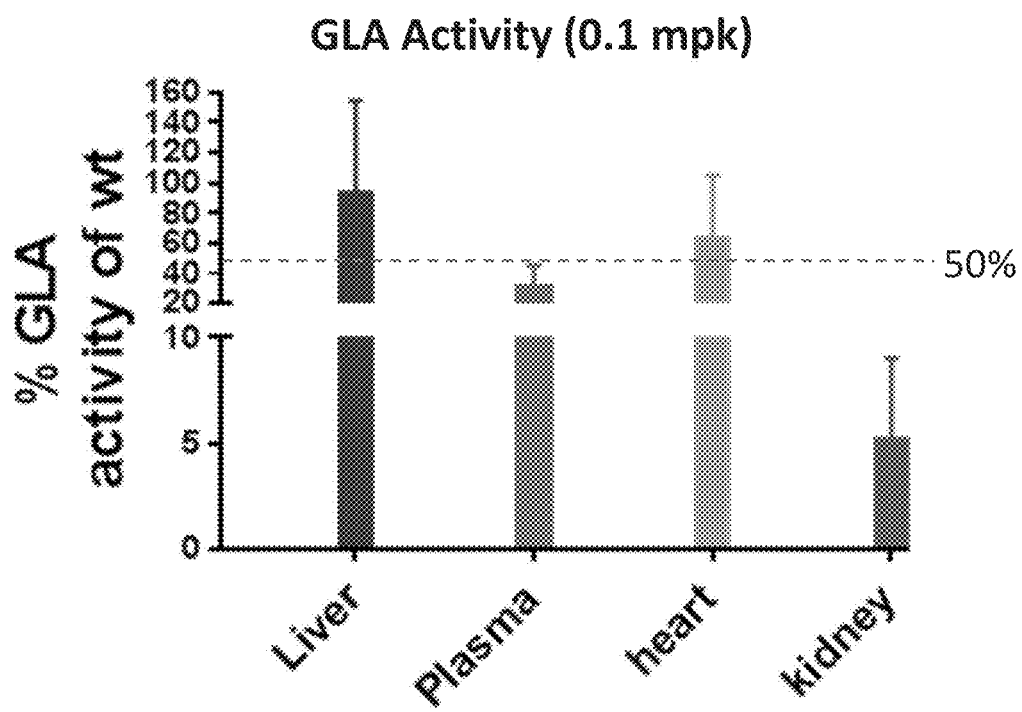
Figure 15C:
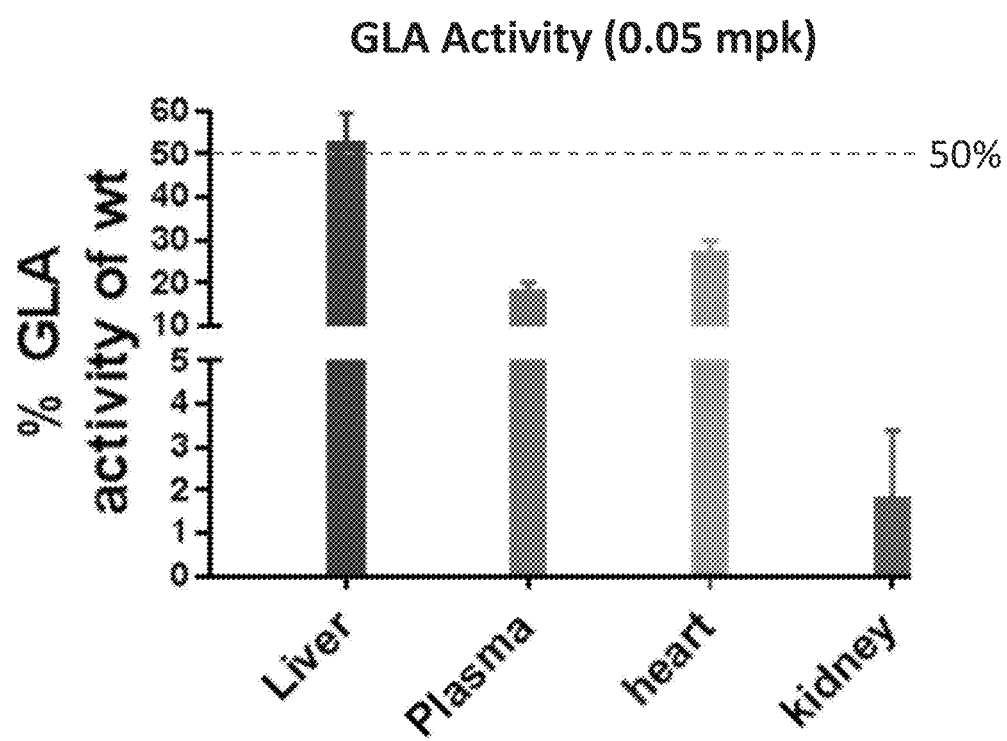

FIGS. 15A, 15B, and 15C show GLA activity in heart, kidney, liver, and spleen tissues, respectively, harvested from the GLA knockout mice 72 hours after administration of GLA mRNA. FIGS. 15A, 15B, and 15C show supraphysiologic (>100%) GLA activity in the liver, plasma, and heart with 0.5 mg/kg GLA mRNA administration, and at least 50% restoration of GLA activity in the kidney with 0.5 mg/kg GLA mRNA administration.

Figure 16A:
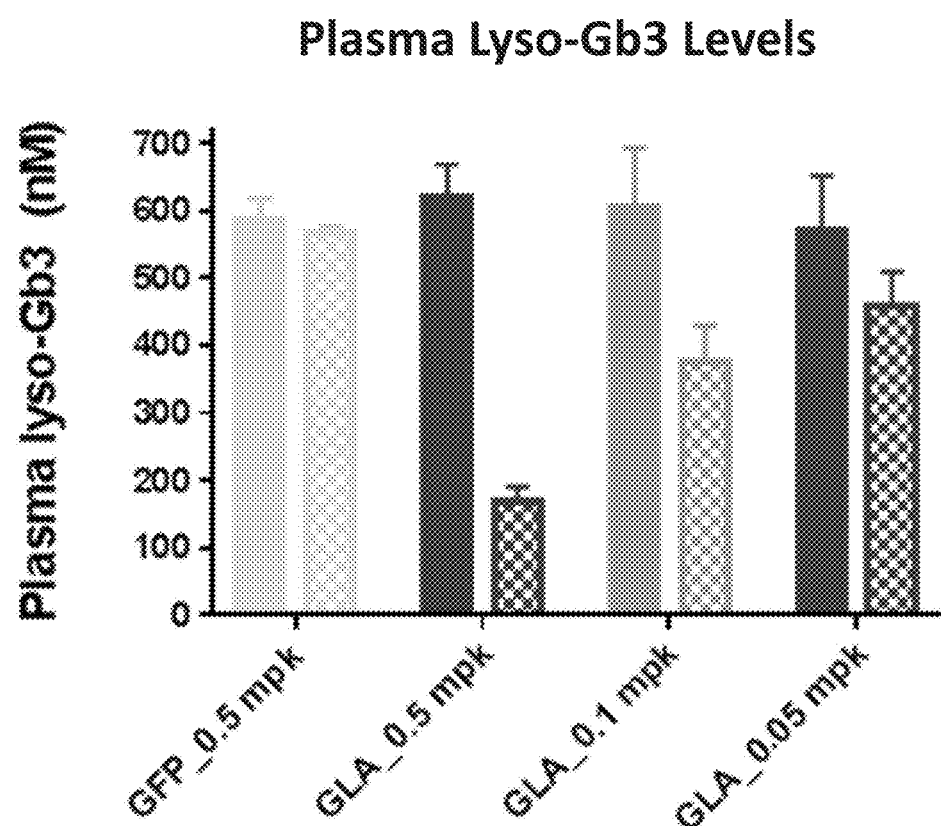
Figure 16B:
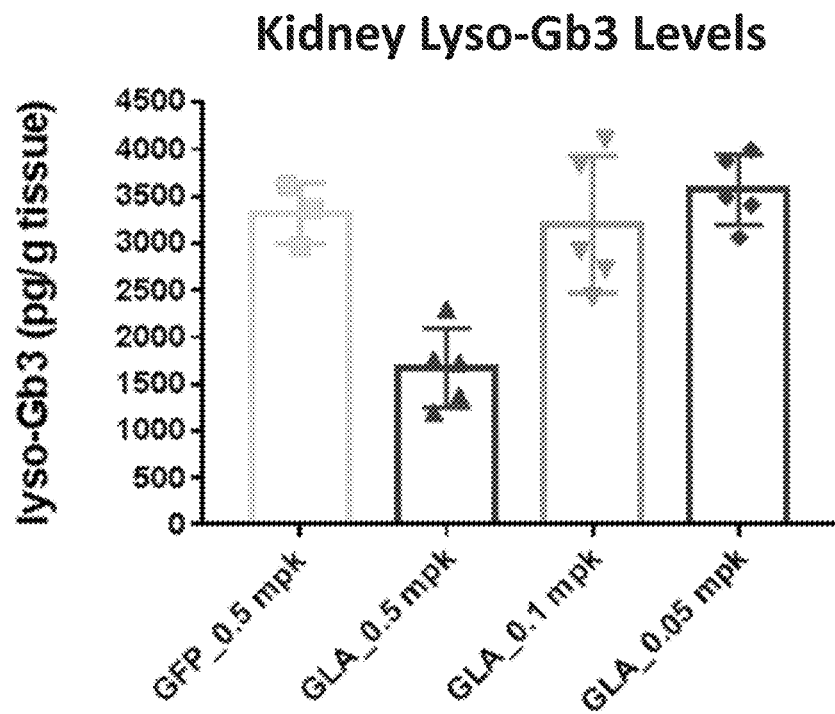
Figure 16C:
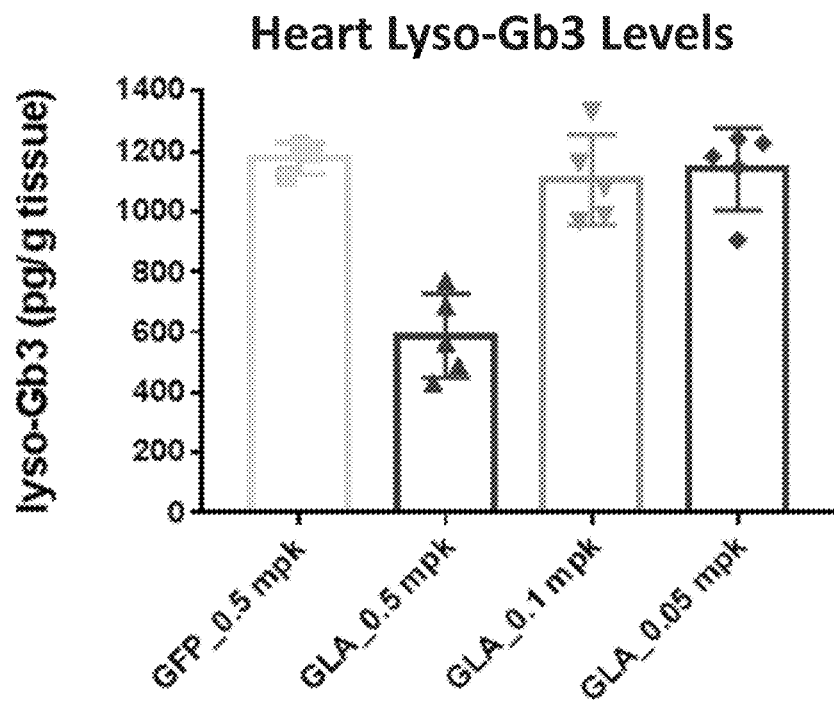
Figures 16D, 16E:
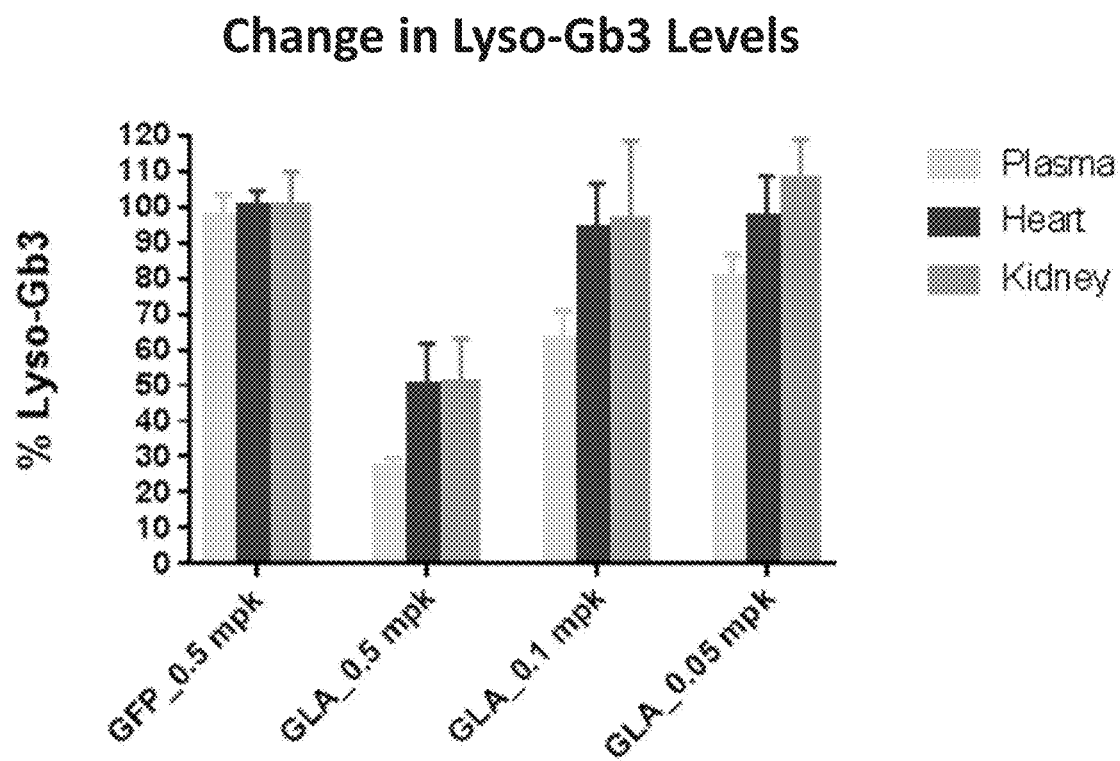

FIGS. 16A to 16E show the level of lyso-Gb3 in plasma and tissue samples from the GLA knockout mice administered GLA mRNA or control GFP mRNA. FIGS. 16A, 16B, and 16C show the lyso-Gb3 levels in plasma, kidney, and heart, respectively, 72 hours after administration of 0.5 mg/kg control GFP mRNA, 0.5 mg/kg GLA mRNA, 0.1 mg/kg GLA mRNA, or 0.05 mg/kg GLA mRNA. These data indicate a dose-dependent decrease in lyso-Gb3 levels in plasma 72 hours after administration of a single dose of GLA mRNA. FIGS. 16D and 16E show the dose-dependent reduction of lyso-Gb3 levels as a percent relative to the lyso-Gb3 levels in the plasma, heart, and kidney of untreated knockout mice.

Figure 16F:
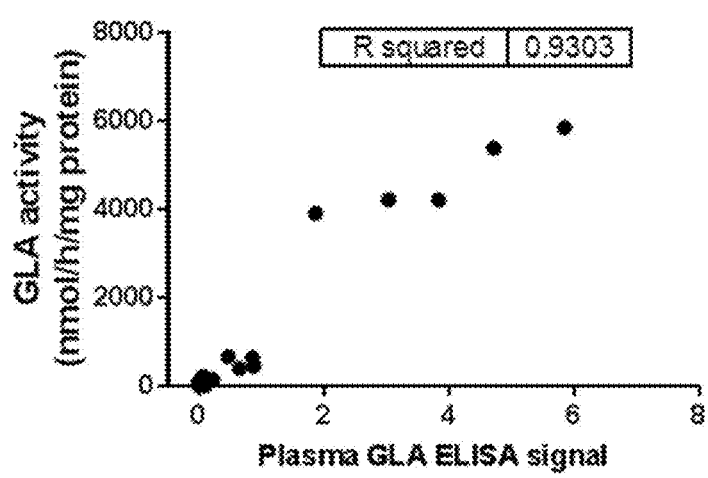
Figure 16G:
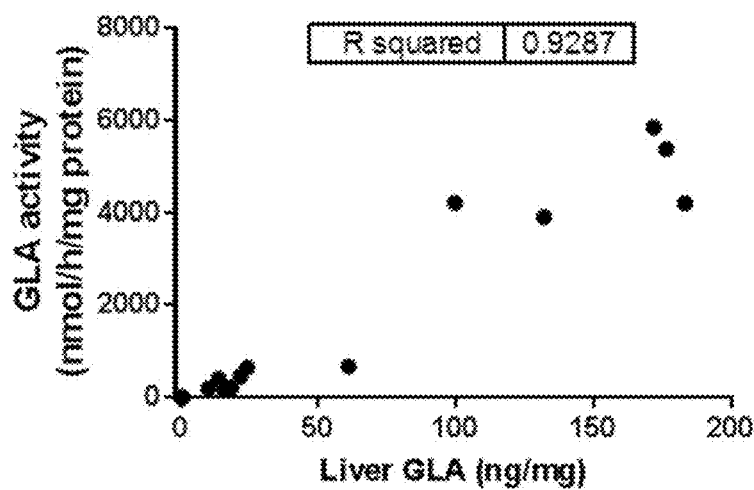
Figure 16H:
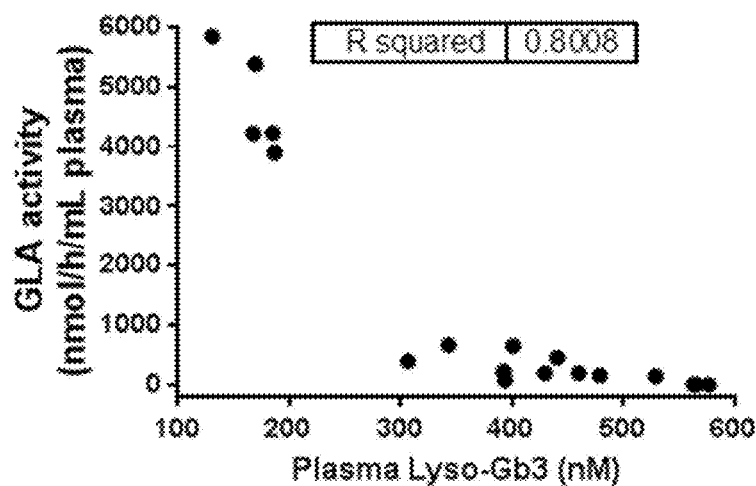

FIGS. 16F, 16G, and 16H show plots of measured GLA activity against other readouts relating to GLA function. FIGS. 16F and 16G show plots of GLA activity against measurements of GLA expression level in the plasma and liver, respectively. In both cases, there is a high degree of correlation (R squared>0.9). These results show that increased GLA expression correlates with increased GLA activity in both the blood and tissues of GLA knockout mice. FIG. 16H shows a plot of GLA activity against the levels of lyso-Gb3 in GLA knockout mice. This plot shows that the increased GLA activity in GLA knockout mice administered a single dose of GLA mRNA correlates with decreased levels of a Fabry Disease biomarker in vivo.

Figure 17A:
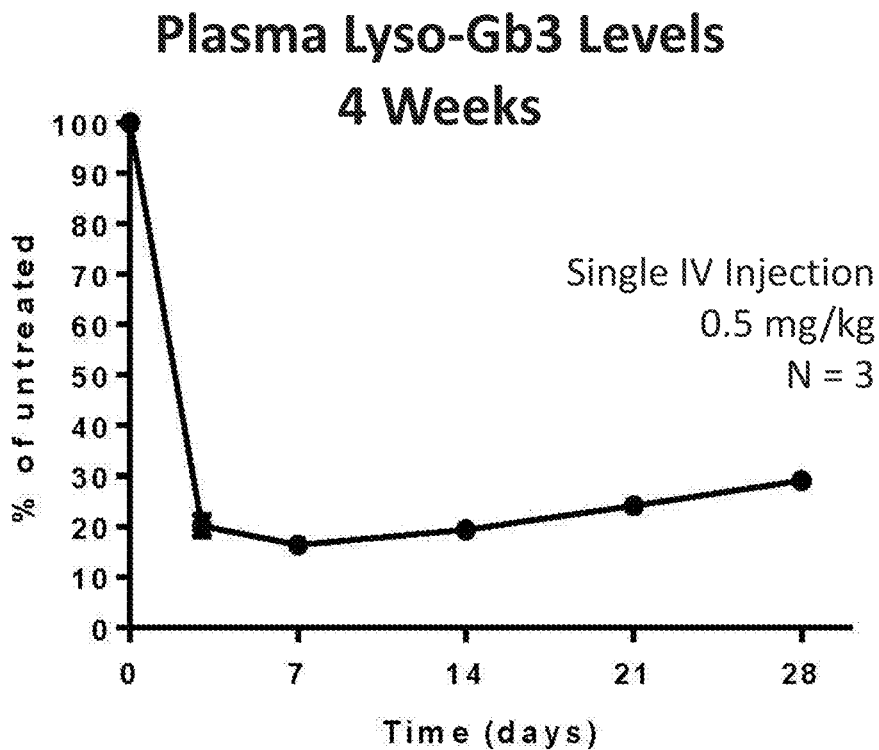
Figure 17B:
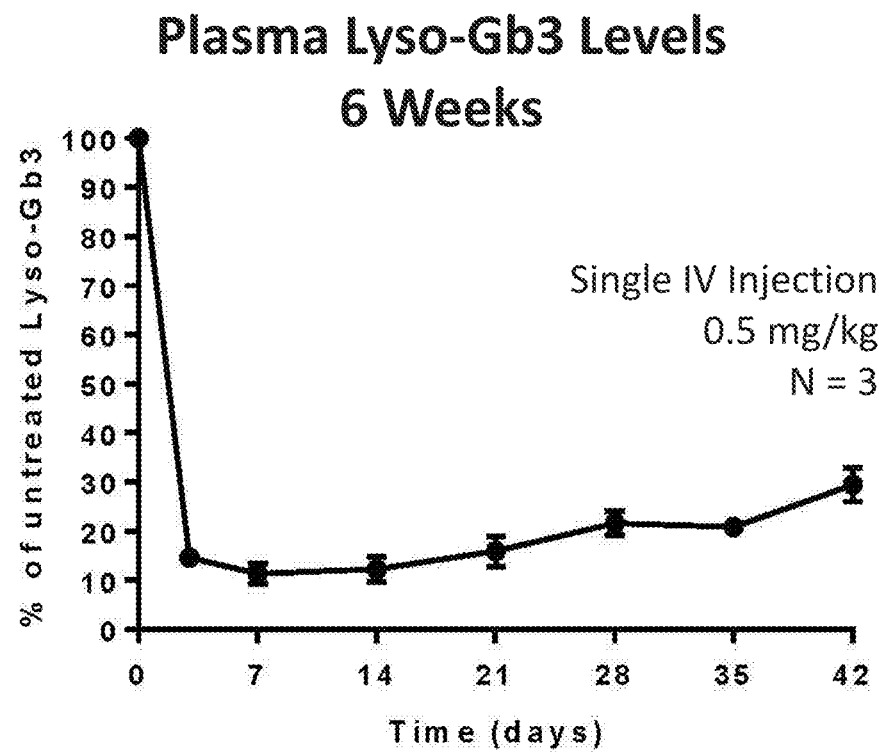

FIGS. 17A, 17B, and 17C show the level of GLA biomarkers in GLA –/– knockout mice treated with single dose GLA mRNA. FIG. 17A shows the percent reduction lyso-Gb3 in mice treated with GLA-mRNA #1, while FIG. 17B shows the percent reduction lyso-Gb3 in mice treated with GLA-mRNA #23. In both cases, lyso-Gb3 was reduced by 80-90% in plasma by 3 days after treatment. Lyso-Gb3 levels remained at levels 70% below initial measurements for the entire 4 week time course for GLA-mRNA #1 (see FIG. 17A), and at levels 70% below initial measurements for the entire 6 week time course for GLA-mRNA #23 (see FIG. 17B). FIG. 17C shows the results of parallel experiments comparing the effects of administering mRNA to administering enzyme replacement therapy (ERT). Both ERT and mRNA therapy reduced Gb3 levels to approximately 20% of baseline levels. FIG. 17C shows a rebound in the level of plasma Gb3 in ERT-treated mice between two and three weeks after treatment, while the Gb3 plasma levels in mice treated with GLA-mRNA #23 remained at approximately 20% baseline levels for at least six weeks after treatment.

Figure 18A:
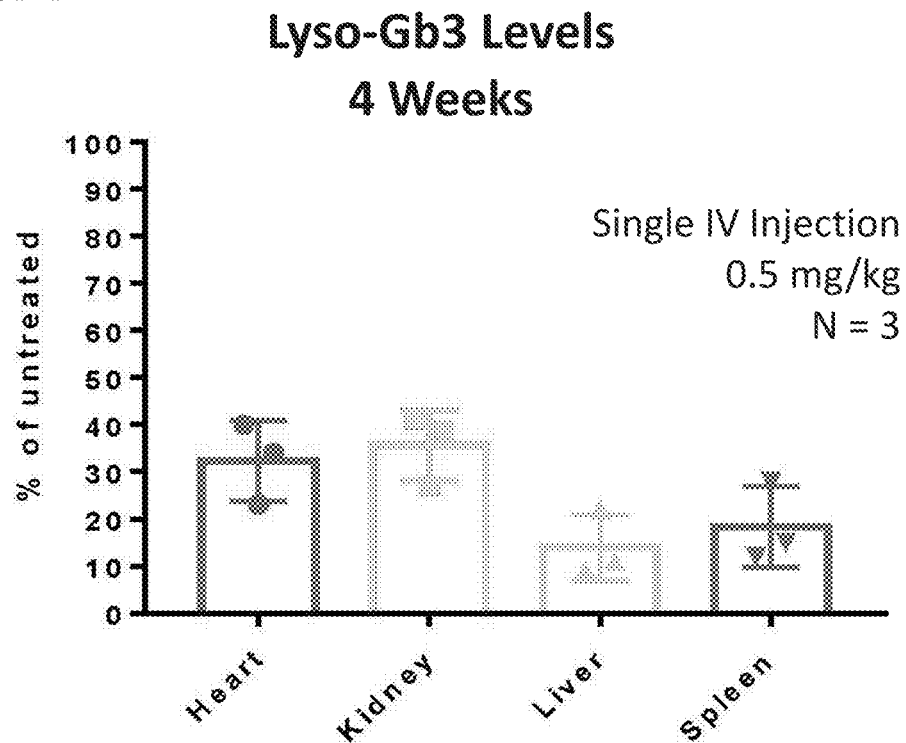
Figure 18B:
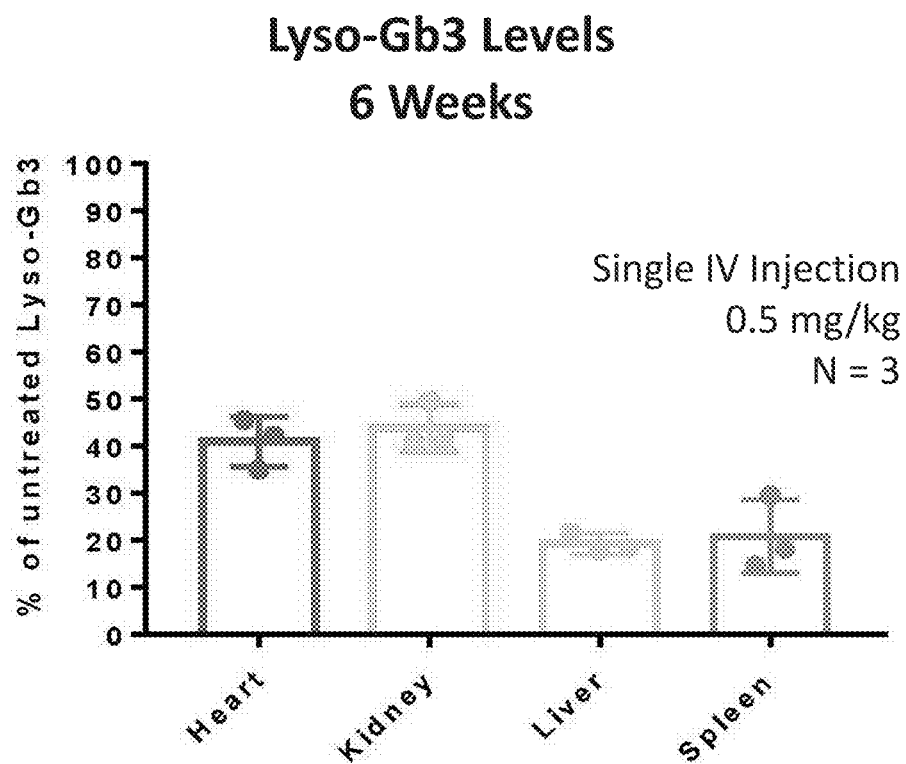

FIGS. 18A and 18B show the level of lyso-Gb3 in heart, kidney, liver, and spleen samples from the GLA knockout mice administered GLA mRNA four and six weeks after administration, respectively. FIG. 18A shows that, four weeks after treatment, the heart and kidney of treated mice had only 30-40% of the lyso-Gb3 observed in untreated knockout mice, and that the liver and spleen of treated mice had only 10-20% of the lyso-Gb3 observed in untreated knockout mice. FIG. 18B shows that, six weeks after treatment, the heart and kidney of treated mice had only 40-45% of the lyso-Gb3 observed in untreated knockout mice, and that the liver and spleen of treated mice had approximately 20% of the lyso-Gb3 observed in untreated knockout mice.

Figure 19:
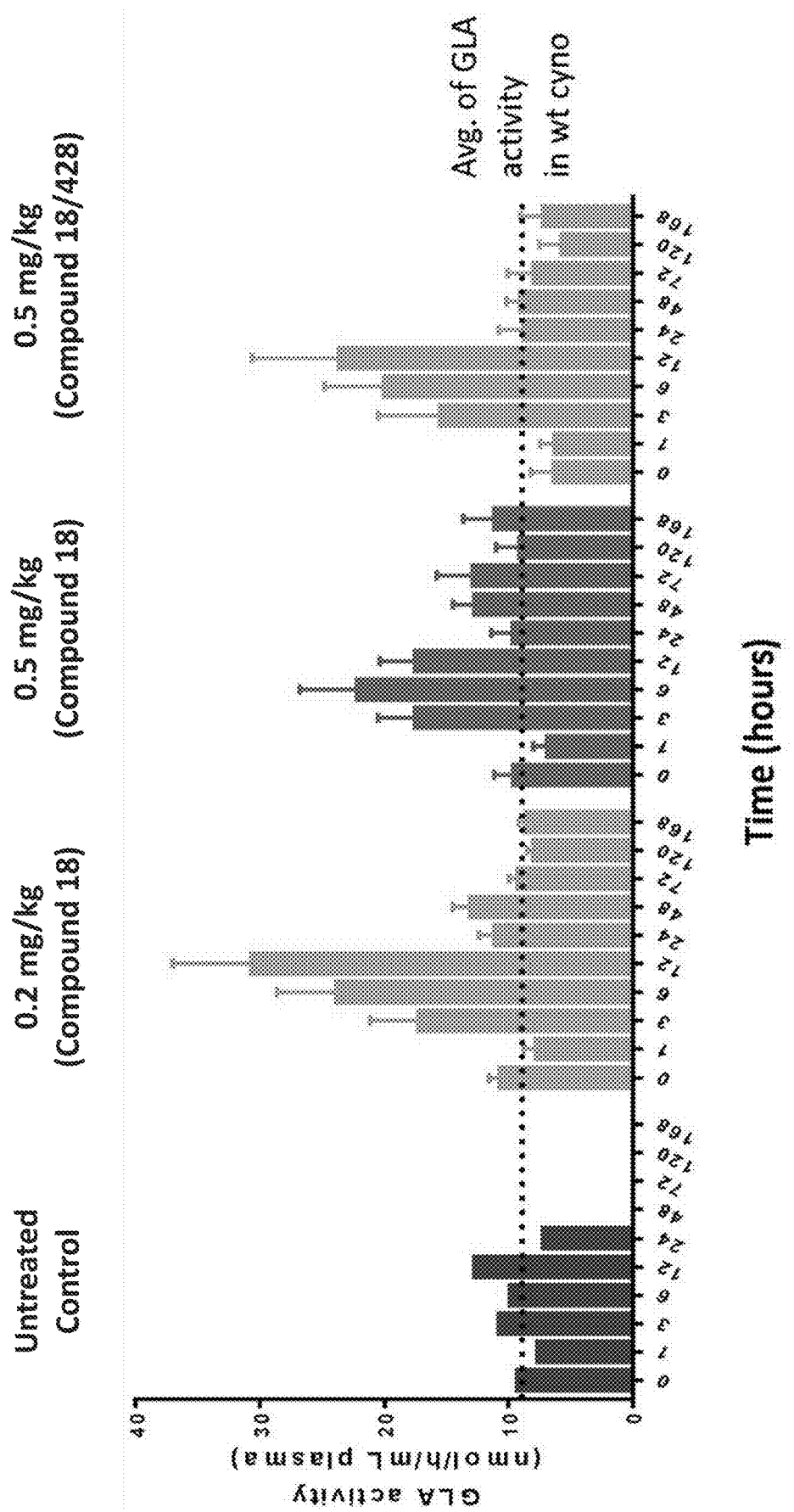

FIG. 19 shows a time-course of GLA activity level in the plasma of monkeys treated with GLA-mRNA relative to untreated monkeys. GLA activity peaked around 6-12 hours after treatment with GLA-mRNA.

Figure 20:
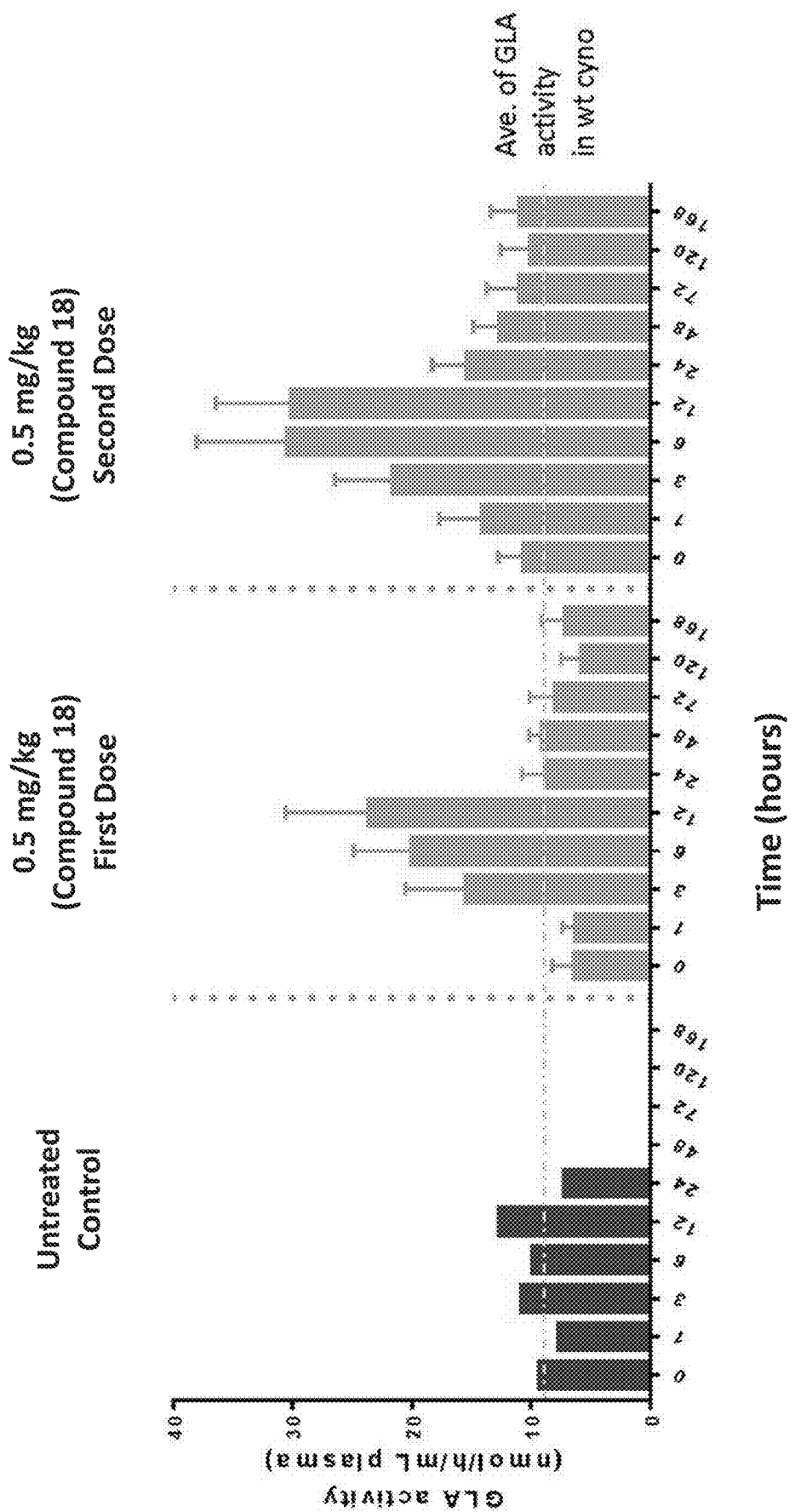

FIG. 20 shows the ability of sequence optimized, chemically modified GLA-encoding mRNAs to facilitate GLA activity in vivo after administration of multiple doses. GLA activity peaked around 6-12 hours after each treatment with GLA-mRNA. Further, FIG. 20 shows that the GLA activity levels were higher at each time point after the second treatment with GLA-mRNA, relative to the equivalent time point after the first treatment with GLA-mRNA.

DETAILED DESCRIPTION

The present invention provides mRNA therapeutics for the treatment of Fabry disease. Fabry disease is a genetic metabolic disorder of glycosphingolipid catabolism that results in the progressive accumulation of globotriaosylceramide (Gb3) and related glycosphingolipids within the lysosomes of multiple cell types. Fabry disease is caused by mutations in the GLA gene, which codes for the enzyme α-galactosidase A (GLA). mRNA therapeutics are particularly well-suited for the treatment of Fabry disease as the technology provides for the intracellular delivery of mRNA encoding GLA followed by de novo synthesis of functional GLA protein within target cells. After delivery of mRNA to the target cells, the desired GLA protein is expressed by the cells' own translational machinery, and hence, fully functional GLA protein replaces the defective or missing protein. Further, mRNA-based therapy of Fabry disease can spread beyond cells to which the mRNA is delivered because a proportion of synthesized GLA is secreted from the cell and taken up by receptor-mediated endocytosis though mannose-6-phosphate receptors.

One challenge associated with delivering nucleic acid-based therapeutics (e.g., mRNA therapeutics) in vivo stems from the innate immune response which can occur when the body's immune system encounters foreign nucleic acids. Foreign mRNAs can activate the immune system via recognition through toll-like receptors (TLRs), in particular TLR7/8, which is activated by single-stranded RNA (ssRNA). In nonimmune cells, the recognition of foreign mRNA can occur through the retinoic acid-inducible gene I (RIG-I). Immune recognition of foreign mRNAs can result in unwanted cytokine effects including interleukin-1β(IL-1β) production, tumor necrosis factor-α (TNF-α) distribution and a strong type I interferon (type I IFN) response. The instant invention features the incorporation of different modified nucleotides within therapeutic mRNAs to minimize the immune activation and optimize the translation efficiency of mRNA to protein. Particular aspects of the invention feature a combination of nucleotide modification to reduce the innate immune response and sequence optimization, in particular, within the open reading frame (ORF) of therapeutic mRNAs encoding GLA to enhance protein expression.

Certain embodiments of the mRNA therapeutic technology of the instant invention also features delivery of mRNA encoding GLA via a lipid nanoparticle (LNP) delivery system. Lipid nanoparticles (LNPs) are an ideal platform for the safe and effective delivery of mRNAs to target cells. LNPs have the unique ability to deliver nucleic acids by a mechanism involving cellular uptake, intracellular transport and endosomal release or endosomal escape. The instant invention features novel ionizable lipid-based LNPs combined with mRNA encoding GLA which have improved properties when administered in vivo. Without being bound in theory, it is believed that the novel ionizable lipid-based LNP formulations have improved properties, for example, cellular uptake, intracellular transport and/or endosomal release or endosomal escape. LNPs administered by systemic route (e.g., intravenous (IV) administration), for example, in a first administration, can accelerate the clearance of subsequently injected LNPs, for example, in further administrations. This phenomenon is known as accelerated blood clearance (ABC) and is a key challenge, in particular, when replacing deficient enzymes (e.g., GLA) in a therapeutic context. This is because repeat administration of mRNA therapeutics is in most instances essential to maintain necessary levels of enzyme in target tissues in subjects (e.g., subjects suffering from Fabry disease). Repeat dosing challenges can be addressed on multiple levels. mRNA engineering and/or efficient delivery by LNPs can result in increased levels and or enhanced duration of protein (e.g., GLA) being expressed following a first dose of administration, which in turn, can lengthen the time between first dose and subsequent dosing. It is known that the ABC phenomenon is, at least in part, transient in nature, with the immune responses underlying ABC resolving after sufficient time following systemic administration. As such, increasing the duration of protein expression and/or activity following systemic delivery of an mRNA therapeutic of the invention in one aspect, combats the ABC phenomenon. Moreover, LNPs can be engineered to avoid immune sensing and/or recognition and can thus further avoid ABC upon subsequent or repeat dosing. Exemplary aspect of the invention feature novel LNPs which have been engineered to have reduced ABC.

1. α-galactosidase A (GLA)

α-galactosidase A (GLA) is a 48,767 Da a polypeptide that is a homodimeric glycoside hydrolase enzyme. It hydrolyzes the terminal alpha-galactosyl moieties from glycolipids and glycoproteins. GLA is encoded by the GLA gene in humans.

Mutations in the GLA gene can affect the synthesis, processing, and stability of α-galactosidase A, and can cause Fabry's disease, a rare lysosomal storage disorder and sphingolipidosis. Fabry's disease results from a failure to catabolize alpha-D-galactosyl glycolipid moieties, and involves an inborn error of glycosphingolipid catabolism in which glycolipid accumulates in many tissues. Patients with Fabry's disease systemically and progressively accumulate of globotriaosylceramide (Gb3) and related glycosphingolipids in plasma and cellular lysosomes throughout the body. For example, a study of Fabry disease patients found an average Gb3 plasma concentration of 11.4±0.8 nmol/mL in affected patients. Schiffmann and O'Brady, Chapter 36 in Fabry Disease: Perspectives from 5 Years of FOS (Oxford: Oxford PharmaGenesis; 2006). Males with Fabry's disease have characteristic skin lesions (angiokeratomas) over the lower trunk. Ocular deposits, febrile episodes, burning pain in the extremities can occur. Renal failure as well as cardiac or cerebral complications of hypertension or other vascular disease can result in death. An attenuated form of Fabry's disease, with characteristics such as corneal opacities, can be present in heterozygous females.

The coding sequence (CDS) for the wild type GLA canonical mRNA sequence is described at the NCBI Reference Sequence database (RefSeq) under accession number NM_000169.2 ("Homo sapiens galactosidase alpha (GLA), mRNA"). The wild type GLA canonical protein sequence is described at the RefSeq database under accession number NP_000160 ("alpha-galactosidase A precursor [Homo sapiens]"). The GLA protein is 429 amino acids long. It is noted that the specific nucleic acid sequences encoding the reference protein sequence in the RefSeq sequences are the coding sequence (CDS) as indicated in the respective RefSeq database entry.

In certain aspects, the invention provides a polynucleotide (e.g., a ribonucleic acid (RNA), e.g., a messenger RNA (mRNA)) comprising a nucleotide sequence (e.g., an open reading frame (ORF)) encoding a GLA polypeptide. In some embodiments, the GLA polypeptide of the invention is a wild type GLA protein. In some embodiments, the GLA polypeptide of the invention is a variant, a peptide or a polypeptide containing a substitution, and insertion and/or an addition, a deletion and/or a covalent modification with respect to a wild-type GLA sequence. In some embodiments, sequence tags or amino acids, can be added to the sequences encoded by the polynucleotides of the invention (e.g., at the N-terminal or C-terminal ends), e.g., for localization. In some embodiments, amino acid residues located at the carboxy, amino terminal, or internal regions of a polypeptide of the invention can optionally be deleted providing for fragments.

In some embodiments, the polynucleotide (e.g., a RNA, e.g., an mRNA) comprising a nucleotide sequence (e.g., an ORF) of the invention encodes a substitutional variant of a GLA sequence, which can comprise one, two, three or more than three substitutions. In some embodiments, the substitutional variant can comprise one or more conservative amino acids substitutions. In other embodiments, the variant is an insertional variant. In other embodiments, the variant is a deletional variant.

As recognized by those skilled in the art, GLA protein fragments, functional protein domains, variants, and homologous proteins (orthologs) are also considered to be within the scope of the GLA polypeptides of the invention. A nonlimiting example of a polypeptide encoded by the polynucleotides of the invention is shown in FIG. 1, which shows the amino acid sequence of human wild type GLA.

2. Polynucleotides and Open Reading Frames (ORFs)

The instant invention features mRNAs for use in treating (i.e., prophylactically and/or therapeutically treating) Fabry disease. The mRNAs featured for use in the invention are administered to subjects and encode human α-galactosidase A (GLA) proteins(s) in vivo. Accordingly, the invention relates to polynucleotides, e.g., mRNA, comprising an open reading frame of linked nucleosides encoding human α-galactosidase A (GLA), isoforms thereof, functional fragments thereof, and fusion proteins comprising GLA. In some embodiments, the open reading frame is sequence-optimized. In particular embodiments, the invention provides sequence-optimized polynucleotides comprising nucleotides encoding the polypeptide sequence of human GLA, or sequence having high sequence identity with those sequence optimized polynucleotides.

In certain aspects, the invention provides polynucleotides (e.g., a RNA, e.g., an mRNA) that comprise a nucleotide sequence (e.g., an ORF) encoding one or more GLA polypeptides. In some embodiments, the encoded GLA polypeptide of the invention can be selected from:
(i) a full length GLA polypeptide (e.g., having the same or essentially the same length as wild-type GLA);
(ii) a functional fragment of wild-type GLA (e.g., a truncated (e.g., deletion of carboxy, amino terminal, or internal regions) sequence shorter than wild-type GLA, but still retaining GLA enzymatic activity);
(iii) a variant thereof (e.g., full length or truncated proteins in which one or more amino acids have been replaced, e.g., variants that retain all or most of the GLA activity of wild-type GLA); or
(iv) a fusion protein comprising (i) a full length GLA protein, a functional fragment or a variant thereof, and (ii) a heterologous protein.

In certain embodiments, the encoded GLA polypeptide is a mammalian GLA polypeptide, such as a human GLA polypeptide, a functional fragment or a variant thereof.

In some embodiments, the polynucleotide (e.g., a RNA, e.g., an mRNA) of the invention increases GLA protein expression levels and/or detectable GLA enzymatic activity levels in cells when introduced in those cells, e.g., by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, compared to GLA protein expression levels and/or detectable GLA enzymatic activity levels in the cells prior to the administration of the polynucleotide of the invention. GLA protein expression levels and/or GLA enzymatic activity can be measured according to methods know in the art. In some embodiments, the polynucleotide is introduced to the cells in vitro. In some embodiments, the polynucleotide is introduced to the cells in vivo.

In some embodiments, the polynucleotides (e.g., a RNA, e.g., an mRNA) of the invention comprise a nucleotide sequence (e.g., an ORF) that encodes a wild-type human GLA, e.g., wild-type human GLA (SEQ ID NO: 1, see FIG. 1).

In some embodiments, the polynucleotide (e.g., a RNA, e.g., an mRNA) of the invention comprises a codon optimized nucleic acid sequence, wherein the open reading frame (ORF) of the codon optimized nucleic sequence is derived from a wild-type GLA sequence.

In some embodiments, the polynucleotides (e.g., a RNA, e.g., an mRNA) of the invention comprise a nucleotide sequence encoding GLA having the full length sequence of human GLA (i.e., including the initiator methionine). In mature human GLA, the initiator methionine can be removed to yield a "mature GLA" comprising amino acid residues of 2-429 of the translated product. Alternatively, the signal peptide can be removed to yield amino acid residues 32-429 of the translated product. The teachings of the present disclosure directed to the full sequence of human GLA (amino acids 1-429) are also applicable to the mature form of human GLA lacking the initiator methionine (amino acids 1-429) and to human GLA lacking the signal peptide (amino acids 32-429). Thus, in some embodiments, the polynucleotides (e.g., a RNA, e.g., an mRNA) of the invention comprise a nucleotide sequence encoding GLA having the mature sequence of human GLA (i.e., lacking the initiator methionine). In some embodiments, the polynucleotides (e.g., a RNA, e.g., an mRNA) of the invention comprise a nucleotide sequence encoding GLA lacking the signal peptide. In some embodiments, the polynucleotide (e.g., a RNA, e.g., an mRNA) of the invention comprising a nucleotide sequence encoding GLA having the full length or mature sequence of human GLA, or encoding GLA lacking the signal peptide, is sequence optimized.

In some embodiments, the polynucleotides (e.g., a RNA, e.g., an mRNA) of the invention comprise a nucleotide sequence (e.g., an ORF) encoding a mutant GLA polypeptide. In some embodiments, the polynucleotides of the invention comprise an ORF encoding a GLA polypeptide that comprises at least one point mutation in the GLA sequence and retains GLA enzymatic activity. In some embodiments, the mutant GLA polypeptide has a GLA activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the GLA activity of the corresponding wild-type GLA (i.e., the same wild-type GLA but without the mutation(s)). In some embodiments, the polynucleotide (e.g., a RNA, e.g., an mRNA) of the invention comprising an ORF encoding a mutant GLA polypeptide is sequence optimized.

In some embodiments, the polynucleotide (e.g., a RNA, e.g., an mRNA) of the invention comprises a nucleotide sequence (e.g., an ORF) that encodes a GLA polypeptide with mutations that do not alter GLA enzymatic activity. Such mutant GLA polypeptides can be referred to as function-neutral. In some embodiments, the polynucleotide comprises an ORF that encodes a mutant GLA polypeptide comprising one or more function-neutral point mutations.

In some embodiments, the mutant GLA polypeptide has higher GLA enzymatic activity than the corresponding wild-type GLA. In some embodiments, the mutant GLA polypeptide has a GLA activity that is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the activity of the corresponding wild-type GLA (i.e., the wild-type GLA but without the mutation(s)).

In some embodiments, the polynucleotides (e.g., a RNA, e.g., an mRNA) of the invention comprise a nucleotide sequence (e.g., an ORF) encoding a functional GLA fragment, e.g., where one or more fragments correspond to a polypeptide subsequence of a wild type GLA polypeptide and retain GLA enzymatic activity. In some embodiments, the GLA fragment has a GLA activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the GLA activity of the corresponding full length GLA. In some embodiments, the polynucleotides (e.g., a RNA, e.g., an mRNA) of the invention comprising an ORF encoding a functional GLA fragment is sequence optimized.

In some embodiments, the polynucleotide (e.g., a RNA, e.g., an mRNA) of the invention comprises a nucleotide sequence (e.g., an ORF) encoding a GLA fragment that has higher GLA enzymatic activity than the corresponding full length GLA. Thus, in some embodiments the GLA fragment has a GLA activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the GLA activity of the corresponding full length GLA.

In some embodiments, the polynucleotide (e.g., a RNA, e.g., an mRNA) of the invention comprises a nucleotide sequence (e.g., an ORF) encoding a GLA fragment that is at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% shorter than wild-type GLA.

In some embodiments, the polynucleotide (e.g., a RNA, e.g., an mRNA) of the invention comprises a nucleotide sequence (e.g., an ORF) encoding a GLA polypeptide (e.g., the wild-type sequence, functional fragment, or variant thereof), wherein the nucleotide sequence has at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from the group consisting of SEQ ID NOs: 3 to 27, 79 to 80, and 141 to 159. See TABLE 2.

In some embodiments, the polynucleotide (e.g., a RNA, e.g., an mRNA) of the invention comprises a nucleotide sequence (e.g., an ORF) encoding a GLA polypeptide (e.g., the wild-type sequence, functional fragment, or variant thereof), wherein the nucleotide sequence has 70% to 100%, 75% to 100%, 80% to 100%, 81% to 100%, 82% to 100%, 83% to 100%, 84% to 100%, 85% to 100%, 86% to 100%, 87% to 100%, 88% to 100%, 89% to 100%, 90% to 100%, 91% to 100%, 92% to 100%, 93% to 100%, 94% to 100%, 95% to 100%, 70% to 75%, 70% to 80%, 70% to 85%, 70% to 90%, 70% to 95%, 75% to 80%, 75% to 85%, 75% to 90%, 75% to 95%, 80% to 85%, 85% to 90%, 85% to 95%, or 90% to 95% sequence identity to a sequence selected from the group consisting of SEQ ID NOs: 3 to 27, 79 to 80, and 141 to 159. See TABLE 2.

In some embodiments, the polynucleotide (e.g., a RNA, e.g., an mRNA) of the invention comprises an ORF encoding a GLA polypeptide (e.g., the wild-type sequence, functional fragment, or variant thereof), wherein the polynucleotide comprises a nucleic acid sequence having 70% to 100%, 75% to 100%, 80% to 100%, 85% to 100%, 70% to 95%, 80% to 95%, 70% to 85%, 75% to 90%, 80% to 95%, 70% to 75%, 75% to 80%, 80% to 85%, 85% to 90%, 90% to 95%, or 95% to 100%, sequence identity to a sequence selected from the group consisting of SEQ ID NOs: 119-120, 122-140, and 160. See TABLE 5.

In some embodiments, the polynucleotide (e.g., a RNA, e.g., an mRNA) of the invention comprises a nucleotide sequence (e.g., an ORF) encoding a GLA polypeptide (e.g., the wild-type sequence, functional fragment, or variant thereof), wherein the nucleotide sequence is at least 70%, at least 71%, at least 72%, at least 73%, at least 74%, 75%, at least 76%, at least 77%, at least 78%, at least 79%, least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence of SEQ ID NO:2 (see, e.g., FIG. 2).

In some embodiments the polynucleotide (e.g., a RNA, e.g., an mRNA) of the invention comprises a nucleotide sequence (e.g., an ORF) encoding a GLA polypeptide (e.g., the wild-type sequence, functional fragment, or variant thereof), wherein the nucleotide sequence is between 70% to 100%, 75% to 100%, 80% to 100%, 81% to 100%, 82% to 100%, 83% to 100%, 84% to 100%, 85% to 100%, 86% to 100%, 87% to 100%, 88% to 100%, 89% to 100%, 90% to 100%, 91% to 100%, 92% to 100%, 93% to 100%, 94% to 100%, 95% to 100%, 70% to 75%, 70% to 80%, 70% to 85%, 70% to 90%, 70% to 95%, 75% to 80%, 75% to 85%, 75% to 90%, 75% to 95%, 80% to 85%, 85% to 90%, 85% to 95%, or 90% to 95% identical to the sequence of SEQ ID NO:2 (see, e.g., FIG. 2).

In some embodiments, the polynucleotide (e.g., a RNA, e.g., an mRNA) of the invention comprises from about 900 to about 100,000 nucleotides (e.g., from 900 to 1,000, from 900 to 1,100, from 900 to 1,200, from 900 to 1,300, from 900 to 1,400, from 900 to 1,500, from 1,000 to 1,100, from 1,000 to 1,100, from 1,000 to 1,200, from 1,000 to 1,300, from 1,000 to 1,400, from 1,000 to 1,500, from 1,194 to 1,400, from 1,194 to 1,600, from 1,194 to 1,800, from 1,194 to 2,000, from 1,194 to 3,000, from 1,194 to 5,000, from 1,194 to 7,000, from 1,194 to 10,000, from 1,194 to 25,000, from 1,194 to 50,000, from 1,194 to 70,000, from 1,194 to 100,000, from 1,287 to 1,400, from 1,287 to 1,600, from 1,287 to 1,800, from 1,287 to 2,000, from 1,287 to 3,000, from 1,287 to 5,000, from 1,287 to 7,000, from 1,287 to 10,000, from 1,287 to 25,000, from 1,287 to 50,000, from 1,287 to 70,000, or from 1,287 to 100,000).

In some embodiments, the polynucleotide of the invention (e.g., a RNA, e.g., an mRNA) comprises a nucleotide sequence (e.g., an ORF) encoding a GLA polypeptide (e.g., the wild-type sequence, functional fragment, or variant thereof), wherein the length of the nucleotide sequence (e.g., an ORF) is at least 500 nucleotides in length (e.g., at least or greater than about 500, 600, 700, 800, 900, 1,000, 1,050, 1,100, 1,150, 1,194, 1,200, 1,250, 1,287, 1,300, 1,400, 1,500, 1,600, 1,700, 1,800, 1,900, 1,959, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 7,000, 8,000, 9,000, 10,000, 20,000, 30,000, 40,000, 50,000, 60,000, 70,000, 80,000, 90,000 or up to and including 100,000 nucleotides).

In some embodiments, the polynucleotide of the invention (e.g., a RNA, e.g., an mRNA) comprises a nucleotide sequence (e.g., an ORF) encoding a GLA polypeptide (e.g., the wild-type sequence, functional fragment, or variant thereof) further comprises at least one nucleic acid sequence that is noncoding, e.g., a miRNA binding site. In some embodiments, the polynucleotide (e.g., a RNA, e.g., an mRNA) of the invention further comprises a 5'-UTR (e.g., selected from the sequences of SEQ ID NOs: 33 to 50, 77, and 115 to 117) and a 3'UTR (e.g., selected from the sequences of SEQ ID NOs: 51 to 75, 81 to 82, 88, 103, 106 to 113, 118, and 161 to 170). In some embodiments, the polynucleotide (e.g., a RNA, e.g., an mRNA) of the invention comprises a sequence selected from the group consisting of SEQ ID NO: 119-120, 122-140, and 160. In a further embodiment, the polynucleotide (e.g., a RNA, e.g., an mRNA) comprises a 5' terminal cap (e.g., Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof) and a poly-A-tail region (e.g., about 100 nucleotides in length). In a further embodiment, the polynucleotide (e.g., a RNA, e.g., an mRNA) a comprises a 3' UTR comprising a nucleic acid sequence selected from the group consisting of SEQ ID NO: 81, 82, 103, and any combination thereof.

In some embodiments, the polynucleotide of the invention (e.g., a RNA, e.g., an mRNA) comprises a nucleotide sequence (e.g., an ORF) encoding a GLA polypeptide is single stranded or double stranded.

In some embodiments, the polynucleotide of the invention comprising a nucleotide sequence (e.g., an ORF) encoding a GLA polypeptide (e.g., the wild-type sequence, functional fragment, or variant thereof) is DNA or RNA. In some embodiments, the polynucleotide of the invention is RNA. In some embodiments, the polynucleotide of the invention is, or functions as, a messenger RNA (mRNA). In some embodiments, the mRNA comprises a nucleotide sequence (e.g., an ORF) that encodes at least one GLA polypeptide, and is capable of being translated to produce the encoded GLA polypeptide in vitro, in vivo, in situ or ex vivo.

In some embodiments, the polynucleotide of the invention (e.g., a RNA, e.g., an mRNA) comprises a sequence-optimized nucleotide sequence (e.g., an ORF) encoding a GLA polypeptide (e.g., the wild-type sequence, functional fragment, or variant thereof), wherein the polynucleotide comprises at least one chemically modified nucleobase, e.g., 5-methoxyuracil. In some embodiments, the polynucleotide further comprises a miRNA binding site, e.g., a miRNA binding site that binds to miR-142 and/or a miRNA binding site that binds to miR-126. In some embodiments, the polynucleotide (e.g., a RNA, e.g., an mRNA) disclosed herein is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

3. Signal Sequences

The polynucleotides (e.g., a RNA, e.g., an mRNA) of the invention can also comprise nucleotide sequences that encode additional features that facilitate trafficking of the encoded polypeptides to therapeutically relevant sites. One such feature that aids in protein trafficking is the signal sequence, or targeting sequence. The peptides encoded by these signal sequences are known by a variety of names, including targeting peptides, transit peptides, and signal peptides. In some embodiments, the polynucleotide (e.g., a RNA, e.g., an mRNA) comprises a nucleotide sequence (e.g., an ORF) that encodes a signal peptide operably linked to a nucleotide sequence that encodes a GLA polypeptide described herein.

In some embodiments, the "signal sequence" or "signal peptide" is a polynucleotide or polypeptide, respectively, which is from about 9 to 200 nucleotides (3-70 amino acids) in length that, optionally, is incorporated at the 5' (or N-terminus) of the coding region or the polypeptide, respectively. Addition of these sequences results in trafficking the encoded polypeptide to a desired site, such as the endoplasmic reticulum or the mitochondria through one or more targeting pathways. Some signal peptides are cleaved from the protein, for example by a signal peptidase after the proteins are transported to the desired site.

In some embodiments, the polynucleotide of the invention comprises a nucleotide sequence encoding a GLA polypeptide, wherein the nucleotide sequence further comprises a 5' nucleic acid sequence encoding a native signal peptide. In another embodiment, the polynucleotide of the invention comprises a nucleotide sequence encoding a GLA polypeptide, wherein the nucleotide sequence lacks the nucleic acid sequence encoding a native signal peptide.

In some embodiments, the polynucleotide of the invention comprises a nucleotide sequence encoding a GLA polypeptide, wherein the nucleotide sequence further comprises a 5' nucleic acid sequence encoding a heterologous signal peptide.

4. Fusion Proteins

In some embodiments, the polynucleotide of the invention (e.g., a RNA, e.g., an mRNA) can comprise more than one nucleic acid sequence (e.g., an ORF) encoding a polypeptide of interest. In some embodiments, polynucleotides of the invention comprise a single ORF encoding a GLA polypeptide, a functional fragment, or a variant thereof. However, in some embodiments, the polynucleotide of the invention can comprise more than one ORF, for example, a first ORF encoding a GLA polypeptide (a first polypeptide of interest), a functional fragment, or a variant thereof, and a second ORF expressing a second polypeptide of interest. In some embodiments, two or more polypeptides of interest can be genetically fused, i.e., two or more polypeptides can be encoded by the same ORF. In some embodiments, the polynucleotide can comprise a nucleic acid sequence encoding a linker (e.g., a $G_4S$ peptide linker or another linker known in the art) between two or more polypeptides of interest.

In some embodiments, a polynucleotide of the invention (e.g., a RNA, e.g., an mRNA) can comprise two, three, four, or more ORFs, each expressing a polypeptide of interest.

In some embodiments, the polynucleotide of the invention (e.g., a RNA, e.g., an mRNA) can comprise a first nucleic acid sequence (e.g., a first ORF) encoding a GLA polypeptide and a second nucleic acid sequence (e.g., a second ORF) encoding a second polypeptide of interest.

5. Sequence Optimization of Nucleotide Sequence Encoding a GLA Polypeptide

In some embodiments, the polynucleotide (e.g., a RNA, e.g., an mRNA) of the invention is sequence optimized. In some embodiments, the polynucleotide (e.g., a RNA, e.g., an mRNA) of the invention comprises a nucleotide sequence (e.g., an ORF) encoding a GLA polypeptide, a nucleotide sequence (e.g., an ORF) encoding another polypeptide of interest, a 5'-UTR, a 3'-UTR, a miRNA, a nucleotide sequence encoding a linker, or any combination thereof) that is sequence optimized. One aspect of sequence optimization A sequence-optimized nucleotide sequence, e.g., an codon-optimized mRNA sequence encoding a GLA polypeptide, is a sequence comprising at least one synonymous nucleobase substitution with respect to a reference sequence (e.g., a wild type nucleotide sequence encoding a GLA polypeptide).

A sequence-optimized nucleotide sequence can be partially or completely different in sequence from the reference sequence. For example, a reference sequence encoding polyserine uniformly encoded by TCT codons can be sequence-optimized by having 100% of its nucleobases substituted (for each codon, T in position 1 replaced by A, C in position 2 replaced by G, and T in position 3 replaced by C) to yield a sequence encoding polyserine which would be uniformly encoded by AGC codons. The percentage of sequence identity obtained from a global pairwise alignment between the reference polyserine nucleic acid sequence and the sequence-optimized polyserine nucleic acid sequence would be 0%. However, the protein products from both sequences would be 100% identical.

Some sequence optimization (also sometimes referred to codon optimization) methods are known in the art (and discussed in more detail below) and can be useful to achieve one or more desired results. These results can include, e.g., matching codon frequencies in certain tissue targets and/or host organisms to ensure proper folding; biasing G/C content to increase mRNA stability or reduce secondary structures; minimizing tandem repeat codons or base runs that can impair gene construction or expression; customizing transcriptional and translational control regions; inserting or removing protein trafficking sequences; removing/adding post translation modification sites in an encoded protein (e.g., glycosylation sites); adding, removing or shuffling protein domains; inserting or deleting restriction sites; modifying ribosome binding sites and mRNA degradation sites; adjusting translational rates to allow the various domains of the protein to fold properly; and/or reducing or eliminating problem secondary structures within the polynucleotide. Sequence optimization tools, algorithms and services are known in the art, non-limiting examples include services from GeneArt (Life Technologies), DNA2.0 (Menlo Park Calif.) and/or proprietary methods.

Codon options for each amino acid are given in TABLE 1.

TABLE 1

Codon Options

| Amino Acid | Single Letter Code | Codon Options |
|---|---|---|
| Isoleucine | I | ATT, ATC, ATA |
| Leucine | L | CTT, CTC, CTA, CTG, TTA, TTG |
| Valine | V | GTT, GTC, GTA, GTG |
| Phenylalanine | F | TTT, TTC |
| Methionine | M | ATG |
| Cysteine | C | TGT, TGC |
| Alanine | A | GCT, GCC, GCA, GCG |
| Glycine | G | GGT, GGC, GGA, GGG |
| Proline | P | CCT, CCC, CCA, CCG |
| Threonine | T | ACT, ACC, ACA, ACG |
| Serine | S | TCT, TCC, TCA, TCG, AGT, AGC |
| Tyrosine | Y | TAT, TAC |
| Tryptophan | W | TGG |
| Glutamine | Q | CAA, CAG |
| Asparagine | N | AAT, AAC |
| Histidine | H | CAT, CAC |
| Glutamic acid | E | GAA, GAG |
| Aspartic acid | D | GAT, GAC |
| Lysine | K | AAA, AAG |
| Arginine | R | CGT, CGC, CGA, CGG, AGA, AGG |
| Selenocysteine | Sec | UGA in mRNA in presence of Selenocysteine insertion element (SECIS) |
| Stop codons | Stop | TAA, TAG, TGA |

In some embodiments, a polynucleotide (e.g., a RNA, e.g., an mRNA) of the invention comprises a sequence-optimized nucleotide sequence (e.g., an ORF) encoding a GLA polypeptide, a functional fragment, or a variant thereof, wherein the GLA polypeptide, functional fragment, or a variant thereof encoded by the sequence-optimized nucleotide sequence has improved properties (e.g., compared to a GLA polypeptide, functional fragment, or a variant thereof encoded by a reference nucleotide sequence that is not sequence optimized), e.g., improved properties related to expression efficacy after administration in vivo. Such properties include, but are not limited to, improving nucleic acid stability (e.g., mRNA stability), increasing translation efficacy in the target tissue, reducing the number of truncated proteins expressed, improving the folding or prevent misfolding of the expressed proteins, reducing toxicity of the expressed products, reducing cell death caused by the expressed products, increasing and/or decreasing protein aggregation.

In some embodiments, the sequence-optimized nucleotide sequence is codon optimized for expression in human subjects, having structural and/or chemical features that avoid one or more of the problems in the art, for example, features which are useful for optimizing formulation and delivery of nucleic acid-based therapeutics while retaining structural and functional integrity; overcoming a threshold of expression; improving expression rates; half-life and/or protein concentrations; optimizing protein localization; and avoiding deleterious bio-responses such as the immune response and/or degradation pathways.

In some embodiments, the polynucleotides of the invention comprise a nucleotide sequence (e.g., a nucleotide sequence (e.g., an ORF) encoding a GLA polypeptide, a nucleotide sequence (e.g., an ORF) encoding another polypeptide of interest, a 5'-UTR, a 3'-UTR, a microRNA binding site, a nucleic acid sequence encoding a linker, or any combination thereof) that is sequence-optimized according to a method comprising:

(i) substituting at least one codon in a reference nucleotide sequence (e.g., an ORF encoding a GLA polypeptide) with an alternative codon to increase or decrease uridine content to generate a uridine-modified sequence;

(ii) substituting at least one codon in a reference nucleotide sequence (e.g., an ORF encoding a GLA polypeptide) with an alternative codon having a higher codon frequency in the synonymous codon set;

(iii) substituting at least one codon in a reference nucleotide sequence (e.g., an ORF encoding a GLA polypeptide) with an alternative codon to increase G/C content; or (iv) a combination thereof.

In some embodiments, the sequence-optimized nucleotide sequence (e.g., an ORF encoding a GLA polypeptide) has at least one improved property with respect to the reference nucleotide sequence.

In some embodiments, the sequence optimization method is multiparametric and comprises one, two, three, four, or more methods disclosed herein and/or other optimization methods known in the art.

Features, which can be considered beneficial in some embodiments of the invention, can be encoded by or within regions of the polynucleotide and such regions can be upstream (5') to, downstream (3') to, or within the region that encodes the GLA polypeptide. These regions can be incorporated into the polynucleotide before and/or after sequence-optimization of the protein encoding region or open reading frame (ORF). Examples of such features include, but are not limited to, untranslated regions (UTRs), microRNA sequences, Kozak sequences, oligo(dT) sequences, poly-A tail, and detectable tags and can include multiple cloning sites that can have XbaI recognition.

In some embodiments, the polynucleotide of the invention comprises a 5' UTR, a 3' UTR and/or a miRNA binding site. In some embodiments, the polynucleotide comprises two or more 5' UTRs and/or 3' UTRs, which can be the same or different sequences. In some embodiments, the polynucleotide comprises two or more miRNA, which can be the same or different sequences. Any portion of the 5' UTR, 3' UTR, and/or miRNA binding site, including none, can be sequence-optimized and can independently contain one or more different structural or chemical modifications, before and/or after sequence optimization.

In some embodiments, after optimization, the polynucleotide is reconstituted and transformed into a vector such as, but not limited to, plasmids, viruses, cosmids, and artificial chromosomes. For example, the optimized polynucleotide can be reconstituted and transformed into chemically competent *E. coli*, yeast, neurospora, maize, drosophila, etc. where high copy plasmid-like or chromosome structures occur by methods described herein.

6. Sequence-Optimized Nucleotide Sequences Encoding GLA Polypeptides

In some embodiments, the polynucleotide of the invention comprises a sequence-optimized nucleotide sequence encoding a GLA polypeptide disclosed herein. In some embodiments, the polynucleotide of the invention comprises an open reading frame (ORF) encoding a GLA polypeptide, wherein the ORF has been sequence optimized.

Exemplary sequence-optimized nucleotide sequences encoding human GLA are set forth as SEQ ID NOs: 3-27 (GLA-CO01, GLA-CO02, GLA-CO03, GLA-CO04, GLA-CO05, GLA-CO06, GLA-CO07, GLA-CO08, GLA-CO09, GLA-CO10, GLA-CO11, GLA-CO12, GLA-CO13, GLA-CO14, GLA-CO15, GLA-CO16, GLA-CO17, GLA-CO18, GLA-CO19, GLA-CO20, GLA-CO21, GLA-CO22, GLA-CO23, GLA-CO24, and GLA-CO25, respectively. Further exemplary sequence optimized nucleotide sequences encoding human GLA are shown in TABLE 2. In some embodiments, the sequence optimized GLA sequences set forth as SEQ ID NOs: 3-27 or shown in TABLE 2, fragments, and variants thereof are used to practice the methods disclosed herein. In some embodiments, the sequence optimized GLA sequences in TABLE 2, fragments and variants thereof are combined with or alternatives to the wild-type sequences disclosed in FIGS. 1-2.

In some embodiments, a polynucleotide of the present disclosure, for example a polynucleotide comprising an mRNA nucleotide sequence encoding a GLA polypeptide, comprises from 5' to 3' end:
(i) a 5' cap provided herein, for example, CAP1;
(ii) a 5' UTR, such as the sequences provided herein, for example, SEQ ID NO: 33;
(iii) an open reading frame encoding a GLA polypeptide, e.g., a sequence optimized nucleic acid sequence encoding GLA set forth as SEQ ID NOs: 3 to 27, 79 to 80, and 141 to 159, or shown in TABLE 2;
(iv) at least one stop codon;
(v) a 3' UTR, such as the sequences provided herein, for example, SEQ ID NOs: 81, 82, or 103; and
(vi) a poly-A tail provided above.

TABLE 2

Sequence-Optimized Sequences for Human GLA

| SEQ ID NO | Name | Sequence |
|---|---|---|
| 3 | GLA-CO01 | See Sequence Listing |
| 4 | GLA-CO02 | See Sequence Listing |
| 5 | GLA-CO03 | See Sequence Listing |
| 6 | GLA-CO04 | See Sequence Listing |
| 7 | GLA-CO05 | See Sequence Listing |
| 8 | GLA-CO06 | See Sequence Listing |
| 9 | GLA-CO07 | See Sequence Listing |
| 10 | GLA-CO08 | See Sequence Listing |
| 11 | GLA-CO09 | See Sequence Listing |
| 12 | GLA-CO10 | See Sequence Listing |
| 13 | GLA-CO11 | See Sequence Listing |
| 14 | GLA-CO12 | See Sequence Listing |
| 15 | GLA-CO13 | See Sequence Listing |
| 16 | GLA-CO14 | See Sequence Listing |
| 17 | GLA-CO15 | See Sequence Listing |
| 18 | GLA-CO16 | See Sequence Listing |
| 19 | GLA-CO17 | See Sequence Listing |
| 20 | GLA-CO18 | See Sequence Listing |
| 21 | GLA-CO19 | See Sequence Listing |
| 22 | GLA-CO20 | See Sequence Listing |
| 23 | GLA-CO21 | See Sequence Listing |

TABLE 2-continued

Sequence-Optimized Sequences for Human GLA

| SEQ ID NO | Name | Sequence |
|---|---|---|
| 24 | GLA-CO22 | See Sequence Listing |
| 25 | GLA-CO23 | See Sequence Listing |
| 26 | GLA-CO24 | See Sequence Listing |
| 27 | GLA-CO25 | See Sequence Listing |
| 79 | GLA-CO26 | AUGCAGCUCCGGAACCCCGAGCUCCACCUUGGCUGCGCCCUCGCCUUGCGGUUCCUCGCACUUGUGAGCUGGGA<br>CAUACCAGGCGCCCGGGCCCUCGACAACGGCCUCGCCCGCACCCCAACCAUGGGCUGGCUCCACUGGGAGCGCU<br>UCAUGUGCAACCUCGACUGCCAGGAGGAGCCCGACUCCUGCAUCUCCGAGAAGCUUUUCAUGGAGAUGGCCGAG<br>CUCAUGGUGUCCGAGGGCUGGAAGGACGCCGGCUACGAGUACCUCUGCAUCGACGACUGCUGGAUGGCCCCGCA<br>GCGCGACAGCGAGGGUCGCCUCCAGGCCGACCCCGCAGCGGUUCCCUCACGGCAUCCGCCAGCUCGCCAACUACG<br>UCCACUCCAAGGGCCUCAAGCUCGGCAUCUACGCCGACGUCGGCAACAAGACCUGCGCCGGCUUCCCCGGCUCC<br>UUCGGCUACUACGACAUCGACGCCCAGACCUUCGCCGACUGGGGCGUCGACCUCCUCAAGUUCGACGGCUGCUA<br>CUGCGACUCCCUCGAGAACCUCCGCGACGGCUACAAGCACAUGUCCCUCGCCCUCAACCGCACCGGCCGCUCCA<br>UCGUCUACUCCUGCGAGUGGCCCCUCUACAUGUGGCCCUUCCAGAAGCCCAACUACACCGAGAUAAGGCAGUAC<br>UGCAACCACUGGCGCAAUUUCGCCGAUAUCGAUGACUCCUGGAAGUCCAUCAAGAGCAUCCUGGACUGGACCUC<br>CUUCAACCAGGAGCGCAUCGUCGACGUCGCCGGCCCCGGCGGCUGGAACGACCCCGACAUGCUCGUCAUCGAA<br>ACUUCGGCCUGUCCUGGAACCAGCAGGUCACCCAGAUGGCCCUCUGGGCCAUCAUGGCCGCCCCCACUGUUCAUG<br>UCCAACGACCUCCGCCACAUCAGCCCGCAGGCCAAGGCCCUCUCCAGGACAAGGACGUCAUCGCCAUCAACCA<br>AGACCCGCUCGGCAAGCAGGGCUACCAGCUCCGCCAGGGCGACAACUUCGAGGUGUGGGAACGUCCCCUCAGCG<br>GCCUGGCGUGGGCCGUCGCCAUGAUCAACCGCCAGGAGAUCGGCGGCCCGCGCUCCUACACCAUCGCCGUGGCC<br>AGCCUGGGCAAGGGCGUCGCCUGCAACCCCGCCUGCUUCAUCACCCAGCUCCUCCCCGUCAAGAGAAAGCUGGG<br>CUUCUACGAGUGGACCAGCCGCCUCCGCUCCCACAUCAACCCCACCGGCACCGUCCUGCUCCAGCUGGAGAACA<br>CCAUGCAGAUGAGCCUCAAGGACCUGCUC |
| 80 | GLA-CO27 | AUGCAGCUGCGGAACCCCGAGCUGCACCUGGGCUGCGCCCUGGCCCUGCGGUUCCUGGCCCUGGUGAGCUGGGA<br>CAUCCCCGGCGCCCGGGCCCUGGACAACGGCCUGGCCCGGACGCCCACCAUGGGCUGGCUGCACUGGGAGCGGU<br>UCAUGUGCAACCUGGACUGCCAGGAGGAGCCCGACAGCUGCAUCAGCGAGAAGCUGUUCAUGGAGAUGGCCGAG<br>CUGAUGGUGAGCGAGGGCUGGAAGGACGCCGGCUACGAGUACCUGUGCAUCGACGACUGCUGGAUGGCGCCCCA<br>GCGGGACAGCGAGGGCCGGCUGCAGGCCGACCCCGCAGCCGGUUCCCUCACGGCAUCCGGCAGCUGGCCAACUACG<br>UGCACAGCAAGGGCCUGAAGCUGGGCAUCUACGCCGACGUGGGCAACAAGACCUGCGCCGGCUUCCCCGGCAGC<br>UUCGGCUACUACGACAUCGACGCCCAGACCUUCGCCGACUGGGGCGUGGACCUGCUGAAGUUCGACGGCUGCUA<br>CUGCGACAGCCUGGAGAACCUGGCCGACGGCUACAAGCACAUGAGCCUGGCCCUGAACCGGACCGGCCGGAGCA<br>UCGUGUACAGCUGCGAGUGGCCCCUGUACAUGUGGCCCUUCCAGAAGCCCAACUACACCGAGAUCCGGCAGUAC<br>UGCAACCACUGGCGGAACUUCGCCGACAUCGACGACAGCUGGAAGAGCAUCAAGAGCAUCCUGGACUGGACCAG<br>CUUCAACCAGGAGCGGAUCGUGGACGUGGCCGGCCCCGGCGGCUGGAACGACCCCGACAUGCUGGUGAUCGGCA<br>ACUUCGGCCUGAGCUGGAACCAGCAGGUGACCCAGAUGGCCCUGUGGGCCAUCAUGGCCGCGCCCCUGUUCAUG<br>AGCAACGACCUGCGGCACAUCAGCCCCUCAGGCCAAGGCCCUGCUGCAGGACAAGGACGUGAUCGCCAUCAACCA<br>GGACCCACUGGGCAAGCAGGGCUACCAGCUGCGGCAGGGCGACAACUUCGAGGUGUGGGAGCGGCCCCUGAGCG<br>GCCUGGCUGGGCCGUGGCCAUGAUCAACCGGCAGGAGAUCGGCGGCCCGCGGAGCUACACCAUCGCCGUGGCC<br>AGCCUGGGCAAGGGCGUGGCCUGCAACCCCGCCUGCUUCAUCACCCAGCUGCUCCCGUGAAGCGGAAGCUGGG<br>CUUCUACGAGUGGACCAGCCGGCUGCGGAGCCACAUCAACCCCACCGGCACCGUGCUGCUGCAGCUGGAGAACA<br>CCAUGCAGAUGAGCCUGAAGGACCUGCUG |
| 141 | GLA-CO28 | AUGCAGCUCAGGAACCCGGAGCUCCACCUCGGCUGCGCCCUCGCCCUCAGGUUCCUCGCUCUUGUGAGCUGGGA<br>CAUCCCGGGCGCCAGGGCCCUCGACAACGGCCUCGCCAGAACCCCGACCAUGGGCUGGCUCCACUGGGAGAGGU<br>UCAUGUGUAAUCUGGACUGCCAGGAGGAGCCGGAUAGCUGCAUCAGCGAGAAGCUGUUCAUGGAGAUGGCCGAG<br>CUGAUGGUGUCCGAGGGCUGGAAGGACGCCGGCUACGAGUACCUUUGCAUCGAUGACUGCUGGAUGGCCCCGCA<br>GCGGGACAGCGAGGGCAGGCUGCAAGCUGACCCCCAGCGUUCCCGCACGGCAUCCGGCAGCUGGCCAACUACG<br>UGCACAGCAAGGGCCUGAAGCUGGGCAUCUACGCGGACGUCGGCAACAAGACCUGCGCCGGCUUCCCGGGAAGC<br>UUCGGCUACUACGACAUCGACGCCCAGACCUUCGCCGACUGGGGCGUGGACCUGCUGAAGUUCGACGGCUGCUA<br>CUGCGACAGCCUGGAGAACCUGGCCGACGGCUACAAGCACAUGUCCCUGGCUCUGAAUAGAACCGGCAGGAGCA<br>UAGUGUACAGCUGCGAGUGGCCACUGUACAUGUGGCCGUUCCAGAAGCCGAACUACACCGAAAUCAGACAAUAC<br>UGCAACCACUGGCGGAAUUUCGCCGAUAUCGACGACUCCUGGAAGUCCAUCAAGUCCAUCCUGGACUGGACCUC<br>CUUCAACCAGGAGAGAAUCGUGGACGUGGCCGGCCCUGGGUGGAUGGAACGAUCCAGACAUGCUGGUUAUCGGCA<br>AUUUCGGCCUGAGCUGGAACCAGCAGGUGACAGAUGGCCCUGUGGGCCAUCAUGGCCGCCCCCACUGUUCAUG<br>UCCAACGACCUCCGCCACAUCAGCCCCGCAGGCCAAGGCCCUCCUCCAAGACAAGGACGUGAUCGCCAUCAACCA<br>AGACCCGCUCGGCAAGCAGGGCUACCAGCUGCGCCAGGGCGACAAUUUCGAGGUCUGGGAGCGCCCGCUGUCUG<br>GUCUGGCGUGGGCCGUGGCCAUGAUCAAUAGACAGGAGAUCGGCGGCCCGCGGAGCUACACCAUCGCCGUAGCC<br>AGCCUGGGCAAGGGCGUGGCCUGCAACCCCGGCUUGUUUCAUCACCCAGCUGCUCCCGGUUAAGAGAAAGCUGGG<br>CUUCUACGAGUGGACCAGCCGGUUGCGGAGCCAUAUCAACCCGACUGGCACCGUGCUGCUGCAGCUGGAGAACA<br>CAAUGCAGAUGUCCCUGAAGGACCUGCUC |
| 142 | GLA-CO29 | AUGCAGCUCCGCAAUCCGGAGCUCCACCUCGGCUGCGCCCUCGCCCUCAGGUUCCUCGCCCUUGUGAGCUGGGA<br>UAUCCCGGGCGCCAGGGCCCUCGACAACGGCUUAGCCAGAACCCCAACGAUGGGCUGGCUCCACUGGGAGAGGU<br>UCAUGUGCAACCUGGACUGCCAGGAGGAACCGGACAGCUGCAUCUCCGAGAAGCUGUUCAUGGAGAUGGCCGAG<br>CUCAUGGUGAGCGAGGGCUGGAAGGACGCCGGCUACGAGUAUCUCUGCAUCGACGACUGCUGGAUGGCCCCACA<br>GAGGGACCUCGAGGGCCGGCUGCAAGCUGACCCCGCAGCGGUUCCUCGCCAUCCGGCAACGCCAACUACG<br>UGCACAGCAAGGGCCUGAAGCUGGGAAUCUACGCCGACGUGGGCAACAAGACCUGCGCUGGCUUCCCGGGCAGC<br>UUCGGCUACUAUGACAUCGAUGCCCAGACCUUCGCCGACUGGGGCGUCGACCUGCUCAAGUUCGACGGCUGUUA<br>CUGCGACAGCCUGGAGAACCUGGCAGACGGCUAUAAGCACAUGAGCCUGGCACUCAACAGGACCGGCAGGUCAA<br>UAGUGUACAGCUGCGAGUGGCCGCUGUACAUGUGGCCAUUCCAGAAGCCGAAUUACACCGAGAUAAGGCAGUAU<br>UGCAACCACUGGCGAAACUUCGCGGAUAUCGAUGACAGCUGGAAGUCGAUAAAGAGCAUCCUGGACUGGACCAG |

TABLE 2-continued

Sequence-Optimized Sequences for Human GLA

| SEQ ID NO | Name | Sequence |
|---|---|---|
| | | CUUCAACCAGGAGAGGAUCGUGGACGUCGCCGGCCCGGGCGGCUGGAACGACCCGGACAUGCUGGUGAUCGGAA<br>ACUUCGGCCUCAGCUGGAACCAACAGGUGACCCAGAUGGCCCUGUGGGCCAUCAUGGCGGCACCUCUGUUCAUG<br>AGCAACGACCUGCGGCAUAUCAGCCCGCAGGCCAAGGCCUGCUCCAGGACAAGGACGUCAUAGCCAUCAACCA<br>GGACCCGCUGGGCAAGCAGGGCUACCAACUGCGGCAGGGAGACAACUUCGAGGUGUGGGAGCGGCCGCUGAGCG<br>GCCUGGCAUGGGCCGUGGCCAUGAUCAAUAGACAGGAGAUCGGCGGCCCGCGGAGCUACACCAUCGCCGUGGCG<br>AGUCUUGGCAAGGGUGUGGCCUGCAAUCCGGCCUGCUUCAUCACCCAGCUGCUGCCAGUCAAGCGCAAGCUCGG<br>AUUCUACGAGUGGACCAGCCGUCUGCGCAGCCACAUCAAUCCUACCGGCACGGUGCUCCUGCAGCUGGAGAACA<br>CCAUGCAAAUGUCUCUCAAGGACCUGCUG |
| 143 | GLA-CO30 | AUGCAGCUCCGGAACCCAGAACUCCACCUCGGCUGCGCCCUCGCCCUCCGGUUCCUUGCCCUCGUGUCCUGGGA<br>CAUUCCAGGCGCCCGGGCCCUCGACAACGGCCUCGCCCGGACCCCAACCAUGGGCUGGCUCCAUUGGGAGAGGU<br>UCAUGUGCAACCUGGACUGCCAAGAGGAGCCUGACUCCUGAGAAGCUGGACGCUGAUCAUGGAGAUGGCCGAG<br>CUCAUGGUGAGCGAGGGCUGGAAGGACGCCGGCUACGAAUAUCUGUGCAUCGACGAUUGCUGGAUGGCCCCUCA<br>AAGAGACAGCGAGGGCAGACUGCAGGCCGACCCGCAGCGCUUCCCUCAUGGCAUCCGGCAACUCGCGAAUUAUG<br>UGCACAGCAAGGGCCUGAAGCUGGGCAUCUACGCCGACGUCGGUAACAAGACCUGCGCCGGCUUCCCAGGCAGC<br>UUCGGCUACUACGACAUCGACGCCCGACCUUCGCCGACUGGGGCGUAGACUCCCUGAAGUUCGACGGUUGCUA<br>CUGCGACUCCCUGGAGAACCUAGCCGACGGCUACAAGCACAUGUCCCUCGCCCUGAACAGAACCGGCCGGUCCA<br>UCGUCUAUUCCUGCGAGUGGCCGCUGUACAUGUGGCCGUUCCAGAAGCCUAACUACACAGAGAUCCGCCAGUAC<br>UGCAACCACUGGCGGAAUUUCGCCGAUAUCGACGACAGUUGGAAGUCCAUCAAGAGCAUACUGGAUUGGACCUC<br>CUUCAACCAGGAGAGGAUCGUGGACGUGGCCGGCCCGGGCGGUUGGAACGACCCAGACAUGCUGGUGAUCGGAA<br>ACUUCGGCCUGAGCUGGAACCAGCAGGUGACCCAGAUGGCCCUCUGGGCCAUCAUGGCCGCCCCUCUGUUCAUG<br>UCCAAUGACCUCAGGCAUAUCUCCCCGCAGGCCAAGGCUCUCCUCCAGGACAAGGACGUGAUCGCCAUCAAUCA<br>GGAUCCGCUGGGGAAAGCAGGGAUACCAGCUGAGGCAGGGCGACAACUUCGAGGUGUGGGAGCGCCCCACUGAGCG<br>GCCUGGCUUGGGCCGUGGCCAUGAUCAACCGGCAAGAGAUCGGCGGCCCGCGGAGCUACACCAUUGCCGUGGCU<br>AGCCUGGGCAAGGGCGUGGCCUGCAACCCGGCCUGCUUCAUCACCCAGCUUCUGCCGGUAAAGCGUAAGCUGGG<br>CUUCUACGAGUGGACCAGCAGACUGAGGAGCCACAUCAACCCCGACCGGCACCGUGCUGCUCCAGCUGGAGAACA<br>CCAUGCAGAUGAGCCUGAAGGAUCUGCUC |
| 144 | GLA-CO31 | AUGCAACUCCGCAAUCGGGAGCUCCACCUCGGCUGUGCGCUCGCCCUUAGAUUCCUCGCCCUCGUGAGCUGGGA<br>CAUCCCAGGCGCCCGGGCCCUCGACAACGGCCUAGCCCGCACUCCUACAAUGGGCUGGUUGCACUGGGAACGCU<br>UCAUGUGUAACCUGGACUGCCAGGAGGAACCGGACAGCUGUAUCUCCGAGAAGCUGUUCAUGGAGAUGGCCGAG<br>CUGAUGGUGAGCGAGGGCUGGAAGGAUGCCGGCUACGAGUACCUGUGUAUCGAUGACUGCUGGAUGGCCCCGCA<br>GCGAGAUAGCGAGGGACGCCUGCAGGCCGACCCGCAGAGAUUCCCGCACGGCAUCCGCCAGCUGGCCAAUUAUG<br>UUCACAGCAAGGGCCUGAAGCUGGGCAUCUACGCCGACGUGGCCAACAAGACCUGCGCCGGAUUCCCGGGCAGC<br>UUCGGCUACUACGAUAUAGAUGCCCAAACAUUCGCCGACUGGGGCGUCGACCUGCUUAAGUUCGACGGCUGCUA<br>CUGCGAUAGCCUGGAGAAUCUGGCCGACGGCUACAAGCACAUGAGCCUGGCCCUCAACAGGACCGGAAGGUCCA<br>UCGUGUACAGCUGCGAAUGGCCUCUGUACAUGUGGCCUUUCCAGAAGCCGAACUACACACCGAGAUCCGCCAGUAC<br>UGUAAUCACUGGAGGAACUUCGCCGACAUCGACGAUUCUUGGAAGUCUAUCAAGUCCAUCCUGGACUGGACCUC<br>CUUCAAUCAGGAGAGAAUUGUCGACGUGGCCGGCCCGGGUGGCUGGAACGACCCGGACAUGCUGGUGAUCGGCA<br>ACUUCGGCCUGAGCUGGAACCAGCAGGUGACCCAGAUGGCCCUGUGGGCCAUAAUGGCCGCCCCACUCUUCAUG<br>UCCAACGACCUGCGGCACAUCAGCCCCAACAGGCCAAGGACCUGCUCCAGGACAAGGACGUGAUCGCCAUCAACCA<br>AGACCCUCUGGGCAAGCAGGGUUACCAGCUUAGACAGGGCGACAACUUCGAGGUGUGGGAGCGCCCGCUUUCCG<br>GCCUCGCCUGGGCCGUGGCCAUGAUCAACAGGCAGGAAAUCGGAGGCCCGCGCUCCUAUACUAUCGCCGUGGCG<br>AGCCUGGGCAAGGGCGUGGCCUGCAACCCGGCCUGCUUCAUCACCCAGCUGCUGCCAGUCAAGAGAAAGCUGGG<br>CUUCUACGAGUGGACCUCCAGACUGAGAUCCCACAUCAAUCCUACCGGCACCGUGCUGCUGCAGCUGGAGAACA<br>CGAUGCAGAUGUCGCUGAAGGACCUCCUG |
| 145 | GLA-CO32 | AUGCAGCUCCGGAACCCAGAGCUUCACCUUGGCUGCGCCCUCGCCCUCAGGUUCCUAGCCCUCGUGUCCUGGGA<br>CAUCCCAGGCGCCCGGGCCCUUGACAACGGCCUCGCCAGAACCCGACCAUGGGCUGGCUCCACUGGGGAGCGCU<br>UCAUGUGCAACCUGGACUGUCAGGAGGAGCCGGACUCAUGUAUCAGCGAGAAGCUGUUCAUGGAAAUGGCCGAA<br>UUAAUGGUGUCCGAGGGCUGGAAGGACGCCGGCUAUGAGUACCUGUGCAUCGACGAUUGCUGGAUGGCCCCGCA<br>GAGAGACAGCGAGGGCAGACUGCAGGCCGACCCACAGAGGUUCCCACACGGCAUCAGGCAGCUGGCCAACUACG<br>UGCACUCCAAGGGCCUGAAGCUGGGCAUCUACGCCGAUGUGGGCAACAAGACCUGCGCCGGCUUCCCGGGCAGC<br>UUCGGCUAUUACGAUAUCGACGCCCAGACGUUCGCCGACUGGGGCGUGGAUCUGCUGAAGUUCGACGGCUGUUA<br>CUGUGACAGCUGGAGAAUCUGGCCGAUGGCUACAAGCAUAUGAGUCUCGCCCUCAACAGGACCGGCCGCUCAA<br>UCGUGUACAGCUGCGAGUGGCCGCUGUACAUGUGGCCGUUCCAGAAGCCAAACUACACCGAGAUCAGGCAAUAC<br>UGCAACCAUUGGCGCAACUUCGCCGAUAUAGAUGACAGCUGGAAGUCCAUCAAGUCCAUCCUGGACUGGACCAG<br>CUUCAAUCAGGAGCGUAUAGUGGACGUGGCCGGCCCGGGUUGGAACGACCCCAGACAUGCUGGUGAUCGGCA<br>ACUUCGGCCUGAGCUGGAACCAGCAGGUGACCCAGAUGGCCCUGUGGGCCAUCAUGGCCGCCCCACUGUUCAUG<br>UCCAACGACCUGCGGCACAUCAGCCCGCAGGCCAAGGCGCUGCUCAGGAUAAGGACGUGAUAGCUAUCAACCA<br>AGACCCCACUGGGCAAGCAGGGAUAUCAGCUGAGGCAAGGCGACAACUUCGAGGUGUGGGAGAGGCCGCUCAGCG<br>GCCUGGCCUGGGCCGUGGCCAUGAUCAACAGGCAAGAGAUCGGCGGACUACACCAUCGCGGUCGCC<br>AGCCUGGGCAAGGGUGUGGCCGUGCAACCCAGCAUGCUUCAUCACCCAGCUGCUGCCGGUGAAGAGGAAGCUGGG<br>AUUCUACGAGUGGACUAGCAGACUGAGGAGCCACAUCAACCCGACCGGCACCGUCCUGCUGCAGCUCGAGAACA<br>CCAUGCAGAUGUCCCUGAAGGAUCUGCUG |
| 146 | GLA-CO33 | AUGCAGCUCCGGAACCCAGAGUUGCAUCUCGGUUGCGCCCUUAGCUCUCCGGUUCCUCGCCCUCGUGAGCUGGGA<br>CAUCCCAGGCGCCCAGGGCUCUCGACAACGGACUUGCAGGACCCCGACAAUGGGCUGGCUCCACUGGGAGCGGU<br>UCAUGUGCAACCUGGAUUGUCAGGAGGAGCCAGACUCCUGCAUCUCCGAGAAGCUGUUCAUGGAGAUGGCCGAA<br>CUCAUGGUGAGCGAGGGAUGGAAGGACGCCGGCUAUGAGUAUCUGUGCAUCGACGAUUGCUGGAUGGCCCGCA<br>GAGGGAUAGCGAGGGCCGCCUCCAGGCCGACCCGCAGCGAUUCCCGCACGGCAUCGACAGCUGGCCAACUACG<br>UGCACUCCAAGGGCCUCAAGCUGGGCAUAUACGCCGACGUCGGAAACAAGACGUGCGCCGGCUUCCCGGGCAGC<br>UUCGGCUACUAUGACAUCGACGCCCAGACGUUCGCGGAUUGGGGCGUGGACCUGCUGAAGUUCGACGGCUGCUA<br>CUGCGAUAGCCUCGAGAAUCUGGCCGACGGAUACAAGCAUAUGAGCCUCGCCCUGAACAGGACCGGCCGGUUCCA<br>UCGUGUACUAUGCGAGUGGCCGCUCUACAUGUGGCCAUUCCAGAAGCCUAAUUACACCGAGAUCCGGCAGUAC |

TABLE 2-continued

Sequence-Optimized Sequences for Human GLA

| SEQ ID NO | Name | Sequence |
|---|---|---|
| | | UGCAACCACUGGCGAAAUUUCGCAGAUAUAGACGAUAGCUGGAAGUCCAUCAAGUCUAUCCUGGACUGGACUUC<br>CUUCAACCAGGAAAGGAUCGUCGACGUGGCGGGCCCGGGCGGCUGGAACGACCCGGACAUGCUGGUGAUCGGCA<br>ACUUCGGCCUGAGCUGGAACCAGCAGGUGACCCAGAUGGCCCUGUGGGCCAUCAUGGCCGCCCCUCUGUUCAUG<br>UCCAAUGACCUGCGGCACAUCAGCCCGCAGGCCAAGGCCCUGCUGCAAGACAAGGAUGUGAUUGCCAUCAAUCA<br>GGACCCUCUCGGCAAGCAGGGCUACCAGCUCCGACAGGGAGAUAACUUCGAAGUGUGGGAGCGGCCGCUGAGCG<br>GCCUGGCCUGGGCCGUCGCCAUGAUCAACCGGCAGGAGAUCGGCGGCCCACGCUCCUACACCAUCGCCGUGGCC<br>UCCCUGGGCAAGGGCGUGGCCUGCAAUCCGGCAUGCUUCAUCACCCAGCUGCUGCAGUCAAGAGGAAGCUGGG<br>CUUCUAUGAAUGGACCAGCAGACUGCGAUCCCACAUCAACCCAACCGGCACCGUGCUGCUGCAGCUGGAGAACA<br>CUAUGCAGAUGAGCCUGAAGGACCUGCUG |
| 147 | GLA-CO34 | AUGCAGCUCAGAAACCCAGAGCUCCAUUUGGGCUGCGCCCUCGCCCUCCGGUUCCUCGCCCUCGUGAGCUGGGA<br>CAUCCCGGGCGCCAGAGCCCUCGACAACGGACUCGCCCGAACACCAACCAUGGGCUGGCUCCAUUGGGAGAGGU<br>UCAUGUGCAACCUGGACUGCCAGGAGGAGCCGGAUAGCUGCAUCAGCGAGAAGCUGUUCAUGGAGAUGGCCGAG<br>CUGAUGGUGUCCGAGGGCUGGAAGGACGCCGGCUAUGAGUAUCUGUGCAUCGACGACUGCUGGAUGGCCCCACA<br>GCGGGACUCCGAGGGAAGGCUGCAGGCCGACCCGCAGAGGUUCCCUCACGGCAUCCGUCAGCUCGCCAACUACG<br>UGCACUCCAAGGGCCUGAAGCUGGGCAUCUACGCCGACGUGGGCAACAAGACCUGCGCCGGCUUCCCAGGCAGC<br>UUCGGAUACUAUGACAUCGACGCCCAGACCUUCGCCGACUGGGGCGUGGAUCUGCUGAAGUUCGACGGCUGCUA<br>CUGCGACAGCUUGGAGAAUCUGGCCGACGGUUACAAGCACAUGAGCCUAGCCCUGAACCGGACCGGAAGGAGCA<br>UCGUGUACAGCUGCGAGUGGCCGCUGUACAUGUGGCCAUUCCAGAAGCCGAACUACACCGAGAUUAGGCAGUAC<br>UGCAACCACUGGAGAAACUUCGCAGAUAUCGACGACGCUGGAAGUCCAUCAAGAGCAUCCUGGAUUGGACCAG<br>CUUCAACCAGGAGCGGAUCGUGGACGUGGCCGGUCCGGGAGGCUGGAACGACCCGGACAUGCUGGUGAUCGGCA<br>ACUUCGGACUGAGCUGGAACCAGCAAGUGACCCAGAUGGCCCUGUGGGCCAUCAUGGCCGCCCCUCUAUUCAUG<br>UCUAACGACCUGCGGCACAUUUCCCCGCAGGCCAAGGCCCUGCUGCAGGACAAGGACGUCAUCGCGAUCAAUCA<br>GGACCCACUGGGCAAGCAGGGCUAUCAGCUGCGUCAGGGCGACAAUUUCGAGGUGUGGGAGCGGCCGCUGAGCG<br>GCCUGGCCUGGGCCGUGGCCAUGAUCAACCGGCAGGAGAUCGGAGGCCCGAGAAGCUACACCAUCGCAGUUGCC<br>AGCCUGGGCAAGGGCGUGGCCUGCAACCCGGCCUGCUUCAUCACCCAGCUGCUACCGGUGAAGCGUAAGCUGGG<br>CUUCUACGAGUGGACCAGCAGGCUCAGGAGCCACAUCAACCCGACCGGCACCGUGCUGCUCCAGCUGGAGAACA<br>CCAUGCAGAUGUCCCUGAAGGAUCUGCUG |
| 148 | GLA-CO35 | AUGCAACUCAGGAACCCGGAGCUCCACCUAGGCUGCGCCCUCGCCCUCCGCUUCCUCGCACUCGUGAGCUGGGA<br>CAUCCCAGGUGCCAGAGCGCUCGACAACGGACUCGCCCGGACCCUACCAUGGGCUGGCUCCACUGGGAGCGCU<br>UCAUGUGCAACCUGGACUGCCAGGAGGAACCGGACAGCUGCAUCUCCGAGAAGCUGUUCAUGGAGAUGGCCGAG<br>CUGAUGGUGAGCGAGGGCUGGAAGGACGCCGGCUACGAGUACCUGUGCAUCGACGACUGGAUGGCCCCUCA<br>GAGGGACAGCGAGGGCAGGCUGCAGGCCGACCCGCAGCGCUUCCCGCACGGCAUCCGGCAGCUGGCUAACUACG<br>UGCACAGCAAGGGCCUGAAGCUCGGCAUCUACGCCGACGUGGGAAACAAGACCUGCGCGGGCUUCCCAGGAUCC<br>UUCGGCUAUUACGACAUCGACGCCCAGACCUUCGCCGACUGGGGCGUGGACCUGCUGAAGUUCGACGGAUGCUA<br>CUGUGACUCCCUCGAGAACCUGGCCGACGGCUACAAGCACAUGAGCCUGGCCCUGAACCGCACCGGCAGGAGCA<br>UCGUGUAUAGCUGUGAAUGGCCGCUGUACAUGUGGCCGUUCCAGAAGCCUAACUACACCGAGAUCAGACAGUAU<br>UGCAACCAUUGGCGGAAUUUCGCCGACAUCGAUGACUCCUGGAAGUCCAUAAAGAGCAUCCUGGAUUGGACCAG<br>CUUCAAUCAAGAGGAUAUGGACGUGGCCGGUCCGGGCGGAUGGAACGACCCGGACAUGCUGGUGAUCGGCA<br>ACUUCGGUCUGAGCUGGAACCAGCAGGUGACUCAGAUGGCCCUGUGGGCCAUCAUGGCCGCCCCUCACUGUUCAUG<br>AGCAACGACCUGAGACACAUCAGCCCGCAGGCCAAGGCCCUGCUGCAGGAUAAGGACGUCAUCGCCAUCAACCA<br>AGAUCCGCUGGGCAAGCAGGGCUACCAGCUGCGCCAGGGCGACAACUUCGAGGUGUGGGAGCGGCCGCUGAGCG<br>GCCUGGCCUGGGCCGUUGCAAUGAUCAACCGUCAGGAGAUCGGCGGCCCGAGGUCCUACACGAUCGCCGUGGCC<br>UCUCUCGGCAAGGGCGUGGCCUGUAACCCGGCCUGCUUCAUCACCCAGCUGCUCCGGUGAAGCGCAAGUUGGG<br>CUUCUACGAGUGGACCAGCCGCUGCGGUCCCACAUCAAUCCAACCGGCACCGUGCUGCUGCAGCUGGAGAACA<br>CCAUGCAAAUGAGCCUCAAGGAUUUGCUG |
| 149 | GLA-CO36 | AUGCAGCUCCGGAACCCCGAGCUCCACCUCGGCUGCGCCCUUGCCUUGCGGUUCCUCGCGCUCGUGAGCUGGGA<br>CAUCCCAGGCGCCAGGGCCCUCGACAACGGCCUCGCCCGGACCCCGACCAUGGGCUGGCUCCACUGGGAGCGGU<br>UCAUGUGCAACCUGGACUGCCAGGAGGAGCCCGACAGCUGCAUCAGCGAGAAGCUGUUCAUGGAGAUGGCCGAG<br>CUGAUGGUGAGCGAGGGCUGGAAGGACGCCGGCUACGAGUACCUGUGCAUCGACGACUGCUGGAUGGCCCCGCA<br>GCGGGACAGCGAGAAGGCCGGCUGCAGGCCGACCCGCAAAGAUUCCCACACGGCAUCCGGCAGCUGGCCAACUACG<br>UGCACAGCAAGGGCCUGAAGCUGGGCAUCUACGCCGACGUGGGCAACAAGACCUGCGCCGGCUUCCCGGGCAGC<br>UUCGGCUACUACGACAUCGACGCCCAGACCUUCGCCGACUGGGGCGUGGACCUGCUGAAGUUCGACGGCUGCUA<br>CUGCGACAGCCUGGAGAACCUGGCCGACGGCUACAAGCACAUGAGCCUCGCCCUGAACCGGACCGGCCGGAGCA<br>UCGUGUACAGCUGCGAGUGGCCCCUGUACAUGUGGCCUUCCAGAAGCCCAACUACACCGAGAUCAGACAGUAC<br>UGCAACCACUGGCGGAACUUCGCCGAUAUCGAUGACAGCUGGAAGUCAAUCAAGAGCAUCCUGGACUGGACCAG<br>CUUCAACCAGGAGCGGAUCGUGGACGUGGCCGGCCCGGCGGCUGGAACGACCCCGACAUGCUGGUGAUCGGCA<br>ACUUCGGCCUGAGCUGGAACCAGCAGGUGACCCAGAUGGCCCUGUGGGCCAUCAUGGCCGCCCCACUCUUCAUG<br>AGCAACGACCUGCGGCACAUCAGCCCGCAGGCCAAGGCCCUGCUGCAGGACAAGGACGUGAUCGCCAUCAAUCA<br>GGACCCUCUGGGCAAGCAGGGCUACCAGCUGUGGGAGGCGGAGAGGCCCCUGAGCG<br>GCCUGGCCUGGGCCGUGGCCAUGAUCAACCGGCAGGAGAUCGGCGGCCCUCGGAGCUACACCAUCGCCGUAGCC<br>AGCCUGGGUAAGGGCGUGGCCUGCAACCCCGCCUGCUUCAUCACCCAGCUGCUCCCGUGAAGCGGAAGCUCGG<br>AUUCUACGAGUGGACCUCCAGACUGCGGAGCCACAUCAACCCCACCGGCACCGUGCUCCUGCAGCUUGAGAACA<br>CCAUGCAGAUGUCACUGAAGGAUCUGCUG |
| 150 | GLA-CO37 | AUGCAGCUCCGGAACCCCGAGCUCCACCUCGGCUGCGCCCUUGCCCUCCGGUUCCUCGCCCUUGUGAGCUGGGA<br>CAUCCCCGGCGCCCGGGCCCUUGACAACGGCCUCGCCCGGACCCCGACCAUGGGCUGGCUCCACUGGGAGCGGU<br>UCAUGUGCAACCUGGACUGCCAGGAGGAGCCCGACAGCUGCAUCAGCGAGAAGCUGUUCAUGGAGAUGGCCGAG<br>CUGAUGGUGAGCGAGGGCUGGAAGGACGCCGGCUACGAGUACCUGUGCAUCGACGACUGCUGGAUGGCCCCGCA<br>GCGGGACAGCGAGGGUCGGCUGCAGGCCGACCCACAGCGCUUCCCUCACGGCAUCCGGCAGCUGGCCAACUACG<br>UGCACAGCAAGGGCCUGAAGCUGGGCAUCUACGCCGACGUGGGCAACAAGACCUGCGCCGGCUUCCCGGGCAGC<br>UUCGGCUACUACGACAUCGACGCCCAGACCUUCGCCGACUGGGGCGUGGACCUGCUGAAGUUCGACGGCUGCUA<br>CUGCGACAGCCUGGAGAACCUGGCCGACGGCUACAAGCACAUGAGCCUCGCGCUGAACCGGACCGGCCGGAGCA |

TABLE 2-continued

Sequence-Optimized Sequences for Human GLA

| SEQ ID NO | Name | Sequence |
|---|---|---|
| | | UCGUGUACAGCUGCGAGUGGCCCCUGUACAUGUGGCCCUUCCAGAAGCCCAACUACACCGAGAUCAGACAGUAC<br>UGCAACCACUGGCGGAAUUUCGCCGAUAUCGAUGACAGCUGGAAGUCCAUCAAGUCCAUCCUGGAUUGGACCAG<br>CUUCAACCAGGAGCGGAUCGUGGACGUGGCCGGCCCCGGCGGCUGGAACGACCCCGACAUGCUGGUGAUCGCA<br>ACUUCGGCCUGAGCUGGAACCAGCAGGUGACCCAGAUGGCCCUGUGGGCAUCAUGGCCGCCCCACUCUUCAUG<br>AGCAACGACCUGCGGCACAUCAGCCCGCAGGCCAAGGCCCUGCUGCAGGACAAGGACGUGAUCGCCAUCAAUCA<br>GGACCCACUGGGCAAGCAGGGCUACCAGCUCCGGCAGGGCGACAACUUCGAGGUGUGGGAGAGGCCGCUGAGCG<br>GCCUUGCGUGGGCCGUGGCCAUGAUCAACCGGCAGGAGAUCGGCGGCCCGCGGAGCUACACCAUCGCCGUGGCA<br>AGCCUGGGAAAGGCGUGGCCUGCAACCCCGCCUGCUUCAUCACCCAGCUGCUGCCCGUGAAGCGGAAGUUAGG<br>CUUCUACGAGUGGACCUCCAGGCUGCGGAGCCACAUCAACCCCACCGGCACCGUGCUGCUGCAACUGGAGAAUA<br>CCAUGCAGAUGAGCCUGAAGGAUCUGCUG |
| 151 | GLA-C038 | AUGCAGCUCCGGAACCCCGAGCUCCACCUCGGCUGCGCCCUCGCCCUCCGGUUCCUAGCCCUCGUGAGCUGGGA<br>CAUACCGGGCGCCAGGGCGCUCGACAACGGCCUCGCCCGGACCCCGACCAUGGGCUGGUCCCACUGGGAGCGGU<br>UCAUGUGCAACCUGGACUGCCAGGAGGAGCCCGACAGCUGCAUCAGCGAGAAGCUGUUCAUGGAGAUGGCCGAG<br>CUGAUGGUGAGCGAGGGCUGGAAGGACGCCGGCUACGAGUACCUGUGCAUCGACGACUGCUGGAUGGCACCUCA<br>GCGGGACUCCGAGGGCCGGCUGCAGGCCGACCUCAGAGAUUCCCGCACGGCAUCCGGCAGCUGGCCAACUACG<br>UGCACAGCAAGGGCCUGAAGCUGGGCAUCUACGCCGACGUGGGCAACAAGACCUGCGCCGGCUUCCCGGGCAGC<br>UUCGGCUACUACGACAUCGACGCCCAGACCUUCGCCGACUGGGGCGUGGACCUGCUGAAGUUCGACGGCUGCUA<br>CUGCGACAGCCUGGAGAACCUGGCCGACGGCUACAAGCACAUGUCUCUCGCCUUGAACCGGACCGGCCGGAGCA<br>UCGUGUACAGCUGCGAGUGGCCCCUGUACAUGUGGCCCUUCCAGAAGCCCAACUACACCGAGAUCCGCCAGUAC<br>UGCAACCACUGGCGGAAUUUCGCCGAUAUUGACGAUAGCUGGAAGUCCAUCAAGUCCAUCCUGGAUUGGACCAG<br>CUUCAACCAGGAGCGGAUCGUGACGUGGCCGGCCCCGGCGGCUGGAACGACCCCGACAUGCUGGUGAUCGCCA<br>ACUUCGCCCUGAGCUGGAACCAGCAGGUGACCCAGAUGGCCCUGUGGGCAUCAUGGCCGCCCCACUCUUCAUG<br>AGCAACGACCUGCGGCACAUCAGCCCGCAGGCCAAGGCCCUGCUGCAGGACAAGGACGUGAUCGCCAUUAAUCA<br>GGACCCGCUGGGCAAGCAGGGCUACCAGCUCAGGCAGGGCGACAACUUCGAGGUGUGGGAGAGGCCUCUGAGCG<br>GUCUGGCCUGGGCCGUGGCCAUGAUCAACCGGCAGGAGAUCGGCGGACCGCGGAGCUACACCAUCGCGGUGGCC<br>AGCCUGGGAAAGGGCGUGGCCUGCAACCCCGCCUGCUUCAUCACCCAGCUGCUGCCCGUGAAGAGAAAGCUCGG<br>CUUCUACGAGUGGACGUCAAGACUGCGGAGCCACAUCAACCCCACCGGCACCGUGCUCCUGCAGCUGGAGAAUA<br>CCAUGCAGAUGUCCCUGAAGGACCUCCUG |
| 152 | GLA-C039 | AUGCAGCUCCGGAACCCCGAGCUUCACCUAGGCUGCGCCCUCGCCCUCCGGUUCCUUGCCCUAGUGAGCUGGGA<br>CAUCCCAGGCGCCCGCGCUCGACAACGGCCUCGCCCGGACCCCUACCAUGGGCUGGUCCCACUGGGAGCGGU<br>UCAUGUGCAACCUGGACUGCCAGGAGGAGCCCGACAGCUGCAUCAGCGAGAAGCUGUUCAUGGAGAUGGCCGAG<br>CUGAUGGUGAGCGAGGGCUGGAAGGACGCCGGCUACGAGUACCUGUGCAUCGACGACUGCUGGAUGGCGCCGCA<br>GCGGGACUCUGAGGGCCGGCUGCAGGCCGACCCCGCAGAGGUUCCCGCACGGCAUCCGGCAGCUGGCCAACUACG<br>UGCACAGCAAGGGCCUGAAGCUGGGCAUCUACGCCGACGUGGGCAACAAGACCUGCGCCGGCUUCCCUGGCAGC<br>UUCGGCUACUACGACAUCGACGCCCAGACCUUCGCCGACUGGGGCGUGGACCUGCUGAAGUUCGACGGCUGCUA<br>CUGCGACAGCCUGGAGAACCUGGCCGACGGCUACAAGCACAUGAGCUUGGCGCUCAACCGGACCGGCCGGAGCA<br>UCGUGUACAGCUGCGAGUGGCCCCUGUACAUGUGGCCCUUCCAGAAGCCCAACUACACCGAGAUCCGCCAGUAC<br>UGCAACCACUGGCGGAAUUUCGCCGAUAUCGAUGAUUCCUGGAAGUCCAUCAAGUCCAUCCUCGACUGGACCAG<br>CUUCAACCAGGAGCGGAUCGUGACGUGGCCGGCCCCGGCGGCUGGAACGACCCCGACAUGCUGGUGAUCGCA<br>ACUUCGGCCUGAGCUGGAACCAGCAGGUGACCCAGAUGGCCCUGUGGGCAUCAUGGCCGCGCCACUCUUCAUG<br>AGCAACGACCUGCGGCACAUCAGCCCGCAGGCCAAGGCCCUGCUGCAGGACAAGGACGUGAUCGCCAUUAACCA<br>GACCCGCUGGGCAAGCAGGGCUACCAGCUGCGCCAGGGCGACAACUUCGAGGUGUGGGAGAGGCCUCUGUCCG<br>GACUGGCUUGGGCCGUGGCCAUGAUCAACCGGCAGGAGAUCGGCGGACCACGGAGCUACACCAUCGCCGUGGCG<br>AGCCUGGGUAAGGGCGUGGCCUGCAACCCCGCCUGCUUCAUCACCCAGCUGCUGCCCGUGAAGAGAAAGCUGGG<br>UUUCUACGAGUGGACCUCGAGACUGCGGAGCCACAUCAACCCCACCGGCACCGUGCUCCUGCAGCUCGAGAACA<br>CCAUGCAGAUGUCCCUCAAGGACCUCCUG |
| 153 | GLA-C040 | AUGCAGCUCCGGAACCCCGAGCUCCACCUCGGCUGCGCCCUCGCCCUCCGGUUCCUCGCGCUCGUGAGCUGGGA<br>CAUCCCAGGCGCCCGGGCUCUCGACAACGGCCUAGCCCGGACCCCGACCAUGGGCUGGUCCCACUGGGAGCGGU<br>UCAUGUGCAACCUGGACUGCCAGGAGGAGCCCGACAGCUGCAUCAGCGAGAAGCUGUUCAUGGAGAUGGCCGAG<br>CUGAUGGUGAGCGAGGGCUGGAAGGACGCCGGCUACGAGUACCUGUGCAUCGACGACUGCUGGAUGGCCCCACA<br>GCGGGACAGCGAGGGACGGCUGCAGGCCGAUCCGCAGCGUUUCCGCACGGCAUCCGGCAGCUGGCCAACUACG<br>UGCACAGCAAGGGCCUGAAGCUGGGCAUCUACGCCGACGUGGGCAACAAGACCUGCGCCGGCUUCCCAGGCAGC<br>UUCGGCUACUACGACAUCGACGCCCAGACCUUCGCCGACUGGGGCGUGGACCUGCUGAAGUUCGACGGCUGUUA<br>CUGCGACAGCCUGGAGAACCUGGCCGACGGCUACAAGCACAUGUCCUGGCUGAACCGGACCGGCCGGAGCA<br>UCGUGUACAGCUGCGAGUGGCCCUGUACAUGUGGCCCUUCCAGAAGCCCAACUACACCGAGAUCAGACAAUAC<br>UGCAACCACUGGCGGAAUUUCGCCGAUAUAGACGAUAGCUGGAAGUCCAUCAAGUCCAUCCUGGAUUGGACCAG<br>CUUCAACCAGGAGCGGAUCGUGACGUGGCCGGCCCCGGCGGCUGGAACGACCCCGACAUGCUGGUGAUCGCA<br>ACUUCGGCCUGAGCUGGAACCAGCAGGUGACCCAGAUGGCCCUGUGGGCAUCAUGGCCGCCCCUCUCUUCAUG<br>AGCAACGACCUGCGGCACAUCAGCCCGCAGGCCAAGGCCCUGCUGCAGGACAAGGACGUGAUCGCCAUCAAUCA<br>AGACCCGCUGGGCAAGCAGGGCUACCAGCUGAGACAGGGCGACAACUUCGAGGUGUGGGAGAGGCCGCUGUCGG<br>GACUGGCCUGGGCCGUGGCCAUGAUCAACCGGCAGGAGAUCGGCGGCCCGCGGAGCUACACCAUCGCGGUGGCC<br>UCGCUGGGAAAGGGCGUGGCCUGCAACCCCGCCUGCUUCAUCACCCAGCUGCUGCCCGUGAAGCGUAAGCUGGG<br>AUUUCUACGAGUGGACCUCCAGACUGCGGAGCCACAUCAACCCCACCGGCACCGUGCUUCUGCAGCUGGAGAAUA<br>CCAUGCAGAUGUCCCUCAAGGACCUCCUG |
| 154 | GLA-C041 | AUGCAGCUCCGGAACCCCGAGCUCCACCUUGGCUGCGCCCUUGCCCUUGCGGUUCUUAGCCCUCGUGAGCUGGGA<br>CAUCCCAGGCGCCCGCGCCUCGACAACGGCCUCGCCCGGACCCCUACCAUGGGCUGGUCCCACUGGGAGGCGCU<br>UCAUGUGCAACCUCGACUGCCAGGAGGAGCCCGACUCCUGCAUCUCCGAAGCUGUUCAUGGAGAUGGCCGAG<br>CUCAUGGUGUCCGAGGGCUGGAAGGACGCCGGCUACGAGUACCUGUGCAUCGACGACUGCUGGAUGGCCCCGCA<br>GCGCGACAGCGAGGGCAGGCUCCAGGCCGACCCACAGAGGUUCCCACACGGCAUCCGCCAGCUGCCAACUACG<br>UCCACUCCAAGGGCCUCAAGCUCGGCAUCUACGCCGACGUCGGCAACAAGACCUGCGCCGGCUUCCCCGGCUCC<br>UUCGGCUACUACGACAUCGACGCCCAGACCUUCGCCGACUGGGGCGUCGACCUCCUCAAGUUCGACGGCUGCUA |

TABLE 2-continued

Sequence-Optimized Sequences for Human GLA

| SEQ ID NO | Name | Sequence |
|---|---|---|
| | | CUGCGACUCCCUCGAGAACCUCGCCGACGGCUACAAGCACAUGUCCCUCGCCCUCAACCGCACCGGCCGCUCCA<br>UCGUCUACUCCUGCGAGUGGCCCCUCUACAUGUGGCCCUUCCAGAAGCCCAACUACACCGAGAUCAGGCAGUAC<br>UGCAACCACUGGCGCAAUUUCGCCGAUAUCGAUGACAGCUGGAAGUCCAUCAAGAGCAUCCUGGACUGGACCUC<br>CUUCAACCAGGAGCGCAUCGUCGACGUCGCCGGCCCCGGCCGGCUGGAACGACCCCGACAUGCUCGUCAUCGGUA<br>ACUUCGGCCUGUCUUGGAACCAGCAGGUCACCCAGAUGGCCCUCUGGGCCAUCAUGGCCGCCCCACUGUUCAUG<br>UCCAACGACCUCCGCCACAUCUCCCCUCAGGCCAAGGCCCUCCUCCAGGACAAGGACGUCAUCGCCAUCAAUCA<br>GGACCCGCUCGGCAAGCAGGGCUACCAGCUCCGCCAGGGCGACAACUUCGAGGUGUGGGAGAGGCCCCUCUCCG<br>GACUCGCCUGGGCCGUCGCCAUGAUCAACCGCCAGGAGAUCGGCGGCCCACGCUCCUACACCAUCGCCGUGGCC<br>UCCCUGGGCAAGGGCGUCGCCCUGCAACCCCGCCUGCUUCAUCACCCAGCUCCUCCCCGUCAAGAGGAAGCUGGG<br>CUUCUACGAGUGGACAAGCCGCCUCCGCUCCCACAUCAACCCCACCGGCACCGUGCUGCUGCAGCUGGAGAACA<br>CCAUGCAGAUGUCCCUGAAGGACCUGCUC |
| 155 | GLA-CO42 | AUGCAGCUUCGGAACCCCGAGCUCCACCUUGGCUGCGCCCUUGCCCUCCGGUUCCUCGCCCUCGUGAGCUGGGA<br>CAUACCGGGCGCCAGGGCCCUCGACAACGGCCUCGCCCGCACCCCGACCAUGGGCUGGCUCCACUGGGAGCGCU<br>UCAUGUGCAACCUCGACUGCCAGGAGGAGCCCGACUCCUGCAUCUCCGAGAAGCUGUUCAUGGAGAUGGCCGAG<br>CUCAUGGUGUCCGAGGGCUGGAAGGACGCCGGCUACGAGUACCUCUGCAUCGACGACUGCUGGAUGGCCCCGCA<br>GCGCGACAGCGAGGGUCGCCUCCAGGCCGACCCACAGAGAUUCCCGCACGGCAUCCGCCAGCUCGCCAACUACG<br>UCCACUCCAAGGGCCUCAAGCUCGGCAUCUACGCCGACGUCGGCAACAAGACCUGCGCCGGCUUCCCCGGCUCC<br>UUCGGCUACUACGACAUCGACGCCCAGACCUUCGCCGACUGGGGCGUCGACCUCCUCAAGUUCGACGGCUGCUA<br>CUGCGACUCCCUCGAGAACCUCGCCGACGGCUACAAGCACAUGAGCUCGCUCUCAACCGCACCGGCCGCUCCA<br>UCGUCUACUCCUGCGAGUGGCCCCUCUACAUGUGGCCCUUCCAGAAGCCCAACUACACCGAGAUUCGCCAGUAC<br>UGCAACCACUGGCGCAAUUUCGCCGAUAUCGAUGACUCCUGGAAGUCCAUCAAGAGCAUCCUGGACUGGACCUC<br>CUUCAACCAGGAGCGCAUCGUCGACGUCGCCGGCCCCGGCGGCUGGAACGACCCCGACAUGCUCGUCAUCGGAA<br>ACUUCGGCCUGAGCUGGAACCAGCAGGUCACCCAGAUGGCCCUCUGGGCCAUCAUGGCCGCCCCAUUGUUCAUG<br>UCCAACGACCUCCGCCACAUCUCCCCGCAGGCCAAGGCCCUCCUCCAGGACAAGGACGUCAUCGCCAUCAAUCA<br>GGACCCGCUCGGCAAGCAGGGCUACCAGCUCCGCCAGGGCGACAACUUCGAGGUGUGGGAGCGGCCCUCUCCG<br>GACUGGCCUGGGCCGUCGCCAUGAUCAACCGCCAGGAGAUCGGCGGCCCACGCUCCUACACCAUCGCCGUGGCC<br>AGCCUGGGCAAGGGCGUCGCCCUGCAACCCCGCCUGCUUCAUCACCCAGCUCCUCCCCGUCAAGAGGAAGCUGGG<br>CUUCUACGAGUGGACCAGCCGCCUCCGCUCCCACAUCAACCCCACCGGCACCGUGCUGCUGCAGCUGGAGAACA<br>CCAUGCAGAUGAGCCUGAAGGACCUGCUC |
| 156 | GLA-CO43 | AUGCAGCUCCGGAACCCCGAGCUCCACCUCGGCUGCGCCCUCGCCCUCCGGUUCCUCGCCCUAGUGAGCUGGGA<br>CAUCCCGGGCGCCAGGGCCCUCGACAACGGCCUCGCCCGCACCCCAACCAUGGGCUGGCUCCACUGGGAGCGCU<br>UCAUGUGCAACCUCGACUGCCAGGAGGAGCCCGACUCCUGCAUCUCCGAGAAGCUGUUCAUGGAGAUGGCCGAG<br>CUCAUGGUGUCCGAGGGCUGGAAGGACGCCGGCUACGAGUACCUCUGCAUCGACGACUGCUGGAUGGCCCCACA<br>GCGCGACAGCGAGGGCCGCCUCCAGGCCGACCCACAGAGGUUCCCGCACGGCAUCCGCCAGCUCGCCAACUACG<br>UCCACUCCAAGGGCCUCAAGCUCGGCAUCUACGCCGACGUCGGCAACAAGACCUGCGCCGGCUUCCCCGGCUCC<br>UUCGGCUACUACGACAUCGACGCCCAGACCUUCGCCGACUGGGGCGUCGACCUCCUCAAGUUCGACGGCUGCUA<br>CUGCGACUCCCUCGAGAACCUCGCCGACGGCUACAAGCACAUGAGCUGGCGCUCAACCGCACCGGCCGCUCCA<br>UCGUCUACUCCUGCGAGUGGCCCCUCUACAUGUGGCCCUUCCAGAAGCCCAACUACACCGAGAUCCGACAGUAC<br>UGCAACCACUGGCGCAAUUUCGCCGAUAUCGAUGAUCUCCUGGAAGUCCAUCAAGAGCAUCCUGGACUGGACCUC<br>CUUCAACCAGGAGCGCAUCGUCGACGUCGCCGGCCCCGGCGGCUGGAACGACCCCGACAUGCUCGUCAUCGGUA<br>ACUUCGGCCUGAGCUGGAACCAGCAGGUCACCCAGAUGGCCCUCUGGGCCAUCAUGGCCGCCCCGCUUUUCAUG<br>UCCAACGACCUCCGCCACAUCUCGCCGCAGGCCAAGGCCCUCCUCCAGGACAAGGACGUCAUCGCCAUCAAUCA<br>GGACCCGCUCGGCAAGCAGGGCUACCAGCUCCGCCAGGGCGACAACUUCGAGGUGUGGGAGCGGCCCCUCAGCG<br>GCCUGGCGUGGGCCGUCGCCAUGAUCAACCGCCAGGAGAUCGGCGGUCCACGCUCCUACACCAUCGCCGUGGCC<br>AGCCUGGGCAAGGGCGUCGCCCUGCAACCCCGCCUGCUUCAUCACCCAGCUCCUCCCCGUCAAGAGGAAGCUGGG<br>AUUCUACGAGUGGACUAGCAGGCUGCGCUCCCACAUCAACCCCACCGGCACCGUGCUCCUGCAGCUGGAGAAUA<br>CCAUGCAGAUGUCCCUGAAGGACCUGCUC |
| 157 | GLA-CO44 | AUGCAGCUGCGGAACCCCGAGCUGCACCUGGGCUGCGCCCUGGCCCUGCGGUUCCUGGCCCUGGUGAGCUGGGA<br>CAUCCCCGGCGCCCGGGCGCUGGACAACGGGCUGGCGAGGACGCCGACGAUGGGGUGGCUGCACUGGGAGAGGU<br>UCAUGUGCAACCUGGACUGCCAGGAGGAGCCGGACAGCUGCAUCAGCGAGAAGCUGUUCAUGGAGAUGGCGGAG<br>CUGAUGGUGAGCGAGGGGUGGAAGGACGCCGGGGUACGAGUACCUGUGCAUCGACGACUGCUGGAUGGCGCCGCA<br>GAGGGACAGCGAGGGAGGCUGCAGGCGGACCCGCAGAGGUUCCCGCACGGGAUCAGGCAGCUGGCAACUACG<br>UGCACAGCAAGGGGCUGAAGCUGGGGAUCUACGCGGACGUGGGGAACAAGACGUGCGCGGGGUUCCCGGGGAGC<br>UUCGGGUACUACGACAUCGACGCGCAGACGUUCGCGGACUGGGGUGGACCUGCUGAAGUUCGACGGGUGCUA<br>CUGCGACAGCCUGGAGAACCUGGCGGACGGGUACAAGCACAUGAGCCUGCUGAACAGGACGGGCGGGCUCCA<br>UCGUGUACAGCUGCGAGUGGCCGCUGUACAUGUGGCCGUUCCAGAAGCCGAACUACACGGAGAUCAGGCAGUAC<br>UGCAACCACUGGAGGAAUUCGCGGACAUCGACGACAGCUGGAAGAGCAUCAAGAGCAUCCUGGACUGGACGAG<br>CUUCAACCAGGAGAGGAUCGUGGACGUGGCGGGCCCGGAGGGUGGAACGACCCGGACAUGCUGGUGAUCGGGA<br>ACUUCGGCCUGAGCUGGAACCAGCAGGUGACCCAGAUGGCGCUGUGGGCGAUCAUGGCCGCCCCGCUGUUCAUG<br>AGCAACGACCUGAGGCACAUCAGCCCGCAGGCAAGGCCGUCGCUGCAGGACAAGGACGUGAUCGCGAUCAACCA<br>GGACCCGCUGGGGAAGCAGGGGUACCAGCUGAGGCAGGGCGACAACUUCGAGGUGUGGGAGAGGCCGCUGAGCG<br>GGCUGGCGUGGCGGUGGCGAUGAUCAACAGGCAGGAGAUCGGAGGGCCGAGGAGCUACACGAUCGCGGUGGCG<br>AGCCUGGGCAAGGGGCUGGCGCUGCAACCCGCGCUGUUCAUCACGCAGCUGCUCGGUGAAGAGGAAGCUGGG<br>GUUCUACGAGUGGACGAGCAGGCUGAGGAGCCACAUCAACCCGACGGGGACGGUGCUGCUGCAGCUGGAGAACA<br>CGAUGCAGAUGAGCCUGAAGGACCUGCUG |
| 158 | GLA-CO45 | AUGCAGCUGCGGAACCCCGAGCUGCACCUGGGCUGCGCCCUGGCCCUGCGGUUCCUGGCCCUGGUGAGCUGGGA<br>CAUCCCCGGCGCCCGGGCCCUCGACAACGGCCUCGCCCGCACGCCCACCAUGGGCUGGCUCCACUGGGAGCGCU<br>UCAUGUGCAACCUCGACUGCCAGGAGGAGCCCGACUCCUGCAUCUCCGAGAAGCUCUUCAUGGAGAUGGCCGAG<br>CUCAUGGUCUCCGAGGGCUGGAAGGACGCCGGCUACGAGUACCUCUGCAUCGACGACUGCUGGAUGGCGCCCCA<br>GCGCGACUCCGAGGGCCGCCUCCAGGCCGACCCUCAGCGCUUCCCGCACGGCAUCCGCCAGCUCGCCAACUACG<br>UCCACUCCAAGGGCCUCAAGCUCGGCAUCUACGCCGACGUCGGCAACAAGACCUGCGCCGGCUUCCCCGGCUCC |

TABLE 2-continued

Sequence-Optimized Sequences for Human GLA

| SEQ ID NO | Name | Sequence |
|---|---|---|
|  |  | UUCGGCUACUACGACAUCGACGCCCAGACCUUCGCCGACUGGGGCGUCGACCUCCUCAAGUUCGACGGCUGCUA<br>CUGCGACUCCCUCGAGAACCUCGCCGACGGCUACAAGCACAUGUCCCUCGCCCUCAACCGCACCGGCCGCUCCA<br>UCGUCUACUCCUGCGAGUGGCCCCUCUACAUGUGGCCCUUCCAGAAGCCCAACUACACCGAGAUCCGCCAGUAC<br>UGCAACCACUGGCGCAACUUCGCCGACAUCGACGACUCCUGGAAGUCCAUCAAGUCCAUCCUCGACUGGACCUC<br>CUUCAACCAGGAGCGCAUCGUCGACGUCGCCGGCCCCGGCGGCUGGAACGACCCCGACAUGCUCGUCAUCGGCA<br>ACUUCGGCCUCUCCUGGAACCAGCAGGUCACCCAGAUGGCCCUCUGGGCCAUCAUGGCCGCGCCCCUCUUCAUG<br>UCCAACGACCUCCGCCACAUCUCGCCCCAGGCCAAGGCCCUCCUCCAGGACAAGGACGUCAUCGCCAUCAACCA<br>GGACCCGCUCGGCAAGCAGGGCUACCAGCUCCGCCAGGGCGACAACUUCGAGGUCUGGGAGCGCCCGCUCUCCG<br>GCCUCGCCUGGGCCGUCGCCAUGAUCAACCGCCAGGAGAUCGGCGGCCCACGCUCCUACACCAUCGCCGUCGCC<br>UCCCUCGGCAAGGGCGUCGCCUGCAACCCCGCCUGCUUCAUCACCCAGCUCCUCCCCGUCAAGCGCAAGCUCGG<br>CUUCUACGAGUGGACCUCCCGCCUCCGCUCCCACAUCAACCCCACCGGCACCGUCCUCCUCCAGCUCGAGAACA<br>CCAUGCAGAUGUCCCUCAAGGACCUCCUC |
| 159 | GLA-CO46 | AUGCAGCUGAGGAACCCAGAACUACAUCUGGGCUGCGCGCUUGCGCUUCGCUUCCUGGCCCUCGUUUCCUGGGA<br>CAUCCCUGGGGCUAGAGCACUGGACAAUGGAUUGGCAAGGACGCCUACCAUGGGCUGGCUGCACUGGGAGCGCU<br>UCAUGUGCAACCUUGACUGCCAGGAAGAGCCAGAUUCCUGCACAGUGAGAAGCUCUUCAUGGAGAUGGCAGAG<br>CUCAUGGUCUCAGAAGGCUGGAAGGAUGCAGGUUAUGAGUACCUCUGCAUUGAUGACUGUUGGAUGGCUCCCCA<br>AAGAGAUUCAGAAGGCAGACUUCAGGCAGACCCUCAGCGCUUUCCUCAUGGGAUUCGCCAGCUAGCUAAUUAUG<br>UUCACAGCAAAGGACUGAAGCUAGGGAUUUAUGCAGAUGUUGGAAAUAAGACCUGCGCAGGCUUCCCUGGGAGU<br>UUUGGAUACUACGACAUUGAUGCCCAGACCUUUGCUGACUGGGGAGUAGAUCUGCUAAAGUUUGAUGGUUGUUA<br>CUGUGACAGUUUGGAGAAUUUGGCAGAUGGUUAUAAGCACAUGUCCUUGGCCCUGAAUAGGACUGGCAGAAGCA<br>UUGUGUACUCCUGUGAGUGGCCUCUUUAUAUGUGGCCCUUUCAGAAGCCCAAUUAUACAGAAAUCCGACAGUAC<br>UGCAAUCACUGGCGAAAUUUUGCUGACAUUGAUGAUUCCUGGAAGAGUAUAAAGAGUAUCUUGGACUGGACAUC<br>UUUUAACCAGGAGAGAAUUGUUGAUGUUGCUGGACCAGGCGGUUGGAAUGACCCAGAUAUGUUAGUGAUUGGCA<br>ACUUUGGCCUCAGCUGGAAUCAGCAAGUAACUCAGAUGGCCCUCUGGGCUAUCAUGGCUGCUCCUUUAUUCAUG<br>UCUAAUGACCUCCGACACAUCAGCCCUCAAGCCAAAGCUCUCCUUCAGGAUAAGGACGUAAUUGCCAUCAAUCA<br>GGACCCCUUGGGCAAGCAAGGGUACCAGCUUAGACAGGGAGACAACUUUGAAGUGUGGGAACGACCUCUCUCAG<br>GCUUAGCCUGGGCUGUAGCUAUGAUAAACCGGCAGGAGAUUGGUGGACCUCGCUCUUAUACCAUCGCAGUUGCU<br>UCCCUGGGUAAAGGAGUGGCCUGUAAUCCUGCCUGCUUCAUCACACAGCUCCUCCCUGUGAAGAGGAAGCUAGG<br>GUUCUAUGAAUGGACUUCAAGGUUAAGAAGUCACAUAAAUCCCACAGGCACUGUUUUGCUUCAGCUAGAGAAUA<br>CAAUGCAGAUGUCAUUAAAGGACUUACUU |

The sequence-optimized nucleotide sequences disclosed herein are distinct from the corresponding wild type nucleotide acid sequences and from other known sequence-optimized nucleotide sequences, e.g., these sequence-optimized nucleic acids have unique compositional characteristics.

In some embodiments, the percentage of uracil or thymine nucleobases in a sequence-optimized nucleotide sequence (e.g., encoding a GLA polypeptide, a functional fragment, or a variant thereof) is modified (e.g., reduced) with respect to the percentage of uracil or thymine nucleobases in the reference wild-type nucleotide sequence. Such a sequence is referred to as a uracil-modified or thymine-modified sequence. The percentage of uracil or thymine content in a nucleotide sequence can be determined by dividing the number of uracils or thymines in a sequence by the total number of nucleotides and multiplying by 100. In some embodiments, the sequence-optimized nucleotide sequence has a lower uracil or thymine content than the uracil or thymine content in the reference wild-type sequence. In some embodiments, the uracil or thymine content in a sequence-optimized nucleotide sequence of the invention is greater than the uracil or thymine content in the reference wild-type sequence and still maintain beneficial effects, e.g., increased expression and/or reduced Toll-Like Receptor (TLR) response when compared to the reference wild-type sequence.

The uracil or thymine content of wild-type GLA is about 26%. In some embodiments, the uracil or thymine content of a uracil- or thymine-modified sequence encoding a GLA polypeptide is less than 26%. In some embodiments, the uracil or thymine content of a uracil- or thymine-modified sequence encoding a GLA polypeptide of the invention is less than 25%, less than 24%, less than 23%, less than 22%, less than 21%, less than 20%, less than 19%, less that 18%, less than 17%, less than 16%, less than 15%, less than 14%, less than 13%, less than 12%, or less than 11%. In some embodiments, the uracil or thymine content is not less than 25%, 24%, 23%, 22%, 21%, 20%, 19%, 18%, 17%, 16%, 15%, 14%, 13%, or 12%. The uracil or thymine content of a sequence disclosed herein, i.e., its total uracil or thymine content is abbreviated herein as % $U_{TL}$ or % $T_{TL}$.

In some embodiments, the uracil or thymine content (% $U_{TL}$ or % $T_{TL}$) of a uracil- or thymine-modified sequence encoding a GLA polypeptide of the invention is between 12% and 26%, between 13% and 26%, between 13% and 25%, between 14% and 25%, between 14% and 24%, between 15% and 24%, between 15% and 23%, between 16% and 23%, between 16% and 22%, between 16% and 21%, between 16% and 20%, between 16% and 19%, between 16% and 18%, or between 16% and 17%.

In some embodiments, the uracil or thymine content (% $U_{TL}$ or % $T_{TL}$) of a uracil- or thymine-modified sequence encoding a GLA polypeptide of the invention is between 15% and 19%, between 16% and 19%, or between 16% and 18%.

In a particular embodiment, the uracil or thymine content (% $U_{TL}$ or % $T_{TL}$) of a uracil- or thymine modified sequence encoding a GLA polypeptide of the invention is between about 16% and about 18%.

A uracil- or thymine-modified sequence encoding a GLA polypeptide of the invention can also be described according to its uracil or thymine content relative to the uracil or thymine content in the corresponding wild-type nucleic acid sequence (% $U_{WT}$ or % $T_{WT}$), or according to its uracil or thymine content relative to the theoretical minimum uracil or thymine content of a nucleic acid encoding the wild-type protein sequence (% $U_{TM}$ or (% $T_{TM}$).

The phrases "uracil or thymine content relative to the uracil or thymine content in the wild type nucleic acid sequence," refers to a parameter determined by dividing the number of uracils or thymines in a sequence-optimized nucleic acid by the total number of uracils or thymines in the corresponding wild-type nucleic acid sequence and multiplying by 100. This parameter is abbreviated herein as % $U_{WT}$ or % $T_{WT}$.

In some embodiments, the % $U_{WT}$ or % $T_{WT}$ of a uracil- or thymine-modified sequence encoding a GLA polypeptide of the invention is above 50%, above 55%, above 60%, above 65%, above 70%, above 75%, above 80%, above 85%, above 90%, or above 95%.

In some embodiments, the % $U_{WT}$ or % $T_{WT}$ of a uracil- or thymine modified sequence encoding a GLA polypeptide of the invention is between 50% and 80%, between 51% and 79%, between 52% and 78%, between 53% and 77%, between 54% and 76%, between 55% and 75%, between 56% and 74%, between 57% and 73%, between 58% and 72%, between 59% and 71%, between 60% and 70%, between 61% and 70%, or between 62% and 70%.

In some embodiments, the % $U_{WT}$ or % $T_{WT}$ of a uracil- or thymine-modified sequence encoding a GLA polypeptide of the invention is between 60% and 72%, between 60.2% and 71.8%, between 60.4% and 71.6%, between 60.6% and 71.4%, between 60.8% and 71.2%, between 61% and 71%, between 61.2% and 70.8%, between 61.4% and 70.6%, between 61.6% and 70.4%, between 61.8% and 70.2%, or between 62% and 70%.

In a particular embodiment, the % $U_{WT}$ or % $T_{WT}$ of a uracil- or thymine-modified sequence encoding a GLA polypeptide of the invention is between about 62% and about 70%, e.g., between 62.73% and 69.70%.

Uracil- or thymine-content relative to the uracil or thymine theoretical minimum, refers to a parameter determined by dividing the number of uracils or thymines in a sequence-optimized nucleotide sequence by the total number of uracils or thymines in a hypothetical nucleotide sequence in which all the codons in the hypothetical sequence are replaced with synonymous codons having the lowest possible uracil or thymine content and multiplying by 100. This parameter is abbreviated herein as % $U_{TM}$ or % $T_{TM}$.

For DNA it is recognized that thymine is present instead of uracil, and one would substitute T where U appears. Thus, all the disclosures related to, e.g., % $U_{TM}$, % $U_{WT}$, or % $U_{TL}$ with respect to RNA are equally applicable to % $T_{TM}$, % $T_{WT}$, or % $T_{TL}$ with respect to DNA.

In some embodiments, the % $U_{TM}$ of a uracil-modified sequence encoding a GLA polypeptide of the invention is below 300%, below 295%, below 290%, below 285%, below 280%, below 275%, below 270%, below 265%, below 260%, below 255%, below 250%, below 245%, below 240%, below 235%, below 230%, below 225%, below 220%, below 215%, below 200%, below 195%, below 190%, below 185%, below 180%, below 175%, below 170%, below 165%, below 160%, below 155%, below 154%, below 153%, below 152%, below 151%, below 150%, below 149%, below 148%, below 147%, below 146%, below 145%, below 144%, below 143%, below 142%, below 141%, below 140%, below 139%, below 138%, below 137%, below 136%, below 135%, below 134%, below 133%, below 132%, below 131%, below 130%, below 129%, below 128%, below 127%, below 126%, below 125%, below 124%, below 123%, below 122%, below 121%, or below 120%.

In some embodiments, the % $U_{TM}$ of a uracil-modified sequence encoding a GLA polypeptide of the invention is above 100%, above 101%, above 102%, above 103%, above 104%, above 105%, above 106%, above 107%, above 108%, above 109%, above 110%, above 111%, above 112%, above 113%, above 114%, above 115%, above 116%, above 117%, above 118%, above 119%, above 120%, above 121%, above 122%, above 123%, above 124%, above 125%, or above 126%, above 127%, above 128%, above 129%, or above 130%, above 135%, above 130%, above 131%, above 132%, above 133%, above 134%, above 135%, above 136%, above 137%, above 138%, above 139%, or above 140%, above 141%, above 142%, above 143%, above 144%, above 145%, above 146%, above 147%, above 148%, above 149%, or above 150%.

In some embodiments, the % $U_{TM}$ of a uracil-modified sequence encoding a GLA polypeptide of the invention is between 131% and 132%, between 130% and 133%, between 129% and 134%, between 128% and 135%, between 127% and 136%, between 126% and 137%, between 125% and 138%, between 124% and 139%, between 123% and 140%, between 122% and 141%, between 121% and 142%, between 120% and 143%, between 119% and 144%, between 118% and 145%, or between 117% and 146%.

In some embodiments, the % $U_{TM}$ of a uracil-modified sequence encoding a GLA polypeptide of the invention is between about 123% and about 138%, e.g., between 123% and 138%.

In some embodiments, a uracil-modified sequence encoding a GLA polypeptide of the invention has a reduced number of consecutive uracils with respect to the corresponding wild-type nucleic acid sequence. For example, two consecutive leucines can be encoded by the sequence CUUUUG, which includes a four uracil cluster. Such a subsequence can be substituted, e.g., with CUGCUC, which removes the uracil cluster.

Phenylalanine can be encoded by UUC or UUU. Thus, even if phenylalanines encoded by UUU are replaced by UUC, the synonymous codon still contains a uracil pair (UU). Accordingly, the number of phenylalanines in a sequence establishes a minimum number of uracil pairs (UU) that cannot be eliminated without altering the number of phenylalanines in the encoded polypeptide. For example, if the polypeptide, e.g., wild type GLA, has 10, 11, 12, 13, 14, 15, 16, or 17 phenylalanines, the absolute minimum number of uracil pairs (UU) that a uracil-modified sequence encoding the polypeptide, e.g., wild type GLA, can contain is 10, 11, 12, 13, 14, 15, 16, or 17, respectively.

Wild type GLA contains 5 uracil pairs (UU), and 12 uracil triplets (UUU). In some embodiments, a uracil-modified sequence encoding a GLA polypeptide of the invention has a reduced number of uracil triplets (UUU) with respect to the wild-type nucleic acid sequence. In some embodiments, a uracil-modified sequence encoding a GLA polypeptide of the invention contains 12, 11, 10, 9, 8, 7, 6, 5, 4, 3, 2, 1 or no uracil triplets (UUU).

In some embodiments, a uracil-modified sequence encoding a GLA polypeptide has a reduced number of uracil pairs (UU) with respect to the number of uracil pairs (UU) in the wild-type nucleic acid sequence. In some embodiments, a uracil-modified sequence encoding a GLA polypeptide of the invention has a number of uracil pairs (UU) corresponding to the minimum possible number of uracil pairs (UU) in the wild-type nucleic acid sequence, e.g., 11 uracil pairs in the case of wild type GLA.

In some embodiments, a uracil-modified sequence encoding a GLA polypeptide of the invention has at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 uracil pairs (UU) less than the number of uracil pairs (UU) in the wild-type nucleic acid sequence. In some embodiments, a uracil-modified sequence encoding a GLA polypeptide of the invention has between 11 and 27 uracil pairs (UU).

The phrase "uracil pairs (UU) relative to the uracil pairs (UU) in the wild type nucleic acid sequence," refers to a parameter determined by dividing the number of uracil pairs (UU) in a sequence-optimized nucleotide sequence by the total number of uracil pairs (UU) in the corresponding wild-type nucleotide sequence and multiplying by 100. This parameter is abbreviated herein as % $UU_{wt}$.

In some embodiments, a uracil-modified sequence encoding a GLA polypeptide of the invention has a % $UU_{wt}$ less than 90%, less than 85%, less than 80%, less than 75%, less than 70%, less than 65%, less than 60%, less than 65%, less than 60%, less than 55%, less than 50%, less than 40%, less than 30%, or less than 25%.

In some embodiments, a uracil-modified sequence encoding a GLA polypeptide has a % $UU_{wt}$ between 16% and 58%. In a particular embodiment, a uracil-modified sequence encoding a GLA polypeptide of the invention has a % $UU_{wt}$ between 21% and 53%.

In some embodiments, the polynucleotide of the invention comprises a uracil-modified sequence encoding a GLA polypeptide disclosed herein. In some embodiments, the uracil-modified sequence encoding a GLA polypeptide comprises at least one chemically modified nucleobase, e.g., 5-methoxyuracil. In some embodiments, at least 95% of a nucleobase (e.g., uracil) in a uracil-modified sequence encoding a GLA polypeptide of the invention are modified nucleobases. In some embodiments, at least 95% of uracil in a uracil-modified sequence encoding a GLA polypeptide is 5-methoxyuracil. In some embodiments, the polynucleotide comprising a uracil-modified sequence further comprises a miRNA binding site, e.g., a miRNA binding site that binds to miR-142 and/or a miRNA binding site that binds to miR-126. In some embodiments, the polynucleotide comprising a uracil-modified sequence is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

In some embodiments, the "guanine content of the sequence optimized ORF encoding GLA with respect to the theoretical maximum guanine content of a nucleotide sequence encoding the GLA polypeptide," abbreviated as % $G_{TMX}$ is at least 64%, at least 65%, at least 70%, at least 75%, at least 75%, at least about 80%, at least about 85%, at least about 90%, at least about 95%, or about 100%. In some embodiments, the % $G_{TMX}$ is between about 70% and about 85%, between about 70% and about 80%, between about 71% and about 80%, or between about 72% and about 80%.

In some embodiments, the "cytosine content of the ORF relative to the theoretical maximum cytosine content of a nucleotide sequence encoding the GLA polypeptide," abbreviated as % $C_{TMX}$, is at least 54%, at least 55%, at least 60%, at least 65%, at least 70%, at least 75%, at least about 80%, at least about 85%, at least about 90%, at least about 95%, or about 100%. In some embodiments, the % $C_{TMX}$ is between about 60% and about 80%, between about 65% and about 80%, between about 70% and about 80%, or between about 70% and about 76%.

In some embodiments, the "guanine and cytosine content (G/C) of the ORF relative to the theoretical maximum G/C content in a nucleotide sequence encoding the GLA polypeptide," abbreviated as % $G/C_{TMX}$ is at least about 73%, at least about 75%, at least about 80%, at least about 85%, at least about 90%, at least about 95%, or about 100% In some embodiments, the % $G/C_{TMX}$ is between about 80% and about 100%, between about 85% and about 99%, between about 90% and about 97%, or between about 91% and about 95%.

In some embodiments, the "G/C content in the ORF relative to the G/C content in the corresponding wild-type ORF," abbreviated as % $G/C_{WT}$ is at least 102%, at least 103%, at least 104%, at least 105%, at least 106%, at least 107%, at least about 110%, at least about 115%, at least about 120%, or at least about 125%.

In some embodiments, the average G/C content in the 3rd codon position in the ORF is at least 30%, at least 31%, at least 32%, at least 33%, at least 34%, at least 35%, at least 36%, at least 37%, at least 38%, at least 39%, or at least 40% higher than the average G/C content in the 3rd codon position in the corresponding wild-type ORF.

In some embodiments, the polynucleotide of the invention comprises an open reading frame (ORF) encoding a GLA polypeptide, wherein the ORF has been sequence optimized, and wherein each of % $U_{TL}$, % $U_{WT}$, % $U_{TM}$, % $G_{TL}$, % $G_{WT}$, % $G_{TMX}$, % $C_{TL}$, % $C_{WT}$, % $C_{TMX}$, % $G/C_{TL}$, % $G/C_{WT}$, or % $G/C_{TMX}$, alone or in a combination thereof is in a range between (i) a maximum corresponding to the parameter's maximum value (MAX) plus about 0.5, 1, 1.5, 2, 2.5, 3, 3.5, 4, 4.5, 5, 5.5, 6, 6.5, 7, 7.5, 8, 8.5, 9, 9.5, or 10 standard deviations (STD DEV), and (ii) a minimum corresponding to the parameter's minimum value (MIN) less 0.5, 1, 1.5, 2, 2.5, 3, 3.5, 4, 4.5, 5, 5.5, 6, 6.5, 7, 7.5, 8, 8.5, 9, 9.5, or 10 standard deviations (STD DEV).

7. Methods for Sequence Optimization

In some embodiments, a polynucleotide, e.g., mRNA, of the invention (e.g., a polynucleotide comprising a nucleotide sequence encoding a GLA polypeptide (e.g., the wild-type sequence, functional fragment, or variant thereof) is sequence optimized. A sequence optimized nucleotide sequence (nucleotide sequence is also referred to as "nucleic acid" herein) comprises at least one codon modification with respect to a reference sequence (e.g., a wild-type sequence encoding a GLA polypeptide). Thus, in a sequence optimized nucleic acid, at least one codon is different from a corresponding codon in a reference sequence (e.g., a wild-type sequence).

In general, sequence optimized nucleic acids are generated by at least a step comprising substituting codons in a reference sequence with synonymous codons (i.e., codons that encode the same amino acid). Such substitutions can be effected, for example, by applying a codon substitution map (i.e., a table providing the codons that will encode each amino acid in the codon optimized sequence), or by applying a set of rules (e.g., if glycine is next to neutral amino acid, glycine would be encoded by a certain codon, but if it is next to a polar amino acid, it would be encoded by another codon). In addition to codon substitutions (i.e., "codon optimization") the sequence optimization methods disclosed herein comprise additional optimization steps which are not strictly directed to codon optimization such as the removal of deleterious motifs (destabilizing motif substitution). Compositions and formulations comprising these sequence optimized nucleic acids (e.g., a RNA, e.g., an mRNA) can be administered to a subject in need thereof to facilitate in vivo expression of functionally active GLA.

The recombinant expression of large molecules in cell cultures can be a challenging task with numerous limitations (e.g., poor protein expression levels, stalled translation resulting in truncated expression products, protein misfolding, etc.) These limitations can be reduced or avoided by administering the polynucleotides (e.g., a RNA, e.g., an mRNA), which encode a functionally active GLA or compositions or formulations comprising the same to a patient suffering from Fabry disease, so the synthesis and delivery of the GLA polypeptide to treat Fabry disease takes place endogenously.

Changing from an in vitro expression system (e.g., cell culture) to in vivo expression requires the redesign of the nucleic acid sequence encoding the therapeutic agent. Redesigning a naturally occurring gene sequence by choosing different codons without necessarily altering the encoded amino acid sequence can often lead to dramatic increases in protein expression levels (Gustafsson et al., 2004, Journal/Trends Biotechnol 22, 346-53). Variables such as codon adaptation index (CAI), mRNA secondary structures, cis-regulatory sequences, GC content and many other similar variables have been shown to somewhat correlate with protein expression levels (Villalobos et al., 2006, "Journal/BMC Bioinformatics 7, 285). However, due to the degeneracy of the genetic code, there are numerous different nucleic acid sequences that can all encode the same therapeutic agent. Each amino acid is encoded by up to six synonymous codons; and the choice between these codons influences gene expression. In addition, codon usage (i.e., the frequency with which different organisms use codons for expressing a polypeptide sequence) differs among organisms (for example, recombinant production of human or humanized therapeutic antibodies frequently takes place in hamster cell cultures).

In some embodiments, a reference nucleic acid sequence can be sequence optimized by applying a codon map. The skilled artisan will appreciate that the T bases in the codon maps disclosed below are present in DNA, whereas the T bases would be replaced by U bases in corresponding RNAs. For example, a sequence optimized nucleic acid disclosed herein in DNA form, e.g., a vector or an in-vitro translation (IVT) template, would have its T bases transcribed as U based in its corresponding transcribed mRNA. In this respect, both sequence optimized DNA sequences (comprising T) and their corresponding RNA sequences (comprising U) are considered sequence optimized nucleic acid of the present invention. A skilled artisan would also understand that equivalent codon-maps can be generated by replaced one or more bases with non-natural bases. Thus, e.g., a TTC codon (DNA map) would correspond to a UUC codon (RNA map), which in turn can correspond to a ΨΨC codon (RNA map in which U has been replaced with pseudouridine).

In one embodiment, a reference sequence encoding GLA can be optimized by replacing all the codons encoding a certain amino acid with only one of the alternative codons provided in a codon map. For example, all the valines in the optimized sequence would be encoded by GTG or GTC or GTT.

Sequence optimized polynucleotides of the invention can be generated using one or more codon optimization methods, or a combination thereof. Sequence optimization methods which can be used to sequence optimize nucleic acid sequences are described in detail herein. This list of methods is not comprehensive or limiting.

It will be appreciated that the design principles and rules described for each one of the sequence optimization methods discussed below can be combined in many different ways, for example high G/C content sequence optimization for some regions or uridine content sequence optimization for other regions of the reference nucleic acid sequence, as well as targeted nucleotide mutations to minimize secondary structure throughout the sequence or to eliminate deleterious motifs.

The choice of potential combinations of sequence optimization methods can be, for example, dependent on the specific chemistry used to produce a synthetic polynucleotide. Such a choice can also depend on characteristics of the protein encoded by the sequence optimized nucleic acid, e.g., a full sequence, a functional fragment, or a fusion protein comprising GLA, etc. In some embodiments, such a choice can depend on the specific tissue or cell targeted by the sequence optimized nucleic acid (e.g., a therapeutic synthetic mRNA).

The mechanisms of combining the sequence optimization methods or design rules derived from the application and analysis of the optimization methods can be either simple or complex. For example, the combination can be:
  (i) Sequential: Each sequence optimization method or set of design rules applies to a different subsequence of the overall sequence, for example reducing uridine at codon positions 1 to 30 and then selecting high frequency codons for the remainder of the sequence;
  (ii) Hierarchical: Several sequence optimization methods or sets of design rules are combined in a hierarchical, deterministic fashion. For example, use the most GC-rich codons, breaking ties (which are common) by choosing the most frequent of those codons.
  (iii) Multifactorial/Multiparametric: Machine learning or other modeling techniques are used to design a single sequence that best satisfies multiple overlapping and possibly contradictory requirements. This approach would require the use of a computer applying a number of mathematical techniques, for example, genetic algorithms.

Ultimately, each one of these approaches can result in a specific set of rules which in many cases can be summarized in a single codon table, i.e., a sorted list of codons for each amino acid in the target protein (i.e., GLA), with a specific rule or set of rules indicating how to select a specific codon for each amino acid position.

a. Uridine Content Optimization

The presence of local high concentrations of uridine in a nucleic acid sequence can have detrimental effects on translation, e.g., slow or prematurely terminated translation, especially when modified uridine analogs are used in the production of synthetic mRNAs. Furthermore, high uridine content can also reduce the in vivo half-life of synthetic mRNAs due to TLR activation.

Accordingly, a nucleic acid sequence can be sequence optimized using a method comprising at least one uridine content optimization step. Such a step comprises, e.g., substituting at least one codon in the reference nucleic acid with an alternative codon to generate a uridine-modified sequence, wherein the uridine-modified sequence has at least one of the following properties:
  (i) increase or decrease in global uridine content;
  (ii) increase or decrease in local uridine content (i.e., changes in uridine content are limited to specific subsequences);

(iii) changes in uridine distribution without altering the global uridine content;
(iv) changes in uridine clustering (e.g., number of clusters, location of clusters, or distance between clusters); or
(v) combinations thereof.

In some embodiments, the sequence optimization process comprises optimizing the global uridine content, i.e., optimizing the percentage of uridine nucleobases in the sequence optimized nucleic acid with respect to the percentage of uridine nucleobases in the reference nucleic acid sequence. For example, 30% of nucleobases can be uridines in the reference sequence and 10% of nucleobases can be uridines in the sequence optimized nucleic acid.

In other embodiments, the sequence optimization process comprises reducing the local uridine content in specific regions of a reference nucleic acid sequence, i.e., reducing the percentage of uridine nucleobases in a subsequence of the sequence optimized nucleic acid with respect to the percentage of uridine nucleobases in the corresponding subsequence of the reference nucleic acid sequence. For example, the reference nucleic acid sequence can have a 5'-end region (e.g., 30 codons) with a local uridine content of 30%, and the uridine content in that same region could be reduced to 10% in the sequence optimized nucleic acid.

In specific embodiments, codons can be replaced in the reference nucleic acid sequence to reduce or modify, for example, the number, size, location, or distribution of uridine clusters that could have deleterious effects on protein translation. Although as a general rule it is desirable to reduce the uridine content of the reference nucleic acid sequence, in certain embodiments the uridine content, and in particular the local uridine content, of some subsequences of the reference nucleic acid sequence can be increased.

The reduction of uridine content to avoid adverse effects on translation can be done in combination with other optimization methods disclosed here to achieve other design goals. For example, uridine content optimization can be combined with ramp design, since using the rarest codons for most amino acids will, with a few exceptions, reduce the U content.

In some embodiments, the uridine-modified sequence is designed to induce a lower Toll-Like Receptor (TLR) response when compared to the reference nucleic acid sequence. Several TLRs recognize and respond to nucleic acids. Double-stranded (ds)RNA, a frequent viral constituent, has been shown to activate TLR3. See Alexopoulou et al. (2001) Nature, 413:732-738 and Wang et al. (2004) Nat. Med., 10:1366-1373. Single-stranded (ss)RNA activates TLR7. See Diebold et al. (2004) Science 303:529-1531. RNA oligonucleotides, for example RNA with phosphorothioate internucleotide linkages, are ligands of human TLR8. See Heil et al. (2004) Science 303:1526-1529. DNA containing unmethylated CpG motifs, characteristic of bacterial and viral DNA, activate TLR9. See Hemmi et al. (2000) Nature, 408: 740-745.

As used herein, the term "TLR response" is defined as the recognition of single-stranded RNA by a TLR7 receptor, and in some embodiments encompasses the degradation of the RNA and/or physiological responses caused by the recognition of the single-stranded RNA by the receptor. Methods to determine and quantitate the binding of an RNA to a TLR7 are known in the art. Similarly, methods to determine whether an RNA has triggered a TLR7-mediated physiological response (e.g., cytokine secretion) are well known in the art. In some embodiments, a TLR response can be mediated by $TLR_3$, TLR8, or TLR9 instead of TLR7.

Suppression of TLR7-mediated response can be accomplished via nucleoside modification. RNA undergoes over hundred different nucleoside modifications in nature (see the RNA Modification Database, available at mods.rna.albany.edu). Human rRNA, for example, has ten times more pseudouridine (T) and 25 times more 2'-O-methylated nucleosides than bacterial rRNA. Bacterial mRNA contains no nucleoside modifications, whereas mammalian mRNAs have modified nucleosides such as 5-methylcytidine (m5C), N6-methyladenosine (m6A), inosine and many 2'-O-methylated nucleosides in addition to N7-methylguanosine (m7G).

Uracil and ribose, the two defining features of RNA, are both necessary and sufficient for TLR7 stimulation, and short single-stranded RNA (ssRNA) act as TLR7 agonists in a sequence-independent manner as long as they contain several uridines in close proximity. See Diebold et al. (2006) Eur. J. Immunol. 36:3256-3267, which is herein incorporated by reference in its entirety. Accordingly, one or more of the optimization methods disclosed herein comprises reducing the uridine content (locally and/or locally) and/or reducing or modifying uridine clustering to reduce or to suppress a TLR7-mediated response.

In some embodiments, the TLR response (e.g., a response mediated by TLR7) caused by the uridine-modified sequence is at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% lower than the TLR response caused by the reference nucleic acid sequence.

In some embodiments, the TLR response caused by the reference nucleic acid sequence is at least about 1-fold, at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2-fold, at least about 3-fold, at least about 4-fold, at least about 5-fold, at least about 6-fold, at least about 7-fold, at least about 8-fold, at least about 9-fold, or at least about 10-fold higher than the TLR response caused by the uridine-modified sequence.

In some embodiments, the uridine content (average global uridine content) (absolute or relative) of the uridine-modified sequence is higher than the uridine content (absolute or relative) of the reference nucleic acid sequence. Accordingly, in some embodiments, the uridine-modified sequence contains at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% more uridine that the reference nucleic acid sequence.

In other embodiments, the uridine content (average global uridine content) (absolute or relative) of the uridine-modified sequence is lower than the uridine content (absolute or relative) of the reference nucleic acid sequence. Accordingly, in some embodiments, the uridine-modified sequence contains at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% less uridine that the reference nucleic acid sequence.

In some embodiments, the uridine content (average global uridine content) (absolute or relative) of the uridine-modified sequence is less than 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% of the total nucleobases in the uridine-modified sequence. In some embodiments, the uridine content of the uridine-modified sequence is between about 10% and about 20%. In some particular embodiments, the uridine content of the uridine-modified sequence is between about 12% and about 16%.

In some embodiments, the uridine content of the reference nucleic acid sequence can be measured using a sliding window. In some embodiments, the length of the sliding window is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleobases. In some embodiments, the sliding window is over 40 nucleobases in length. In some embodiments, the sliding window is 20 nucleobases in length. Based on the uridine content measured with a sliding window, it is possible to generate a histogram representing the uridine content throughout the length of the reference nucleic acid sequence and sequence optimized nucleic acids.

In some embodiments, a reference nucleic acid sequence can be modified to reduce or eliminate peaks in the histogram that are above or below a certain percentage value. In some embodiments, the reference nucleic acid sequence can be modified to eliminate peaks in the sliding-window representation which are above 65%, 60%, 55%, 50%, 45%, 40%, 35%, or 30% uridine. In another embodiment, the reference nucleic acid sequence can be modified so no peaks are over 30% uridine in the sequence optimized nucleic acid, as measured using a 20 nucleobase sliding window. In some embodiments, the reference nucleic acid sequence can be modified so no more or no less than a predetermined number of peaks in the sequence optimized nucleic sequence, as measured using a 20 nucleobase sliding window, are above or below a certain threshold value. For example, in some embodiments, the reference nucleic acid sequence can be modified so no peaks or no more than 1, 2, 3, 4, 5, 6, 7, 8, 9 or 10 peaks in the sequence optimized nucleic acid are above 10%, 15%, 20%, 25% or 30% uridine. In another embodiment, the sequence optimized nucleic acid contains between 0 peaks and 2 peaks with uridine contents 30% of higher.

In some embodiments, a reference nucleic acid sequence can be sequence optimized to reduce the incidence of consecutive uridines. For example, two consecutive leucines could be encoded by the sequence CUUUUG, which would include a four uridine cluster. Such subsequence could be substituted with CUGCUC, which would effectively remove the uridine cluster. Accordingly, a reference nucleic sequence can be sequence optimized by reducing or eliminating uridine pairs (UU), uridine triplets (UUU) or uridine quadruplets (UUUU). Higher order combinations of U are not considered combinations of lower order combinations. Thus, for example, UUUU is strictly considered a quadruplet, not two consecutive U pairs; or UUUUUU is considered a sextuplet, not three consecutive U pairs, or two consecutive U triplets, etc.

In some embodiments, all uridine pairs (UU) and/or uridine triplets (UUU) and/or uridine quadruplets (UUUU) can be removed from the reference nucleic acid sequence. In other embodiments, uridine pairs (UU) and/or uridine triplets (UUU) and/or uridine quadruplets (UUUU) can be reduced below a certain threshold, e.g., no more than 1, 2, 3, 4, 5, 6, 7, 8, 9, 10, 11, 12, 13, 14, 15, 16, 17, 18, 19, or 20 occurrences in the sequence optimized nucleic acid. In a particular embodiment, the sequence optimized nucleic acid contains less than 20, 19, 18, 17, 16, 15, 14, 13, 12, 11, 10, 9, 8, 7, 6, 5, 4, 3, 2, or 1 uridine pairs. In another particular embodiment, the sequence optimized nucleic acid contains no uridine pairs and/or triplets.

Phenylalanine codons, i.e., UUC or UUU, comprise a uridine pair or triples and therefore sequence optimization to reduce uridine content can at most reduce the phenylalanine U triplet to a phenylalanine U pair. In some embodiments, the occurrence of uridine pairs (UU) and/or uridine triplets (UUU) refers only to non-phenylalanine U pairs or triplets. Accordingly, in some embodiments, non-phenylalanine uridine pairs (UU) and/or uridine triplets (UUU) can be reduced below a certain threshold, e.g., no more than 1, 2, 3, 4, 5, 6, 7, 8, 9, 10, 11, 12, 13, 14, 15, 16, 17, 18, 19, or 20 occurrences in the sequence optimized nucleic acid. In a particular embodiment, the sequence optimized nucleic acid contains less than 20, 19, 18, 17, 16, 15, 14, 13, 12, 11, 10, 9, 8, 7, 6, 5, 4, 3, 2, or 1 non-phenylalanine uridine pairs and/or triplets. In another particular embodiment, the sequence optimized nucleic acid contains no non-phenylalanine uridine pairs and/or triplets.

In some embodiments, the reduction in uridine combinations (e.g., pairs, triplets, quadruplets) in the sequence optimized nucleic acid can be expressed as a percentage reduction with respect to the uridine combinations present in the reference nucleic acid sequence.

In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine pairs present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine triplets present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine quadruplets present in the reference nucleic acid sequence.

In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of non-phenylalanine uridine pairs present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of non-phenylalanine uridine triplets present in the reference nucleic acid sequence.

In some embodiments, the uridine content in the sequence optimized sequence can be expressed with respect to the theoretical minimum uridine content in the sequence. The term "theoretical minimum uridine content" is defined as the uridine content of a nucleic acid sequence as a percentage of the sequence's length after all the codons in the sequence have been replaced with synonymous codon with the lowest uridine content. In some embodiments, the uridine content of the sequence optimized nucleic acid is identical to the theoretical minimum uridine content of the reference sequence (e.g., a wild type sequence). In some aspects, the uridine content of the sequence optimized nucleic acid is about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195% or about 200% of the theoretical minimum uridine content of the reference sequence (e.g., a wild type sequence).

In some embodiments, the uridine content of the sequence optimized nucleic acid is identical to the theoretical minimum uridine content of the reference sequence (e.g., a wild type sequence).

The reference nucleic acid sequence (e.g., a wild type sequence) can comprise uridine clusters which due to their number, size, location, distribution or combinations thereof have negative effects on translation. As used herein, the term "uridine cluster" refers to a subsequence in a reference nucleic acid sequence or sequence optimized nucleic acid sequence with contains a uridine content (usually described as a percentage) which is above a certain threshold. Thus, in certain embodiments, if a subsequence comprises more than about 10%, 15%, 20%, 25%, 30%, 35%, 40%, 45%, 50%, 55%, 60% or 65% uridine content, such subsequence would be considered a uridine cluster.

The negative effects of uridine clusters can be, for example, eliciting a TLR7 response. Thus, in some implementations of the nucleic acid sequence optimization methods disclosed herein it is desirable to reduce the number of clusters, size of clusters, location of clusters (e.g., close to the 5' and/or 3' end of a nucleic acid sequence), distance between clusters, or distribution of uridine clusters (e.g., a certain pattern of cluster along a nucleic acid sequence, distribution of clusters with respect to secondary structure elements in the expressed product, or distribution of clusters with respect to the secondary structure of an mRNA).

In some embodiments, the reference nucleic acid sequence comprises at least one uridine cluster, wherein said uridine cluster is a subsequence of the reference nucleic acid sequence wherein the percentage of total uridine nucleobases in said subsequence is above a predetermined threshold. In some embodiments, the length of the subsequence is at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 nucleobases. In some embodiments, the subsequence is longer than 100 nucleobases. In some embodiments, the threshold is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% uridine content. In some embodiments, the threshold is above 25%.

For example, an amino acid sequence comprising A, D, G, S and R could be encoded by the nucleic acid sequence GCU, GAU, GGU, AGU, CGU. Although such sequence does not contain any uridine pairs, triplets, or quadruplets, one third of the nucleobases would be uridines. Such a uridine cluster could be removed by using alternative codons, for example, by using GCC, GAC, GGC, AGC, and CGC, which would contain no uridines.

In other embodiments, the reference nucleic acid sequence comprises at least one uridine cluster, wherein said uridine cluster is a subsequence of the reference nucleic acid sequence wherein the percentage of uridine nucleobases of said subsequence as measured using a sliding window that is above a predetermined threshold. In some embodiments, the length of the sliding window is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleobases. In some embodiments, the sliding window is over 40 nucleobases in length. In some embodiments, the threshold is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% uridine content. In some embodiments, the threshold is above 25%.

In some embodiments, the reference nucleic acid sequence comprises at least two uridine clusters. In some embodiments, the uridine-modified sequence contains fewer uridine-rich clusters than the reference nucleic acid sequence. In some embodiments, the uridine-modified sequence contains more uridine-rich clusters than the reference nucleic acid sequence. In some embodiments, the uridine-modified sequence contains uridine-rich clusters with are shorter in length than corresponding uridine-rich clusters in the reference nucleic acid sequence. In other embodiments, the uridine-modified sequence contains uridine-rich clusters which are longer in length than the corresponding uridine-rich cluster in the reference nucleic acid sequence. See, Kariko et al. (2005) Immunity 23:165-175; Kormann et al. (2010) Nature Biotechnology 29:154-157; or Sahin et al. (2014) Nature Reviews Drug Discovery AOP, published online 19 Sep. 2014m doi:10.1038/nrd4278; all of which are herein incorporated by reference their entireties.

b. Guanine/Cytosine (G/C) Content

A reference nucleic acid sequence can be sequence optimized using methods comprising altering the Guanine/Cytosine (G/C) content (absolute or relative) of the reference nucleic acid sequence. Such optimization can comprise altering (e.g., increasing or decreasing) the global G/C content (absolute or relative) of the reference nucleic acid sequence; introducing local changes in G/C content in the reference nucleic acid sequence (e.g., increase or decrease G/C in selected regions or subsequences in the reference nucleic acid sequence); altering the frequency, size, and distribution of G/C clusters in the reference nucleic acid sequence, or combinations thereof.

In some embodiments, the sequence optimized nucleic acid encoding GLA comprises an overall increase in G/C content (absolute or relative) relative to the G/C content (absolute or relative) of the reference nucleic acid sequence. In some embodiments, the overall increase in G/C content (absolute or relative) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the reference nucleic acid sequence.

In some embodiments, the sequence optimized nucleic acid encoding GLA comprises an overall decrease in G/C content (absolute or relative) relative to the G/C content of the reference nucleic acid sequence. In some embodiments, the overall decrease in G/C content (absolute or relative) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the reference nucleic acid sequence.

In some embodiments, the sequence optimized nucleic acid encoding GLA comprises a local increase in Guanine/Cytosine (G/C) content (absolute or relative) in a subsequence (i.e., a G/C modified subsequence) relative to the G/C content (absolute or relative) of the corresponding subsequence in the reference nucleic acid sequence. In some embodiments, the local increase in G/C content (absolute or relative) is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the corresponding subsequence in the reference nucleic acid sequence.

In some embodiments, the sequence optimized nucleic acid encoding GLA comprises a local decrease in Guanine/Cytosine (G/C) content (absolute or relative) in a subsequence (i.e., a G/C modified subsequence) relative to the G/C content (absolute or relative) of the corresponding subsequence in the reference nucleic acid sequence. In some embodiments, the local decrease in G/C content (absolute or relative) is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the corresponding subsequence in the reference nucleic acid sequence.

In some embodiments, the G/C content (absolute or relative) is increased or decreased in a subsequence which is at least about 5, 10, 15, 20, 25, 30, 35, 40, 45, 50, 55, 60, 65, 70, 75, 80, 85, 90, 95, or 100 nucleobases in length.

In some embodiments, the G/C content (absolute or relative) is increased or decreased in a subsequence which is at least about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleobases in length.

In some embodiments, the G/C content (absolute or relative) is increased or decreased in a subsequence which is at least about 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, or 10000 nucleobases in length.

The increases or decreases in G and C content (absolute or relative) described herein can be conducted by replacing synonymous codons with low G/C content with synonymous codons having higher G/C content, or vice versa. For example, L has 6 synonymous codons: two of them have 2 G/C (CUC, CUG), 3 have a single G/C (UUG, CUU, CUA), and one has no G/C (UUA). So if the reference nucleic acid had a CUC codon in a certain position, G/C content at that position could be reduced by replacing CUC with any of the codons having a single G/C or the codon with no G/C.

See, U.S. Publ. Nos. US20140228558, US20050032730 A1; Gustafsson et al. (2012) Protein Expression and Purification 83: 37-46; all of which are incorporated herein by reference in their entireties.

c. Codon Frequency—Codon Usage Bias

Numerous codon optimization methods known in the art are based on the substitution of codons in a reference nucleic acid sequence with codons having higher frequencies. Thus, in some embodiments, a nucleic acid sequence encoding GLA disclosed herein can be sequence optimized using methods comprising the use of modifications in the frequency of use of one or more codons relative to other synonymous codons in the sequence optimized nucleic acid with respect to the frequency of use in the non-codon optimized sequence.

As used herein, the term "codon frequency" refers to codon usage bias, i.e., the differences in the frequency of occurrence of synonymous codons in coding DNA/RNA. It is generally acknowledged that codon preferences reflect a balance between mutational biases and natural selection for translational optimization. Optimal codons help to achieve faster translation rates and high accuracy. As a result of these factors, translational selection is expected to be stronger in highly expressed genes. In the field of bioinformatics and computational biology, many statistical methods have been proposed and used to analyze codon usage bias. See, e.g., Comeron & Aguadé (1998) J. Mol. Evol. 47: 268-74. Methods such as the 'frequency of optimal codons' (Fop) (Ikemura (1981) J. Mol. Biol. 151 (3): 389-409), the Relative Codon Adaptation (RCA) (Fox & Eril (2010) DNA Res. 17 (3): 185-96) or the 'Codon Adaptation Index' (CAI) (Sharp & Li (1987) Nucleic Acids Res. 15 (3): 1281-95) are used to predict gene expression levels, while methods such as the 'effective number of codons' (Nc) and Shannon entropy from information theory are used to measure codon usage evenness. Multivariate statistical methods, such as correspondence analysis and principal component analysis, are widely used to analyze variations in codon usage among genes (Suzuki et al. (2008) DNA Res. 15 (6): 357-65; Sandhu et al., In Silico Biol. 2008; 8(2):187-92).

The nucleic acid sequence encoding a GLA polypeptide disclosed herein (e.g., a wild type nucleic acid sequence, a mutant nucleic acid sequence, a chimeric nucleic sequence, etc. which can be, for example, an mRNA), can be codon optimized using methods comprising substituting at least one codon in the reference nucleic acid sequence with an alternative codon having a higher or lower codon frequency in the synonymous codon set; wherein the resulting sequence optimized nucleic acid has at least one optimized property with respect to the reference nucleic acid sequence.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the reference nucleic acid sequence encoding GLA are substituted with alternative codons, each alternative codon having a codon frequency higher than the codon frequency of the substituted codon in the synonymous codon set.

In some embodiments, at least one codon in the reference nucleic acid sequence encoding GLA is substituted with an alternative codon having a codon frequency higher than the codon frequency of the substituted codon in the synonymous codon set, and at least one codon in the reference nucleic acid sequence is substituted with an alternative codon having a codon frequency lower than the codon frequency of the substituted codon in the synonymous codon set.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% of the codons in the reference nucleic acid sequence encoding GLA are substituted with alternative codons, each alternative codon having a codon frequency higher than the codon frequency of the substituted codon in the synonymous codon set.

In some embodiments, at least one alternative codon having a higher codon frequency has the highest codon frequency in the synonymous codon set. In other embodiments, all alternative codons having a higher codon frequency have the highest codon frequency in the synonymous codon set.

In some embodiments, at least one alternative codon having a lower codon frequency has the lowest codon frequency in the synonymous codon set. In some embodiments, all alternative codons having a higher codon frequency have the highest codon frequency in the synonymous codon set.

In some specific embodiments, at least one alternative codon has the second highest, the third highest, the fourth highest, the fifth highest or the sixth highest frequency in the synonymous codon set. In some specific embodiments, at least one alternative codon has the second lowest, the third lowest, the fourth lowest, the fifth lowest, or the sixth lowest frequency in the synonymous codon set.

Optimization based on codon frequency can be applied globally, as described above, or locally to the reference nucleic acid sequence encoding a GLA polypeptide. In some embodiments, when applied locally, regions of the reference nucleic acid sequence can modified based on codon frequency, substituting all or a certain percentage of codons in a certain subsequence with codons that have higher or lower frequencies in their respective synonymous codon sets. Thus, in some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in a subsequence of the reference nucleic acid sequence are substituted with alternative codons, each alternative codon having a codon frequency higher than the codon frequency of the substituted codon in the synonymous codon set.

In some embodiments, at least one codon in a subsequence of the reference nucleic acid sequence encoding a GLA polypeptide is substituted with an alternative codon having a codon frequency higher than the codon frequency of the substituted codon in the synonymous codon set, and at least one codon in a subsequence of the reference nucleic acid sequence is substituted with an alternative codon having a codon frequency lower than the codon frequency of the substituted codon in the synonymous codon set.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% of the codons in a subsequence of the reference nucleic acid sequence encoding a GLA polypeptide are substituted with alternative codons, each alternative codon having a codon frequency higher than the codon frequency of the substituted codon in the synonymous codon set.

In some embodiments, at least one alternative codon substituted in a subsequence of the reference nucleic acid sequence encoding a GLA polypeptide and having a higher codon frequency has the highest codon frequency in the synonymous codon set. In other embodiments, all alternative codons substituted in a subsequence of the reference nucleic acid sequence and having a lower codon frequency have the lowest codon frequency in the synonymous codon set.

In some embodiments, at least one alternative codon substituted in a subsequence of the reference nucleic acid sequence encoding a GLA polypeptide and having a lower codon frequency has the lowest codon frequency in the synonymous codon set. In some embodiments, all alternative codons substituted in a subsequence of the reference nucleic acid sequence and having a higher codon frequency have the highest codon frequency in the synonymous codon set.

In specific embodiments, a sequence optimized nucleic acid encoding a GLA polypeptide can comprise a subsequence having an overall codon frequency higher or lower than the overall codon frequency in the corresponding subsequence of the reference nucleic acid sequence at a specific location, for example, at the 5' end or 3' end of the sequence optimized nucleic acid, or within a predetermined distance from those region (e.g., at least 1, 2, 3, 4, 5, 6, 7, 8, 9, 10, 15, 20, 25, 30, 35, 40, 45, 50, 55, 60, 65, 70, 75, 80, 85, 90, 95 or 100 codons from the 5' end or 3' end of the sequence optimized nucleic acid).

In some embodiments, an sequence optimized nucleic acid encoding a GLA polypeptide can comprise more than one subsequence having an overall codon frequency higher or lower than the overall codon frequency in the corresponding subsequence of the reference nucleic acid sequence. A skilled artisan would understand that subsequences with overall higher or lower overall codon frequencies can be organized in innumerable patterns, depending on whether the overall codon frequency is higher or lower, the length of the subsequence, the distance between subsequences, the location of the subsequences, etc. See, U.S. Pat. Nos. 5,082,767, 8,126,653, 7,561,973, 8,401,798; U.S. Publ. No. US 20080046192, US 20080076161; Intl. Publ. No. WO2000018778; Welch et al. (2009) PLoS ONE 4(9): e7002; Gustafsson et al. (2012) Protein Expression and Purification 83: 37-46; Chung et al. (2012) BMC Systems Biology 6:134; all of which are incorporated herein by reference in their entireties.

d. Destabilizing Motif Substitution

There is a variety of motifs that can affect sequence optimization, which fall into various non-exclusive categories, for example:

(i) Primary sequence based motifs: Motifs defined by a simple arrangement of nucleotides.
(ii) Structural motifs: Motifs encoded by an arrangement of nucleotides that tends to form a certain secondary structure.
(iii) Local motifs: Motifs encoded in one contiguous subsequence.
(iv) Distributed motifs: Motifs encoded in two or more disjoint subsequences.
(v) Advantageous motifs: Motifs which improve nucleotide structure or function.
(vi) Disadvantageous motifs: Motifs with detrimental effects on nucleotide structure or function.

There are many motifs that fit into the category of disadvantageous motifs. Some examples include, for example, restriction enzyme motifs, which tend to be relatively short, exact sequences such as the restriction site motifs for Xba 1 (TCTAGA), EcoRI (GAATTC), EcoRII (CCWGG, wherein W means A or T, per the IUPAC ambiguity codes), or HindIII (AAGCTT); enzyme sites, which tend to be longer and based on consensus not exact sequence, such in the T7 RNA polymerase (GnnnnWnCRnCTCnCnnWnD, wherein n means any nucleotide, R means A or G, W means A or T, D means A or G or T but not C); structural motifs, such as GGGG repeats (Kim et al. (1991) Nature 351(6324):331-2); or other motifs such as CUG-triplet repeats (Querido et al. (2014) J. Cell Sci. 124:1703-1714).

Accordingly, the nucleic acid sequence encoding a GLA polypeptide disclosed herein can be sequence optimized using methods comprising substituting at least one destabilizing motif in a reference nucleic acid sequence, and removing such disadvantageous motif or replacing it with an advantageous motif.

In some embodiments, the optimization process comprises identifying advantageous and/or disadvantageous motifs in the reference nucleic sequence, wherein such motifs are, e.g., specific subsequences that can cause a loss of stability in the reference nucleic acid sequence prior or during the optimization process. For example, substitution of specific bases during optimization can generate a subsequence (motif) recognized by a restriction enzyme. Accordingly, during the optimization process the appearance of disadvantageous motifs can be monitored by comparing the sequence optimized sequence with a library of motifs known to be disadvantageous. Then, the identification of disadvantageous motifs could be used as a post-hoc filter, i.e., to determine whether a certain modification which potentially could be introduced in the reference nucleic acid sequence should be actually implemented or not.

In some embodiments, the identification of disadvantageous motifs can be used prior to the application of the sequence optimization methods disclosed herein, i.e., the identification of motifs in the reference nucleic acid sequence encoding a GLA polypeptide and their replacement with alternative nucleic acid sequences can be used as a preprocessing step, for example, before uridine reduction.

In other embodiments, the identification of disadvantageous motifs and their removal is used as an additional sequence optimization technique integrated in a multiparametric nucleic acid optimization method comprising two or more of the sequence optimization methods disclosed herein. When used in this fashion, a disadvantageous motif identified during the optimization process would be removed, for example, by substituting the lowest possible number of nucleobases in order to preserve as closely as possible the original design principle(s) (e.g., low U, high frequency, etc.). See, e.g., U.S. Publ. Nos. US20140228558, US20050032730, or US20140228558, which are herein incorporated by reference in their entireties.

e. Limited Codon Set Optimization

In some particular embodiments, sequence optimization of a reference nucleic acid sequence encoding a GLA polypeptide can be conducted using a limited codon set, e.g., a codon set wherein less than the native number of codons is used to encode the 20 natural amino acids, a subset of the 20 natural amino acids, or an expanded set of amino acids including, for example, non-natural amino acids.

The genetic code is highly similar among all organisms and can be expressed in a simple table with 64 entries which would encode the 20 standard amino acids involved in protein translation plus start and stop codons. The genetic code is degenerate, i.e., in general, more than one codon specifies each amino acid. For example, the amino acid leucine is specified by the UUA, UUG, CUU, CUC, CUA, or CUG codons, while the amino acid serine is specified by UCA, UCG, UCC, UCU, AGU, or AGC codons (difference in the first, second, or third position). Native genetic codes comprise 62 codons encoding naturally occurring amino acids. Thus, in some embodiments of the methods disclosed herein optimized codon sets (genetic codes) comprising less than 62 codons to encode 20 amino acids can comprise 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 30, 29, 28, 27, 26, 25, 24, 23, 22, 21, or 20 codons.

In some embodiments, the limited codon set comprises less than 20 codons. For example, if a protein contains less than 20 types of amino acids, such protein could be encoded by a codon set with less than 20 codons. Accordingly, in some embodiments, an optimized codon set comprises as many codons as different types of amino acids are present in the protein encoded by the reference nucleic acid sequence. In some embodiments, the optimized codon set comprises 19, 18, 17, 16, 15, 14, 13, 12, 11, 10, 9, 8, 7, 6, 5, 4, 3, 2 or even 1 codon.

In some embodiments, at least one amino acid selected from the group consisting of Ala, Arg, Asn, Asp, Cys, Gln, Glu, Gly, His, Ile, Leu, Lys, Phe, Pro, Ser, Thr, Tyr, and Val, i.e., amino acids which are naturally encoded by more than one codon, is encoded with less codons than the naturally occurring number of synonymous codons. For example, in some embodiments, Ala can be encoded in the sequence optimized nucleic acid by 3, 2 or 1 codons; Cys can be encoded in the sequence optimized nucleic acid by 1 codon; Asp can be encoded in the sequence optimized nucleic acid by 1 codon; Glu can be encoded in the sequence optimized nucleic acid by 1 codon; Phe can be encoded in the sequence optimized nucleic acid by 1 codon; Gly can be encoded in the sequence optimized nucleic acid by 3 codons, 2 codons or 1 codon; His can be encoded in the sequence optimized nucleic acid by 1 codon; Ile can be encoded in the sequence optimized nucleic acid by 2 codons or 1 codon; Lys can be encoded in the sequence optimized nucleic acid by 1 codon; Leu can be encoded in the sequence optimized nucleic acid by 5 codons, 4 codons, 3 codons, 2 codons or 1 codon; Asn can be encoded in the sequence optimized nucleic acid by 1 codon; Pro can be encoded in the sequence optimized nucleic acid by 3 codons, 2 codons, or 1 codon; Gln can be encoded in the sequence optimized nucleic acid by 1 codon; Arg can be encoded in the sequence optimized nucleic acid by 5 codons, 4 codons, 3 codons, 2 codons, or 1 codon; Ser can be encoded in the sequence optimized nucleic acid by 5 codons, 4 codons, 3 codons, 2 codons, or 1 codon; Thr can be encoded in the sequence optimized nucleic acid by 3 codons, 2 codons, or 1 codon; Val can be encoded in the sequence optimized nucleic acid by 3 codons, 2 codons, or 1 codon; and, Tyr can be encoded in the sequence optimized nucleic acid by 1 codon.

In some embodiments, at least one amino acid selected from the group consisting of Ala, Arg, Asn, Asp, Cys, Gln, Glu, Gly, His, Ile, Leu, Lys, Phe, Pro, Ser, Thr, Tyr, and Val, i.e., amino acids which are naturally encoded by more than one codon, is encoded by a single codon in the limited codon set.

In some specific embodiments, the sequence optimized nucleic acid is a DNA and the limited codon set consists of 20 codons, wherein each codon encodes one of 20 amino acids. In some embodiments, the sequence optimized nucleic acid is a DNA and the limited codon set comprises at least one codon selected from the group consisting of GCT, GCC, GCA, and GCG; at least a codon selected from the group consisting of CGT, CGC, CGA, CGG, AGA, and AGG; at least a codon selected from AAT or ACC; at least a codon selected from GAT or GAC; at least a codon selected from TGT or TGC; at least a codon selected from CAA or CAG; at least a codon selected from GAA or GAG; at least a codon selected from the group consisting of GGT, GGC, GGA, and GGG; at least a codon selected from CAT or CAC; at least a codon selected from the group consisting of ATT, ATC, and ATA; at least a codon selected from the group consisting of TTA, TTG, CTT, CTC, CTA, and CTG; at least a codon selected from AAA or AAG; an ATG codon; at least a codon selected from TTT or TTC; at least a codon selected from the group consisting of CCT, CCC, CCA, and CCG; at least a codon selected from the group consisting of TCT, TCC, TCA, TCG, AGT, and AGC; at least a codon selected from the group consisting of ACT, ACC, ACA, and ACG; a TGG codon; at least a codon selected from TAT or TAC; and, at least a codon selected from the group consisting of GTT, GTC, GTA, and GTG.

In other embodiments, the sequence optimized nucleic acid is an RNA (e.g., an mRNA) and the limited codon set consists of 20 codons, wherein each codon encodes one of 20 amino acids. In some embodiments, the sequence optimized nucleic acid is an RNA and the limited codon set comprises at least one codon selected from the group consisting of GCU, GCC, GCA, and GCG; at least a codon selected from the group consisting of CGU, CGC, CGA, CGG, AGA, and AGG; at least a codon selected from AAU or ACC; at least a codon selected from GAU or GAC; at least a codon selected from UGU or UGC; at least a codon selected from CAA or CAG; at least a codon selected from GAA or GAG; at least a codon selected from the group consisting of GGU, GGC, GGA, and GGG; at least a codon selected from CAU or CAC; at least a codon selected from the group consisting of AUU, AUC, and AUA; at least a codon selected from the group consisting of UUA, UUG, CUU, CUC, CUA, and CUG; at least a codon selected from AAA or AAG; an AUG codon; at least a codon selected from UUU or UUC; at least a codon selected from the group consisting of CCU, CCC, CCA, and CCG; at least a codon selected from the group consisting of UCU, UCC, UCA, UCG, AGU, and AGC; at least a codon selected from the group consisting of ACU, ACC, ACA, and ACG; a UGG codon; at least a codon selected from UAU or UAC; and, at least a codon selected from the group consisting of GUU, GUC, GUA, and GUG.

In some specific embodiments, the limited codon set has been optimized for in vivo expression of a sequence optimized nucleic acid (e.g., a synthetic mRNA) following administration to a certain tissue or cell.

In some embodiments, the optimized codon set (e.g., a 20 codon set encoding 20 amino acids) complies at least with one of the following properties:
(i) the optimized codon set has a higher average G/C content than the original or native codon set; or,
(ii) the optimized codon set has a lower average U content than the original or native codon set; or,
(iii) the optimized codon set is composed of codons with the highest frequency; or,
(iv) the optimized codon set is composed of codons with the lowest frequency; or,
(v) a combination thereof.

In some specific embodiments, at least one codon in the optimized codon set has the second highest, the third highest, the fourth highest, the fifth highest or the sixth highest frequency in the synonymous codon set. In some specific embodiments, at least one codon in the optimized codon has the second lowest, the third lowest, the fourth lowest, the fifth lowest, or the sixth lowest frequency in the synonymous codon set.

As used herein, the term "native codon set" refers to the codon set used natively by the source organism to encode the reference nucleic acid sequence. As used herein, the term "original codon set" refers to the codon set used to encode the reference nucleic acid sequence before the beginning of sequence optimization, or to a codon set used to encode an optimized variant of the reference nucleic acid sequence at the beginning of a new optimization iteration when sequence optimization is applied iteratively or recursively.

In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the highest frequency. In other embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the lowest frequency.

In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the highest uridine content. In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the lowest uridine content.

In some embodiments, the average G/C content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% higher than the average G/C content (absolute or relative) of the original codon set. In some embodiments, the average G/C content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% lower than the average G/C content (absolute or relative) of the original codon set.

In some embodiments, the uracil content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% higher than the average uracil content (absolute or relative) of the original codon set. In some embodiments, the uracil content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% lower than the average uracil content (absolute or relative) of the original codon set.

See also U.S. Appl. Publ. No. 2011/0082055, and Int'l. Publ. No. WO2000018778, both of which are incorporated herein by reference in their entireties.

8. Characterization of Sequence Optimized Nucleic Acids

In some embodiments of the invention, the polynucleotide (e.g., a RNA, e.g., an mRNA) comprising a sequence optimized nucleic acid disclosed herein encoding a GLA polypeptide can be tested to determine whether at least one nucleic acid sequence property (e.g., stability when exposed to nucleases) or expression property has been improved with respect to the non-sequence optimized nucleic acid.

As used herein, "expression property" refers to a property of a nucleic acid sequence either in vivo (e.g., translation efficacy of a synthetic mRNA after administration to a subject in need thereof) or in vitro (e.g., translation efficacy of a synthetic mRNA tested in an in vitro model system). Expression properties include but are not limited to the amount of protein produced by an mRNA encoding a GLA polypeptide after administration, and the amount of soluble or otherwise functional protein produced. In some embodiments, sequence optimized nucleic acids disclosed herein can be evaluated according to the viability of the cells expressing a protein encoded by a sequence optimized nucleic acid sequence (e.g., a RNA, e.g., an mRNA) encoding a GLA polypeptide disclosed herein.

In a particular embodiment, a plurality of sequence optimized nucleic acids disclosed herein (e.g., a RNA, e.g., an mRNA) containing codon substitutions with respect to the non-optimized reference nucleic acid sequence can be characterized functionally to measure a property of interest, for example an expression property in an in vitro model system, or in vivo in a target tissue or cell.

a. Optimization of Nucleic Acid Sequence Intrinsic Properties

In some embodiments of the invention, the desired property of the polynucleotide is an intrinsic property of the nucleic acid sequence. For example, the nucleotide sequence (e.g., a RNA, e.g., an mRNA) can be sequence optimized for in vivo or in vitro stability. In some embodiments, the nucleotide sequence can be sequence optimized for expression in a particular target tissue or cell. In some embodiments, the nucleic acid sequence is sequence optimized to increase its plasma half life by preventing its degradation by endo and exonucleases.

In other embodiments, the nucleic acid sequence is sequence optimized to increase its resistance to hydrolysis in solution, for example, to lengthen the time that the sequence optimized nucleic acid or a pharmaceutical composition comprising the sequence optimized nucleic acid can be stored under aqueous conditions with minimal degradation.

In other embodiments, the sequence optimized nucleic acid can be optimized to increase its resistance to hydrolysis in dry storage conditions, for example, to lengthen the time that the sequence optimized nucleic acid can be stored after lyophilization with minimal degradation.

b. Nucleic Acids Sequence Optimized for Protein Expression

In some embodiments of the invention, the desired property of the polynucleotide is the level of expression of a GLA polypeptide encoded by a sequence optimized sequence disclosed herein. Protein expression levels can be measured using one or more expression systems. In some embodiments, expression can be measured in cell culture systems, e.g., CHO cells or HEK293 cells. In some embodiments, expression can be measured using in vitro expression systems prepared from extracts of living cells, e.g., rabbit reticulocyte lysates, or in vitro expression systems prepared by assembly of purified individual components. In other embodiments, the protein expression is measured in an in vivo system, e.g., mouse, rabbit, monkey, etc.

In some embodiments, protein expression in solution form can be desirable. Accordingly, in some embodiments, a reference sequence can be sequence optimized to yield a sequence optimized nucleic acid sequence having optimized levels of expressed proteins in soluble form. Levels of protein expression and other properties such as solubility, levels of aggregation, and the presence of truncation products (i.e., fragments due to proteolysis, hydrolysis, or defective translation) can be measured according to methods known in the art, for example, using electrophoresis (e.g., native or SDS-PAGE) or chromatographic methods (e.g., HPLC, size exclusion chromatography, etc.).

c. Optimization of Target Tissue or Target Cell Viability

In some embodiments, the expression of heterologous therapeutic proteins encoded by a nucleic acid sequence can have deleterious effects in the target tissue or cell, reducing protein yield, or reducing the quality of the expressed product (e.g., due to the presence of protein fragments or precipitation of the expressed protein in inclusion bodies), or causing toxicity.

Accordingly, in some embodiments of the invention, the sequence optimization of a nucleic acid sequence disclosed herein, e.g., a nucleic acid sequence encoding a GLA polypeptide, can be used to increase the viability of target cells expressing the protein encoded by the sequence optimized nucleic acid.

Heterologous protein expression can also be deleterious to cells transfected with a nucleic acid sequence for autologous or heterologous transplantation. Accordingly, in some embodiments of the present disclosure the sequence optimization of a nucleic acid sequence disclosed herein can be used to increase the viability of target cells expressing the protein encoded by the sequence optimized nucleic acid sequence. Changes in cell or tissue viability, toxicity, and other physiological reaction can be measured according to methods known in the art.

d. Reduction of Immune and/or Inflammatory Response

In some cases, the administration of a sequence optimized nucleic acid encoding GLA polypeptide or a functional fragment thereof can trigger an immune response, which could be caused by (i) the therapeutic agent (e.g., an mRNA encoding a GLA polypeptide), or (ii) the expression product of such therapeutic agent (e.g., the GLA polypeptide encoded by the mRNA), or (iv) a combination thereof. Accordingly, in some embodiments of the present disclosure the sequence optimization of nucleic acid sequence (e.g., an mRNA) disclosed herein can be used to decrease an immune or inflammatory response triggered by the administration of a nucleic acid encoding a GLA polypeptide or by the expression product of GLA encoded by such nucleic acid.

In some aspects, an inflammatory response can be measured by detecting increased levels of one or more inflammatory cytokines using methods known in the art, e.g., ELISA. The term "inflammatory cytokine" refers to cytokines that are elevated in an inflammatory response. Examples of inflammatory cytokines include interleukin-6 (IL-6), CXCL1 (chemokine (C-X-C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL-12), interleukin-13 (11-13), interferon α (IFN-α), etc.

9. Modified Nucleotide Sequences Encoding GLA Polypeptides

In some embodiments, the polynucleotide (e.g., a RNA, e.g., an mRNA) of the invention comprises a chemically modified nucleobase, e.g., 5-methoxyuracil. In some embodiments, the mRNA is a uracil-modified sequence comprising an ORF encoding a GLA polypeptide, wherein the mRNA comprises a chemically modified nucleobase, e.g., 5-methoxyuracil.

In certain aspects of the invention, when the 5-methoxyuracil base is connected to a ribose sugar, as it is in polynucleotides, the resulting modified nucleoside or nucleotide is referred to as 5-methoxyuridine. In some embodiments, uracil in the polynucleotide is at least about 25%, at least about 30%, at least about 40%, at least about 50%, at least about 60%, at least about 70%, at least about 80%, at least 90%, at least 95%, at least 99%, or about 100% 5-methoxyuracil. In one embodiment, uracil in the polynucleotide is at least 95% 5-methoxyuracil. In another embodiment, uracil in the polynucleotide is 100% 5-methoxyuracil.

In embodiments where uracil in the polynucleotide is at least 95% 5-methoxyuracil, overall uracil content can be adjusted such that an mRNA provides suitable protein expression levels while inducing little to no immune response. In some embodiments, the uracil content of the ORF is between about 110% and about 150%, about 115% and about 150%, about 120% and about 150%, about 110% and about 145%, about 115% and about 145%, about 120% and about 145%, about 110% and about 140%, about 115% and about 140%, or about 120% and about 140% of the theoretical minimum uracil content in the corresponding wild-type ORF (% $U_{TM}$). In other embodiments, the uracil content of the ORF is between about 120% and about 143% or between 123% and 138% of the % UTM. In some embodiments, the uracil content of the ORF encoding a GLA polypeptide is about 120%, about 125%, about 130%, about 135%, or about 140% of the % $U_{TM}$. In this context, the term "uracil" can refer to 5-methoxyuracil and/or naturally occurring uracil.

In some embodiments, the uracil content in the ORF of the mRNA encoding a GLA polypeptide of the invention is less than about 50%, about 40%, about 30%, or about 20% of the total nucleobase content in the ORF. In some embodiments, the uracil content in the ORF is between about 12% and about 26% of the total nucleobase content in the ORF. In other embodiments, the uracil content in the ORF is between about 16% and about 18% of the total nucleobase content in the ORF. In one embodiment, the uracil content in the ORF of the mRNA encoding a GLA polypeptide is less than about 26% of the total nucleobase content in the open reading frame. In this context, the term "uracil" can refer to 5-methoxyuracil and/or naturally occurring uracil.

In further embodiments, the ORF of the mRNA encoding a GLA polypeptide having 5-methoxyuracil and adjusted uracil content has increased Cytosine (C), Guanine (G), or Guanine/Cytosine (G/C) content (absolute or relative). In some embodiments, the overall increase in C, G, or G/C content (absolute or relative) of the ORF is at least about 2%, at least about 3%, at least about 4%, at least about 5%, at least about 6%, at least about 7%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the wild-type ORF. In some embodiments, the G, the C, or the G/C content in the ORF is less than about 100%, less than about 95%, less than about 90%, less than about 85%, less than about 80%, or less than about 75% of the theoretical maximum G, C, or G/C content of the corresponding wild type nucleotide sequence encoding the GLA polypeptide (% $G_{TMX}$; % $C_{TMX}$, or % $G/C_{TMX}$). In other embodiments, the G, the C, or the G/C content in the ORF is between about 72% and about 80%, about 70% and about 76%, or about 91% and about 95% of the % $G_{TMX}$, % $Cm_{TMX}$, or % $G/C_{TMX}$, respectively. In some embodiments, the increases in G and/or C content (absolute or relative) described herein can be conducted by replacing synonymous codons with low G, C, or G/C content with synonymous codons having higher G, C, or G/C content. In other embodiments, the increase in G and/or C content (absolute or relative) is conducted by replacing a codon ending with U with a synonymous codon ending with G or C.

In further embodiments, the ORF of the mRNA encoding a GLA polypeptide of the invention comprises 5-methoxyuracil and has an adjusted uracil content containing less uracil pairs (UU) and/or uracil triplets (UUU) and/or uracil quadruplets (UUUU) than the corresponding wild-type nucleotide sequence encoding the GLA polypeptide. In some embodiments, the ORF of the mRNA encoding a GLA polypeptide of the invention contains no uracil pairs and/or uracil triplets and/or uracil quadruplets. In some embodiments, uracil pairs and/or uracil triplets and/or uracil quadruplets are reduced below a certain threshold, e.g., no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 34, 35, 36, 37, 38, 39, 40, 41, 42, 43, 44, 45, 46, 47, 48, 49, 50, or 51 occurrences in the ORF of the mRNA encoding the GLA polypeptide. In a particular embodiment, the ORF of the mRNA encoding the GLA polypeptide of the invention contains less than 40, 39, 38, 37, 36, 35, 34, 33, 32, 31, 39, 29, 28, 27, 26, 25, 24, 23, 22, 21, 20, 19, 18, 17, 16, 15, 14, 13, 12, 11, 10, 9, 8, 7, 6, 5, 4, 3, 2, or 1 non-phenylalanine uracil pairs and/or triplets. In another embodiment, the ORF of the mRNA encoding the GLA polypeptide contains no non-phenylalanine uracil pairs and/or triplets.

In further embodiments, the ORF of the mRNA encoding a GLA polypeptide of the invention comprises 5-methoxyuracil and has an adjusted uracil content containing less uracil-rich clusters than the corresponding wild-type nucleotide sequence encoding the GLA polypeptide. In some embodiments, the ORF of the mRNA encoding the GLA polypeptide of the invention contains uracil-rich clusters that are shorter in length than corresponding uracil-rich clusters in the corresponding wild-type nucleotide sequence encoding the GLA polypeptide.

In further embodiments, alternative lower frequency codons are employed. At least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the GLA polypeptide-encoding ORF of the 5-methoxyuracil-comprising mRNA are substituted with alternative codons, each alternative codon having a codon frequency lower than the codon frequency of the substituted codon in the synonymous codon set. The ORF also has adjusted uracil content, as described above. In some embodiments, at least one codon in the ORF of the mRNA encoding the GLA polypeptide is substituted with an alternative codon having a codon frequency lower than the codon frequency of the substituted codon in the synonymous codon set.

In some embodiments, the adjusted uracil content, GLA polypeptide-encoding ORF of the 5-methoxyuracil-comprising mRNA exhibits expression levels of GLA when administered to a mammalian cell that are higher than expression levels of GLA from the corresponding wild-type mRNA. In other embodiments, the expression levels of GLA when administered to a mammalian cell are increased relative to a corresponding mRNA containing at least 95% 5-methoxyuracil and having a uracil content of about 160%, about 170%, about 180%, about 190%, or about 200% of the theoretical minimum. In yet other embodiments, the expression levels of GLA when administered to a mammalian cell are increased relative to a corresponding mRNA, wherein at least about 50%, at least about 60%, at least about 70%, at least about 80%, at least about 90%, or about 100% of uracils are 1-methylpseudouracil or pseudouracils. In some embodiments, the mammalian cell is a mouse cell, a rat cell, or a rabbit cell. In other embodiments, the mammalian cell is a monkey cell or a human cell. In some embodiments, the human cell is a HeLa cell, a BJ fibroblast cell, or a peripheral blood mononuclear cell (PBMC). In some embodiments, GLA is expressed when the mRNA is administered to a mammalian cell in vivo. In some embodiments, the mRNA is administered to mice, rabbits, rats, monkeys, or humans. In one embodiment, mice are null mice. In some embodiments, the mRNA is administered to mice in an amount of about 0.01 mg/kg, about 0.05 mg/kg, about 0.1 mg/kg, or about 0.15 mg/kg. In some embodiments, the mRNA is administered intravenously or intramuscularly. In other embodiments, the GLA polypeptide is expressed when the mRNA is administered to a mammalian cell in vitro. In some embodiments, the expression is increased by at least about 2-fold, at least about 5-fold, at least about 10-fold, at least about 50-fold, at least about 500-fold, at least about 1500-fold, or at least about 3000-fold. In other embodiments, the expression is increased by at least about 10%, about 20%, about 30%, about 40%, about 50%, 60%, about 70%, about 80%, about 90%, or about 100%.

In some embodiments, adjusted uracil content, GLA polypeptide-encoding ORF of the 5-methoxyuracil-comprising mRNA exhibits increased stability. In some embodiments, the mRNA exhibits increased stability in a cell relative to the stability of a corresponding wild-type mRNA under the same conditions. In some embodiments, the mRNA exhibits increased stability including resistance to nucleases, thermal stability, and/or increased stabilization of secondary structure. In some embodiments, increased stability exhibited by the mRNA is measured by determining the half-life of the mRNA (e.g., in a plasma, cell, or tissue sample) and/or determining the area under the curve (AUC) of the protein expression by the mRNA over time (e.g., in vitro or in vivo). An mRNA is identified as having increased stability if the half-life and/or the AUC is greater than the half-life and/or the AUC of a corresponding wild-type mRNA under the same conditions.

In some embodiments, the mRNA of the present invention induces a detectably lower immune response (e.g., innate or acquired) relative to the immune response induced by a corresponding wild-type mRNA under the same conditions. In other embodiments, the mRNA of the present disclosure induces a detectably lower immune response (e.g., innate or acquired) relative to the immune response induced by an mRNA that encodes for a GLA polypeptide but does not comprise 5-methoxyuracil under the same conditions, or relative to the immune response induced by an mRNA that encodes for a GLA polypeptide and that comprises 5-methoxyuracil but that does not have adjusted uracil content under the same conditions. The innate immune response can be manifested by increased expression of pro-inflammatory cytokines, activation of intracellular PRRs (RIG-I, MDA5, etc.), cell death, and/or termination or reduction in protein translation. In some embodiments, a reduction in the innate immune response can be measured by expression or activity level of Type 1 interferons (e.g., IFN-α, IFN-β, IFN-κ, IFN-δ, IFN-ε, IFN-τ, IFN-ω, and IFN-ζ) or the expression of interferon-regulated genes such as the toll-like receptors (e.g., TLR7 and TLR8), and/or by decreased cell death following one or more administrations of the mRNA of the invention into a cell.

In some embodiments, the expression of Type-1 interferons by a mammalian cell in response to the mRNA of the present disclosure is reduced by at least 10%, 20%, 30%, 40%, 50%, 60%, 70%, 80%, 90%, 95%, 99%, 99.9%, or greater than 99.9% relative to a corresponding wild-type mRNA, to an mRNA that encodes a GLA polypeptide but does not comprise 5-methoxyuracil, or to an mRNA that encodes a GLA polypeptide and that comprises 5-methoxyuracil but that does not have adjusted uracil content. In some embodiments, the interferon is IFN-β. In some embodiments, cell death frequency caused by administration of mRNA of the present disclosure to a mammalian cell is 10%, 25%, 50%, 75%, 85%, 90%, 95%, or over 95% less than the cell death frequency observed with a corresponding wild-type mRNA, an mRNA that encodes for a GLA polypeptide but does not comprise 5-methoxyuracil, or an mRNA that encodes for a GLA polypeptide and that comprises 5-methoxyuracil but that does not have adjusted uracil content. In some embodiments, the mammalian cell is a BJ fibroblast cell. In other embodiments, the mammalian cell is a splenocyte. In some embodiments, the mammalian cell is that of a mouse or a rat. In other embodiments, the mammalian cell is that of a human. In one embodiment, the mRNA of the present disclosure does not substantially induce an innate immune response of a mammalian cell into which the mRNA is introduced.

In some embodiments, the polynucleotide is an mRNA that comprises an ORF that encodes a GLA polypeptide, wherein uracil in the mRNA is at least about 95% 5-methoxyuracil, wherein the uracil content of the ORF is between about 120% and about 140% of the theoretical minimum uracil content in the corresponding wild-type ORF, and wherein the uracil content in the ORF encoding the GLA polypeptide is less than about 26% of the total nucleobase content in the ORF. In some embodiments, the ORF that encodes the GLA polypeptide is further modified to increase G/C content of the ORF (absolute or relative) by at least about 40%, as compared to the corresponding wild-type ORF. In yet other embodiments, the ORF encoding the GLA polypeptide contains less than 20 non-phenylalanine uracil pairs and/or triplets. In some embodiments, at least one codon in the ORF of the mRNA encoding the GLA polypeptide is further substituted with an alternative codon having a codon frequency lower than the codon frequency of the substituted codon in the synonymous codon set. In some embodiments, the expression of the GLA polypeptide encoded by an mRNA comprising an ORF wherein uracil in the mRNA is at least about 95% 5-methoxyuracil, and wherein the uracil content of the ORF is between about 120% and about 140% of the theoretical minimum uracil content in the corresponding wild-type ORF, is increased by at least about 10-fold when compared to expression of the GLA polypeptide from the corresponding wild-type mRNA. In some embodiments, the mRNA comprises an open ORF wherein uracil in the mRNA is at least about 95% 5-methoxyuracil, and wherein the uracil content of the ORF is between about 120% and about 140% of the theoretical minimum uracil content in the corresponding wild-type ORF, and wherein the mRNA does not substantially induce an innate immune response of a mammalian cell into which the mRNA is introduced.

10. Methods for Modifying Polynucleotides

The invention includes modified polynucleotides comprising a polynucleotide described herein (e.g., a polynucleotide, e.g., mRNA, comprising a nucleotide sequence encoding a GLA polypeptide). The modified polynucleotides can be chemically modified and/or structurally modified. When the polynucleotides of the present invention are chemically and/or structurally modified the polynucleotides can be referred to as "modified polynucleotides."

The present disclosure provides for modified nucleosides and nucleotides of a polynucleotide (e.g., RNA polynucleotides, such as mRNA polynucleotides) encoding a GLA polypeptide. A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside including a phosphate group. Modified nucleotides can by synthesized by any useful method, such as, for example, chemically, enzymatically, or recombinantly, to include one or more modified or non-natural nucleosides. Polynucleotides can comprise a region or regions of linked nucleosides. Such regions can have variable backbone linkages. The linkages can be standard phosphodiester linkages, in which case the polynucleotides would comprise regions of nucleotides.

The modified polynucleotides disclosed herein can comprise various distinct modifications. In some embodiments, the modified polynucleotides contain one, two, or more (optionally different) nucleoside or nucleotide modifications. In some embodiments, a modified polynucleotide, introduced to a cell can exhibit one or more desirable properties, e.g., improved protein expression, reduced immunogenicity, or reduced degradation in the cell, as compared to an unmodified polynucleotide.

a. Structural Modifications

In some embodiments, a polynucleotide of the present invention (e.g., a polynucleotide comprising a nucleotide sequence encoding a GLA polypeptide) is structurally modified. As used herein, a "structural" modification is one in which two or more linked nucleosides are inserted, deleted, duplicated, inverted or randomized in a polynucleotide without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" can be chemically modified to "AT-5meC-G". The same polynucleotide can be structurally modified from "ATCG" to "ATCCCG". Here, the dinucleotide "CC" has been inserted, resulting in a structural modification to the polynucleotide.

b. Chemical Modifications

In some embodiments, the polynucleotides of the present invention are chemically modified. As used herein in reference to a polynucleotide, the terms "chemical modification" or, as appropriate, "chemically modified" refer to modification with respect to adenosine (A), guanosine (G), uridine (U), thymidine (T) or cytidine (C) ribo- or deoxyribonucleosides in one or more of their position, pattern, percent or population. Generally, herein, these terms are not intended to refer to the ribonucleotide modifications in naturally occurring 5'-terminal mRNA cap moieties.

In some embodiments, the polynucleotides of the present invention can have a uniform chemical modification of all or any of the same nucleoside type or a population of modifications produced by mere downward titration of the same starting modification in all or any of the same nucleoside type, or a measured percent of a chemical modification of all any of the same nucleoside type but with random incorporation, such as where all uridines are replaced by a uridine analog, e.g., pseudouridine or 5-methoxyuridine. In another embodiment, the polynucleotides can have a uniform chemical modification of two, three, or four of the same nucleoside type throughout the entire polynucleotide (such as all uridines and all cytosines, etc. are modified in the same way).

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil. Any combination of base/sugar or linker may be incorporated into polynucleotides of the present disclosure.

The skilled artisan will appreciate that, except where otherwise noted, polynucleotide sequences set forth in the instant application will recite "T"s in a representative DNA sequence but where the sequence represents RNA, the "T"s would be substituted for "U"s.

Modifications of polynucleotides (e.g., RNA polynucleotides, such as mRNA polynucleotides) that are useful in the compositions, methods and synthetic processes of the present disclosure include, but are not limited to the following nucleotides, nucleosides, and nucleobases: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyl adenosine; N6-threonylcarbamoyladenosine; 1,2'-O-dimethyl adenosine; 1-methyladenosine; 2'-O-methyladenosine; 2'-O-ribosyladenosine (phosphate); 2-methyl adenosine; 2-methylthio-N6 isopentenyladenosine; 2-methylthio-N6-hydroxynorvalyl carbamoyl adenosine; 2'-O-methyladenosine; 2'-O-ribosyladenosine (phosphate); Isopentenyladenosine; N6-(cis-hydroxyisopentenyl)adenosine; N6,2'-O-dimethyl adenosine; N6,2'-O-dimethyladenosine; N6,N6,2'-O-trimethyladenosine; N6,N6-dimethyl adenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6, N6 (dimethyl)adenine; N6-cis-hydroxy-isopentenyl-adenosine; α-thio-adenosine; 2

(amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo)adenine; 2-(halo)adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methyl cytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl)cytosine; 5-(alkynyl)cytosine; 5-(halo)cytosine; 5-(propynyl)cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynyl cytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azidocytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thioguanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-(alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deaza-guanosine TP; N2-isobutyl-guanosine TP; 1-methylinosine; Inosine; dimethylinosine; 2'-O-methylinosine; 7-methyl-inosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl) pseudouridine; 1-methylpseudouridine; 1-ethyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methyluridine,), 5-methoxyuridine; 5-methyl-2-thiouridine; 5-methyl aminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uracil; N1-ethyl-pseudo-uracil; uridine 5-oxyacetic acid; uridine 5-oxyacetic acid methyl ester; 3-(3-Amino-3-carboxypropyl)-Uridine TP; 5-(i so-Pentenylaminomethyl)-2-thiouridine TP; 5-(iso-Pentenylaminomethyl)-2'-O-methyluridine TP; 5-(iso-Pentenylaminomethyl)uridine T P; 5-propynyl uracil; α-thio-uridine; 1 (aminoalkylamino-carbonylethylenyl)-2(thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio) pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl)pseudo-UTP; 1-Methyl-pseudo-UTP; 1-Ethyl-pseudo-UTP; 2 (thio) pseudouracil; 2' deoxy uridine; 2' fluorouridine; 2-(thio) uracil; 2,4-(dithio)psuedouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl)uracil; 4 (thio)pseudouracil; 4-(thio) pseudouracil; 4-(thio)uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio)uracil; 5 (methylaminomethyl)-4 (thio)uracil; 5 (propynyl)uracil; 5 (trifluoromethyl)uracil; 5-(2-aminopropyl)uracil; 5-(alkyl)-2-(thio) pseudouracil; 5-(alkyl)-2,4 (dithio)pseudouracil; 5-(alkyl)-4 (thio)pseudouracil; 5-(alkyl)pseudouracil; 5-(alkyl)uracil; 5-(alkynyl)uracil; 5-(allylamino)uracil; 5-(cyanoalkyl)uracil; 5-(dialkylaminoalkyl)uracil; 5-(dimethylaminoalkyl) uracil; 5-(guanidiniumalkyl)uracil; 5-(halo)uracil; 5-(1,3-diazole-1-alkyl)uracil; 5-(methoxy)uracil; 5-(methoxycarbonylmethyl)-2-(thio)uracil; 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio)uracil; 5-(methylaminomethyl)-4-(thio) uracil; 5-(propynyl)uracil; 5-(trifluoromethyl)uracil; 5-aminoallyl-uridine; 5-bromouridine; 5-iodo-uridine; 5-uracil; 6 (azo)uracil; 6-(azo)uracil; 6-aza-uridine; allyamino-uracil; aza uracil; deaza uracil; N3 (methyl)uracil; Pseudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1-(2-Hydroxypropyl)pseudouridine TP; (2R)-1-(2-Hydroxypropyl)pseudouridine TP; (2 S)-1-(2-Hydroxypropyl) pseudouridine TP; (E)-5-(2-Bromo-vinyl)ara-uridine TP; (E)-5-(2-Bromo-vinyl)uridine TP; (Z)-5-(2-Bromo-vinyl) ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl) pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP; 1-(3,4-Bis-trifluoromethoxybenzyl)pseudouridine TP; 1-(3, 4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carb oxybutyl)p s eudo-UTP; i-(4-Amino-benzyl) pseudo-UTP; 1-(4-Amino-butyl)pseudo-UTP; 1-(4-Amino-phenyl)pseudo-UTP; 1-(4-Azidobenzyl)pseudouridine TP; 1-(4-Bromobenzyl)pseudouridine TP; 1-(4-Chlorobenzyl) pseudouridine TP; 1-(4-Fluorobenzyl)pseudouridine TP; 1-(4-Iodobenzyl)pseudouridine TP; 1-(4-Methanesulfonyl-benzyl)pseudouridine TP; 1-(4-Methoxybenzyl)pseudouridine TP; 1-(4-Methoxy-benzyl)pseudo-UTP; 1-(4-Methoxy-phenyl)pseudo-UTP; 1-(4-Methylbenzyl)pseudouridine TP; 1-(4-Methyl-benzyl)pseudo-UTP; 1-(4-Nitrobenzyl) pseudouridine TP; 1-(4-Nitro-benzyl)pseudo-UTP; 1(4-Nitro-phenyl)pseudo-UTP; 1-(4-Thiomethoxybenzyl) pseudouridine TP; 1-(4-Trifluoromethoxybenzyl) pseudouridine TP; 1-(4-Trifluoromethylbenzyl) pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl}pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP;

1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy)-ethoxy}-ethoxy]-ethoxy)-ethoxy}]propionic acid; Pseudouridine TP 1-[3-{2-(2-(2-ethoxy)-ethoxy}]propionic acid; Pseudouridine TP 1-[3-{2-(2-ethoxy)-ethoxy}] propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'flurocytidine; 2' methyl, 2'amino, 2'azido, 2'fluro-adenine; 2'methyl, 2'amino, 2'azido, 2'fluro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; O6-substituted purines; 0-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3- yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl, pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, the polynucleotide (e.g., RNA polynucleotide, such as mRNA polynucleotide) includes a combination of at least two (e.g., 2, 3, 4 or more) of the aforementioned modified nucleobases.

In some embodiments, the mRNA comprises at least one chemically modified nucleoside. In some embodiments, the at least one chemically modified nucleoside is selected from the group consisting of pseudouridine (ψ), 2-thiouridine (s2U), 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (m1ψ), 1-ethyl-pseudouridine (e1ψ), 5-methoxy-uridine (mo5U), 5-methyl-cytidine (m5C), α-thio-guanosine, α-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methylinosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, 2,8-dimethyladenosine, 2-geranylthiouridine, 2-lysidine, 2-selenouridine, 3-(3-amino-3-carboxypropyl)-5,6-dihydrouridine, 3-(3-amino-3-carboxypropyl)pseudouridine, 3-methylpseudouridine, 5-(carboxyhydroxymethyl)-2'-O-methyluridine methyl ester, 5-aminomethyl-2-geranylthiouridine, 5-aminomethyl-2-selenouridine, 5-aminomethyluridine, 5-carbamoylhydroxymethyluridine, 5-carbamoylmethyl-2-thiouridine, 5-carboxymethyl-2-thiouridine, 5-carboxymethylaminomethyl-2-geranylthiouridine, 5-carboxymethylaminomethyl-2-selenouridine, 5-cyanomethyluridine, 5-hydroxycytidine, 5-methylaminomethyl-2-geranylthiouridine, 7-aminocarboxypropyl-demethylwyosine, 7-aminocarboxypropylwyosine, 7-aminocarboxypropylwyosine methyl ester, 8-methyladenosine, N4,N4-dimethylcytidine, N6-formyladenosine, N6-hydroxymethyladenosine, agmatidine, cyclic N6-threonylcarbamoyladenosine, glutamylqueuosine, methylated undermodified hydroxywybutosine, N4,N4,2'-O-trimethylcytidine, geranylated 5-methylaminomethyl-2-thiouridine, geranylated 5-carboxymethylaminomethyl-2-thiouridine, Qbase, preQ0base, preQ1base, and two or more combinations thereof. In some embodiments, the at least one chemically modified nucleoside is selected from the group consisting of pseudouridine, 1-methyl-pseudouridine, 1-ethyl-pseudouridine, 5-methylcytosine, 5-methoxyuridine, and a combination thereof. In some embodiments, the polynucleotide (e.g., RNA polynucleotide, such as mRNA polynucleotide) includes a combination of at least two (e.g., 2, 3, 4 or more) of the aforementioned modified nucleobases.

(i) Base Modifications

In certain embodiments, the chemical modification is at nucleobases in the polynucleotides (e.g., RNA polynucleotide, such as mRNA polynucleotide). In some embodiments, modified nucleobases in the polynucleotide (e.g., RNA polynucleotide, such as mRNA polynucleotide) are selected from the group consisting of 1-methyl-pseudouridine (m1ψ), 1-ethyl-pseudouridine (e1ψ), 5-methoxy-uridine (mo5U), 5-methyl-cytidine (m5C), pseudouridine (ψ), α-thio-guanosine and α-thio-adenosine. In some embodiments, the polynucleotide includes a combination of at least two (e.g., 2, 3, 4 or more) of the aforementioned modified nucleobases.

In some embodiments, the polynucleotide (e.g., RNA polynucleotide, such as mRNA polynucleotide) comprises pseudouridine (ψ) and 5-methyl-cytidine (m5C). In some embodiments, the polynucleotide (e.g., RNA polynucleotide, such as mRNA polynucleotide) comprises 1-methyl-pseudouridine (m1ψ). In some embodiments, the polynucleotide (e.g., RNA polynucleotide, such as mRNA polynucleotide) comprises 1-ethyl-pseudouridine (e1ψ). In some embodiments, the polynucleotide (e.g., RNA polynucleotide, such as mRNA polynucleotide) comprises 1-methyl-pseudouridine (m1ψ) and 5-methyl-cytidine (m5C). In some embodiments, the polynucleotide (e.g., RNA polynucleotide, such as mRNA polynucleotide) comprises 1-ethyl-pseudouridine (e1ψ) and 5-methyl-cytidine (m5C). In some embodiments, the polynucleotide (e.g., RNA polynucleotide, such as mRNA polynucleotide) comprises 2-thiouridine (s2U). In some embodiments, the polynucleotide (e.g., RNA polynucleotide, such as mRNA polynucleotide) comprises 2-thiouridine and 5-methyl-cytidine (m5C). In some embodiments, the polynucleotide (e.g., RNA polynucleotide, such as mRNA polynucleotide) comprises methoxy-uridine (mo5U). In some embodiments, the polynucleotide (e.g., RNA polynucleotide, such as mRNA polynucleotide) comprises 5-methoxy-uridine (mo5U) and 5-methyl-cytidine (m5C). In some embodiments, the polynucleotide (e.g., RNA polynucleotide, such as mRNA polynucleotide) comprises 2'-O-methyl uridine. In some embodiments, the polynucleotide (e.g., RNA polynucleotide, such as mRNA polynucleotide) comprises 2'-O-methyl uridine and 5-methyl-cytidine (m5C). In some embodiments, the polynucleotide (e.g., RNA polynucleotide, such as mRNA polynucleotide) comprises N6-methyl-adenosine (m6A). In some embodiments, the polynucleotide (e.g., RNA polynucleotide, such as mRNA polynucleotide) comprises N6-methyl-adenosine (m6A) and 5-methyl-cytidine (m5C).

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methyl-cytidine (m5C), meaning that all cytosine residues in the mRNA sequence are replaced with 5-methyl-cytidine (m5C). Similarly, a polynucleotide can be uniformly modified for any type of nucleoside residue present in the sequence by replacement with a modified residue such as any of those set forth above.

In some embodiments, the chemically modified nucleosides in the open reading frame are selected from the group consisting of uridine, adenine, cytosine, guanine, and any combination thereof.

In some embodiments, the modified nucleobase is a modified cytosine. Examples of nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethylcytidine (hm5C), 1-methyl-pseudoisocytidine, 2-thio-cytidine (s2C), 2-thio-5-methyl-cytidine.

In some embodiments, a modified nucleobase is a modified uridine. Example nucleobases and nucleosides having a modified uridine include 5-cyano uridine or 4'-thio uridine.

In some embodiments, a modified nucleobase is a modified adenine. Example nucleobases and nucleosides having a modified adenine include 7-deaza-adenine, 1-methyl-adenosine (m1A), 2-methyl-adenine (m2A), N6-methyl-adenine (m6A), and 2,6-Diaminopurine.

In some embodiments, a modified nucleobase is a modified guanine. Example nucleobases and nucleosides having a modified guanine include inosine (I), 1-methylinosine (m1I), wyosine (imG), methylwyosine (mimG), 7-deaza-guanosine, 7-cyano-7-deaza-guanosine (preQO), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

In some embodiments, the nucleobase modified nucleotides in the polynucleotide (e.g., RNA polynucleotide, such as mRNA polynucleotide) are 5-methoxyuridine.

In some embodiments, the polynucleotide (e.g., RNA polynucleotide, such as mRNA polynucleotide) includes a combination of at least two (e.g., 2, 3, 4 or more) of modified nucleobases.

In some embodiments, at least 95% of a type of nucleobases (e.g., uracil) in a polynucleotide of the invention (e.g., an mRNA polynucleotide encoding GLA) are modified nucleobases. In some embodiments, at least 95% of uracil in a polynucleotide of the present invention (e.g., an mRNA polynucleotide encoding GLA) is 5-methoxyuracil.

In some embodiments, the polynucleotide (e.g., RNA polynucleotide, such as mRNA polynucleotide) comprises 5-methoxyuridine (5mo5U) and 5-methyl-cytidine (m5C).

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methoxyuridine, meaning that substantially all uridine residues in the mRNA sequence are replaced with 5-methoxyuridine. Similarly, a polynucleotide can be uniformly modified for any type of nucleoside residue present in the sequence by replacement with a modified residue such as any of those set forth above.

In some embodiments, the modified nucleobase is a modified cytosine.

In some embodiments, a modified nucleobase is a modified uracil. Example nucleobases and nucleosides having a modified uracil include 5-methoxyuracil.

In some embodiments, a modified nucleobase is a modified adenine.

In some embodiments, a modified nucleobase is a modified guanine.

In some embodiments, the nucleobases, sugar, backbone, or any combination thereof in the open reading frame encoding a GLA polypeptide are chemically modified by at least 10%, at least 20%, at least 30%, at least 40%, at least 50%, at least 60%, at least 70%, at least 80%, at least 90%, at least 95%, at least 99%, or 100%.

In some embodiments, the uridine nucleosides in the open reading frame encoding a GLA polypeptide are chemically modified by at least 10%, at least 20%, at least 30%, at least 40%, at least 50%, at least 60%, at least 70%, at least 80%, at least 90%, at least 95%, at least 99%, or 100%.

In some embodiments, the adenosine nucleosides in the open reading frame encoding a GLA polypeptide are chemically modified by at least 10%, at least 20%, at least 30%, at least 40%, at least 50%, at least 60%, at least 70%, at least 80%, at least 90%, at least 95%, at least 99%, or 100%.

In some embodiments, the cytidine nucleosides in the open reading frame encoding a GLA polypeptide are chemically modified by at least at least 10%, at least 20%, at least 30%, at least 40%, at least 50%, at least 60%, at least 70%, at least 80%, at least 90%, at least 95%, at least 99%, or 100%.

In some embodiments, the guanosine nucleosides in the open reading frame encoding a GLA polypeptide are chemically modified by at least at least 10%, at least 20%, at least 30%, at least 40%, at least 50%, at least 60%, at least 70%, at least 80%, at least 90%, at least 95%, at least 99%, or 100%.

In some embodiments, the polynucleotides can include any useful linker between the nucleosides. Such linkers, including backbone modifications, that are useful in the composition of the present disclosure include, but are not limited to the following: 3'-alkylene phosphonates, 3'-amino phosphoramidate, alkene containing backbones, aminoalkylphosphoramidates, aminoalkylphosphotriesters, boranophosphates, —$CH_2$—O—N($CH_3$)—$CH_2$—, —$CH_2$—N($CH_3$)—N($CH_3$)—$CH_2$—, —$CH_2$—NH—$CH_2$—, chiral phosphonates, chiral phosphorothioates, formacetyl and thioformacetyl backbones, methylene (methylimino), methylene formacetyl and thioformacetyl backbones, methyleneimino and methylenehydrazino backbones, morpholino linkages, —N($CH_3$)—$CH_2$—$CH_2$—, oligonucleosides with heteroatom internucleoside linkage, phosphinates, phosphoramidates, phosphorodithioates, phosphorothioate internucleoside linkages, phosphorothioates, phosphotriesters, PNA, siloxane backbones, sulfamate backbones, sulfide sulfoxide and sulfone backbones, sulfonate and sulfonamide backbones, thionoalkylphosphonates, thionoalkylphosphotriesters, and thionophosphoramidates.

(ii) Sugar Modifications

The modified nucleosides and nucleotides (e.g., building block molecules), which can be incorporated into a polynucleotide (e.g., RNA or mRNA, as described herein), can be modified on the sugar of the ribonucleic acid. For example, the 2' hydroxyl group (OH) can be modified or replaced with a number of different substituents. Exemplary substitutions at the 2'-position include, but are not limited to, H, halo, optionally substituted $C_{1-6}$ alkyl; optionally substituted $C_{1-6}$ alkoxy; optionally substituted $C_{6-10}$ aryloxy; optionally substituted $C_{3-8}$ cycloalkyl; optionally substituted $C_{3-8}$ cycloalkoxy; optionally substituted $C_{6-10}$ aryloxy; optionally substituted $C_{6-10}$ aryl-$C_{1-10}$ alkoxy, optionally substituted $C_{1-12}$ (heterocyclyl)oxy; a sugar (e.g., ribose, pentose, or any described herein); a polyethyleneglycol (PEG), —O($CH_2CH_2O$)$_n CH_2CH_2OR$, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxyl is connected by a $C_{1-6}$ alkylene or $C_{1-6}$ heteroalkylene bridge to the 4'-carbon of the same ribose sugar, where exemplary bridges included methylene, propylene, ether, or amino bridges; aminoalkyl, as defined herein;

aminoalkoxy, as defined herein; amino as defined herein; and amino acid, as defined herein Generally, RNA includes the sugar group ribose, which is a 5-membered ring having an oxygen. Exemplary, non-limiting modified nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone); multicyclic forms (e.g., tricyclo; and "unlocked" forms, such as glycol nucleic acid (GNA) (e.g., R-GNA or S-GNA, where ribose is replaced by glycol units attached to phosphodiester bonds); threose nucleic acid (TNA, where ribose is replace with α-L-threofuranosyl-(3'→2)), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar. Such sugar modifications are taught International Patent Publication Nos. WO2013052523 and WO2014093924, the contents of each of which are incorporated herein by reference in their entireties.

(iii) Combinations of Modifications

The polynucleotides of the invention (e.g., a polynucleotide comprising a nucleotide sequence encoding a GLA polypeptide or a functional fragment or variant thereof) can include a combination of modifications to the sugar, the nucleobase, and/or the internucleoside linkage. These combinations can include any one or more modifications described herein.

Combinations of modified nucleotides can be used to form the polynucleotides of the invention. Unless otherwise noted, the modified nucleotides can be completely substituted for the natural nucleotides of the polynucleotides of the invention. As a non-limiting example, the natural nucleotide uridine can be substituted with a modified nucleoside described herein. In another non-limiting example, the natural nucleotide uridine can be partially substituted or replaced (e.g., about 0.1%, 1%, 5%, 10%, 15%, 20%, 25%, 30%, 35%, 40%, 45%, 50%, 55%, 60%, 65%, 70%, 75%, 80%, 85%, 90%, 95% or 99.9%) with at least one of the modified nucleoside disclosed herein. Any combination of base/sugar or linker can be incorporated into the polynucleotides of the invention and such modifications are taught in International Patent Publications WO2013052523 and WO2014093924, and U.S. Publ. Nos. US 20130115272 and US20150307542, the contents of each of which are incorporated herein by reference in its entirety.

11. Untranslated Regions (UTRs)

Untranslated regions (UTRs) are nucleic acid sections of a polynucleotide before a start codon (5'UTR) and after a stop codon (3'UTR) that are not translated. In some embodiments, a polynucleotide (e.g., a ribonucleic acid (RNA), e.g., a messenger RNA (mRNA)) of the invention comprising an open reading frame (ORF) encoding a GLA polypeptide further comprises UTR (e.g., a 5'UTR or functional fragment thereof, a 3'UTR or functional fragment thereof, or a combination thereof).

A UTR can be homologous or heterologous to the coding region in a polynucleotide. In some embodiments, the UTR is homologous to the ORF encoding the GLA polypeptide. In some embodiments, the UTR is heterologous to the ORF encoding the GLA polypeptide. In some embodiments, the polynucleotide comprises two or more 5'UTRs or functional fragments thereof, each of which has the same or different nucleotide sequences. In some embodiments, the polynucleotide comprises two or more 3'UTRs or functional fragments thereof, each of which has the same or different nucleotide sequences.

In some embodiments, the 5'UTR or functional fragment thereof, 3' UTR or functional fragment thereof, or any combination thereof is sequence optimized.

In some embodiments, the 5'UTR or functional fragment thereof, 3' UTR or functional fragment thereof, or any combination thereof comprises at least one chemically modified nucleobase, e.g., 1-methylpseudouridine or 5-methoxyuracil.

UTRs can have features that provide a regulatory role, e.g., increased or decreased stability, localization and/or translation efficiency. A polynucleotide comprising a UTR can be administered to a cell, tissue, or organism, and one or more regulatory features can be measured using routine methods. In some embodiments, a functional fragment of a 5'UTR or 3'UTR comprises one or more regulatory features of a full length 5' or 3' UTR, respectively.

Natural 5'UTRs bear features that play roles in translation initiation. They harbor signatures like Kozak sequences that are commonly known to be involved in the process by which the ribosome initiates translation of many genes. Kozak sequences have the consensus CCR(A/G)CCAUGG, where R is a purine (adenine or guanine) three bases upstream of the start codon (AUG), which is followed by another 'G'. 5'UTRs also have been known to form secondary structures that are involved in elongation factor binding.

By engineering the features typically found in abundantly expressed genes of specific target organs, one can enhance the stability and protein production of a polynucleotide. For example, introduction of 5'UTR of liver-expressed mRNA, such as albumin, serum amyloid A, Apolipoprotein AB/E, transferrin, alpha fetoprotein, erythropoietin, or Factor VIII, can enhance expression of polynucleotides in hepatic cell lines or liver. Likewise, use of 5'UTR from other tissue-specific mRNA to improve expression in that tissue is possible for muscle (e.g., MyoD, Myosin, Myoglobin, Myogenin, Herculin), for endothelial cells (e.g., Tie-1, CD36), for myeloid cells (e.g., C/EBP, AML1, G-CSF, GM-CSF, CD11b, MSR, Fr-1, i-NOS), for leukocytes (e.g., CD45, CD18), for adipose tissue (e.g., CD36, GLUT4, ACRP30, adiponectin) and for lung epithelial cells (e.g., SP-A/B/C/D).

In some embodiments, UTRs are selected from a family of transcripts whose proteins share a common function, structure, feature or property. For example, an encoded polypeptide can belong to a family of proteins (i.e., that share at least one function, structure, feature, localization, origin, or expression pattern), which are expressed in a particular cell, tissue or at some time during development. The UTRs from any of the genes or mRNA can be swapped for any other UTR of the same or different family of proteins to create a new polynucleotide.

In some embodiments, the 5'UTR and the 3'UTR can be heterologous. In some embodiments, the 5'UTR can be derived from a different species than the 3'UTR. In some embodiments, the 3'UTR can be derived from a different species than the 5'UTR.

Co-owned International Patent Application No. PCT/US2014/021522 (Publ. No. WO/2014/164253, incorporated herein by reference in its entirety) provides a listing of exemplary UTRs that can be utilized in the polynucleotide of the present invention as flanking regions to an ORF.

Exemplary UTRs of the application include, but are not limited to, one or more 5'UTR and/or 3'UTR derived from the nucleic acid sequence of: a globin, such as an α- or β-globin (e.g., a *Xenopus*, mouse, rabbit, or human globin); a strong Kozak translational initiation signal; a CYBA (e.g., human cytochrome b-245 α polypeptide); an albumin (e.g., human albumin7); a HSD17B4 (hydroxysteroid (17-β) dehydrogenase); a virus (e.g., a tobacco etch virus (TEV), a Venezuelan equine encephalitis virus (VEEV), a Dengue virus, a cytomegalovirus (CMV) (e.g., CMV immediate early 1 (IE1)), a hepatitis virus (e.g., hepatitis B virus), a sindbis virus, or a PAV barley yellow dwarf virus); a heat shock protein (e.g., hsp70); a translation initiation factor (e.g., eIF4G); a glucose transporter (e.g., hGLUT1 (human glucose transporter 1)); an actin (e.g., human a or (3 actin); a GAPDH; a tubulin; a histone; a citric acid cycle enzyme; a topoisomerase (e.g., a 5'UTR of a TOP gene lacking the 5' TOP motif (the oligopyrimidine tract)); a ribosomal protein Large 32 (L32); a ribosomal protein (e.g., human or mouse ribosomal protein, such as, for example, rps9); an ATP synthase (e.g., ATP5A1 or the β subunit of mitochondrial H+-ATP synthase); a growth hormone e (e.g., bovine (bGH) or human (hGH)); an elongation factor (e.g., elongation factor 1 α1 (EEF1A1)); a manganese superoxide dismutase (MnSOD); a myocyte enhancer factor 2A (MEF2A); a β-F1-ATPase, a creatine kinase, a myoglobin, a granulocyte-colony stimulating factor (G-CSF); a collagen (e.g., collagen type I, alpha 2 (Col1A2), collagen type I, alpha 1 (Col1A1), collagen type VI, alpha 2 (Col6A2), collagen type VI, alpha 1 (Col6A1)); a ribophorin (e.g., ribophorin I (RPNI)); a low density lipoprotein receptor-related protein (e.g., LRP1); a cardiotrophin-like cytokine factor (e.g., Nnt1); calreticulin (Calr); a procollagen-lysine, 2-oxoglutarate 5-dioxygenase 1 (Plod1); and a nucleobindin (e.g., Nucb1).

In some embodiments, the 5'UTR is selected from the group consisting of a (3-globin 5'UTR; a 5'UTR containing a strong Kozak translational initiation signal; a cytochrome b-245 α polypeptide (CYBA) 5'UTR; a hydroxysteroid (17-β) dehydrogenase (HSD17B4) 5'UTR; a Tobacco etch virus (TEV) 5'UTR; a Venezuelen equine encephalitis virus (TEEV) 5'UTR; a 5' proximal open reading frame of rubella virus (RV) RNA encoding nonstructural proteins; a Dengue virus (DEN) 5'UTR; a heat shock protein 70 (Hsp70) 5'UTR; a eIF4G 5'UTR; a GLUT1 5'UTR; functional fragments thereof and any combination thereof.

In some embodiments, the 3'UTR is selected from the group consisting of a β-globin 3'UTR; a CYBA 3'UTR; an albumin 3'UTR; a growth hormone (GH) 3'UTR; a VEEV 3'UTR; a hepatitis B virus (HBV) 3'UTR; α-globin 3'UTR; a DEN 3'UTR; a PAV barley yellow dwarf virus (BYDV-PAV) 3'UTR; an elongation factor 1 al (EEF1A1) 3'UTR; a manganese superoxide dismutase (MnSOD) 3'UTR; a β subunit of mitochondrial H(+)-ATP synthase ((3-mRNA) 3'UTR; a GLUT1 3'UTR; a MEF2A 3'UTR; a β-F1-ATPase 3'UTR; functional fragments thereof and combinations thereof.

Wild-type UTRs derived from any gene or mRNA can be incorporated into the polynucleotides of the invention. In some embodiments, a UTR can be altered relative to a wild type or native UTR to produce a variant UTR, e.g., by changing the orientation or location of the UTR relative to the ORF; or by inclusion of additional nucleotides, deletion of nucleotides, swapping or transposition of nucleotides. In some embodiments, variants of 5' or 3' UTRs can be utilized, for example, mutants of wild type UTRs, or variants wherein one or more nucleotides are added to or removed from a terminus of the UTR.

Additionally, one or more synthetic UTRs can be used in combination with one or more non-synthetic UTRs. See, e.g., Mandal and Rossi, Nat. Protoc. 2013 8(3):568-82, and sequences available at www.addgene.org/Derrick_Rossi/, the contents of each are incorporated herein by reference in their entirety. UTRs or portions thereof can be placed in the same orientation as in the transcript from which they were selected or can be altered in orientation or location. Hence, a 5' and/or 3' UTR can be inverted, shortened, lengthened, or combined with one or more other 5' UTRs or 3' UTRs.

In some embodiments, the polynucleotide comprises multiple UTRs, e.g., a double, a triple or a quadruple 5'UTR or 3'UTR. For example, a double UTR comprises two copies of the same UTR either in series or substantially in series. For example, a double beta-globin 3'UTR can be used (see US2010/0129877, the contents of which are incorporated herein by reference in its entirety).

In certain embodiments, the polynucleotides of the invention comprise a 5'UTR and/or a 3'UTR selected from any of the UTRs disclosed herein.

In some embodiments, the 5'UTR comprises:

```
5'UTR-001 (Upstream UTR)
                                           (SEQ ID NO. 33)
(GGGAAAUAAGAGAGAAAAGAAGAGUAAGAAGAAAUAUAAGAGCCACC);

5'UTR-002 (Upstream UTR)
                                           (SEQ ID NO. 34)
(GGGAGAUCAGAGAGAAAAGAAGAGUAAGAAGAAAUAUAAGAGCCACC);

5'UTR-003 (Upstream UTR)
(See SEQ ID NO. 35);

5'UTR-004 (Upstream UTR)
                                           (SEQ ID NO. 36)
(GGGAGACAAGCUUGGCAUUCCGGUACUGUUGGUAAAGCCACC);

5'UTR-005 (Upstream UTR)
                                           (SEQ ID NO. 37)
(GGGAGAUCAGAGAGAAAAGAAGAGUAAGAAGAAAUAUAAGAGCCACC);

5'UTR-006 (Upstream UTR)
                                           (SEQ ID NO. 38)
(GGAAUAAAAGUCUCAACACAACAUAUACAAAACAAACGAAUCUCAAGCA

AUCAAGCAUUCUACUUCUAUUGCAGCAAUUUAAAUCAUUUCUUUUAAAGC

AAAAGCAAUUUUCUGAAAAUUUUCACCAUUUACGAACGAUAGCAAC);

5'UTR-007 (Upstream UTR)
                                           (SEQ ID NO. 39)
(GGGAGACAAGCUUGGCAUUCCGGUACUGUUGGUAAAGCCACC);

5'UTR-008 (Upstream UTR)
                                           (SEQ ID NO. 40)
(GGGAAUUAACAGAGAAAAGAAGAGUAAGAAGAAAUAUAAGAGCCACC);

5'UTR-009 (Upstream UTR)
                                           (SEQ ID NO. 41)
(GGGAAAUUAGACAGAAAAGAAGAGUAAGAAGAAAUAUAAGAGCCACC);

5'UTR-010, Upstream
                                           (SEQ ID NO. 42)
(GGGAAAUAAGAGAGUAAAGAACAGUAAGAAGAAAUAUAAGAGCCACC);

5'UTR-011 (Upstream UTR)
                                           (SEQ ID NO. 43)
(GGGAAAAAGAGAGAAAAGAAGACUAAGAAGAAAUAUAAGAGCCACC);
```

-continued

5'UTR-012 (Upstream UTR)
(SEQ ID NO. 44)
(GGGAAAUAAGAGAGAAAAGAAGAGUAAGAAGAUAUAUAAGAGCCACC);

5'UTR-013 (Upstream UTR)
(SEQ ID NO. 45)
(GGGAAAUAAGAGACAAAACAAGAGUAAGAAGAAAUAUAAGAGCCACC);

5'UTR-014 (Upstream UTR)
(SEQ ID NO. 46)
(GGGAAAUUAGAGAGUAAAGAACAGUAAGUAGAAUUAAAAGAGCCACC);

5'UTR-15 (Upstream UTR)
(SEQ ID NO. 47)
(GGGAAAUAAGAGAGAAUAGAAGAGUAAGAAGAAAUAUAAGAGCCACC);

5'UTR-016 (Upstream UTR)
(SEQ ID NO. 48)
(GGGAAAUAAGAGAGAAAAGAAGAGUAAGAAGAAAAUUAAGAGCCACC);

5'UTR-017 (Upstream UTR)
(SEQ ID NO. 49)
(GGGAAAUAAGAGAGAAAAGAAGAGUAAGAAGAAAUUUAAGAGCCACC);
or 5'UTR-018 (Upstream UTR)
(SEQ ID NO. 50)
(UCAAGCUUUUGGACCCUCGUACAGAAGCUAAUACGACUCACUAUAGGGA

AAUAAGAGAGAAAAGAAGAGUAAGAAGAAAUAUAAGAGCCACC).

In some embodiments, the 3'UTR comprises:

142-3p 3'UTR (UTR including miR142-3p)
(SEQ ID NO. 51)
(UGAUAAUAGUCCAUAAAGUAGGAAACACUACAGCUGGAGCCUCGGUGGC

CAUGCUUCUUGCCCCUUGGGCCUCCCCCCAGCCCCUCCUCCCCUUCCUGC

ACCCGUACCCCCGUGGUCUUUGAAUAAAGUCUGAGUGGGCGGC);

142-3p 3'UTR (UTR including miR142-3p)
(SEQ ID NO. 52)
(UGAUAAUAGGCUGGAGCCUCGGUGGCUCCAUAAAGUAGGAAACACUACA

CAUGCUUCUUGCCCCUUGGGCCUCCCCCCAGCCCCUCCUCCCCUUCCUGC

ACCCGUACCCCCGUGGUCUUUGAAUAAAGUCUGAGUGGGCGGC);

142-3p 3'UTR (UTR including miR142-3p)
(SEQ ID NO. 53)
(UGAUAAUAGGCUGGAGCCUCGGUGGCCAUGCUUCUUGCCCCUUCCAUAA

AGUAGGAAACACUACAUGGGCCUCCCCCCAGCCCCUCCUCCCCUUCCUGC

ACCCGUACCCCCGUGGUCUUUGAAUAAAGUCUGAGUGGGCGGC);

142-3p 3'UTR (UTR including miR142-3p)
(SEQ ID NO. 54)
(UGAUAAUAGGCUGGAGCCUCGGUGGCCAUGCUUCUUGCCCCUUGGGCCU

CCCCCCAGUCCAUAAAGUAGGAAACACUACACCCCUCCUCCCCUUCCUGC

ACCCGUACCCCCGUGGUCUUUGAAUAAAGUCUGAGUGGGCGGC);

142-3p 3'UTR (UTR including miR142-3p)
(SEQ ID NO. 55)
(UGAUAAUAGGCUGGAGCCUCGGUGGCCAUGCUUCUUGCCCCUUGGGCCU

CCCCCAGCCCCUCCUCCCCUUCUCCAUAAAGUAGGAAACACUACACUGC

ACCCGUACCCCCGUGGUCUUUGAAUAAAGUCUGAGUGGGCGGC);

142-3p 3'UTR (UTR including miR142-3p)
(SEQ ID NO. 56)
(UGAUAAUAGGCUGGAGCCUCGGUGGCCAUGCUUCUUGCCCCUUGGGCCU

CCCCCAGCCCCUCCUCCCCUUCCUGCACCCGUACCCCUCCAUAAAGUA

GGAAACACUACAGUGGUCUUUGAAUAAAGUCUGAGUGGGCGGC);

142-3p 3'UTR (UTR including miR142-3p)
(SEQ ID NO. 57)
(UGAUAAUAGGCUGGAGCCUCGGUGGCCAUGCUUCUUGCCCCUUGGGCCU

CCCCCCAGCCCCUCCUCCCCUUCCUGCACCCGUACCCCCGUGGUCUUUGA

AUAAAGUUCCAUAAAGUAGGAAACACUACACUGAGUGGGCGGC);

3'UTR-001 (Creatine Kinase UTR)
(See SEQ ID NO. 58);

3'UTR-002 (Myoglobin UTR)
(See SEQ ID NO. 59);

3'UTR-003 (α-actin UTR)
(See SEQ ID NO. 60);

3'UTR-004 (Albumin UTR)
(See SEQ ID NO. 61);

3'UTR-005 (a-globin UTR)
(See SEQ ID NO. 62);

3'UTR-006 (G-CSF UTR)
(See SEQ ID NO. 63);

3'UTR-007 (Col1a2; collagen, type I, alpha 2 UTR)
(See SEQ ID NO. 64);

3'UTR-008 (Col6a2; collagen, type VI, alpha 2 UTR)
(See SEQ ID NO. 65);

3'UTR-009 (RPN1; ribophorin I UTR)
(See SEQ ID NO. 66);

3'UTR-010 (LRP1; low density lipoprotein receptor related protein 1 UTR)
(See SEQ ID NO. 67);

3'UTR-011 (Nnt1; cardiotrophin-like cytokine factor 1 UTR)
(See SEQ ID NO. 68);

3'UTR-012 (Col6a1; collagen, type VI, alpha 1 UTR)
(See SEQ ID NO. 69);

3'UTR-013 (Calr; calreticulin UTR)
(See SEQ ID NO. 70);

3'UTR-014 (Col1a1; collagen, type I, alpha 1 UTR)
(See SEQ ID NO. 71);

3'UTR-015 (Plod1; procollagen-lysine, 2-oxo-glutarate 5-dioxygenase 1 UTR)
(See SEQ ID NO. 72);

3'UTR-016 (Nucb1; nucleobindin 1 UTR)
(See SEQ ID NO. 73);

3'UTR-017 (α-globin)
(See SEQ ID NO. 74);

3'UTR-018
(See SEQ ID NO. 75);

3'UTR (miR142 + miR126 variant 1)
(SEQ ID NO. 81)
UGAUAAUAGUCCAUAAAGUAGGAAACACUACAGCUGGAGCCUCGGUGGCC

AUGCUUCUUGCCCCUUGGGCCUCCCCCCAGCCCCUCCUCCCCUUCCUGCA

CCCGUACCCCCGCAUUAUUACUCACGGUACGAGUGGUCUUUGAAUAAAG

UCUGAGUGGGCGGC;

3'UTR (miR 142-3p and miR 126-3p binding sites variant 2)
(SEQ ID NO. 82)
UGAUAAUAGUCCAUAAAGUAGGAAACACUACAGCUGGAGCCUCGGUGGCC

UAGCUUCUUGCCCCUUGGGCCUCCCCCCAGCCCCUCCUCCCCUUCCUGCA

```
                          -continued
CCCGUACCCCCCGCAUUAUUACUCACGGUACGAGUGGUCUUUGAAUAAAG UCUGAGUGGGCGGC;
or 3'UTR (miR142 binding site)
                                            (SEQ ID NO. 161)
UGAUAAUAGGCUGGAGCCUCGGUGGCCUAGCUUCUUGCCCCUUGGGCCUC

CCCCCAGCCCCUCCUCCCCUUCCUGCACCCGUACCCCCUCCAUAAAGUAG

GAAACACUACAGUGGUCUUUGAAUAAAGUCUGAGUGGGCGGC.
```

In certain embodiments, the 5'UTR and/or 3'UTR sequence of the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 5'UTR sequences comprising any of SEQ ID NOs: 33-50, 77, and 115-117 and/or 3'UTR sequences comprising any of SEQ ID NOs: 51-75, 81-82, 88, 103, 106-113, 118, and 161-170, and any combination thereof.

The polynucleotides of the invention can comprise combinations of features. For example, the ORF can be flanked by a 5'UTR that comprises a strong Kozak translational initiation signal and/or a 3'UTR comprising an oligo(dT) sequence for templated addition of a poly-A tail. A 5'UTR can comprise a first polynucleotide fragment and a second polynucleotide fragment from the same and/or different UTRs (see, e.g., US2010/0293625, herein incorporated by reference in its entirety).

Other non-UTR sequences can be used as regions or subregions within the polynucleotides of the invention. For example, introns or portions of intron sequences can be incorporated into the polynucleotides of the invention. Incorporation of intronic sequences can increase protein production as well as polynucleotide expression levels. In some embodiments, the polynucleotide of the invention comprises an internal ribosome entry site (IRES) instead of or in addition to a UTR (see, e.g., Yakubov et al., Biochem. Biophys. Res. Commun. 2010 394(1):189-193, the contents of which are incorporated herein by reference in their entirety). In some embodiments, the polynucleotide comprises an IRES instead of a 5'UTR sequence. In some embodiments, the polynucleotide comprises an ORF and a viral capsid sequence. In some embodiments, the polynucleotide comprises a synthetic 5'UTR in combination with a non-synthetic 3'UTR.

In some embodiments, the UTR can also include at least one translation enhancer polynucleotide, translation enhancer element, or translational enhancer elements (collectively, "TEE," which refers to nucleic acid sequences that increase the amount of polypeptide or protein produced from a polynucleotide. As a non-limiting example, the TEE can include those described in US2009/0226470, incorporated herein by reference in its entirety, and others known in the art. As a non-limiting example, the TEE can be located between the transcription promoter and the start codon. In some embodiments, the 5'UTR comprises a TEE.

In one aspect, a TEE is a conserved element in a UTR that can promote translational activity of a nucleic acid such as, but not limited to, cap-dependent or cap-independent translation.

In one non-limiting example, the TEE comprises the TEE sequence in the 5'-leader of the Gtx homeodomain protein. See Chappell et al., PNAS 2004 101:9590-9594, incorporated herein by reference in its entirety.

In some embodiments, the polynucleotide of the invention comprises one or multiple copies of a TEE. The TEE in a translational enhancer polynucleotide can be organized in one or more sequence segments. A sequence segment can harbor one or more of the TEEs provided herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the TEE provided herein, identical or different number of copies of each of the TEE, and/or identical or different organization of the TEE within each sequence segment. In one embodiment, the polynucleotide of the invention comprises a translational enhancer polynucleotide sequence. Non-limiting examples of TEE sequences are described in U.S. Publication 2014/0200261, the contents of which are incorporated herein by reference in their entirety.

12. MicroRNA (miRNA) Binding Sites

Polynucleotides of the invention can include regulatory elements, for example, microRNA (miRNA) binding sites, transcription factor binding sites, structured mRNA sequences and/or motifs, artificial binding sites engineered to act as pseudo-receptors for endogenous nucleic acid binding molecules, and combinations thereof. In some embodiments, polynucleotides including such regulatory elements are referred to as including "sensor sequences". Non-limiting examples of sensor sequences are described in U.S. Publication 2014/0200261, the contents of which are incorporated herein by reference in their entirety.

In some embodiments, a polynucleotide (e.g., a ribonucleic acid (RNA), e.g., a messenger RNA (mRNA)) of the invention comprises an open reading frame (ORF) encoding a polypeptide of interest and further comprises one or more miRNA binding site(s). Inclusion or incorporation of miRNA binding site(s) provides for regulation of polynucleotides of the invention, and in turn, of the polypeptides encoded therefrom, based on tissue-specific and/or cell-type specific expression of naturally-occurring miRNAs.

The present invention also provides pharmaceutical compositions and formulations that comprise any of the polynucleotides described above. In some embodiments, the composition or formulation further comprises a delivery agent.

In some embodiments, the composition or formulation can contain a polynucleotide comprising a sequence optimized nucleic acid sequence disclosed herein which encodes a polypeptide. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes a polypeptide. In some embodiments, the polynucleotide further comprises a miRNA binding site, e.g., a miRNA binding site that binds.

A miRNA, e.g., a natural-occurring miRNA, is a 19-25 nucleotide long noncoding RNA that binds to a polynucleotide and down-regulates gene expression either by reducing stability or by inhibiting translation of the polynucleotide. A miRNA sequence comprises a "seed" region, i.e., a sequence in the region of positions 2-8 of the mature miRNA. A miRNA seed can comprise positions 2-8 or 2-7 of the mature miRNA. In some embodiments, a miRNA seed can comprise 7 nucleotides (e.g., nucleotides 2-8 of the mature miRNA), wherein the seed-complementary site in the corresponding miRNA binding site is flanked by an adenosine (A) opposed to miRNA position 1. In some embodiments, a miRNA seed can comprise 6 nucleotides (e.g., nucleotides 2-7 of the mature miRNA), wherein the seed-complementary site in the corresponding miRNA binding site is flanked by an adenosine (A) opposed to miRNA position 1. See, for example, Grimson A, Farh K K, Johnston W K, Garrett-Engele P, Lim L P, Bartel D P; Mol. Cell. 2007 Jul. 6; 27(1):91-105. miRNA profiling of the target cells or tissues can be conducted to determine the presence or absence of miRNA in the cells or tissues. In some embodiments, a polynucleotide (e.g., a ribonucleic acid (RNA), e.g., a messenger RNA (mRNA)) of the invention comprises one or more microRNA binding sites, microRNA target sequences, microRNA complementary sequences, or microRNA seed complementary sequences. Such sequences can correspond to, e.g., have complementarity to, any known microRNA such as those taught in US Publication US2005/0261218 and US Publication US2005/0059005, the contents of each of which are incorporated herein by reference in their entirety.

microRNAs derive enzymatically from regions of RNA transcripts that fold back on themselves to form short hairpin structures often termed a pre-miRNA (precursor-miRNA). A pre-miRNA typically has a two-nucleotide overhang at its 3' end, and has 3' hydroxyl and 5' phosphate groups. This precursor-mRNA is processed in the nucleus and subsequently transported to the cytoplasm where it is further processed by DICER (a RNase III enzyme), to form a mature microRNA of approximately 22 nucleotides. The mature microRNA is then incorporated into a ribonuclear particle to form the RNA-induced silencing complex, RISC, which mediates gene silencing. Art-recognized nomenclature for mature miRNAs typically designates the arm of the pre-miRNA from which the mature miRNA derives; "5p" means the microRNA is from the 5 prime arm of the pre-miRNA hairpin and "3p" means the microRNA is from the 3 prime end of the pre-miRNA hairpin. A miR referred to by number herein can refer to either of the two mature microRNAs originating from opposite arms of the same pre-miRNA (e.g., either the 3p or 5p microRNA). All miRs referred to herein are intended to include both the 3p and 5p arms/sequences, unless particularly specified by the 3p or 5p designation.

As used herein, the term "microRNA (miRNA or miR) binding site" refers to a sequence within a polynucleotide, e.g., within a DNA or within an RNA transcript, including in the 5'UTR and/or 3'UTR, that has sufficient complementarity to all or a region of a miRNA to interact with, associate with or bind to the miRNA. In some embodiments, a polynucleotide of the invention comprising an ORF encoding a polypeptide of interest and further comprises one or more miRNA binding site(s). In exemplary embodiments, a 5'UTR and/or 3'UTR of the polynucleotide (e.g., a ribonucleic acid (RNA), e.g., a messenger RNA (mRNA)) comprises the one or more miRNA binding site(s).

A miRNA binding site having sufficient complementarity to a miRNA refers to a degree of complementarity sufficient to facilitate miRNA-mediated regulation of a polynucleotide, e.g., miRNA-mediated translational repression or degradation of the polynucleotide. In exemplary aspects of the invention, a miRNA binding site having sufficient complementarity to the miRNA refers to a degree of complementarity sufficient to facilitate miRNA-mediated degradation of the polynucleotide, e.g., miRNA-guided RNA-induced silencing complex (RISC)-mediated cleavage of mRNA. The miRNA binding site can have complementarity to, for example, a 19-25 nucleotide long miRNA sequence, to a 19-23 long nucleotide miRNA sequence, or to a 22 nucleotide long miRNA sequence. A miRNA binding site can be complementary to only a portion of a miRNA, e.g., to a portion less than 1, 2, 3, or 4 nucleotides of the full length of a naturally-occurring miRNA sequence, or to a portion less than 1, 2, 3, or 4 nucleotides shorter than a naturally-occurring miRNA sequence. Full or complete complementarity (e.g., full complementarity or complete complementarity over all or a significant portion of the length of a naturally-occurring miRNA) is preferred when the desired regulation is mRNA degradation.

In some embodiments, a miRNA binding site includes a sequence that has complementarity (e.g., partial or complete complementarity) with an miRNA seed sequence. In some embodiments, the miRNA binding site includes a sequence that has complete complementarity with a miRNA seed sequence. In some embodiments, a miRNA binding site includes a sequence that has complementarity (e.g., partial or complete complementarity) with an miRNA sequence. In some embodiments, the miRNA binding site includes a sequence that has complete complementarity with a miRNA sequence. In some embodiments, a miRNA binding site has complete complementarity with a miRNA sequence but for 1, 2, or 3 nucleotide substitutions, terminal additions, and/or truncations.

In some embodiments, the miRNA binding site is the same length as the corresponding miRNA. In other embodiments, the miRNA binding site is one, two, three, four, five, six, seven, eight, nine, ten, eleven or twelve nucleotide(s) shorter than the corresponding miRNA at the 5' terminus, the 3' terminus, or both. In still other embodiments, the microRNA binding site is two nucleotides shorter than the corresponding microRNA at the 5' terminus, the 3' terminus, or both. The miRNA binding sites that are shorter than the corresponding miRNAs are still capable of degrading the mRNA incorporating one or more of the miRNA binding sites or preventing the mRNA from translation.

In some embodiments, the miRNA binding site binds the corresponding mature miRNA that is part of an active RISC containing Dicer. In another embodiment, binding of the miRNA binding site to the corresponding miRNA in RISC degrades the mRNA containing the miRNA binding site or prevents the mRNA from being translated. In some embodiments, the miRNA binding site has sufficient complementarity to miRNA so that a RISC complex comprising the miRNA cleaves the polynucleotide comprising the miRNA binding site. In other embodiments, the miRNA binding site has imperfect complementarity so that a RISC complex comprising the miRNA induces instability in the polynucleotide comprising the miRNA binding site. In another embodiment, the miRNA binding site has imperfect complementarity so that a RISC complex comprising the miRNA represses transcription of the polynucleotide comprising the miRNA binding site.

In some embodiments, the miRNA binding site has one, two, three, four, five, six, seven, eight, nine, ten, eleven or twelve mismatch(es) from the corresponding miRNA.

In some embodiments, the miRNA binding site has at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one contiguous nucleotides complementary to at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one, respectively, contiguous nucleotides of the corresponding miRNA.

By engineering one or more miRNA binding sites into a polynucleotide of the invention, the polynucleotide can be targeted for degradation or reduced translation, provided the miRNA in question is available. This can reduce off-target effects upon delivery of the polynucleotide. For example, if a polynucleotide of the invention is not intended to be delivered to a tissue or cell but ends up is said tissue or cell, then a miRNA abundant in the tissue or cell can inhibit the expression of the gene of interest if one or multiple binding sites of the miRNA are engineered into the 5'UTR and/or 3'UTR of the polynucleotide. Thus, in some embodiments, incorporation of one or more miRNA binding sites into an mRNA of the disclosure may reduce the hazard of off-target effects upon nucleic acid molecule delivery and/or enable tissue-specific regulation of expression of a polypeptide encoded by the mRNA. In yet other embodiments, incorporation of one or more miRNA binding sites into an mRNA of the disclosure can modulate immune responses upon nucleic acid delivery in vivo. In further embodiments, incorporation of one or more miRNA binding sites into an mRNA of the disclosure can modulate accelerated blood clearance (ABC) of lipid-comprising compounds and compositions described herein.

Conversely, miRNA binding sites can be removed from polynucleotide sequences in which they naturally occur in order to increase protein expression in specific tissues. For example, a binding site for a specific miRNA can be removed from a polynucleotide to improve protein expression in tissues or cells containing the miRNA.

Regulation of expression in multiple tissues can be accomplished through introduction or removal of one or more miRNA binding sites, e.g., one or more distinct miRNA binding sites. The decision whether to remove or insert a miRNA binding site can be made based on miRNA expression patterns and/or their profilings in tissues and/or cells in development and/or disease. Identification of miRNAs, miRNA binding sites, and their expression patterns and role in biology have been reported (e.g., Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein; each of which is incorporated herein by reference in its entirety).

miRNAs and miRNA binding sites can correspond to any known sequence, including non-limiting examples described in U.S. Publication Nos. 2014/0200261, 2005/0261218, and 2005/0059005, each of which are incorporated herein by reference in their entirety.

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126).

Specifically, miRNAs are known to be differentially expressed in immune cells (also called hematopoietic cells), such as antigen presenting cells (APCs) (e.g., dendritic cells and macrophages), macrophages, monocytes, B lymphocytes, T lymphocytes, granulocytes, natural killer cells, etc. Immune cell specific miRNAs are involved in immunogenicity, autoimmunity, the immune-response to infection, inflammation, as well as unwanted immune response after gene therapy and tissue/organ transplantation. Immune cells specific miRNAs also regulate many aspects of development, proliferation, differentiation and apoptosis of hematopoietic cells (immune cells). For example, miR-142 and miR-146 are exclusively expressed in immune cells, particularly abundant in myeloid dendritic cells. It has been demonstrated that the immune response to a polynucleotide can be shut-off by adding miR-142 binding sites to the 3'-UTR of the polynucleotide, enabling more stable gene transfer in tissues and cells. miR-142 efficiently degrades exogenous polynucleotides in antigen presenting cells and suppresses cytotoxic elimination of transduced cells (e.g., Annoni A et al., blood, 2009, 114, 5152-5161; Brown B D, et al., Nat med. 2006, 12(5), 585-591; Brown B D, et al., blood, 2007, 110(13): 4144-4152, each of which is incorporated herein by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing a miR-142 binding site into the 5'UTR and/or 3'UTR of a polynucleotide of the invention can selectively repress gene expression in antigen presenting cells through miR-142 mediated degradation, limiting antigen presentation in antigen presenting cells (e.g., dendritic cells) and thereby preventing antigen-mediated immune response after the delivery of the polynucleotide. The polynucleotide is then stably expressed in target tissues or cells without triggering cytotoxic elimination.

In one embodiment, binding sites for miRNAs that are known to be expressed in immune cells, in particular, antigen presenting cells, can be engineered into a polynucleotide of the invention to suppress the expression of the polynucleotide in antigen presenting cells through miRNA mediated RNA degradation, subduing the antigen-mediated immune response. Expression of the polynucleotide is maintained in non-immune cells where the immune cell specific miRNAs are not expressed. For example, in some embodiments, to prevent an immunogenic reaction against a liver specific protein, any miR-122 binding site can be removed and a miR-142 (and/or mirR-146) binding site can be engineered into the 5'UTR and/or 3'UTR of a polynucleotide of the invention.

To further drive the selective degradation and suppression in APCs and macrophage, a polynucleotide of the invention can include a further negative regulatory element in the 5'UTR and/or 3'UTR, either alone or in combination with miR-142 and/or miR-146 binding sites. As a non-limiting example, the further negative regulatory element is a Constitutive Decay Element (CDE).

Immune cell specific miRNAs include, but are not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-5p, hsa-let-7i-3p, hsa-let-7i-5p, miR-10a-3p, miR-10a-5p, miR-1184, hsa-let-7f-1-3p, hsa-let-7f-2-5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR- 150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-197-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-5p, miR-29c-3p, miR-29c-5p-miR-30e-3p, miR-30e-5p, miR-331-5p, miR-339-3p, miR-339-5p, miR-345-3p, miR-345-5p, miR-346, miR-34a-3p, miR-34a-5p, miR-363-3p, miR-363-5p, miR-372, miR-377-3p, miR-377-5p, miR-493-3p, miR-493-5p, miR-542, miR-548b-5p, miR548c-5p, miR-548i, miR-548j, miR-548n, miR-574-3p, miR-598, miR-718, miR-935, miR-99a-3p, miR-99a-5p, miR-99b-3p, and miR-99b-5p. Furthermore, novel miRNAs can be identified in immune cell through micro-array hybridization and microtome analysis (e.g., Jima D D et al, Blood, 2010, 116:e118-e127; Vaz C et al., BMC Genomics, 2010, 11,288, the content of each of which is incorporated herein by reference in its entirety.)

miRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR-199b-3p, miR-199b-5p, miR-296-5p, miR-557, miR-581, miR-939-3p, and miR-939-5p. MiRNA binding sites from any liver specific miRNA can be introduced to or removed from a polynucleotide of the invention to regulate expression of the polynucleotide in the liver. Liver specific miRNA binding sites can be engineered alone or further in combination with immune cell (e.g., APC) miRNA binding sites in a polynucleotide of the invention.

miRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, and miR-381-5p. miRNA binding sites from any lung specific miRNA can be introduced to or removed from a polynucleotide of the invention to regulate expression of the polynucleotide in the lung. Lung specific miRNA binding sites can be engineered alone or further in combination with immune cell (e.g., APC) miRNA binding sites in a polynucleotide of the invention.

miRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451b, miR-499a-3p, miR-499a-5p, miR-499b-3p, miR-499b-5p, miR-744-3p, miR-744-5p, miR-92b-3p, and miR-92b-5p. miRNA binding sites from any heart specific microRNA can be introduced to or removed from a polynucleotide of the invention to regulate expression of the polynucleotide in the heart. Heart specific miRNA binding sites can be engineered alone or further in combination with immune cell (e.g., APC) miRNA binding sites in a polynucleotide of the invention.

miRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-30c-5p, miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510, miR-516a-3p, miR-548b-5p, miR-548c-5p, miR-571, miR-7-1-3p, miR-7-2-3p, miR-7-5p, miR-802, miR-922, miR-9-3p, and miR-9-5p. miRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, and miR-657. miRNA binding sites from any CNS specific miRNA can be introduced to or removed from a polynucleotide of the invention to regulate expression of the polynucleotide in the nervous system. Nervous system specific miRNA binding sites can be engineered alone or further in combination with immune cell (e.g., APC) miRNA binding sites in a polynucleotide of the invention.

miRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p, and miR-944. MiRNA binding sites from any pancreas specific miRNA can be introduced to or removed from a polynucleotide of the invention to regulate expression of the polynucleotide in the pancreas. Pancreas specific miRNA binding sites can be engineered alone or further in combination with immune cell (e.g. APC) miRNA binding sites in a polynucleotide of the invention.

miRNAs that are known to be expressed in the kidney include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-30c-1-3p, miR-30c-2-3p, miR30c-5p, miR-324-3p, miR-335-3p, miR-335-5p, miR-363-3p, miR-363-5p, and miR-562. miRNA binding sites from any kidney specific miRNA can be introduced to or removed from a polynucleotide of the invention to regulate expression of the polynucleotide in the kidney. Kidney specific miRNA binding sites can be engineered alone or further in combination with immune cell (e.g., APC) miRNA binding sites in a polynucleotide of the invention.

miRNAs that are known to be expressed in the muscle include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p, and miR-25-5p. MiRNA binding sites from any muscle specific miRNA can be introduced to or removed from a polynucleotide of the invention to regulate expression of the polynucleotide in the muscle. Muscle specific miRNA binding sites can be engineered alone or further in combination with immune cell (e.g., APC) miRNA binding sites in a polynucleotide of the invention.

miRNAs are also differentially expressed in different types of cells, such as, but not limited to, endothelial cells, epithelial cells, and adipocytes.

miRNAs that are known to be expressed in endothelial cells include, but are not limited to, let-7b-3p, let-7b-5p, miR-100-3p, miR-100-5p, miR-101-3p, miR-101-5p, miR-126-3p, miR-126-5p, miR-1236-3p, miR-1236-5p, miR-130a-3p, miR-130a-5p, miR-17-5p, miR-17-3p, miR-18a-3p, miR-18a-5p, miR-19a-3p, miR-19a-5p, miR-19b-1-5p, miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p, and miR-92b-5p. Many novel miRNAs are discovered in endothelial cells from deep-sequencing analysis (e.g., Voellenkle C et al., RNA, 2012, 18, 472-484, herein incorporated by reference in its entirety). miRNA binding sites from any endothelial cell specific miRNA can be introduced to or removed from a polynucleotide of the invention to regulate expression of the polynucleotide in the endothelial cells.

miRNAs that are known to be expressed in epithelial cells include, but are not limited to, let-7b-3p, let-7b-5p, miR-1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR-34a, miR-34b-5p, miR-34c-5p, miR-449a, miR-449b-3p, miR-449b-5p specific in respiratory ciliated epithelial cells, let-7 family, miR-133a, miR-133b, miR-126 specific in lung epithelial cells, miR-382-3p, miR-382-5p specific in renal epithelial cells, and miR-762 specific in corneal epithelial cells. miRNA binding sites from any epithelial cell specific miRNA can be introduced to or removed from a polynucleotide of the invention to regulate expression of the polynucleotide in the epithelial cells.

In addition, a large group of miRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (e.g., Kuppusamy K T et al., Curr. Mol Med, 2013, 13(5), 757-764; Vidigal J A and Ventura A, Semin Cancer Biol. 2012, 22(5-6), 428-436; Goff L A et al., PLoS One, 2009, 4:e7192; Morin R D et al., Genome Res, 2008, 18, 610-621; Yoo J K et al., Stem Cells Dev. 2012, 21(11), 2049-2057, each of which is herein incorporated by reference in its entirety). MiRNAs abundant in embryonic stem cells include, but are not limited to, let-7a-2-3p, let-a-3p, let-7a-5p, let7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR-200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-5481, miR-548m, miR-548n, miR-5480-3p, miR-5480-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel miRNAs are discovered by deep sequencing in human embryonic stem cells (e.g., Morin R D et al., Genome Res, 2008, 18, 610-621; Goff L A et al., PLoS One, 2009, 4:e7192; Bar M et al., Stem cells, 2008, 26, 2496-2505, the content of each of which is incorporated herein by reference in its entirety).

In one embodiment, the binding sites of embryonic stem cell specific miRNAs can be included in or removed from the 3'UTR of a polynucleotide of the invention to modulate the development and/or differentiation of embryonic stem cells, to inhibit the senescence of stem cells in a degenerative condition (e.g. degenerative diseases), or to stimulate the senescence and apoptosis of stem cells in a disease condition.

In some embodiments, miRNAs are selected based on expression and abundance in immune cells of the hematopoietic lineage, such as B cells, T cells, macrophages, dendritic cells, and cells that are known to express TLR7/TLR8 and/or able to secrete cytokines such as endothelial cells and platelets. In some embodiments, the miRNA set thus includes miRs that may be responsible in part for the immunogenicity of these cells, and such that a corresponding miR-site incorporation in polynucleotides of the present invention (e.g., mRNAs) could lead to destabilization of the mRNA and/or suppression of translation from these mRNAs in the specific cell type. Non-limiting representative examples include miR-142, miR-144, miR-150, miR-155 and miR-223, which are specific for many of the hematopoietic cells; miR-142, miR150, miR-16 and miR-223, which are expressed in B cells; miR-223, miR-451, miR-26a, miR-16, which are expressed in progenitor hematopoietic cells; and miR-126, which is expressed in plasmacytoid dendritic cells, platelets and endothelial cells. For further discussion of tissue expression of miRs see e.g., Teruel-Montoya, R. et al. (2014) *PLoS One* 9:e102259; Landgraf, P. et al. (2007) Cell 129:1401-1414; Bissels, U. et al. (2009) *RNA* 15:2375-2384. Any one miR-site incorporation in the 3'UTR and/or 5' UTR may mediate such effects in multiple cell types of interest (e.g., miR-142 is abundant in both B cells and dendritic cells).

In some embodiments, it may be beneficial to target the same cell type with multiple miRs and to incorporate binding sites to each of the 3p and 5p arm if both are abundant (e.g., both miR-142-3p and miR142-5p are abundant in hematopoietic stem cells). Thus, in certain embodiments, polynucleotides of the invention contain two or more (e.g., two, three, four or more) miR bindings sites from: (i) the group consisting of miR-142, miR-144, miR-150, miR-155 and miR-223 (which are expressed in many hematopoietic cells); or (ii) the group consisting of miR-142, miR150, miR-16 and miR-223 (which are expressed in B cells); or the group consisting of miR-223, miR-451, miR-26a, miR-16 (which are expressed in progenitor hematopoietic cells).

In some embodiments, it may also be beneficial to combine various miRs such that multiple cell types of interest are targeted at the same time (e.g., miR-142 and miR-126 to target many cells of the hematopoietic lineage and endothelial cells). Thus, for example, in certain embodiments, polynucleotides of the invention comprise two or more (e.g., two, three, four or more) miRNA bindings sites, wherein: (i) at least one of the miRs targets cells of the hematopoietic lineage (e.g., miR-142, miR-144, miR-150, miR-155 or miR-223) and at least one of the miRs targets plasmacytoid dendritic cells, platelets or endothelial cells (e.g., miR-126); or (ii) at least one of the miRs targets B cells (e.g., miR-142, miR150, miR-16 or miR-223) and at least one of the miRs targets plasmacytoid dendritic cells, platelets or endothelial cells (e.g., miR-126); or (iii) at least one of the miRs targets progenitor hematopoietic cells (e.g., miR-223, miR-451, miR-26a or miR-16) and at least one of the miRs targets plasmacytoid dendritic cells, platelets or endothelial cells (e.g., miR-126); or (iv) at least one of the miRs targets cells of the hematopoietic lineage (e.g., miR-142, miR-144, miR-150, miR-155 or miR-223), at least one of the miRs targets B cells (e.g., miR-142, miR150, miR-16 or miR-223) and at least one of the miRs targets plasmacytoid dendritic cells, platelets or endothelial cells (e.g., miR-126); or any other possible combination of the foregoing four classes of miR binding sites (i.e., those targeting the hematopoietic lineage, those targeting B cells, those targeting progenitor hematopoietic cells and/or those targeting plamacytoid dendritic cells/platelets/endothelial cells).

In one embodiment, to modulate immune responses, polynucleotides of the present invention can comprise one or more miRNA binding sequences that bind to one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) reduces or inhibits immune cell activation (e.g., B cell activation, as measured by frequency of activated B cells) and/or cytokine production (e.g., production of IL-6, IFN-γ and/or TNFα). Furthermore, it has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) can reduce or inhibit an anti-drug antibody (ADA) response against a protein of interest encoded by the mRNA.

In another embodiment, to modulate accelerated blood clearance of a polynucleotide delivered in a lipid-comprising compound or composition, polynucleotides of the invention can comprise one or more miR binding sequences that bind to one or more miRNAs expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miR binding sites reduces or inhibits accelerated blood clearance (ABC) of the lipid-comprising compound or composition for use in delivering the mRNA. Furthermore, it has now been discovered that incorporation of one or more miR binding sites into an mRNA reduces serum levels of anti-PEG anti-IgM (e.g., reduces or inhibits the acute production of IgMs that recognize polyethylene glycol (PEG) by B cells) and/or reduces or inhibits proliferation and/or activation of plasmacytoid dendritic cells following administration of a lipid-comprising compound or composition comprising the mRNA.

In some embodiments, miR sequences may correspond to any known microRNA expressed in immune cells, including but not limited to those taught in US Publication US2005/0261218 and US Publication US2005/0059005, the contents of which are incorporated herein by reference in their entirety. Non-limiting examples of miRs expressed in immune cells include those expressed in spleen cells, myeloid cells, dendritic cells, plasmacytoid dendritic cells, B cells, T cells and/or macrophages. For example, miR-142-3p, miR-142-5p, miR-16, miR-21, miR-223, miR-24 and miR-27 are expressed in myeloid cells, miR-155 is expressed in dendritic cells, B cells and T cells, miR-146 is upregulated in macrophages upon TLR stimulation and miR-126 is expressed in plasmacytoid dendritic cells. In certain embodiments, the miR(s) is expressed abundantly or preferentially in immune cells. For example, miR-142 (miR-142-3p and/or miR-142-5p), miR-126 (miR-126-3p and/or miR-126-5p), miR-146 (miR-146-3p and/or miR-146-5p) and miR-155 (miR-155-3p and/or miR155-5p) are expressed abundantly in immune cells. These microRNA sequences are known in the art and, thus, one of ordinary skill in the art can readily design binding sequences or target sequences to which these microRNAs will bind based upon Watson-Crick complementarity.

Accordingly, in various embodiments, polynucleotides of the present invention comprise at least one microRNA binding site for a miR selected from the group consisting of miR-142, miR-146, miR-155, miR-126, miR-16, miR-21, miR-223, miR-24 and miR-27. In another embodiment, the mRNA comprises at least two miR binding sites for microRNAs expressed in immune cells. In various embodiments, the polynucleotide of the invention comprises 1-4, one, two, three or four miR binding sites for microRNAs expressed in immune cells. In another embodiment, the polynucleotide of the invention comprises three miR binding sites. These miR binding sites can be for microRNAs selected from the group consisting of miR-142, miR-146, miR-155, miR-126, miR-16, miR-21, miR-223, miR-24, miR-27, and combinations thereof. In one embodiment, the polynucleotide of the invention comprises two or more (e.g., two, three, four) copies of the same miR binding site expressed in immune cells, e.g., two or more copies of a miR binding site selected from the group of miRs consisting of miR-142, miR-146, miR-155, miR-126, miR-16, miR-21, miR-223, miR-24, miR-27.

In one embodiment, the polynucleotide of the invention comprises three copies of the same miR binding site. In certain embodiments, use of three copies of the same miR binding site can exhibit beneficial properties as compared to use of a single miR binding site. Non-limiting examples of sequences for 3' UTRs containing three miR bindings sites are shown in SEQ ID NO: 106 (three miR-142-3p binding sites) and SEQ ID NO: 108 (three miR-142-5p binding sites).

In another embodiment, the polynucleotide of the invention comprises two or more (e.g., two, three, four) copies of at least two different miR binding sites expressed in immune cells. Non-limiting examples of sequences of 3' UTRs containing two or more different miR binding sites are shown in SEQ ID NO: 81 (one miR-142-3p binding site and one miR-126-3p binding site), SEQ ID NO. 82 (one miR-142-3p binding site and one miR-126-3p binding site); SEQ ID NO: 103 (one miR 126-3p binding site), SEQ ID NO: 109 (two miR-142-5p binding sites and one miR-142-3p binding sites) and SEQ ID NO: 112 (two miR-155-5p binding sites and one miR-142-3p binding sites).

In another embodiment, the polynucleotide of the invention comprises at least two miR binding sites for microRNAs expressed in immune cells, wherein one of the miR binding sites is for miR-142-3p. In various embodiments, the polynucleotide of the invention comprises binding sites for miR-142-3p and miR-155 (miR-155-3p or miR-155-5p), miR-142-3p and miR-146 (miR-146-3 or miR-146-5p), or miR-142-3p and miR-126 (miR-126-3p or miR-126-5p).

In another embodiment, the polynucleotide of the invention comprises at least two miR binding sites for microRNAs expressed in immune cells, wherein one of the miR binding sites is for miR-126-3p. In various embodiments, the polynucleotide of the invention comprises binding sites for miR-126-3p and miR-155 (miR-155-3p or miR-155-5p), miR-126-3p and miR-146 (miR-146-3p or miR-146-5p), or miR-126-3p and miR-142 (miR-142-3p or miR-142-5p).

In another embodiment, the polynucleotide of the invention comprises at least two miR binding sites for microRNAs expressed in immune cells, wherein one of the miR binding sites is for miR-142-5p. In various embodiments, the polynucleotide of the invention comprises binding sites for miR-142-5p and miR-155 (miR-155-3p or miR-155-5p), miR-142-5p and miR-146 (miR-146-3 or miR-146-5p), or miR-142-5p and miR-126 (miR-126-3p or miR-126-5p).

In yet another embodiment, the polynucleotide of the invention comprises at least two miR binding sites for microRNAs expressed in immune cells, wherein one of the miR binding sites is for miR-155-5p. In various embodiments, the polynucleotide of the invention comprises binding sites for miR-155-5p and miR-142 (miR-142-3p or miR-142-5p), miR-155-5p and miR-146 (miR-146-3 or miR-146-5p), or miR-155-5p and miR-126 (miR-126-3p or miR-126-5p).

miRNA can also regulate complex biological processes such as angiogenesis (e.g., miR-132) (Anand and Cheresh Curr Opin Hematol 2011 18:171-176). In the polynucleotides of the invention, miRNA binding sites that are involved in such processes can be removed or introduced, in order to tailor the expression of the polynucleotides to biologically relevant cell types or relevant biological processes. In this context, the polynucleotides of the invention are defined as auxotrophic polynucleotides.

In some embodiments, a polynucleotide of the invention comprises a miRNA binding site, wherein the miRNA binding site comprises one or more nucleotide sequences selected from TABLE 3 or TABLE 4, including one or more copies of any one or more of the miRNA binding site sequences. In some embodiments, a polynucleotide of the invention further comprises at least one, two, three, four, five, six, seven, eight, nine, ten, or more of the same or different miRNA binding sites selected from TABLE 3 or TABLE 4, including any combination thereof.

In some embodiments, the miRNA binding site binds to miR-142 or is complementary to miR-142. In some embodiments, the miR-142 comprises SEQ ID NO:28. In some embodiments, the miRNA binding site binds to miR-142-3p or miR-142-5p. In some embodiments, the miR-142-3p binding site comprises SEQ ID NO:30. In some embodiments, the miR-142-5p binding site comprises SEQ ID NO:32. In some embodiments, the miRNA binding site comprises a nucleotide sequence at least 80%, at least 85%, at least 90%, at least 95%, or 100% identical to SEQ ID NO:30 or SEQ ID NO:32.

In some embodiments, the miRNA binding site binds to miR-126 or is complementary to miR-126. In some embodiments, the miR-126 comprises SEQ ID NO: 83. In some embodiments, the miRNA binding site binds to miR-126-3p or miR-126-5p. In some embodiments, the miR-126-3p binding site comprises SEQ ID NO: 85. In some embodiments, the miR-126-5p binding site comprises SEQ ID NO: 87. In some embodiments, the miRNA binding site comprises a nucleotide sequence at least 80%, at least 85%, at least 90%, at least 95%, or 100% identical to SEQ ID NO: 85 or SEQ ID NO: 87.

In one embodiment, the 3' UTR comprises two miRNA binding sites, wherein a first miRNA binding site binds to miR-142 and a second miRNA binding site binds to miR-126. In a specific embodiment, the 3' UTR binding to miR-142 and miR-126 comprises, consists, or consists essentially of the sequence of SEQ ID NO: 81 or 82.

miR-142, miR-126, and miR-142 and miR-126 binding sites

| SEQ ID NO. | Description | Sequence |
|---|---|---|
| 28 | miR-142 | GACAGUGCAGUCACCCAUAAAGUAGAAAGCACUACUAACAGCACUGGAGGGUGUAGUGUUUCCUACUUUAUGGAUGAGUGUACUGUG |
| 29 | miR-142-3p | UGUAGUGUUUCCUACUUUAUGGA |
| 30 | miR-142-3p binding site | UCCAUAAAGUAGGAAACACUACA |
| 31 | miR-142-5p | CAUAAAGUAGAAAGCACUACU |
| 32 | miR-142-5p binding site | AGUAGUGCUUUCUACUUUAUG |
| 83 | miR-126 | CGCUGGCGACGGGACAUUAUUACUUUUGGUACGCGCUGUGACACUUCAAACUCGUACCGUGAGUAAUAAUGCGCCGUCCACGGCA |
| 84 | miR-126-3p | UCGUACCGUGAGUAAUAAUGCG |
| 85 | miR-126-3p binding site | CGCAUUAUUACUCACGGUACGA |
| 86 | miR-126-5p | CAUUAUUACUUUUGGUACGCG |
| 87 | miR-126-5p binding site | CGCGUACCAAAAGUAAUAAUG |

In some embodiments, a miRNA binding site is inserted in the polynucleotide of the invention in any position of the polynucleotide (e.g., the 5'UTR and/or 3'UTR). In some embodiments, the 5'UTR comprises a miRNA binding site. In some embodiments, the 3'UTR comprises a miRNA binding site. In some embodiments, the 5'UTR and the 3'UTR comprise a miRNA binding site. The insertion site in the polynucleotide can be anywhere in the polynucleotide as long as the insertion of the miRNA binding site in the polynucleotide does not interfere with the translation of a functional polypeptide in the absence of the corresponding miRNA; and in the presence of the miRNA, the insertion of the miRNA binding site in the polynucleotide and the binding of the miRNA binding site to the corresponding miRNA are capable of degrading the polynucleotide or preventing the translation of the polynucleotide.

In some embodiments, a miRNA binding site is inserted in at least about 30 nucleotides downstream from the stop codon of an ORF in a polynucleotide of the invention comprising the ORF. In some embodiments, a miRNA binding site is inserted in at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides downstream from the stop codon of an ORF in a polynucleotide of the invention. In some embodiments, a miRNA binding site is inserted in about 10 nucleotides to about 100 nucleotides, about 20 nucleotides to about 90 nucleotides, about 30 nucleotides to about 80 nucleotides, about 40 nucleotides to about 70 nucleotides, about 50 nucleotides to about 60 nucleotides, about 45 nucleotides to about 65 nucleotides downstream from the stop codon of an ORF in a polynucleotide of the invention.

In some embodiments, a miRNA binding site is inserted within the 3' UTR immediately following the stop codon of the coding region within the polynucleotide of the invention, e.g., mRNA. In some embodiments, if there are multiple copies of a stop codon in the construct, a miRNA binding site is inserted immediately following the final stop codon. In some embodiments, a miRNA binding site is inserted further downstream of the stop codon, in which case there are 3' UTR bases between the stop codon and the miR binding site(s). In some embodiments, three non-limiting examples of possible insertion sites for a miR in a 3' UTR are shown in SEQ ID NOs: 51, 52, and 113, which show a 3' UTR sequence with a miR-142-3p site inserted in one of three different possible insertion sites, respectively, within the 3' UTR.

In some embodiments, one or more miRNA binding sites can be positioned within the 5' UTR at one or more possible insertion sites. For example, three non-limiting examples of possible insertion sites for a miR in a 5' UTR are shown in SEQ ID NOs: 115, 116, and 117, which show a 5' UTR sequence with a miR-142-3p site inserted into one of three different possible insertion sites, respectively, within the 5' UTR.

In one embodiment, a codon optimized open reading frame encoding a polypeptide of interest comprises a stop codon and the at least one microRNA binding site is located within the 3' UTR 1-100 nucleotides after the stop codon. In one embodiment, the codon optimized open reading frame encoding the polypeptide of interest comprises a stop codon and the at least one microRNA binding site for a miR expressed in immune cells is located within the 3' UTR 30-50 nucleotides after the stop codon. In another embodiment, the codon optimized open reading frame encoding the polypeptide of interest comprises a stop codon and the at least one microRNA binding site for a miR expressed in immune cells is located within the 3' UTR at least 50 nucleotides after the stop codon. In other embodiments, the codon optimized open reading frame encoding the polypeptide of interest comprises a stop codon and the at least one microRNA binding site for a miR expressed in immune cells is located within the 3' UTR immediately after the stop codon, or within the 3' UTR 15-20 nucleotides after the stop codon or within the 3' UTR 70-80 nucleotides after the stop codon. In other embodiments, the 3'UTR comprises more than one miRNA binding site (e.g., 2-4 miRNA binding sites), wherein there can be a spacer region (e.g., of 10-100, 20-70 or 30-50 nucleotides in length) between each miRNA binding site. In another embodiment, the 3' UTR comprises a spacer region between the end of the miRNA binding site(s) and the poly A tail nucleotides. For example, a spacer region of 10-100, 20-70 or 30-50 nucleotides in length can be situated between the end of the miRNA binding site(s) and the beginning of the poly A tail.

In one embodiment, a codon optimized open reading frame encoding a polypeptide of interest comprises a start codon and the at least one microRNA binding site is located within the 5' UTR 1-100 nucleotides before (upstream of) the start codon. In one embodiment, the codon optimized open reading frame encoding the polypeptide of interest comprises a start codon and the at least one microRNA binding site for a miR expressed in immune cells is located within the 5' UTR 10-50 nucleotides before (upstream of) the start codon. In another embodiment, the codon optimized open reading frame encoding the polypeptide of interest comprises a start codon and the at least one microRNA binding site for a miR expressed in immune cells is located within the 5' UTR at least 25 nucleotides before (upstream of) the start codon. In other embodiments, the codon optimized open reading frame encoding the polypeptide of interest comprises a start codon and the at least one microRNA binding site for a miR expressed in immune cells is located within the 5' UTR immediately before the start codon, or within the 5' UTR 15-20 nucleotides before the start codon or within the 5' UTR 70-80 nucleotides before the start codon. In other embodiments, the 5'UTR comprises more than one miRNA binding site (e.g., 2-4 miRNA binding sites), wherein there can be a spacer region (e.g., of 10-100, 20-70 or 30-50 nucleotides in length) between each miRNA binding site.

In one embodiment, the 3' UTR comprises more than one stop codon, wherein at least one miRNA binding site is positioned downstream of the stop codons. For example, a 3' UTR can comprise 1, 2 or 3 stop codons. Non-limiting examples of triple stop codons that can be used include: UGAUAAUAG, UGAUAGUAA, UAAUGAUAG, UGAUAAUAA, UGAUAGUAG, UAAUGAUGA, UAAUAGUAG, UGAUGAUGA, UAAUAAUAA and UAGUAGUAG. Within a 3' UTR, for example, 1, 2, 3 or 4 miRNA binding sites, e.g., miR-142-3p binding sites, can be positioned immediately adjacent to the stop codon(s) or at any number of nucleotides downstream of the final stop codon. When the 3' UTR comprises multiple miRNA binding sites, these binding sites can be positioned directly next to each other in the construct (i.e., one after the other) or, alternatively, spacer nucleotides can be positioned between each binding site.

In one embodiment, the 3' UTR comprises three stop codons with a single miR-142-3p binding site located downstream of the 3rd stop codon. Non-limiting examples of sequences of 3' UTR having three stop codons and a single miR-142-3p binding site located at different positions downstream of the final stop codon are shown in Table 4 below.

Table 4 contains non-limiting examples of miR sequences, miR binding sites, and UTRs of use in the claimed invention.

TABLE 4

3' UTRs, miR Sequences, and miR Binding Sites

| SEQ ID NO: | Sequence |
|---|---|
| 29 | UGUAGUGUUUCCUACUUUAUGGA<br><br>(miR 142-3p sequence) |

TABLE 4-continued 3' UTRs, miR Sequences, and miR Binding Sites

| SEQ ID NO: | Sequence |
|---|---|
| 30 | UCCAUAAAGUAGGAAACACUACA (miR 142-3p binding site) |
| 31 | CAUAAAGUAGAAAGCACUACU (miR 142-5p sequence) |
| 85 | CGCAUUAUUACUCACGGUACGA (miR 126-3p binding site) |
| 89 | CCUCUGAAAUUCAGUUCUUCAG (miR 146-3p sequence) |
| 90 | UGAGAACUGAAUUCCAUGGGUU (miR 146-5p sequence) |
| 91 | CUCCUACAUAUUAGCAUUAACA (miR 155-3p sequence) |
| 92 | UUAAUGCUAAUCGUGAUAGGGGU (miR 155-5p sequence) |
| 84 | UCGUACCGUGAGUAAUAAUGCG (miR 126-3p sequence) |
| 86 | CAUUAUUACUUUUGGUACGCG (miR 126-5p sequence) |
| 93 | CCAGUAUUAACUGUGCUGCUGA (miR 16-3p sequence) |
| 94 | UAGCAGCACGUAAAUAUUGGCG (miR 16-5p sequence) |
| 95 | CAACACCAGUCGAUGGGCUGU (miR 21-3p sequence) |
| 96 | UAGCUUAUCAGACUGAUGUUGA (miR 21-5p sequence) |
| 97 | UGUCAGUUUGUCAAAUACCCCA (miR 223-3p sequence) |
| 98 | CGUGUAUUUGACAAGCUGAGUU (miR 223-5p sequence) |
| 99 | UGGCUCAGUUCAGCAGGAACAG (miR 24-3p sequence) |
| 100 | UGCCUACUGAGCUGAUAUCAGU (miR 24-5p sequence) |
| 101 | UUCACAGUGGCUAAGUUCCGC (miR 27-3p sequence) |
| 102 | AGGGCUUAGCUGCUUGUGAGCA (miR 27-5p sequence) |

TABLE 4-continued

3' UTRs, miR Sequences, and miR Binding Sites

| SEQ ID NO: | Sequence |
|---|---|
| 104 | UUAAUGCUAAUUGUGAUAGGGGU |
| | (miR 155-5p sequence) |
| 105 | ACCCCUAUCACAAUUAGCAUUAA |
| | (miR 155-5p binding site) |
| 51 | UGAUAAUAGUCCAUAAAGUAGGAAACACUACAGCUGGAGCCUCGGUGGCCA UGCUUCUUGCCCCUUGGGCCUCCCCCCAGCCCCUCCUCCCCUUCCUGCACC CGUACCCCCGUGGUCUUUGAAUAAAGUCUGAGUGGGCGGC |
| | (3'UTR with miR 142-3p binding site, P1 insertion) |
| 52 | UGAUAAUAGGCUGGAGCCUCGGUGGCUCCAUAAAGUAGGAAACACUACACA UGCUUCUUGCCCCUUGGGCCUCCCCCCAGCCCCUCCUCCCCUUCCUGCACC CGUACCCCCGUGGUCUUUGAAUAAAGUCUGAGUGGGCGGC |
| | (3'UTR with miR 142-3p binding site, P2 insertion) |
| 53 | UGAUAAUAGGCUGGAGCCUCGGUGGCCAUGCUUCUUGCCCCUUCCAUAAAG UAGGAAACACUACAUGGGCCUCCCCCCAGCCCCUCCUCCCCUUCCUGCACC CGUACCCCCGUGGUCUUUGAAUAAAGUCUGAGUGGGCGGC |
| | (3 'UTR including miR142-3p binding site) |
| 54 | UGAUAAUAGGCUGGAGCCUCGGUGGCCAUGCUUCUUGCCCCUUGGGCCUCC CCCCAGUCCAUAAAGUAGGAAACACUACACCCCUCCUCCCCUUCCUGCACC CGUACCCCCGUGGUCUUUGAAUAAAGUCUGAGUGGGCGGC |
| | (3'UTR including miR142-3p binding site) |
| 55 | UGAUAAUAGGCUGGAGCCUCGGUGGCCAUGCUUCUUGCCCCUUGGGCCUCC CCCCAGCCCCUCCUCCCCUUCUCCAUAAAGUAGGAAACACUACACUGCACC CGUACCCCCGUGGUCUUUGAAUAAAGUCUGAGUGGGCGGC |
| | (3'UTR including miR142-3p binding site) |
| 56 | UGAUAAUAGGCUGGAGCCUCGGUGGCCAUGCUUCUUGCCCCUUGGGCCUCC CCCCAGCCCCUCCUCCCCUUCCUGCACCCGUACCCCCUCCAUAAAGUAGGA AACACUACAGUGGUCUUUGAAUAAAGUCUGAGUGGGCGGC |
| | (3' UTR with miR 142-3p binding site) |
| 57 | UGAUAAUAGGCUGGAGCCUCGGUGGCCAUGCUUCUUGCCCCUUGGGCCUCC CCCCAGCCCCUCCUCCCCUUCCUGCACCCGUACCCCCGUGGUCUUUGAAUA AAGUUCCAUAAAGUAGGAAACACUACAUGAGUGGGCGGC |
| | (3'UTR including miR142-3p binding site) |
| 75 | UGAUAAUAGGCUGGAGCCUCGGUGGCCAUGCUUCUUGCCCCUUGGGCCUCC CCCCAGCCCCUCCUCCCCUUCCUGCACCCGUACCCCCGUGGUCUUUGAAUA AAGUCUGAGUGGGCGGC |
| | (3' UTR, no miR binding sites) |
| 81 | UGAUAAUAGUCCAUAAAGUAGGAAACACUACAGCUGGAGCCUCGGUGGCCA UGCUUCUUGCCCCUUGGGCCUCCCCCCAGCCCCUCCUCCCCUUCCUGCACC |

TABLE 4-continued

3' UTRs, miR Sequences, and miR Binding Sites

| SEQ ID NO: | Sequence |
|---|---|
| | CGUACCCCCCGCAUUAUUACUCACGGUACGAGUGGUCUUUGAAUAAAGUCU |
| | GAGUGGGCGGC |
| | (3' UTR with miR 142-3p and miR 126-3p binding sites) |
| 82 | UGAUAAUAGUCCAUAAAGUAGGAAACACUACAGCUGGAGCCUCGGUGGCCU |
| | AGCUUCUUGCCCCUUGGGCCUCCCCCCAGCCCCUCCUCCCCUUCCUGCACC |
| | CGUACCCCCCGCAUUAUUACUCACGGUACGAGUGGUCUUUGAAUAAAGUCU |
| | GAGUGGGCGGC |
| | (3' UTR with miR 142-3p and miR 126-3p binding sites variant 2) |
| 88 | GCUGGAGCCUCGGUGGCCAUGCUUCUUGCCCCUUGGGCCUCCCCCAGCCC |
| | CUCCUCCCCUUCCUGCACCCGUACCCCCUCCAUAAAGUAGGAAACACUACA |
| | GUGGUCUUUGAAUAAAGUCUGAGUGGGCGGC |
| | (3'UTR with miR 142-3p binding site) |
| 103 | UGAUAAUAGGCUGGAGCCUCGGUGGCCAUGCUUCUUGCCCCUUGGGCCUCC |
| | CCCAGCCCCUCCUCCCCUUCCUGCACCCGUACCCCCCGCAUUAUUACUCA |
| | CGGUACGAGUGGUCUUUGAAUAAAGUCUGAGUGGGCGGC |
| | (3'UTR with miR 126-3p binding site) |
| 106 | UGAUAAUAGUCCAUAAAGUAGGAAACACUACAGCUGGAGCCUCGGUGGCCA |
| | UGCUUCUUGCCCCUUGGGCCUCCAUAAAGUAGGAAACACUACAUCCCCCCA |
| | GCCCCUCCUCCCCUUCCUGCACCCGUACCCCCUCCAUAAAGUAGGAAACAC |
| | UACAGUGGUCUUUGAAUAAAGUCUGAGUGGGCGGC |
| | (3' UTR with 3 miR 142-3p binding sites) |
| 107 | UGAUAAUAGGCUGGAGCCUCGGUGGCCAUGCUUCUUGCCCCUUGGGCCUCC |
| | CCCAGCCCCUCCUCCCCUUCCUGCACCCGUACCCCCAGUAGUGCUUUCUA |
| | CUUUAUGGUGGUCUUUGAAUAAAGUCUGAGUGGGCGGC |
| | (3'UTR with miR 142-5p binding site) |
| 108 | UGAUAAUAGAGUAGUGCUUUCUACUUUAUGGCUGGAGCCUCGGUGGCCAUG |
| | CUUCUUGCCCCUUGGGCCAGUAGUGCUUUCUACUUUAUGUCCCCCAGCCC |
| | CUCCUCCCCUUCCUGCACCCGUACCCCAGUAGUGCUUUCUACUUUAUGGU |
| | GGUCUUUGAAUAAAGUCUGAGUGGGCGGC |
| | (3'UTR with 3 miR 142-5p binding sites) |
| 109 | UGAUAAUAGAGUAGUGCUUUCUACUUUAUGGCUGGAGCCUCGGUGGCCAUG |
| | CUUCUUGCCCCUUGGGCCUCCAUAAAGUAGGAAACACUACAUCCCCCAGC |
| | CCCUCCUCCCCUUCCUGCACCCGUACCCCCAGUAGUGCUUUCUACUUUAUG |
| | GUGGUCUUUGAAUAAAGUCUGAGUGGGCGGC |

TABLE 4-continued

3' UTRs, miR Sequences, and miR Binding Sites

| SEQ ID NO: | Sequence |
|---|---|

(3'UTR with 2 miR 142-5p binding sites and 1 miR 142-3p binding site)

110 UGAUAAUAGGCUGGAGCCUCGGUGGCCAUGCUUCUUGCCCCUUGGGCCUCC
CCCCAGCCCCUCCUCCCCUUCCUGCACCCGUACCCCACCCCUAUCACAAU
UAGCAUUAAGUGGUCUUUGAAUAAAGUCUGAGUGGGCGGC
(3'UTR with miR 155-5p binding site)

111 UGAUAAUAGACCCCUAUCACAAUUAGCAUUAAGCUGGAGCCUCGGUGGCCA
UGCUUCUUGCCCCUUGGGCCACCCCUAUCACAAUUAGCAUUAAUCCCCCCA
GCCCCUCCUCCCCUUCCUGCACCCGUACCCCCACCCCUAUCACAAUUAGCA
UUAAGUGGUCUUUGAAUAAAGUCUGAGUGGGCGGC
(3' UTR with 3 miR 155-5p binding sites)

112 UGAUAAUAGACCCCUAUCACAAUUAGCAUUAAGCUGGAGCCUCGGUGGCCA
UGCUUCUUGCCCCUUGGGCCUCCAUAAAGUAGGAAACACUACAUCCCCCCA
GCCCCUCCUCCCCUUCCUGCACCCGUACCCCCACCCCUAUCACAAUUAGCA
UUAAGUGGUCUUUGAAUAAAGUCUGAGUGGGCGGC
(3'UTR with 2 miR 155-5p binding sites and 1 miR 142-3p binding site)

113 UGAUAAUAGGCUGGAGCCUCGGUGGCCAUGCUUCUUGCCCCUUGGGCCUCC
AUAAAGUAGGAAACACUACAUCCCCCCAGCCCCUCCUCCCCUUCCUGCACC
CGUACCCCCGUGGUCUUUGAAUAAAGUCUGAGUGGGCGGC
(3'UTR with miR 142-3p binding site, P3 insertion)

114 AGUAGUGCUUUCUACUUUAUG
(miR-142-5p binding site)

115 GGGAAAUAAGAGUCCAUAAAGUAGGAAACACUACAAGAAAAGAAGAGUAAG
AAGAAAUAUAAGAGCCACC
(5' UTR with miR142-3p binding site at position p1)

116 GGGAAAUAAGAGAGAAAAGAAGAGUAAUCCAUAAAGUAGGAAACACUACAG
AAGAAAUAUAAGAGCCACC
(5' UTR with miR142-3p binding site at position p2)

117 GGGAAAUAAGAGAGAAAAGAAGAGUAAGAAGAAAUAUAAUCCAUAAAGUAG
GAAACACUACAGAGCCACC
(5' UTR with miR142-3p binding site at position p3)

118 UGAUAAUAGAGUAGUGCUUUCUACUUUAUGGCUGGAGCCUCGGUGGCCAUG
CUUCUUGCCCCUUGGGCCAGUAGUGCUUUCUACUUUAUGUCCCCCCAGCCC
CUCUCCCUUCCUGCACCCGUACCCCCAGUAGUGCUUUCUACUUUAUGGUG
GUCUUUGAAUAAAGUCUGAGUGGGCGGC

TABLE 4-continued

3' UTRs, miR Sequences, and miR Binding Sites

| SEQ ID NO: | Sequence |
|---|---|

(3'UTR with 3 miR 142-5p binding sites)

161 UGAUAAUAGGCUGGAGCCUCGGUGGCCUAGCUUCUUGCCCCUUGGGCCUCC
CCCCAGCCCCUCCUCCCCUUCCUGCACCCGUACCCCCUCCAUAAAGUAGGA
AACACUACAGUGGUCUUUGAAUAAAGUCUGAGUGGGCGGC (3' UTR with miR 142-3p binding site variant 2)

162 UGAUAAUAGGCUGGAGCCUCGGUGGCCUAGCUUCUUGCCCCUUGGGCCUCC
CCCCAGCCCCUCCUCCCCUUCCUGCACCCGUACCCCCGUGGUCUUUGAAUA
AAGUCUGAGUGGGCGGC (3' UTR, no miR binding sites variant 2)

163 UGAUAAUAGGCUGGAGCCUCGGUGGCCUAGCUUCUUGCCCCUUGGGCCUCC
CCCCAGCCCCUCCUCCCCUUCCUGCACCCGUACCCCCGCAUUAUUACUCA
CGGUACGAGUGGUCUUUGAAUAAAGUCUGAGUGGGCGGC (3' UTR with miR 126-3p binding site variant 3)

164 UGAUAAUAGUCCAUAAAGUAGGAAACACUACAGCUGGAGCCUCGGUGGCCU
AGCUUCUUGCCCCUUGGGCCUCCAUAAAGUAGGAAACACUACAUCCCCCCA
GCCCCUCCUCCCCUUCCUGCACCCGUACCCCCUCCAUAAAGUAGGAAACAC
UACAGUGGUCUUUGAAUAAAGUCUGAGUGGGCGGC (3' UTR with 3 miR 142-3p binding sites variant 2)

165 UGAUAAUAGUCCAUAAAGUAGGAAACACUACAGCUGGAGCCUCGGUGGCCU
AGCUUCUUGCCCCUUGGGCCUCCCCCCAGCCCCUCCUCCCCUUCCUGCACC
CGUACCCCCGUGGUCUUUGAAUAAAGUCUGAGUGGGCGGC (3'UTR with miR 142-3p binding site, P1 insertion variant 2)

166 UGAUAAUAGGCUGGAGCCUCGGUGGCUCCAUAAAGUAGGAAACACUACACU
AGCUUCUUGCCCCUUGGGCCUCCCCCCAGCCCCUCCUCCCCUUCCUGCACC
CGUACCCCCGUGGUCUUUGAAUAAAGUCUGAGUGGGCGGC (3'UTR with miR 142-3p binding site, P2 insertion variant 2)

167 UGAUAAUAGGCUGGAGCCUCGGUGGCCUAGCUUCUUGCCCCUUGGGCCUCC
AUAAAGUAGGAAACACUACAUCCCCCAGCCCCUCCUCCCCUUCCUGCACC
CGUACCCCCGUGGUCUUUGAAUAAAGUCUGAGUGGGCGGC (3'UTR with miR 142-3p binding site, P3 insertion variant 2)

168 UGAUAAUAGGCUGGAGCCUCGGUGGCCUAGCUUCUUGCCCCUUGGGCCUCC
CCCCAGCCCCUCCUCCCCUUCCUGCACCCGUACCCCCACCCCUAUCACAAU
UAGCAUUAAGUGGUCUUUGAAUAAAGUCUGAGUGGGCGGC (3'UTR with miR 155-5p binding site variant 2)

169 UGAUAAUAGACCCCUAUCACAAUUAGCAUUAAGCUGGAGCCUCGGUGGCCU
AGCUUCUUGCCCCUUGGGCCACCCCUAUCACAAUUAGCAUUAAUCCCCCCA
GCCCCUCCUCCCCUUCCUGCACCCGUACCCCCACCCCUAUCACAAUUAGCA
UUAAGUGGUCUUUGAAUAAAGUCUGAGUGGGCGGC

TABLE 4-continued

3' UTRs, miR Sequences, and miR Binding Sites

SEQ ID NO: Sequence (3' UTR with 3 miR 155-5p binding sites variant 2)

170    UGAUAAUAGACCCCUAUCACAAUUAGCAUUAAGCUGGAGCCUCGGUGGCCU

AGCUUCUUGCCCCUUGGGCCUCCAUAAAGUAGGAAACACUACAUCCCCCCA

GCCCCUCCUCCCCUUCCUGCACCCGUACCCCCACCCCUAUCACAAUUAGCA

UUAAGUGGUCUUUGAAUAAAGUCUGAGUGGGCGGC (3'UTR with 2 miR 155-5p binding sites and 1 miR 142-3p binding site variant 2)

Stop codon = bold
miR 142-3p binding site = underline
miR 126-3p binding site = bold underline
miR 155-5p binding site = shaded
miR 142-5p binding site = shaded and bold underline In one embodiment, the polynucleotide of the invention comprises a 5' UTR, a codon optimized open reading frame encoding a polypeptide of interest, a 3' UTR comprising the at least one miRNA binding site for a miR expressed in immune cells, and a 3' tailing region of linked nucleosides. In various embodiments, the 3' UTR comprises 1-4, at least two, one, two, three or four miRNA binding sites for miRs expressed in immune cells, preferably abundantly or preferentially expressed in immune cells.

In one embodiment, the at least one miRNA expressed in immune cells is a miR-142-3p microRNA binding site. In one embodiment, the miR-142-3p microRNA binding site comprises the sequence shown in SEQ ID NO: 30. In one embodiment, the 3' UTR of the mRNA comprising the miR-142-3p microRNA binding site comprises the sequence shown in SEQ ID NO: 88.

In one embodiment, the at least one miRNA expressed in immune cells is a miR-126 microRNA binding site. In one embodiment, the miR-126 binding site is a miR-126-3p binding site. In one embodiment, the miR-126-3p microRNA binding site comprises the sequence shown in SEQ ID NO: 85. In one embodiment, the 3' UTR of the mRNA of the invention comprising the miR-126-3p microRNA binding site comprises the sequence shown in SEQ ID NO: 103.

Non-limiting exemplary sequences for miRs to which a microRNA binding site(s) of the disclosure can bind include the following: miR-142-3p (SEQ ID NO: 29), miR-142-5p (SEQ ID NO: 31), miR-146-3p (SEQ ID NO: 89), miR-146-5p (SEQ ID NO: 90), miR-155-3p (SEQ ID NO: 91), miR-155-5p (SEQ ID NO: 92), miR-126-3p (SEQ ID NO: 84), miR-126-5p (SEQ ID NO: 86), miR-16-3p (SEQ ID NO: 93), miR-16-5p (SEQ ID NO: 94), miR-21-3p (SEQ ID NO: 95), miR-21-5p (SEQ ID NO: 96), miR-223-3p (SEQ ID NO: 97), miR-223-5p (SEQ ID NO: 98), miR-24-3p (SEQ ID NO: 99), miR-24-5p (SEQ ID NO: 100), miR-27-3p (SEQ ID NO: 101) and miR-27-5p (SEQ ID NO: 102). Other suitable miR sequences expressed in immune cells (e.g., abundantly or preferentially expressed in immune cells) are known and available in the art, for example at the University of Manchester's microRNA database, miRBase. Sites that bind any of the aforementioned miRs can be designed based on Watson-Crick complementarity to the miR, typically 100% complementarity to the miR, and inserted into an mRNA construct of the disclosure as described herein.

In another embodiment, a polynucleotide of the present invention (e.g., and mRNA, e.g., the 3' UTR thereof) can comprise at least one miRNA binding site to thereby reduce or inhibit accelerated blood clearance, for example by reducing or inhibiting production of IgMs, e.g., against PEG, by B cells and/or reducing or inhibiting proliferation and/or activation of pDCs, and can comprise at least one miRNA binding site for modulating tissue expression of an encoded protein of interest.

The distance between the miRNA binding sites can vary considerably; a number of different constructs have been tested with differing placement of the two miRNA binding sites and all have been functional. In certain embodiments, a nucleotide spacer is positioned between the two miRNA binding sites of a sufficient length to allow binding of RISC to each one. In one embodiment, the two miRNA binding sites are positioned about 40 bases apart from each other and the overall length of the 3' UTR is approximately 100-110 bases.

miRNA gene regulation can be influenced by the sequence surrounding the miRNA such as, but not limited to, the species of the surrounding sequence, the type of sequence (e.g., heterologous, homologous, exogenous, endogenous, or artificial), regulatory elements in the surrounding sequence and/or structural elements in the surrounding sequence. The miRNA can be influenced by the 5'UTR and/or 3'UTR. As a non-limiting example, a non-human 3'UTR can increase the regulatory effect of the miRNA sequence on the expression of a polypeptide of interest compared to a human 3'UTR of the same sequence type.

In one embodiment, other regulatory elements and/or structural elements of the 5'UTR can influence miRNA mediated gene regulation. One example of a regulatory element and/or structural element is a structured IRES (Internal Ribosome Entry Site) in the 5'UTR, which is necessary for the binding of translational elongation factors to initiate protein translation. EIF4A$_2$ binding to this secondarily structured element in the 5'-UTR is necessary for miRNA mediated gene expression (Meijer H A et al., Science, 2013, 340, 82-85, herein incorporated by reference in its entirety). The polynucleotides of the invention can further include this structured 5'UTR in order to enhance microRNA mediated gene regulation.

At least one miRNA binding site can be engineered into the 3'UTR of a polynucleotide of the invention. In this context, at least two, at least three, at least four, at least five, at least six, at least seven, at least eight, at least nine, at least ten, or more miRNA binding sites can be engineered into a 3'UTR of a polynucleotide of the invention. For example, 1 to 10, 1 to 9, 1 to 8, 1 to 7, 1 to 6, 1 to 5, 1 to 4, 1 to 3, 2, or 1 miRNA binding sites can be engineered into the 3'UTR of a polynucleotide of the invention. In one embodiment, miRNA binding sites incorporated into a polynucleotide of the invention can be the same or can be different miRNA sites. A combination of different miRNA binding sites incorporated into a polynucleotide of the invention can include combinations in which more than one copy of any of the different miRNA sites are incorporated. In another embodiment, miRNA binding sites incorporated into a polynucleotide of the invention can target the same or different tissues in the body. As a non-limiting example, through the introduction of tissue-, cell-type-, or disease-specific miRNA binding sites in the 3'-UTR of a polynucleotide of the invention, the degree of expression in specific cell types (e.g., myeloid cells, endothelial cells, etc.) can be reduced.

In one embodiment, a miRNA binding site can be engineered near the 5' terminus of the 3'UTR, about halfway between the 5' terminus and 3' terminus of the 3'UTR and/or near the 3' terminus of the 3'UTR in a polynucleotide of the invention. As a non-limiting example, a miRNA binding site can be engineered near the 5' terminus of the 3'UTR and about halfway between the 5' terminus and 3' terminus of the 3'UTR. As another non-limiting example, a miRNA binding site can be engineered near the 3' terminus of the 3'UTR and about halfway between the 5' terminus and 3' terminus of the 3'UTR. As yet another non-limiting example, a miRNA binding site can be engineered near the 5' terminus of the 3'UTR and near the 3' terminus of the 3'UTR.

In another embodiment, a 3'UTR can comprise 1, 2, 3, 4, 5, 6, 7, 8, 9, or 10 miRNA binding sites. The miRNA binding sites can be complementary to a miRNA, miRNA seed sequence, and/or miRNA sequences flanking the seed sequence.

In some embodiments, the expression of a polynucleotide of the invention can be controlled by incorporating at least one sensor sequence in the polynucleotide and formulating the polynucleotide for administration. As a non-limiting example, a polynucleotide of the invention can be targeted to a tissue or cell by incorporating a miRNA binding site and formulating the polynucleotide in a lipid nanoparticle comprising an ionizable lipid, including any of the lipids described herein.

A polynucleotide of the invention can be engineered for more targeted expression in specific tissues, cell types, or biological conditions based on the expression patterns of miRNAs in the different tissues, cell types, or biological conditions. Through introduction of tissue-specific miRNA binding sites, a polynucleotide of the invention can be designed for optimal protein expression in a tissue or cell, or in the context of a biological condition.

In some embodiments, a polynucleotide of the invention can be designed to incorporate miRNA binding sites that either have 100% identity to known miRNA seed sequences or have less than 100% identity to miRNA seed sequences. In some embodiments, a polynucleotide of the invention can be designed to incorporate miRNA binding sites that have at least: 60%, 65%, 70%, 75%, 80%, 85%, 90%, 95%, 96%, 97%, 98%, or 99% identity to known miRNA seed sequences. The miRNA seed sequence can be partially mutated to decrease miRNA binding affinity and as such result in reduced downmodulation of the polynucleotide. In essence, the degree of match or mis-match between the miRNA binding site and the miRNA seed can act as a rheostat to more finely tune the ability of the miRNA to modulate protein expression. In addition, mutation in the non-seed region of a miRNA binding site can also impact the ability of a miRNA to modulate protein expression.

In one embodiment, a miRNA sequence can be incorporated into the loop of a stem loop.

In another embodiment, a miRNA seed sequence can be incorporated in the loop of a stem loop and a miRNA binding site can be incorporated into the 5' or 3' stem of the stem loop.

In one embodiment, a translation enhancer element (TEE) can be incorporated on the 5'end of the stem of a stem loop and a miRNA seed can be incorporated into the stem of the stem loop. In another embodiment, a TEE can be incorporated on the 5' end of the stem of a stem loop, a miRNA seed can be incorporated into the stem of the stem loop and a miRNA binding site can be incorporated into the 3' end of the stem or the sequence after the stem loop. The miRNA seed and the miRNA binding site can be for the same and/or different miRNA sequences.

In one embodiment, the incorporation of a miRNA sequence and/or a TEE sequence changes the shape of the stem loop region which can increase and/or decrease translation. (see e.g., Kedde et al., "A Pumilio-induced RNA structure switch in p27-3'UTR controls miR-221 and miR-22 accessibility." Nature Cell Biology. 2010, incorporated herein by reference in its entirety).

In one embodiment, the 5'-UTR of a polynucleotide of the invention can comprise at least one miRNA sequence. The miRNA sequence can be, but is not limited to, a 19 or 22 nucleotide sequence and/or a miRNA sequence without the seed.

In one embodiment the miRNA sequence in the 5'UTR can be used to stabilize a polynucleotide of the invention described herein.

In another embodiment, a miRNA sequence in the 5'UTR of a polynucleotide of the invention can be used to decrease the accessibility of the site of translation initiation such as, but not limited to a start codon. See, e.g., Matsuda et al., PLoS One. 2010 11(5):e15057; incorporated herein by reference in its entirety, which used antisense locked nucleic acid (LNA) oligonucleotides and exon junction complexes (EJCs) around a start codon (−4 to +37 where the A of the AUG codons is +1) in order to decrease the accessibility to the first start codon (AUG). Matsuda showed that altering the sequence around the start codon with an LNA or EJC affected the efficiency, length and structural stability of a polynucleotide. A polynucleotide of the invention can comprise a miRNA sequence, instead of the LNA or EJC sequence described by Matsuda et al, near the site of translation initiation in order to decrease the accessibility to the site of translation initiation. The site of translation initiation can be prior to, after or within the miRNA sequence. As a non-limiting example, the site of translation initiation can be located within a miRNA sequence such as a seed sequence or binding site.

In some embodiments, a polynucleotide of the invention can include at least one miRNA in order to dampen the antigen presentation by antigen presenting cells. The miRNA can be the complete miRNA sequence, the miRNA seed sequence, the miRNA sequence without the seed, or a combination thereof. As a non-limiting example, a miRNA incorporated into a polynucleotide of the invention can be specific to the hematopoietic system. As another non-limiting example, a miRNA incorporated into a polynucleotide of the invention to dampen antigen presentation is miR-142-3p.

In some embodiments, a polynucleotide of the invention can include at least one miRNA in order to dampen expression of the encoded polypeptide in a tissue or cell of interest. As a non-limiting example, a polynucleotide of the invention can include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence.

In some embodiments, a polynucleotide of the invention can comprise at least one miRNA binding site in the 3'UTR in order to selectively degrade mRNA therapeutics in the immune cells to subdue unwanted immunogenic reactions caused by therapeutic delivery. As a non-limiting example, the miRNA binding site can make a polynucleotide of the invention more unstable in antigen presenting cells. Non-limiting examples of these miRNAs include mir-142-5p, mir-142-3p, mir-146a-5p, and mir-146-3p.

In one embodiment, a polynucleotide of the invention comprises at least one miRNA sequence in a region of the polynucleotide that can interact with a RNA binding protein.

In some embodiments, the polynucleotide of the invention (e.g., a RNA, e.g., an mRNA) comprising (i) a sequence-optimized nucleotide sequence (e.g., an ORF) encoding a GLA polypeptide (e.g., the wild-type sequence, functional fragment, or variant thereof) and (ii) a miRNA binding site (e.g., a miRNA binding site that binds to miR-142).

In some embodiments, the polynucleotide of the invention comprises a uracil-modified sequence encoding a GLA polypeptide disclosed herein and a miRNA binding site disclosed herein, e.g., a miRNA binding site that binds to miR-142 and/or a miRNA binding site that binds to miR-126. In some embodiments, the polynucleotide of the invention comprises a uracil-modified sequence encoding a polypeptide disclosed herein and a miRNA binding site disclosed herein, e.g., a miRNA binding site that binds to miR-142miR-126, miR-142, miR-144, miR-146, miR-150, miR-155, miR-16, miR-21, miR-223, miR-24, miR-27 or miR-26a. In some embodiments, the miRNA binding site binds to miR126-3p, miR-142-3p, miR-142-5p, or miR-155. In some embodiments, the polynucleotide of the invention comprises a uracil-modified sequence encoding a polypeptide disclosed herein and at least two different microRNA binding sites, wherein the microRNA is expressed in an immune cell of hematopoietic lineage or a cell that expresses TLR7 and/or TLR8 and secretes pro-inflammatory cytokines and/or chemokines, and wherein the polynucleotide comprises one or more modified nucleobases. In some embodiments, the uracil-modified sequence encoding a GLA polypeptide comprises at least one chemically modified nucleobase, e.g., 5-methoxyuracil. In some embodiments, at least 95% of a type of nucleobase (e.g., uracil) in a uracil-modified sequence encoding a GLA polypeptide of the invention are modified nucleobases. In some embodiments, at least 95% of uracil in a uracil-modified sequence encoding a GLA polypeptide is 5-methoxyuridine. In some embodiments, the polynucleotide (e.g., a RNA, e.g., an mRNA) disclosed herein, e.g., comprising an miRNA binding site, is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5: 1.5.

13. 3' UTRs

In certain embodiments, a polynucleotide of the present invention (e.g., a polynucleotide comprising a nucleotide sequence encoding a GLA polypeptide of the invention) further comprises a 3' UTR.

3'-UTR is the section of mRNA that immediately follows the translation termination codon and often contains regulatory regions that post-transcriptionally influence gene expression. Regulatory regions within the 3'-UTR can influence polyadenylation, translation efficiency, localization, and stability of the mRNA. In one embodiment, the 3'-UTR useful for the invention comprises a binding site for regulatory proteins or microRNAs.

In certain embodiments, the 3' UTR useful for the polynucleotides of the invention comprises a 3'UTR selected from the group consisting of SEQ ID NO: 51-75, 81-82, 88, 103, 106-113, 118, and 161-170, or any combination thereof. In some embodiments, the 3' UTR comprises a nucleic acid sequence selected from the group consisting of SEQ ID NOs: 81, 82, 103, or any combination thereof.

In certain embodiments, the 3' UTR sequence useful for the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of SEQ ID NO: 51-75, 81-82, 88, 103, 106-113, 118, and 161-170, or any combination thereof.

14. Regions Having a 5' Cap

The invention also includes a polynucleotide that comprises both a 5' Cap and a polynucleotide of the present invention (e.g., a polynucleotide comprising a nucleotide sequence encoding a GLA polypeptide).

The 5' cap structure of a natural mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns during mRNA splicing.

Endogenous mRNA molecules can be 5'-end capped generating a 5'-ppp-5'-triphosphate linkage between a terminal guanosine cap residue and the 5'-terminal transcribed sense nucleotide of the mRNA molecule. This 5'-guanylate cap can then be methylated to generate an N7-methyl-guanylate residue. The ribose sugars of the terminal and/or anteterminal transcribed nucleotides of the 5' end of the mRNA can optionally also be 2'-O-methylated. 5'-decapping through hydrolysis and cleavage of the guanylate cap structure can target a nucleic acid molecule, such as an mRNA molecule, for degradation.

In some embodiments, the polynucleotides of the present invention (e.g., a polynucleotide comprising a nucleotide sequence encoding a GLA polypeptide) incorporate a cap moiety.

In exemplary embodiments, a polynucleotide of the invention, e.g., an mRNA, or in particular, the 5' UTR of a polynucleotide (or mRNA) comprises a Cap structure, or is capped.

In exemplary embodiments, the portions or segments of a polynucleotide of the invention, e.g., an mRNA, for example, the 5' UTR, open reading frame, 3' UTR and polyA tail are operably linked.

In some embodiments, polynucleotides of the present invention (e.g., a polynucleotide comprising a nucleotide sequence encoding a GLA polypeptide) comprise a non-hydrolyzable cap structure preventing decapping and thus increasing mRNA half-life. Because cap structure hydrolysis requires cleavage of 5'-ppp-5' phosphorodiester linkages, modified nucleotides can be used during the capping reaction. For example, a Vaccinia Capping Enzyme from New England Biolabs (Ipswich, Mass.) can be used with α-thio-guanosine nucleotides according to the manufacturer's instructions to create a phosphorothioate linkage in the 5'-ppp-5' cap. Additional modified guanosine nucleotides can be used such as α-methyl-phosphonate and seleno-phosphate nucleotides.

Additional modifications include, but are not limited to, 2'-O-methylation of the ribose sugars of 5'-terminal and/or 5'-anteterminal nucleotides of the polynucleotide (as mentioned above) on the 2'-hydroxyl group of the sugar ring. Multiple distinct 5'-cap structures can be used to generate the 5'-cap of a nucleic acid molecule, such as a polynucleotide that functions as an mRNA molecule. Cap analogs, which herein are also referred to as synthetic cap analogs, chemical caps, chemical cap analogs, or structural or functional cap analogs, differ from natural (i.e., endogenous, wild-type or physiological) 5'-caps in their chemical structure, while retaining cap function. Cap analogs can be chemically (i.e., non-enzymatically) or enzymatically synthesized and/or linked to the polynucleotides of the invention.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine (m$^7$G-3'mppp-G; which can equivalently be designated 3' O-Me-m7G(5')ppp(5')G). The 3'-O atom of the other, unmodified, guanine becomes linked to the 5'-terminal nucleotide of the capped polynucleotide. The N7- and 3'-O-methlyated guanine provides the terminal moiety of the capped polynucleotide.

Another exemplary cap is mCAP, which is similar to ARCA but has a 2'-O-methyl group on guanosine (i.e., N7,2'-O-dimethyl-guanosine-5'-triphosphate-5'-guanosine, m$^7$Gm-ppp-G).

In some embodiments, the cap is a dinucleotide cap analog. As a non-limiting example, the dinucleotide cap analog can be modified at different phosphate positions with a boranophosphate group or a phophoroselenoate group such as the dinucleotide cap analogs described in U.S. Pat. No. 8,519,110, the contents of which are herein incorporated by reference in its entirety.

In another embodiment, the cap is a cap analog is a N7-(4-chlorophenoxyethyl) substituted dicucleotide form of a cap analog known in the art and/or described herein. Non-limiting examples of a N7-(4-chlorophenoxyethyl) substituted dicucleotide form of a cap analog include a N7-(4-chlorophenoxyethyl)-G(5')ppp(5')G and a N7-(4-chlorophenoxyethyl)-m$^{3'-O}$G(5)ppp(5')G cap analog (See, e.g., the various cap analogs and the methods of synthesizing cap analogs described in Kore et al. Bioorganic & Medicinal Chemistry 2013 21:4570-4574; the contents of which are herein incorporated by reference in its entirety). In another embodiment, a cap analog of the present invention is a 4-chloro/bromophenoxyethyl analog.

While cap analogs allow for the concomitant capping of a polynucleotide or a region thereof, in an in vitro transcription reaction, up to 20% of transcripts can remain uncapped. This, as well as the structural differences of a cap analog from an endogenous 5'-cap structures of nucleic acids produced by the endogenous, cellular transcription machinery, can lead to reduced translational competency and reduced cellular stability.

Polynucleotides of the invention (e.g., a polynucleotide comprising a nucleotide sequence encoding a GLA polypeptide) can also be capped post-manufacture (whether IVT or chemical synthesis), using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'cap structures of the present invention are those that, among other things, have enhanced binding of cap binding proteins, increased half-life, reduced susceptibility to 5' endonucleases and/or reduced 5'decapping, as compared to synthetic 5'cap structures known in the art (or to a wild-type, natural or physiological 5'cap structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include, but are not limited to, 7mG(5')ppp(5')N, pN2p (cap 0), 7mG(5')ppp(5')NlmpNp (cap 1), and 7mG(5')-ppp(5')NlmpN2mp (cap 2).

As a non-limiting example, capping chimeric polynucleotides post-manufacture can be more efficient as nearly 100% of the chimeric polynucleotides can be capped. This is in contrast to ~80% when a cap analog is linked to a chimeric polynucleotide in the course of an in vitro transcription reaction.

According to the present invention, 5' terminal caps can include endogenous caps or cap analogs. According to the present invention, a 5' terminal cap can comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

15. Poly-A Tails

In some embodiments, the polynucleotides of the present disclosure (e.g., a polynucleotide comprising a nucleotide sequence encoding a GLA polypeptide) further comprise a poly-A tail. In further embodiments, terminal groups on the poly-A tail can be incorporated for stabilization. In other embodiments, a poly-A tail comprises des-3' hydroxyl tails.

During RNA processing, a long chain of adenine nucleotides (poly-A tail) can be added to a polynucleotide such as an mRNA molecule in order to increase stability. Immediately after transcription, the 3' end of the transcript can be cleaved to free a 3' hydroxyl. Then poly-A polymerase adds a chain of adenine nucleotides to the RNA. The process, called polyadenylation, adds a poly-A tail that can be between, for example, approximately 80 to approximately 250 residues long, including approximately 80, 90, 100, 110, 120, 130, 140, 150, 160, 170, 180, 190, 200, 210, 220, 230, 240 or 250 residues long.

PolyA tails can also be added after the construct is exported from the nucleus.

According to the present invention, terminal groups on the poly A tail can be incorporated for stabilization. Polynucleotides of the present invention can include des-3' hydroxyl tails. They can also include structural moieties or 2'-Omethyl modifications as taught by Junjie Li, et al. (Current Biology, Vol. 15, 1501-1507, Aug. 23, 2005, the contents of which are incorporated herein by reference in its entirety).

The polynucleotides of the present invention can be designed to encode transcripts with alternative polyA tail structures including histone mRNA. According to Norbury, "Terminal uridylation has also been detected on human replication-dependent histone mRNAs. The turnover of these mRNAs is thought to be important for the prevention of potentially toxic histone accumulation following the completion or inhibition of chromosomal DNA replication. These mRNAs are distinguished by their lack of a 3' poly(A) tail, the function of which is instead assumed by a stable stem-loop structure and its cognate stem-loop binding protein (SLBP); the latter carries out the same functions as those of PABP on polyadenylated mRNAs" (Norbury, "Cytoplasmic RNA: a case of the tail wagging the dog," Nature Reviews Molecular Cell Biology; AOP, published online 29 Aug. 2013; doi:10.1038/nrm3645) the contents of which are incorporated herein by reference in its entirety.

Unique poly-A tail lengths provide certain advantages to the polynucleotides of the present invention. Generally, the length of a poly-A tail, when present, is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides).

In some embodiments, the polynucleotide or region thereof includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In some embodiments, the poly-A tail is designed relative to the length of the overall polynucleotide or the length of a particular region of the polynucleotide. This design can be based on the length of a coding region, the length of a particular feature or region or based on the length of the ultimate product expressed from the polynucleotides.

In this context, the poly-A tail can be 10, 20, 30, 40, 50, 60, 70, 80, 90, or 100% greater in length than the polynucleotide or feature thereof. The poly-A tail can also be designed as a fraction of the polynucleotides to which it belongs. In this context, the poly-A tail can be 10, 20, 30, 40, 50, 60, 70, 80, or 90% or more of the total length of the construct, a construct region or the total length of the construct minus the poly-A tail. Further, engineered binding sites and conjugation of polynucleotides for Poly-A binding protein can enhance expression.

Additionally, multiple distinct polynucleotides can be linked together via the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In some embodiments, the polynucleotides of the present invention are designed to include a polyA-G Quartet region. The G-quartet is a cyclic hydrogen bonded array of four guanine nucleotides that can be formed by G-rich sequences in both DNA and RNA. In this embodiment, the G-quartet is incorporated at the end of the poly-A tail. The resultant polynucleotide is assayed for stability, protein production and other parameters including half-life at various time points. It has been discovered that the polyA-G quartet results in protein production from an mRNA equivalent to at least 75% of that seen using a poly-A tail of 120 nucleotides alone.

16. Start Codon Region

The invention also includes a polynucleotide that comprises both a start codon region and the polynucleotide described herein (e.g., a polynucleotide comprising a nucleotide sequence encoding a GLA polypeptide). In some embodiments, the polynucleotides of the present invention can have regions that are analogous to or function like a start codon region.

In some embodiments, the translation of a polynucleotide can initiate on a codon that is not the start codon AUG. Translation of the polynucleotide can initiate on an alternative start codon such as, but not limited to, ACG, AGG, AAG, CTG/CUG, GTG/GUG, ATA/AUA, ATT/AUU, TTG/UUG (see Touriol et al. Biology of the Cell 95 (2003) 169-178 and Matsuda and Mauro PLoS ONE, 2010 5:11; the contents of each of which are herein incorporated by reference in its entirety).

As a non-limiting example, the translation of a polynucleotide begins on the alternative start codon ACG. As another non-limiting example, polynucleotide translation begins on the alternative start codon CTG or CUG. As yet another non-limiting example, the translation of a polynucleotide begins on the alternative start codon GTG or GUG.

Nucleotides flanking a codon that initiates translation such as, but not limited to, a start codon or an alternative start codon, are known to affect the translation efficiency, the length and/or the structure of the polynucleotide. (See, e.g., Matsuda and Mauro PLoS ONE, 2010 5:11; the contents of which are herein incorporated by reference in its entirety). Masking any of the nucleotides flanking a codon that initiates translation can be used to alter the position of translation initiation, translation efficiency, length and/or structure of a polynucleotide.

In some embodiments, a masking agent can be used near the start codon or alternative start codon in order to mask or hide the codon to reduce the probability of translation initiation at the masked start codon or alternative start codon. Non-limiting examples of masking agents include antisense locked nucleic acids (LNA) polynucleotides and exon-junction complexes (EJCs) (See, e.g., Matsuda and Mauro describing masking agents LNA polynucleotides and EJCs (PLoS ONE, 2010 5:11); the contents of which are herein incorporated by reference in its entirety).

In another embodiment, a masking agent can be used to mask a start codon of a polynucleotide in order to increase the likelihood that translation will initiate on an alternative start codon. In some embodiments, a masking agent can be used to mask a first start codon or alternative start codon in order to increase the chance that translation will initiate on a start codon or alternative start codon downstream to the masked start codon or alternative start codon.

In some embodiments, a start codon or alternative start codon can be located within a perfect complement for a miRNA binding site. The perfect complement of a miRNA binding site can help control the translation, length and/or structure of the polynucleotide similar to a masking agent. As a non-limiting example, the start codon or alternative start codon can be located in the middle of a perfect complement for a miRNA binding site. The start codon or alternative start codon can be located after the first nucleotide, second nucleotide, third nucleotide, fourth nucleotide, fifth nucleotide, sixth nucleotide, seventh nucleotide, eighth nucleotide, ninth nucleotide, tenth nucleotide, eleventh nucleotide, twelfth nucleotide, thirteenth nucleotide, fourteenth nucleotide, fifteenth nucleotide, sixteenth nucleotide, seventeenth nucleotide, eighteenth nucleotide, nineteenth nucleotide, twentieth nucleotide or twenty-first nucleotide.

In another embodiment, the start codon of a polynucleotide can be removed from the polynucleotide sequence in order to have the translation of the polynucleotide begin on a codon that is not the start codon. Translation of the polynucleotide can begin on the codon following the removed start codon or on a downstream start codon or an alternative start codon. In a non-limiting example, the start codon ATG or AUG is removed as the first 3 nucleotides of the polynucleotide sequence in order to have translation initiate on a downstream start codon or alternative start codon. The polynucleotide sequence where the start codon was removed can further comprise at least one masking agent for the downstream start codon and/or alternative start codons in order to control or attempt to control the initiation of translation, the length of the polynucleotide and/or the structure of the polynucleotide.

17. Stop Codon Region

The invention also includes a polynucleotide that comprises both a stop codon region and the polynucleotide described herein (e.g., a polynucleotide comprising a nucleotide sequence encoding a GLA polypeptide). In some embodiments, the polynucleotides of the present invention can include at least two stop codons before the 3' untranslated region (UTR). The stop codon can be selected from TGA, TAA and TAG in the case of DNA, or from UGA, UAA and UAG in the case of RNA. In some embodiments, the polynucleotides of the present invention include the stop codon TGA in the case or DNA, or the stop codon UGA in the case of RNA, and one additional stop codon. In a further embodiment the addition stop codon can be TAA or UAA. In another embodiment, the polynucleotides of the present invention include three consecutive stop codons, four stop codons, or more.

18. Insertions and Substitutions

The invention also includes a polynucleotide of the present disclosure that further comprises insertions and/or substitutions.

In some embodiments, the 5'UTR of the polynucleotide can be replaced by the insertion of at least one region and/or string of nucleosides of the same base. The region and/or string of nucleotides can include, but is not limited to, at least 3, at least 4, at least 5, at least 6, at least 7 or at least 8 nucleotides and the nucleotides can be natural and/or unnatural. As a non-limiting example, the group of nucleotides can include 5-8 adenine, cytosine, thymine, a string of any of the other nucleotides disclosed herein and/or combinations thereof.

In some embodiments, the 5'UTR of the polynucleotide can be replaced by the insertion of at least two regions and/or strings of nucleotides of two different bases such as, but not limited to, adenine, cytosine, thymine, any of the other nucleotides disclosed herein and/or combinations thereof. For example, the 5'UTR can be replaced by inserting 5-8 adenine bases followed by the insertion of 5-8 cytosine bases. In another example, the 5'UTR can be replaced by inserting 5-8 cytosine bases followed by the insertion of 5-8 adenine bases.

In some embodiments, the polynucleotide can include at least one substitution and/or insertion downstream of the transcription start site that can be recognized by an RNA polymerase. As a non-limiting example, at least one substitution and/or insertion can occur downstream of the transcription start site by substituting at least one nucleic acid in the region just downstream of the transcription start site (such as, but not limited to, +1 to +6). Changes to region of nucleotides just downstream of the transcription start site can affect initiation rates, increase apparent nucleotide triphosphate (NTP) reaction constant values, and increase the dissociation of short transcripts from the transcription complex curing initial transcription (Brieba et al, Biochemistry (2002) 41: 5144-5149; herein incorporated by reference in its entirety). The modification, substitution and/or insertion of at least one nucleoside can cause a silent mutation of the sequence or can cause a mutation in the amino acid sequence.

In some embodiments, the polynucleotide can include the substitution of at least 1, at least 2, at least 3, at least 4, at least 5, at least 6, at least 7, at least 8, at least 9, at least 10, at least 11, at least 12 or at least 13 guanine bases downstream of the transcription start site.

In some embodiments, the polynucleotide can include the substitution of at least 1, at least 2, at least 3, at least 4, at least 5 or at least 6 guanine bases in the region just downstream of the transcription start site. As a non-limiting example, if the nucleotides in the region are GGGAGA, the guanine bases can be substituted by at least 1, at least 2, at least 3 or at least 4 adenine nucleotides. In another non-limiting example, if the nucleotides in the region are GGGAGA the guanine bases can be substituted by at least 1, at least 2, at least 3 or at least 4 cytosine bases. In another non-limiting example, if the nucleotides in the region are GGGAGA the guanine bases can be substituted by at least 1, at least 2, at least 3 or at least 4 thymine, and/or any of the nucleotides described herein.

In some embodiments, the polynucleotide can include at least one substitution and/or insertion upstream of the start codon. For the purpose of clarity, one of skill in the art would appreciate that the start codon is the first codon of the protein coding region whereas the transcription start site is the site where transcription begins. The polynucleotide can include, but is not limited to, at least 1, at least 2, at least 3, at least 4, at least 5, at least 6, at least 7 or at least 8 substitutions and/or insertions of nucleotide bases. The nucleotide bases can be inserted or substituted at 1, at least 1, at least 2, at least 3, at least 4 or at least 5 locations upstream of the start codon. The nucleotides inserted and/or substituted can be the same base (e.g., all A or all C or all T or all G), two different bases (e.g., A and C, A and T, or C and T), three different bases (e.g., A, C and T or A, C and T) or at least four different bases.

As a non-limiting example, the guanine base upstream of the coding region in the polynucleotide can be substituted with adenine, cytosine, thymine, or any of the nucleotides described herein. In another non-limiting example the substitution of guanine bases in the polynucleotide can be designed so as to leave one guanine base in the region downstream of the transcription start site and before the start codon (see Esvelt et al. Nature (2011) 472(7344):499-503; the contents of which is herein incorporated by reference in its entirety). As a non-limiting example, at least 5 nucleotides can be inserted at 1 location downstream of the transcription start site but upstream of the start codon and the at least 5 nucleotides can be the same base type.

19. Polynucleotide Comprising an mRNA Encoding a GLA Polypeptide

In certain embodiments, a polynucleotide of the present disclosure, for example a polynucleotide comprising an mRNA nucleotide sequence encoding a GLA polypeptide, comprises from 5' to 3' end:
(i) a 5' cap provided above;
(ii) a 5' UTR, such as the sequences provided above;
(iii) an open reading frame encoding a GLA polypeptide, e.g., a sequence optimized nucleic acid sequence encoding GLA disclosed herein;
(iv) at least one stop codon;
(v) a 3' UTR, such as the sequences provided above; and
(vi) a poly-A tail provided above.

In some embodiments, the polynucleotide further comprises a miRNA binding site, e.g., a miRNA binding site that binds to miRNA-142. In some embodiments, the 5'UTR comprises the miRNA binding site.

In some embodiments, a polynucleotide of the present disclosure comprises a nucleotide sequence encoding a polypeptide sequence at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the protein sequence of a wild type GLA.

In some embodiments, a polynucleotide of the present disclosure, for example a polynucleotide comprising an mRNA nucleotide sequence encoding a GLA polypeptide, comprises (1) a 5' cap provided above, for example, CAP1, (2) a nucleotide sequence selected form the group consisting of SEQ ID NO: 119, 120, 122 to 140 and 160, and (3) a poly-A tail provided above, for example, a poly A tail of approximately 100 residues, wherein SEQ ID NO: 119 comprises from 5' to 3' end: 5' UTR of SEQ ID NO:33, GLA polypeptide ORF of SEQ ID NO: 79, and 3'UTR of SEQ ID NO: 81;

SEQ ID NO: 120 comprises from 5' to 3' end: 5' UTR of SEQ ID NO:33, GLA polypeptide ORF of SEQ ID NO: 80, and 3'UTR of SEQ ID NO: 81;

SEQ ID NO: 122 comprises from 5' to 3' end: 5' UTR of SEQ ID NO:33, GLA polypeptide ORF of SEQ ID NO: 141, and 3'UTR of SEQ ID NO: 81;

SEQ ID NO: 123 comprises from 5' to 3' end: 5' UTR of SEQ ID NO:33, GLA polypeptide ORF of SEQ ID NO: 142, and 3'UTR of SEQ ID NO: 81;

SEQ ID NO: 124 comprises from 5' to 3' end: 5' UTR of SEQ ID NO:33, GLA polypeptide ORF of SEQ ID NO: 143, and 3'UTR of SEQ ID NO: 81;

SEQ ID NO: 125 comprises from 5' to 3' end: 5' UTR of SEQ ID NO:33, GLA polypeptide ORF of SEQ ID NO: 144, and 3'UTR of SEQ ID NO: 81;

SEQ ID NO: 126 comprises from 5' to 3' end: 5' UTR of SEQ ID NO:33, GLA polypeptide ORF of SEQ ID NO: 145, and 3'UTR of SEQ ID NO: 81;

SEQ ID NO: 127 comprises from 5' to 3' end: 5' UTR of SEQ ID NO:33, GLA polypeptide ORF of SEQ ID NO: 146, and 3'UTR of SEQ ID NO: 81;

SEQ ID NO: 128 comprises from 5' to 3' end: 5' UTR of SEQ ID NO:33, GLA polypeptide ORF of SEQ ID NO: 147, and 3'UTR of SEQ ID NO: 81;

SEQ ID NO: 129 comprises from 5' to 3' end: 5' UTR of SEQ ID NO:33, GLA polypeptide ORF of SEQ ID NO: 148, and 3'UTR of SEQ ID NO: 81;

SEQ ID NO: 130 comprises from 5' to 3' end: 5' UTR of SEQ ID NO:33, GLA polypeptide ORF of SEQ ID NO: 149, and 3'UTR of SEQ ID NO: 81;

SEQ ID NO: 131 comprises from 5' to 3' end: 5' UTR of SEQ ID NO:33, GLA polypeptide ORF of SEQ ID NO: 150, and 3'UTR of SEQ ID NO: 81;

SEQ ID NO: 132 comprises from 5' to 3' end: 5' UTR of SEQ ID NO:33, GLA polypeptide ORF of SEQ ID NO: 151, and 3'UTR of SEQ ID NO: 81;

SEQ ID NO: 133 comprises from 5' to 3' end: 5' UTR of SEQ ID NO:33, GLA polypeptide ORF of SEQ ID NO: 152, and 3'UTR of SEQ ID NO: 81;

SEQ ID NO: 134 comprises from 5' to 3' end: 5' UTR of SEQ ID NO:33, GLA polypeptide ORF of SEQ ID NO: 153, and 3'UTR of SEQ ID NO: 81;

SEQ ID NO: 135 comprises from 5' to 3' end: 5' UTR of SEQ ID NO:33, GLA polypeptide ORF of SEQ ID NO: 154, and 3'UTR of SEQ ID NO: 81;

SEQ ID NO: 136 comprises from 5' to 3' end: 5' UTR of SEQ ID NO:33, GLA polypeptide ORF of SEQ ID NO: 155, and 3'UTR of SEQ ID NO: 81;

SEQ ID NO: 137 comprises from 5' to 3' end: 5' UTR of SEQ ID NO:33, GLA polypeptide ORF of SEQ ID NO: 156, and 3'UTR of SEQ ID NO: 81;

SEQ ID NO: 138 comprises from 5' to 3' end: 5' UTR of SEQ ID NO:33, GLA polypeptide ORF of SEQ ID NO: 157, and 3'UTR of SEQ ID NO: 81;

SEQ ID NO: 139 comprises from 5' to 3' end: 5' UTR of SEQ ID NO:33, GLA polypeptide ORF of SEQ ID NO: 158, and 3'UTR of SEQ ID NO: 81;

SEQ ID NO: 140 comprises from 5' to 3' end: 5' UTR of SEQ ID NO:33, GLA polypeptide ORF of SEQ ID NO: 159, and 3'UTR of SEQ ID NO: 81;

SEQ ID NO: 160 comprises from 5' to 3' end: 5' UTR of SEQ ID NO:33, GLA polypeptide ORF of SEQ ID NO: 79, and 3'UTR of SEQ ID NO: 103;

| | | mRNA Constructs |
|---|---|---|
| SEQ ID NO | Construct | Sequence<br>5' UTR = bold underline;<br>3' UTR comprising a stop codon = bold italics |
| 119 | GLA-mRNA #1 | <u>GGGAAAUAAGAGAGAAAAGAAGAGUAAGAAGAAAUAUAAGAGCCACC</u>AUGCAGCUCCGGAACCCC<br>GAGCUCCACCUUGGCUGCGCCCUCGCCUUGCGGUUCCUCGCACUUGUGAGCUGGGACAUACCAGG<br>CGCCCGGGCCCUCGACAACGGCCUCGCCCGCACCCCAACCAUGGGCUGGCUCCACUGGGAGCGCU<br>UCAUGUGCAACCUCGACUGCCAGGAGGAGCCCGACUCCUGCAUCUCCGAGAAGCUUUUCAUGGAG<br>AUGGCCGAGCUCAUGGUGUCCGAGGGCUGGAAGGACGCCGGCUACGAGUACCUCUGCAUCGACGA<br>CUGCUGGAUGGCCCCGCAGCGCGACAGCGAGGGUCGCCUCCAGGCCGACCCGCAGCGGUUCCCUC<br>ACGGCAUCCGCCAGCUCGCCAACUACGUCCACUCCAAGGGCCUCAAGCUCGGCAUCUACGCCGAC<br>GUCGGCAACAAGACCUGCGCCGGCUUCCCCGGCUCCUUCGGCUACUACGACAUCGACGCCCAGAC<br>CUUCGCCGACUGGGGCGUCGACCUCCUCAAGUUCGACGGCUGCUACUGCGACUCCCUCGAGAACC<br>UCGCCGACGGCUACAAGCACAUGUCCCUCGCCCUCAACCGCACCGGCCGCUCCAUCGUCUACUCC<br>UGCGAGUGGCCCCUCUACAUGUGGCCCUUCCAGAAGCCCAACUACACCGAGAUAAGGCAGUACUG<br>CAACCACUGGCGCAAUUUCGCCGAUAUCGAUGACUCCUGGAAGUCCAUCAAGAGCAUCCUGGACU<br>GGACCUCCUUCAACCAGGAGCGCAUCGUCGACGUCGCCGGCCCCGGCGGCUGGAACGACCCCGAC<br>AUGCUCGUCAUCGGAAACUUCGGCCUGUCCUGGAACCAGCAGGUCACCCAGAUGGCCCUCUGGGC<br>CAUCAUGGCCGCCCCACUGUUCAUGUCCAACGACCUCCGCCACAUCAGCCCGCAGGCCAAGGCCC<br>UCCUCCAGGACAAGGACGUCAUCGCCAUCAACCAAGACCCGCUGGCAAGCAGGGCUACCAGCUC<br>CGCCAGGGCGACAACUUCGAGGUGUGGGAACGUCCCCUCAGCGGCCUGGCGUGGGCCGUCGCCAU<br>GAUCAACCGCCAGGAGAUCGGCGGCCCGCGCUCCUACACCAUCGCCGUGGCCAGCCUGGGCAAGG<br>GCGUCGCCUGCAACCCCGCCUGCUUCAUCACCCAGCUCCUCCCCGUCAAGAGAAAGCUGGGCUUC<br>UACGAGUGGACCAGCCGCCUCCGCUCCCACAUCAACCCCACCGGCACCGUCCUGCUCCAGCUGGA<br>GAACACCAUGCAGAUGAGCCUCAAGGACCUGCU*GAUAAUAGUCCAUAAAGUAGGAAACACUAC*<br>*AGCUGGAGCCUCGGUGGCCAUGCUUCUUGCCCUUGGGCCUCCCCCCAGCCCCUCCUCCCCUUCC*<br>*UGCACCCGUACCCCCCGCAUUAUUACUCACGGUACGAGUGGUCUUUGAAUAAAGUCUGAGUGGGC*<br>*GGC* |
| 120 | GLA-mRNA #2 | <u>GGGAAAUAAGAGAGAAAAGAAGAGUAAGAAGAAAUAUAAGAGCCACC</u>AUGCAGCUGCGGAACCCC<br>GAGCUGCACCUGGGCUGCGCCCUGGCCCUGCGGUUCCUGGCCCUGGUGAGCUGGGACAUCCCCGG<br>CGCCCGGGCCCUGGACAACGGCCUGGCCUGGACGCCCACCAUGGGGCUGGCUGCACUGGGAGCGCU<br>UCAUGUGCAACCUGGACUGCCAGGAGGAGCCCGACAGCUGCAUCAGCGAGAAGCUGUUCAUGGAG<br>AUGGCCGAGCUGAUGGUGAGCGAGGGCUGGAAGGACGCCGGCUACGAGUACCUGUGCAUCGACGA<br>CUGCUGGAUGGCGCCCAGCGGGACAGCGAGGGCCGGCUGCAGGCCGACCCGCAGCGGUUCCCUC<br>ACGGCAUCCGCCAGCUGGCCAACUACGUGCACAGCAAGGGCCUGAAGCUGGGCAUCUACGCCGAC<br>GUGGGCAACAAGACCUGCGCCGGCUUCCCCGGCAGCUUCGGCUACUACGACAUCGACGCCCAGAC<br>CUUCGCCGACUGGGGCGUGGACCUGCUGAAGUUCGACGGCUGCUACUGCGACAGCCUGGAGAACC<br>UGGCCGACGGCUACAAGCACAUGAGCCUGGCCCUGAACCGGACCGGCCGGAGCAUCGUGUACAGC<br>UGCGAGUGGCCCCUGUACAUGUGGCCCUUCCAGAAGCCCAACUACACCGAGAUCCGGCAGUACUG<br>CAACCACUGGCGGAACUUCGCCGACAUCGACGACAGCUGGAAGAGCAUCAAGAGCAUCCUGGACU<br>GGACCAGCUUCAACCAGGAGCGGAUCGUGGACGUGGCCGGCCCCGGCGGCUGGAACGACCCCGAC<br>AUGCUGGUGAUCGGCAACUUCGGCCUGAGCUGGAACCAGCAGGUGACCCAGAUGGCCCUGUGGGC<br>CAUCAUGGCCGCGCCCCUGUUCAUGAGCAACGACCUGCGGCACAUCAGCCCUCAGGCCAAGGCCC<br>UGCUGCAGGACAAGGACGUGAUCGCCAUCAACCAGGACCCGCUGGGCAAGCAGGGCUACCAGCUG<br>CGGCAGGGCGACAACUUCGAGGUGUGGGAGCGGCCCCUGAGCGGCCUGGCCUGGGCGUGGCCAU<br>GAUCAACCGCCAGGAGAUCGGCGGCCCGCGGAGCUACACCAUCGCCGUGGCCAGCCUGGGCAAGG<br>GCGUGGCCUGCAACCCCGCCUGCUUCAUCACCCAGCUGCUGCCCGUGAAGCGGAAGCUGGGCUUC<br>UACGAGUGGACCAGCCGGCUGCGGAGCCACAUCAACCCCACCGGCACCGUGCUGCUGCAGCUGGA<br>GAACACCAUGCAGAUGAGCCUGAAGGACCUGCU*GAUAAUAGUCCAUAAAGUAGGAAACACUAC*<br>*AGCUGGAGCCUCGGUGGCCAUGCUUCUUGCCCUUGGGCCUCCCCCCAGCCCCUCCUCCCCUUCC*<br>*UGCACCCGUACCCCCCGCAUUAUUACUCACGGUACGAGUGGUCUUUGAAUAAAGUCUGAGUGGGC*<br>*GGC* |
| 121 | GLA-mRNA #3 | <u>GGGAAAUAAGAGAGAAAAGAAGAGUAAGAAGAAAUAUAAGAGCCACC</u>AUGCAGCUGAGGAACCCA<br>GAACUACAUCUGGGCUGCGCGCUUGCGCUUCGCUUCCUGGCCCUCGUUUCCUGGGACAUCCCCUGG<br>GGCUAGAGCACUGGACAAUGGAUUGGCAAGGACGCCUACCAUGGGCUGGCUGCACUGGGAGCGCU<br>UCAUGUGCAACCUUGACUGCCAGGAAGAGCCAGAUUCCUGCAUCAGUGAGAAGCUCUUCAUGGAG<br>AUGGCAGAGCUCAUGGUCUCAGAAGGCUGGAAGGAUGCAGGUUAUGAGUACCUCUGCAUUGAUGA<br>CUGUUGGAUGGCUCCCCAAAGAGAUUCAGAAGGCAGACUUCAGGCAGACCCUCAGCGCUUUCCUC<br>AUGGGAUUCGCCAGCUAGCUAAUUAUGUUCACAGCAAAGGACUGAAGCUAGGGAUUUAUGCAGAU<br>GUUGGAAAUAAAACCUGCGCAGGCUUCCCUGGGAGUUUUGGAUACUACGACAUUGAUGCCCAGAC<br>CUUUGCUGACUGGGGAGUAGAUCUGCUAAAAUUUGAUGGUUGUUACUGUGACAGUUUGGAAAAUU<br>UGGCAGAUGGUUAUAAGCACAUGUCCUUGGCCCUGAAUAGGACUGGCAGAAGCAUUGUGUACUCC<br>UGUGAGUGGCCUCUUUAUAUGUGGCCCUUUCAAAAGCCCAAUUAUACAGAAAUCCGACAGUACUG<br>CAAUCACUGGCGAAAUUUUGCUGACAUUGAUGAUUCCUGGAAAAGUAUAAAGAGUAUCUUGGACU<br>GGACAUCUUUUAACCAGGAGAGAAUUGUUGAUGUUGCUGGACAGGGGGUUGGAAUGACCCAGAU<br>AUGUUAGUGAUUGGCAACUUUGGCCUCAGCUGGAAUCAGCAAGUAACUCAGAUGGCCCUCUGGGC<br>UAUCAUGGCUGCUCCCUUAUUCAUGUCUAAUGACCUCCGACACAUCAGCCCUCAAGCCAAAGCUC<br>UCCUUCAGGAUAAGGACGUAAUUGCCAUCAAUCAGGACCCCUUGGGCAAGCAGGGUUACCAGCUU<br>AGACAGGGAGACAACUUUGAAGUGUGGGAACGACCUCUCUCAGGCUUAGCCUGGGCUGUAGCUAU<br>GAUAAACCGCCAGGAGAUUGGUGGACCUCGCUCUUUAUACCAUCGCAGUUGCUUCCUGGGGUAAAG<br>GAGUGGCCUGUAAUCCUGCCUGCUUCAUCACACAGCUCCUCCCUGUGAAAAGGAAGCUAGGGUUC<br>UAUGAAUGGACUUCAAGGUUAAGAAGUCACAUAAUCCCACAGGCACUGUUUUGCUUCCAGCUAGA<br>AAAUACAAUGCAGAUGUCAUUAAAAGACUUACUU*GAUAAUAGUCCAUAAAGUAGGAAACACUAC*<br>*AGCUGGAGCCUCGGUGGCCAUGCUUCUUGCCCUUGGGCCUCCCCCCAGCCCCUCCUCCCCUUCC*<br>*UGCACCCGUACCCCCCGCAUUAUUACUCACGGUACGAGUGGUCUUUGAAUAAAGUCUGAGUGGGC*<br>*GGC* |

-continued mRNA Constructs

| SEQ ID NO | Construct | Sequence<br>5' UTR = bold underline;<br>3' UTR comprising a stop codon = bold italics |
|---|---|---|
| 122 | GLA-mRNA #4 | <u>GGGAAAUAAGAGAGAAAAGAAGAGUAAGAAGAAAUAUAAGAGCCACC</u>AUGCAGCUCAGGAACCCG<br>GAGCUCCACCUCGGCUGCGCCCUCGCCCUCAGGUUCCUCGCUCUUGUGAGCUGGGACAUCCCGGG<br>CGCCAGGGCCCUCGACAACGGCCUCGCCAGAACCCCGACCAUGGGCUGGCUCCACUGGGAGAGGU<br>UCAUGUGUAAUCUGGACUGCCAGGAGGAGCCGGAUAGCUGCAUCAGCGAGAAGCUGUUCAUGGAG<br>AUGGCCGAGCUGAUGGUGUCCGAGGGCUGGAAGGACGCCGGCUAUGAGUACUUUGCAUCGAUGA<br>CUGCUGGAUGGCCCCGCAGCGGGACAGCGAGGGCAGGCUGCAAGCUGACCCUCAGCGUUUCCCGC<br>ACGGCAUCCGGCAGCUGGCCAACUACGUGCACAGCAAGGGCCUGAAGCUGGGCAUCUACGCGGAC<br>GUCGGCAACAAGACCUGCGCCGGCUUCCCGGGAAGCUUCGGCUACUACGACAUCGACGCCCAGAC<br>CUUCGCCGACUGGGGCGUGGACCUGCUGAAGUUCGACGGCUGCUACUGUGACAGCCUGGAGAACC<br>UGGCCGACGGCUACAAGCACAUGUCCCUGGCUCUGAAUAGAACCGGCAGGAGCAUAGUGUACAGC<br>UGCGAGUGGCCACUGUACAUGUGGCCGUUCCAGAAGCCGAACUACACCGAAAUCAGACAAUACUG<br>CAACCACUGGCGGAAUUUCGCCGAUAUCGACGACUCCUGGAAGUCCAUCAAGUCCAUCCUGGACU<br>GGACCUCCUUCAACCAGGAGAGAAUCGUGGACGUGGCCGGCCUGGUGGAUGGAACGAUCCAGAC<br>AUGCUGGUUAUCGGCAAUUUCGGCCUGAGCUGGAACCAGCAGGUGACGCAGAUGGCCCUGUGGGC<br>CAUCAUGGCCGCCCCACUGUUCAUGUCCAACGACCUCCGCCACAUCAGCCCGCAGGCCAAGGCCC<br>UCCUCCAAGACAAGGACGUGAUCGCCAUCAACCAAGACCCGCUCGGCAAGCAGGGCUACCAGCUG<br>CGCCAGGGCGACAAUUUCGAGGUCUGGGAGCGCCCGCUGUCUGGUCUGGCGUGGGCCGUGGCCAU<br>GAUCAAUAGACAGGAGAUCGGCGGCCCGGAGCUACACCAUCGCCGUAGCCAGCCUGGGCAAGG<br>GCGUGGCCUGCAACCCGGCUUGUUUCAUCACCCAGCUGCUCCGGUUAAGAGAAAGCUGGGCUUC<br>UACGAGUGGACCAGCCGGUUGCGCAGCCAUAUCAACCCGACUGGCACCGUGCUGCUGCAGCUGGA<br>GAACACAAUGCAGAUGUCCCUGAAGGACCUGCUC*UGAUAAUAGUCCAUAAAGUAGGAAACACUAC*<br>*AGCUGGAGCCUCGGUGGCCAUGCUUCUUGCCCCUUGGGCCUCCCCCCAGCCCCUCCUCCCCUUCC*<br>*UGCACCCGUACCCCCCGCAUUAUUACUCACGGUACGAGUGGUCUUUGAAUAAAGUCUGAGUGGGC*<br>*GGC* |
| 123 | GLA-mRNA #5 | <u>GGGAAAUAAGAGAGAAAAGAAGAGUAAGAAGAAAUAUAAGAGCCACC</u>AUGCAGCUCCGCAAUCCG<br>GAGCUCCACCUCGGCUGCGCCCUCGCCCUCAGGUUCCUCGCCCUUGUGAGCUGGGAUAUCCCGGG<br>CGCCAGGGCCCUCGACAACGGCCUUAGCCAGAACCCCAACGAUGGGCUGGCUCACUGGGAGAGGU<br>UCAUGUGCAACCUGGACUGCCAGGAGGAACCGGACAGCUGCAUCUCCGAGAAGCUGUUCAUGGAG<br>AUGGCCGAGCUCAUGGUGAGCGAGGGCUGGAAGGACGCCGGCUACGAGUAUCUCUGCAUCGACGA<br>CUGCUGGAUGGCCCCACAGAGGGACUCCGAGGGCAGGCUGCAGGCCGACCCGCAGAGAUUCCCUC<br>ACGGCAUCCGGCAACUGGCCAACUACGUGCACAGCAAGGGCCUGAAGCUGGGGAAUCUACGCCGAC<br>GUGGGCAACAAGACCUGUGCUGGCUUCCCGGGCAGCUUCGGCUACUAUGACAUCGAUGCCCAGAC<br>CUUCGCCGACUGGGGCGUCGACCUGCUCAAGUUCGACGGCUGUUACUGCGACAGCCUGGAGAACC<br>UGGCAGACGGCUAUAAGCACAUGAGCCUGGCACUCAACAGGACCGGCAGGUCAAUAGUGUACAGC<br>UGCGAGUGGCCGCUGUACAUGUGGCCAUUCCAGAAGCCGAAUUACACCGAGAUAAGGCAGUAUUG<br>CAACCACUGGCGAAACUUCGCGGAUAUCGAUGACAGCUGGAAGUCGAUAAAGAGCAUCCUGGACU<br>GGACCAGCUUCAACCAGGAGAGGAUCGUGGACGUCGCCGGCCUGGCGGCUGGAACGACCCGGAC<br>AUGCUGGUGAUCGGAAACUUCGGCCUCAGCUGGAACCAACAGGUGACCCAGAUGGCCCUGUGGGC<br>CAUCAUGGCGGCACCUCUGUUCAUGAGCAAUGACCUGCGGCAUAUCAGCCCGCAGGCCAAGGCCC<br>UGCUCCAGGACAAGGACGUCAUAGCCAUCAAUCAGGACCCGUGGGCAAGCAGGGCUACCAACUG<br>CGGCAGGGAGACAACUUCGAGGUGUGGGAGCGGCCGCUGAGCGGCCUGGCAUGGGCCGUGGCCAU<br>GAUCAAUAGACAGGAGAUCGGCGGCCCGCGGAGCUACACCAUCGCCGUGGCGAGUCUUGGCAAGG<br>GUGUGGCCUGCAAUCCGGCCUGCUUCAUCACCCAGCUGCUCCAGUCAAGCGCAAGCUCGGAUUC<br>UACGAGUGGACCAGCCGUCUGCGCAGCCACAUCAAUCCUACCGGCACGGUGCUCCUGCAGCUGGA<br>GAACACCAUGCAAAUGUCUCUCAAGGACCUGCUG*UGAUAAUAGUCCAUAAAGUAGGAAACACUAC*<br>*AGCUGGAGCCUCGGUGGCCAUGCUUCUUGCCCCUUGGGCCUCCCCCCAGCCCCUCCUCCCCUUCC*<br>*UGCACCCGUACCCCCCGCAUUAUUACUCACGGUACGAGUGGUCUUUGAAUAAAGUCUGAGUGGGC*<br>*GGC* |
| 124 | GLA-mRNA #6 | <u>GGGAAAUAAGAGAGAAAAGAAGAGUAAGAAGAAAUAUAAGAGCCACC</u>AUGCAGCUCCGGAACCCA<br>GAACUCCACCUCGGCUGCGCCCUCGCCCUCCGGUUCCUUGCCCUCGUGUCCUGGGACAUUCCAGG<br>CGCCCGGGCCCUCGACAACGGCCUCGCCCGGACCCCAACCAUGGGCUGGCUCCAUUGGGAGAGGU<br>UCAUGUGCAACCUGGACUGCCAAGAGGAGCUGGACUCCUGCAUCUCCGAGAAGCUGUUCAUGGAG<br>AUGGCCGAGCUCAUGGUGAGCGAGGGCUGGAAGGACGCCGGCUACGAAUAUCUGUGCAUCGACGA<br>UUGCUGGAUGGCCCCUCAAAGAGACAGCGAGGGCAGACUGCAGGCCGACCCGCAGCGCUUCCCUC<br>AUGGCAUCCGGCAACUCGCGAAUUAUGUGCACAGCAAGGGCCUGAAGCUGGGCAUCUACGCCGAC<br>GUCGGUAACAAGACCUGCGCCGGCUUCCCAGGCAGCUUCGGCUACUACGACAUCGACGCCCAGAC<br>CUUCGCCGACUGGGGCGUAGACCUCCUGAAGUUCGACGGUUGUACUGCGACUCCCUGGAGAACC<br>UAGCCGACGGCUACAAGCACAUGUCCCUCGCCCUGAACAGAACCGGCCGGUCCAUCGUCUAUUCC<br>UGCGAGUGGCCGCUGUACAUGUGGCCCGUUCCAGAAGCCUAACUACACAGAGAUCCGCCAGUACUG<br>CAACCACUGGCGGAAUUUCGCCGAUAUCGACGACAGUUGGAAGUCCAUCAAGAGCAUACUGGAUU<br>GGACCUCCUUCAACCAGGAGAGGAUCGUGGACGUGGCCGGCCCGGGCGGUUGGAACGACCCAGAC<br>AUGCUGGUGAUCGGAAACUUCGGCCUGAGCUGGAACCAGCAGGUGACCCAGAUGGCCCUCUGGGC<br>CAUCAUGGCCGCCCCUCUGUUCAUGUCCAAUGACCUCAGGCAUAUCUCCCCGCAGGCCAAGGCUC<br>UCCUCCAGGACAAGGACGUGAUCGCCAUCAAUCAGGAUCCGCUGGGAAAGCAGGGAUACCAGCUG<br>AGGCAGGGCGACAACUUCGAGGUGUGGGAGCGCCCACUGAGCGGCCUGGCUUGGGCCGUGGCCAU<br>GAUCAACCGGCAAGAGAUCGGCGGCCCGCGGAGCUACACCAUUGCCGUGGCUAGCCUGGGCAAGG<br>GCGUGGCCUGCAACCCGGCCUGCUUCAUCACCCAGCUUUCUCGCGGUAAAGCGUAAGCUGGGCUUC<br>UACGAGUGGACCAGCAGACUGAGGAGCCACAUCAACCCGACCGGCACCGUGCUGCUCCAGCUGGA |

| SEQ ID NO | Construct | Sequence<br>5' UTR = bold underline;<br>3' UTR comprising a stop codon = bold italics |
|---|---|---|
| | | GAACACCAUGCAGAUGAGCCUGAAGGAUCUGCUC*UGAUAAUAGUCCAUAAAGUAGGAAACACUAC<br>AGCUGGAGCCUCGGUGGCCAUGCUUCUUGCCCCUUGGGCCUCCCCCCAGCCCCUCCUCCCCUUCC<br>UGCACCCGUACCCCCCGCAUUAUUACUCACGGUACGAGUGGUCUUUGAAUAAAGUCUGAGUGGGC<br>GGC* |
| 125 | GLA-mRNA #7 | GGGAAAUAAGAGAGAAAAGAAGAGUAAGAAGAAAUAUAAGAGCCACCAUGCAACUCCGCAAUCCG<br>GAGCUCCACCUCGGCUGUGCGCUCGCCCUUAGAUUCCUCGCCCUCGUGAGCUGGGACAUCCCAGG<br>CGCCCGGGCCCUCGACAACGGCCUAGCCCGCACUCCUACAAUGGGCUGGUUGCACUGGGAACGCU<br>UCAUGUGUAACCUGGACUGCCAGGAGGAACCGGACAGCUGUAUCUCCGAGAAGCUGUUCAUGGAG<br>AUGGCCGAGCUGAUGGUGAGCGAGGGCUGGAAGGAUGCCGGCUACGAGUACCUGUGUAUCGAUGA<br>CUGCUGGAUGGCCCCGCAGCGAGAUAGCGAGGGACGCCUGCAGGCCGACCCGACCCGCAGAGAUUCCCGC<br>ACGGCAUCCGCCAGCUGGCCAAUUAUGUUCACAGCAAGGGCCUGAAGCUGGGCAUCUACGCCGAC<br>GUGGGCAACAAGACCUGCGCCGGAUUCCCGGGCAGCUUCGGCUACUACGAUAUAGAUGCCCAAAC<br>AUUCGCCGACUGGGGCGUCGACCUGCUUAAGUUCGACGGCUGCUACUGCGAUAGCCUGGAGAAUC<br>UGGCCGACGGCUACAAGCACAUGAGCCUGGCCCUCAACAGGACCGGAAGGUCCAUCGUGUACAGC<br>UGCGAAUGGCCUCUGUACAUGUGGCCUUUCCAGAAGCCGAACACACCGAGAUCCGGCAGUACUG<br>UAAUCACUGGAGGAACUUCGCCGACAUCGACGAUUCUUGGAAGUCUAUCAAGUCCAUCCUGGACU<br>GGACCUCCUUCAAUCAGGAGAGAAUUGUCGACGUGGCCGGCCCGGGUGGCUGGAACGACCCGGAC<br>AUGCUGGUGAUCGGCAACUUCGGCCUGAGCUGGAACCAGCAGGUGACCCAGAUGGCCCUGUGGGC<br>CAUAAUGGCCGCCCCACUCUUCAUGUCCAACGACCUGCACAUCAGCCCACAGGCCAAGGCAC<br>UGCUCCAGGACAAGGACGUGAUCGCCAUCAACCAAGACCCUCUGGGCAAGCAGGGUUACCAGCUU<br>AGACAGGGCGACAACUUCGAGGUGUGGGAGCGCCCGCUUUCCGGCCUCGCCUGGGCCGUGGCCAU<br>GAUCAACAGGCAGGAAAUCGGAGGCCCGCGCUCCUAUACUAUCGCCGUGGCGAGCCUGGGCAAGG<br>GCGUGGCCUGCAACCCGGCCUGCUUCAUCACCCAGCUGCUGCCAGUCAAGAGAAAGCUGGGCUUC<br>UACGAGUGGACCUCCAGACUGAGAUCCCACAUCAAUCCUACCGGCACCGUGCUGCUGCAGCUGGA<br>GAACACGAUGCAGAUGUCGCUGAAGGACCUCCUG*UGAUAAUAGUCCAUAAAGUAGGAAACACUAC<br>AGCUGGAGCCUCGGUGGCCAUGCUUCUUGCCCCUUGGGCCUCCCCCCAGCCCCUCCUCCCCUUCC<br>UGCACCCGUACCCCCCGCAUUAUUACUCACGGUACGAGUGGUCUUUGAAUAAAGUCUGAGUGGGC<br>GGC* |
| 126 | GLA-mRNA #8 | GGGAAAUAAGAGAGAAAAGAAGAGUAAGAAGAAAUAUAAGAGCCACCAUGCAGCUCCGGAACCCA<br>GAGCUUCACCUUGGCUGCGCCCUCGCCCUCAGGUAUCCUAGCCCUCGUGAUCCUGGGACAUCCCAGG<br>CGCCCGGGCCCUUGACAACGGCCUCGCCAGAACCCCGACCAUGGGCUGGCUCCACUGGGAGCGCU<br>UCAUGUGCAACCUGGACUGUCAGGAGGAGCCGGACUCAUGUAUCAGCGAGAAGCUGUUCAUGGAA<br>AUGGCCGAAUUAAUGGUGUCCGAGGGCUGGAAGGACGCCGGCUAUGAGUACCUGUGCAUCGACGA<br>UUGCUGGAUGGCCCCGCAGAGAGACAGCGAGGGCAGACUGCAGGCCGACCCCACAGAGGUUCCCAC<br>ACGGCAUCAGGCAGCUGGCCAACUACGUGCACUCCAAGGGCCUGAAGCUGGGCAUCUACGCCGAU<br>GUGGGCAAUAAGACCUGCGCCGGCUUCCCGGGCAGCUUCGGCUAUUACGAUAUCGACGCCCAGAC<br>GUUCGCCGACUGGGGCGUGGAUCUGCUGAAGUUCGACGGCUGUUACUGUGACAGCCUGGAGAAUC<br>UGGCCGAUGGCUACAAGCAUAUGAGUCUCGCCCUCAACAGGACCGGCCGCUCAAUCGUGUACAGC<br>UGCGAGUGGCCGCUGUACAUGUGGCCGUUCCAGAAGCCAAACUACACCGAGAUCAGGCAAUACUG<br>CAACCAUUGGCGCAACUUCGCCGAUAUAGAUGACAGCUGGAAGUCCAUCAAGUCCAUCCUGGACU<br>GGACCAGCUUCAAUCAGGAGCGUAUAGUGGACGUGGCCGGCCCGGGCGGUUGGAACGACCCAGAC<br>AUGCUGGUGAUCGGCAACUUCGGCCUGAGCUGGAACCAGCAGGUGACCCAGAUGGCCCUGUGGGC<br>CAUCAUGGCCGCCCCACUGUUCAUGUCCAACGACCUGCGCAUCAGCCCGCAGGCCAAGGCCC<br>UGCUGCAGGAUAAGGACGUGAUAGCUAUCAACCAAGACCCACUGGGCAAGCAGGGAUACCAGCUG<br>AGGCAAGGCGACAACUUCGAGGUGUGGGAGAGGCCGCUCAGCGGCCUGGCCUGGGCCGUGGCCAU<br>GAUCAACAGGCAAGAGAUCGGAGGCCCGAGAAGCUACACCAUCGCGGUCGCCAGCCUGGGCAAGG<br>GUGUGGCGUGCAACCCAGCAUGCUUCAUCACCCAGCUGCUGCCGGUGAAGAGGAAGCUGGGAUUC<br>UACGAGUGGACUAGCAGACUGAGGAGCCACAUCAACCCCGACCGGCACCGUCCUGCUGCAGCUCGA<br>GAACACCAUGCAGAUGUCCCUGAAGGAUCUGCUG*UGAUAAUAGUCCAUAAAGUAGGAAACACUAC<br>AGCUGGAGCCUCGGUGGCCAUGCUUCUUGCCCCUUGGGCCUCCCCCCAGCCCCUCCUCCCCUUCC<br>UGCACCCGUACCCCCCGCAUUAUUACUCACGGUACGAGUGGUCUUUGAAUAAAGUCUGAGUGGGC<br>GGC* |
| 127 | GLA-mRNA #9 | GGGAAAUAAGAGAGAAAAGAAGAGUAAGAAGAAAUAUAAGAGCCACCAUGCAGCUCCGGAACCCA<br>GAGUUGCAUCUCGGUUGCGCCUUAGCUCUCCGGUUCCUCGCCCUCGUGAGCUGGGACAUCCCAGG<br>CGCCAGGGCUCUCGACAACGGACUUGCCAGGACCCCGACAAUGGGCUGGCUCCACUGGGAGCGGU<br>UCAUGUGCAACCUGGAUUGUCAGGAGGAGCCAGACUCCUGCAUCUCCGAGAAGCUGUUCAUGGAG<br>AUGGCCGAACUCAUGGUGAGCGAGGGAUGGAAGGACGCCGGCUAUGAGUAUCUGUGCAUCGACGA<br>UUGCUGGAUGGCCCCGCAGAGGGAUAGCGAGGGCCGCCUCCAGGCCGACCCGCAGCGAUUCCCGC<br>ACGGCAUCCGACAGCUGGCCAACUACGUGCAUCUCAAGGGCCUCAAGCUGGGCAUAUACGCCGAC<br>GUCGGAAACAAGACGUGCGCCGGCUUCCCGGGCAGCUUCGGCUACUAUGACAUCGACGCCCAGAC<br>GUUCGCGGAUUGGGGCGUGGACCUGCUGAAGUUCGACGGCUGCUACUGCGAUAGCCUCGAGAAUC<br>UGGCCGACGGAUACAAGCAUAUGAGCCUCGCCCUGAACAGGACCGGCCGUUCCAUCGUGUACUCA<br>UGCGAGUGGCCGCUCUACAUGUGGCCAUUCCAGAAGCCUAAUUACACCGAGAUCCGGCAGUACUG<br>CAACCACUGGCGAAAUUUCGCAGAUAUAGACGAUAGCUGGAAGUCCAUCAAGUCUAUCCUGGACU<br>GGACUUCCUUCAACCAGGAAAGGAUCGUCGACGUGGCCGGCCCGGGCGGCUGGAACGACCCGGAC<br>AUGCUGGUGAUCGGCAACUUCGGCCUGAGCUGGAACCAGCAGGUGACCCAGAUGGCCCUGUGGGC<br>CAUCAUGGCCGCCCCUCUGUUCAUGUCCAAUGACCUGCGGCACAUCAGCCCGCAGGCCAAGGCCC<br>UGCUGCAAGACAAGGAUGUGAUUGCCAUCAAUCAGGACCCUCUCGGCAAGCAGGGCUACCAGCUC<br>CGACAGGGAGAUAACUUCGAAGUGUGGGAGCGGCCGCUGAGCGGCCUGGCCUGGGCCGUCGCCAU<br>GAUCAACCGGCAGGAGAUCGGCGGCCCACGCUCCUACACCAUCGCCGUGGCCUCCCUGGGCAAGG

| SEQ ID NO | Construct | Sequence 5' UTR = bold underline; 3' UTR comprising a stop codon = bold italics |
|---|---|---|
|  |  | GCGUGGCCUGCAAUCCGGCAUGCUUCAUCACCCAGCUGCUGCCAGUCAAGAGGAAGCUGGGCUUC<br>UAUGAAUGGACCAGCAGACUGCGAUCCCACAUCAACCCAACCGGCACCGUGCUGCUGCAGCUGGA<br>GAACACUAUGCAGAUGAGCCUGAAGGACCUGCUG*UGAUAAUAGUCCAUAAAGUAGGAAACACUAC<br>AGCUGGAGCCUCGUGGCCAUGCUUCUUGCCCCUUGGGCCUCCCCCCAGCCCCUCCUCCCCUUCC<br>UGCACCCGUACCCCCCGCAUUAUUACUCACGGUACGAGUGGUCUUUGAAUAAAGUCUGAGUGGGC<br>GGC* |
| 128 | GLA-mRNA #10 | <u>GGGAAAUAAGAGAGAAAAGAAGAGUAAGAAGAAAUAUAAGAGCCACC</u>AUGCAGCUCAGAAACCCA<br>GAGCUCCAUUUGGGCUGCGCCCUCGCCCUCCGGUUCCUCGCCCUCGUGAGCUGGGACAUCCCGGG<br>CGCCAGAGCCCUCGACAACGGACUCGCCCGAACACCAACCAUGGGCUGGCUCCAUUGGGAGAGGU<br>UCAUGUGCAACCUGGACUGCCAGGAGGAGCCGGAUAGCUGCAUCAGCGAGAAGCUGUUCAUGGAG<br>AUGGCCGAGCUGAUGGUGUCCGAGGGCUGGAAGGACGCCGGCUAUGAGUAUCUGUGCAUCGACGA<br>CUGCUGGAUGGCCCCACAGCGGGACUCCGAGGGAAGGCUGCAGGCCGACCCGCAGAGGUUCCCUC<br>ACGGCAUCCGUCAGCUCGCCAACUACGUGCACUCCAAGGGCCUGAAGCUGGGCAUCUACGCCGAC<br>GUGGGCAACAAGACCUGCGCCGGCUUCCCAGGCAGCUUCGGAUACUAUGACAUCGACGCCCAGAC<br>CUUCGCCGACUGGGGCGUGGAUCUGCUGAAGUUCGACGGCUGCUACUGCGACAGCUUGGAGAAUC<br>UGGCCGACGUUACAAGCACAUGAGCCUAGCCCUGAACCGGACCGGAAGGAGCAUCGUGUACAGC<br>UGCGAGUGGCCGCUGUACAUGUGGCCAUUCCAGAAGCCGAACUACACCGAGAUUAGGCAGUACUG<br>CAACCACUGGAGAAACUUCGCAGAUAUCGACGACAGCUGGAAGUCCAUCAAGAGCAUCCUGGAUU<br>GGACCAGCUUCAACCAGGAGCGGAUCGUGGACGUGGCCGGUCCGGGAGGCUGGAACGACCCGGAC<br>AUGCUGGUGAUCGGCAACUUCGGACUGAGCUGGAACCAGCAAGUGACCCAGAUGGCCCUGUGGGC<br>CAUCAUGGCCGCCCCUCUAUUCAUGUCUAACGACCUGCGGCACAUUCCCCGCAGGCCAAGGCCC<br>UGCUGCAGGACAAGGACGUCAUCGCGAUCAAUCAGGACCCACUGGGCAAGCAGGGCUAUCAGCUG<br>CGUCAGGGCGACAAUUUCGAGGUGUGGGAGCGGCCGCUGAGCGGCCUGGCCUGGGCCGUGGCCAU<br>GAUCAACCGGCAGGAGAUCGGAGGCCCGAGAAGCUACACCAUCGCAGUUGCCAGCCUGGGCAAGG<br>GCGUGGCCUGCAACCCGGCCUGCUUCAUCACCCAGCUGCUACCGGUGAAGCGUAAGCUGGGCUUC<br>UACGAGUGGACCAGCAGGCUCAGGAGCCACAUCAACCCGACCGGCACCGUGCUGCUCCAGCUGGA<br>GAACACCAUGCAGAUGUCCCUGAAGGAUCUGCUG*UGAUAAUAGUCCAUAAAGUAGGAAACACUAC<br>AGCUGGAGCCUCGUGGCCAUGCUUCUUGCCCCUUGGGCCUCCCCCCAGCCCCUCCUCCCCUUCC<br>UGCACCCGUACCCCCCGCAUUAUUACUCACGGUACGAGUGGUCUUUGAAUAAAGUCUGAGUGGGC<br>GGC* |
| 129 | GLA-mRNA #11 | <u>GGGAAAUAAGAGAGAAAAGAAGAGUAAGAAGAAAUAUAAGAGCCACC</u>AUGCAACUCAGGAACCCG<br>GAGCUCCACCUAGGCUGCGCCCUCGCCCUCCGCUUCCUCGCACUCGUGAGCUGGGACAUCCCAGG<br>UGCCAGAGCGCUCGACAACGGACUCGCCCGGACCCCUACCAUGGGCUGGCUCCACUGGGAGCGCU<br>UCAUGUGCAACCUGGACUGCCAGGAGGAACCGGACAGCUGCAUCUCCGAGAAGCUGUUCAUGGAG<br>AUGGCCGAGCUGAUGGUGAGCGAGGGCUGGAAGGACGCCGGCUACGAGUACCUGUGCAUCGACGA<br>CUGCUGGAUGGCCCCUCAGAGGGACAGCGAGGGCAGGCUGCAGGCCGACCCGCAGCGCUUCCCGC<br>ACGGCAUCCGGCAGCUGGCUAACUACGUGCACAGCAAGGGCCUGAAGCUCGGCAUCUACGCCGAC<br>GUGGGAAACAAGACCUGCGCGGGCUUCCCAGGAUCCUUCGGCUAUUACGACAUCGACGCCCAGAC<br>CUUCGCCGACUGGGGCGUGGACCUGCUGAAGUUCGACGGCUGCUACUGUGACUCCCUCGAGAACC<br>UGGCUGACGGCUACAAGCACAUGAGCCUGGCCCUGAACCGCACCGGCAGGAGCAUCGUGUAUAGC<br>UGUGAAUGGCCGCUGUACAUGUGGCCGUUCCAGAAGCCUAACUACACCGAGAUCAGACAGUAUUG<br>CAACCAUUGGCGGAAUUUCGCCGACAUCGAUGACUCCUGGAAGUCCAUAAAGAGCAUCCUGGAUU<br>GGACCAGCUUCAACCAAGAGAGGAUAUGGACGUGGCCGGUCCGGGCGGAUGGAACGACCCCGGAC<br>AUGCUGGUGAUCGGCAACUUCGGCUCGAGCUGGAACCAGCAGGUGACUCAGAUGGCCCUGUGGGC<br>CAUCAUGGCCGCUCCACUGUUCAUGAGCAACGACCUGAGACACAUCAGCCCGCAGGCCAAGGCCC<br>UGCUGCAGGAUAAGGACGUCAUCGCCAUCAACCAAGAUCCGCUGGGCAAGCAGGGCUACCAGCUG<br>CGCCAGGGCGACAACUUCGAGGUGUGGGAGCGGCCGCUGAGCGGCCUGGCCUGGGCCGUGCAAU<br>GAUCAACCGUCAGGAGAUCGGCGGCCCGAGGUCCUACACGAUCGCCGUGGCCUCUCUCGGCAAGG<br>GCGUGGCCUGUAACCCGGCCUGCUUCAUCACCCAGCUGCUGCGGUGAAGCGCAAGUUGGGCUUC<br>UACGAGUGGACCAGCCGGCUGCGGUCCCACAUCAAUCCAACCGGCACCGUGCUGCUGCAGCUGGA<br>GAACACCAUGCAAAUGAGCCUCAAGGAUUAUGCUG*UGAUAAUAGUCCAUAAAGUAGGAAACACUAC<br>AGCUGGAGCCUCGUGGCCAUGCUUCUUGCCCCUUGGGCCUCCCCCCAGCCCCUCCUCCCCUUCC<br>UGCACCCGUACCCCCCGCAUUAUUACUCACGGUACGAGUGGUCUUUGAAUAAAGUCUGAGUGGGC<br>GGC* |
| 130 | GLA-mRNA #12 | <u>GGGAAAUAAGAGAGAAAAGAAGAGUAAGAAGAAAUAUAAGAGCCACC</u>AUGCAGCUCCGGAACCCC<br>GAGCUCCACCUCGGCUGCGCCCUUGCCUUGCGGUUCCUCGCGCUCGUGAGCUGGGACAUCCCAGG<br>CGCCAGGGCCCUCGACAACGGCCUCGCCCGGACCCCGACCAUGGGCUGGCUCCACUGGGAGCGGU<br>UCAUGUGCAACCUGGACUGCCAGGAGGAGCCCGACAGCUGCAUCAGCGAGAAGCUGUUCAUGGAG<br>AUGGCCGAGCUGAUGGUGAGCGAGGGCUGGAAGGACGCCGGCUACGAGUACCUGUGCAUCGACGA<br>CUGCUGGAUGGCCCCGCAGCGGGACAGCGAAGGCCGGCUGCAGGCCGACCCGCAAAGAUUCCCAC<br>ACGGCAUCCGGCAGCUGGCCAACUACGUGCACAGCAAGGGCCUGAAGCUGGGCAUCUACGCCGAC<br>GUGGGCAACAAGACCUGCGCCGGCUUCCCGGGCAGCUUCGGCUACUACGACAUCGACGCCCAGAC<br>CUUCGCCGACUGGGGCGUGGACCUGCUGAAGUUCGACGGCUGCUACUGCGACAGCCUGGAGAACC<br>UGGCCGACGGCUACAAGCACAUGAGCCUCGCCCUGAACCGGACCGGCCGGAGCAUCGUGUACAGC<br>UGCGAGUGGCCCCUGUACAUGUGGCCCUUCCAGAAGCCCAACUACACCGAGAUCAGACAGUACUG<br>CAACCACUGGCGGAACUUCGCCGACAUCGAUGACAGCUGGAAGUCAAUCAAGAGCAUACUGGACU<br>GGACCAGCUUCAACCAGGAGCGGAUCGUGGACGUGGCCGGCCCGGCGGCUGGAACGACCCCGAC<br>AUGCUGGUGAUCGGCAACUUCGGCCUGAGCUGGAACCAGCAGGUGACCCAGAUGGCCCUGUGGGC<br>CAUCAUGGCCGCCCCACUCUUCAUGAGCAACGACCUGCGGCACAUCAGCCCGCAGGCCAAGGCCC<br>UGCUGCAGGACAAGGACGUGAUCGCCAUCAAUCAGGACCCUCUGGGCAAGCAGGGCUACCAGCUG | mRNA Constructs

| SEQ ID NO | Construct | Sequence<br>5' UTR = bold underline;<br>3' UTR comprising a stop codon = bold italics |
|---|---|---|
| | | AGGCAGGGCGACAACUUCGAGGUGUGGGAGAGGCCCCUGAGCGGCCUGGCCUGGGCCGUGGCCAU GAUCAACCGGCAGGAGAUCGGCGGCCCUCGGAGCUACACCAUCGCCGUAGCCAGCCUGGGUAAGG GCGUGGCCUGCAACCCCGCCUGCUUCAUCACCCAGCUGCUGCCGUGAAGCGGAAGCUCGGAUUC UACGAGUGGACCUCCAGACUGCGGAGCCACAUCAACCCCACCGGCACCGUCUCCUGCAGCUUGA GAACACCAUGCAGAUGUCACUGAAGGAUCUGCUG*UGAUAAUAGUCCAUAAAGUAGGAAACACUAC AGCUGGAGCCUCGGUGGCCAUGCUUCUUGCCCCUUGGGCCUCCCCCCAGCCCCUCCUCCCCUUCC UGCACCCGUACCCCCCGCAUUAUUACUCACGGUACGAGUGGUCUUUGAAUAAAGUCUGAGUGGGC GGC* |
| 131 | GLA-mRNA #13 | <u>GGGAAAUAAGAGAGAAAAGAAGAGUAAGAAGAAAUAUAAGAGCCACC</u>AUGCAGCUCCGGAACCCC GAGCUCCACCUCGGCUGCGCCCUUGCCCUCCGGUUCCUCGCCCUUGUGAGCUGGGACAUCCCCGG CGCCCGGGCCCUUGACAACGGCCUCGCCCGGACCCCGACCAUGGGCUGGCUCCACUGGGAGCGGU UCAUGUGCAACCUGGACUGCCAGGAGGAGCCCGACAGCUGCAUCAGCGAGAAGCUGUUCAUGGAG AUGGCCGAGCUGAUGGUGAGCGAGGGCUGGAAGGACGCCGGCUACGAGUACCUGUGCAUCGACGA CUGCUGGAUGGCCCCGCAGCGGGACAGCGAGGGUCGGCUGCAGGCCGACCCACAGCGCUUCCCUC ACGGCAUCCGGCAGCUGGCCAACUACGUGCACAGCAAGGGCCUGAAGCUGGGCAUCUACGCCGAC GUGGGCAACAAGACCUGCGCCGGCUUCCCGGGCAGCUUCGGCUACUACGACAUCGACGCCCAGAC CUUCGCCGACUGGGGCGUGGACCUGCUGAAGUUCGACGGCUGCUACUGCGACAGCCUGGAGAACC UGGCCGACGGCUACAAGCACAUGAGCCUCGCGCUGAACCGGACCGGCCGGAGCAUCGUGUACAGC UGCGAGUGGCCCCUGUACAUGUGGCCCUUCCAGAAGCCCAACUACACCGAGAUCAGACAGUACUG CAACCACUGGCGGAAUUUCGCCGAUAUCGAUGACAGCUGGAAGUCCAUCAAGUCCAUCCUGGAUU GGACCAGCUUCAACCAGGAGCGGAUCGUGGACGUGGCCGGCCCCGGCGGCUGGAACGACCCCGAC AUGCUGGUGAUCGGCAACUUCGGCCUGAGCUGGAACCAGCAGGUGACCCAGAUGGCCCUGUGGGC CAUCAUGGCCGCCCACUCUUCAUGAGCAACGACCUGCUGCACAUCAGCCCGCAGGCCAGGCCC UGCUGCAGGACAAGGACGUGAUCGCCAUCAAUCAGGACCCACUGGGCAAGCAGGGCUACCAGCUC CGGCAGGGCGACAACUUCGAGGUGUGGGAGAGGCCGCUGAGCGGCCUUGCGUGGGCCGUGGCCAU GAUCAACCGGCAGGAGAUCGGCGGCCCGCGGAGCUACACCAUCGCCGUGGCAAGCCUGGGAAAGG GCGUGGCCUGCAACCCCGCCUGCUUCAUCACCCAGCUGCUGCCGUGAAGCGGAAGUUAGGCUUC UACGAGUGGACCUCCAGGCUGCGGAGCCACAUCAACCCCACCGGCACCGUCUGCUGCAACUGGA GAAUACCAUGCAGAUGAGCCUGAAGGAUCUGCUG*UGAUAAUAGUCCAUAAAGUAGGAAACACUAC AGCUGGAGCCUCGGUGGCCAUGCUUCUUGCCCCUUGGGCCUCCCCCCAGCCCCUCCUCCCCUUCC UGCACCCGUACCCCCCGCAUUAUUACUCACGGUACGAGUGGUCUUUGAAUAAAGUCUGAGUGGGC GGC* |
| 132 | GLA-mRNA #14 | <u>GGGAAAUAAGAGAGAAAAGAAGAGUAAGAAGAAAUAUAAGAGCCACC</u>AUGCAGCUCCGGAACCCC GAGCUCCACCUCGGCUGCGCCCUCGCCCUCCGGUUCCUAGCCCUCGUGAGCUGGGACAUACCGGG CGCCAGGGCGCUCGACAACGGCCUCGCCCGGACCCCGACCAUGGGCUGGCUCCACUGGGAGCGGU UCAUGUGCAACCUGGACUGCCAGGAGGAGCCCGACAGCUGCAUCAGCGAGAAGCUGUUCAUGGAG AUGGCCGAGCUGAUGGUGAGCGAGGGCUGGAAGGACGCCGGCUACGAGUACCUGUGCAUCGACGA CUGCUGGAUGGCACCUCAGCGGGACUCCGAGGGCCGGCUGCAGGCCGACCCUCAGAGAUUCCCGC ACGGCAUCCGGCAGCUGGCCAACUACGUGCACAGCAAGGGCCUGAAGCUGGGCAUCUACGCCGAC GUGGGCAACAAGACCUGCGCCGGCUUCCCGGGCAGCUUCGGCUACUACGACAUCGACGCCCAGAC CUUCGCCGACUGGGGCGUGGACCUGCUGAAGUUCGACGGCUGCUACUGCGACAGCCUGGAGAACC UGGCCGACGGCUACAAGCACAUGUCUCUCGCCUUGAACCGGACCGGCCGGAGCAUCGUGUACAGC UGCGAGUGGCCCCUGUACAUGUGGCCCUUCCAGAAGCCCAACUACACCGAGAUCCGCCAGUACUG CAACCACUGGCGGAAUUUCGCCGAUAUUGACGAUAGCUGGAAGUCCAUCAAGUCCAUCCUGGAUU GGACCAGCUUCAACCAGGAGCGGAUCGUGGACGUGGCCGGCCCCGGCGGCUGGAACGACCCCGAC AUGCUGGUGAUCGGCAACUUCGGCCUGAGCUGGAACCAGCAGGUGACCCAGAUGGCCCUGUGGGC CAUCAUGGCCGCCCACUCUUCAUGAGCAACGACCUGCUGCACAUCAGCCCGCAGGCCAGGCCC UGCUGCAGGACAAGGACGUGAUCGCCAUUAAUCAGGACCCGUGGGCAAGCAGGGCUACCAGCUC AGGCAGGGCGACAACUUCGAGGUGUGGGAGAGGCCUCGAGCGGUCUGGCUGGGCCGUGGCCAU GAUCAACCGGCAGGAGAUCGGCGGACCGCGGAGCUACACCAUCGCGGUGGCCAGCCUGGGAAAGG GCGUGGCCUGCAACCCCGCCUGCUUCAUCACCCAGCUGCUGCCGUGAAGAGAAAGCUCGGCUUC UACGAGUGGACGUCAAGACUGCGGAGCCACAUCAACCCCACCGGCACCGUCUCCUGCAGCUGGA GAAUACCAUGCAGAUGUCCCGAAGGACCUCCUG*UGAUAAUAGUCCAUAAAGUAGGAAACACUAC AGCUGGAGCCUCGGUGGCCAUGCUUCUUGCCCCUUGGGCCUCCCCCCAGCCCCUCCUCCCCUUCC UGCACCCGUACCCCCCGCAUUAUUACUCACGGUACGAGUGGUCUUUGAAUAAAGUCUGAGUGGGC GGC* |
| 133 | GLA-mRNA #15 | <u>GGGAAAUAAGAGAGAAAAGAAGAGUAAGAAGAAAUAUAAGAGCCACC</u>AUGCAGCUCCGGAACCCC GAGCUUCACCUAGGCUGCGCCCUCGCCCUCCGGUUCCUGCCCUAGUGAGCUGGGACAUCCCAGG CGCCCGCGCCCUCGACAACGGCCUCGCCCGGACCCCUACCAUGGGCUGGCUCCACUGGGAGCGGU UCAUGUGCAACCUGGACUGCCAGGAGGAGCCCGACAGCUGCAUCAGCGAGAAGCUGUUCAUGGAG AUGGCCGAGCUGAUGGUGAGCGAGGGCUGGAAGGACGCCGGCUACGAGUACCUGUGCAUCGACGA CUGCUGGAUGGCGCCGCAGCGGGACUCUGAGGGCCGGCUGCAGGCCGACCCGCAGAGGUUCCCGC ACGGCAUCCGGCAGCUGGCCAACUACGUGCACAGCAAGGGCCUGAAGCUGGGCAUCUACGCCGAC GUGGGCAACAAGACCUGCGCCGGCUUCCCUGGCAGCUUCGGCUACUACGACAUCGACGCCCAGAC CUUCGCCGACUGGGGCGUGGACCUGCUGAAGUUCGACGGCUGCUACUGCGACAGCCUGGAGAACC UGGCCGACGGCUACAAGCACAUGAGCCUUGCGCUCAACCGGACCGGCCGGAGCAUCGUGUACAGC UGCGAGUGGCCCCUGUACAUGUGGCCCUUCCAGAAGCCCAACUACACCGAGAUCCGCCAGUACUG CAACCACUGGCGGAAUUUCGCCGAUAUCGAUGAUUCCUGGAAGUCCAUCAAGUCCAUCCUCGACU GGACCAGCUUCAACCAGGAGCGGAUCGUGGACGUGGCCGGCCCCGGCGGCUGGAACGACCCCGAC AUGCUGGUGAUCGGCAACUUCGGCCUGAGCUGGAACCAGCAGGUGACCCAGAUGGCCCUGUGGGC | mRNA Constructs

| SEQ ID NO | Construct | Sequence<br>5' UTR = bold underline;<br>3' UTR comprising a stop codon = bold italics |
|---|---|---|
| | | CAUCAUGGCCGCGCCACUCUUCAUGAGCAACGACCUGCGGCACAUCAGCCCGCAGGCCAAGGCCC<br>UGCUGCAGGACAAGGACGUGAUCGCCAUUAACCAAGACCCGCUGGGCAAGCAGGGCUACCAGCUG<br>CGCCAGGGCGACAACUUCGAGGUGUGGGAGAGGCCUCUGUCCGGACUGGCUUGGGCCGUGGCCAU<br>GAUCAACCGGCAGGAGAUCGGCGGACCACGGAGCUACACCAUCGCCGUGGCGAGCCUGGGUAAGG<br>GCGUGGCCUGCAACCCCGCCUGCUUCAUCACCCAGCUGCUGCCCGUGAAGAGAAAGCUGGGUUUC<br>UACGAGUGGACCUCGAGACUGCGGAGCCACAUCAACCCCACCGGCACCGUGCUCCUGCAGCUCGA<br>GAACACCAUGCAGAUGUCCCUCAAGGACCUCCUG*UGAUAAUAGUCCAUAAAGUAGGAAACACUAC*<br>*AGCUGGAGCCUCGUGGCCAUGCUUCUUGCCCCUUGGGCCUCCCCCCAGCCCCUCCUCCCCUUCC*<br>*UGCACCCGUACCCCCCGCAUUAUUACUCACGGUACGAGUGGUCUUUGAAUAAAGUCUGAGUGGGC*<br>*GGC* |
| 134 | GLA-mRNA #16 | <u>GGGAAAUAAGAGAGAAAAGAAGAGUAAGAAGAAAUAUAAGAGCCACC</u>AUGCAGCUCCGGAACCCC<br>GAGCUCCACCUCGGCUGCGCCCUCGCCCUCCGGUUCUCGCGCUCGUGAGCUGGGACAUCCCAGG<br>CGCCCGGGCUCUCGACAACGGCCUAGCCCGGACCCCGACCAUGGGCUGGCUCCACUGGGAGCGGU<br>UCAUGUGCAACCUGGACUGCCAGGAGGAGCCCGACAGCUGCAUCAGCGAGAAGCUGUUCAUGGAG<br>AUGGCCGAGCUGAUGGUGAGCGAGGGCUGGAAGGACGCCGGCUACGAGUACCUGUGCAUCGACGA<br>CUGCUGGAUGGCCCCACAGCGGGACAGCGAGGGACGCUGCAGGCCGAUCCGCAGCGUUUCCCGC<br>ACGGCAUCCGGCAGCUGGCCAACUACGUGCACAGCAAGGGCCUGAAGCUGGCAUCUACGCCGAC<br>GUGGGCAACAAGACCUGCGCCGGCUUCCCAGGCAGCUUCGGCUACUACGACAUCGACGCCCAGAC<br>CUUCGCCGACUGGGGCGUGGACCUGCUGAAGUUCGACGGCUGUUACUGCGACAGCCUGGAGAACC<br>UGGCCGACGGCUACAAGCACAUGUCCCUGGCACUGAACCGGACCGGCCGGAGCAUCGUGUACAGC<br>UGCGAGUGGCCCCUGUACAUGUGGCCCUUCCAGAAGCCCAACUACACCGAGAUCAGACAAUACUG<br>CAACCACUGGCGGAAUUUCGCCGAUAUAGACGAUAGCUGGAAGUCCAUCAAGUCCAUCCUGGAUU<br>GGACCAGCUUCAACCAGGAGCGGAUCGUGGACGUGGCCCGGCCCCGGCGGCUGGAACGACCCCGAC<br>AUGCUGGUGAUCGGCAACUUCGGCCUGAGCUGGAACCAGCAGGUGACCCAGAUGGCCCUGUGGGC<br>CAUCAUGGCCGCCCCUCUCUUCAUGAGCAACGACCUGCGGCACAUCAGCCCGCAGGCCAAGGCCC<br>UGCUGCAGGACAAGGACGUGAUCGCCAUCAAUCAAGACCCGCUGGGCAAGCAGGGCUACCAGCUG<br>AGACAGGGCGACAACUUCGAGGUGUGGGAGAGGCCGCUGUCGGGACUGGCCUGGGCCGUGGCCAU<br>GAUCAACCGGCAGGAGAUCGGCGGCCCGGGAGCUACACCAUCGCGGUGGCCUCGCUGGGAAAGG<br>GCGUGGCCUGCAACCCCGCCUGCUUCAUCACCCAGCUGCUGCCCGUGAAGCUAAGCUGGGAUUC<br>UACGAGUGGACCUCCAGACUGCGGAGCCACAUCAACCCCACCGGCACCGUGCUUCUGCAGCUGGA<br>GAAUACCAUGCAGAUGUCCCUCAAGGACCUCCUG*UGAUAAUAGUCCAUAAAGUAGGAAACACUAC*<br>*AGCUGGAGCCUCGUGGCCCAUGCUUCUUGCCCCUUGGGCCUCCCCCCAGCCCCUCCUCCCCUUCC*<br>*UGCACCCGUACCCCCCGCAUUAUUACUCACGGUACGAGUGGUCUUUGAAUAAAGUCUGAGUGGGC*<br>*GGC* |
| 135 | GLA-mRNA #17 | <u>GGGAAAUAAGAGAGAAAAGAAGAGUAAGAAGAAAUAUAAGAGCCACC</u>AUGCAGCUCCGGAACCCC<br>GAGCUCCACCUUGGCUGCGCCCUUGCCUUGCGGUUCUUAGCCCUCGUGAGCUGGGACAUCCCAGG<br>CGCCCGCGCCCUCGACAACGGCCUCGCCCGCACCCCUACCAUGGGCUGGCUCCACUGGGAGCGCU<br>UCAUGUGCAACCUCGACUGCCAGGAGGAGCCCGACUCCUGCAUCUCCGAGAAGCUGUUCAUGGAG<br>AUGGCCGAGCUCAUGGUGUCCGAGGGCUGGAAGGACGCCGGCUACGAGUACCUCUGCAUCGACGA<br>CUGCUGGAUGGCCCCGCAGCGCGACAGCGAGGGCAGGCUCCAGGCCGACCCACAGAGGUUCCCAC<br>ACGGCAUCCGCCAGCUCGCCAACUACGUCCACUCCAAGGGCCUCAAGCUCGGCAUCUACGCCGAC<br>GUCGGCAACAAGACCUGCGCCGGCUUCCCCGGCUCCUUCGGCUACUACGACAUCGACGCCCAGAC<br>CUUCGCCGACUGGGGCGUCGACCUCCUCAAGUUCGACGGCUGCUACUGCGACUCCCUCGAGAACC<br>UCGCCGACGGCUACAAGCACAUGUCCCUCGCCCUCAACCGCACCGGCCGCUCCAUCGUCUACUCC<br>UGCGAGUGGCCCCUCUACAUGUGGCCCUUCCAGAAGCCCAACUACACCGAGAUCAGGCAGUACUG<br>CAACCACUGGCGCAAUUUCGCCGAUAUCGAUGACAGCUGGAAGUCCAUCAAGAGCAUCCUGGACU<br>GGACCUCCUUCAACCAGGAGCGCAUCGUCGACGUCGCCCGGCCCCGGCGGCUGGAACGACCCCGAC<br>AUGCUCGUCAUCGGUAACUUCGGCCUGUCUUGGAACCAGCAGGUCACCCAGAUGGCCCUCUGGGC<br>CAUCAUGGCCGCCCACUGUUCAUGUCCAACGACCUCCGCCACAUCUCCCCUCAGGCCAAGGCCC<br>UCCUCCAGGACAAGGACGUCAUCGCCAUCAAUCAGGACCCGCUCGGCAAGCAGGGCUACCAGCUC<br>CGCCAGGGCGACAACUUCGAGGUGUGGGAGAGGCCCCUCUCCGGACUCGCCUGGGCCGUCGCCAU<br>GAUCAACCGCCAGGAGAUCGGCGGCCCACGCUCCUACACCAUCGCCGUGGCCUCCCUGGGCAAGG<br>GCGUCGCCUGCAACCCCGCCUGCUUCAUCACCCAGCUCCUCCCCGUCAAGAGGAAGCUGGGCUUC<br>UACGAGUGGACAAGCCGCCUCCGCUCCCACAUCAACCCCACCGGCACCGUGCUGCUGCAGCUGGA<br>GAACACCAUGCAGAUGUCCCUGAAGGACCUGCUG*UGAUAAUAGUCCAUAAAGUAGGAAACACUAC*<br>*AGCUGGAGCCUCGUGGCCAUGCUUCUUGCCCCUUGGGCCUCCCCCCAGCCCCUCCUCCCCUUCC*<br>*UGCACCCGUACCCCCCGCAUUAUUACUCACGGUACGAGUGGUCUUUGAAUAAAGUCUGAGUGGGC*<br>*GGC* |
| 136 | GLA-mRNA #18 | <u>GGGAAAUAAGAGAGAAAAGAAGAGUAAGAAGAAAUAUAAGAGCCACC</u>AUGCAGCUUCGGAACCCC<br>GAGCUCCACCUUGGCUGCGCCCUUGCCCUCCGGUUCCUCGCCCUCGUGAGCUGGGACAUACCGGG<br>CGCCAGGGCCCUCGACAACGGCCUCGCCCGCACCCCGACCAUGGGCUGGCUCCACUGGGAGCGCU<br>UCAUGUGCAACCUCGACUGCCAGGAGGAGCCCGACUCCUGCAUCUCCGAGAAGCUGUUCAUGGAG<br>AUGGCCGAGCUCAUGGUGUCCGAGGGCUGGAAGGACGCCGGCUACGAGUACCUCUGCAUCGACGA<br>CUGCUGGAUGGCCCCGCAGCGCGACAGCGAGGGCGCCCUCAGGCCGACCCACAGAGAUUCCCGC<br>ACGGCAUCCGCCAGCUCGCCAACUACGUCCACUCCAAGGGCCUCAAGCUCGGCAUCUACGCCGAC<br>GUCGGCAACAAGACCUGCGCCGGCUUCCCCGGCUCCUUCGGCUACUACGACAUCGACGCCCAGAC<br>CUUCGCCGACUGGGGCGUCGACCUCCUCAAGUUCGACGGCUGCUACUGCGACUCCCUCGAGAACC<br>UCGCCGACGGCUACAAGCACAUGAGCCUCGCUCUCAACCGCACCGGCCGCUCCAUCGUCUACUCC<br>UGCGAGUGGCCCCUCUACAUGUGGCCCUUCCAGAAGCCCAACUACACCGAGAUCCGCCAGUACUG<br>CAACCACUGGCGCAAUUUCGCCGAUAUCGAUGACUCCUGGAAGUCCAUCAAGAGCAUCCUGGACU |

-continued mRNA Constructs

| SEQ ID NO | Construct | Sequence<br>5' UTR = bold underline;<br>3' UTR comprising a stop codon = bold italics |
|---|---|---|
| | | GGACCUCCUUCAACCAGGAGCGCAUCGUCGACGUCGCCGGCCCCGGCGGCUGGAACGACCCCGAC<br>AUGCUCGUCAUCGGAAACUUCGGCCUGAGCUGGAACCAGCAGGUCACCCAGAUGGCCCUCUGGGC<br>CAUCAUGGCCGCCCCAUUGUUCAUGUCCAACGACCUCCGCCACAUCUCCCCGCAGGCCAAGGCCC<br>UCCUCCAGGACAAGGACGUCAUCGCCAUCAAUCAGGACCCGCUCGGCAAGCAGGGCUACCAGCUC<br>CGCCAGGGCGACAACUUCGAGGUGUGGGAGCGGCCUCUCUCCGGACUGGCCUGGGCCGUCGCCAU<br>GAUCAACCGCCAGGAGAUCGGCGGCCCACGCUCCUACACCAUCGCCGUGGCCAGCCUGGGCAAGG<br>GCGUCGCCUGCAACCCCGCCUGCUUCAUCACCCAGCUCCUCCCCGUCAAGAGGAAGCUGGGCUUC<br>UACGAGUGGACCAGCCGCCUCCGCUCCCACAUCAACCCCACCGGCACCGUGCUGCUGCAGCUGGA<br>GAACACCAUGCAGAUGAGCCUGAAGGACCUCCU*UGAUAAUAGUCCAUAAAGUAGGAAACACUAC*<br>*AGCUGGAGCCUCGGUGGCCAUGCUUCUUGCCCCUUGGGCCUCCCCCCAGCCCCUCCUCCCCUUCC*<br>*UGCACCCGUACCCCCCGCAUUAUUACUCACGGUACGAGUGGUCUUUGAAUAAAGUCUGAGUGGGC*<br>*GGC* |
| 137 | GLA-mRNA #19 | <u>GGGAAAUAAGAGAGAAAAGAAGAGUAAGAAGAAAUAUAAGAGCCACC</u>AUGCAGCUCCGGAACCCC<br>GAGCUCCACCUCGGCUGCGCCCUCGCCCUCCGGUUCUCGCCCUAGUGAGCUGGGACAUCCCGGG<br>CGCCAGGGCCCUCGACAACGGCCUCGCCCGCACCCCAACCAUGGGCUGGCUCACUGGGAGCGCU<br>UCAUGUGCAACCUCGACUGCCAGGAGGAGCCCGACUCCUGCAUCUCCGAGAAGCUGUUCAUGGAG<br>AUGGCCGAGCUCAUGGUGUCCGAGGGCUGGAAGGACGCCGGCUACGAGUACCUCUGCAUCGACGA<br>CUGCUGGAUGGCCCCACAGCGCGACAGCGAGGGCCGCCUCCAGGCCGACCCACAGAGGUUCCCGC<br>ACGGCAUCCGCCAGCUCGCCAACUACGUCCACUCCAAGGGCCUCAAGCUCGGCAUCUACGCCGAC<br>GUCGGCAACAAGACCUGCGCCGGCUUCCCCGGCUCCUUCGGCUACUACGACAUCGACGCCCAGAC<br>CUUCGCCGACUGGGGCGUCGACCUCCUCAAGUUCGACGGCUGCUACUGCGACUCCCUCGAGAACC<br>UCGCCGACGGCUACAAGCACAUGAGCCUGGCGCUCAACCGCACCGGCCGCUCCAUCGUCUACUCC<br>UGCGAGUGGCCCUCUACAUGUGGCCUUCCAGAAGCCCAACUACACCGGAGAUCCGACAGUACUG<br>CAACCACUGGCGCAAUUUCGCCGAUAUCGAUGAUUCCUGGAAGUCCAUCAAGGAGCAUCCUCGAUU<br>GGACCUCCUUCAACCAGGAGCGCAUCGUCGACGUCGCCGGCCCCGGCGGCUGGAACGACCCCGAC<br>AUGCUCGUCAUCGGUAACUUCGGCCUGAGCUGGAACCAGCAGGUCACCCAGAUGGCCCUCUGGGC<br>CAUCAUGGCCGCCCCGCUUUUCAUGUCCAACGACCUCCGCCACAUCUCGCCGCAGGCCAAGGCCC<br>UCCUCCAGGACAAGGACGUCAUCGCCAUCAAUCAGGACCCGCUCGGCAAGCAGGGCUACCAGCUC<br>CGCCAGGGCGACAACUUCGAGGUGUGGGAGCGGCCCCUCAGCGGCUGGCGUGGGCCGUCGCCAU<br>GAUCAACCGCCAGGAGAUCGGCGGUCCACGCUCCUACACCAUCGCCGUGGCCAGCCUGGGCAAGG<br>GCGUCGCCUGCAACCCCGCCUGCUUCAUCACCCAGCUCCUCCCCGUCAAGAGGAAGCUGGGAUUC<br>UACGAGUGGACUAGCAGGCUGCGCUCCCACAUCAACCCCACCGGCACCGUGCUCCUGCAGCUGGA<br>GAAUACCAUGCAGAUGUCCCUGAAGGACCUGCU*UGAUAAUAGUCCAUAAAGUAGGAAACACUAC*<br>*AGCUGGAGCCUCGGUGGCCAUGCUUCUUGCCCCUUGGGCCUCCCCCCAGCCCCUCCUCCCCUUCC*<br>*UGCACCCGUACCCCCCGCAUUAUUACUCACGGUACGAGUGGUCUUUGAAUAAAGUCUGAGUGGGC*<br>*GGC* |
| 138 | GLA-mRNA #20 | <u>GGGAAAUAAGAGAGAAAAGAAGAGUAAGAAGAAAUAUAAGAGCCACC</u>AUGCAGCUGCGGAACCCC<br>GAGCUGCACCUGGGCUGCGCCCUGGCCCUGCGGUUCCUGGCCCUGGUGAGCUGGGACAUCCCGG<br>CGCCCGGGCGCUGGACAACGGGCUGGCGAGGACGCCGACGAUGGGGUGGCUGCACUGGGAGGU<br>UCAUGUGCAACCUGGACUGCCAGGAGGAGCCGGACAGCUGCAUCAGCGAGAAGCUGUUCAUGGAG<br>AUGGCGGAGCUGAUGGUGAGCGAGGGCUGGAAGGACGCGGGUACGAGUACCUGUGCAUCGACGA<br>CUGCUGGAUGGCGCCGCAGAGGGACAGCGAGGGGAGGCUGCAGGCGGACCCGCAGAGGUUCCCGC<br>ACGGGAUCAGGCAGCUGGCGAACUACGUGCACAGCAAGGGGCUGAAGCUGGGGAUCUACGCGGAC<br>GUGGGGAACAAGACGUGCGCGGGGUUCCCGGGGAGCUUCGGGUACUACGACAUCGACGCGCAGAC<br>GUUCGCGGACUGGGGCGUGGACCUGCUGAAGUUCGACGGGUGCUACUGCGACAGCCUGGAGAACC<br>UGGCGGACGGGUACAAGCACAUGAGCCUGGCGCUGAACAGGACGGGGAGGAGCAUCGUGUACAGC<br>UGCGAGUGGCCGCUGUACAUGUGGCCGUUCCAGAAGCCCAACUACACGGGAGAUCAGGCAGUACUG<br>CAACCACUGGAGGAACUUCGCGGACAUCGACGACAGCUGGAAGAGCAUCAAGAGCAUCCUGGACU<br>GGACGAGCUUCAACCAGGAGAGGAUCGUGGACGUGGGGGCCGGGAGGGUGGAACGACCCGGAC<br>AUGCUGGUGAUCGGGAACUUCGGGCUGAGCUGGAACCAGCAGGUGACGCAGAUGGCGCUGUGGGC<br>GAUCAUGGCGGCGCGCUGUUCAUGAGCAACGACCUGAGGCACAUCAGCCCGCAGGCGAAGGCGC<br>UGCUGCAGGACAAGGACGUGAUCGCGAUCAACCAGGACCCGCUGGGGAAGCAGGGGUACCAGCUG<br>AGGCAGGGUGACAACUUCGAGGUGUGGGAGAGGCCGCUGAGCGGGUGGCGUGGGCGGUGGCGAU<br>GAUCAACAGGCAGGAGAUCGGAGGGCCGAGGAGCUACACGAUCGCGGUGGCGAGCCUGGGGAAGG<br>GCGUGGCGUGCAACCCGGCGUGCUUCAUCACGCAGCUGCUGCCGGUGAAGAGGAAGCUGGGGUUC<br>UACGAGUGGACGAGCAGGCUGAGGAGCCACAUCAACCCGACGGGACGGUGCUGCUGCAGCUGGA<br>GAACACGAUGCAGAUGAGCCUGAAGGACCUGCU*UGAUAAUAGUCCAUAAAGUAGGAAACACUAC*<br>*AGCUGGAGCCUCGGUGGCCAUGCUUCUUGCCCCUUGGGCCUCCCCCCAGCCCCUCCUCCCCUUCC*<br>*UGCACCCGUACCCCCCGCAUUAUUACUCACGGUACGAGUGGUCUUUGAAUAAAGUCUGAGUGGGC*<br>*GGC* |
| 139 | GLA-mRNA #21 | <u>GGGAAAUAAGAGAGAAAAGAAGAGUAAGAAGAAAUAUAAGAGCCACC</u>AUGCAGCUGCGGAACCCC<br>GAGCUGCACCUGGGCUGCGCCCUGGCCCUGCGGUUCCUGGCCCUGGUGAGCUGGGACAUCCCCGG<br>CGCCCGGGCCCUCGACAACGGCCUCGCCCGCACGCCCACCAUGGGCUGGCUCCACUGGGAGCGCU<br>UCAUGUGCAACCUCGACUGCCAGGAGGAGCCCGACUCCUGCAUCUCCGAGAAGCUCUUCAUGGAG<br>AUGGCCGAGCUCAUGGUCUCCGAGGGCUGGAAGGACGCCGGCUACGAGUACCUCUGCAUCGACGA<br>CUGCUGGAUGGCGCCCAGCGCGACUCCGAGGGCCGCCUCCAGGCCGACCCUCAGCGCUUCCCGC<br>ACGGCAUCCGCCAGCUCGCCAACUACGUCCACUCCAAGGGCCUCAAGCUCGGCAUCUACGCCGAC<br>GUCGGCAACAAGACCUGCGCCGGCUUCCCCGGCUCCUUCGGCUACUACGACAUCGACGCCCAGAC<br>CUUCGCCGACUGGGGCGUCGACCUCCUCAAGUUCGACGGCUGCUACUGCGACUCCCUCGAGAACC<br>UCGCCGACGGCUACAAGCACAUGUCCCUCGCCCUCAACCGCACCGGCCGCUCCAUCGUCUACUCC |

| SEQ ID NO | Construct | Sequence<br>5' UTR = bold underline;<br>3' UTR comprising a stop codon = bold italics |
|---|---|---|
| | | UGCGAGUGGCCCCUCUACAUGUGGCCCUUCCAGAAGCCCAACUACACCGAGAUCCGCCAGUACUG<br>CAACCACUGGCGCAACUUCGCCGACAUCGACGUCCUGGAAGUCCAUCAAGUCCAUCCUCGACU<br>GGACCUCCUUCAACCAGGAGCGCAUCGUCGACGUCGCCGGCCCCGGCGGCUGGAACGACCCCGAC<br>AUGCUCGUCAUCGGCAACUUCGGCCUCUCCUGGAACCAGCAGGUCACCCAGAUGGCCCUCUGGGC<br>CAUCAUGGCCGCGCCCCUCUUCAUGUCCAACGACCUCCGCCACAUCUCGCCCCAGGCCAAGGCCC<br>UCCUCCAGGACAAGGACGUCAUCGCCAUCAACCAGGACCCGCUCGGCAAGCAGGGCUACCAGCUC<br>CGCCAGGGCGACAACUUCGAGGUCUGGGAGCGCCCGCUCUCCGGCCUCGCCUGGGCCGUCGCCAU<br>GAUCAACCGCCAGGAGAUCGGCGGCCCACGCUCCUACACCAUCGCCGUCGCCUCCCUCGGCAAGG<br>GCGUCGCCUGCAACCCCGCCUGCUUCAUCACCAGCUCUCCCCGUCAAGCGCAAGCUCGGCUUC<br>UACGAGUGGACCUCCCGCCUCCGCUCCCACAUCAACCCCACCGGCACCGUCCUCCUCCAGCUCGA<br>GAACACCAUGCAGAUGUCCCUCAAGGACCUCCU*UGAUAAUAGUCCAUAAAGUAGGAAACACUAC*<br>*AGCUGGAGCCUCGGUGGCCAUGCUUCUUGCCCCUUGGGCCUCCCCCCAGCCCCUCCUCCCCUUCC*<br>*UGCACCCGUACCCCCCGCAUUAUUACUCACGGUACGAGUGGUCUUUGAAUAAAGUCUGAGUGGGC*<br>*GGC* |
| 140 | GLA-mRNA #22 | <u>GGGAAAUAAGAGAGAAAAGAAGAGUAAGAAGAAAUAUAAGAGCCACC</u>AUGCAGCUGAGGAACCCA<br>GAACUACAUCUGGGCUGCGCGCUUGCGCUUCGCUUCCUGGCCCCUCGUUUCCUGGGACAUCCCUGG<br>GGCUAGAGCACUGGACAAUGGAUUGGCAAGGACGCCUACCAUGGGCUGGCUGCACUGGGAGCGCU<br>UCAUGUGCAACCUUGACUGCCAGGAAGAGCCAGAUUCCUGCAUCAGUGAGAAGCUCUUCAUGGAG<br>AUGGCAGAGCUCAUGGUCUCAGAAGGCUGGAAGGAUGCAGGUUAUGAGUACCUCUGCAUUGAUGA<br>CUGUUGGAUGGCUCCCCAAAGAGAUUCAGAAGGCAGACUUCAGGCAGACCCUCAGCGCUUUCCUC<br>AUGGGAUUCGCCAGCUAGCUAAUUAUGUUCACAGCAAAGGACUGAAGCUAGGGAUUUAUGCAGAU<br>GUUGGAAAUAAGACCUGCGCAGGCUUCCCUGGGAGUUUUGGAUACUACGACAUUGAUGCCCAGAC<br>CUUUGCUGACUGGGGAGUAGAUCUGCUAAAGUUUGAUGGUUGUUACUGUGACAGUUUGGAGAAUU<br>UGGCAGAUGGUUAUAAGCACAUGUCCUUGGCCCUGAAUAGGACUGGCAGAAGCAUUGUGUACUCC<br>UGUGAGUGGCCUCUUUAUAUGUGGCCCUUUCAGAAGCCCAAUUAUACAGAAAUCCGACAGUACUG<br>CAAUCACUGGCGAAAUUUUGCUGACAUUGAUGAUUCCUGGAAGAGUAUAAAGAGUAUCUUGGACU<br>GGACAUCUUUUAACCAGGAGAGAAUUGUUGAUGUUGCUGGACCAGGCGGUUGGAAUGACCCAGAU<br>AUGUUAGUGAUUGGCAACUUUGGCCUCAGCUGGAAUCAGCAAGUAACUCAGAUGGCCCUCUGGGC<br>UAUCAUGGCUGCUCCUUUAUUCAUGUCUAAUGACCUCCGACACAUCAGCCCUCAAGCCAAAGCUC<br>UCCUUCAGGAUAAGGACGUAAUUGCCAUCAAUCAGGACCCCUUGGGCAAGCAAGGGUACCAGCUU<br>AGACAGGGAGACAACUUUGAAGUGUGGGAACGACCUCUCUCAGGCUUAGCCUGGGCUGUAGCUAU<br>GAUAAACCGGCAGGAGAUUGGUGGACCUCGCUCUUUAUACCAUCGCAGUUGCUUCCCUGGGUAAAG<br>GAGUGGCCUGUAAUCCUGCCUGCUUCAUCACACAGCUCCUCCCUGUGAAGAGGAAGCUAGGGUUC<br>UAUGAAUGGACUUCAAGGUUAAGAAGUCACAUAAAUCCCACAGGCACUGUUUUGCUUCAGCUAGA<br>GAAUACAAUGCAGAUGUCAUUAAAGGACUUACUU*UGAUAAUAGUCCAUAAAGUAGGAAACACUAC*<br>*AGCUGGAGCCUCGGUGGCCAUGCUUCUUGCCCCUUGGGCCUCCCCCCAGCCCCUCCUCCCCUUCC*<br>*UGCACCCGUACCCCCCGCAUUAUUACUCACGGUACGAGUGGUCUUUGAAUAAAGUCUGAGUGGGC*<br>*GGC* |
| 160 | GLA-mRNA #23 | <u>GGGAAAUAAGAGAGAAAAGAAGAGUAAGAAGAAAUAUAAGAGCCACC</u>AUGCAGCUCCGGAACCCC<br>GAGCUCCACCUUGGCUGCGCCCUCGCCUUGCGGUUCCUCGCACUUGUGAGCUGGGACAUACCAGG<br>CGCCCGGGCCCUCGACAACGGCCUCGCCCGCACCCCAACCAUGGGCUGGCUCCACUGGGAGCGCU<br>UCAUGUGCAACCUCGACUGCCAGGAGGAGCCGACUCCUGCAUCUCCGAGAAGCUUUUCAUGGAG<br>AUGGCCGAGCUCAUGGUGUCCGAGGGCUGGAAGGACGCCGGCUACGAGUACCUCUGCAUCGACGA<br>CUGCUGGAUGGCCCCGCAGCGCGACAGCGAGGGUCGCCUCCAGGCCGACCCGCAGCGGUUCCCUC<br>ACGGCAUCCGCCAGCUCGCCAACUACGUCCACUCCAAGGGCCUCAAGCUCGGCAUCUACGCCGAC<br>GUCGGCAACAAGACCUGCGCCGGCUUCCCCGGCUCCUUCGGCUACUACGACAUCGACGCCCAGAC<br>CUUCGCCGACUGGGGCGUCGACCUCCUCAAGUUCGACGGCUGCUACUGCGACUCCCUCGAGAACC<br>UCGCCGACGGCUACAAGCACAUGUCCCUCGCCCUCAACCGCACCGGCCGCUCCAUCGUCUACUCC<br>UGCGAGUGGCCCCUCUACAUGUGGCCCUUCCAGAAGCCCAACUACACCGAGAUAAGGCAGUACUG<br>CAACCACUGGCGCAAUUUCGCCGAUAUCGAUGACUCCUGGAAGUCCAUCAAGAGCAUCCUGGACU<br>GGACCUCCUUCAACCAGGAGCGCAUCGUCGACGUCGCCGGCCCCGGCGGCUGGAACGACCCCGAC<br>AUGCUCGUCAUCGGAAACUUCGGCCUGUCCUGGAACCAGCAGGUCACCCAGAUGGCCCUCUGGGC<br>CAUCAUGGCCGCCCACUGUUCAUGUCCAACGACCUCCGCCACAUCAGCCCGCAGGCCAAGGCCC<br>UCCUCCAGGACAAGGACGUCAUCGCCAUCAACCAAGACCCGCUCGGCAAGCAGGGCUACCAGCUC<br>CGCCAGGGCGACAACUUCGAGGUGUGGGAACGUCCCCUCAGCGGCCUGGCGUGGGCCGUCGCCAU<br>GAUCAACCGCCAGGAGAUCGGCGGCCCGCGCUCCUACACCAUCGCCGUGGCCAGCUGGGCAAGG<br>GCGUCGCCUGCAACCCCGCCUGCUUCAUCACCCAGCUCCUCCCCGUCAAGAGAAAGCUGGGCUUC<br>UACGAGUGGACCAGCCGCCUCCGCUCCCACAUCAACCCCACCGGCACCGUCCUGCUCCAGCUGGA<br>GAACACCAUGCAGAUGAGCCUCAAGGACCUGCUC*UGAUAAUAGGCUGGAGCCUCGGUGGCCAUGC*<br>*UUGCCCCUUGGGCCUCCCCCCAGCCCCUCCUCCCCUUCCUGCACCCGUACCCCCCGCAUUAU*<br>*UACUCACGGUACGAGUGGUCUUUGAAUAAAGUCUGAGUGGGCGGC* |

20. Methods of Making Polynucleotides

The present disclosure also provides methods for making a polynucleotide of the invention (e.g., a polynucleotide comprising a nucleotide sequence encoding a GLA polypeptide) or a complement thereof.

In some aspects, a polynucleotide (e.g., a RNA, e.g., an mRNA) disclosed herein, and encoding a GLA polypeptide, can be constructed using in vitro transcription. In other aspects, a polynucleotide (e.g., a RNA, e.g., an mRNA) disclosed herein, and encoding a GLA polypeptide, can be constructed by chemical synthesis using an oligonucleotide synthesizer.

In other aspects, a polynucleotide (e.g., a RNA, e.g., an mRNA) disclosed herein, and encoding a GLA polypeptide is made by using a host cell. In certain aspects, a polynucleotide (e.g., a RNA, e.g., an mRNA) disclosed herein, and encoding a GLA polypeptide is made by one or more combination of the IVT, chemical synthesis, host cell expression, or any other methods known in the art.

Naturally occurring nucleosides, non-naturally occurring nucleosides, or combinations thereof, can totally or partially naturally replace occurring nucleosides present in the candidate nucleotide sequence and can be incorporated into a sequence-optimized nucleotide sequence (e.g., a RNA, e.g., an mRNA) encoding a GLA polypeptide. The resultant polynucleotides, e.g., mRNAs, can then be examined for their ability to produce protein and/or produce a therapeutic outcome.

a. In Vitro Transcription/Enzymatic Synthesis

The polynucleotides of the present invention disclosed herein (e.g., a polynucleotide comprising a nucleotide sequence encoding a GLA polypeptide) can be transcribed using an in vitro transcription (IVT) system. The system typically comprises a transcription buffer, nucleotide triphosphates (NTPs), an RNase inhibitor and a polymerase. The NTPs can be selected from, but are not limited to, those described herein including natural and unnatural (modified) NTPs. The polymerase can be selected from, but is not limited to, T7 RNA polymerase, T3 RNA polymerase and mutant polymerases such as, but not limited to, polymerases able to incorporate polynucleotides disclosed herein. See U.S. Publ. No. US20130259923, which is herein incorporated by reference in its entirety.

Any number of RNA polymerases or variants can be used in the synthesis of the polynucleotides of the present invention. RNA polymerases can be modified by inserting or deleting amino acids of the RNA polymerase sequence. As a non-limiting example, the RNA polymerase can be modified to exhibit an increased ability to incorporate a 2'-modified nucleotide triphosphate compared to an unmodified RNA polymerase (see International Publication WO2008078180 and U.S. Pat. No. 8,101,385; herein incorporated by reference in their entireties).

Variants can be obtained by evolving an RNA polymerase, optimizing the RNA polymerase amino acid and/or nucleic acid sequence and/or by using other methods known in the art. As a non-limiting example, T7 RNA polymerase variants can be evolved using the continuous directed evolution system set out by Esvelt et al. (Nature 472:499-503 (2011); herein incorporated by reference in its entirety) where clones of T7 RNA polymerase can encode at least one mutation such as, but not limited to, lysine at position 93 substituted for threonine (K93T), I4M, A7T, E63V, V64D, A65E, D66Y, T76N, C125R, S128R, A136T, N165S, G175R, H176L, Y178H, F182L, L196F, G198V, D208Y, E222K, S228A, Q239R, T243N, G259D, M267I, G280C, H300R, D351A, $A_{354}S$, E356D, L360P, $A_{383}V$, Y385C, D388Y, S397R, M401T, N410S, K450R, P451T, G452V, E484A, H523L, H524N, G542V, E565K, K577E, K577M, N601S, S684Y, L699I, K713E, N748D, Q754R, E775K, A827V, D851N or L864F. As another non-limiting example, T7 RNA polymerase variants can encode at least mutation as described in U.S. Pub. Nos. 20100120024 and 20070117112; herein incorporated by reference in their entireties. Variants of RNA polymerase can also include, but are not limited to, substitutional variants, conservative amino acid substitution, insertional variants, and/or deletional variants.

In one aspect, the polynucleotide can be designed to be recognized by the wild type or variant RNA polymerases. In doing so, the polynucleotide can be modified to contain sites or regions of sequence changes from the wild type or parent chimeric polynucleotide.

Polynucleotide or nucleic acid synthesis reactions can be carried out by enzymatic methods utilizing polymerases. Polymerases catalyze the creation of phosphodiester bonds between nucleotides in a polynucleotide or nucleic acid chain. Currently known DNA polymerases can be divided into different families based on amino acid sequence comparison and crystal structure analysis. DNA polymerase I (pol I) or A polymerase family, including the Klenow fragments of E. coli, Bacillus DNA polymerase I, Thermus aquaticus (Taq) DNA polymerases, and the T7 RNA and DNA polymerases, is among the best studied of these families. Another large family is DNA polymerase α (pol α) or B polymerase family, including all eukaryotic replicating DNA polymerases and polymerases from phages T4 and RB69. Although they employ similar catalytic mechanism, these families of polymerases differ in substrate specificity, substrate analog-incorporating efficiency, degree and rate for primer extension, mode of DNA synthesis, exonuclease activity, and sensitivity against inhibitors.

DNA polymerases are also selected based on the optimum reaction conditions they require, such as reaction temperature, pH, and template and primer concentrations. Sometimes a combination of more than one DNA polymerases is employed to achieve the desired DNA fragment size and synthesis efficiency. For example, Cheng et al. increase pH, add glycerol and dimethyl sulfoxide, decrease denaturation times, increase extension times, and utilize a secondary thermostable DNA polymerase that possesses a 3' to 5' exonuclease activity to effectively amplify long targets from cloned inserts and human genomic DNA. (Cheng et al., PNAS 91:5695-5699 (1994), the contents of which are incorporated herein by reference in their entirety). RNA polymerases from bacteriophage T3, T7, and SP6 have been widely used to prepare RNAs for biochemical and biophysical studies. RNA polymerases, capping enzymes, and poly-A polymerases are disclosed in the co-pending International Publication No. WO2014028429, the contents of which are incorporated herein by reference in their entirety.

In one aspect, the RNA polymerase which can be used in the synthesis of the polynucleotides of the present invention is a Syn5 RNA polymerase. (see Zhu et al. Nucleic Acids Research 2013, doi:10.1093/nar/gkt1193, which is herein incorporated by reference in its entirety). The Syn5 RNA polymerase was recently characterized from marine cyanophage Syn5 by Zhu et al. where they also identified the promoter sequence (see Zhu et al. Nucleic Acids Research 2013, the contents of which is herein incorporated by reference in its entirety). Zhu et al. found that Syn5 RNA polymerase catalyzed RNA synthesis over a wider range of temperatures and salinity as compared to T7 RNA polymerase. Additionally, the requirement for the initiating nucleotide at the promoter was found to be less stringent for Syn5 RNA polymerase as compared to the T7 RNA polymerase making Syn5 RNA polymerase promising for RNA synthesis.

In one aspect, a Syn5 RNA polymerase can be used in the synthesis of the polynucleotides described herein. As a non-limiting example, a Syn5 RNA polymerase can be used in the synthesis of the polynucleotide requiring a precise 3'-terminus.

In one aspect, a Syn5 promoter can be used in the synthesis of the polynucleotides. As a non-limiting example, the Syn5 promoter can be 5"-ATTGGGCACCCG-TAAGGG-3' (SEQ ID NO: 76) as described by Zhu et al. (Nucleic Acids Research 2013).

In one aspect, a Syn5 RNA polymerase can be used in the synthesis of polynucleotides comprising at least one chemical modification described herein and/or known in the art (see e.g., the incorporation of pseudo-UTP and 5Me-CTP described in Zhu et al. Nucleic Acids Research 2013).

In one aspect, the polynucleotides described herein can be synthesized using a Syn5 RNA polymerase which has been purified using modified and improved purification procedure described by Zhu et al. (Nucleic Acids Research 2013).

Various tools in genetic engineering are based on the enzymatic amplification of a target gene which acts as a template. For the study of sequences of individual genes or specific regions of interest and other research needs, it is necessary to generate multiple copies of a target gene from a small sample of polynucleotides or nucleic acids. Such methods can be applied in the manufacture of the polynucleotides of the invention.

For example, polymerase chain reaction (PCR), strand displacement amplification (SDA), nucleic acid sequence-based amplification (NASBA), also called transcription mediated amplification (TMA), and/or rolling-circle amplification (RCA) can be utilized in the manufacture of one or more regions of the polynucleotides of the present invention.

Assembling polynucleotides or nucleic acids by a ligase is also widely used.

b. Chemical Synthesis

Standard methods can be applied to synthesize an isolated polynucleotide sequence encoding an isolated polypeptide of interest, such as a polynucleotide of the invention (e.g., a polynucleotide comprising a nucleotide sequence encoding a GLA polypeptide). For example, a single DNA or RNA oligomer containing a codon-optimized nucleotide sequence coding for the particular isolated polypeptide can be synthesized. In other aspects, several small oligonucleotides coding for portions of the desired polypeptide can be synthesized and then ligated. In some aspects, the individual oligonucleotides typically contain 5' or 3' overhangs for complementary assembly.

A polynucleotide disclosed herein (e.g., a RNA, e.g., an mRNA) can be chemically synthesized using chemical synthesis methods and potential nucleobase substitutions known in the art. See, for example, International Publication Nos. WO2014093924, WO2013052523; WO2013039857, WO2012135805, WO2013151671; U.S. Publ. No. US20130115272; or U.S. Pat. No. 8,999,380 or 8,710,200, all of which are herein incorporated by reference in their entireties.

c. Purification of Polynucleotides Encoding GLA

Purification of the polynucleotides described herein (e.g., a polynucleotide comprising a nucleotide sequence encoding a GLA polypeptide) can include, but is not limited to, polynucleotide clean-up, quality assurance and quality control. Clean-up can be performed by methods known in the arts such as, but not limited to, AGENCOURT® beads (Beckman Coulter Genomics, Danvers, Mass.), poly-T beads, LNA™ oligo-T capture probes (EXIQON® Inc., Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC).

The term "purified" when used in relation to a polynucleotide such as a "purified polynucleotide" refers to one that is separated from at least one contaminant. As used herein, a "contaminant" is any substance that makes another unfit, impure or inferior. Thus, a purified polynucleotide (e.g., DNA and RNA) is present in a form or setting different from that in which it is found in nature, or a form or setting different from that which existed prior to subjecting it to a treatment or purification method.

In some embodiments, purification of a polynucleotide of the invention (e.g., a polynucleotide comprising a nucleotide sequence encoding a GLA polypeptide) removes impurities that can reduce or remove an unwanted immune response, e.g., reducing cytokine activity.

In some embodiments, the polynucleotide of the invention (e.g., a polynucleotide comprising a nucleotide sequence encoding a GLA polypeptide) is purified prior to administration using column chromatography (e.g., strong anion exchange HPLC, weak anion exchange HPLC, reverse phase HPLC (RP-HPLC), and hydrophobic interaction HPLC (HIC-HPLC), or (LCMS)).

In some embodiments, the polynucleotide of the invention (e.g., a polynucleotide comprising a nucleotide sequence a GLA polypeptide) purified using column chromatography (e.g., strong anion exchange HPLC, weak anion exchange HPLC, reverse phase HPLC (RP-HPLC, hydrophobic interaction HPLC (HIC-HPLC), or (LCMS)) presents increased expression of the encoded GLA protein compared to the expression level obtained with the same polynucleotide of the present disclosure purified by a different purification method.

In some embodiments, a column chromatography (e.g., strong anion exchange HPLC, weak anion exchange HPLC, reverse phase HPLC (RP-HPLC), hydrophobic interaction HPLC (HIC-HPLC), or (LCMS)) purified polynucleotide comprises a nucleotide sequence encoding a GLA polypeptide comprising one or more of the point mutations known in the art.

In some embodiments, the use of RP-HPLC purified polynucleotide increases GLA protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the expression levels of GLA protein in the cells before the RP-HPLC purified polynucleotide was introduced in the cells, or after a non-RP-HPLC purified polynucleotide was introduced in the cells.

In some embodiments, the use of RP-HPLC purified polynucleotide increases functional GLA protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the functional expression levels of GLA protein in the cells before the RP-HPLC purified polynucleotide was introduced in the cells, or after a non-RP-HPLC purified polynucleotide was introduced in the cells.

In some embodiments, the use of RP-HPLC purified polynucleotide increases detectable GLA activity in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the activity levels of functional GLA in the cells before the RP-HPLC purified polynucleotide was introduced in the cells, or after a non-RP-HPLC purified polynucleotide was introduced in the cells.

In some embodiments, the purified polynucleotide is at least about 80% pure, at least about 85% pure, at least about 90% pure, at least about 95% pure, at least about 96% pure, at least about 97% pure, at least about 98% pure, at least about 99% pure, or about 100% pure.

A quality assurance and/or quality control check can be conducted using methods such as, but not limited to, gel electrophoresis, UV absorbance, or analytical HPLC. In another embodiment, the polynucleotide can be sequenced by methods including, but not limited to reverse-transcriptase-PCR.

d. Quantification of Expressed Polynucleotides Encoding GLA

In some embodiments, the polynucleotides of the present invention (e.g., a polynucleotide comprising a nucleotide sequence encoding a GLA polypeptide), their expression products, as well as degradation products and metabolites can be quantified according to methods known in the art.

In some embodiments, the polynucleotides of the present invention can be quantified in exosomes or when derived from one or more bodily fluid. As used herein "bodily fluids" include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes can be retrieved from an organ selected from the group consisting of lung, heart, pancreas, stomach, intestine, bladder, kidney, ovary, testis, skin, colon, breast, prostate, brain, esophagus, liver, and placenta.

In the exosome quantification method, a sample of not more than 2 mL is obtained from the subject and the exosomes isolated by size exclusion chromatography, density gradient centrifugation, differential centrifugation, nanomembrane ultrafiltration, immunoabsorbent capture, affinity purification, microfluidic separation, or combinations thereof. In the analysis, the level or concentration of a polynucleotide can be an expression level, presence, absence, truncation or alteration of the administered construct. It is advantageous to correlate the level with one or more clinical phenotypes or with an assay for a human disease biomarker.

The assay can be performed using construct specific probes, cytometry, qRT-PCR, real-time PCR, PCR, flow cytometry, electrophoresis, mass spectrometry, or combinations thereof while the exosomes can be isolated using immunohistochemical methods such as enzyme linked immunosorbent assay (ELISA) methods. Exosomes can also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of polynucleotides remaining or delivered. This is possible because the polynucleotides of the present invention differ from the endogenous forms due to the structural or chemical modifications.

In some embodiments, the polynucleotide can be quantified using methods such as, but not limited to, ultraviolet visible spectroscopy (UV/Vis). A non-limiting example of a UV/Vis spectrometer is a NANODROP® spectrometer (ThermoFisher, Waltham, Mass.). The quantified polynucleotide can be analyzed in order to determine if the polynucleotide can be of proper size, check that no degradation of the polynucleotide has occurred. Degradation of the polynucleotide can be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

21. Pharmaceutical Compositions and Formulations

The present invention provides pharmaceutical compositions and formulations that comprise any of the polynucleotides described above. In some embodiments, the composition or formulation further comprises a delivery agent.

In some embodiments, the composition or formulation can contain a polynucleotide comprising a sequence optimized nucleic acid sequence disclosed herein which encodes a GLA polypeptide. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes a GLA polypeptide. In some embodiments, the polynucleotide further comprises a miRNA binding site, e.g., a miRNA binding site that binds miR-126, miR-142, miR-144, miR-146, miR-150, miR-155, miR-16, miR-21, miR-223, miR-24, miR-27 and miR-26a.

Pharmaceutical compositions or formulation can optionally comprise one or more additional active substances, e.g., therapeutically and/or prophylactically active substances. Pharmaceutical compositions or formulation of the present invention can be sterile and/or pyrogen-free. General considerations in the formulation and/or manufacture of pharmaceutical agents can be found, for example, in *Remington: The Science and Practice of Pharmacy* 21$^{st}$ ed., Lippincott Williams & Wilkins, 2005 (incorporated herein by reference in its entirety). In some embodiments, compositions are administered to humans, human patients or subjects. For the purposes of the present disclosure, the phrase "active ingredient" generally refers to polynucleotides to be delivered as described herein.

Formulations and pharmaceutical compositions described herein can be prepared by any method known or hereafter developed in the art of pharmacology. In general, such preparatory methods include the step of associating the active ingredient with an excipient and/or one or more other accessory ingredients, and then, if necessary and/or desirable, dividing, shaping and/or packaging the product into a desired single- or multi-dose unit.

A pharmaceutical composition or formulation in accordance with the present disclosure can be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure can vary, depending upon the identity, size, and/or condition of the subject being treated and further depending upon the route by which the composition is to be administered.

In some embodiments, the compositions and formulations described herein can contain at least one polynucleotide of the invention. As a non-limiting example, the composition or formulation can contain 1, 2, 3, 4 or 5 polynucleotides of the invention. In some embodiments, the compositions or formulations described herein can comprise more than one type of polynucleotide. In some embodiments, the composition or formulation can comprise a polynucleotide in linear and circular form. In another embodiment, the composition or formulation can comprise a circular polynucleotide and an in vitro transcribed (IVT) polynucleotide. In yet another embodiment, the composition or formulation can comprise an IVT polynucleotide, a chimeric polynucleotide and a circular polynucleotide.

Although the descriptions of pharmaceutical compositions and formulations provided herein are principally directed to pharmaceutical compositions and formulations that are suitable for administration to humans, it will be understood by the skilled artisan that such compositions are generally suitable for administration to any other animal, e.g., to non-human animals, e.g. non-human mammals.

The present invention provides pharmaceutical formulations that comprise a polynucleotide described herein (e.g., a polynucleotide comprising a nucleotide sequence encoding a GLA polypeptide). The polynucleotides described herein can be formulated using one or more excipients to: (1) increase stability; (2) increase cell transfection; (3) permit the sustained or delayed release (e.g., from a depot formulation of the polynucleotide); (4) alter the biodistribution (e.g., target the polynucleotide to specific tissues or cell types); (5) increase the translation of encoded protein in vivo; and/or (6) alter the release profile of encoded protein in vivo. In some embodiments, the pharmaceutical formulation further comprises a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

A pharmaceutically acceptable excipient, as used herein, includes, but are not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cyoprotectants, and/or bulking agents, as suited to the particular dosage form desired. Various excipients for formulating pharmaceutical compositions and techniques for preparing the composition are known in the art (see Remington: The Science and Practice of Pharmacy, 21st Edition, A. R. Gennaro (Lippincott, Williams & Wilkins, Baltimore, Md., 2006; incorporated herein by reference in its entirety).

Exemplary diluents include, but are not limited to, calcium or sodium carbonate, calcium phosphate, calcium hydrogen phosphate, sodium phosphate, lactose, sucrose, cellulose, microcrystalline cellulose, kaolin, mannitol, sorbitol, etc., and/or combinations thereof.

Exemplary granulating and/or dispersing agents include, but are not limited to, starches, pregelatinized starches, or microcrystalline starch, alginic acid, guar gum, agar, poly (vinyl-pyrrolidone), (providone), cross-linked poly(vinylpyrrolidone) (crospovidone), cellulose, methylcellulose, carboxymethyl cellulose, cross-linked sodium carboxymethyl cellulose (croscarmellose), magnesium aluminum silicate (VEEGUM®), sodium lauryl sulfate, etc., and/or combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), sorbitan fatty acid esters (e.g., polyoxyethylene sorbitan monooleate [TWEEN®80], sorbitan monopalmitate [SPAN®40], glyceryl monooleate, polyoxyethylene esters, polyethylene glycol fatty acid esters (e.g., CREMOPHOR®), polyoxyethylene ethers (e.g., polyoxyethylene lauryl ether [BRU®30]), PLUORINC® F 68, POLOXAMER®188, etc. and/or combinations thereof.

Exemplary binding agents include, but are not limited to, starch, gelatin, sugars (e.g., sucrose, glucose, dextrose, dextrin, molasses, lactose, lactitol, mannitol), amino acids (e.g., glycine), natural and synthetic gums (e.g., acacia, sodium alginate), ethylcellulose, hydroxyethylcellulose, hydroxypropyl methylcellulose, etc., and combinations thereof.

Oxidation is a potential degradation pathway for mRNA, especially for liquid mRNA formulations. In order to prevent oxidation, antioxidants can be added to the formulations. Exemplary antioxidants include, but are not limited to, alpha tocopherol, ascorbic acid, acorbyl palmitate, benzyl alcohol, butylated hydroxyanisole, m-cresol, methionine, butylated hydroxytoluene, monothioglycerol, sodium or potassium metabisulfite, propionic acid, propyl gallate, sodium ascorbate, etc., and combinations thereof.

Exemplary chelating agents include, but are not limited to, ethylenediaminetetraacetic acid (EDTA), citric acid monohydrate, disodium edetate, fumaric acid, malic acid, phosphoric acid, sodium edetate, tartaric acid, trisodium edetate, etc., and combinations thereof.

Exemplary antimicrobial or antifungal agents include, but are not limited to, benzalkonium chloride, benzethonium chloride, methyl paraben, ethyl paraben, propyl paraben, butyl paraben, benzoic acid, hydroxybenzoic acid, potassium or sodium benzoate, potassium or sodium sorbate, sodium propionate, sorbic acid, etc., and combinations thereof.

Exemplary preservatives include, but are not limited to, vitamin A, vitamin C, vitamin E, beta-carotene, citric acid, ascorbic acid, butylated hydroxyanisol, ethylenediamine, sodium lauryl sulfate (SLS), sodium lauryl ether sulfate (SLES), etc., and combinations thereof.

In some embodiments, the pH of polynucleotide solutions are maintained between pH 5 and pH 8 to improve stability. Exemplary buffers to control pH can include, but are not limited to sodium phosphate, sodium citrate, sodium succinate, histidine (or histidine-HCl), sodium malate, sodium carbonate, etc., and/or combinations thereof.

Exemplary lubricating agents include, but are not limited to, magnesium stearate, calcium stearate, stearic acid, silica, talc, malt, hydrogenated vegetable oils, polyethylene glycol, sodium benzoate, sodium or magnesium lauryl sulfate, etc., and combinations thereof.

The pharmaceutical composition or formulation described here can contain a cryoprotectant to stabilize a polynucleotide described herein during freezing. Exemplary cryoprotectants include, but are not limited to mannitol, sucrose, trehalose, lactose, glycerol, dextrose, etc., and combinations thereof.

The pharmaceutical composition or formulation described here can contain a bulking agent in lyophilized polynucleotide formulations to yield a "pharmaceutically elegant" cake, stabilize the lyophilized polynucleotides during long term (e.g., 36 month) storage. Exemplary bulking agents of the present invention can include, but are not limited to sucrose, trehalose, mannitol, glycine, lactose, raffinose, and combinations thereof.

In some embodiments, the pharmaceutical composition or formulation further comprises a delivery agent. The delivery agent of the present disclosure can include, without limitation, liposomes, lipid nanoparticles, lipidoids, polymers, lipoplexes, microvesicles, exosomes, peptides, proteins, cells transfected with polynucleotides, hyaluronidase, nanoparticle mimics, nanotubes, conjugates, and combinations thereof.

22. Delivery Agents a. Lipid Compound

The present disclosure provides pharmaceutical compositions with advantageous properties. The lipid compositions described herein may be advantageously used in lipid nanoparticle compositions for the delivery of therapeutic and/or prophylactic agents, e.g., mRNAs, to mammalian cells or organs. For example, the lipids described herein have little or no immunogenicity. For example, the lipid compounds disclosed herein have a lower immunogenicity as compared to a reference lipid (e.g., MC3, KC2, or DLinDMA). For example, a formulation comprising a lipid disclosed herein and a therapeutic or prophylactic agent, e.g., mRNA, has an increased therapeutic index as compared to a corresponding formulation which comprises a reference lipid (e.g., MC3, KC2, or DLinDMA) and the same therapeutic or prophylactic agent.

In certain embodiments, the present application provides pharmaceutical compositions comprising:
(a) a polynucleotide comprising a nucleotide sequence encoding a GLA polypeptide; and
(b) a delivery agent.

In some embodiments, the delivery agent comprises a lipid compound having the Formula (I)

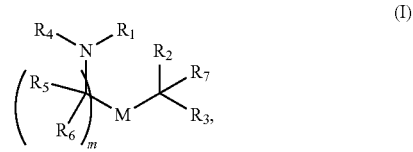

wherein
$R_1$ is selected from the group consisting of $C_{5-30}$ alkyl, $C_{5-20}$ alkenyl, —R*YR", —YR", and —R"M'R';
$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;
$R_7$ is selected from the group consisting of $C_{1-3}$ alkyl, $C_{2-3}$ alkenyl, and H;
$R_8$ is selected from the group consisting of $C_{3-6}$ carbocycle and heterocycle;
$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;
each R is independently selected from the group consisting of $C_{1-3}$ alkyl, $C_{2-3}$ alkenyl, and H;
each R' is independently selected from the group consisting of $C_{1-18}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{2-12}$ alkenyl;
each Y is independently a $C_{3-6}$ carbocycle;
each X is independently selected from the group consisting of F, Cl, Br, and I; and m is selected from 5, 6, 7, 8, 9, 10, 11, 12, and 13,
or salts or stereoisomers thereof.

In some embodiments, a subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof, wherein alkyl and alkenyl groups may be linear or branched.

In some embodiments, a subset of compounds of Formula (I) includes those in which when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In other embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and a 5- to 14-membered heterocycloalkyl having one or more heteroatoms selected from N, O, and S which is substituted with one or more substituents selected from oxo (=O), OH, amino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In other embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, and a 5- to 14-membered heterocycloalkyl having one or more heteroatoms selected from N, O, and S which is substituted with one or more substituents selected from oxo (=O), OH, amino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet other embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5; and when Q is a 5- to 14-membered heterocycle and (i) $R_4$ is —(CH$_2$)$_n$Q in which n is 1 or 2, or (ii) $R_4$ is —(CH$_2$)$_n$CHQR in which n is 1, or (iii) $R_4$ is —CHQR, and —CQ(R)$_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet other embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, and each n is independently selected from 1, 2, 3, 4, and 5; and when Q is a 5- to 14-membered heterocycle and (i) $R_4$ is —(CH$_2$)$_n$Q in which n is 1 or 2, or (ii) $R_4$ is —(CH$_2$)$_n$CHQR in which n is 1, or (iii) $R_4$ is —CHQR, and —CQ(R)$_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still another embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet other embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —(CH$_2$)$_n$Q or —(CH$_2$)$_n$CHQR, where Q is —N(R)$_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13,
or salts or stereoisomers thereof.

In yet other embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_n$Q or —$(CH_2)_n$CHQR, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13,
or salts or stereoisomers thereof.

In still other embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —CQ$(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13,
or salts or stereoisomers thereof.

In still other embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —CQ$(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13,
or salts or stereoisomers thereof.

In certain embodiments, a subset of compounds of Formula (I) includes those of Formula (IA):

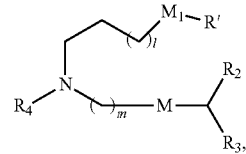

(IA)

or a salt or stereoisomer thereof, wherein l is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_n$Q, in which Q is OH, —NHC(S)N$(R)_2$, —NHC(O)N$(R)_2$, N(R)C(O)R, —N(R)S(O)$_2$R, —N(R)R$_8$, —NHC(=NR$_9$)N$(R)_2$, —NHC(=CHR$_9$)N$(R)_2$, —OC(O)N$(R)_2$, —N(R)C(O)OR, heteroaryl, or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IA), or a salt or stereoisomer thereof, wherein l is selected from 1, 2, 3, 4, and 5; m is selected from 5, 6, 7, 8, and 9;

$M_1$ is a bond or M';

$R_4$ is unsubstituted $C_{1-3}$ alkyl, or —$(CH_2)_nQ$, in which Q is OH, —$NHC(S)N(R)_2$, or —$NHC(O)N(R)_2$;

M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

In certain embodiments, a subset of compounds of Formula (I) includes those of Formula (II):

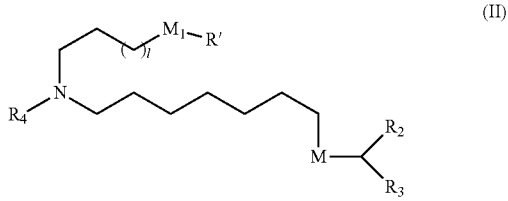

(II)

or a salt or stereoisomer thereof, wherein l is selected from 1, 2, 3, 4, and 5; $M_1$ is a bond or M'; $R_4$ is unsubstituted $C_{1-3}$ alkyl, or —$(CH_2)_nQ$, in which n is 2, 3, or 4, and Q is OH, —$NHC(S)N(R)_2$, —$NHC(O)N(R)_2$, —$N(R)C(O)R$, —$N(R)S(O)_2R$, —$N(R)R_8$, —$NHC(=NR_9)N(R)_2$, —$NHC(=CHR_9)N(R)_2$, —$OC(O)N(R)_2$, —$N(R)C(O)OR$, heteroaryl, or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II), or a salt or stereoisomer thereof, wherein l is selected from 1, 2, 3, 4, and 5;

$M_1$ is a bond or M';

$R_4$ is unsubstituted $C_{1-3}$ alkyl, or —$(CH_2)_nQ$, in which n is 2, 3, or 4, and Q is OH, —$NHC(S)N(R)_2$, or —$NHC(O)N(R)_2$;

M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

In some embodiments, the compound of Formula (I) is of the Formula (IIa),

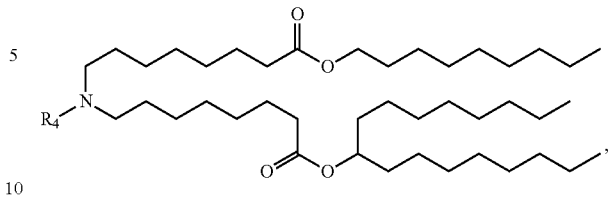

(IIa)

or a salt thereof, wherein $R_4$ is as described above.

In some embodiments, the compound of Formula (I) is of the Formula (IIb),

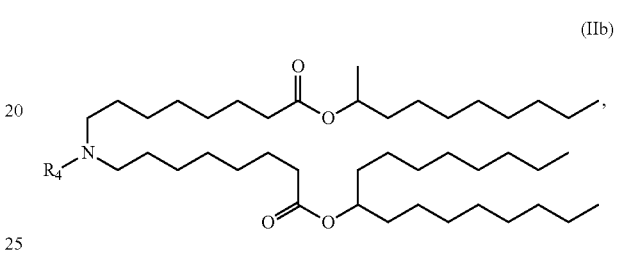

(IIb)

or a salt thereof, wherein $R_4$ is as described above.

In some embodiments, the compound of Formula (I) is of the Formula (IIc),

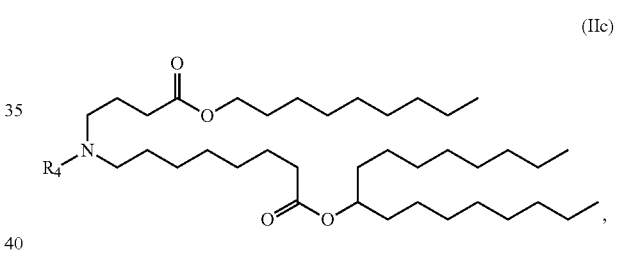

(IIc)

or a salt thereof, wherein $R_4$ is as described above.

In some embodiments, the compound of Formula (I) is of the Formula (IIe):

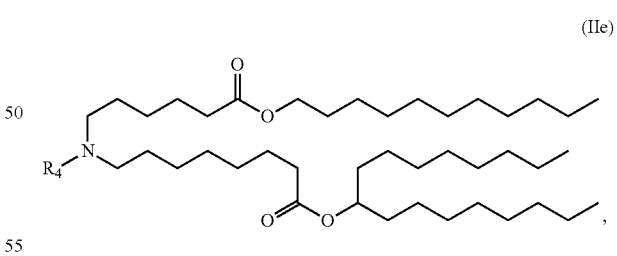

(IIe)

or a salt thereof, wherein $R_4$ is as described above.

In some embodiments, the compound of Formula (IIa), (IIb), (IIc), or (IIe) comprises an $R_4$ which is selected from —$(CH_2)_nQ$ and —$(CH_2)_nCHQR$, wherein Q, R and n are as defined above.

In some embodiments, Q is selected from the group consisting of —OR, —OH, —$O(CH_2)_nN(R)_2$, —OC(O)R, —$CX_3$, —CN, —$N(R)C(O)R$, —$N(H)C(O)R$, —$N(R)S(O)_2R$, —$N(H)S(O)_2R$, —$N(R)C(O)N(R)_2$, —$N(H)C(O)N(R)_2$, —$N(H)C(O)N(H)(R)$, —$N(R)C(S)N(R)_2$, —$N(H)C(S)N(R)_2$, —$N(H)C(S)N(H)(R)$, and a heterocycle, wherein R is as defined above. In some aspects, n is 1 or 2. In some embodiments, Q is OH, —NHC(S)N(R)$_2$, or —NHC(O)N(R)$_2$.

In some embodiments, the compound of Formula (I) is of the Formula (IId),

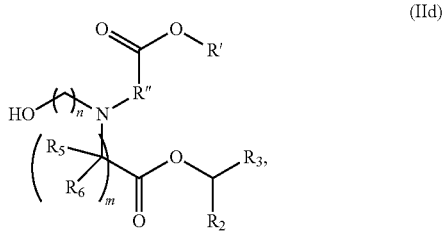

(IId)

or a salt thereof, wherein R$_2$ and R$_3$ are independently selected from the group consisting of C$_{5-14}$ alkyl and C$_{5-14}$ alkenyl, n is selected from 2, 3, and 4, and R', R", R$_5$, R$_6$ and m are as defined above.

In some aspects of the compound of Formula (IId), R$_2$ is C$_8$ alkyl. In some aspects of the compound of Formula (IId), R$_3$ is C$_5$-C$_9$ alkyl. In some aspects of the compound of Formula (IId), m is 5, 7, or 9. In some aspects of the compound of Formula (IId), each R$_5$ is H. In some aspects of the compound of Formula (IId), each R$_6$ is H.

In another aspect, the present application provides a lipid composition (e.g., a lipid nanoparticle (LNP)) comprising: (1) a compound having the Formula (I); (2) optionally a helper lipid (e.g. a phospholipid); (3) optionally a structural lipid (e.g. a sterol); and (4) optionally a lipid conjugate (e.g. a PEG-lipid). In exemplary embodiments, the lipid composition (e.g., LNP) further comprises a polynucleotide encoding a GLA polypeptide, e.g., a polynucleotide encapsulated therein.

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms).

The notation "C$_{1-14}$ alkyl" means a linear or branched, saturated hydrocarbon including 1-14 carbon atoms. An alkyl group can be optionally substituted.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond.

The notation "C$_{2-14}$ alkenyl" means a linear or branched hydrocarbon including 2-14 carbon atoms and at least one double bond. An alkenyl group can include one, two, three, four, or more double bonds. For example, C$_{18}$ alkenyl can include one or more double bonds. A C$_{18}$ alkenyl group including two double bonds can be a linoleyl group. An alkenyl group can be optionally substituted.

As used herein, the term "carbocycle" or "carbocyclic group" means a mono- or multi-cyclic system including one or more rings of carbon atoms. Rings can be three, four, five, six, seven, eight, nine, ten, eleven, twelve, thirteen, fourteen, or fifteen membered rings.

The notation "C$_{3-6}$ carbocycle" means a carbocycle including a single ring having 3-6 carbon atoms. Carbocycles can include one or more double bonds and can be aromatic (e.g., aryl groups). Examples of carbocycles include cyclopropyl, cyclopentyl, cyclohexyl, phenyl, naphthyl, and 1,2-dihydronaphthyl groups. Carbocycles can be optionally substituted.

As used herein, the term "heterocycle" or "heterocyclic group" means a mono- or multi-cyclic system including one or more rings, where at least one ring includes at least one heteroatom. Heteroatoms can be, for example, nitrogen, oxygen, or sulfur atoms. Rings can be three, four, five, six, seven, eight, nine, ten, eleven, or twelve membered rings. Heterocycles can include one or more double bonds and can be aromatic (e.g., heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. Heterocycles can be optionally substituted.

As used herein, a "biodegradable group" is a group that can facilitate faster metabolism of a lipid in a subject. A biodegradable group can be, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group.

As used herein, an "aryl group" is a carbocyclic group including one or more aromatic rings. Examples of aryl groups include phenyl and naphthyl groups.

As used herein, a "heteroaryl group" is a heterocyclic group including one or more aromatic rings. Examples of heteroaryl groups include pyrrolyl, furyl, thiophenyl, imidazolyl, oxazolyl, and thiazolyl. Both aryl and heteroaryl groups can be optionally substituted. For example, M and M' can be selected from the non-limiting group consisting of optionally substituted phenyl, oxazole, and thiazole. In the formulas herein, M and M' can be independently selected from the list of biodegradable groups above.

Alkyl, alkenyl, and cyclyl (e.g., carbocyclyl and heterocyclyl) groups can be optionally substituted unless otherwise specified. Optional substituents can be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR or —OC(O)R), an aldehyde (e.g., —C(O)H), a carbonyl (e.g., —C(O)R, alternatively represented by C=O), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., —C(OR)$_2$R"", in which each OR are alkoxy groups that can be the same or different and R"" is an alkyl or alkenyl group), a phosphate (e.g., P(O)$_4$$^{3-}$), a thiol (e.g., —SH), a sulfoxide (e.g., —S(O)R), a sulfinic acid (e.g., —S(O)OH), a sulfonic acid (e.g., —S(O)$_2$OH), a thial (e.g., —C(S)H), a sulfate (e.g., S(O)$_4$$^{2-}$), a sulfonyl (e.g., —S(O)$_2$—), an amide (e.g., —C(O)NR$_2$, or —N(R)C(O)R), an azido (e.g., —N$_3$), a nitro (e.g., —NO$_2$), a cyano (e.g., —CN), an isocyano (e.g., —NC), an acyloxy (e.g., —OC(O)R), an amino (e.g., —NR$_2$, —NRH, or —NH$_2$), a carbamoyl (e.g., —OC(O)NR$_2$, —OC(O)NRH, or —OC(O)NH$_2$), a sulfonamide (e.g., —S(O)$_2$NR$_2$, —S(O)$_2$NRH, —S(O)$_2$NH$_2$, —N(R)S(O)$_2$R, —N(H)S(O)$_2$R, —N(R)S(O)$_2$H, or —N(H)S(O)$_2$H), an alkyl group, an alkenyl group, and a cyclyl (e.g., carbocyclyl or heterocyclyl) group.

In any of the preceding, R is an alkyl or alkenyl group, as defined herein. In some embodiments, the substituent groups themselves can be further substituted with, for example, one, two, three, four, five, or six substituents as defined herein. For example, a $C_{1-6}$ alkyl group can be further substituted with one, two, three, four, five, or six substituents as described herein.

The compounds of any one of Formulae (I), (IA), (II), (IIa), (IIb), (IIc), (IId), and (IIe) include one or more of the following features when applicable.

In some embodiments, $R_4$ is selected from the group consisting of a $C_{3-6}$ carbocycle, —$(CH_2)_nQ$, —$(CH_2)_n$CHQR, —CHQR, and —$CQ(R)_2$, where Q is selected from a $C_{3-6}$ carbocycle, 5- to 14-membered aromatic or non-aromatic heterocycle having one or more heteroatoms selected from N, O, S, and P, —OR, —$O(CH_2)_nN(R)_2$, —C(O)OR, —OC(O)R, —$CX_3$, —$CX_2H$, —$CXH_2$, —CN, —$N(R)_2$, —$C(O)N(R)_2$, —N(R)C(O)R, —N(R)S(O)$_2$R, —N(R)C(O)N(R)$_2$, —N(R)C(S)N(R)$_2$, and —C(R)N(R)$_2$C(O)OR, and each n is independently selected from 1, 2, 3, 4, and 5.

In another embodiment, $R_4$ is selected from the group consisting of a $C_{3-6}$ carbocycle, —$(CH_2)_nQ$, —$(CH_2)_n$CHQR, —CHQR, and —$CQ(R)_2$, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —N(R)S(O)$_2$R, —N(R)C(O)N(R)$_2$, —N(R)C(S)N(R)$_2$, —C(R)N(R)$_2$C(O)OR, and a 5- to 14-membered heterocycloalkyl having one or more heteroatoms selected from N, O, and S which is substituted with one or more substituents selected from oxo (=O), OH, amino, and $C_{1-3}$ alkyl, and each n is independently selected from 1, 2, 3, 4, and 5.

In another embodiment, $R_4$ is selected from the group consisting of a $C_{3-6}$ carbocycle, —$(CH_2)_nQ$, —$(CH_2)_n$CHQR, —CHQR, and —$CQ(R)_2$, where Q is selected from a $C_{3-6}$ carbocycle, a 5- to 14-membered heterocycle having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —N(R)S(O)$_2$R, —N(R)C(O)N(R)$_2$, —N(R)C(S)N(R)$_2$, —C(R)N(R)$_2$C(O)OR, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_n$CHQR in which n is 1, or (iii) $R_4$ is —CHQR, and —$CQ(R)_2$, then Q is either a 5- to 14-membered heteroaryl or 8- to 14-membered heterocycloalkyl.

In another embodiment, $R_4$ is selected from the group consisting of a $C_{3-6}$ carbocycle, —$(CH_2)_nQ$, —$(CH_2)_n$CHQR, —CHQR, and —$CQ(R)_2$, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —N(R)S(O)$_2$R, —N(R)C(O)N(R)$_2$, —N(R)C(S)N(R)$_2$, —C(R)N(R)$_2$C(O)OR, and each n is independently selected from 1, 2, 3, 4, and 5.

In another embodiment, $R_4$ is unsubstituted $C_{1-4}$ alkyl, e.g., unsubstituted methyl.

In certain embodiments, the disclosure provides a compound having the Formula (I), wherein $R_4$ is —$(CH_2)_nQ$ or —$(CH_2)_n$CHQR, where Q is —$N(R)_2$, and n is selected from 3, 4, and 5.

In certain embodiments, the disclosure provides a compound having the Formula (I), wherein $R_4$ is selected from the group consisting of —$(CH_2)_nQ$, —$(CH_2)_n$CHQR, —CHQR, and —$CQ(R)_2$, where Q is —$N(R)_2$, and n is selected from 1, 2, 3, 4, and 5.

In certain embodiments, the disclosure provides a compound having the Formula (I), wherein $R_2$ and $R_3$ are independently selected from the group consisting of $C_{2-14}$ alkyl, $C_{2-14}$ alkenyl, —R*YR", —YR", and —R*OR", or $R_2$ and $R_3$, together with the atom to which they are attached, form a heterocycle or carbocycle, and $R_4$ is —$(CH_2)_nQ$ or —$(CH_2)_n$CHQR, where Q is —$N(R)_2$, and n is selected from 3, 4, and 5.

In certain embodiments, $R_2$ and $R_3$ are independently selected from the group consisting of $C_{2-14}$ alkyl, $C_{2-14}$ alkenyl, —R*YR", —YR", and —R*OR", or $R_2$ and $R_3$, together with the atom to which they are attached, form a heterocycle or carbocycle.

In some embodiments, $R_1$ is selected from the group consisting of $C_{5-20}$ alkyl and $C_{5-20}$ alkenyl.

In other embodiments, $R_1$ is selected from the group consisting of —R*YR", —YR", and —R"M'R'.

In certain embodiments, $R_1$ is selected from —R*YR" and —YR". In some embodiments, Y is a cyclopropyl group. In some embodiments, R* is $C_8$ alkyl or $C_8$ alkenyl. In certain embodiments, R" is $C_{3-12}$ alkyl. For example, R" can be $C_3$ alkyl. For example, R" can be $C_{4-8}$ alkyl (e.g., $C_4$, $C_5$, $C_6$, $C_7$, or $C_8$ alkyl).

In some embodiments, $R_1$ is $C_{5-20}$ alkyl. In some embodiments, $R_1$ is $C_6$ alkyl. In some embodiments, $R_1$ is $C_8$ alkyl. In other embodiments, $R_1$ is $C_9$ alkyl. In certain embodiments, $R_1$ is $C_{14}$ alkyl. In other embodiments, $R_1$ is $C_{18}$ alkyl.

In some embodiments, $R_1$ is $C_{5-20}$ alkenyl. In certain embodiments, $R_1$ is $C_{18}$ alkenyl. In some embodiments, $R_1$ is linoleyl.

In certain embodiments, $R_1$ is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl, or heptadeca-9-yl). In certain embodiments, $R_1$ is

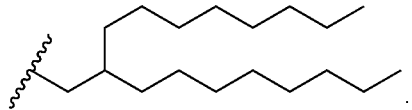 [SMILES: *CC(CCCCCCCC)CCCCCCCC]

In certain embodiments, $R_1$ is unsubstituted $C_{5-20}$ alkyl or $C_{5-20}$ alkenyl. In certain embodiments, R' is substituted $C_{5-20}$ alkyl or $C_{5-20}$ alkenyl (e.g., substituted with a $C_{3-6}$ carbocycle such as 1-cyclopropylnonyl).

In other embodiments, $R_1$ is —R"M'R'.

In some embodiments, R' is selected from —R*YR" and —YR". In some embodiments, Y is $C_{3-8}$ cycloalkyl. In some embodiments, Y is $C_{6-10}$ aryl. In some embodiments, Y is a cyclopropyl group. In some embodiments, Y is a cyclohexyl group. In certain embodiments, R* is $C_1$ alkyl.

In some embodiments, R" is selected from the group consisting of $C_{3-12}$ alkyl and $C_{3-12}$ alkenyl. In some embodiments, R" adjacent to Y is $C_1$ alkyl. In some embodiments, R" adjacent to Y is $C_{4-9}$ alkyl (e.g., $C_4$, $C_5$, $C_6$, $C_7$ or $C_8$ or $C_9$ alkyl).

In some embodiments, R' is selected from $C_4$ alkyl and $C_4$ alkenyl. In certain embodiments, R' is selected from $C_5$ alkyl and $C_5$ alkenyl. In some embodiments, R' is selected from $C_6$ alkyl and $C_6$ alkenyl. In some embodiments, R' is selected from $C_7$ alkyl and $C_7$ alkenyl. In some embodiments, R' is selected from $C_9$ alkyl and $C_9$ alkenyl.

In other embodiments, R' is selected from $C_{11}$ alkyl and $C_{11}$ alkenyl. In other embodiments, R' is selected from $C_{12}$ alkyl, $C_{12}$ alkenyl, $C_{13}$ alkyl, $C_{13}$ alkenyl, $C_{14}$ alkyl, $C_{14}$ alkenyl, $C_{15}$ alkyl, $C_{15}$ alkenyl, $C_{16}$ alkyl, $C_{16}$ alkenyl, $C_{17}$ alkyl, $C_{17}$ alkenyl, $C_{18}$ alkyl, and $C_{18}$ alkenyl. In certain embodiments, R' is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl or heptadeca-9-yl). In certain embodiments, R' is

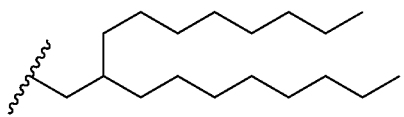

In certain embodiments, R' is unsubstituted $C_{1-18}$ alkyl. In certain embodiments, R' is substituted $C_{1-18}$ alkyl (e.g., $C_{1-15}$ alkyl substituted with a $C_{3-6}$ carbocycle such as 1-cyclopropylnonyl).

In some embodiments, R" is selected from the group consisting of $C_{3-14}$ alkyl and $C_{3-14}$ alkenyl. In some embodiments, R" is $C_3$ alkyl, $C_4$ alkyl, $C_5$ alkyl, $C_6$ alkyl, $C_7$ alkyl, or $C_8$ alkyl. In some embodiments, R" is $C_9$ alkyl, $C_{10}$ alkyl, $C_{11}$ alkyl, $C_{12}$ alkyl, $C_{13}$ alkyl, or $C_{14}$ alkyl.

In some embodiments, M' is —C(O)O—, In some embodiments, M' is —OC(O)—.

In other embodiments, M' is an aryl group or heteroaryl group. For example, M' can be selected from the group consisting of phenyl, oxazole, and thiazole.

In some embodiments, M is —C(O)O—. In some embodiments, M is —OC(O)—. In some embodiments, M is —C(O)N(R')—. In some embodiments, M is —P(O)(OR')O—.

In other embodiments, M is an aryl group or heteroaryl group. For example, M can be selected from the group consisting of phenyl, oxazole, and thiazole.

In some embodiments, M is the same as M'. In other embodiments, M is different from M'.

In some embodiments, each $R_5$ is H. In certain such embodiments, each $R_6$ is also H.

In some embodiments, $R_7$ is H. In other embodiments, $R_7$ is $C_{1-3}$ alkyl (e.g., methyl, ethyl, propyl, or i-propyl).

In some embodiments, $R_2$ and $R_3$ are independently $C_{5-14}$ alkyl or $C_{5-14}$ alkenyl.

In some embodiments, $R_2$ and $R_3$ are the same. In some embodiments, $R_2$ and $R_3$ are $C_8$ alkyl. In certain embodiments, $R_2$ and $R_3$ are $C_2$ alkyl. In other embodiments, $R_2$ and $R_3$ are $C_3$ alkyl. In some embodiments, $R_2$ and $R_3$ are $C_4$ alkyl. In certain embodiments, $R_2$ and $R_3$ are $C_5$ alkyl. In other embodiments, $R_2$ and $R_3$ are $C_6$ alkyl. In some embodiments, $R_2$ and $R_3$ are $C_7$ alkyl.

In other embodiments, $R_2$ and $R_3$ are different. In certain embodiments, $R_2$ is $C_8$ alkyl. In some embodiments, $R_3$ is $C_{1-7}$ (e.g., $C_1$, $C_2$, $C_3$, $C_4$, $C_5$, $C_6$, or $C_7$ alkyl) or $C_9$ alkyl.

In some embodiments, $R_7$ and $R_3$ are H.

In certain embodiments, $R_2$ is H.

In some embodiments, m is 5, 7, or 9.

In some embodiments, $R_4$ is selected from —$(CH_2)_n$Q and —$(CH_2)_n$CHQR.

In some embodiments, Q is selected from the group consisting of —OR, —OH, —O$(CH_2)_n$N$(R)_2$, —OC(O)R, —$CX_3$, —CN, —N(R)C(O)R, —N(H)C(O)R, —N(R)S(O)$_2$R, —N(H)S(O)$_2$R, —N(R)C(O)N$(R)_2$, —N(H)C(O)N$(R)_2$, —N(H)C(O)N(H)(R)—, —N(R)C(S)N$(R)_2$, —N(H)C(S)N$(R)_2$, —N(H)C(S)N(H)(R)—, —C(R)N$(R)_2$C(O)OR, a carbocycle, and a heterocycle.

In certain embodiments, Q is —OH.

In certain embodiments, Q is a substituted or unsubstituted 5- to 10-membered heteroaryl, e.g., Q is an imidazole, a pyrimidine, a purine, 2-amino-1,9-dihydro-6H-purin-6-one-9-yl (or guanin-9-yl), adenin-9-yl, cytosin-1-yl, or uracil-1-yl. In certain embodiments, Q is a substituted 5- to 14-membered heterocycloalkyl, e.g., substituted with one or more substituents selected from oxo (=O), OH, amino, and $C_{1-3}$ alkyl. For example, Q is 4-methylpiperazinyl, 4-(4-methoxybenzyl)piperazinyl, or isoindolin-2-yl-1,3-dione.

In certain embodiments, Q is an unsubstituted or substituted $C_{6-10}$ aryl (such as phenyl) or $C_{3-6}$ cycloalkyl.

In some embodiments, n is 1. In other embodiments, n is 2. In further embodiments, n is 3. In certain other embodiments, n is 4. For example, $R_4$ can be —$(CH_2)_2$OH. For example, $R_4$ can be —$(CH_2)_3$OH. For example, $R_4$ can be —$(CH_2)_4$OH. For example, $R_4$ can be benzyl. For example, $R_4$ can be 4-methoxybenzyl.

In some embodiments, $R_4$ is a $C_{3-6}$ carbocycle. In some embodiments, $R_4$ is a $C_{3-6}$ cycloalkyl. For example, $R_4$ can be cyclohexyl optionally substituted with e.g., OH, halo, $C_{1-6}$ alkyl, etc. For example, $R_4$ can be 2-hydroxycyclohexyl.

In some embodiments, R is H.

In some embodiments, R is unsubstituted $C_{1-3}$ alkyl or unsubstituted $C_{2-3}$ alkenyl. For example, $R_4$ can be —$CH_2CH(OH)CH_3$ or —$CH_2CH(OH)CH_2CH_3$.

In some embodiments, R is substituted $C_{1-3}$ alkyl, e.g., $CH_2OH$. For example, $R_4$ can be —$CH_2CH(OH)CH_2OH$.

In some embodiments, $R_2$ and $R_3$, together with the atom to which they are attached, form a heterocycle or carbocycle. In some embodiments, $R_2$ and $R_3$, together with the atom to which they are attached, form a 5- to 14-membered aromatic or non-aromatic heterocycle having one or more heteroatoms selected from N, O, S, and P. In some embodiments, $R_2$ and $R_3$, together with the atom to which they are attached, form an optionally substituted $C_{3-20}$ carbocycle (e.g., $C_{3-18}$ carbocycle, $C_{3-15}$ carbocycle, $C_{3-12}$ carbocycle, or $C_{3-10}$ carbocycle), either aromatic or non-aromatic. In some embodiments, $R_2$ and $R_3$, together with the atom to which they are attached, form a $C_{3-6}$ carbocycle. In other embodiments, $R_2$ and $R_3$, together with the atom to which they are attached, form a $C_6$ carbocycle, such as a cyclohexyl or phenyl group. In certain embodiments, the heterocycle or $C_{3-6}$ carbocycle is substituted with one or more alkyl groups (e.g., at the same ring atom or at adjacent or non-adjacent ring atoms). For example, $R_2$ and $R_3$, together with the atom to which they are attached, can form a cyclohexyl or phenyl group bearing one or more $C_5$ alkyl substitutions. In certain embodiments, the heterocycle or $C_{3-6}$ carbocycle formed by $R_2$ and $R_3$, is substituted with a carbocycle groups. For example, $R_2$ and $R_3$, together with the atom to which they are attached, can form a cyclohexyl or phenyl group that is substituted with cyclohexyl. In some embodiments, $R_2$ and $R_3$, together with the atom to which they are attached, form a $C_{7-15}$ carbocycle, such as a cycloheptyl, cyclopentadecanyl, or naphthyl group.

In some embodiments, $R_4$ is selected from —$(CH_2)_n$Q and —$(CH_2)_n$CHQR. In some embodiments, Q is selected from the group consisting of —OR, —OH, —O$(CH_2)_n$N$(R)_2$, —OC(O)R, —$CX_3$, —CN, —N(R)C(O)R, —N(H)C(O)R, —N(R)S(O)$_2$R, —N(H)S(O)$_2$R, —N(R)C(O)N$(R)_2$, —N(H)C(O)N$(R)_2$, —N(H)C(O)N(H)(R), —N(R)C(S)N$(R)_2$, —N(H)C(S)N$(R)_2$, —N(H)C(S)N(H)(R), and a heterocycle. In other embodiments, Q is selected from the group consisting of an imidazole, a pyrimidine, and a purine.

In some embodiments, $R_2$ and $R_3$, together with the atom to which they are attached, form a heterocycle or carbocycle. In some embodiments, $R_2$ and $R_3$, together with the atom to which they are attached, form a $C_{3-6}$ carbocycle, such as a phenyl group. In certain embodiments, the heterocycle or $C_{3-6}$ carbocycle is substituted with one or more alkyl groups (e.g., at the same ring atom or at adjacent or non-adjacent ring atoms). For example, $R_2$ and $R_3$, together with the atom to which they are attached, can form a phenyl group bearing one or more $C_5$ alkyl substitutions.

In some embodiments, the pharmaceutical compositions of the present disclosure, the compound of Formula (I) is selected from the group consisting of:

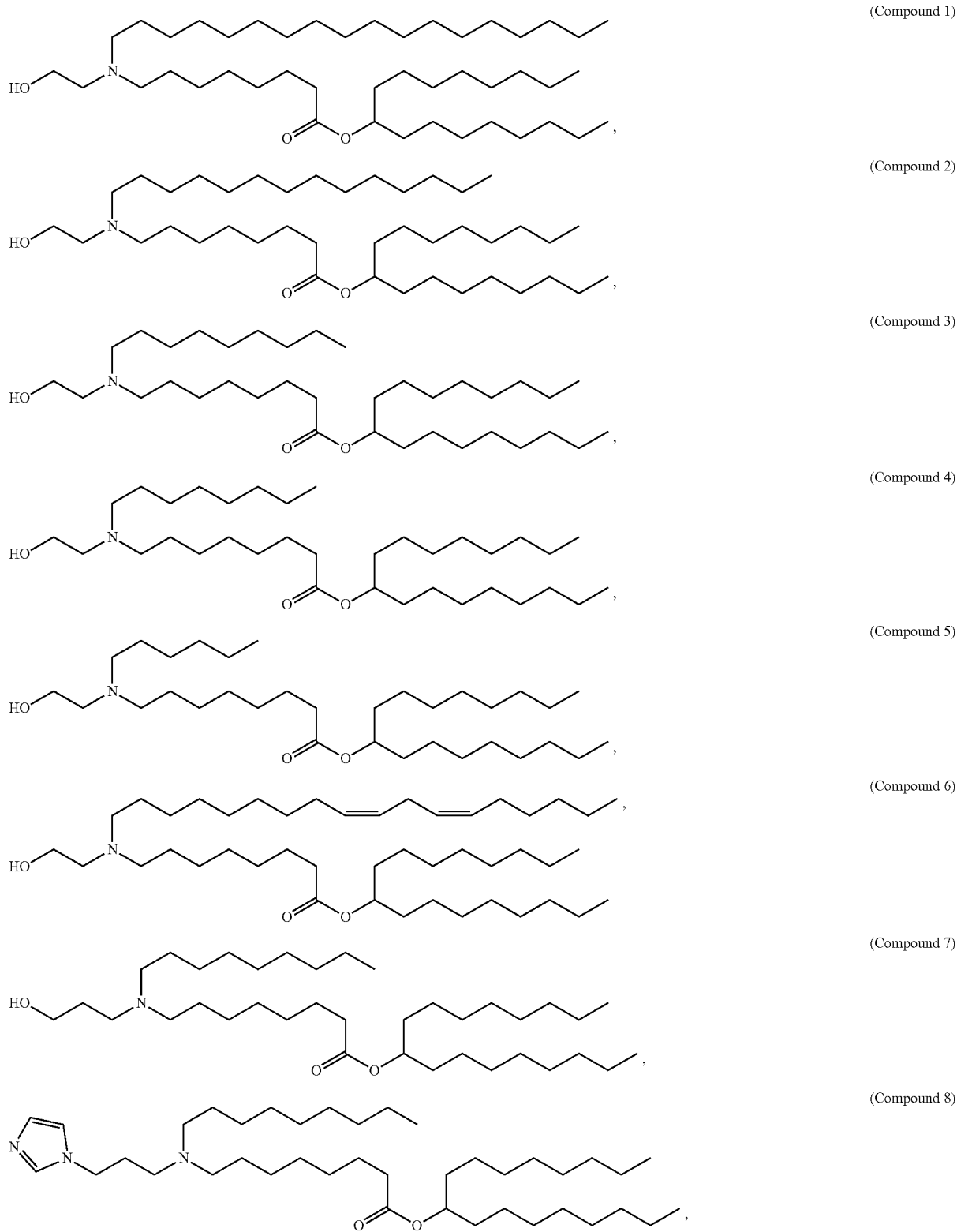

(Compound 9)
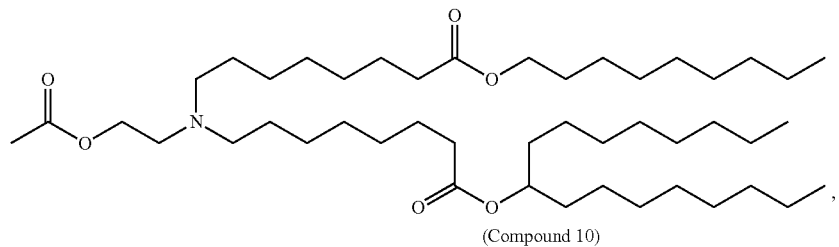
(Compound 10) (Compound 11)
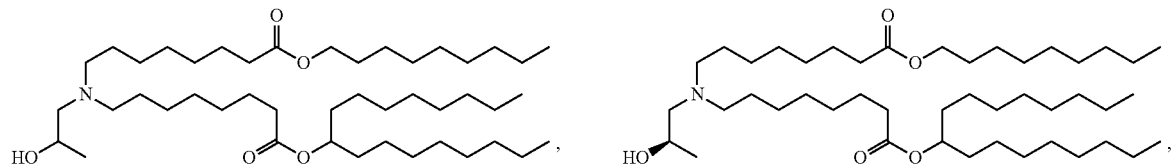
(Compound 12)
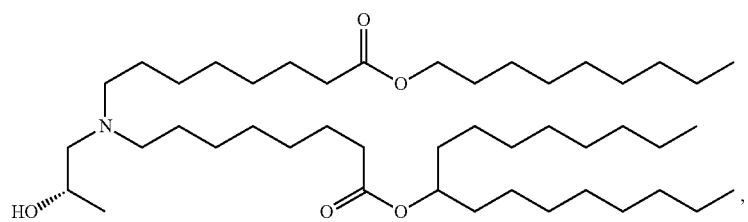
(Compound 13)
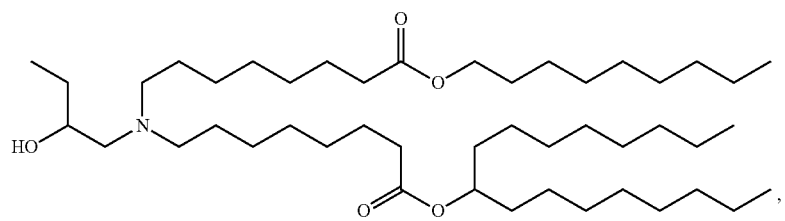
(Compound 14)
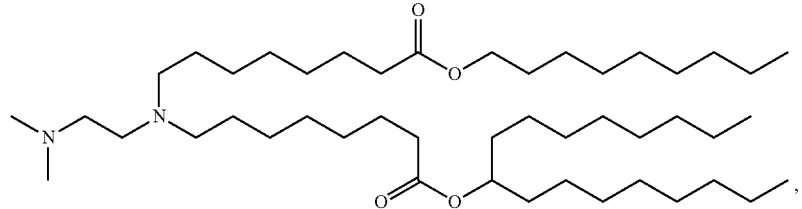
(Compound 15)
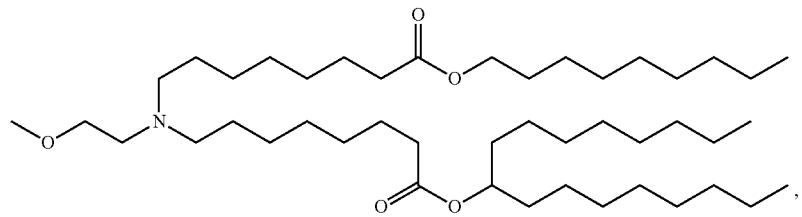
(Compound 16)
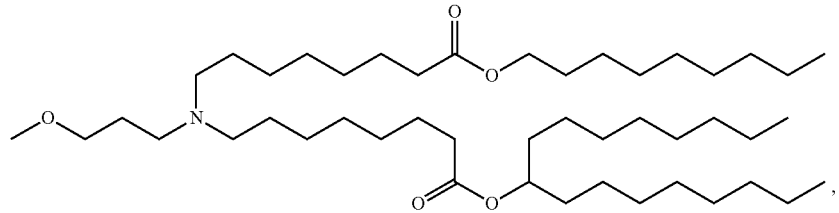

(Compound 17)
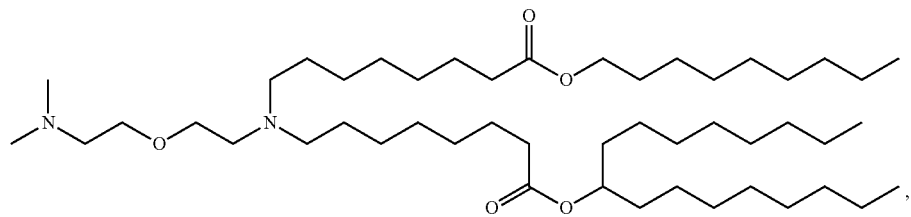
(Compound 18)
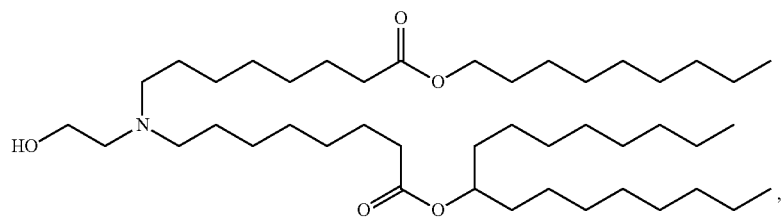
(Compound 19)
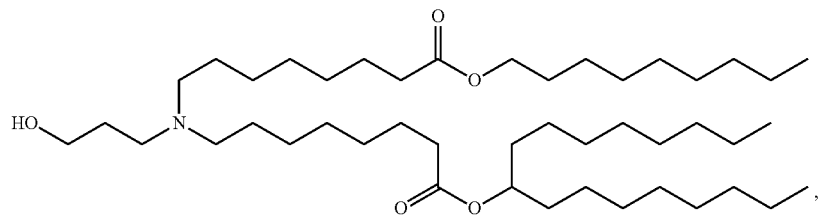
(Compound 20)
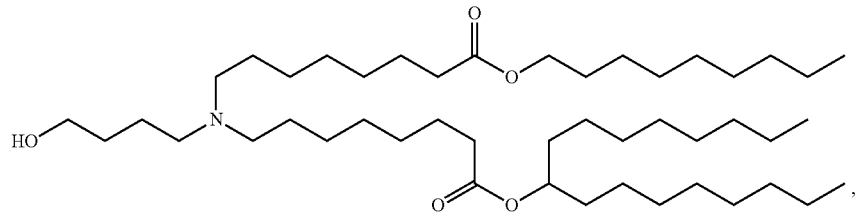
(Compound 21)
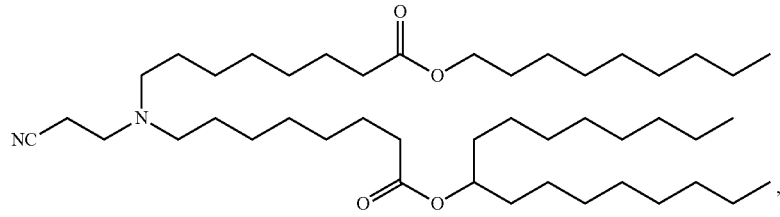
(Compound 22)
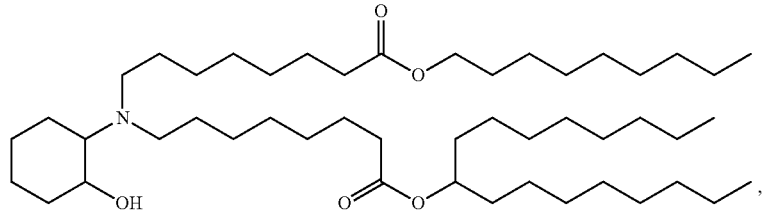
(Compound 23)
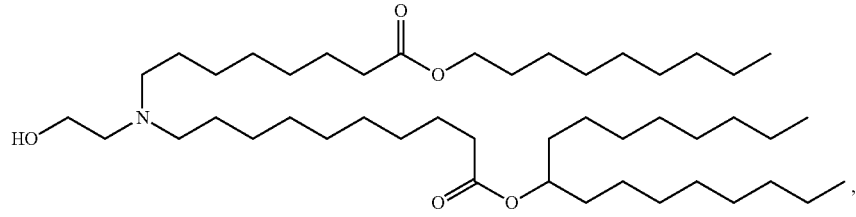

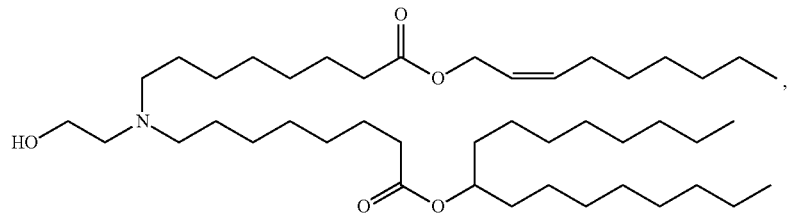
(Compound 24)
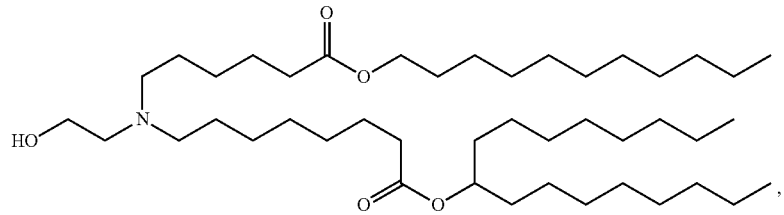
(Compound 25)
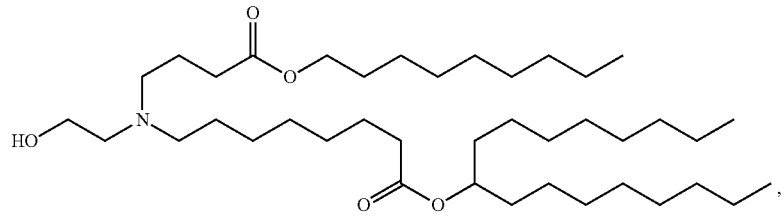
(Compound 26)
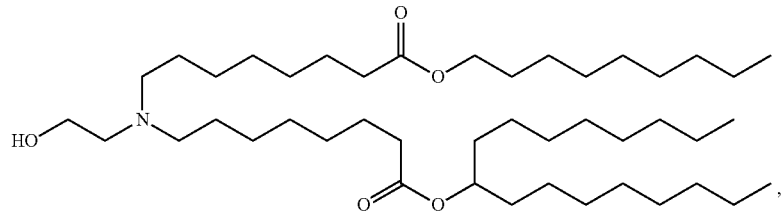
(Compound 27)
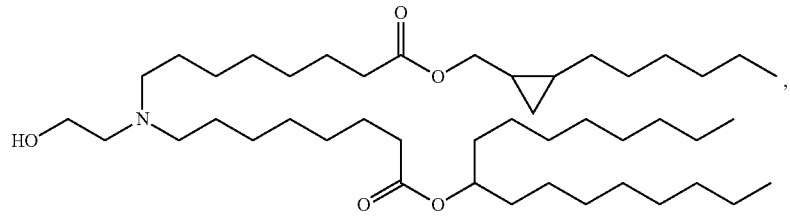
(Compound 28)
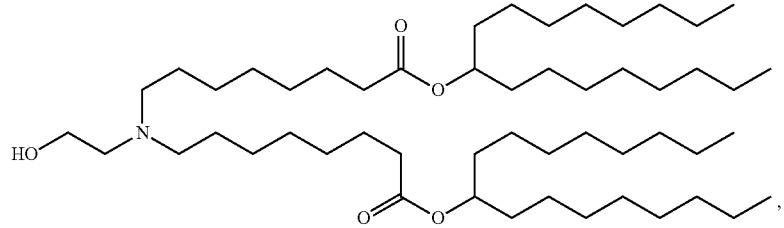
(Compound 29)
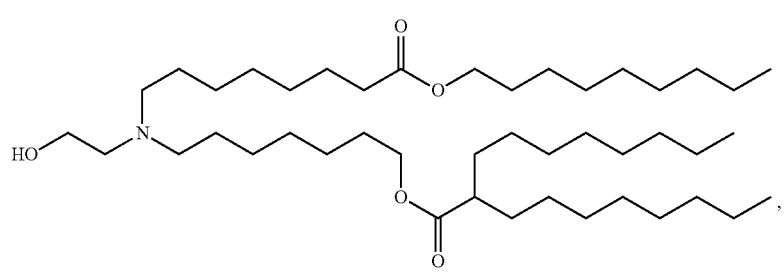
(Compound 30)

-continued
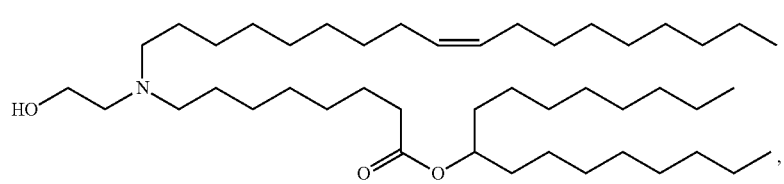
(Compound 31)
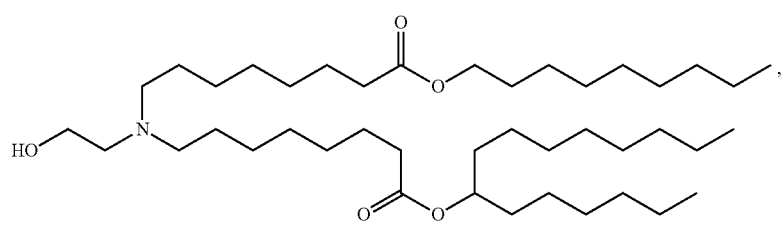
(Compound 32)
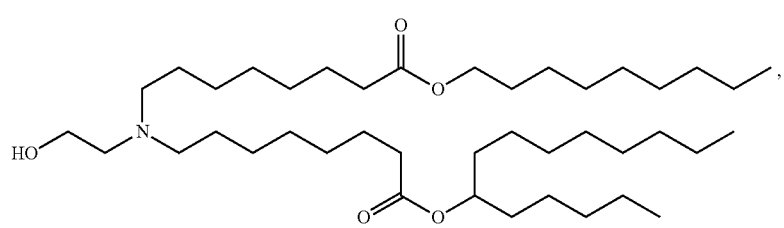
(Compound 33)
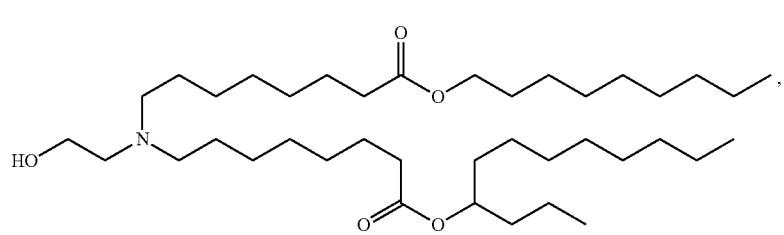
(Compound 34)
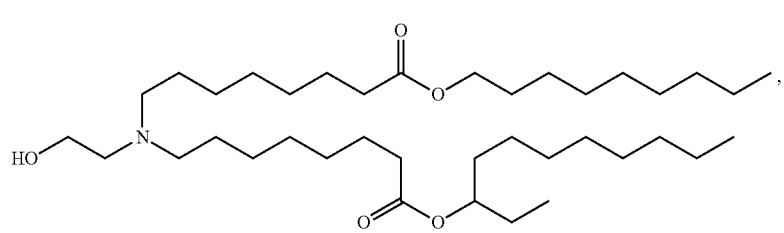
(Compound 35)
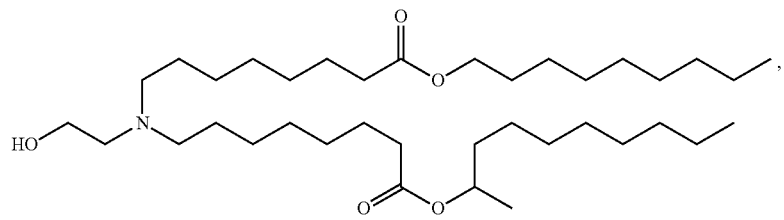
(Compound 36)
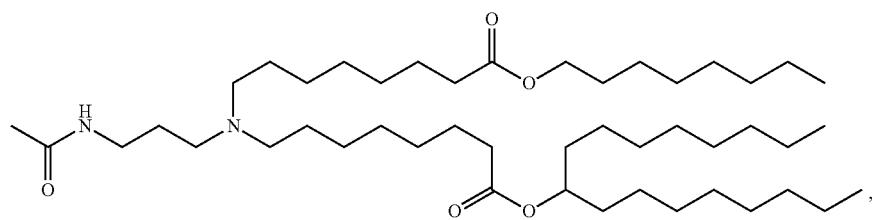
(Compound 37)

(Compound 38)
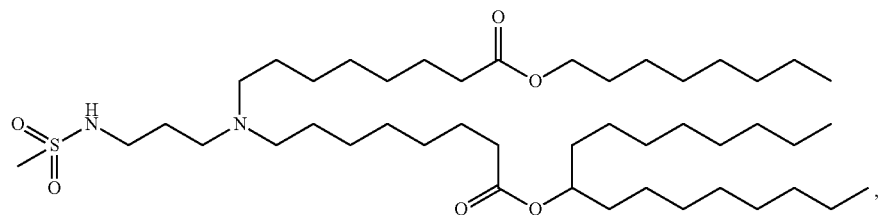
(Compound 39)
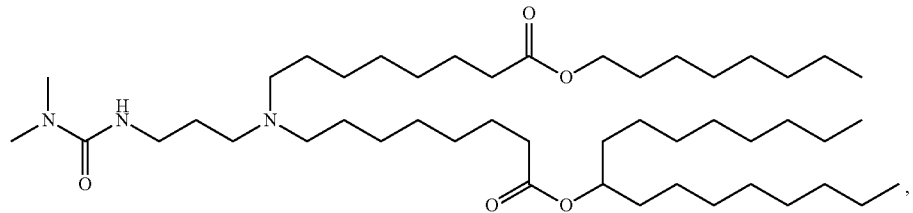
(Compound 40)
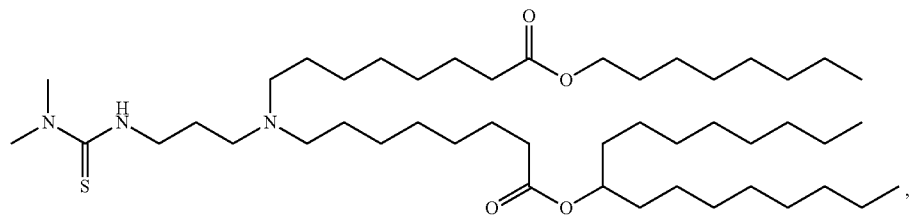
(Compound 41)
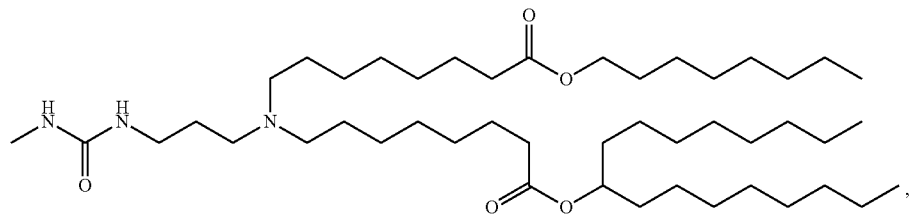
(Compound 42)
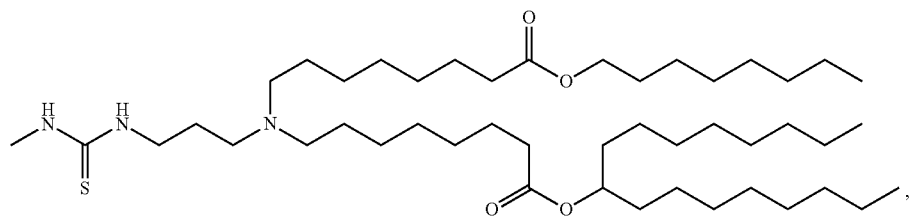
(Compound 43)
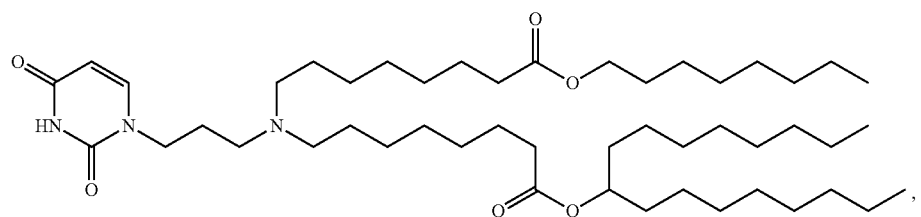
(Compound 44)
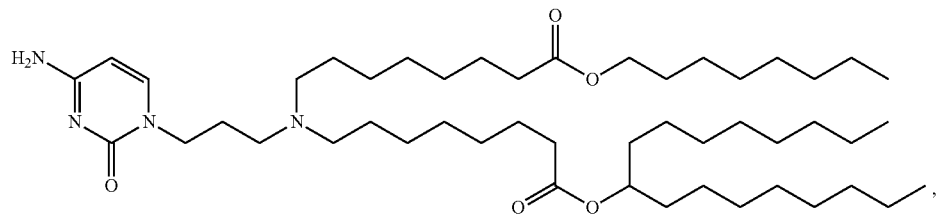

(Compound 45)
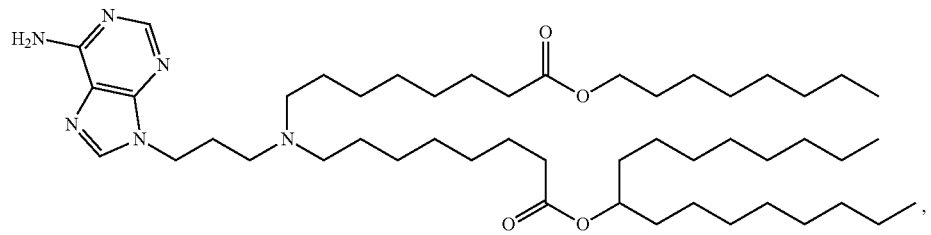
(Compound 46)
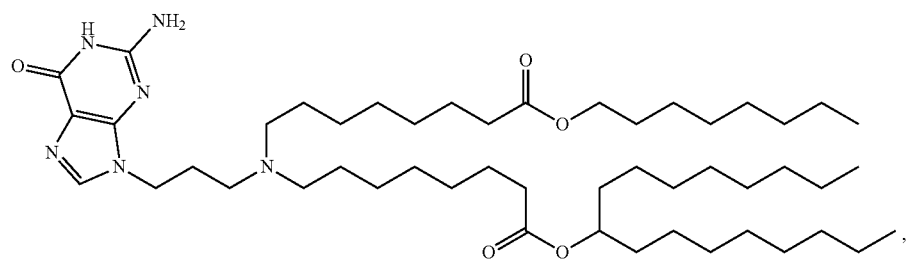
(Compound 47)
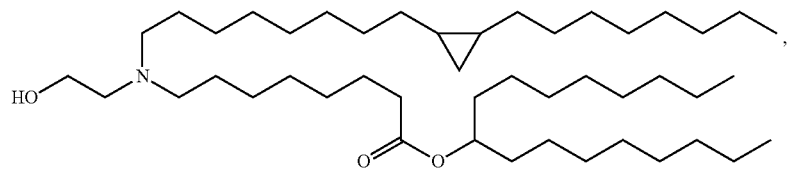
(Compound 48)
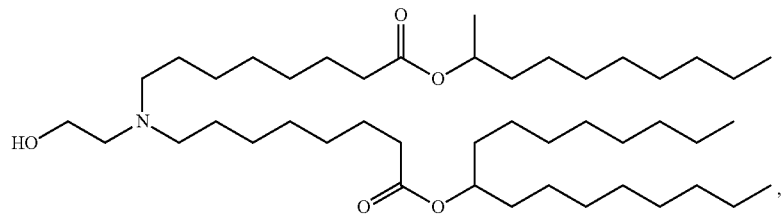
(Compound 49)
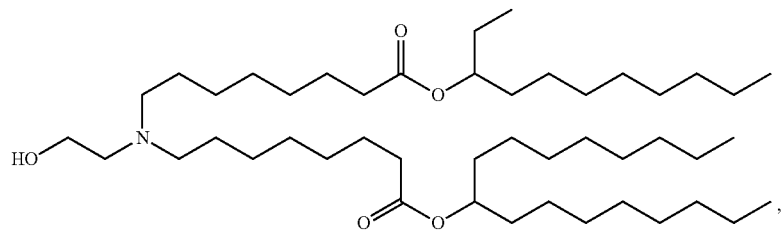
(Compound 50)
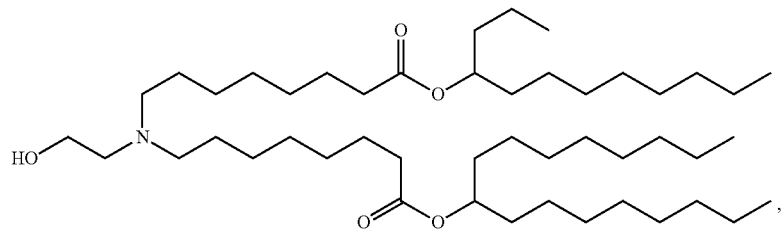
(Compound 51)
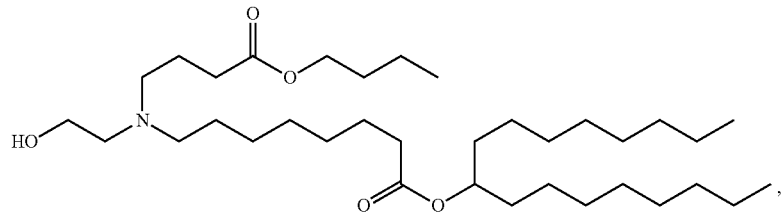

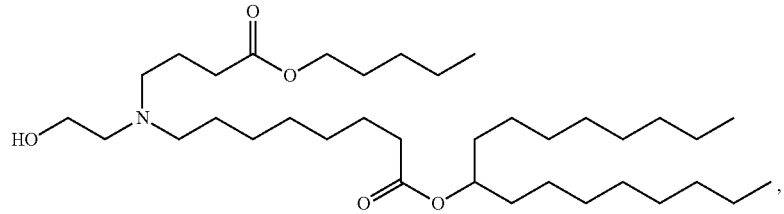
(Compound 52)
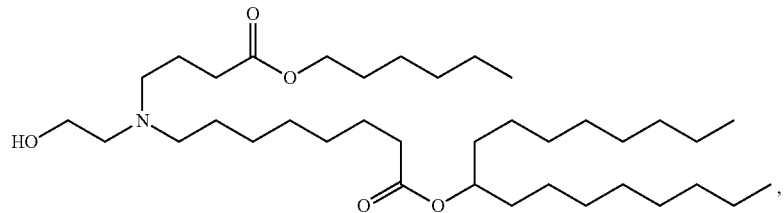
(Compound 53)
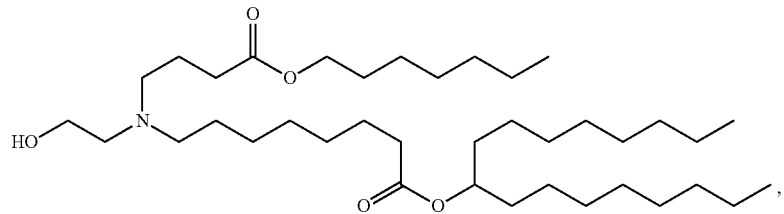
(Compound 54)
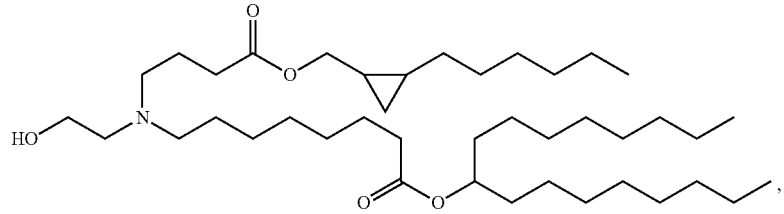
(Compound 55)
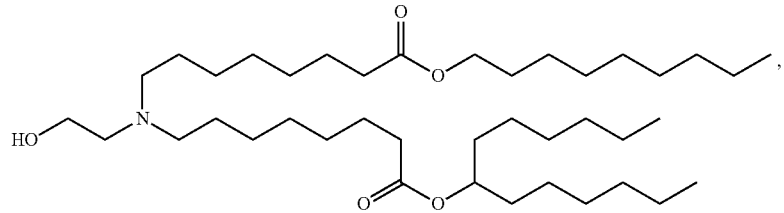
(Compound 56)
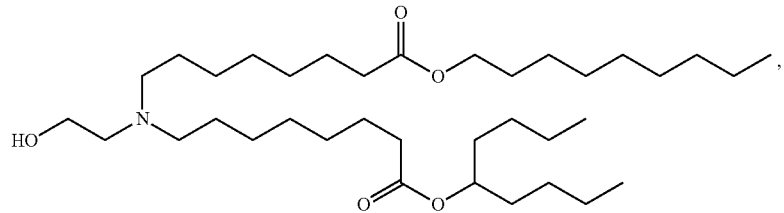
(Compound 57)
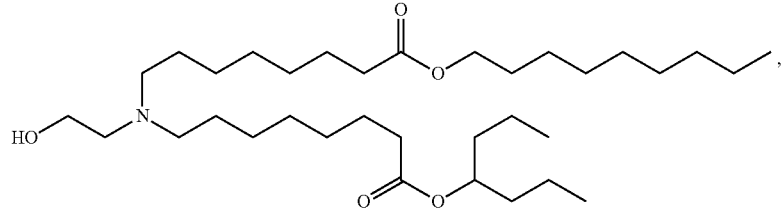
(Compound 58)

(Compound 59)
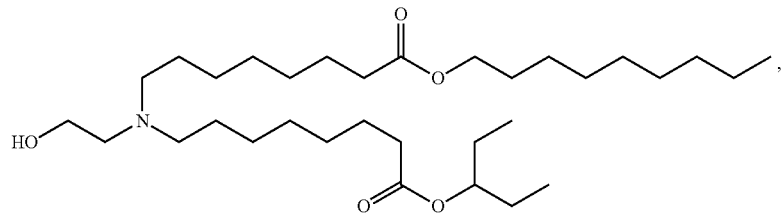
(Compound 60)
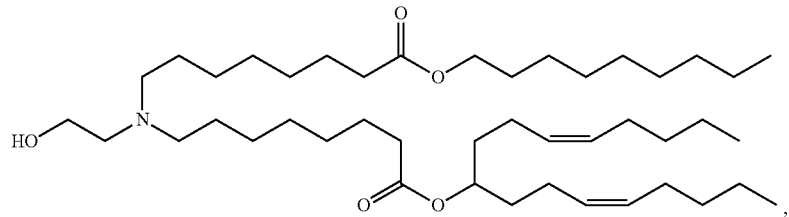
(Compound 61)
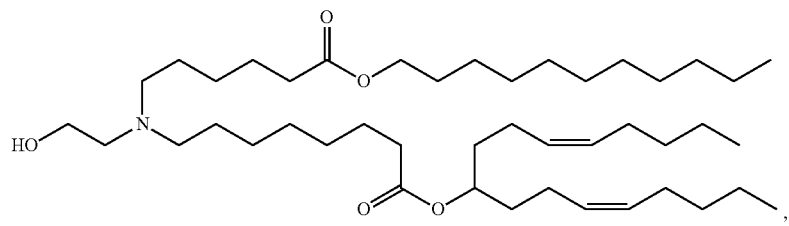
(Compound 62) (Compound 63)
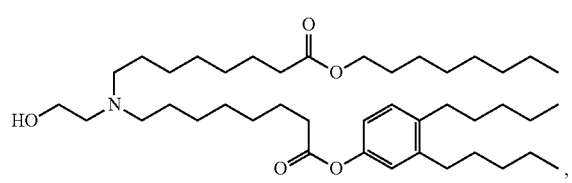
(Compound 64)
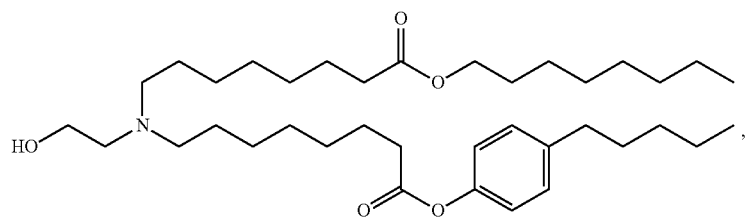
(Compound 65)
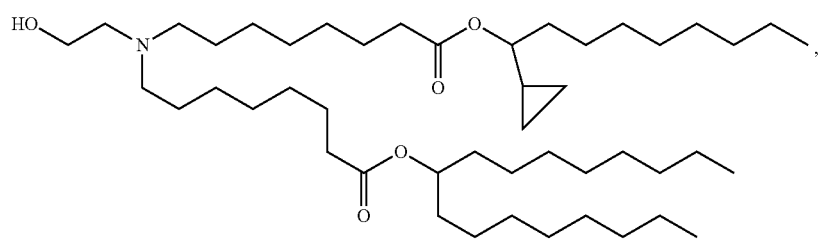
(Compound 66)
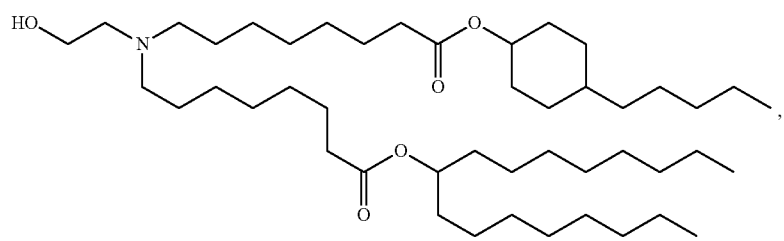

-continued
(Compound 67)
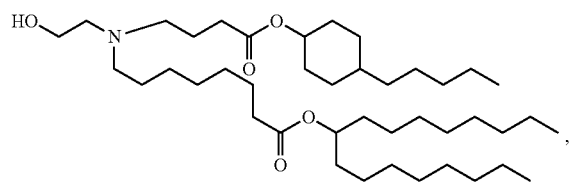
(Compound 68)
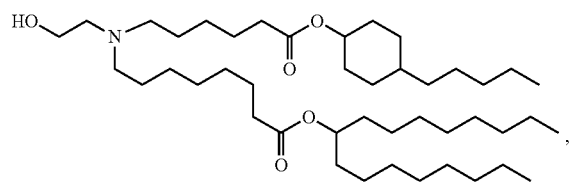
(Compound 69)
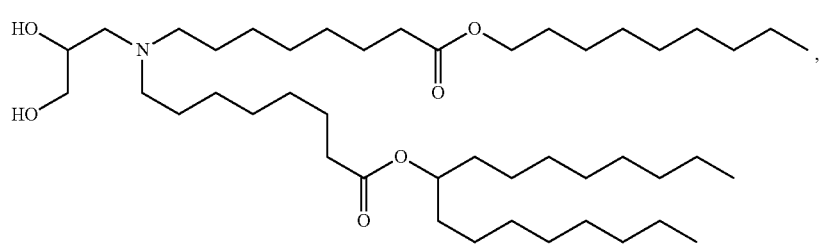
(Compound 70)
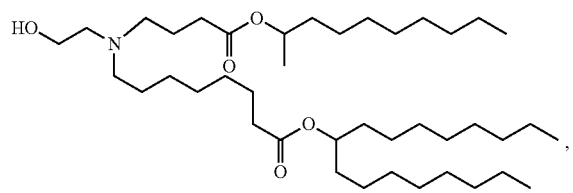
(Compound 71)
(Compound 72)
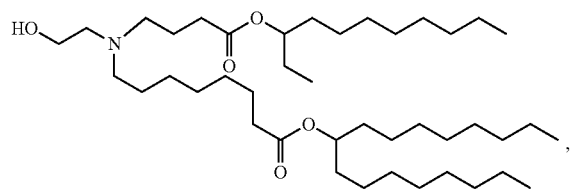
(Compound 73)
(Compound 74)
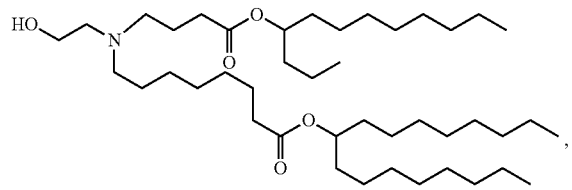
(Compound 75)
(Compound 76)
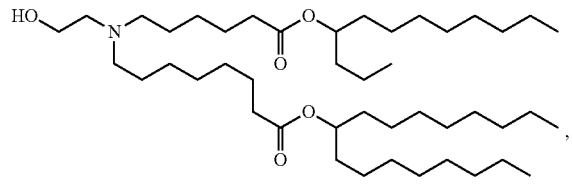
(Compound 77)
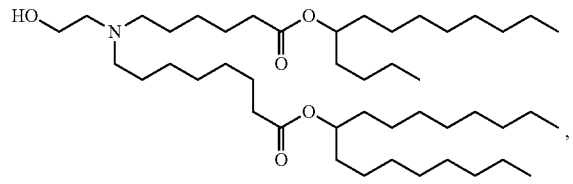
(Compound 78)
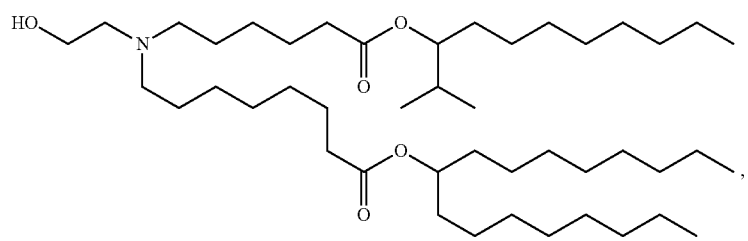

-continued
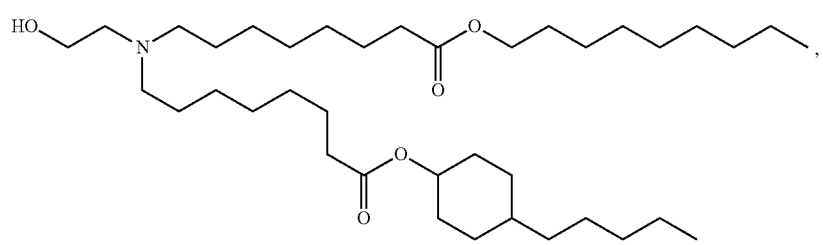
(Compound 79)
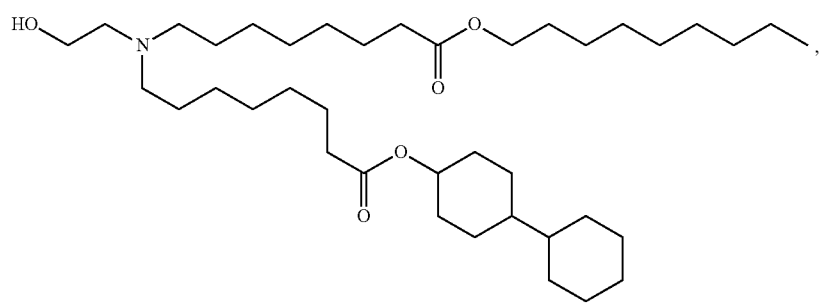
(Compound 80)
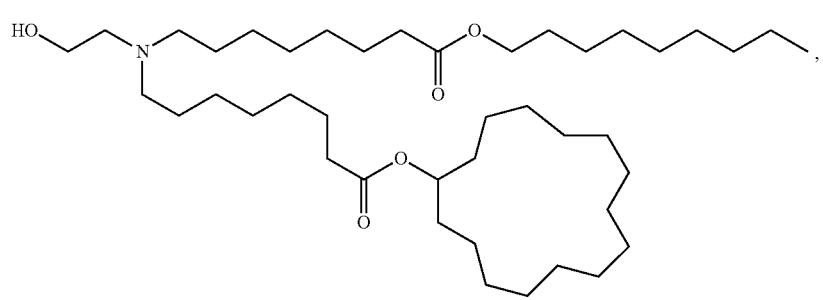
(Compound 81)
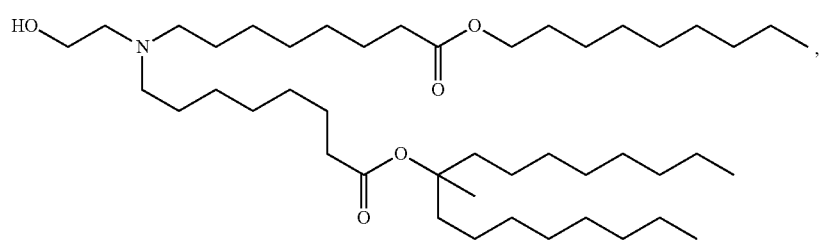
(Compound 82)
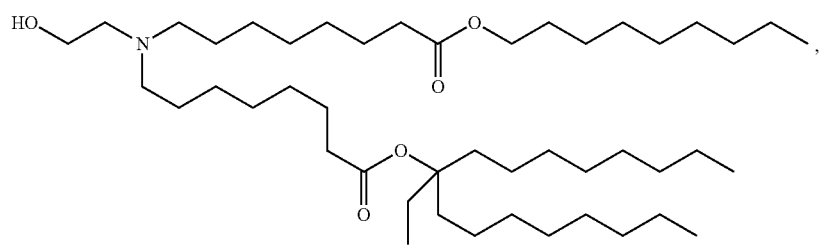
(Compound 83)
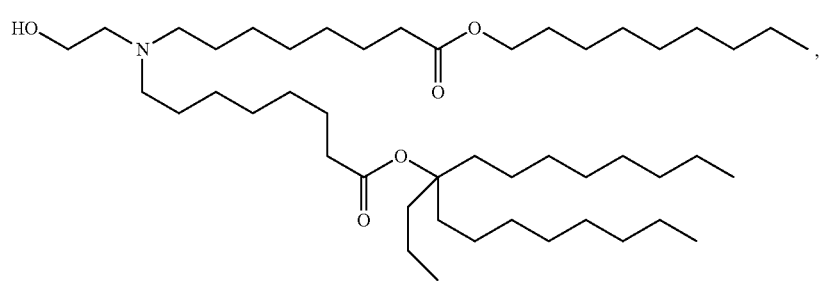
(Compound 84)

-continued
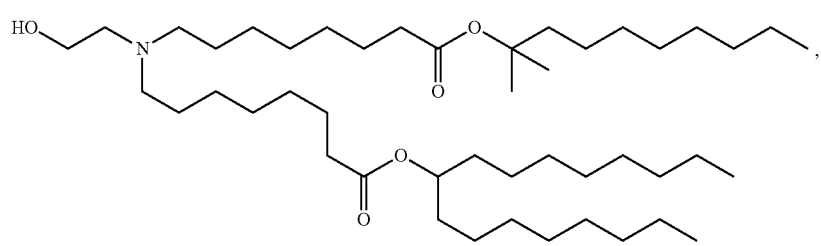
(Compound 85)
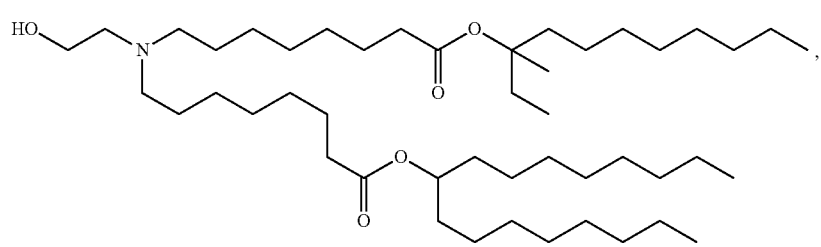
(Compound 86)
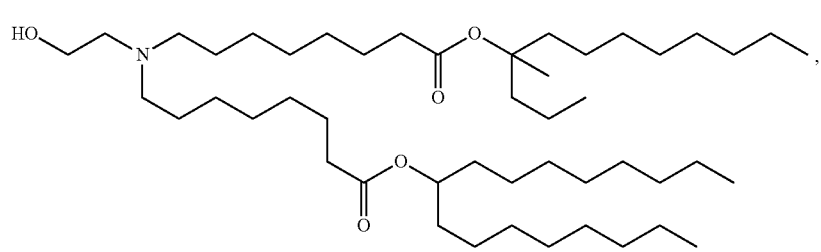
(Compound 87)
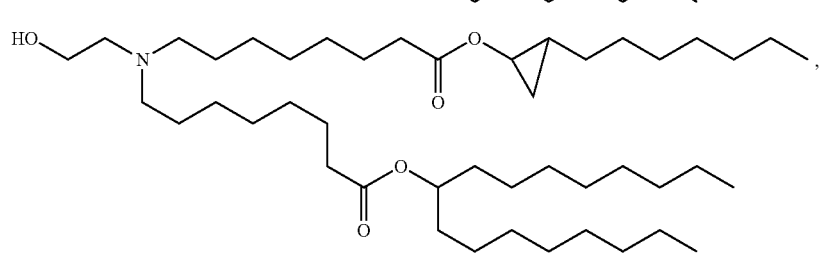
(Compound 88)
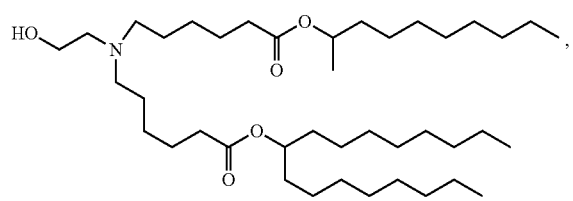
(Compound 89)
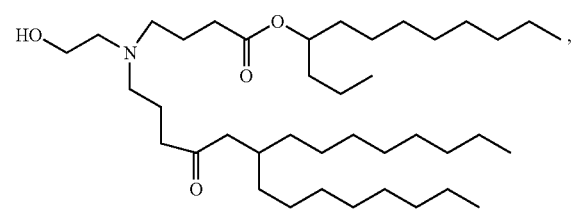
(Compound 90)
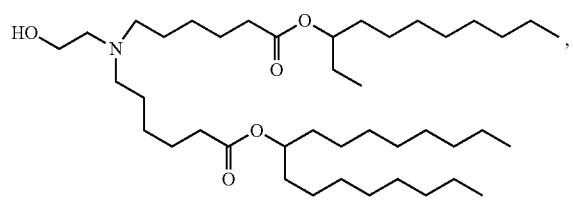
(Compound 91)
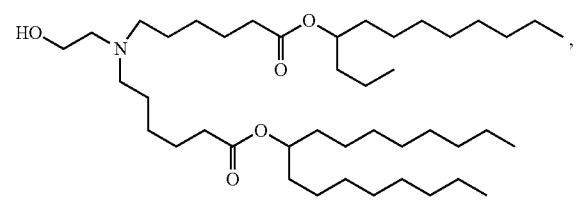
(Compound 92)
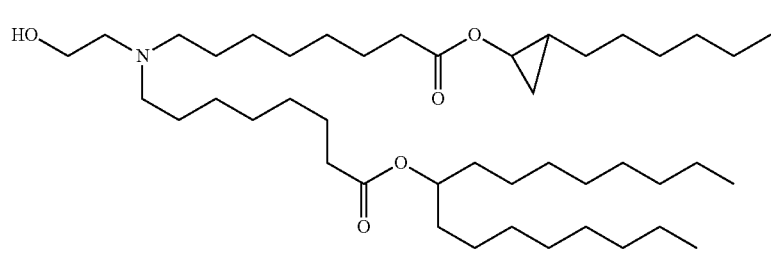
(Compound 93)

-continued
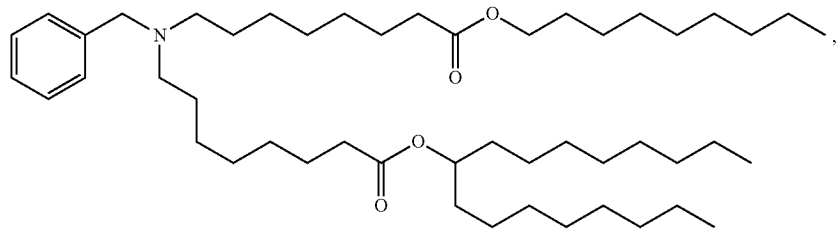
(Compound 94)
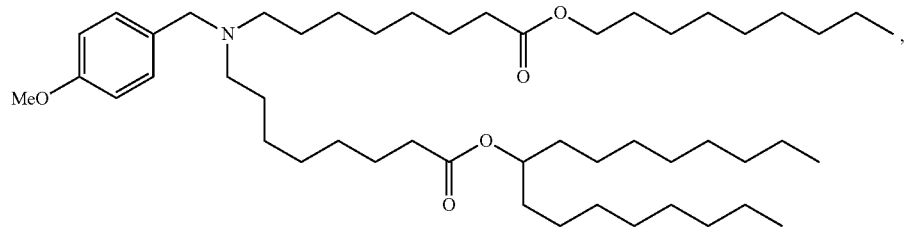
(Compound 95)
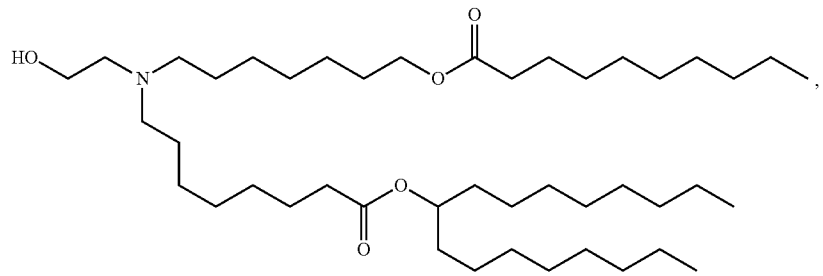
(Compound 96)
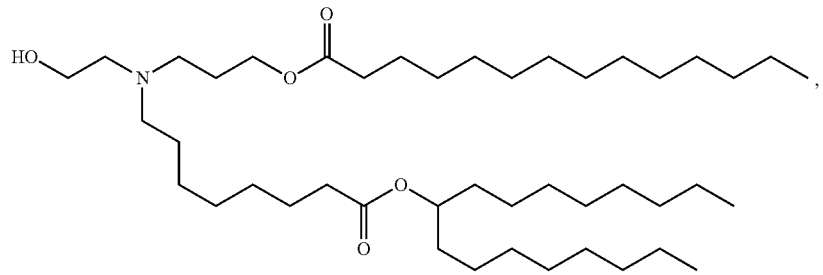
(Compound 97)
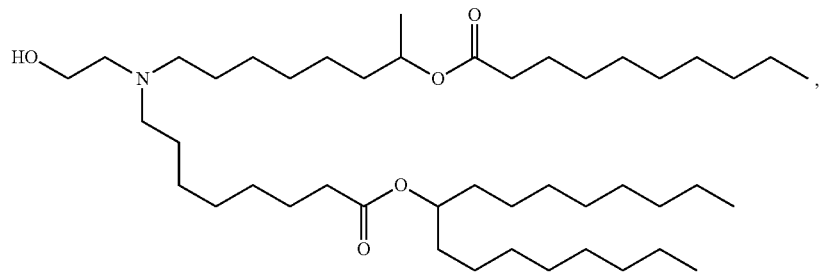
(Compound 98)
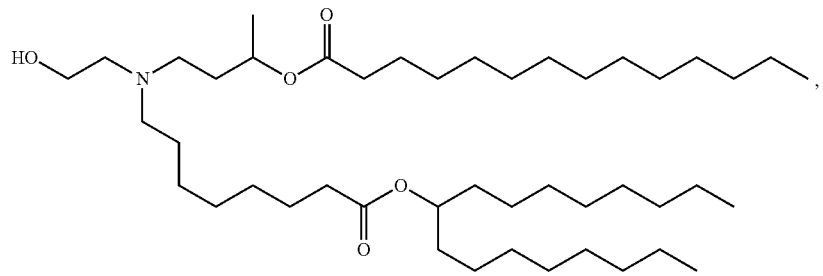
(Compound 99)

-continued
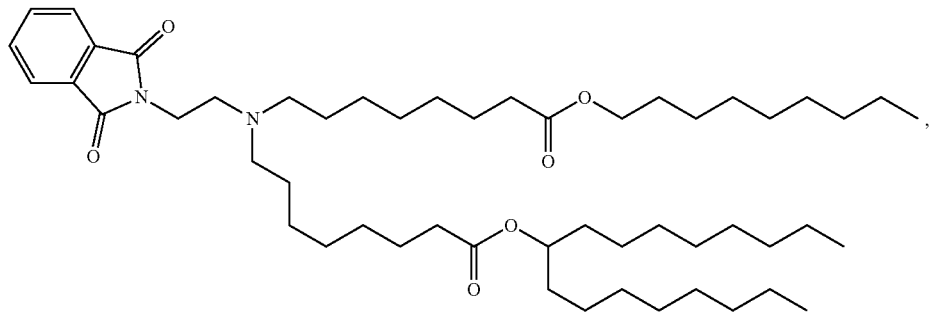
(Compound 100)
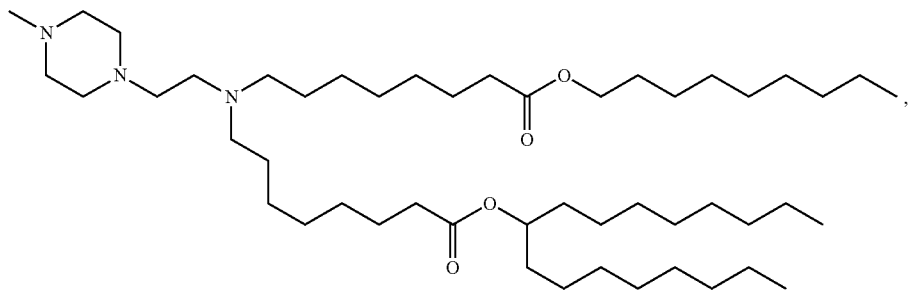
(Compound 101)
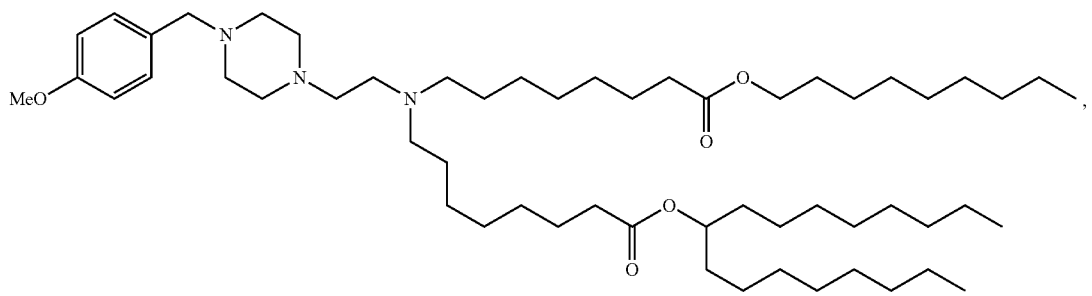
(Compound 102)
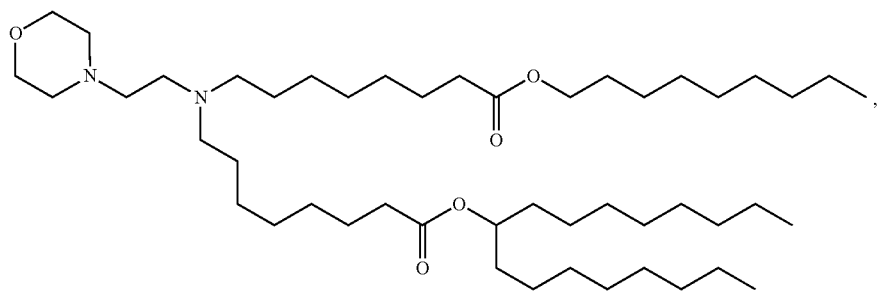
(Compound 103)
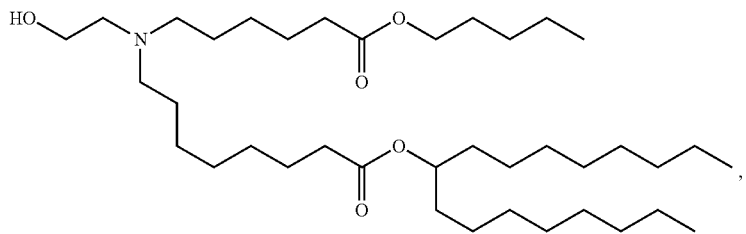
(Compound 104)

-continued
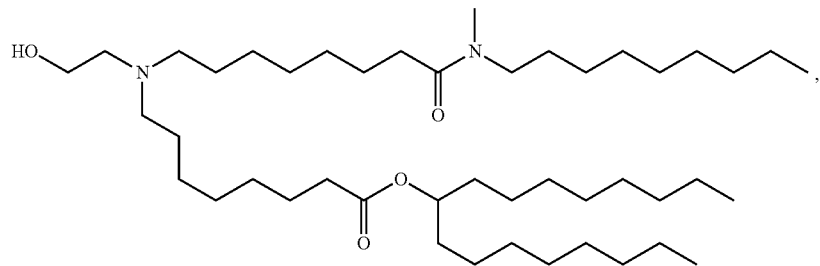
(Compound 105)
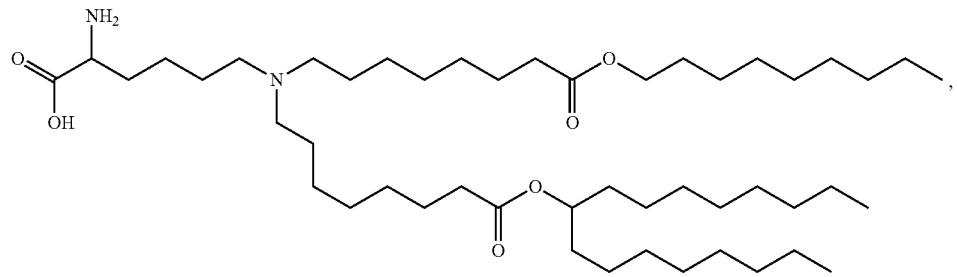
(Compound 106)
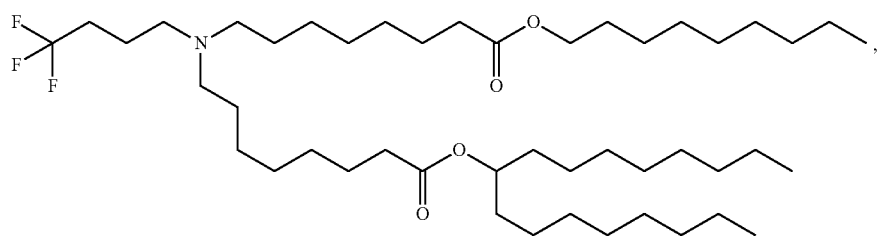
(Compound 107)
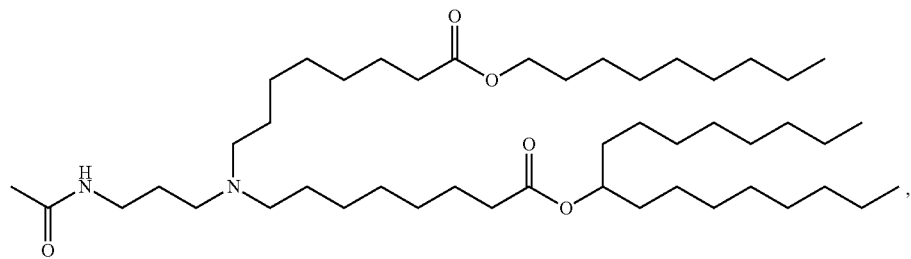
(Compound 108)
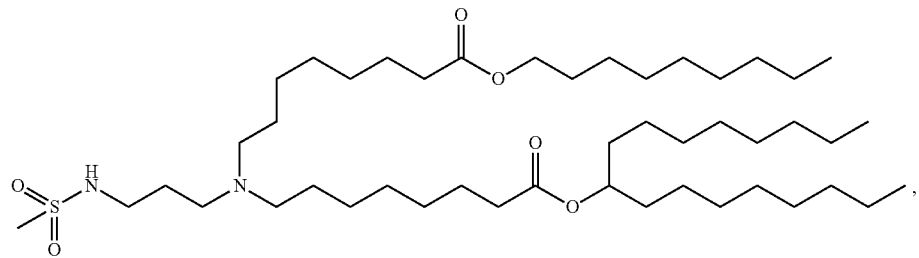
(Compound 109)
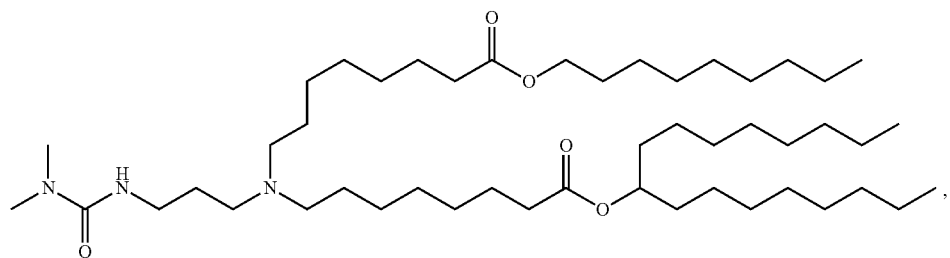
(Compound 110)

-continued
(Compound 111)
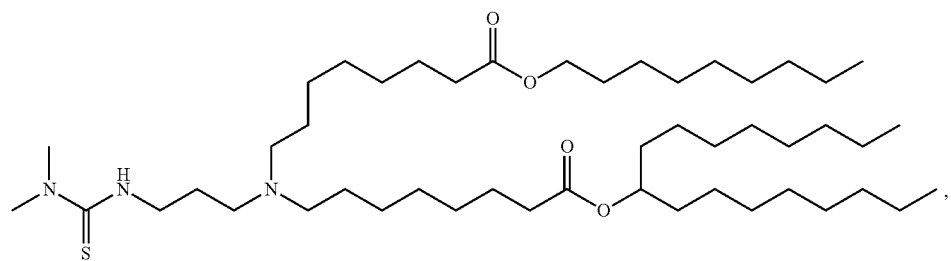
(Compound 112)
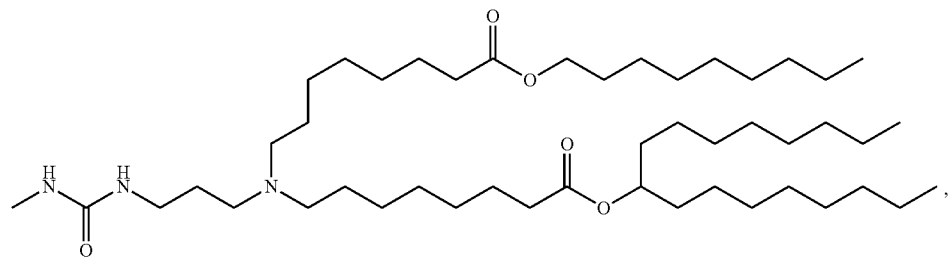
(Compound 113)
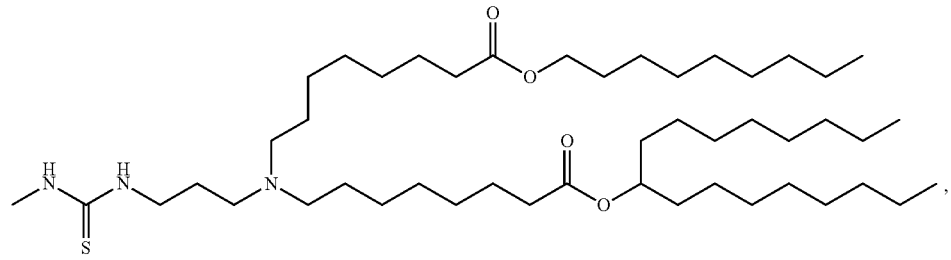
(Compound 114)
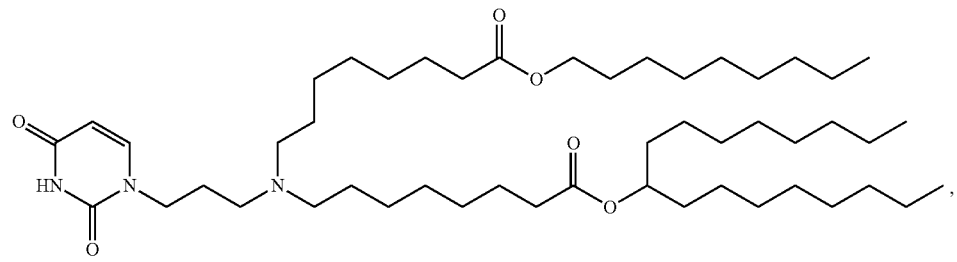
(Compound 115)
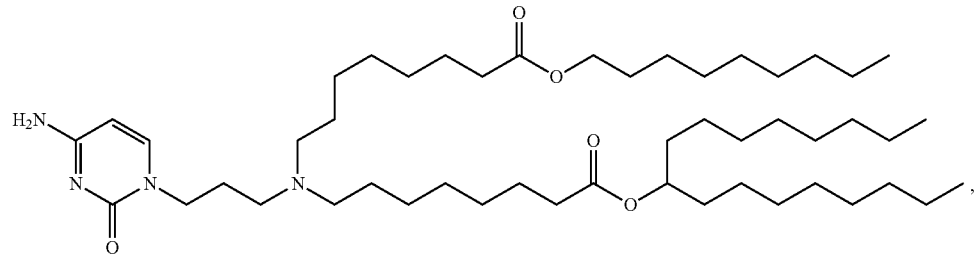
(Compound 116)
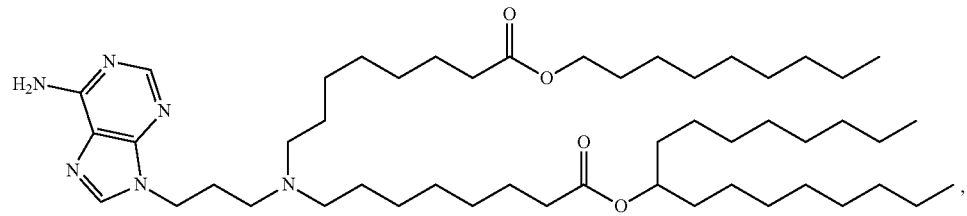

(Compound 117)
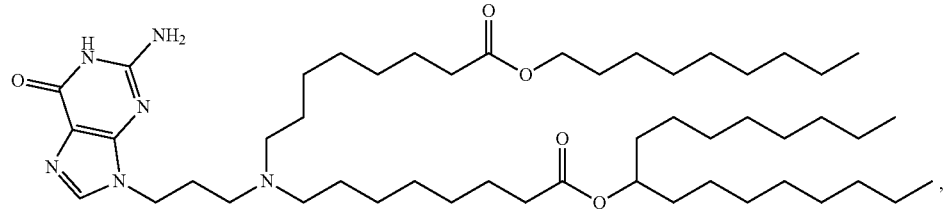
(Compound 118)
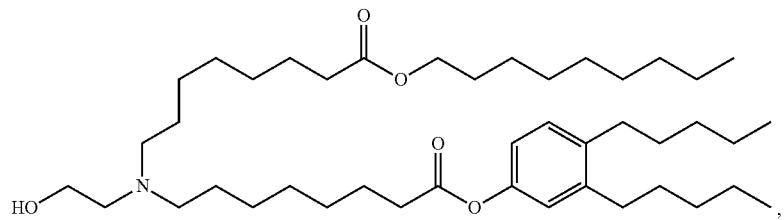
(Compound 119)
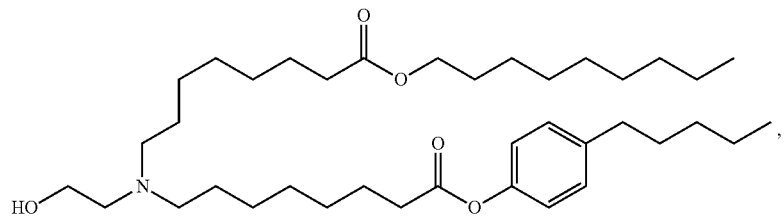
(Compound 120)
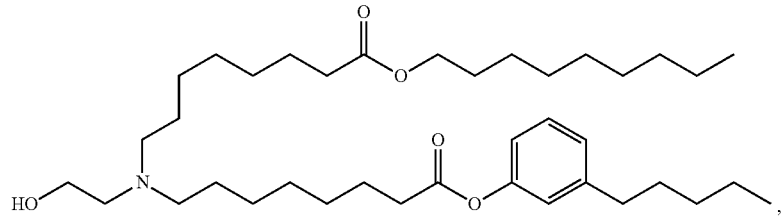
(Compound 121)
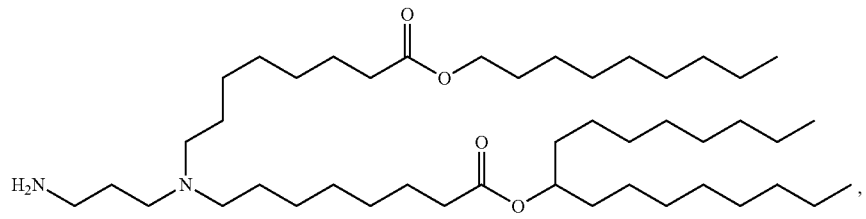
(Compound 122)
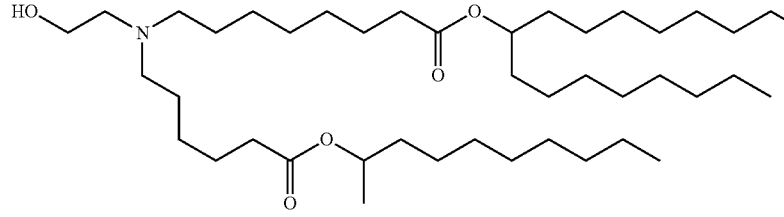
(Compound 123)
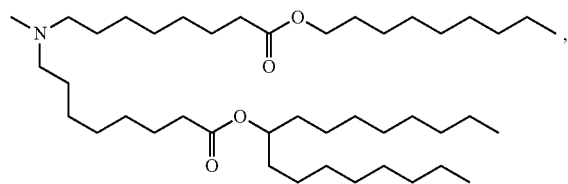
(Compound 124)
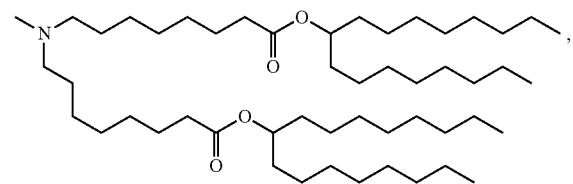

(Compound 125)
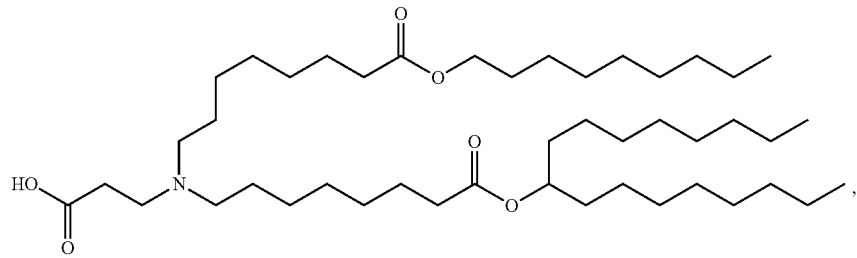
(Compound 126)
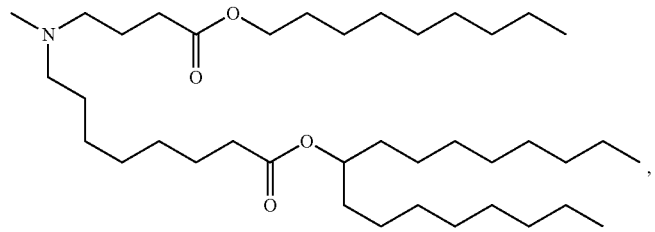
(Compound 127)
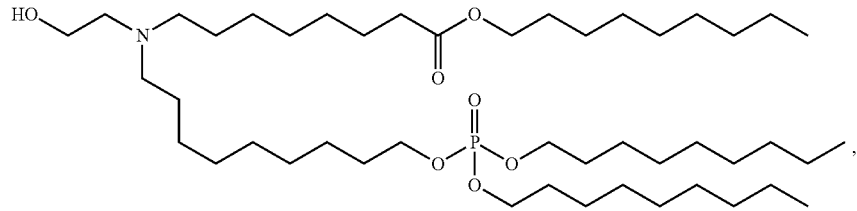
(Compound 128)
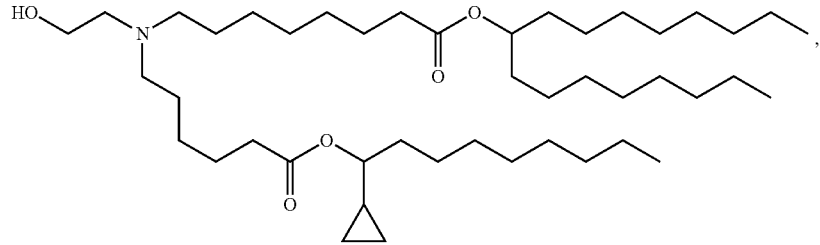
(Compound 129)
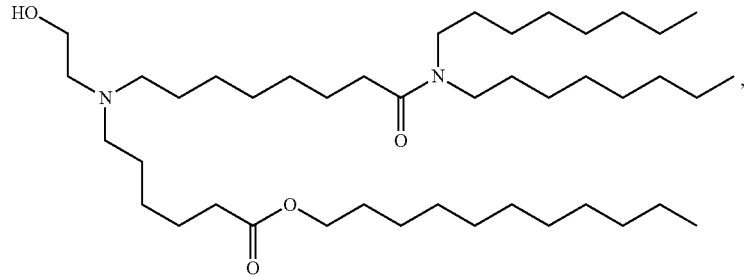
(Compound 130)
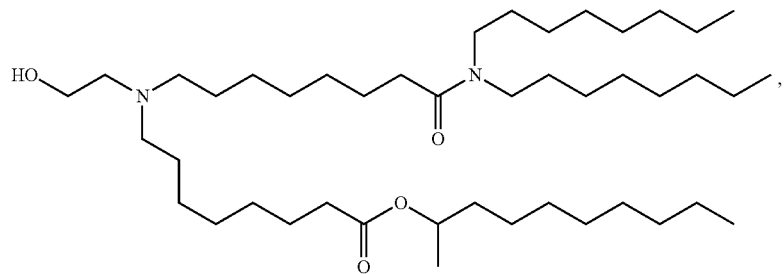

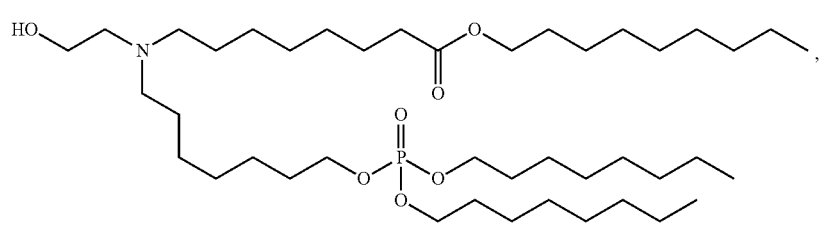
(Compound 131)
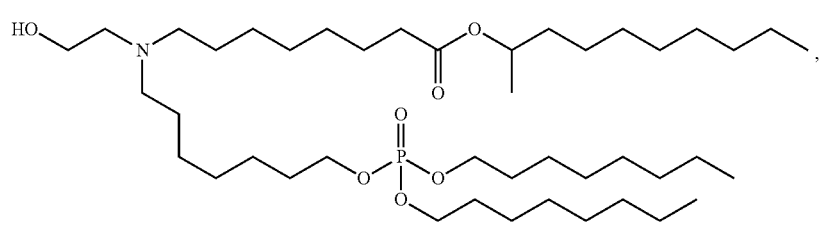
(Compound 132)
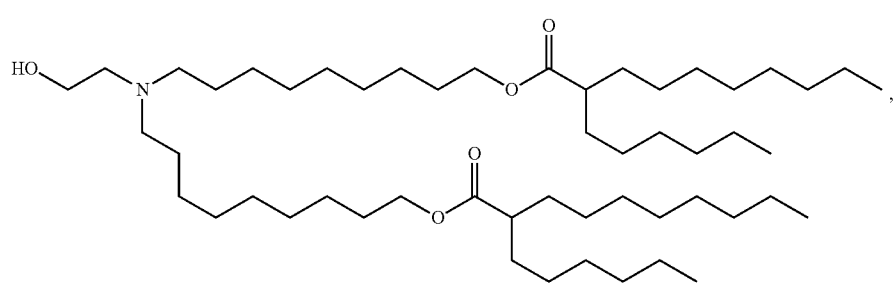
(Compound 133)
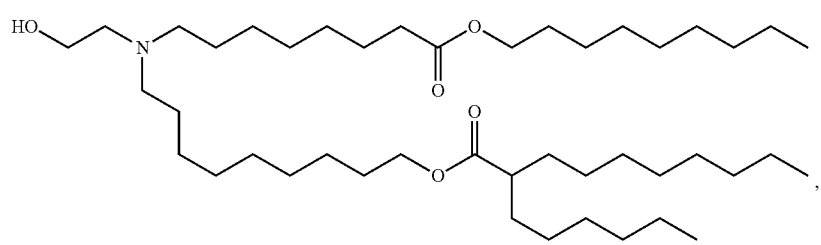
(Compound 134)
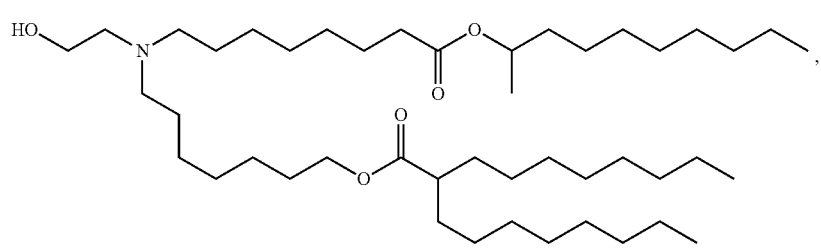
(Compound 135)
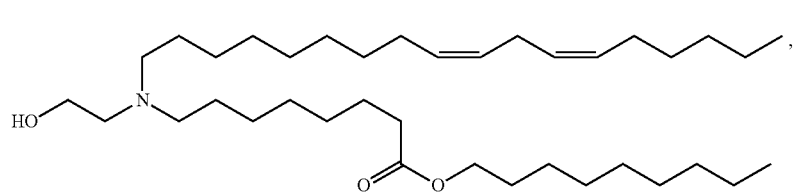
(Compound 136)
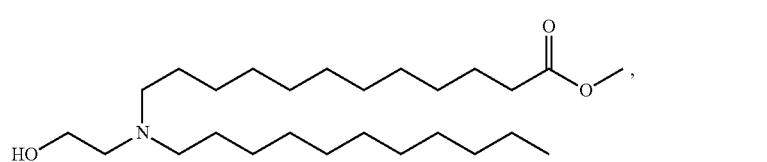
(Compound 137)

(Compound 138)
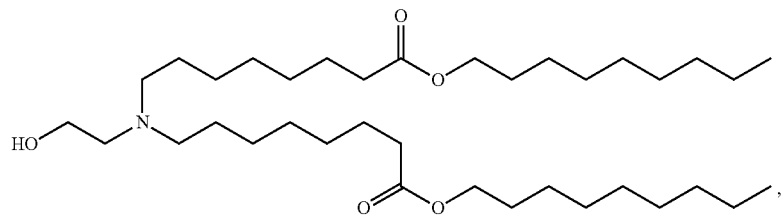
(Compound 139)
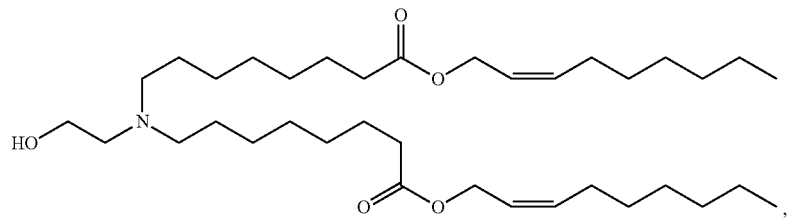
(Compound 140)
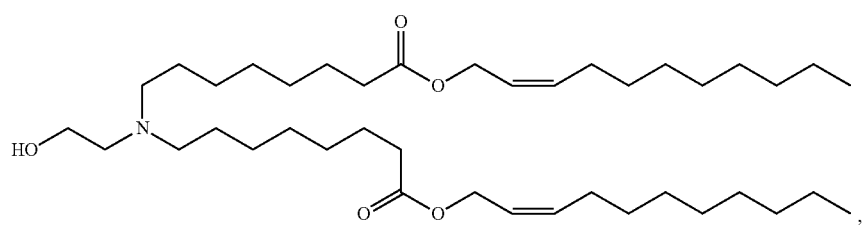
(Compound 141)
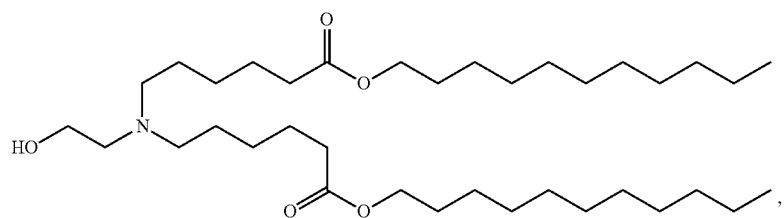
(Compound 142)
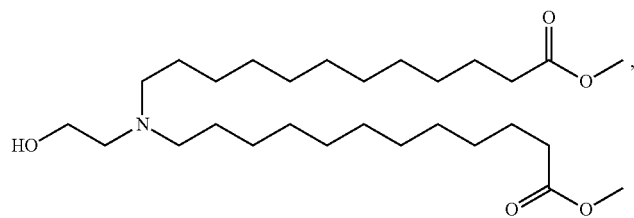
(Compound 143)
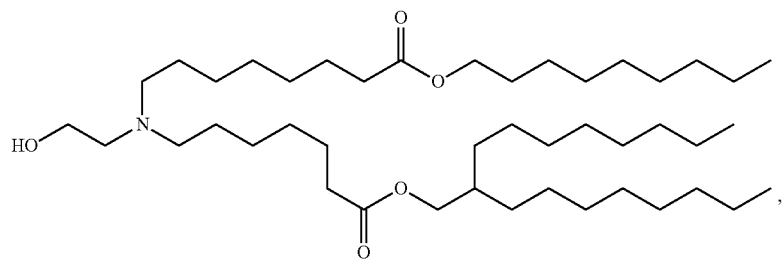

(Compound 144)
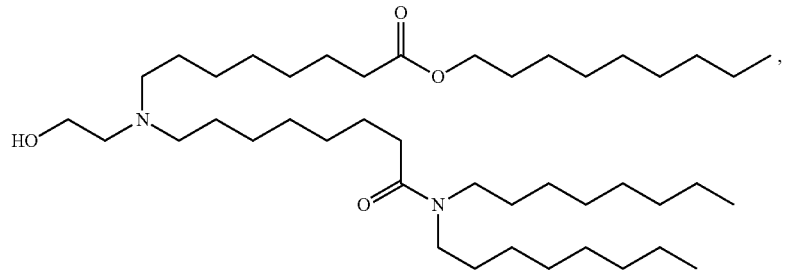
(Compound 145)
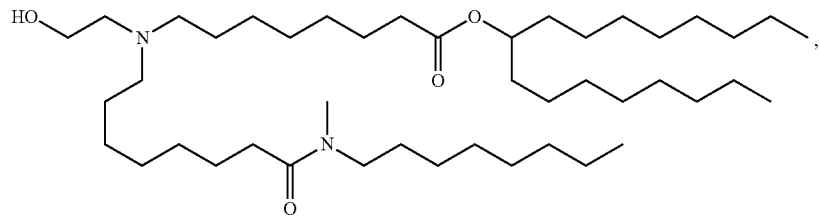
(Compound 146)
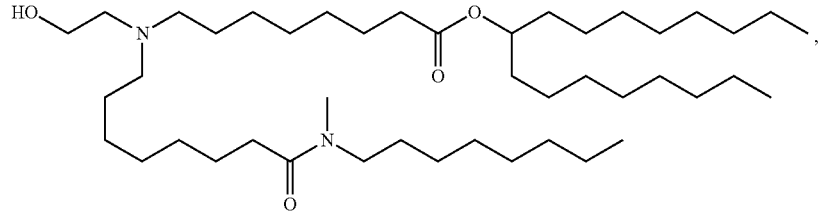
(Compound 147)
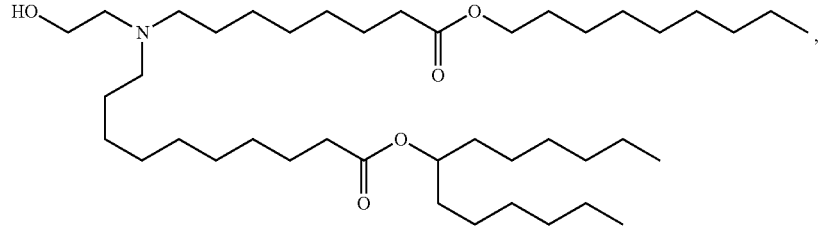
(Compound 148)
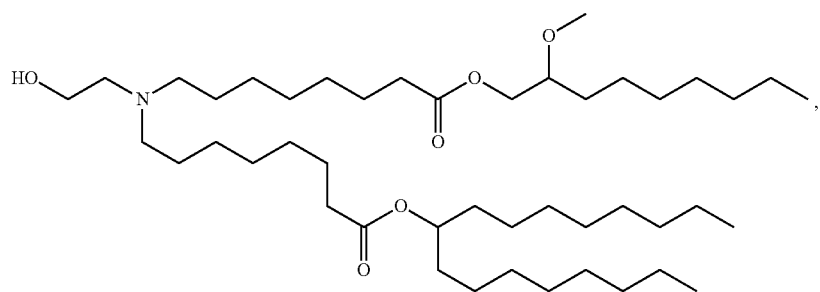
(Compound 149)
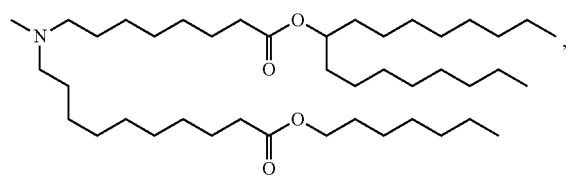
(Compound 150)
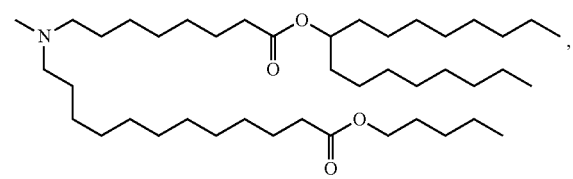

-continued
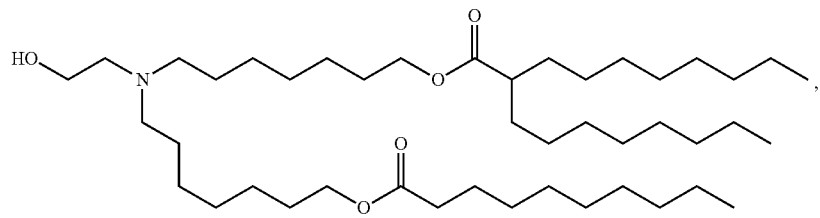
(Compound 151)
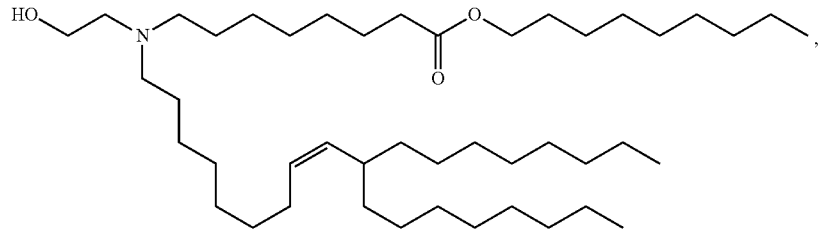
(Compound 152)
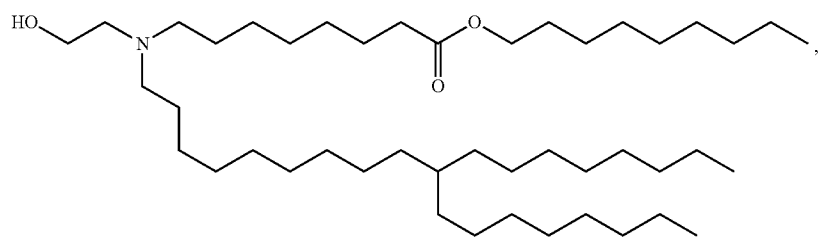
(Compound 153)
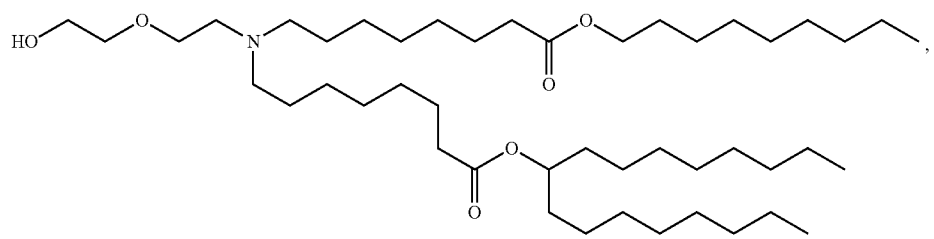
(Compound 154)
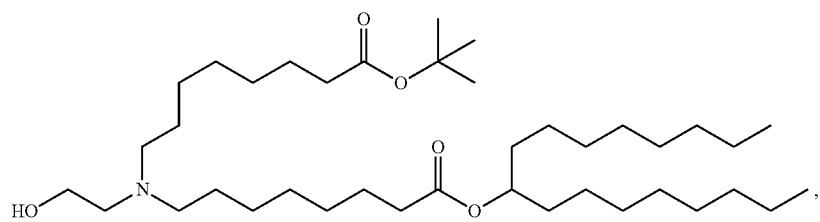
(Compound 155)
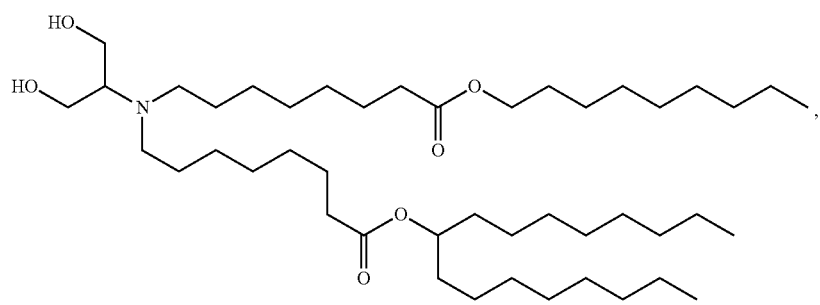
(Compound 156)

(Compound 157)
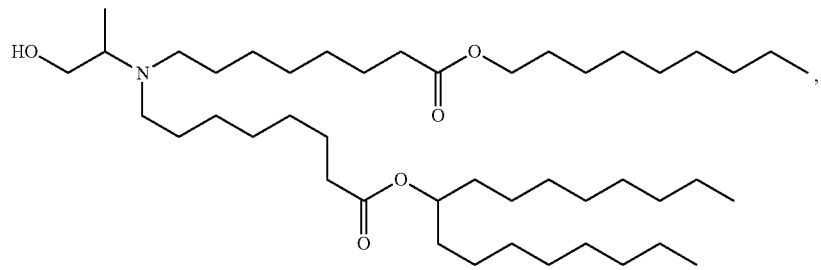
(Compound 158)
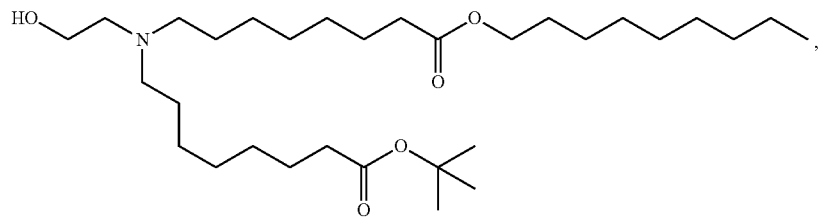
(Compound 159)
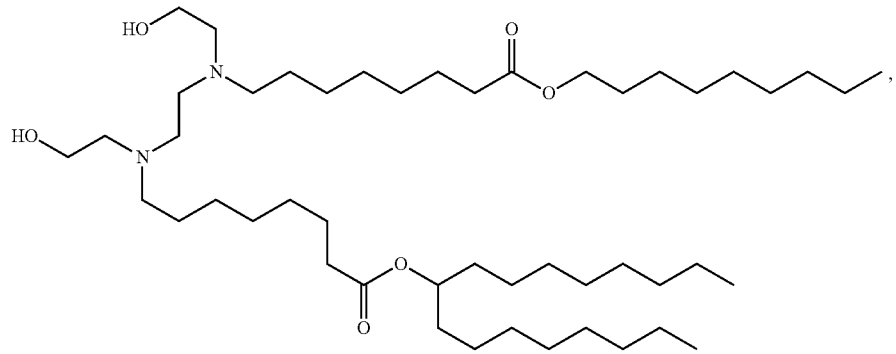
(Compound 160)
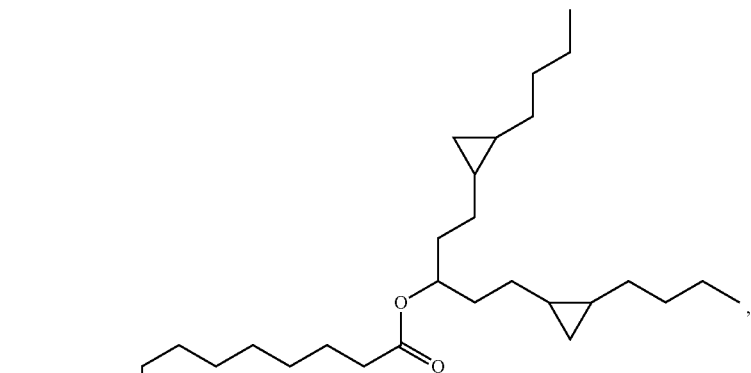
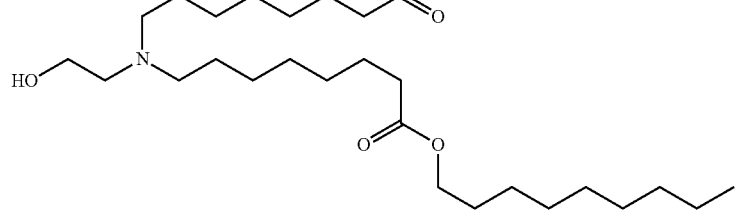
(Compound 161)
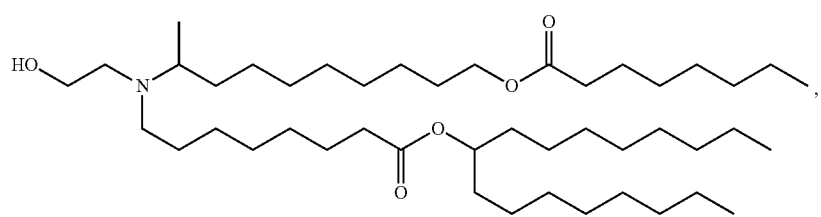

-continued
(Compound 162)
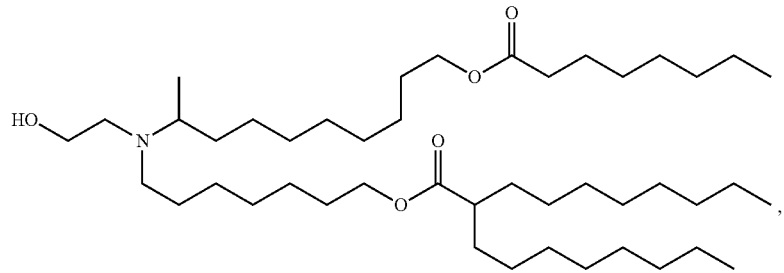
(Compound 163)
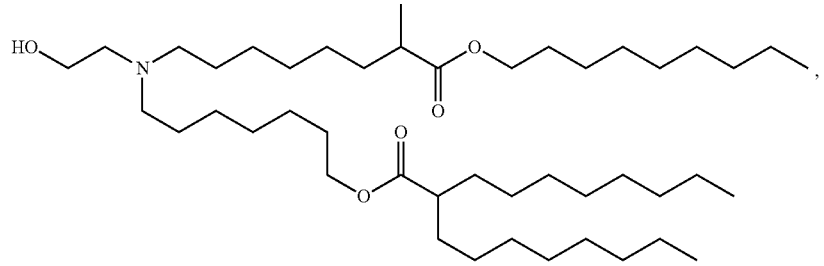
(Compound 164)
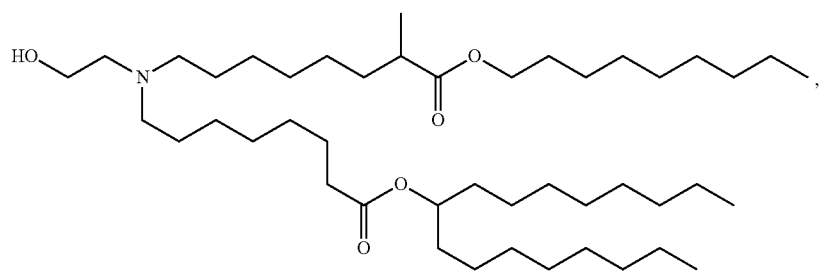
(Compound 165)
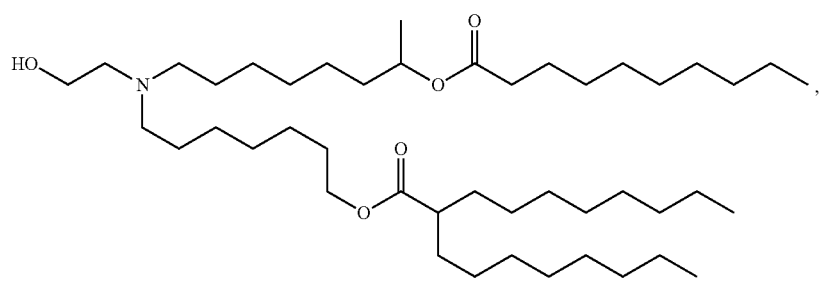
(Compound 166)
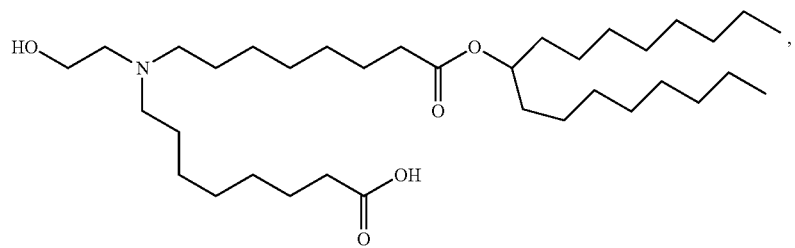
(Compound 167)
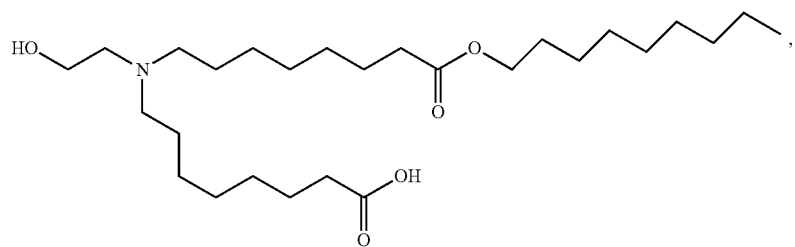

(Compound 168)
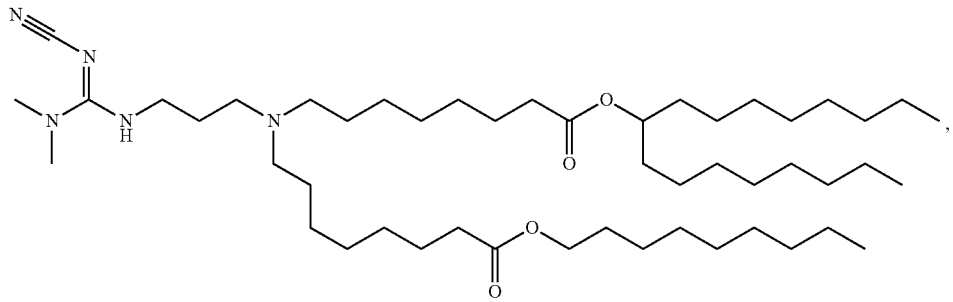
(Compound 169)
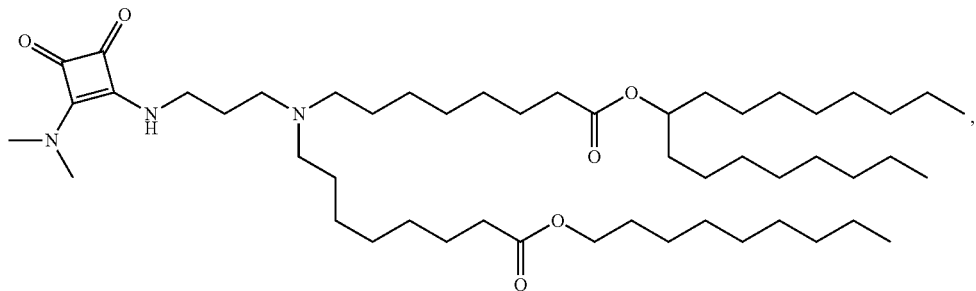
(Compound 170)
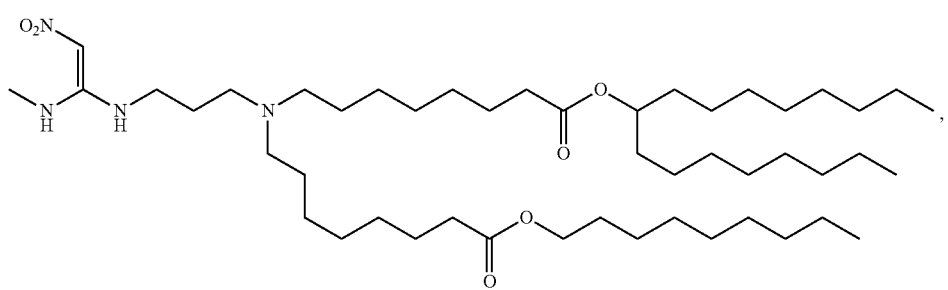
(Compound 171)
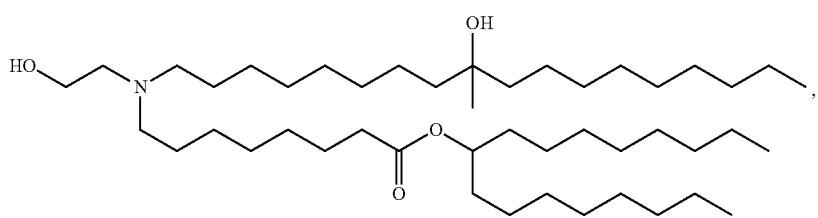
(Compound 172)
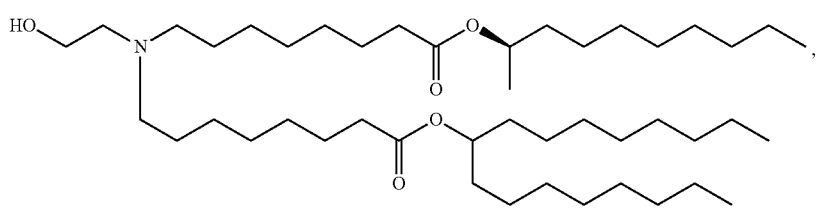
(Compound 173)
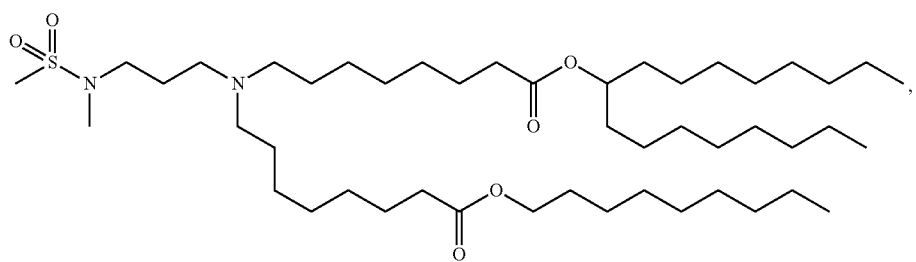

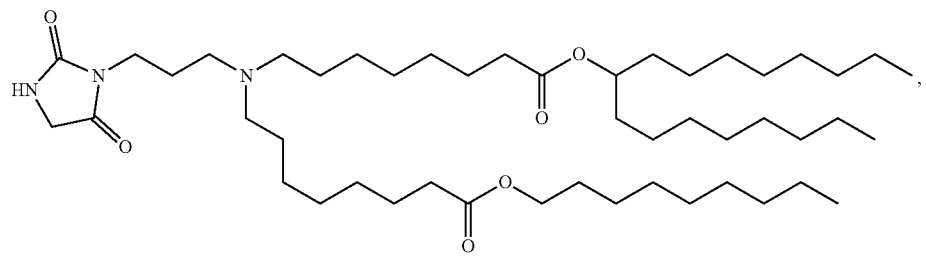
(Compound 174)
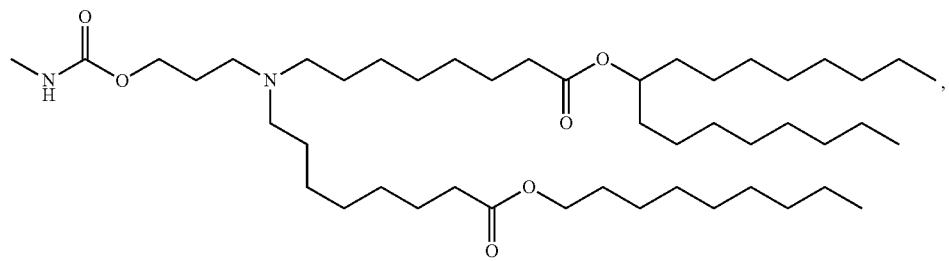
(Compound 175)
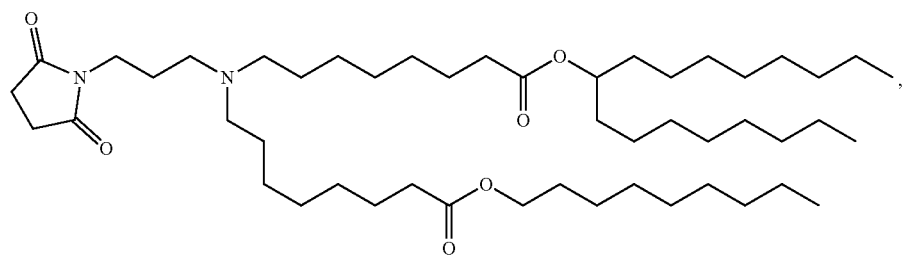
(Compound 176)
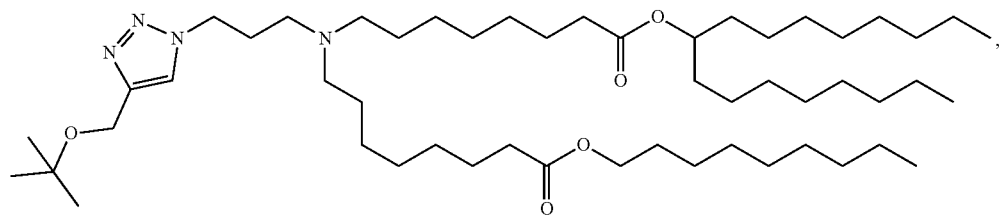
(Compound 177)
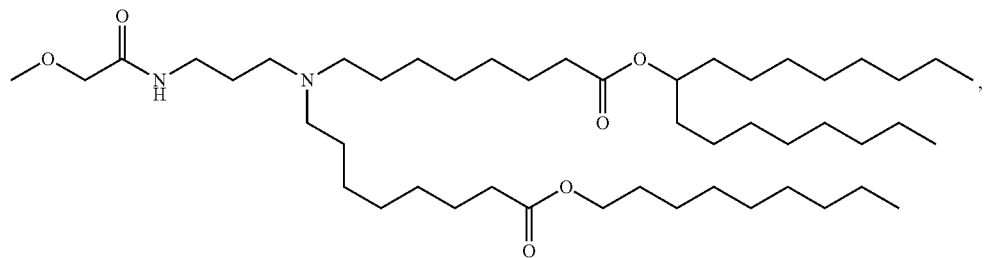
(Compound 178)
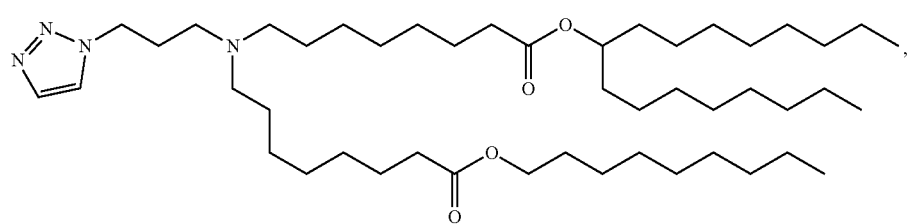
(Compound 179)

(Compound 180)
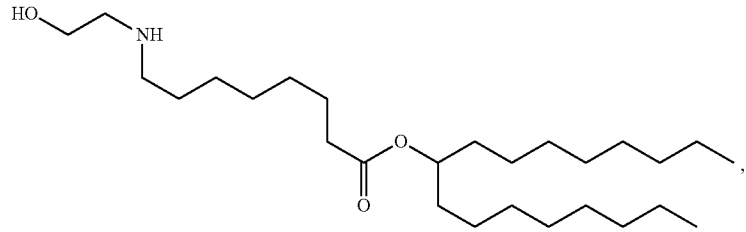
(Compound 181)
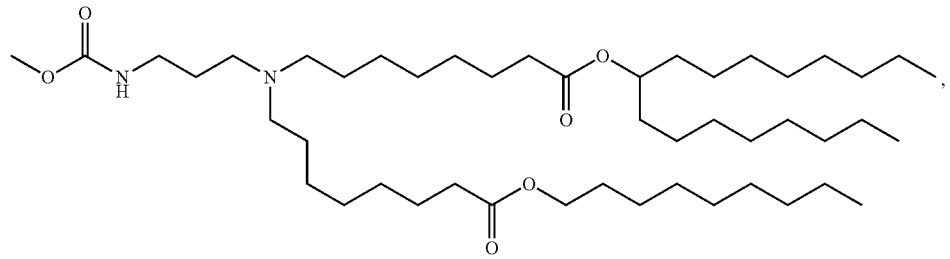
(Compound 182)
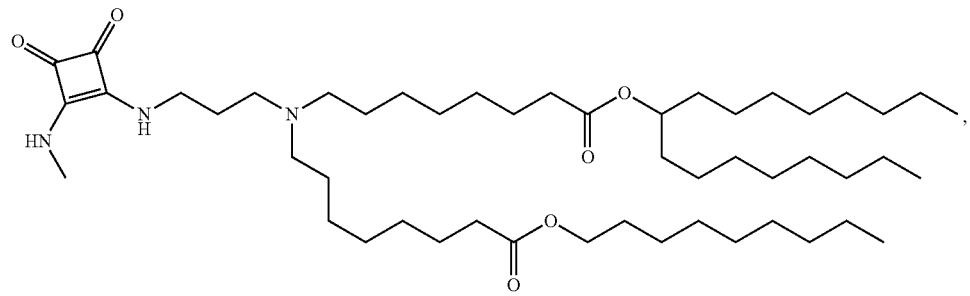
(Compound 183)
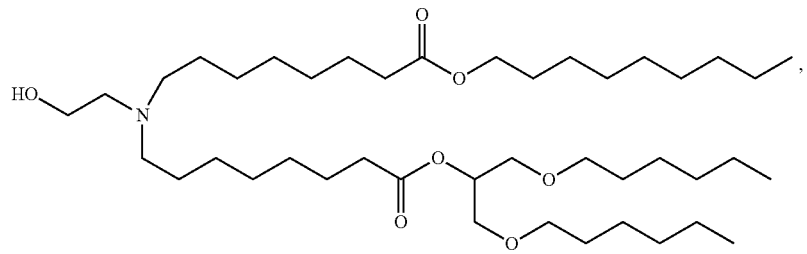
(Compound 184)
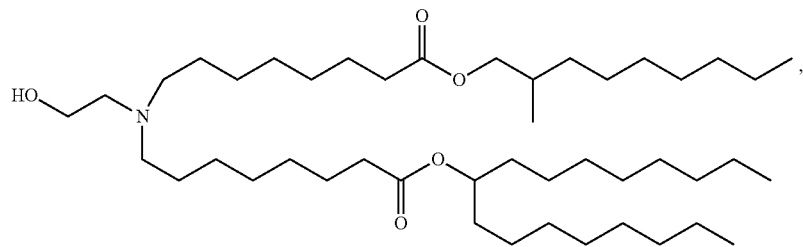
(Compound 185)
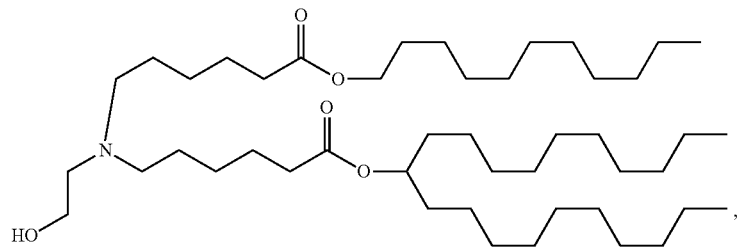

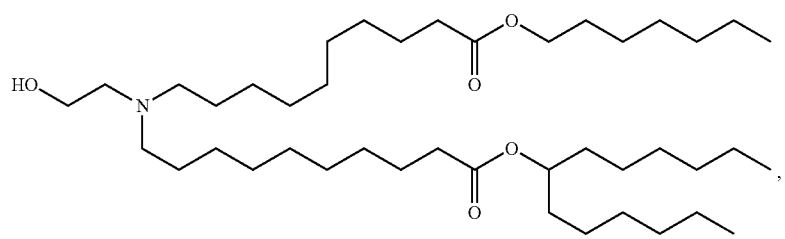
(Compound 186)
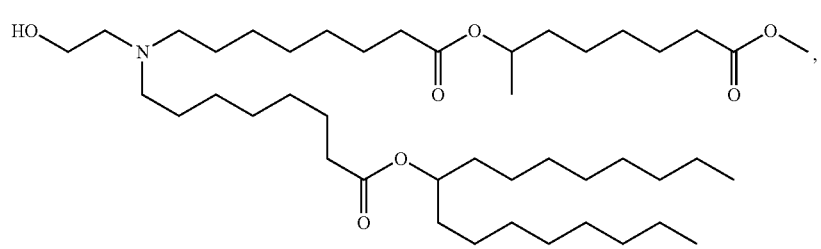
(Compound 187)
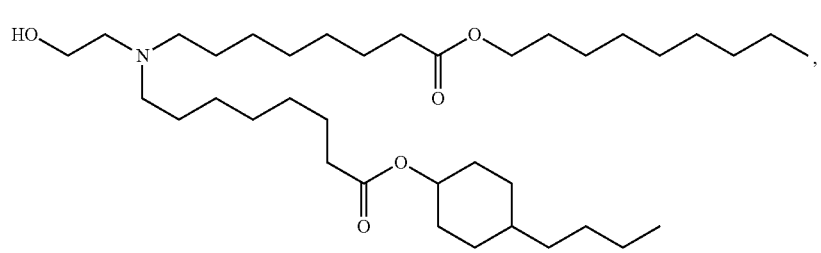
(Compound 188)
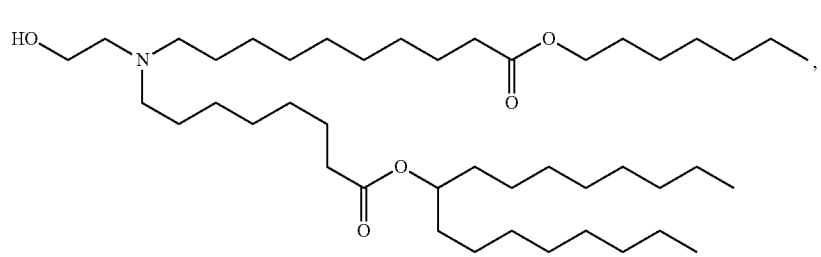
(Compound 189)
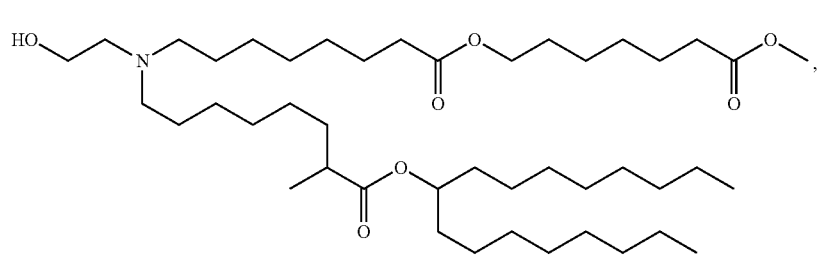
(Compound 190)
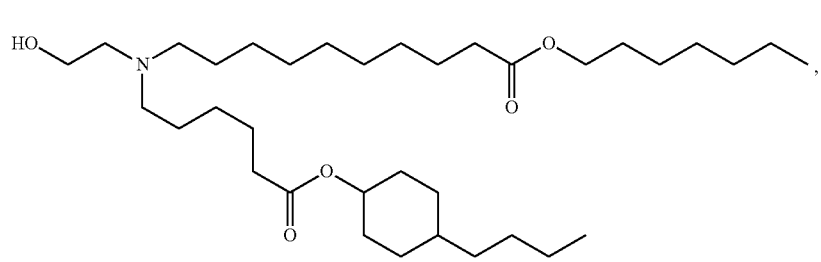
(Compound 191)

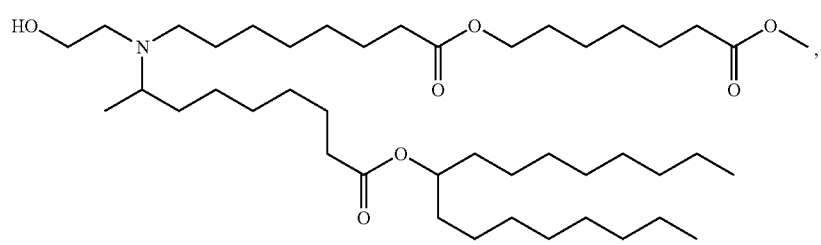
(Compound 192)
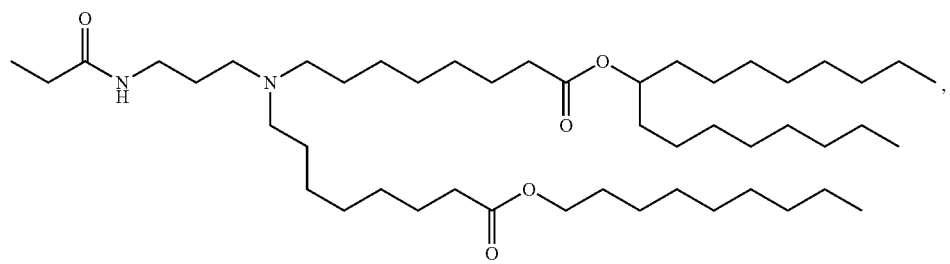
(Compound 193)
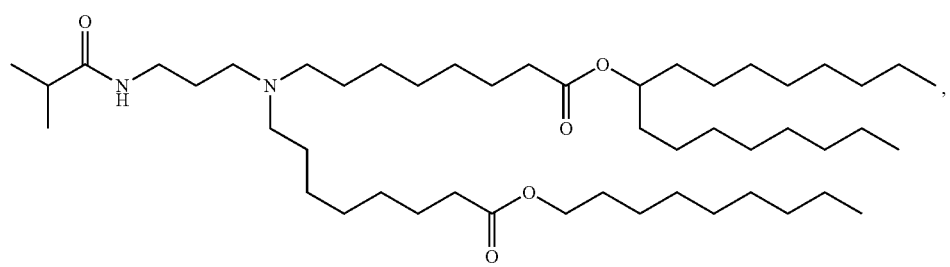
(Compound 194)
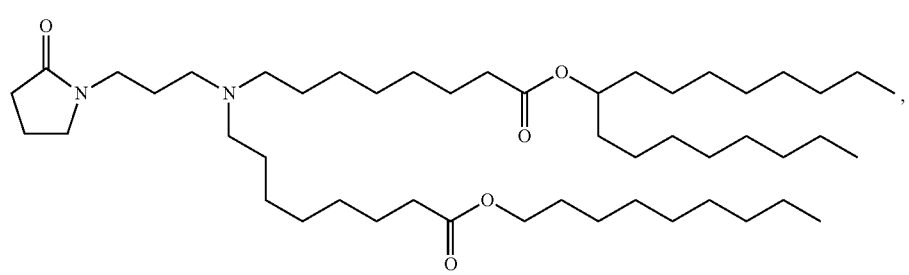
(Compound 195)
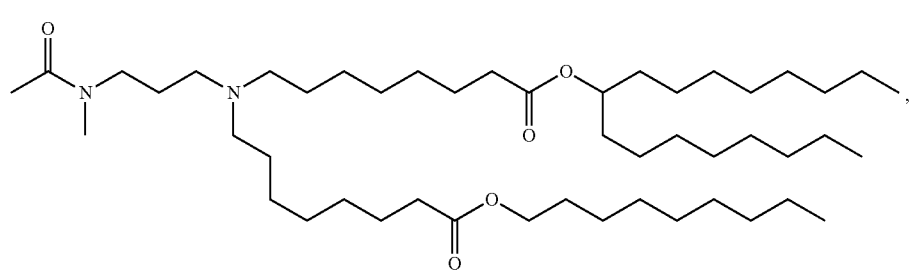
(Compound 196)
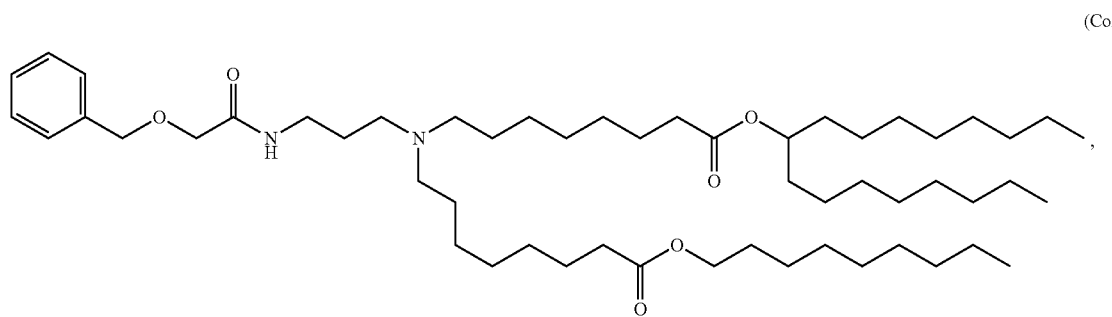
(Compound 197)

(Compound 198)
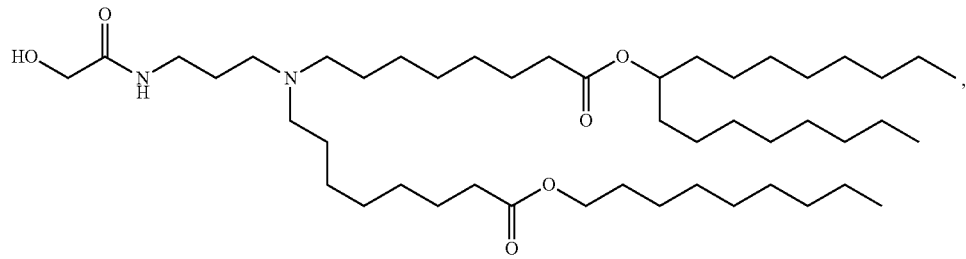
(Compound 199)
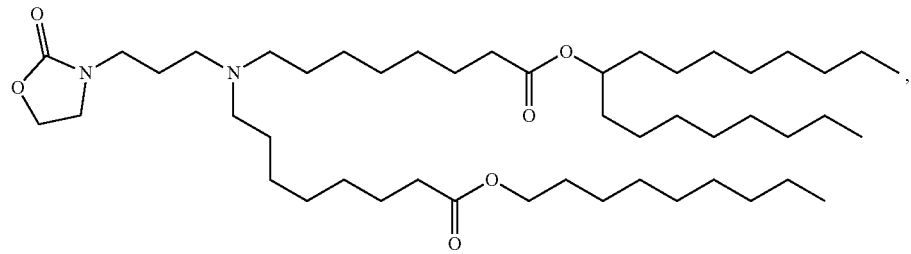
(Compound 200)
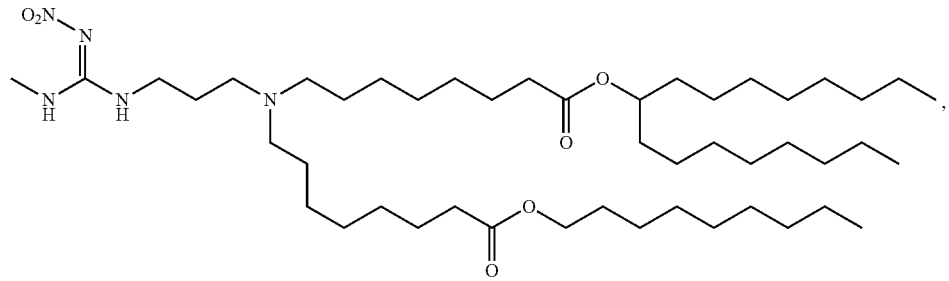
(Compound 201)
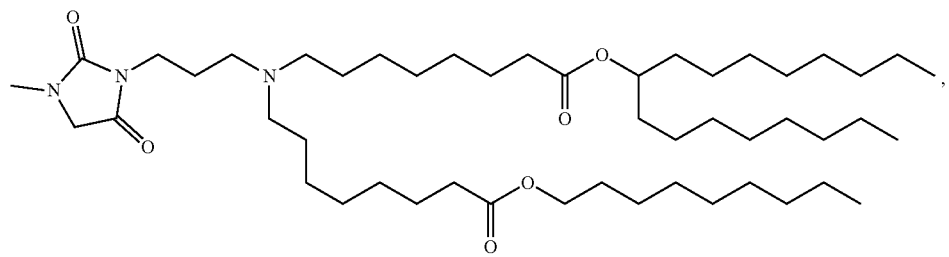
(Compound 202)
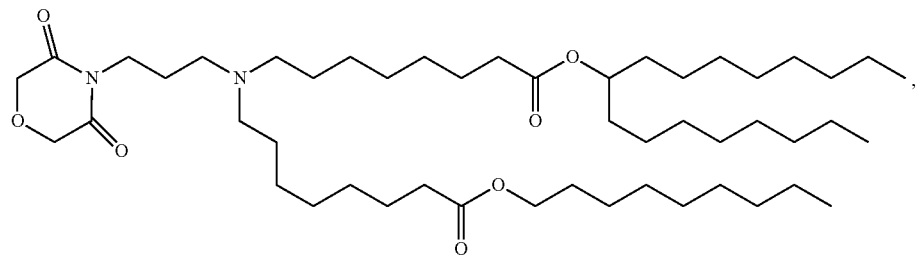
(Compound 203)
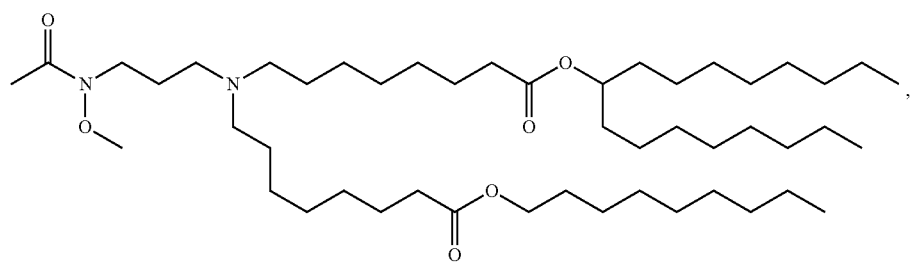

(Compound 204)
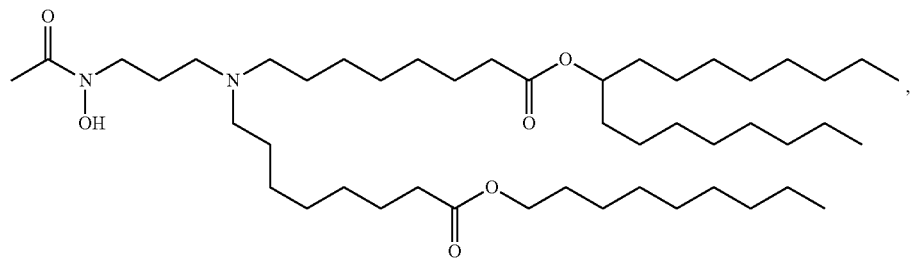
(Compound 205)
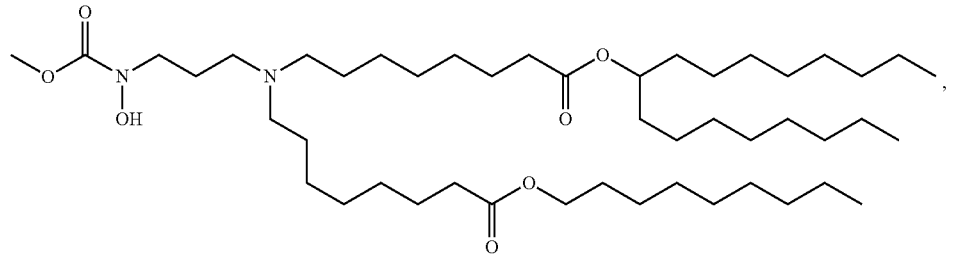
(Compound 206)
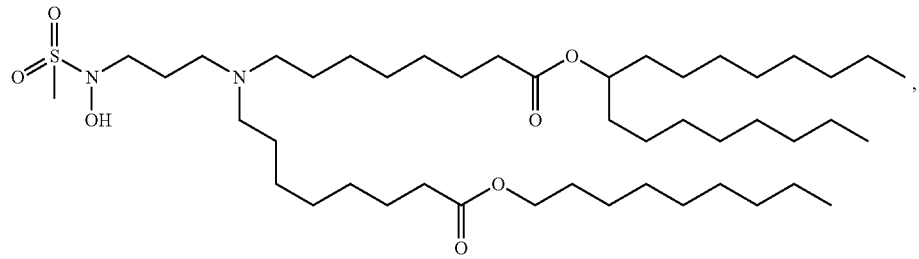
(Compound 207)
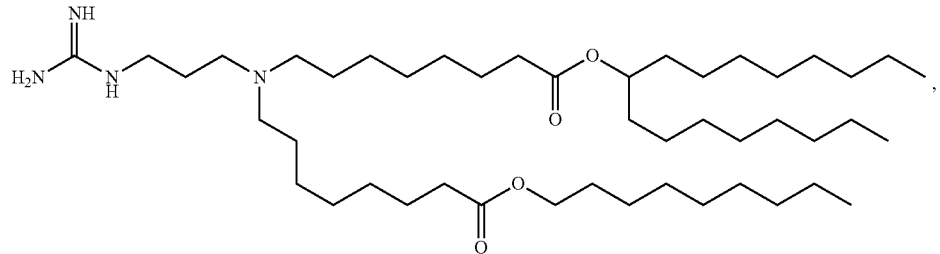
(Compound 208)
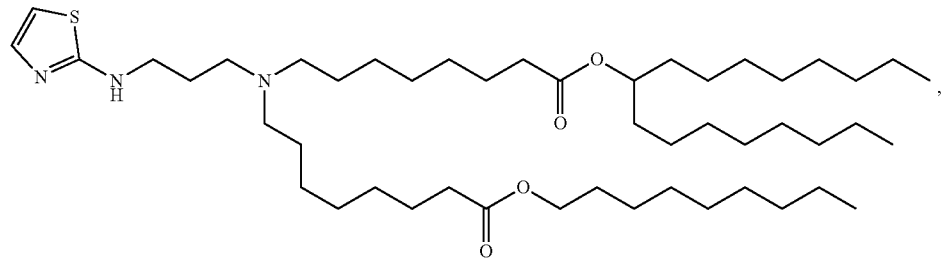
(Compound 209)
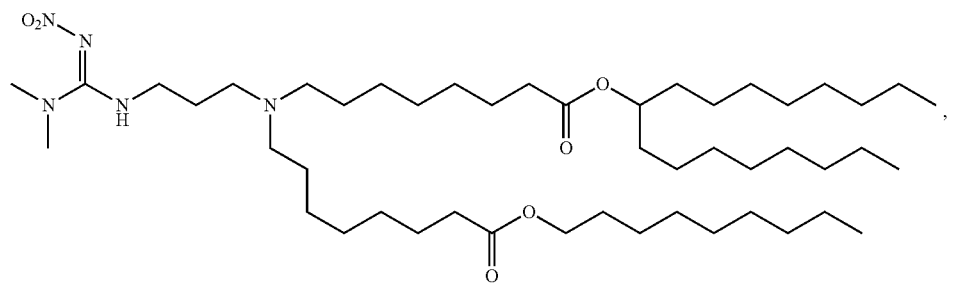

-continued
(Compound 210)
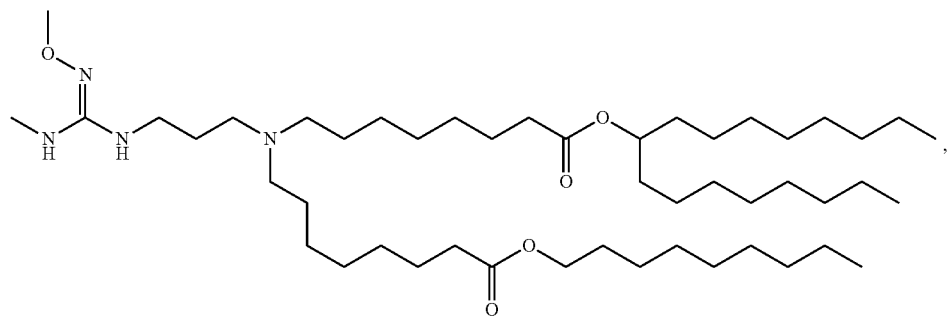
(Compound 211)
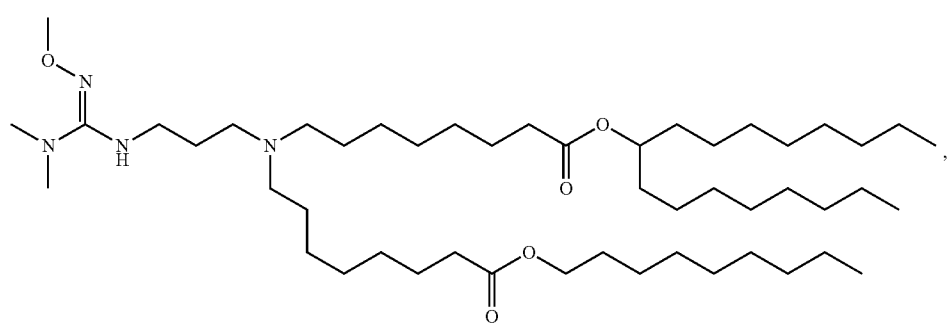
(Compound 212)
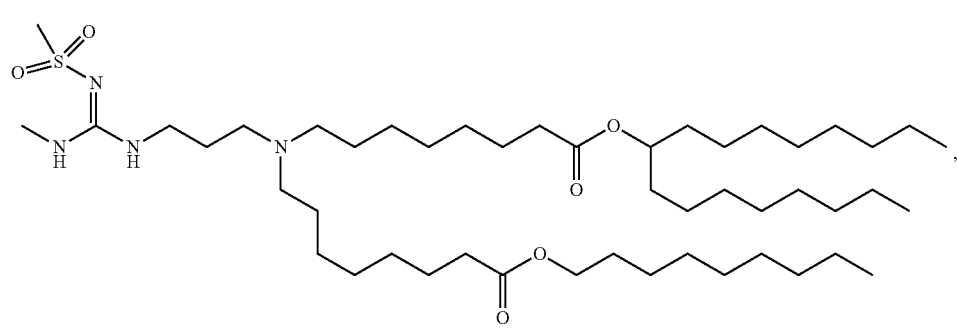
(Compound 213)
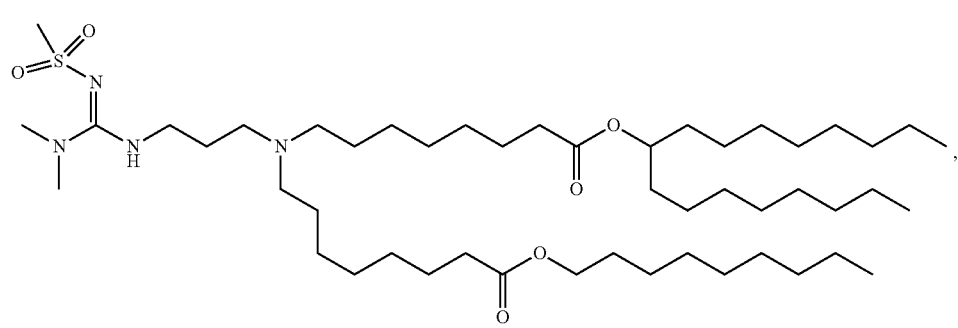
(Compound 214)
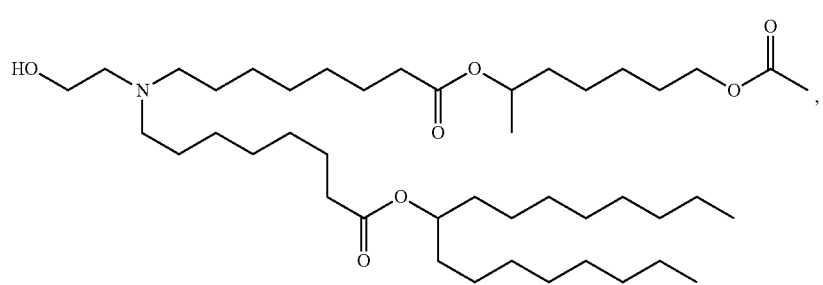

-continued
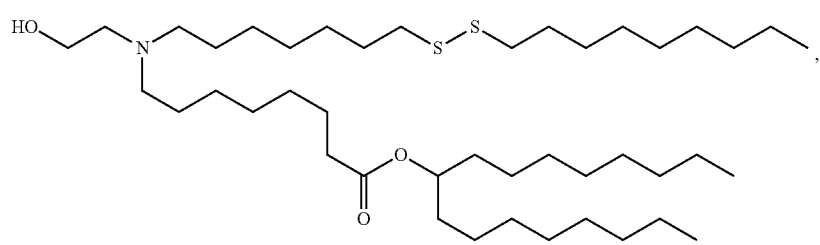
(Compound 215)
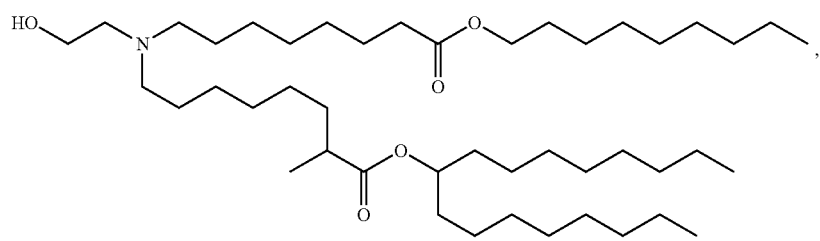
(Compound 216)
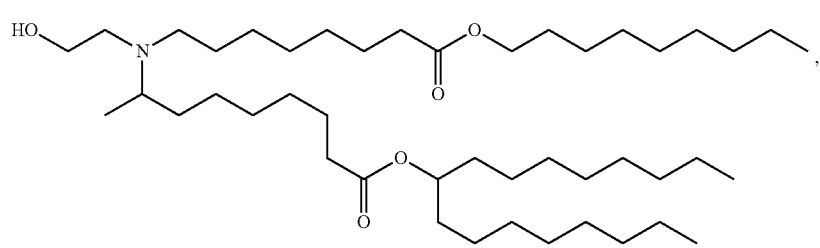
(Compound 217)
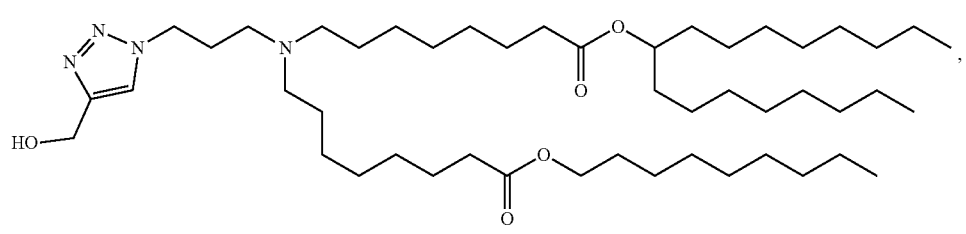
(Compound 218)
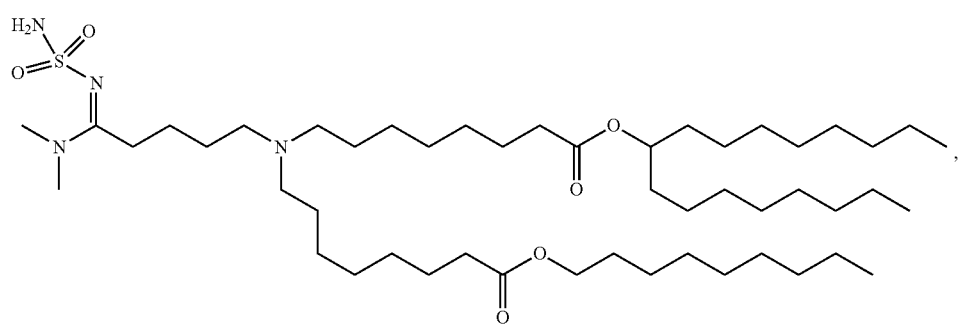
(Compound 219)
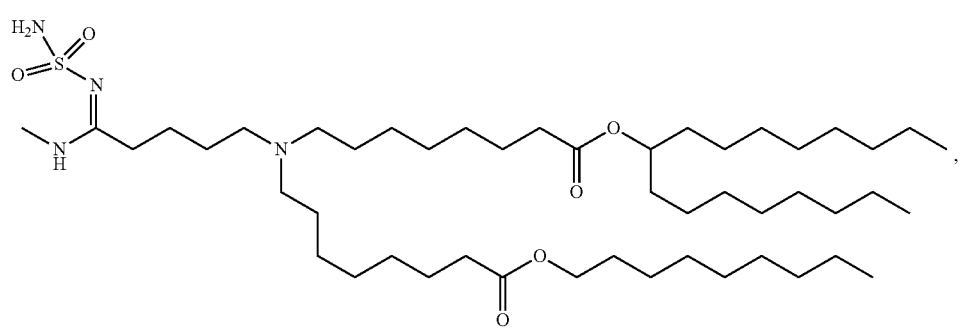
(Compound 220)

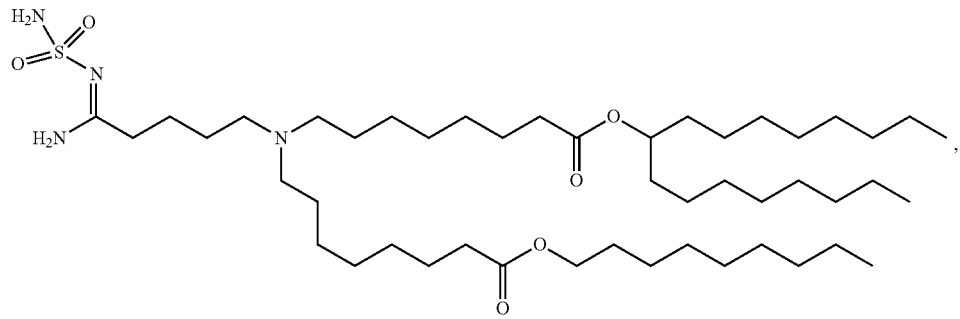
(Compound 221)
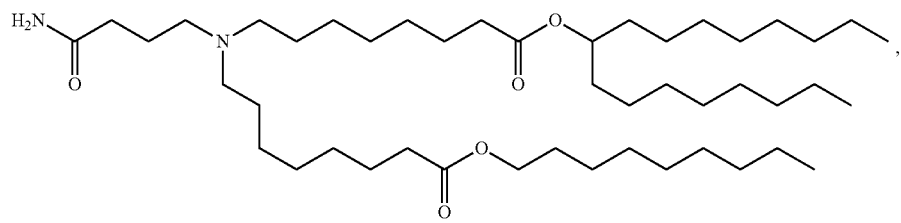
(Compound 222)
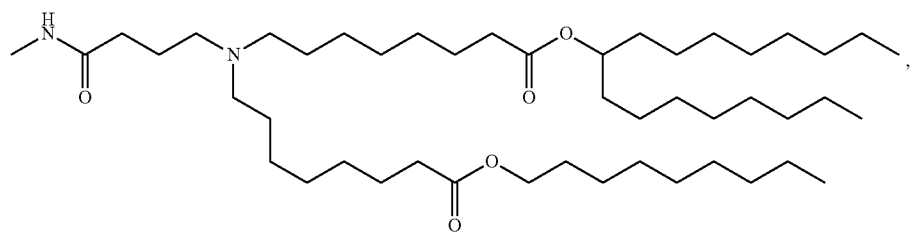
(Compound 223)
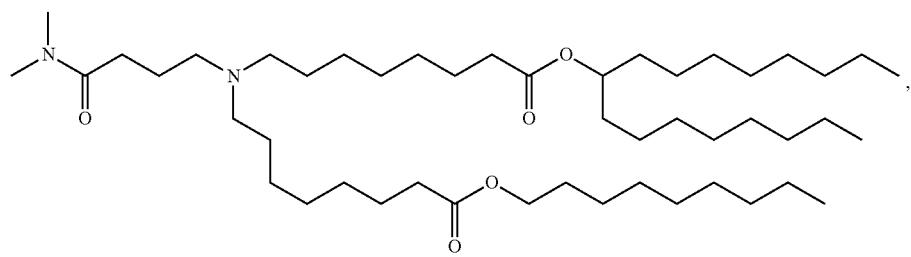
(Compound 224)
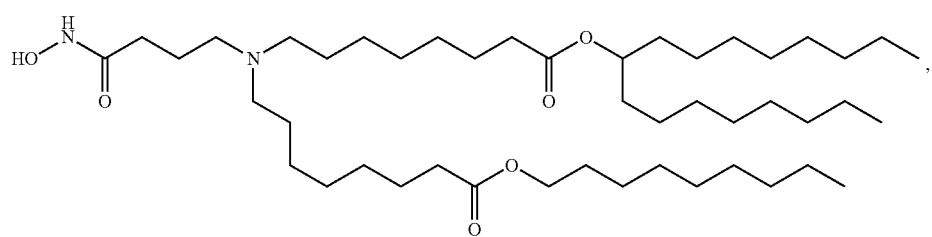
(Compound 225)
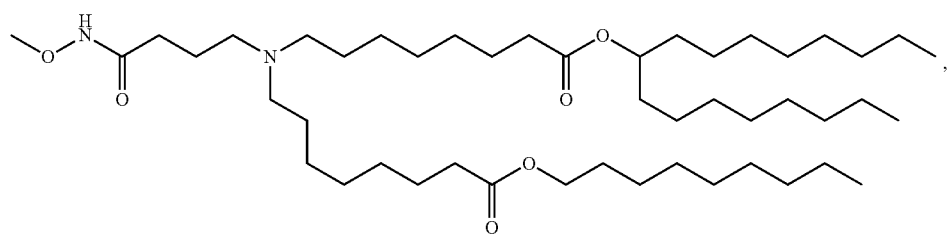
(Compound 226)

-continued

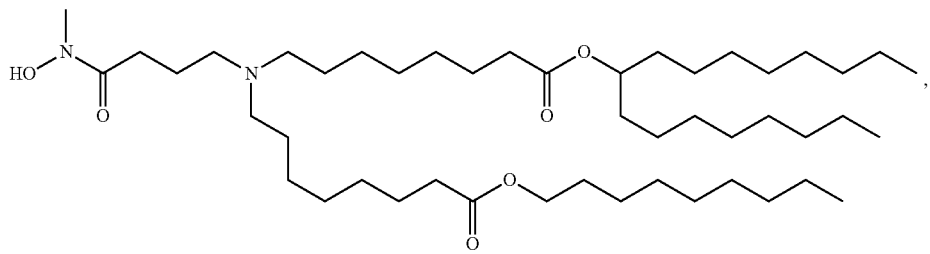
(Compound 227)

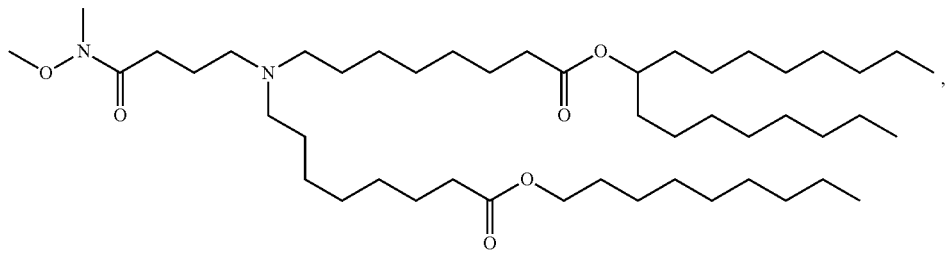
(Compound 228)

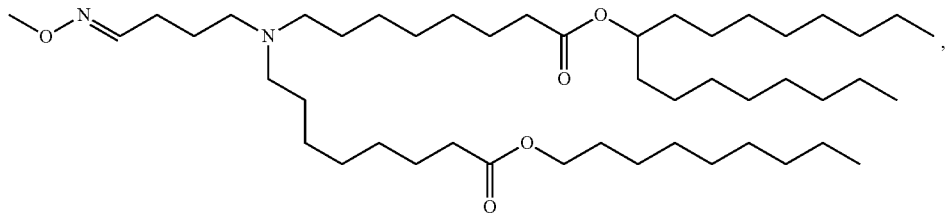
(Compound 229)

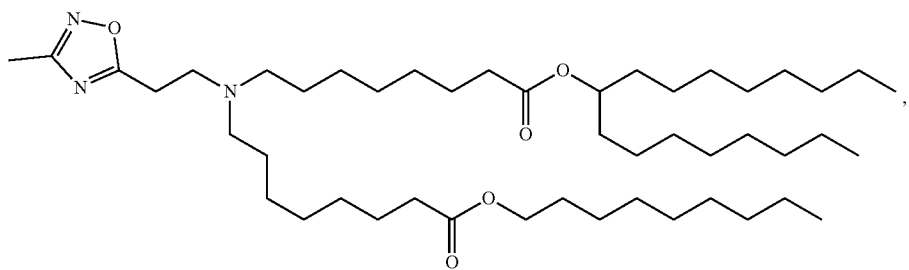
(Compound 230)

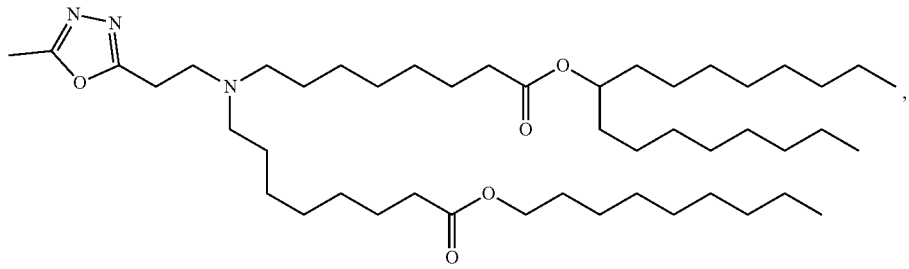
(Compound 231)

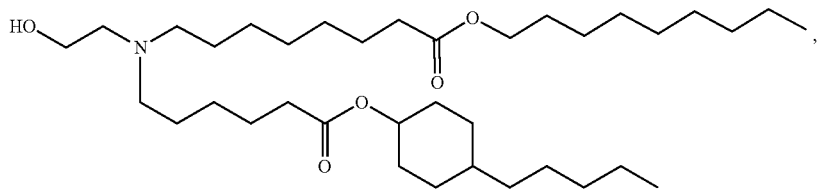
(Compound 232)

and salts or stereoisomers thereof.

In other embodiments, the compound of Formula (I) is selected from the group consisting of Compound 1-Compound 147, or salt or stereoisomers thereof.

In some embodiments ionizable lipids including a central piperazine moiety are provided.

In some embodiments, the delivery agent comprises a lipid compound having the Formula (III)

(III)

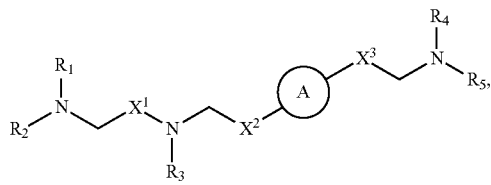

or salts or stereoisomers thereof, wherein

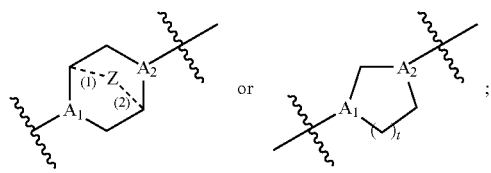

ring A is
t is 1 or 2;
$A_1$ and $A_2$ are each independently selected from CH or N;
Z is $CH_2$ or absent wherein when Z is $CH_2$, the dashed lines (1) and (2) each represent a single bond; and when Z is absent, the dashed lines (1) and (2) are both absent;
$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";
each M is independently selected from the group consisting of —C(O)O—, —OC(O)—, —OC(O)O—, —C(O)N(R')—, —N(R')C(O)—, —C(O)—, —C(S)—, —C(S)S—, —S C(S)—, —CH(OH)—, —P(O)(OR')O—, —S(O)$_2$—, an aryl group, and a heteroaryl group;
$X^1$, $X^2$, and $X^3$ are independently selected from the group consisting of a bond, —CH$_2$—, —(CH$_2$)$_2$—, —CHR—, —CHY—, —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, —CH$_2$—OC(O)—, —CH(OH)—, —C(S)—, and —CH(SH)—;
each Y is independently a $C_{3-6}$ carbocycle;
each R* is independently selected from the group consisting of $C_{1-12}$ alkyl and $C_{2-12}$ alkenyl;
each R is independently selected from the group consisting of $C_{1-3}$ alkyl and a $C_{3-6}$ carbocycle;
each R' is independently selected from the group consisting of $C_{1-12}$ alkyl, $C_{2-12}$ alkenyl, and H; and
each R" is independently selected from the group consisting of $C_{3-12}$ alkyl and $C_{3-12}$ alkenyl,
wherein when ring A is

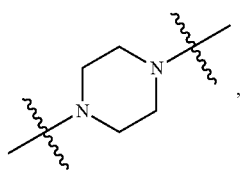 [SMILES: *N1CCN(*)CC1]

then
i) at least one of $X^1$, $X^2$, and $X^3$ is not —CH$_2$—; and/or
ii) at least one of $R_1$, $R_2$, $R_3$, $R_4$, and $R_5$ is —R"MR'.

In some embodiments, the compound is of any of Formulae (IIIa1)-(IIIa6):

(IIIa1)

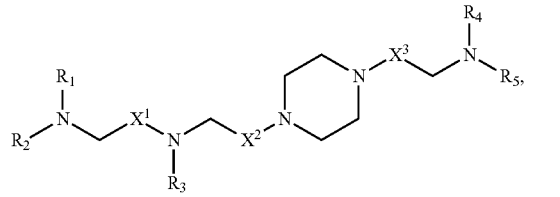

(IIIa2)

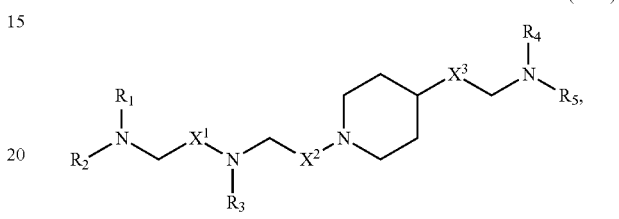

(IIIa3)

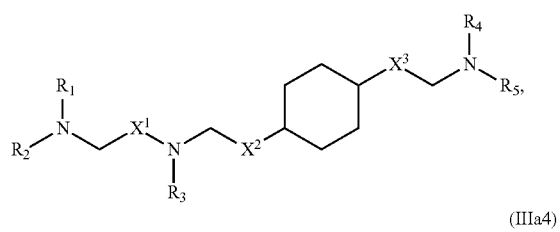

(IIIa4)

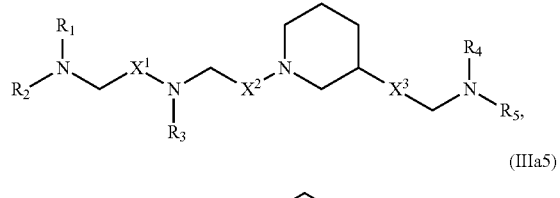

(IIIa5)

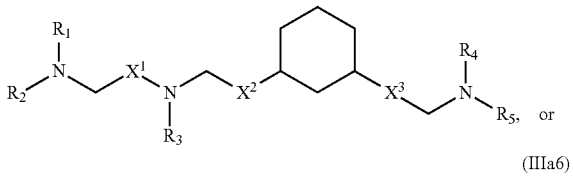

or (IIIa6)

The compounds of Formula (III) or any of (IIIa1)-(IIIa6) include one or more of the following features when applicable.

In some embodiments, ring A is

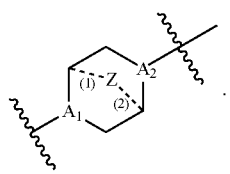

In some embodiments, ring A is

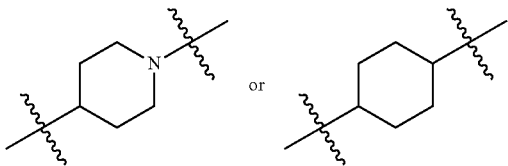

In some embodiments, ring A is

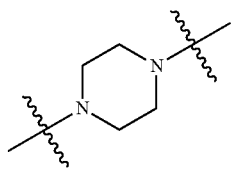

In some embodiments, ring A is

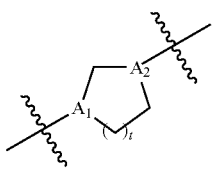

In some embodiments, ring A is

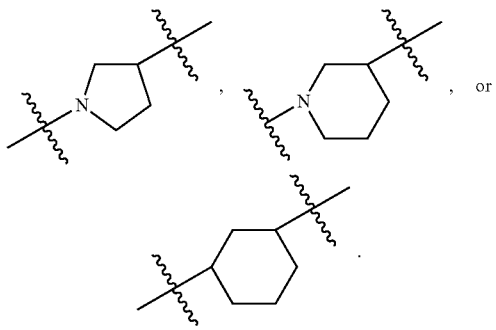

In some embodiments, ring A is

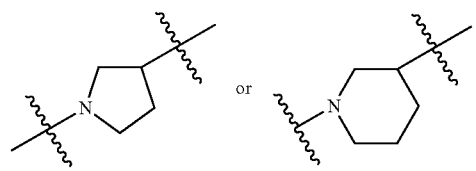 [SMILES: *C1CCN(*)C1 ; *C1CCCN(*)C1]

wherein ring, in which the N atom is connected with $X^2$.

In some embodiments, Z is $CH_2$.
In some embodiments, Z is absent.
In some embodiments, at least one of $A_1$ and $A_2$ is N.
In some embodiments, each of $A_1$ and $A_2$ is N.
In some embodiments, each of $A_1$ and $A_2$ is CH.
In some embodiments, $A_1$ is N and $A_2$ is CH.
In some embodiments, $A_1$ is CH and $A_2$ is N.
In some embodiments, at least one of $X^1$, $X^2$, and $X^3$ is not —$CH_2$—. For example, in certain embodiments, $X^1$ is not —$CH_2$—. In some embodiments, at least one of $X^1$, $X^2$, and $X^3$ is —C(O)—.
In some embodiments, $X^2$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—.
In some embodiments, $X^3$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—. In other embodiments, $X^3$ is —$CH_2$—.
In some embodiments, $X^3$ is a bond or —$(CH_2)_2$—.
In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.
In some embodiments, at least one of $R_1$, $R_2$, $R_3$, $R_4$, and $R_5$ is —R"MR'. In some embodiments, at most one of $R_1$, $R_2$, $R_3$, $R_4$, and $R_5$ is —R"MR'. For example, at least one of $R_1$, $R_2$, and $R_3$ may be —R"MR', and/or at least one of $R_4$ and $R_5$ is —R"MR'. In certain embodiments, at least one M is —C(O)O—, In some embodiments, each M is —C(O)O—, In some embodiments, at least one M is —OC(O)—. In some embodiments, each M is —OC(O)—. In some embodiments, at least one M is —OC(O)O—. In some embodiments, each M is —OC(O)O—. In some embodiments, at least one R" is $C_3$ alkyl. In certain embodiments, each R" is $C_3$ alkyl. In some embodiments, at least one R" is $C_5$ alkyl. In certain embodiments, each R" is $C_5$ alkyl. In some embodiments, at least one R" is $C_6$ alkyl. In certain embodiments, each R" is $C_6$ alkyl. In some embodiments, at least one R" is $C_7$ alkyl. In certain embodiments, each R" is $C_7$ alkyl. In some embodiments, at least one R' is $C_5$ alkyl. In certain embodiments, each R' is $C_5$ alkyl. In other embodiments, at least one R' is $C_1$ alkyl. In certain embodiments, each R' is $C_1$ alkyl. In some embodiments, at least one R' is $C_2$ alkyl. In certain embodiments, each R' is $C_2$ alkyl.
In some embodiments, at least one of $R_1$, $R_2$, $R_3$, $R_4$, and $R_5$ is $C_{12}$ alkyl. In certain embodiments, each of $R_1$, $R_2$, $R_3$, $R_4$, and $R_5$ are $C_{12}$ alkyl.
In certain embodiments, the compound is selected from the group consisting of:

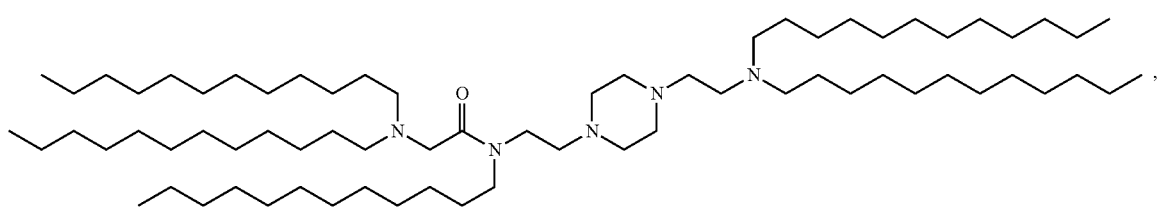

(Compound 233)

-continued
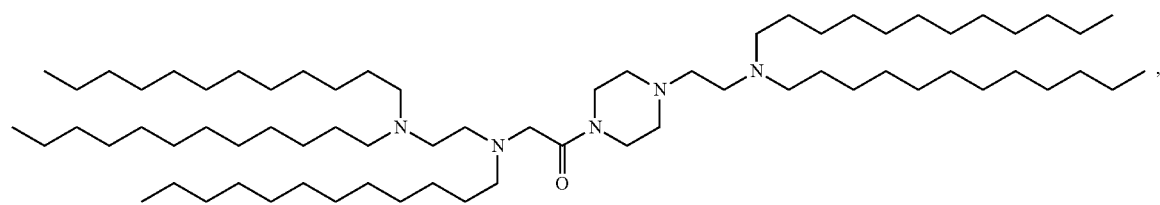
(Compound 234)
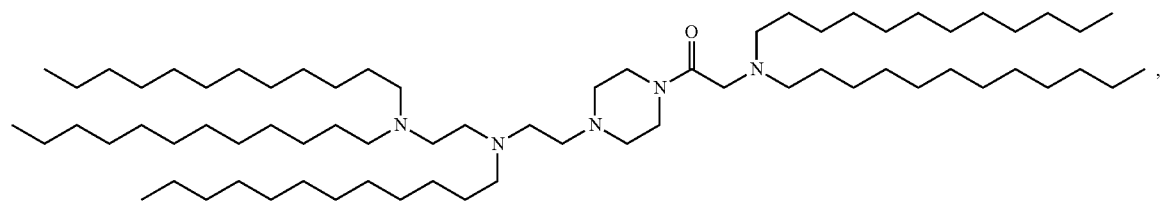
(Compound 235)
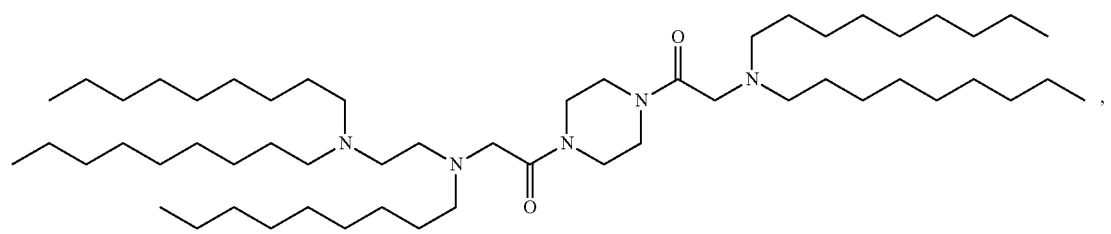
(Compound 236)
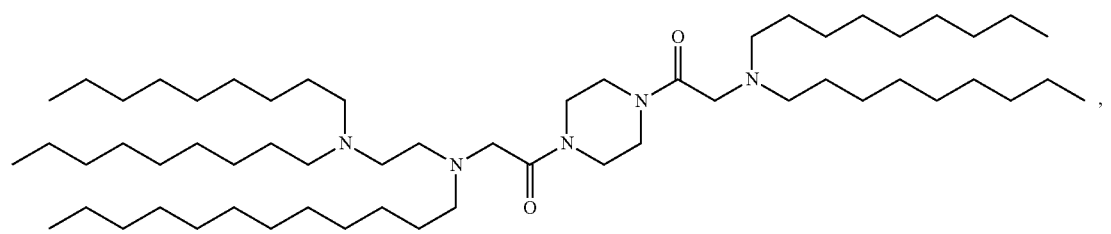
(Compound 237)
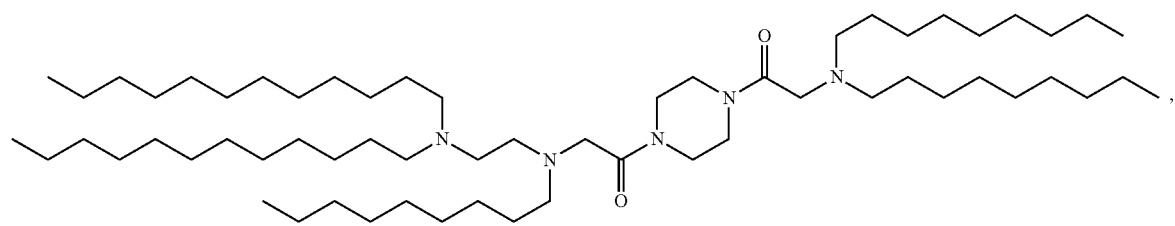
(Compound 238)
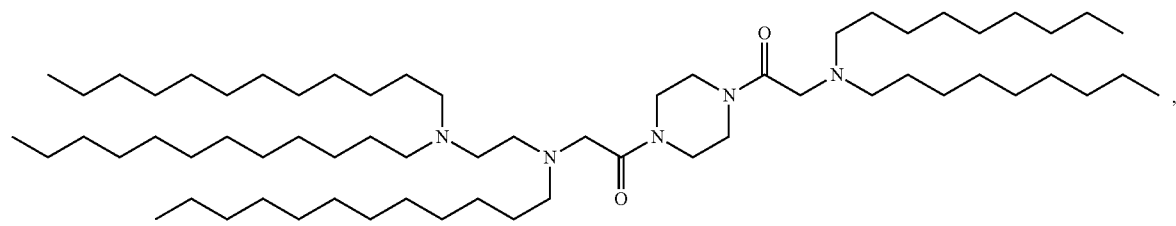
(Compound 239)

(Compound 240)
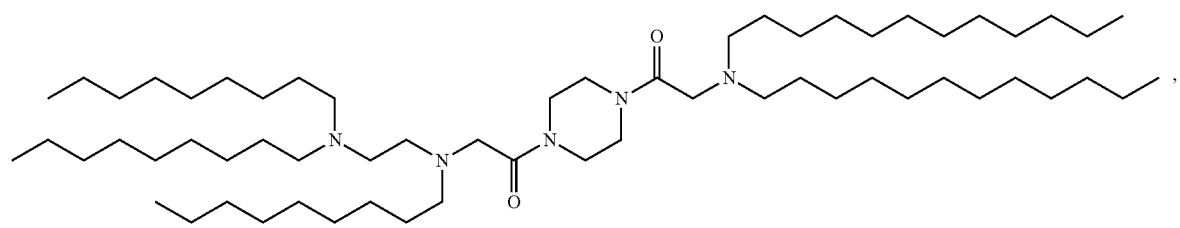
(Compound 241)
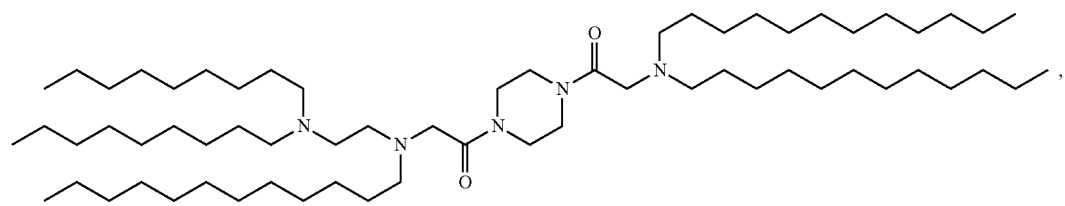
(Compound 242)
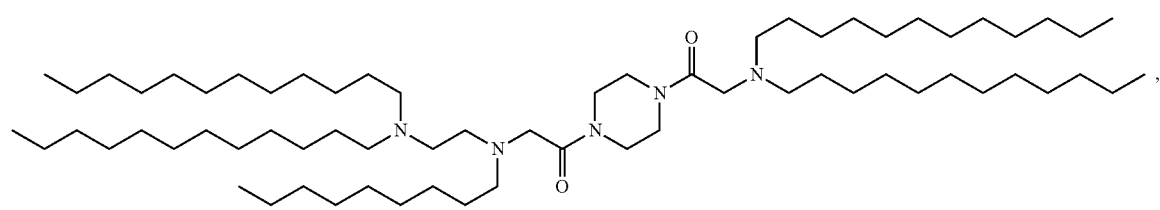
(Compound 243)
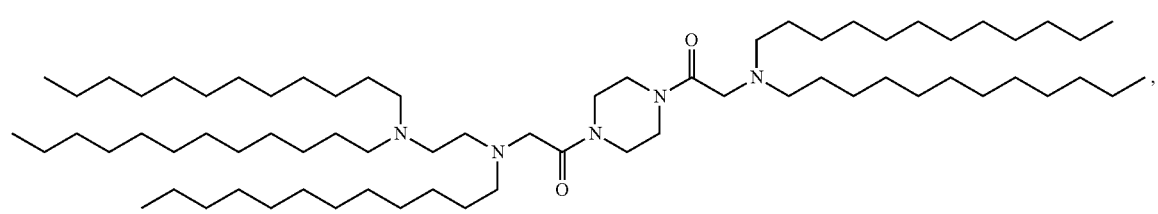
(Compound 244)
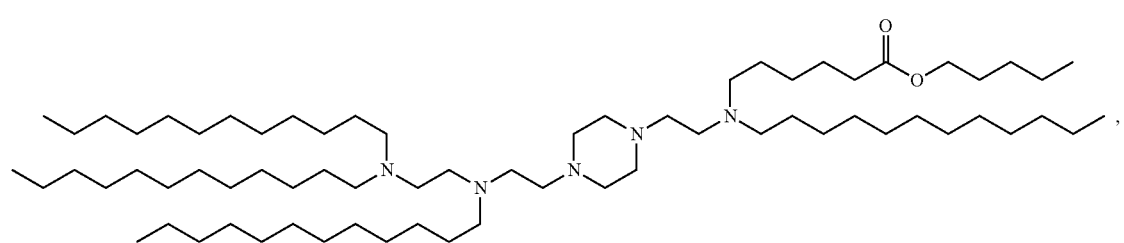
(Compound 245)
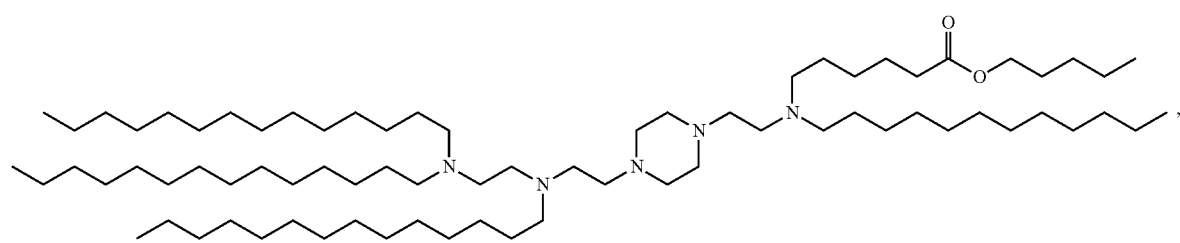

(Compound 246)
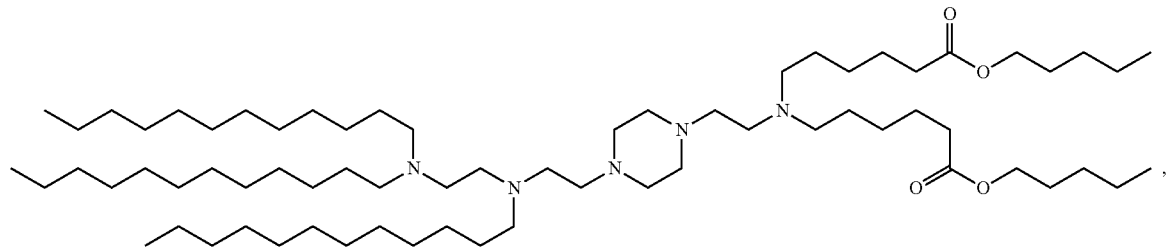
(Compound 247)
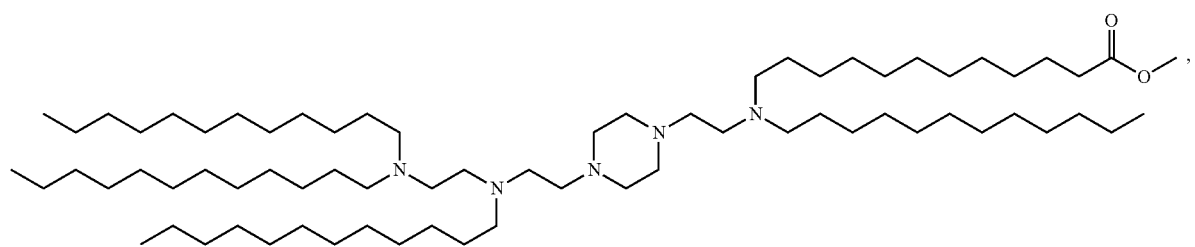
(Compound 248)
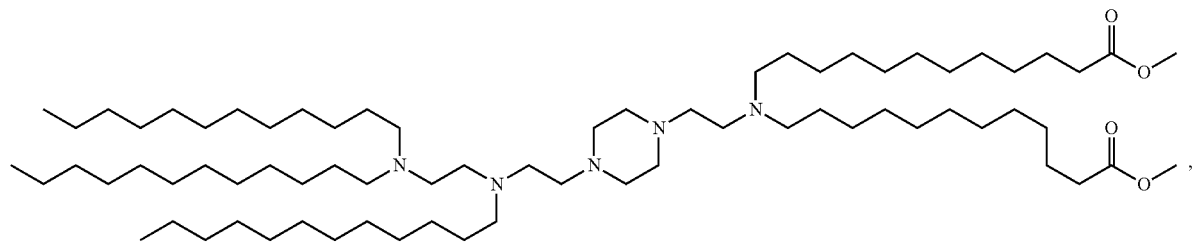
(Compound 274)
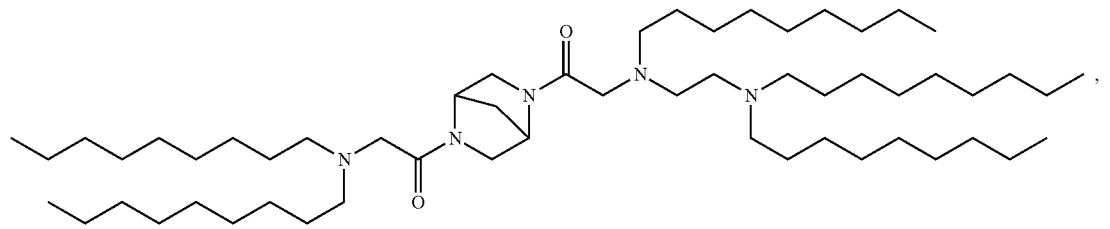
(Compound 275)
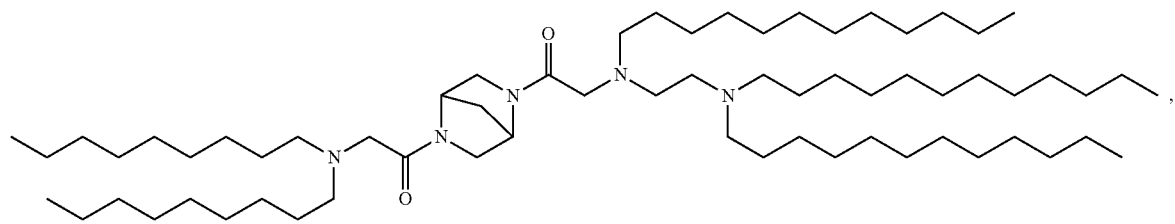
(Compound 276)
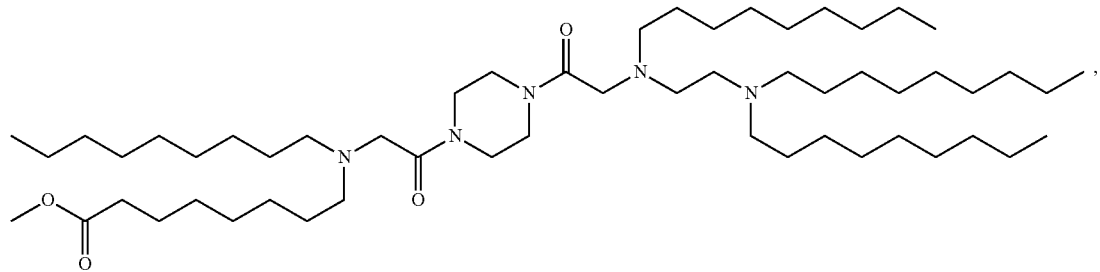

-continued
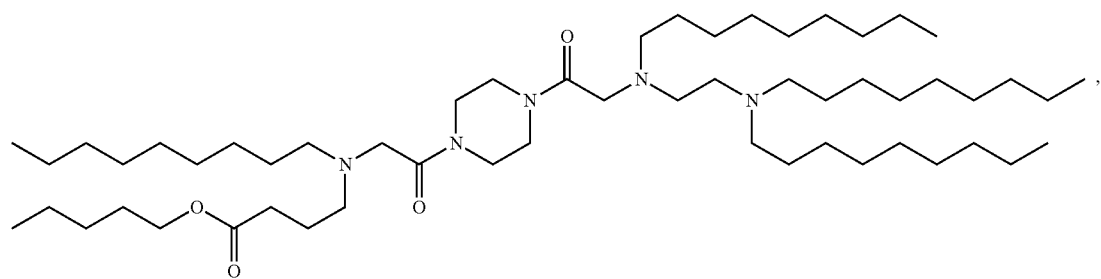
(Compound 277)
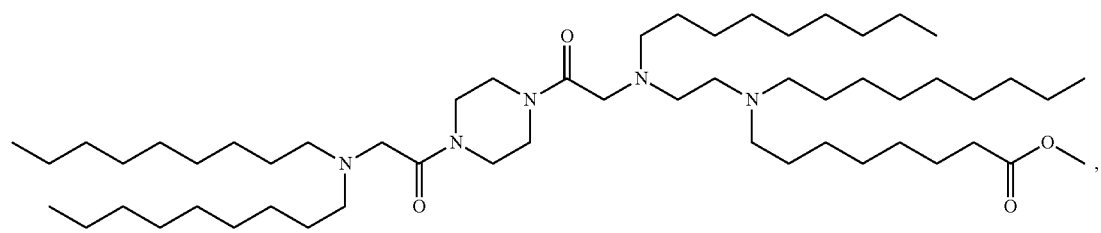
(Compound 278)
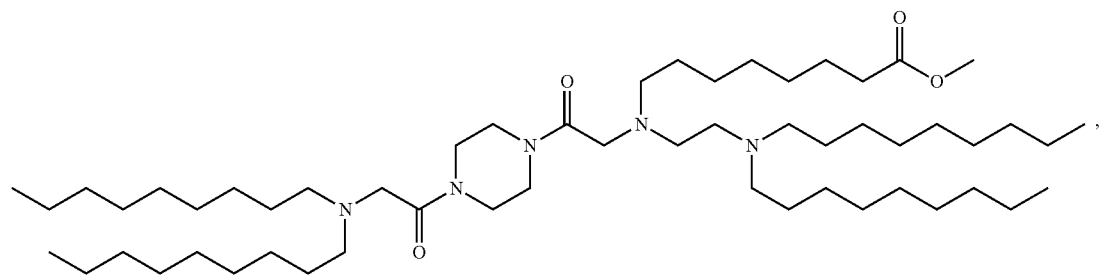
(Compound 279)
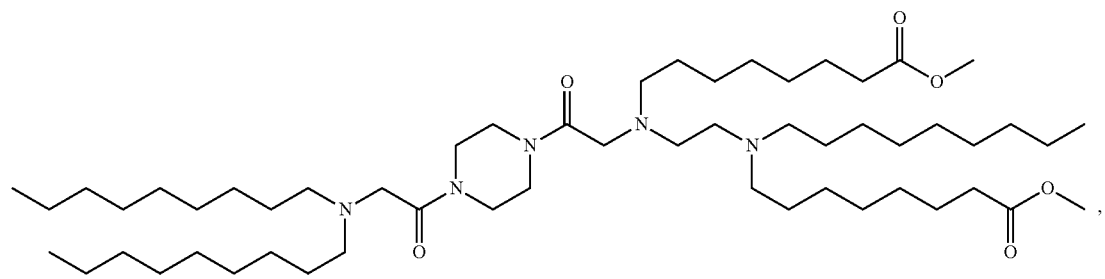
(Compound 280)
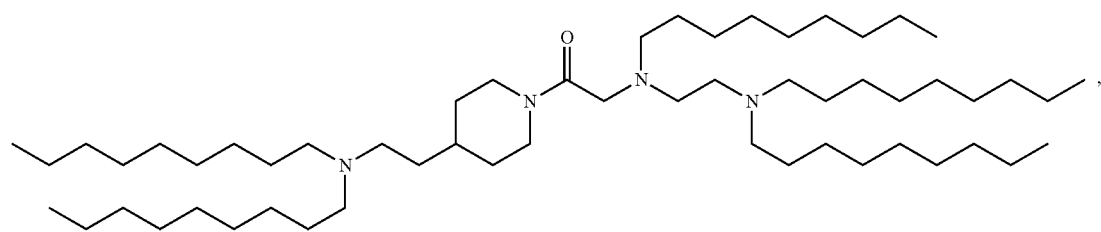
(Compound 281)

-continued
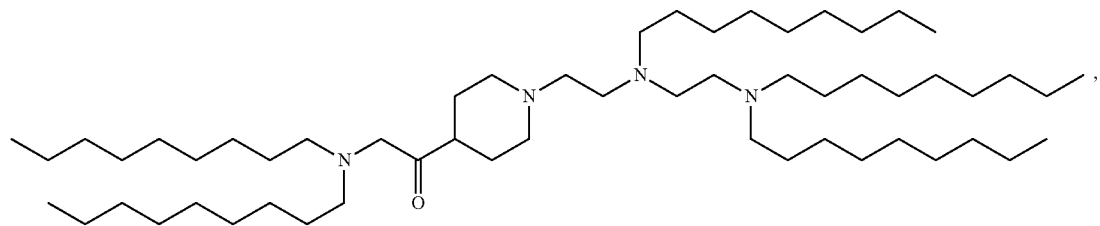
(Compound 282)
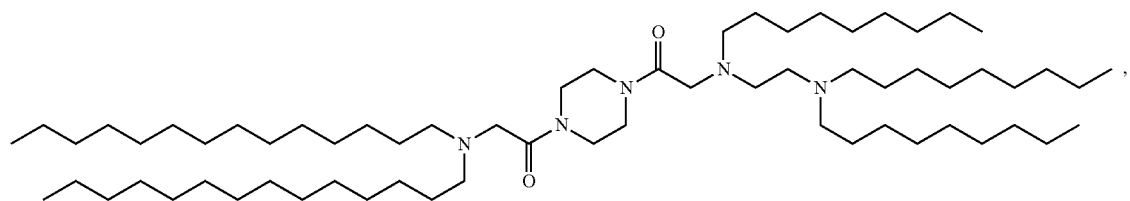
(Compound 283)
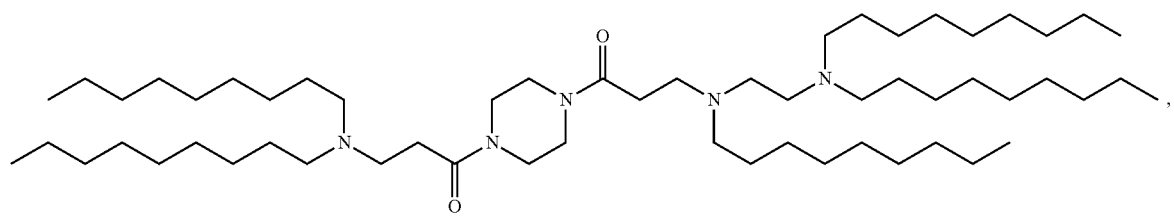
(Compound 284)
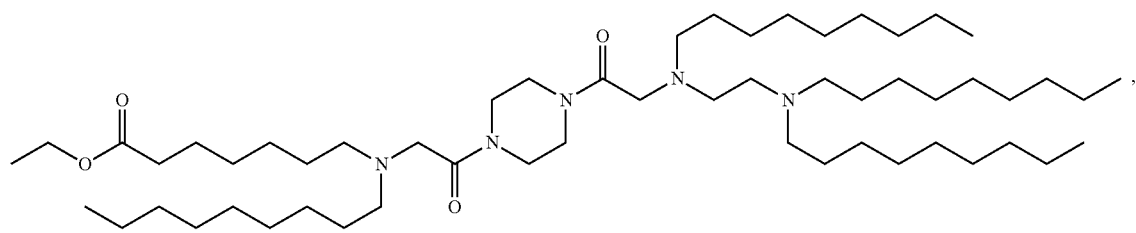
(Compound 285)
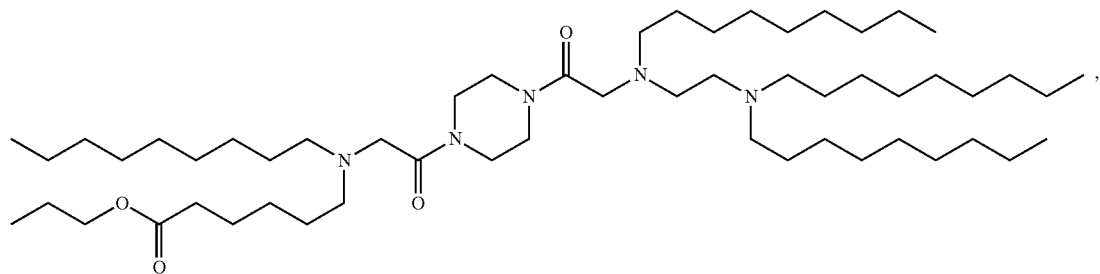
(Compound 286)
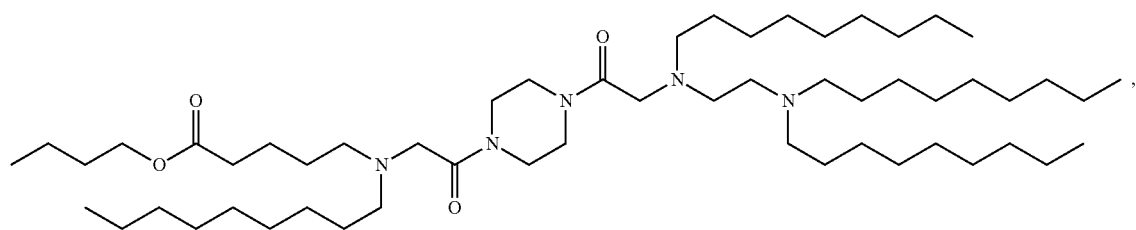
(Compound 287)

(Compound 288)
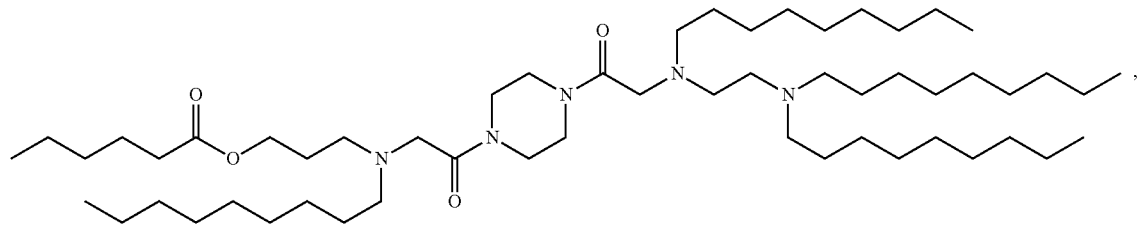
(Compound 289)
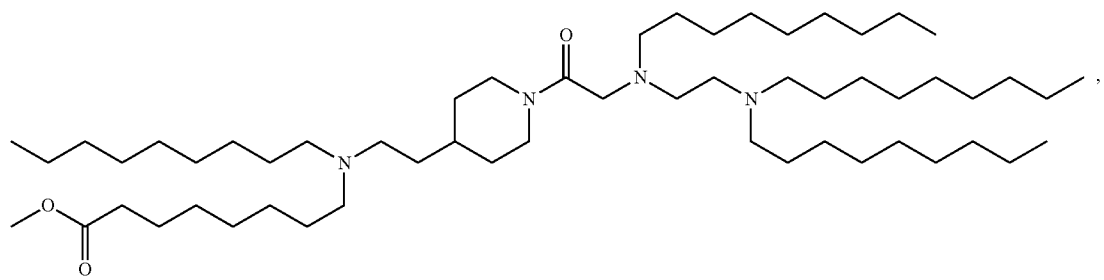
(Compound 290)
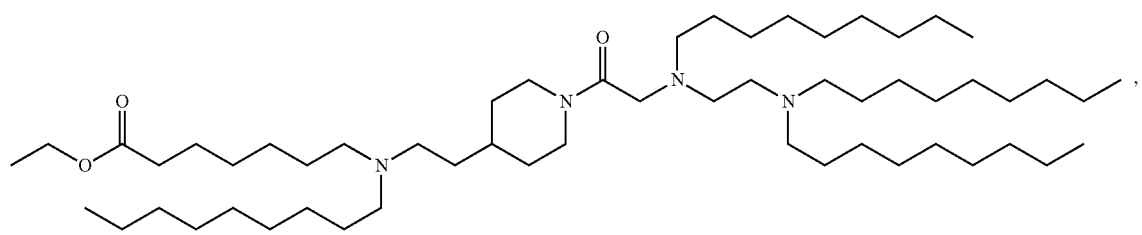
(Compound 291)
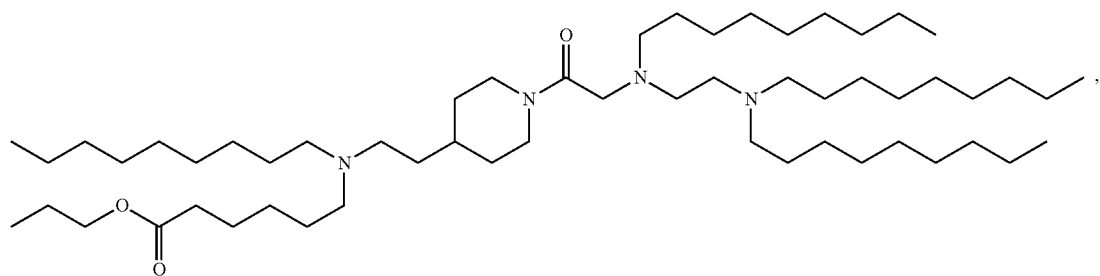
(Compound 292)
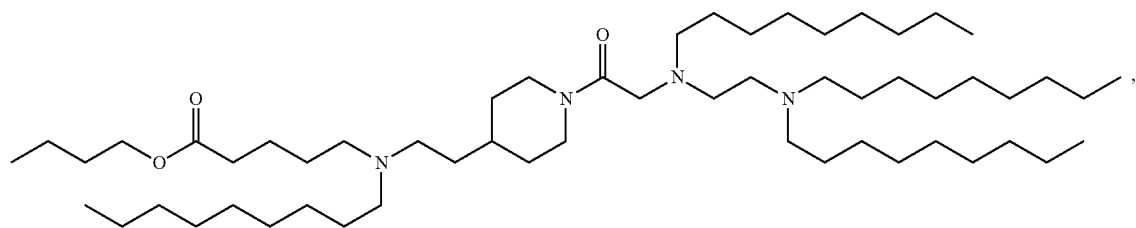
(Compound 293)
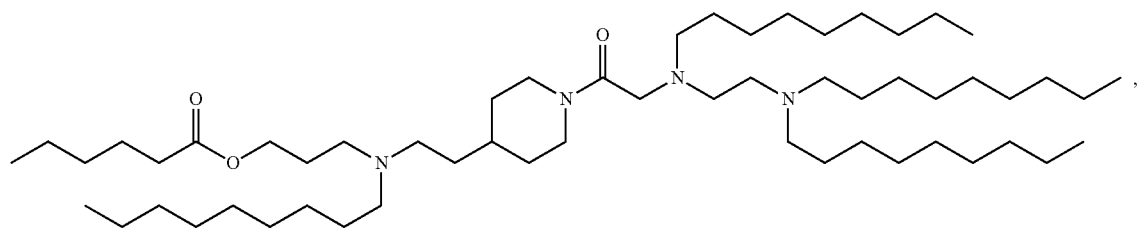

(Compound 294)
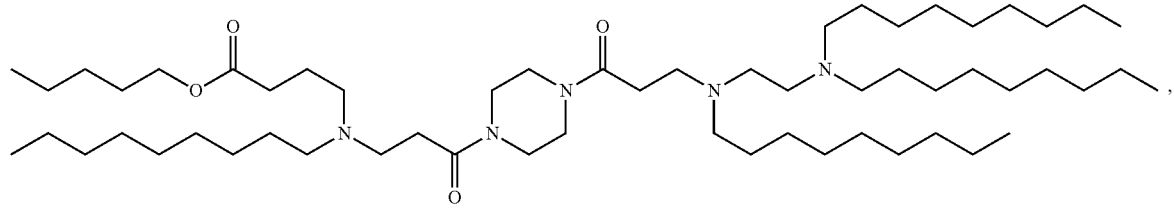
(Compound 295)
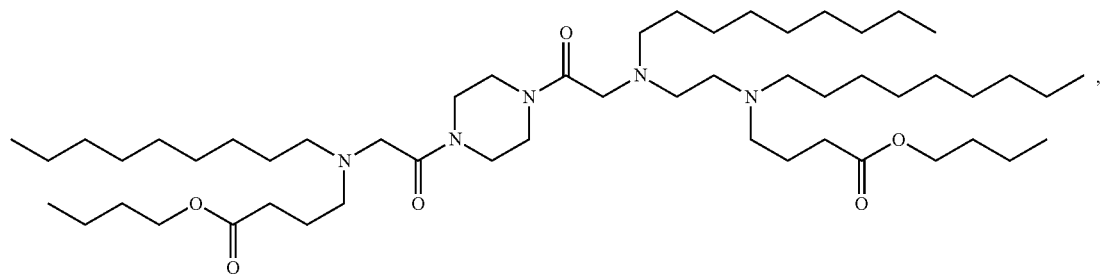
(Compound 296)
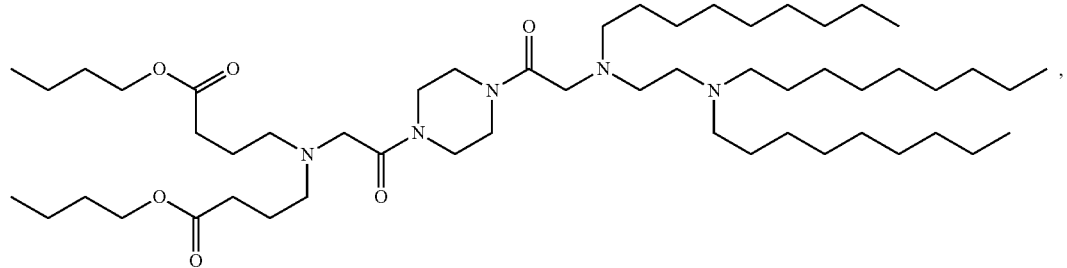
(Compound 297)
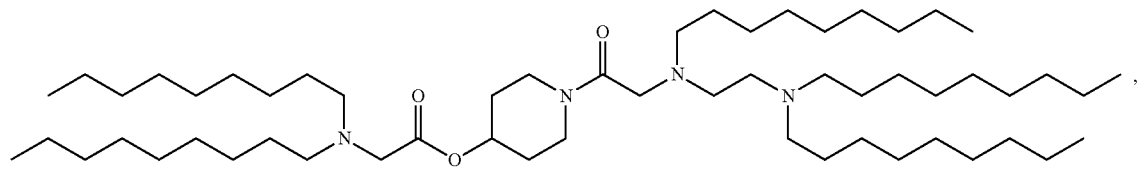
(Compound 298)
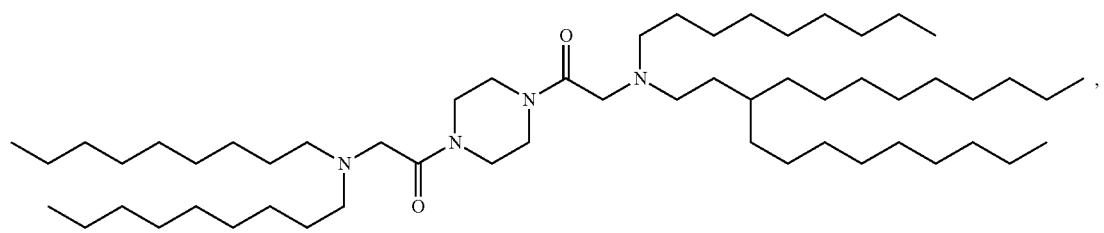
(Compound 300)
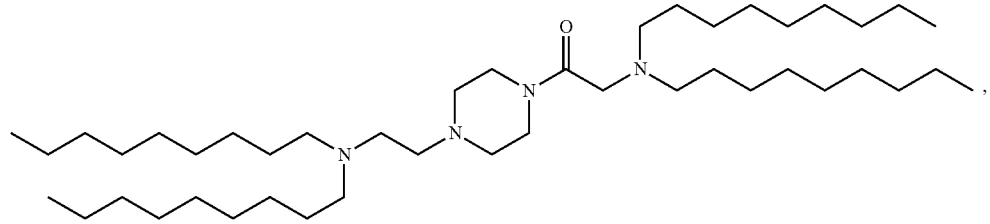

-continued
(Compound 301)
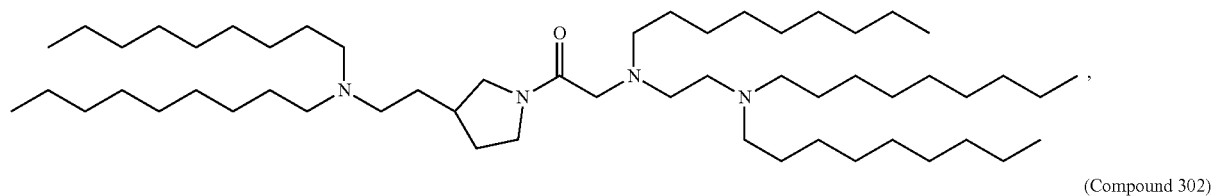
(Compound 302)
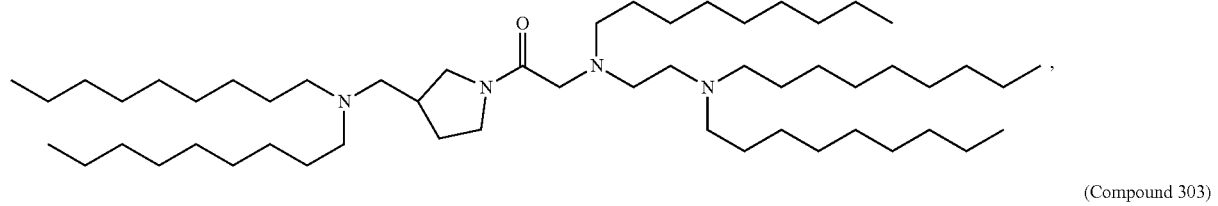
(Compound 303)
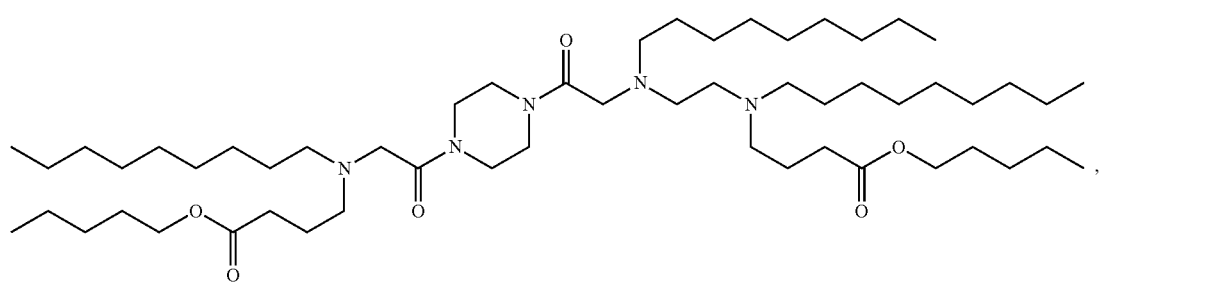
(Compound 304)
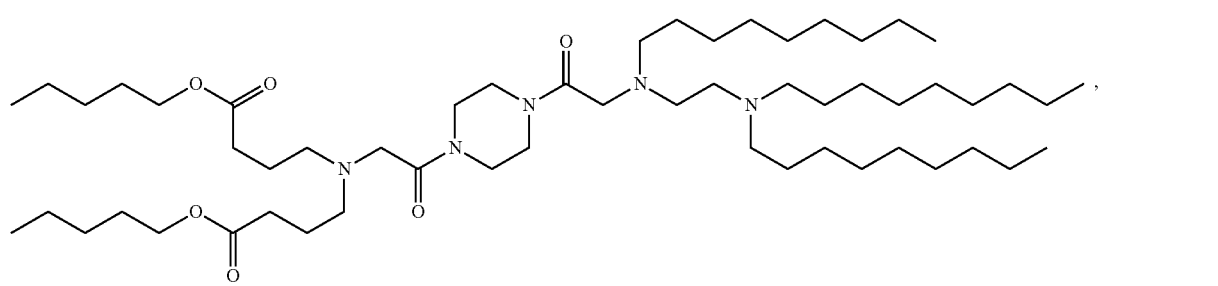
(Compound 305)
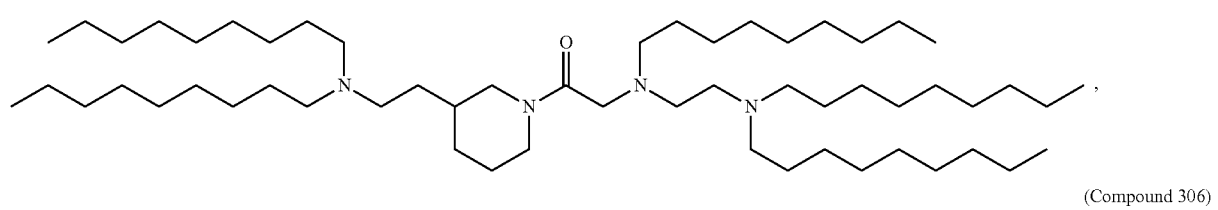
(Compound 306)
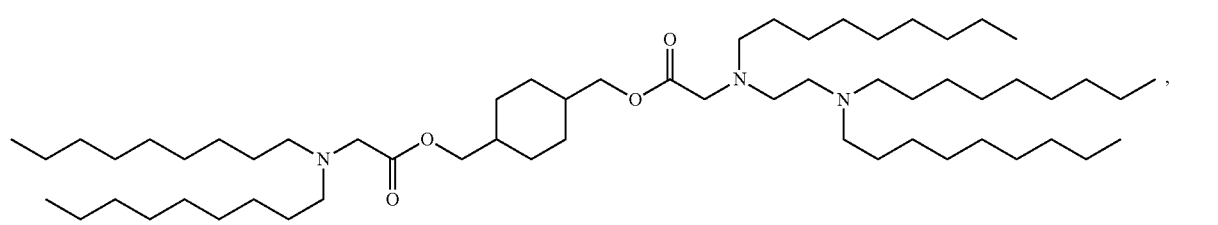
(Compound 307)
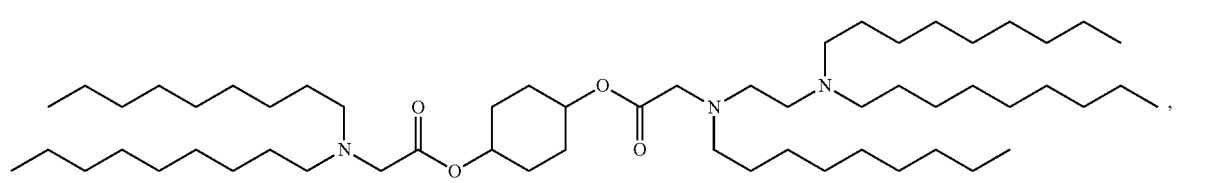

-continued
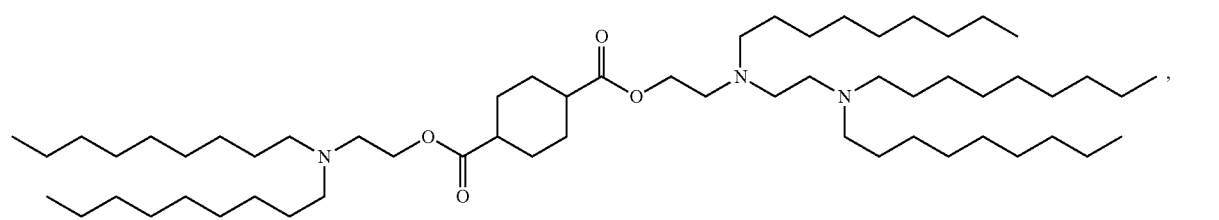
(Compound 308)
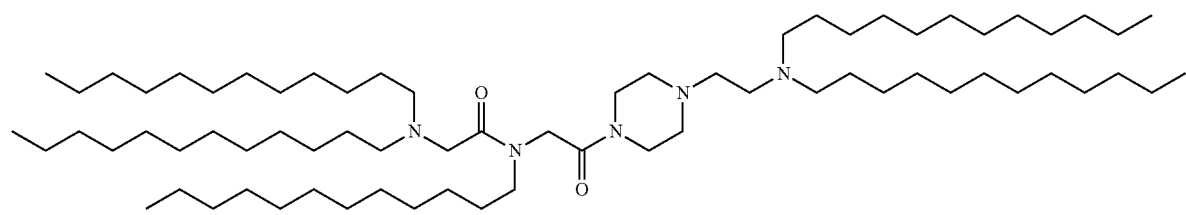
(Compound 310)
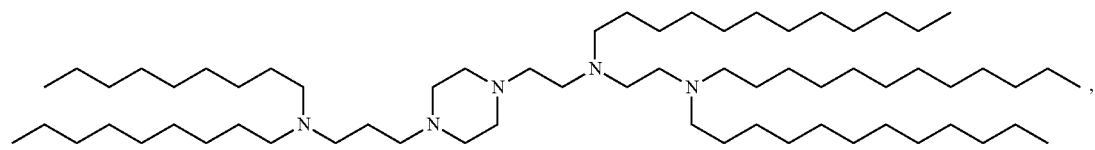
(Compound 311)
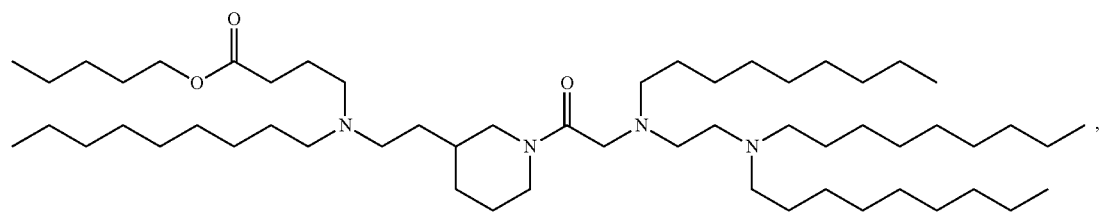
(Compound 312)
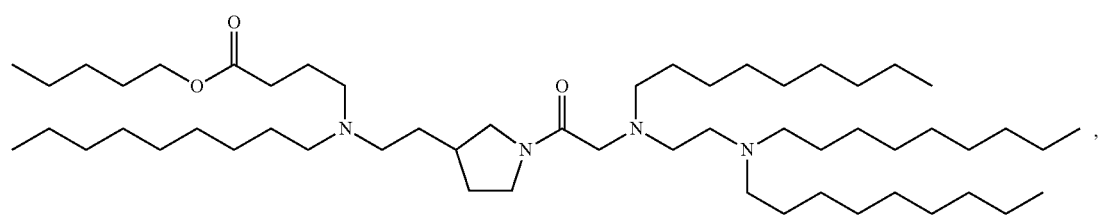
(Compound 313)
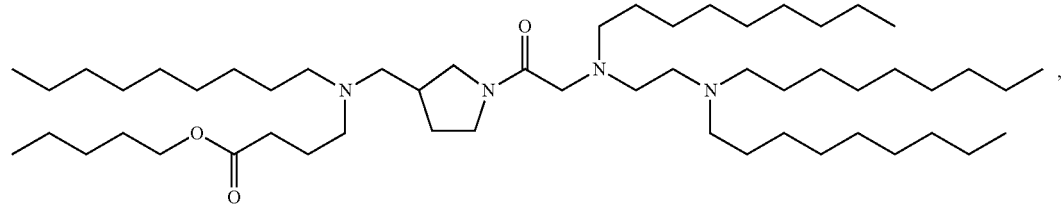
(Compound 314)
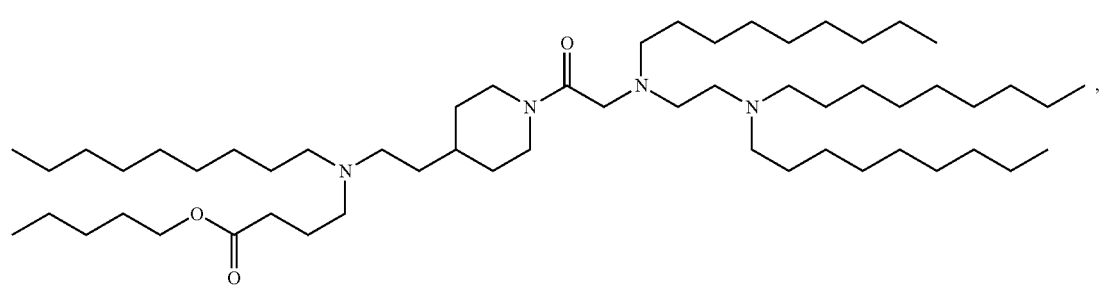
(Compound 315)

(Compound 316)
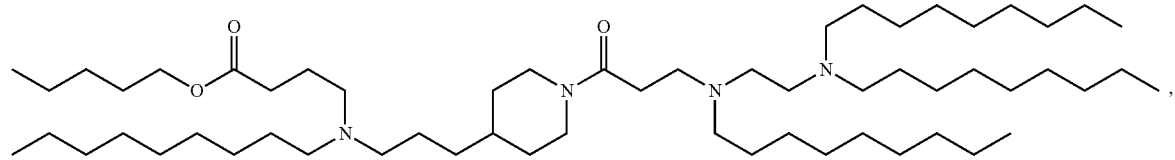
(Compound 317)
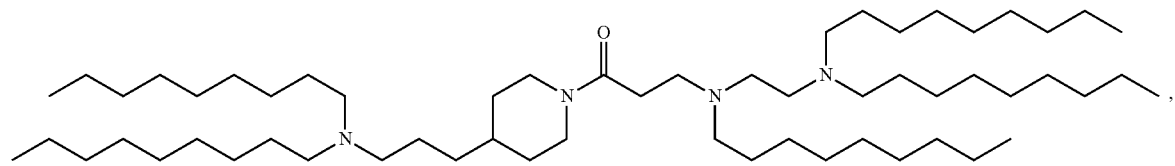
(Compound 318)
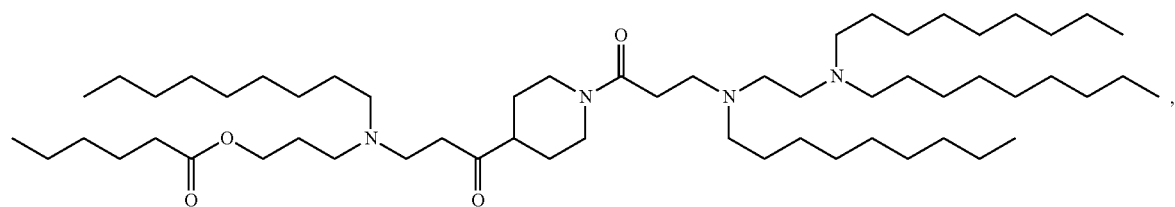
(Compound 319)
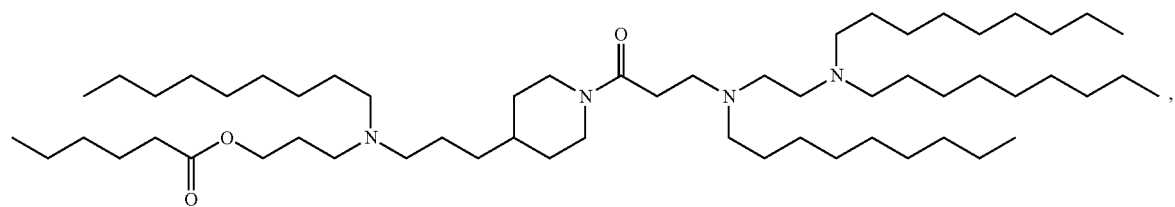
(Compound 320)
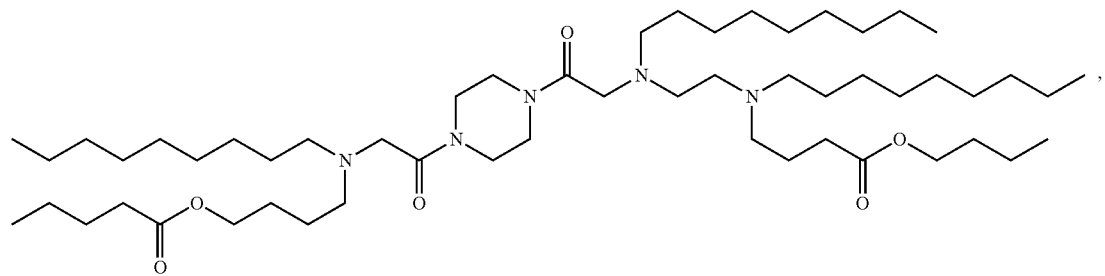
(Compound 321)
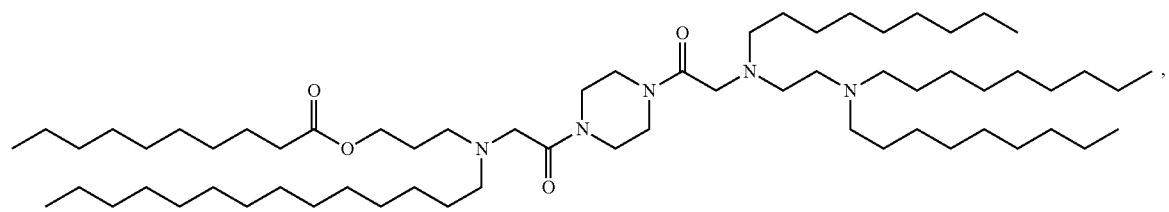

(Compound 322)
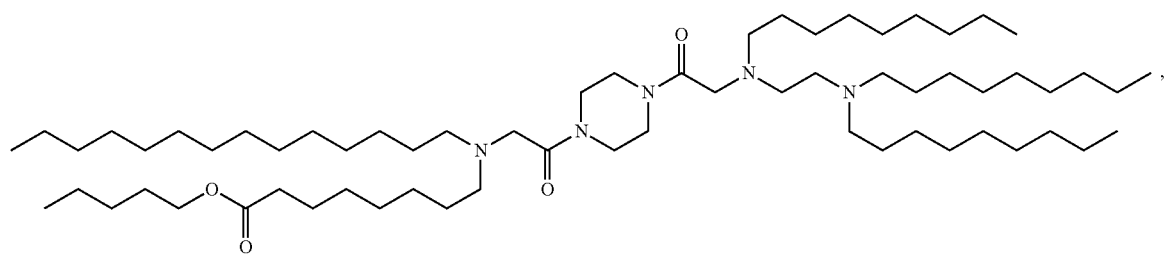
(Compound 323)
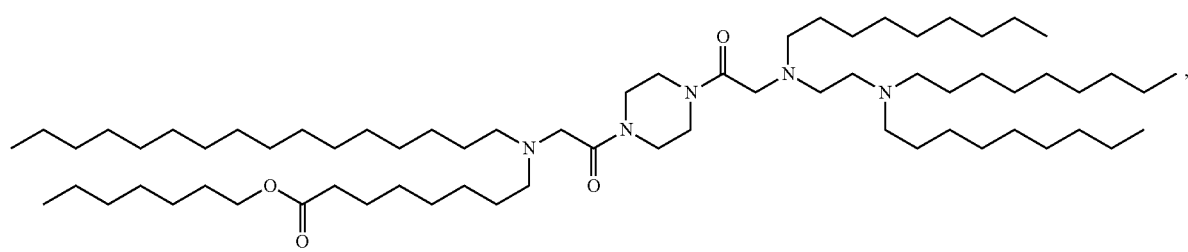
(Compound 324)
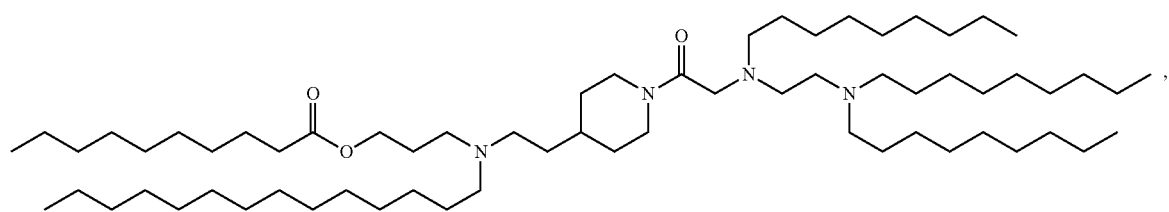
(Compound 325)
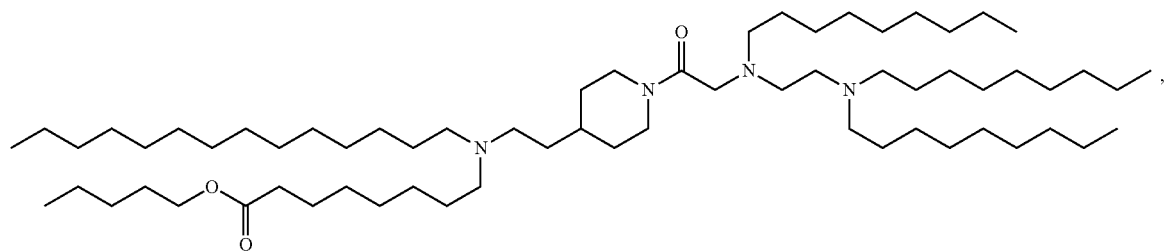
(Compound 326)
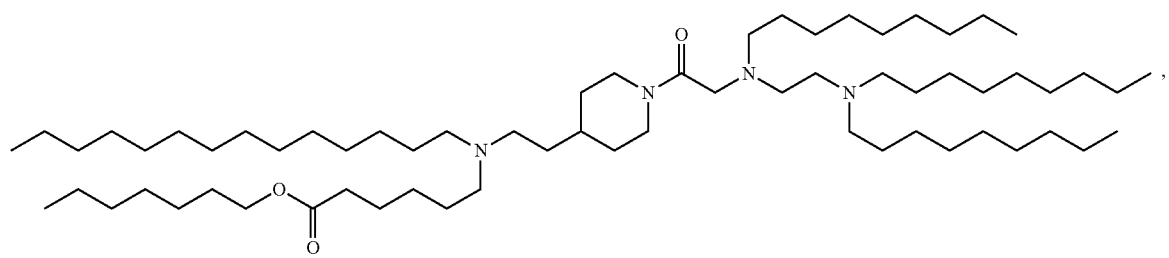
(Compound 327)
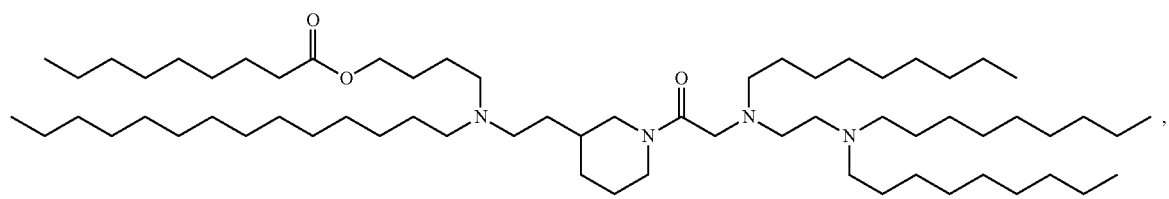

-continued
(Compound 328)
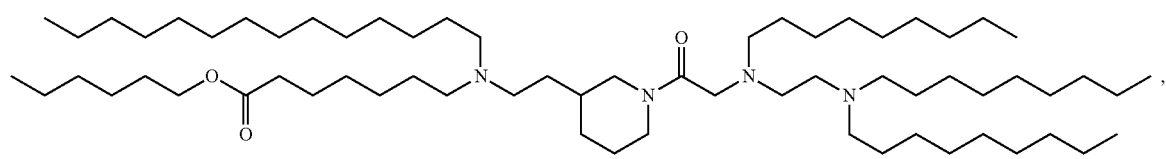
(Compound 329)
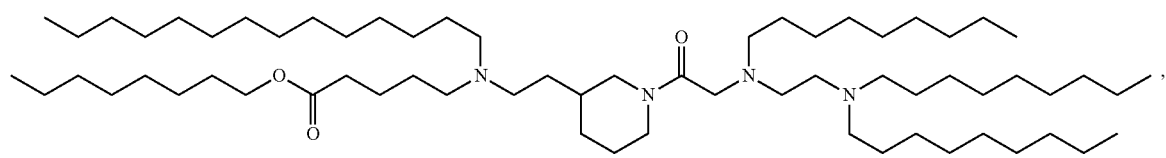
(Compound 330)
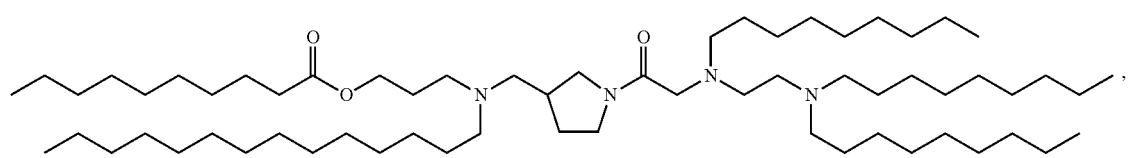
(Compound 331)
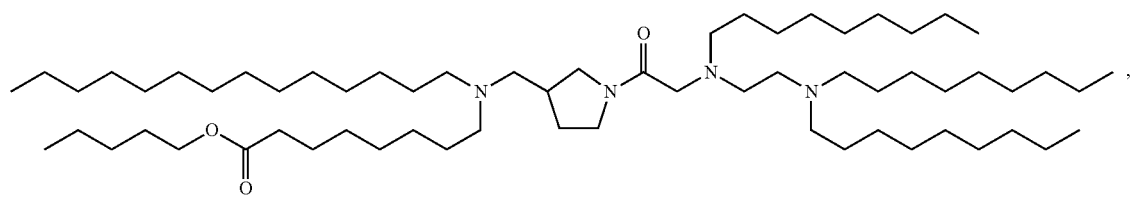
(Compound 332)
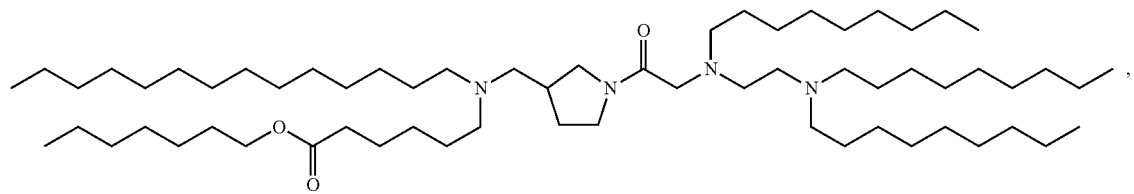
(Compound 333)
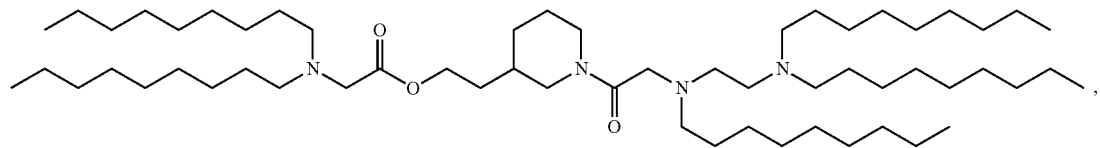
(Compound 334)
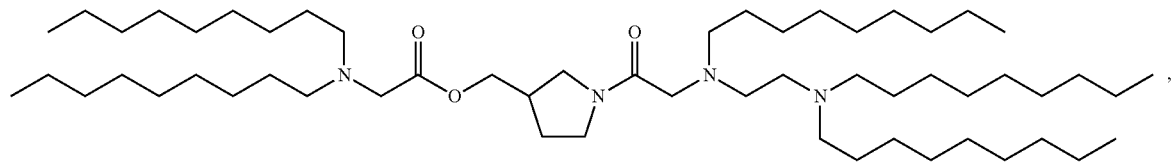
(Compound 335)
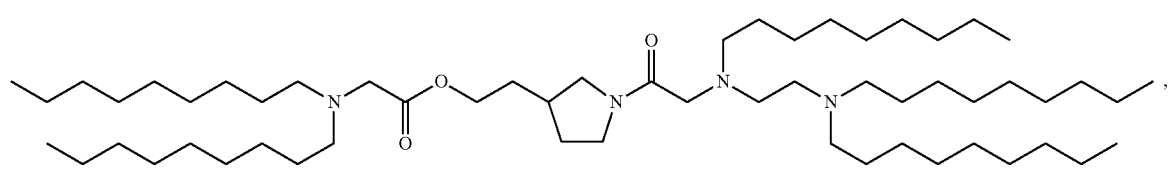

(Compound 336)
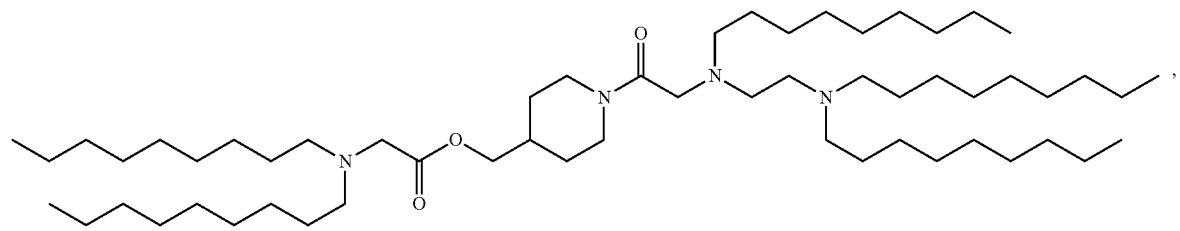
(Compound 337)
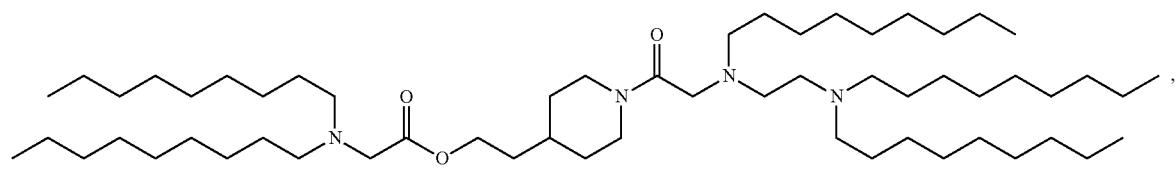
(Compound 338)
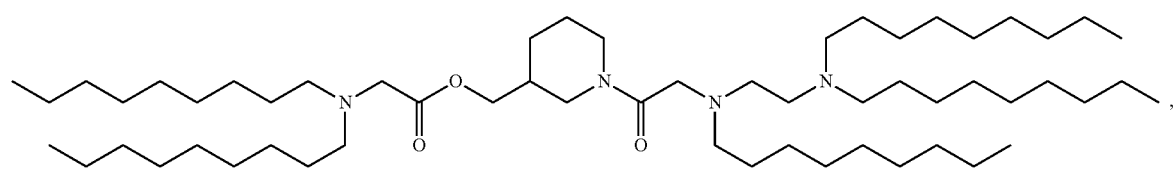
(Compound 339)
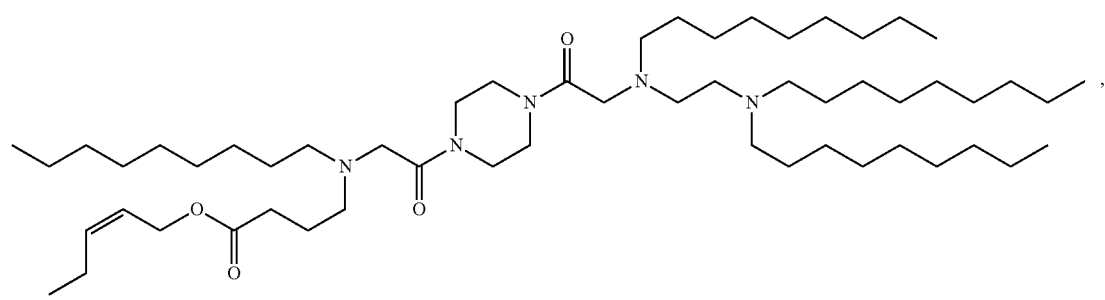
(Compound 340)
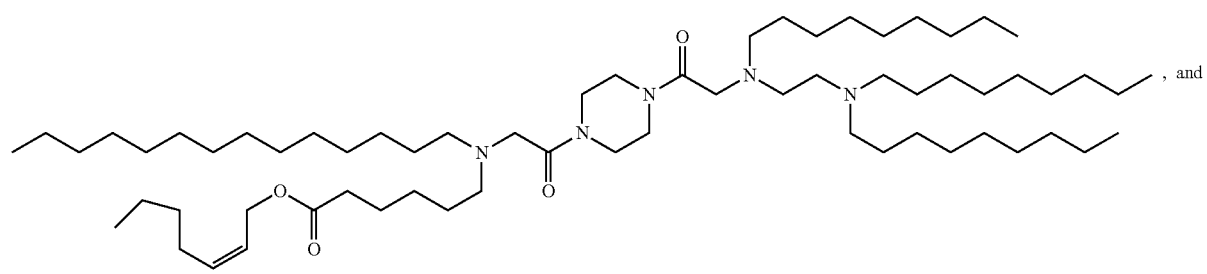, and
(Compound 341)
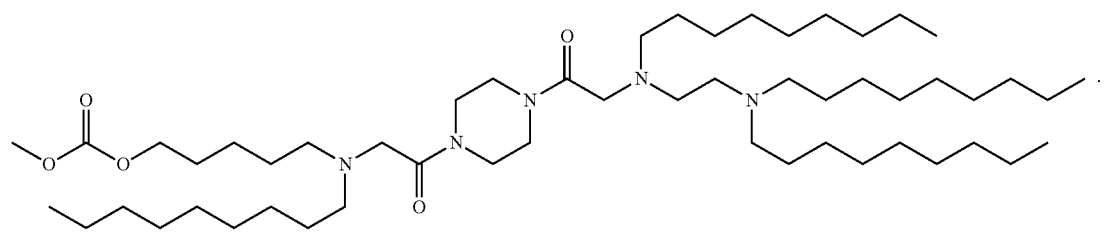

In some embodiments, the delivery agent comprises Compound 236. In another embodiment, the PEG lipid is Compound 428.

In some embodiments, the delivery agent comprises a compound having the Formula (IV)

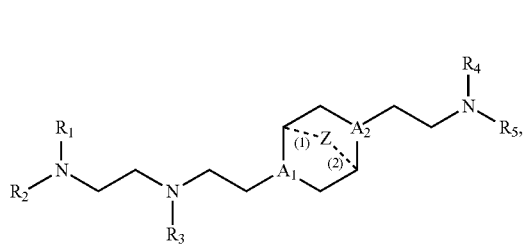

(IV)

or salts or stereoisomer thereof, wherein $A_1$ and $A_2$ are each independently selected from CH or N and at least one of $A_1$ and $A_2$ is N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{6-20}$ alkyl and $C_{6-20}$ alkenyl;

wherein when ring A is

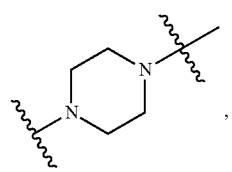 [SMILES: *N1CCN(*)CC1]

then i) $R_1$, $R_2$, $R_3$, $R_4$, and $R_5$ are the same, wherein $R_1$ is not $C_{12}$ alkyl, $C_{18}$ alkyl, or $C_{18}$ alkenyl;

ii) only one of $R_1$, $R_2$, $R_3$, $R_4$, and $R_5$ is selected from $C_{6-20}$ alkenyl;

iii) at least one of $R_1$, $R_2$, $R_3$, $R_4$, and $R_5$ have a different number of carbon atoms than at least one other of $R_1$, $R_2$, $R_3$, $R_4$, and $R_5$;

iv) $R_1$, $R_2$, and $R_3$ are selected from $C_{6-20}$ alkenyl, and $R_4$ and $R_5$ are selected from $C_{6-20}$ alkyl; or v) $R_1$, $R_2$, and $R_3$ are selected from $C_{6-20}$ alkyl, and $R_4$ and $R_5$ are selected from $C_{6-20}$ alkenyl.

In some embodiments, the compound is of Formula (IVa):

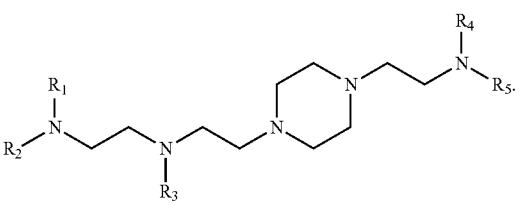

(IVa)

The compounds of Formula (IV) or (IVa) include one or more of the following features when applicable.

In some embodiments, Z is $CH_2$.

In some embodiments, Z is absent.

In some embodiments, at least one of $A_1$ and $A_2$ is N.

In some embodiments, each of $A_1$ and $A_2$ is N.

In some embodiments, each of $A_1$ and $A_2$ is CH.

In some embodiments, $A_1$ is N and $A_2$ is CH.

In some embodiments, $A_1$ is CH and $A_2$ is N.

In some embodiments, $R_1$, $R_2$, $R_3$, $R_4$, and $R_5$ are the same, and are not $C_{12}$ alkyl, $C_{18}$ alkyl, or $C_{18}$ alkenyl. In some embodiments, $R_1$, $R_2$, $R_3$, $R_4$, and $R_5$ are the same and are $C_9$ alkyl or $C_{14}$ alkyl.

In some embodiments, only one of $R_1$, $R_2$, $R_3$, $R_4$, and $R_5$ is selected from $C_{6-20}$ alkenyl. In certain such embodiments, $R_1$, $R_2$, $R_3$, $R_4$, and $R_5$ have the same number of carbon atoms. In some embodiments, $R_4$ is selected from $C_{5-20}$ alkenyl. For example, $R_4$ may be $C_{12}$ alkenyl or $C_{18}$ alkenyl.

In some embodiments, at least one of $R_1$, $R_2$, $R_3$, $R_4$, and $R_5$ have a different number of carbon atoms than at least one other of $R_1$, $R_2$, $R_3$, $R_4$, and $R_5$.

In certain embodiments, $R_1$, $R_2$, and $R_3$ are selected from $C_{6-20}$ alkenyl, and $R_4$ and $R_5$ are selected from $C_{6-20}$ alkyl. In other embodiments, $R_1$, $R_2$, and $R_3$ are selected from $C_{6-20}$ alkyl, and $R_4$ and $R_5$ are selected from $C_{6-20}$ alkenyl.

In some embodiments, $R_1$, $R_2$, and $R_3$ have the same number of carbon atoms, and/or $R_4$ and $R_5$ have the same number of carbon atoms. For example, $R_1$, $R_2$, and $R_3$, or $R_4$ and $R_5$, may have 6, 8, 9, 12, 14, or 18 carbon atoms. In some embodiments, $R_1$, $R_2$, and $R_3$, or $R_4$ and $R_5$, are $C_{18}$ alkenyl (e.g., linoleyl). In some embodiments, $R_1$, $R_2$, and $R_3$, or $R_4$ and $R_5$, are alkyl groups including 6, 8, 9, 12, or 14 carbon atoms.

In some embodiments, $R_1$ has a different number of carbon atoms than $R_2$, $R_3$, $R_4$, and $R_5$. In other embodiments, $R_3$ has a different number of carbon atoms than $R_1$, $R_2$, $R_4$, and $R_5$. In further embodiments, $R_4$ has a different number of carbon atoms than $R_1$, $R_2$, $R_3$, and $R_5$.

In some embodiments, the compound is selected from the group consisting of:

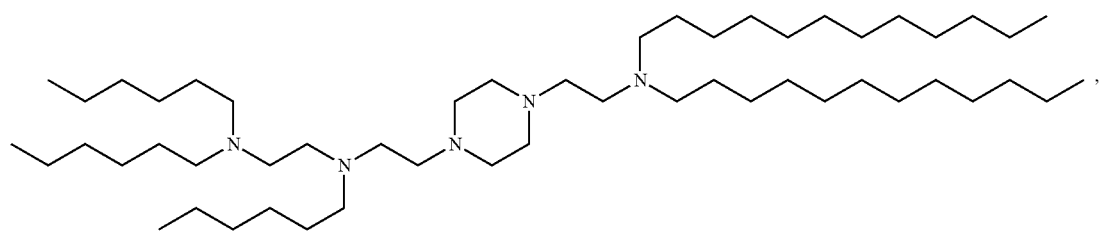

(Compound 249)

-continued
(Compound 250)
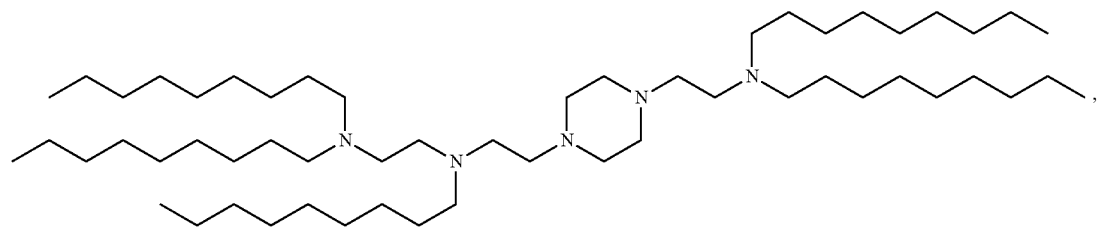
(Compound 251)
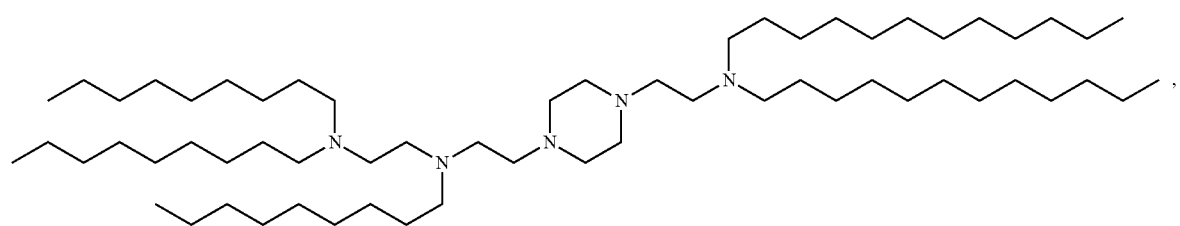
(Compound 252)
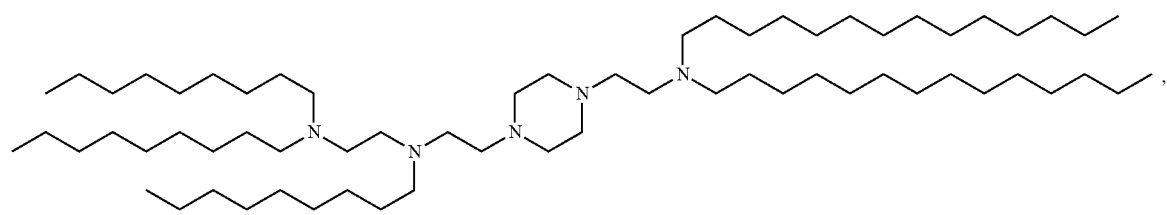
(Compound 253)
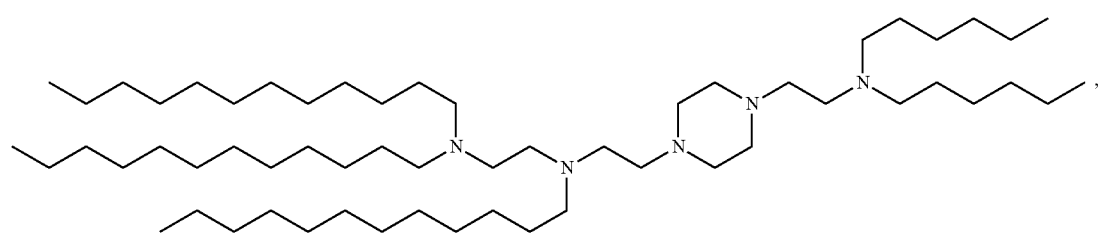
(Compound 254)
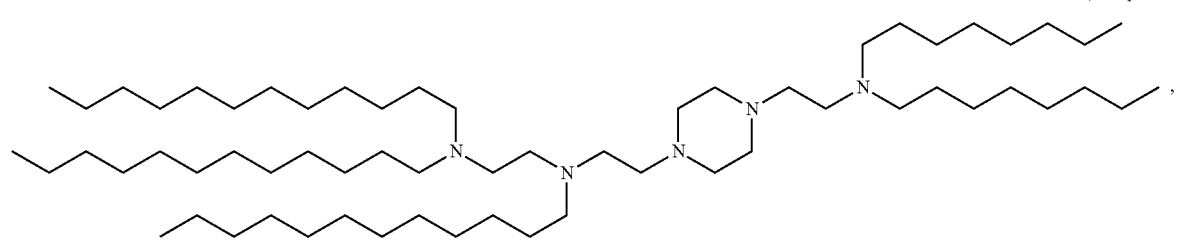
(Compound 255)
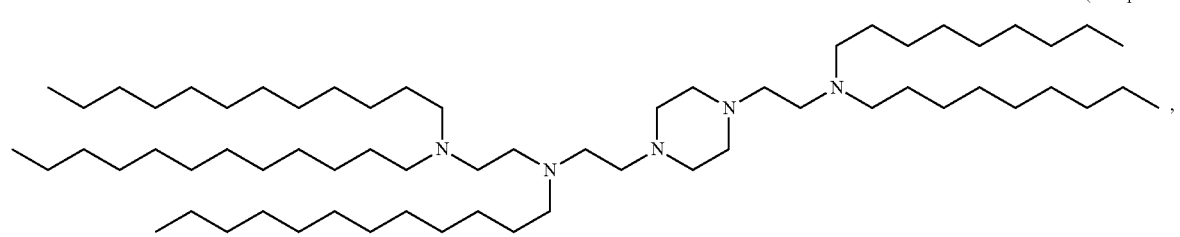

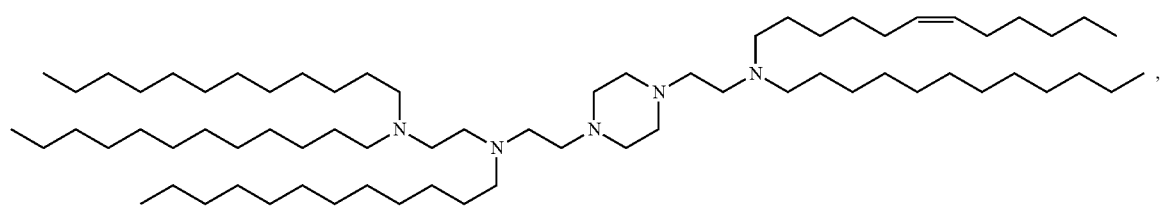
(Compound 256)
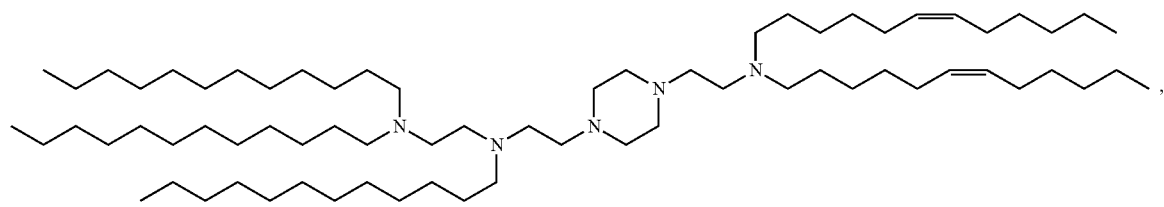
(Compound 257)
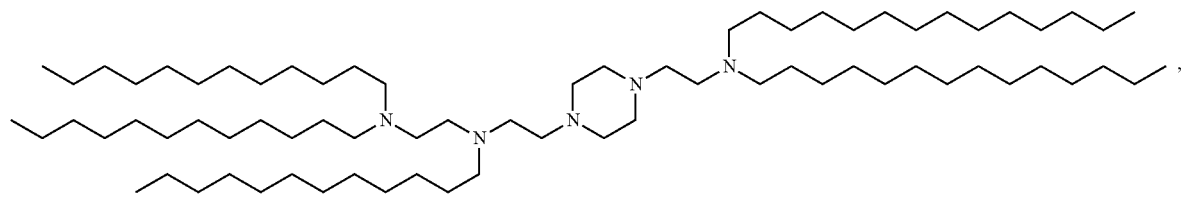
(Compound 258)
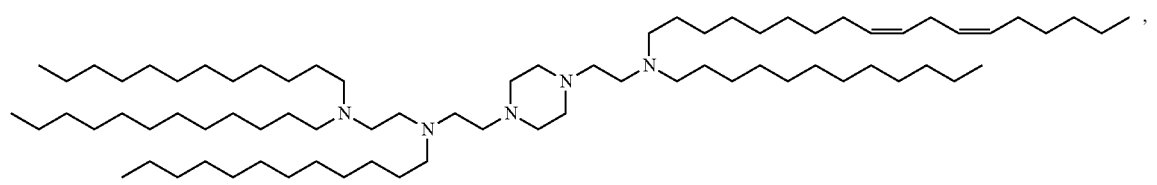
(Compound 259)
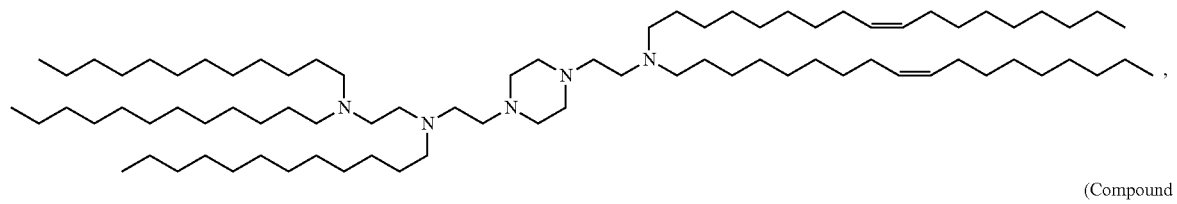
(Compound 260)
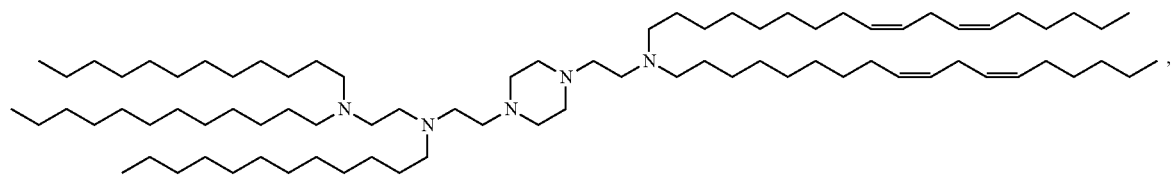
(Compound 261)
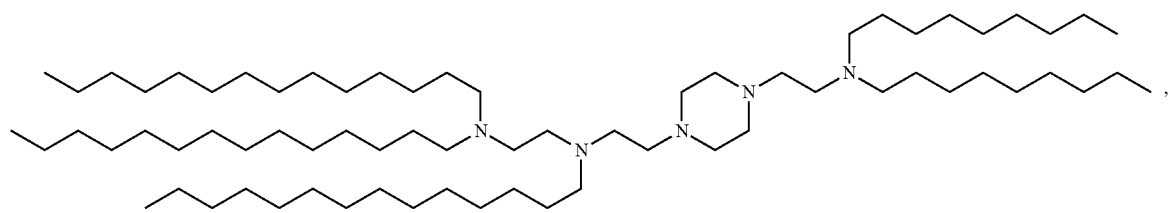
(Compound 262)

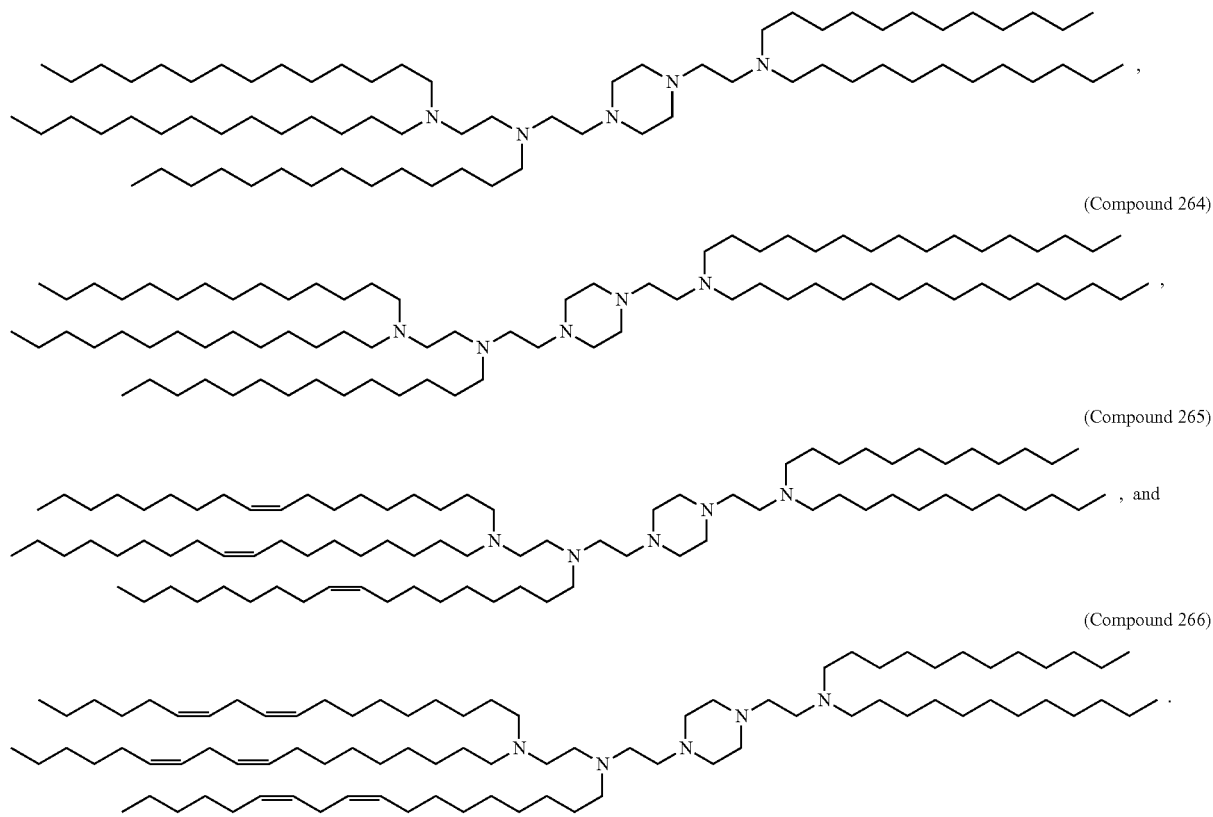

(Compound 263)

(Compound 264)

(Compound 265)

(Compound 266)

In other embodiments, the delivery agent comprises a compound having the Formula (V)

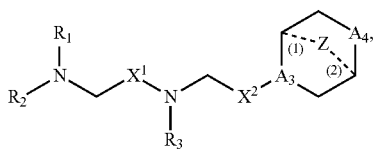

(V)

or salts or stereoisomers thereof, in which
$A_3$ is CH or N;
$A_4$ is $CH_2$ or NH; and at least one of $A_3$ and $A_4$ is N or NH;
Z is $CH_2$ or absent wherein when Z is $CH_2$, the dashed lines (1) and (2) each represent a single bond; and when Z is absent, the dashed lines (1) and (2) are both absent;
$R_1$, $R_2$, and $R_3$ are independently selected from the group consisting of $C_{5-20}$ alkyl, $C_{5-20}$ alkenyl, —R"MR', —R*YR", —YR", and —R*OR";
each M is independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;
$X^1$ and $X^2$ are independently selected from the group consisting of —CH$_2$—, —(CH$_2$)$_2$—, —CHR—, —CHY—, —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, —CH$_2$—OC(O)—, —CH(OH)—, —C(S)—, and —CH(SH)—;

each Y is independently a $C_{3-6}$ carbocycle;
each R* is independently selected from the group consisting of $C_{1-12}$ alkyl and $C_{2-12}$ alkenyl;
each R is independently selected from the group consisting of $C_{1-3}$ alkyl and a $C_{3-6}$ carbocycle;
each R' is independently selected from the group consisting of $C_{1-12}$ alkyl, $C_{2-12}$ alkenyl, and H; and
each R" is independently selected from the group consisting of $C_{3-12}$ alkyl and $C_{3-12}$ alkenyl.

In some embodiments, the compound is of Formula (Va):

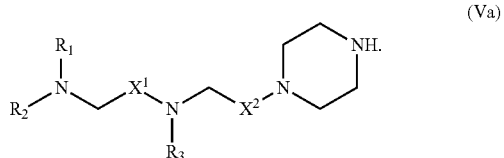

(Va)

The compounds of Formula (V) or (Va) include one or more of the following features when applicable.

In some embodiments, Z is $CH_2$.
In some embodiments, Z is absent.
In some embodiments, at least one of $A_3$ and $A_4$ is N or NH.
In some embodiments, $A_3$ is N and $A_4$ is NH.
In some embodiments, $A_3$ is N and $A_4$ is $CH_2$.
In some embodiments, $A_3$ is CH and $A_4$ is NH.
In some embodiments, at least one of $X^1$ and $X^2$ is not —CH$_2$—. For example, in certain embodiments, $X^1$ is not —CH$_2$—. In some embodiments, at least one of $X^1$ and $X^2$ is —C(O)—.

In some embodiments, $X^2$ is —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, or —CH$_2$—OC(O)—.

In some embodiments, $R_1$, $R_2$, and $R_3$ are independently selected from the group consisting of $C_{5-20}$ alkyl and $C_{5-20}$ alkenyl. In some embodiments, $R_1$, $R_2$, and $R_3$ are the same. In certain embodiments, $R_1$, $R_2$, and $R_3$ are $C_6$, $C_9$, $C_{12}$, or $C_{14}$ alkyl. In other embodiments, $R_1$, $R_2$, and $R_3$ are $C_{18}$ alkenyl. For example, $R_1$, $R_2$, and $R_3$ may be linoleyl.

In some embodiments, the compound is selected from the group consisting of:

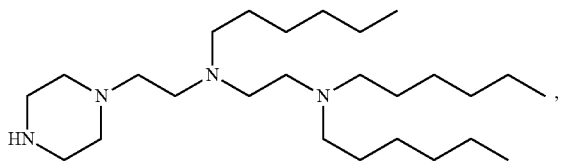

(Compound 267)

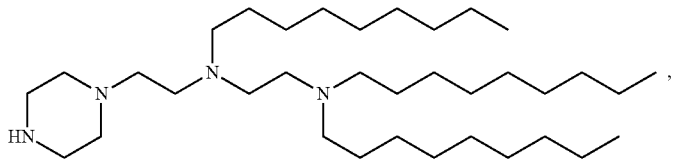

(Compound 268)

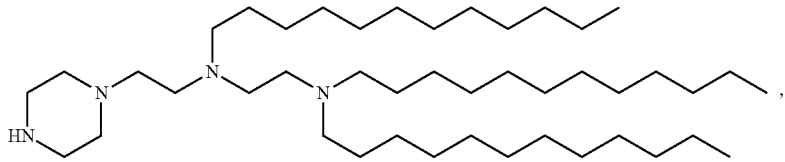

(Compound 269)

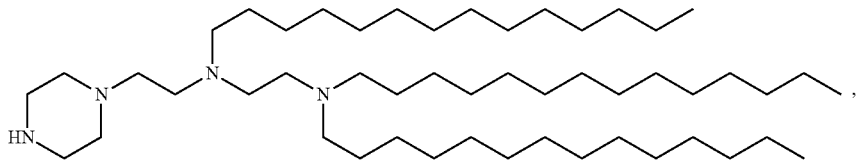

(Compound 270)

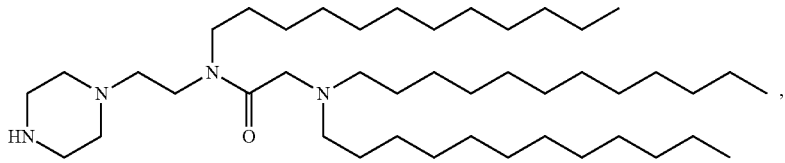

(Compound 271)

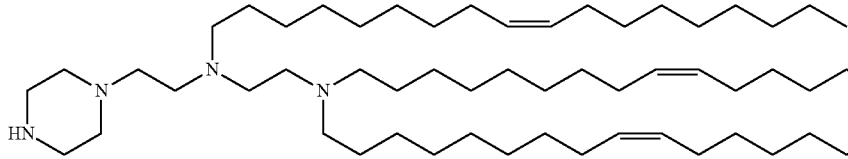

(Compound 272)

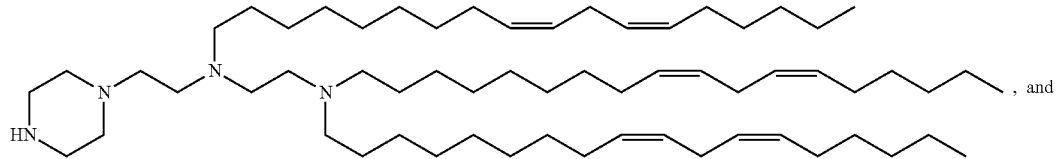

(Compound 273)

, and

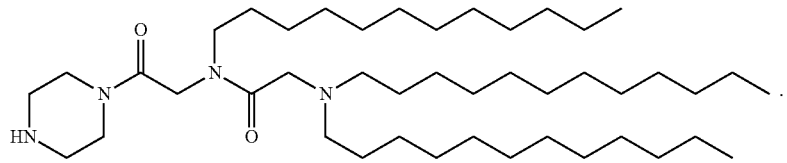

(Compound 309)

.

In other embodiments, the delivery agent comprises a compound having the Formula (VI):

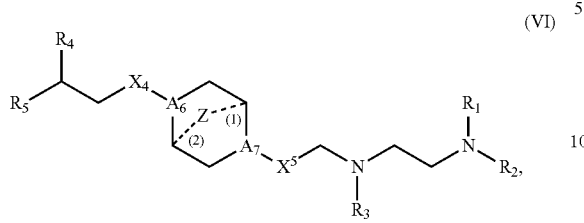

(VI)

or salts or stereoisomers thereof, in which $A_6$ and $A_7$ are each independently selected from CH or N, wherein at least one of $A_6$ and $A_7$ is N;

Z is $CH_2$ or absent wherein when Z is $CH_2$, the dashed lines (1) and (2) each represent a single bond; and when Z is absent, the dashed lines (1) and (2) are both absent;

$X^4$ and $X^5$ are independently selected from the group consisting of —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;

$R_1$, $R_2$, $R_3$, $R_4$, and $R_5$ each are independently selected from the group consisting of $C_{5-20}$ alkyl, $C_{5-20}$ alkenyl, —R"MR', —R*YR", —YR", and —R*OR";

each M is independently selected from the group consisting of —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl.

In some embodiments, $R_1$, $R_2$, $R_3$, $R_4$, and $R_5$ each are independently selected from the group consisting of $C_{6-20}$ alkyl and $C_{6-20}$ alkenyl.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is $C_{9-12}$ alkyl. In certain embodiments, each of $R_1$, $R_2$, $R_3$, $R_4$, and $R_5$ independently is $C_9$, $C_{12}$ or $C_{14}$ alkyl. In certain embodiments, each of $R_1$, $R_2$, $R_3$, $R_4$, and $R_5$ is $C_9$ alkyl.

In some embodiments, $A_6$ is N and $A_7$ is N. In some embodiments, $A_6$ is CH and $A_7$ is N.

In some embodiments, $X^4$ is —$CH_2$— and $X^5$ is —C(O)—. In some embodiments, $X^4$ and $X^5$ are —C(O)—.

In some embodiments, when $A_6$ is N and $A_7$ is N, at least one of $X^4$ and $X^5$ is not —$CH_2$—, e.g., at least one of $X^4$ and $X^5$ is —C(O)—. In some embodiments, when $A_6$ is N and $A_7$ is N, at least one of $R_1$, $R_2$, $R_3$, $R_4$, and $R_5$ is —R"MR'.

In some embodiments, at least one of $R_1$, $R_2$, $R_3$, $R_4$, and $R_5$ is not —R"MR'.

In some embodiments, the compound is (Compound 299)

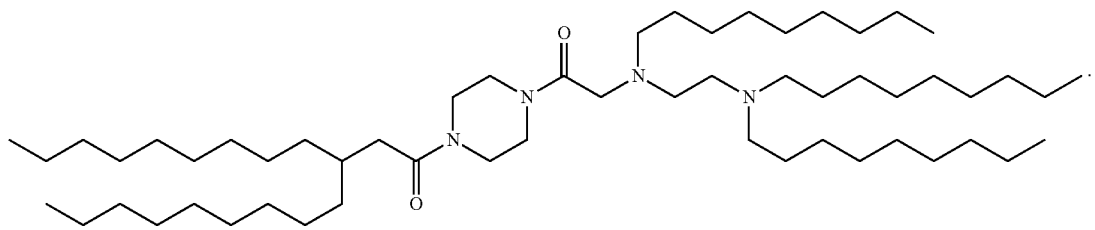

In other embodiments, the delivery agent comprises a compound having the Formula:

(Compound 342)

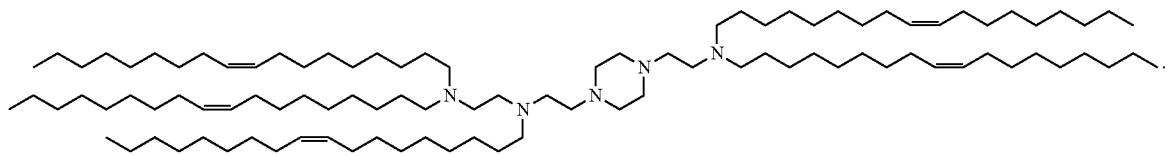

Amine moieties of the lipid compounds disclosed herein can be protonated under certain conditions. For example, the central amine moiety of a lipid according to Formula (I) is typically protonated (i.e., positively charged) at a pH below the pKa of the amino moiety and is substantially not charged at a pH above the pKa. Such lipids can be referred to as ionizable amino lipids.

In one specific embodiment, ionizable amino lipid is Compound 18. In another embodiment, the ionizable amino lipid is Compound 236.

In some embodiments, the amount the ionizable amino lipid, e.g., compound of Formula (I), ranges from about 1 mol % to 99 mol % in the lipid composition.

In one embodiment, the amount of the ionizable amino lipid, e.g., compound of Formula (I), is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 mol % in the lipid composition.

In one embodiment, the amount of the ionizable amino lipid, e.g., the compound of Formula (I), ranges from about 30 mol % to about 70 mol %, from about 35 mol % to about 65 mol %, from about 40 mol % to about 60 mol %, and from about 45 mol % to about 55 mol % in the lipid composition.

In one specific embodiment, the amount of the ionizable amino lipid, e.g., the compound of Formula (I), is about 50 mol % in the lipid composition.

In addition to the ionizable amino lipid disclosed herein, e.g., compound of Formula (I), the lipid composition of the pharmaceutical compositions disclosed herein can comprise additional components such as phospholipids, structural lipids, PEG-lipids, and any combination thereof.

b. Additional Components in the Lipid Composition (i) Phospholipids

The lipid composition of the pharmaceutical composition disclosed herein can comprise one or more phospholipids, for example, one or more saturated or (poly)unsaturated phospholipids or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

Examples of phospholipids include, but are not limited to, the following:

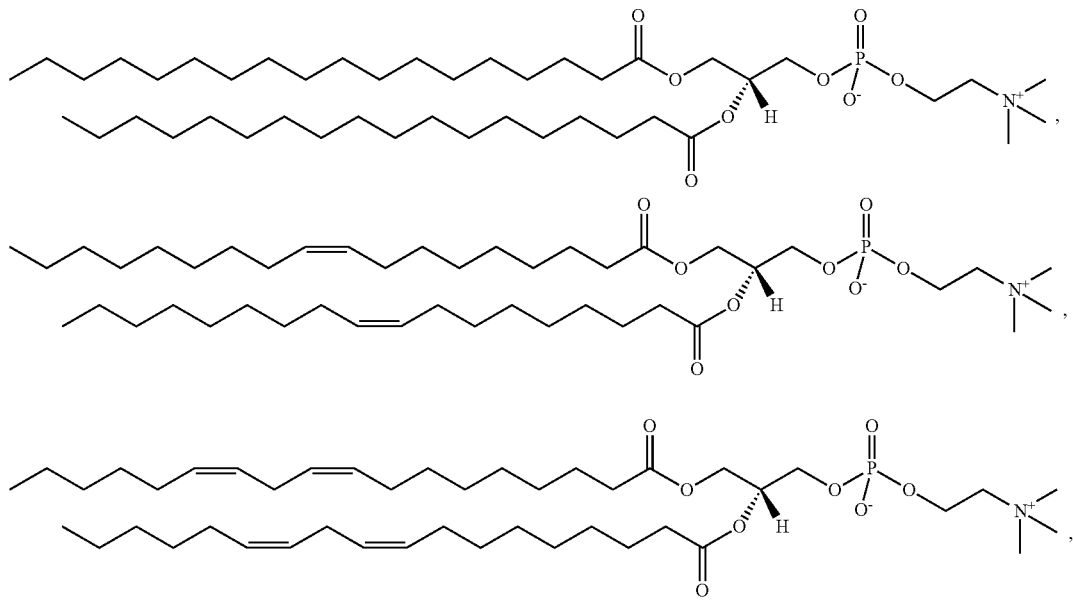

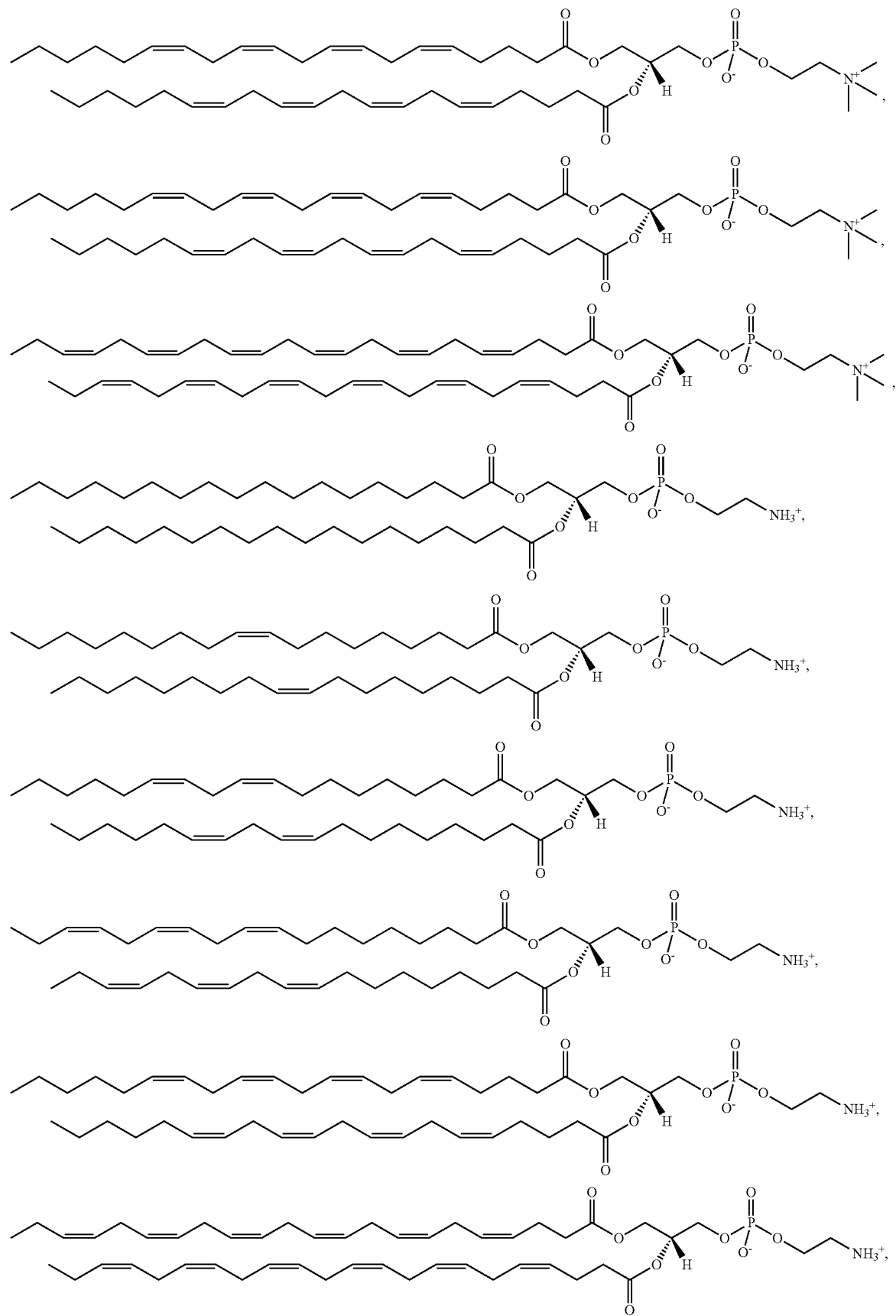

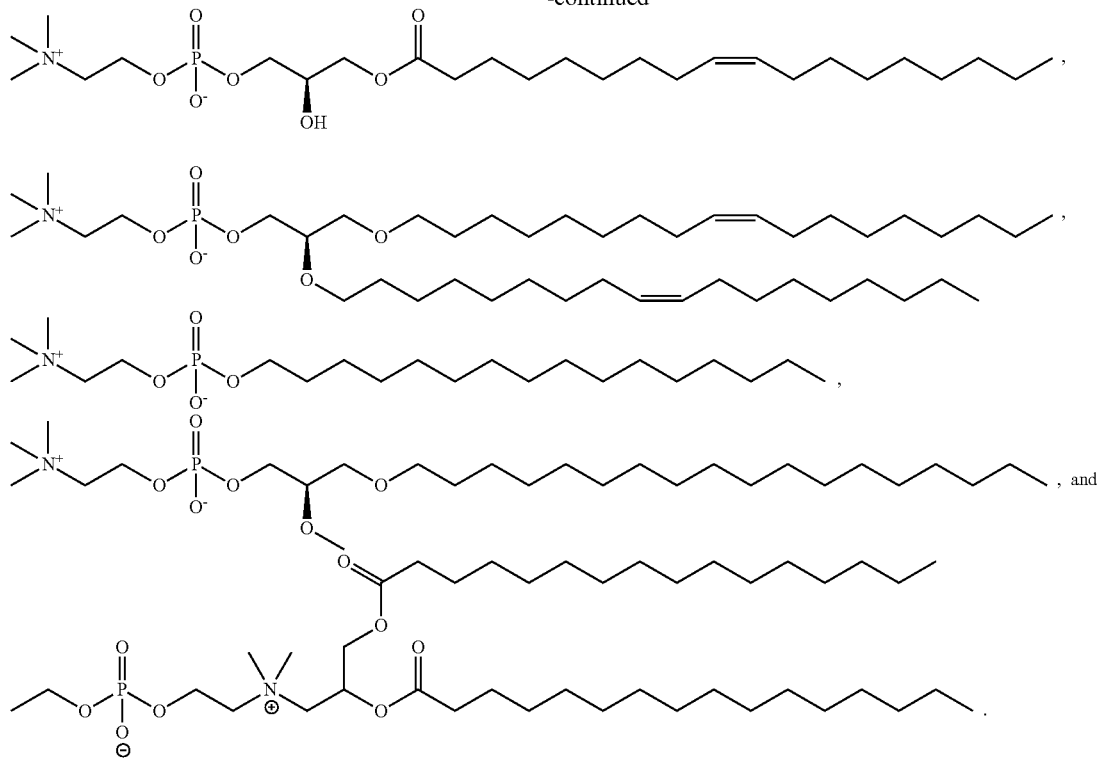

In certain embodiments, a phospholipid useful or potentially useful in the present invention is an analog or variant of DSPC. In certain embodiments, a phospholipid useful or potentially useful in the present invention is a compound of Formula (IX):

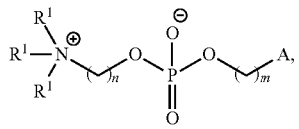

(IX)

or a salt thereof, wherein:
each $R^1$ is independently optionally substituted alkyl; or optionally two $R^1$ are joined together with the intervening atoms to form optionally substituted monocyclic carbocyclyl or optionally substituted monocyclic heterocyclyl; or optionally three $R^1$ are joined together with the intervening atoms to form optionally substituted bicyclic carbocyclyl or optionally substitute bicyclic heterocyclyl;
n is 1, 2, 3, 4, 5, 6, 7, 8, 9, or 10;
m is 0, 1, 2, 3, 4, 5, 6, 7, 8, 9, or 10;
A is of the formula:

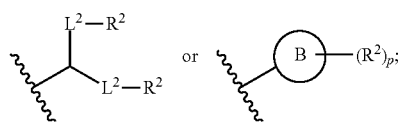

each instance of $L^2$ is independently a bond or optionally substituted $C_{1-6}$ alkylene, wherein one methylene unit of the optionally substituted $C_{1-6}$ alkylene is optionally replaced with —O—, —N($R^N$)—, —S—, —C(O)—, —C(O)N($R^N$)—, —$NR^NC(O)$—, —C(O)—O—, —OC(O)—, —OC(O)O—, —OC(O)N($R^N$)—, —$NR^NC(O)O$—, or —$NR^NC(O)N(R^N)$—;
each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —(O)—, —C(O)N($R^N$)—, —$NR^NC(O)$—, —$NR^NC(O)N(R^N)$—, —C(O)O—, —OC(O)—, —OC(O)O—, —OC(O)N($R^N$)—, —$NR^NC(O)O$—, —C(O)S—, —SC(O)—, —C(=$NR^N$)—, —C(=$NR^N$)N($R^N$)—, —$NR^NC(=NR^N)$—, —$NR^NC(=NR^N)N(R^N)$—, —C(S)—, —C(S)N($R^N$)—, —$NR^NC(S)$—, —$NR^NC(S)N(R^N)$—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—;
each instance of $R^N$ is independently hydrogen, optionally substituted alkyl, or a nitrogen protecting group;
Ring B is optionally substituted carbocyclyl, optionally substituted heterocyclyl, optionally substituted aryl, or optionally substituted heteroaryl; and
p is 1 or 2;

provided that the compound is not of the formula:

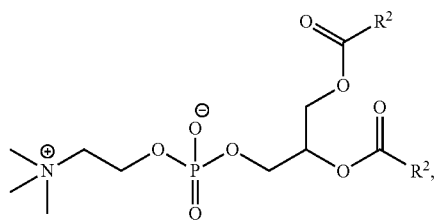

wherein each instance of $R^2$ is independently unsubstituted alkyl, unsubstituted alkenyl, or unsubstituted alkynyl.

Phospholipid Head Modifications

In certain embodiments, a phospholipid useful or potentially useful in the present invention comprises a modified phospholipid head (e.g., a modified choline group). In certain embodiments, a phospholipid with a modified head is DSPC, or analog thereof, with a modified quaternary amine. For example, in embodiments of Formula (IX), at least one of $R^1$ is not methyl. In certain embodiments, at least one of $R^1$ is not hydrogen or methyl. In certain embodiments, the compound of Formula (IX) is of one of the following formulae:

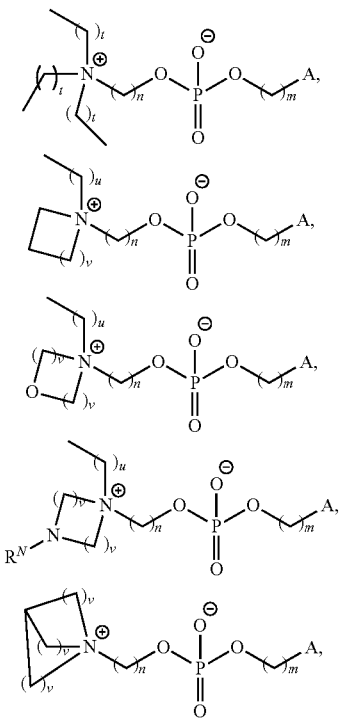

or a salt thereof, wherein:
each t is independently 1, 2, 3, 4, 5, 6, 7, 8, 9, or 10;
each u is independently 0, 1, 2, 3, 4, 5, 6, 7, 8, 9, or 10; and
each v is independently 1, 2, or 3.

In certain embodiments, the compound of Formula (IX) is of one of the following formulae:

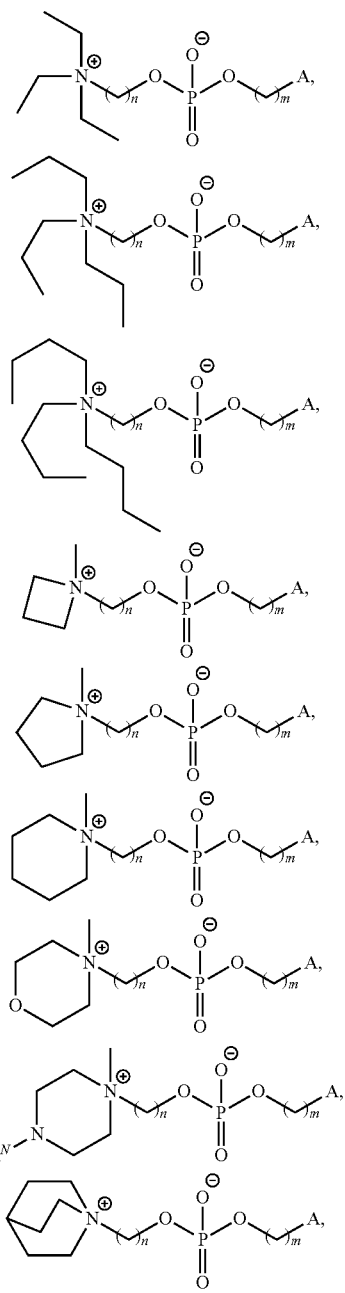

or a salt thereof.

In certain embodiments, a compound of Formula (IX) is one of the following:

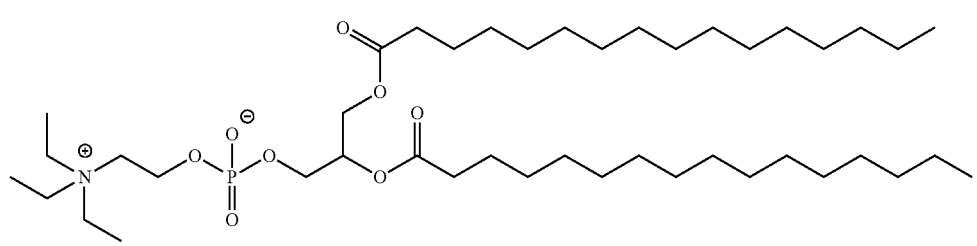

(Compound 400)

-continued
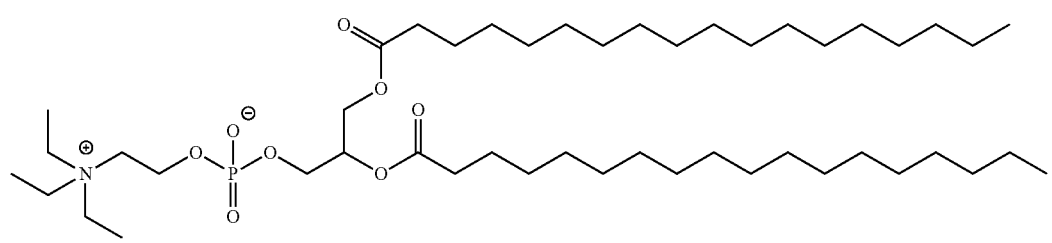
(Compound 401)
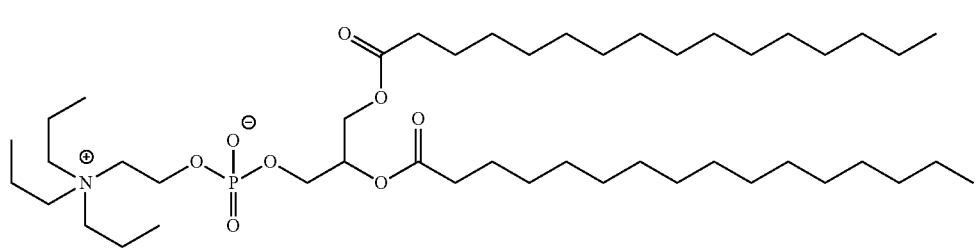
(Compound 402)
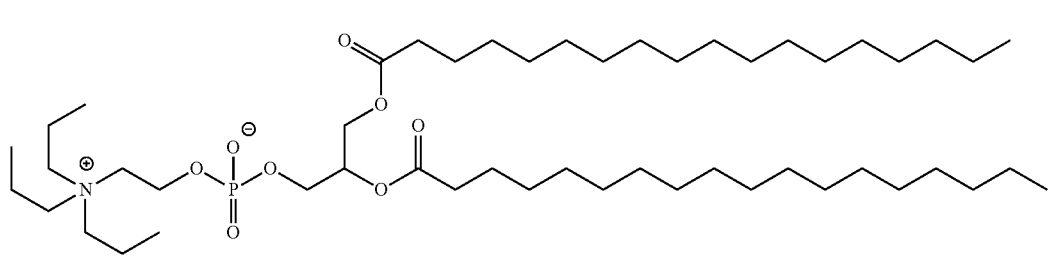
(Compound 403)
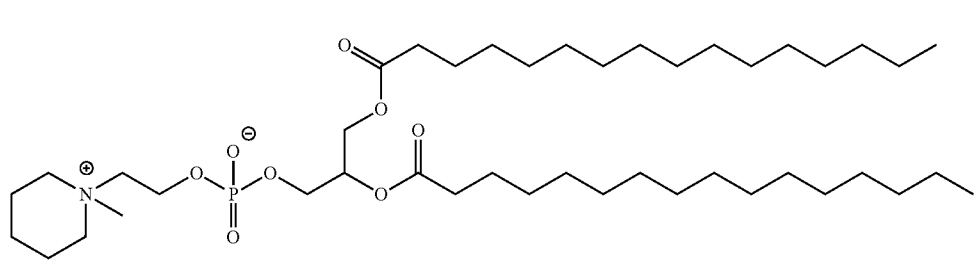
(Compound 404)
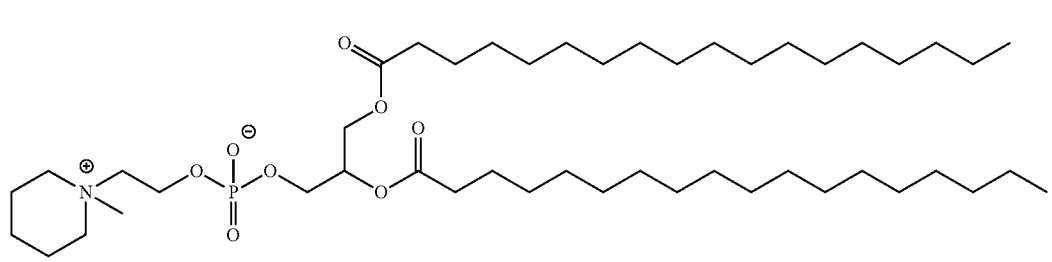
(Compound 405)
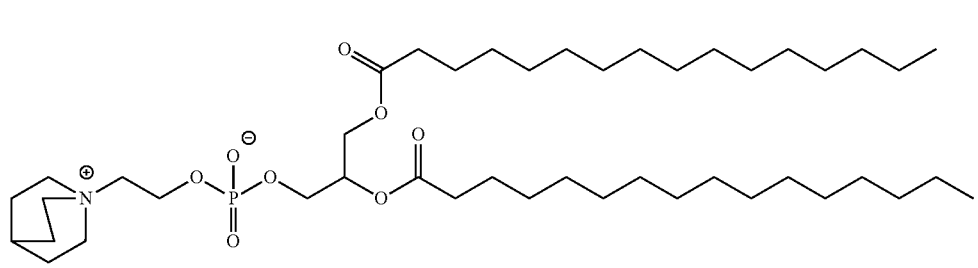
(Compound 406)

(Compound 407)

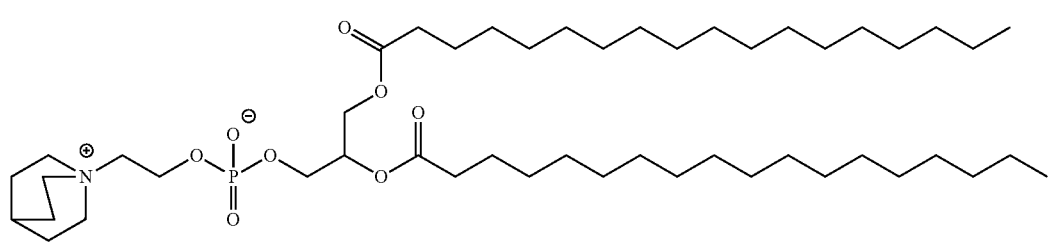

(Compound 408)

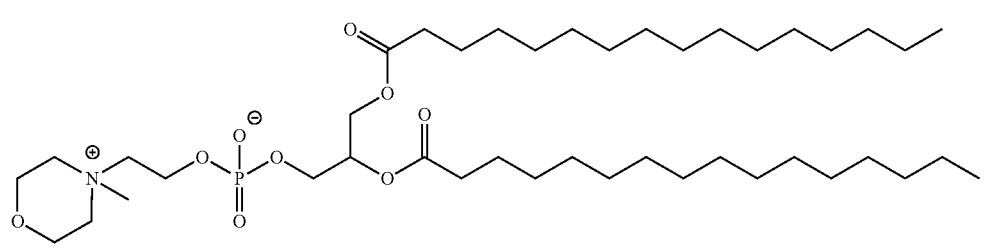

(Compound 409)

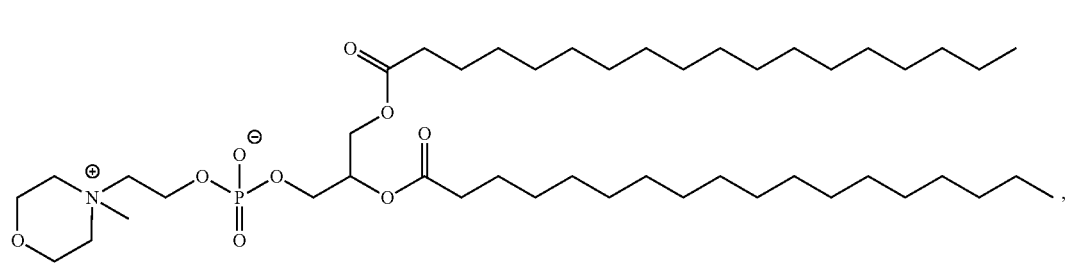

or a salt thereof.

In certain embodiments, a compound of Formula (IX) is of Formula (IX-a):

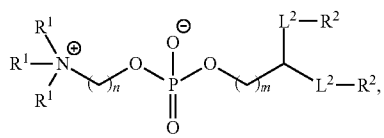 (IX-a)

or a salt thereof.

In certain embodiments, phospholipids useful or potentially useful in the present invention comprise a modified core. In certain embodiments, a phospholipid with a modified core described herein is DSPC, or analog thereof, with a modified core structure. For example, in certain embodiments of Formula (IX-a), group A is not of the following formula:

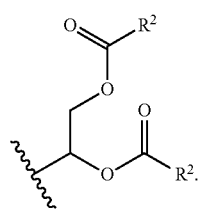

In certain embodiments, the compound of Formula (IX-a) is of one of the following formulae:

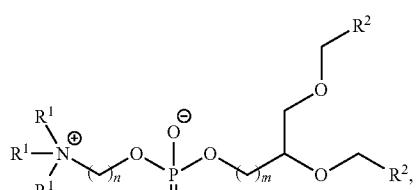

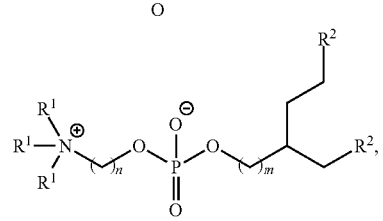

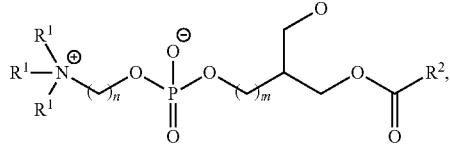

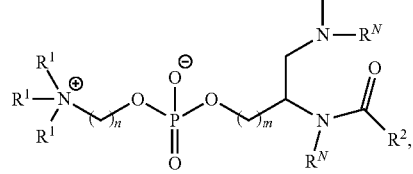

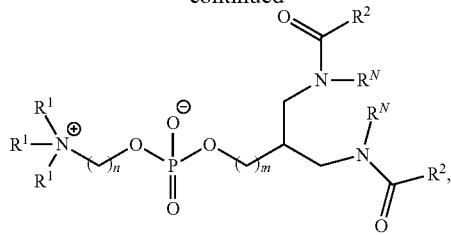

or a salt thereof.

In certain embodiments, a compound of Formula (IX) is one of the following:

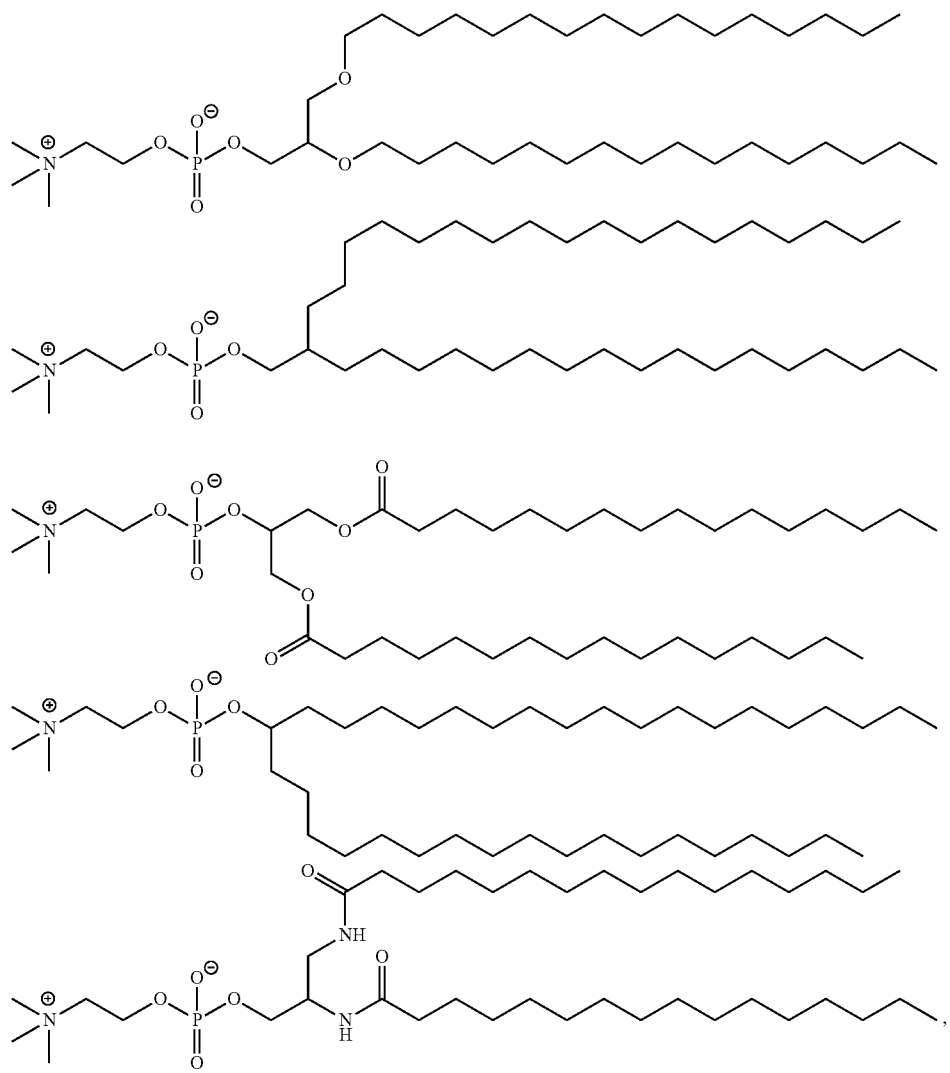

or salts thereof.

In certain embodiments, a phospholipid useful or potentially useful in the present invention comprises a cyclic moiety in place of the glyceride moiety. In certain embodiments, a phospholipid useful in the present invention is DSPC, or analog thereof, with a cyclic moiety in place of the glyceride moiety. In certain embodiments, the compound of Formula (IX) is of Formula (IX-b):

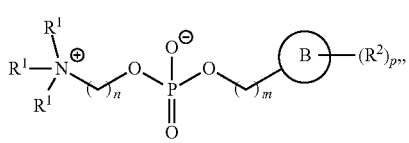

or a salt thereof.

In certain embodiments, the compound of Formula (IX-b) is of Formula (IX-b-1):

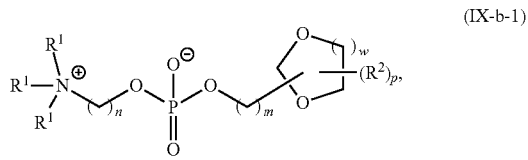

(IX-b-1)

or a salt thereof, wherein:
w is 0, 1, 2, or 3.

In certain embodiments, the compound of Formula (IX-b) is of Formula (IX-b-2):

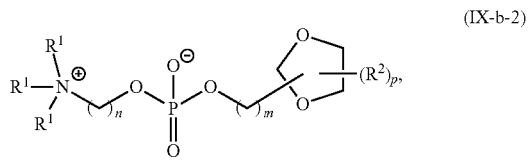

(IX-b-2)

or a salt thereof.

In certain embodiments, the compound of Formula (IX-b) is of Formula (IX-b-3):

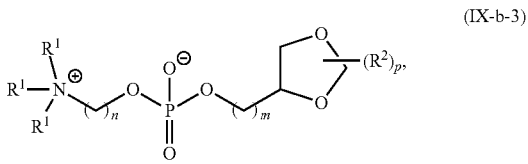

(IX-b-3)

or a salt thereof.

In certain embodiments, the compound of Formula (IX-b) is of Formula (IX-b-4):

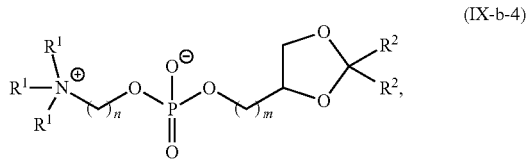

(IX-b-4)

or a salt thereof.

In certain embodiments, the compound of Formula (IX-b) is one of the following:

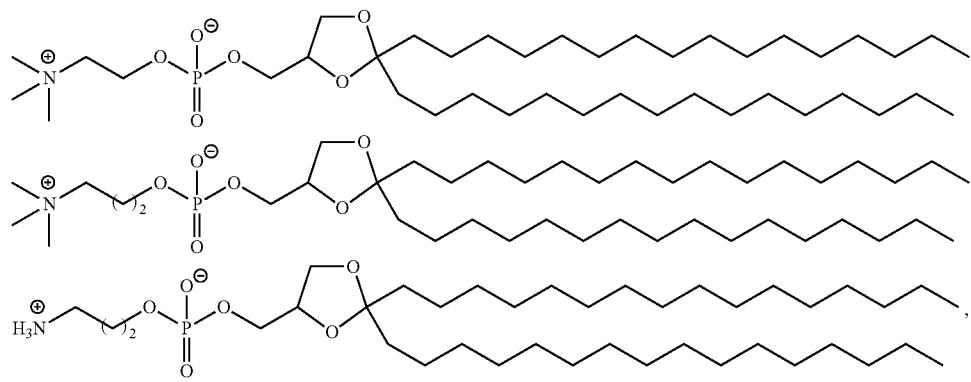

or salts thereof.

Phospholipid Tail Modifications

In certain embodiments, a phospholipid useful or potentially useful in the present invention comprises a modified tail. In certain embodiments, a phospholipid useful or potentially useful in the present invention is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. For example, in certain embodiments, the compound of (IX) is of Formula (IX-a), or a salt thereof, wherein at least one instance of $R^2$ is each instance of $R^2$ is optionally substituted $C_{1-30}$ alkyl, wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R_N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—.

In certain embodiments, the compound of Formula (IX) is of Formula (IX-c):

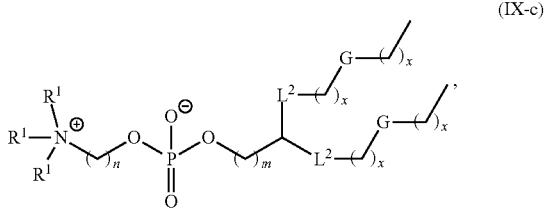

(IX-c)

or a salt thereof, wherein:
each x is independently an integer between 0-30, inclusive; and
each instance is G is independently selected from the group consisting of optionally substituted carbocyclylene, optionally substituted heterocyclylene, optionally substituted arylene, optionally substituted heteroarylene, —N(R$^N$)—, —O—, —S—, —C(O)—, —C(O)N(R$^N$)—, —NR$^N$C(O)—, —NR$^N$C(O)N(R$^N$)—, —C(O)O—, —OC(O)—, —OC(O)O—, —OC(O)N(R$^N$)—, —NR$^N$C(O)O—, —C(O)S—, —SC(O)—, —C(=NR$^N$)—, —C(=NR$^N$)N(R$^N$)—, —NR$^N$C(=NR$^N$)—, —NR$^N$C(=NR$^N$)N(R$^N$)—, —C(S)—, —C(S)N(R$^N$)—, —NR$^N$C(S)—, —NR$^N$C(S)N(R$^N$)—, —S(O)—, —OS(O)—, —S(O)O—, —OS(O)O—, —OS(O)$_2$—, —S(O)$_2$O—, —OS(O)$_2$O—, —N(R$^N$)S(O)—, —S(O)N(R$^N$)—, —N(R$^N$)S(O)N(R$^N$)—, —OS(O)N(R$^N$)—, —N(R$^N$)S(O)O—, —S(O)$_2$—, —N(R$^N$)S(O)$_2$—, —S(O)$_2$N(R$^N$)—, —N(R$^N$)S(O)$_2$N(R$^N$)—, —OS(O)$_2$N(R$^N$)—, or —N(R$^N$)S(O)$_2$O—. Each possibility represents a separate embodiment of the present invention.

In certain embodiments, the compound of Formula (IX-c) is of Formula (IX-c-1):

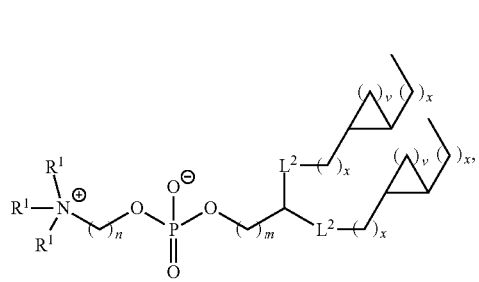

(IX-c-1)

or salt thereof, wherein:
each instance of v is independently 1, 2, or 3.

In certain embodiments, the compound of Formula (IX-c) is of Formula (IX-c-2):

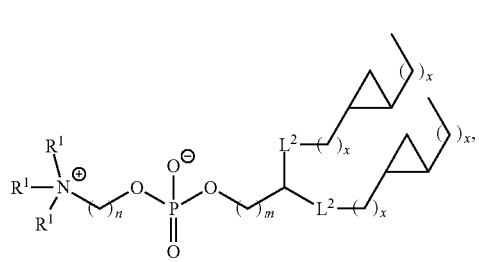

(IX-c-2)

or a salt thereof.

In certain embodiments, the compound of Formula (IX-c) is of the following formula:

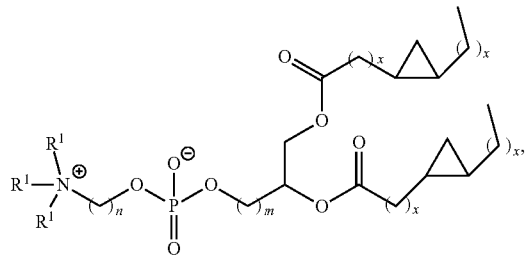

or a salt thereof.

In certain embodiments, the compound of Formula (IX-c) is the following:

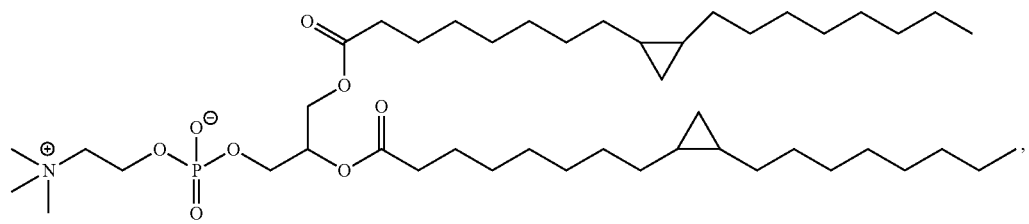 [SMILES: CCCCCCCCC1CC1CCCCCCCC(=O)OCC(COP(=O)([O-])OCC[N+](C)(C)C)OC(=O)CCCCCCCC1CC1CCCCCCCC]

or a salt thereof.

In certain embodiments, the compound of Formula (IX-c) is of Formula (IX-c-3):

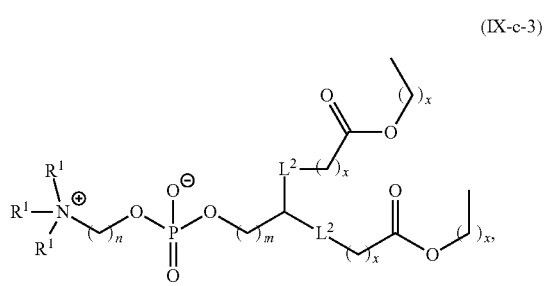

(IX-c-3)

or a salt thereof.

In certain embodiments, the compound of Formula (IX-c) is of the following formulae:

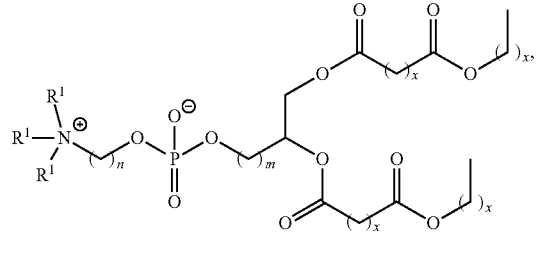

or a salt thereof.

In certain embodiments, the compound of Formula (IX-c) is the following:

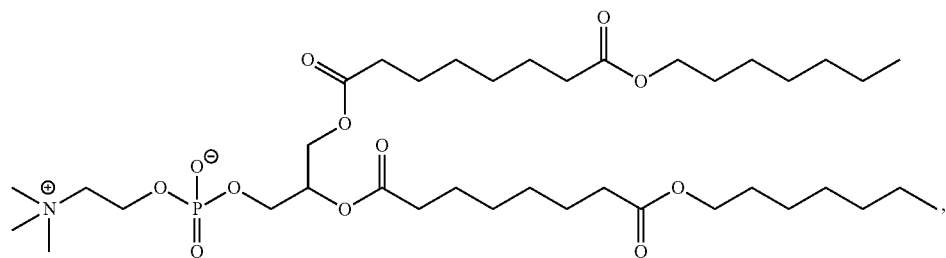 [SMILES: CCCCCCCOC(=O)CCCCCCC(=O)OCC(COP(=O)([O-])OCC[N+](C)(C)C)OC(=O)CCCCCCC(=O)OCCCCCCC]

or a salt thereof.

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful or potentially useful in the present invention is a compound of Formula (IX), wherein n is 1, 3, 4, 5, 6, 7, 8, 9, or 10. For example, in certain embodiments, a compound of Formula (IX) is of one of the following formulae:

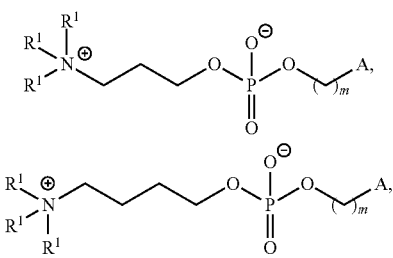

or a salt thereof.

In certain embodiments, a compound of Formula (IX) is one of the following:

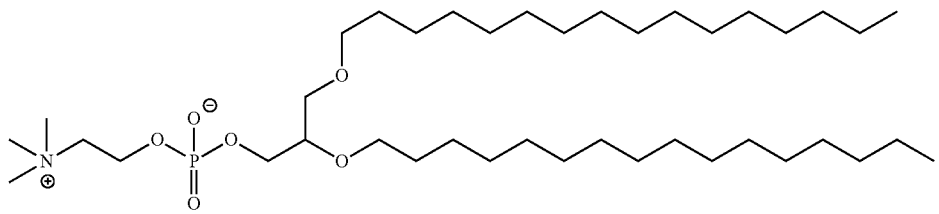

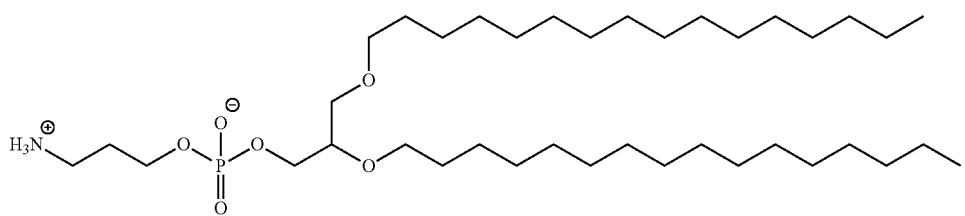

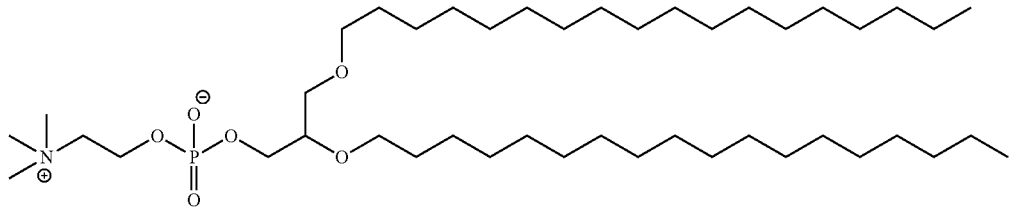

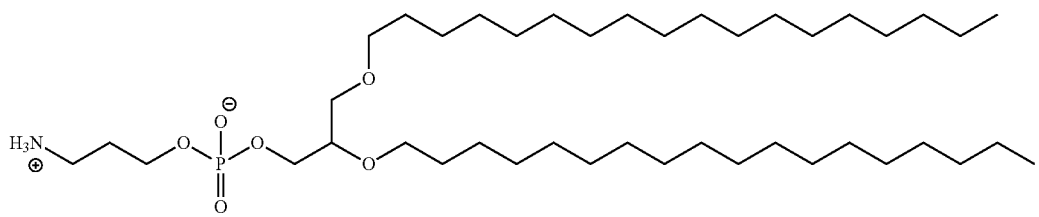

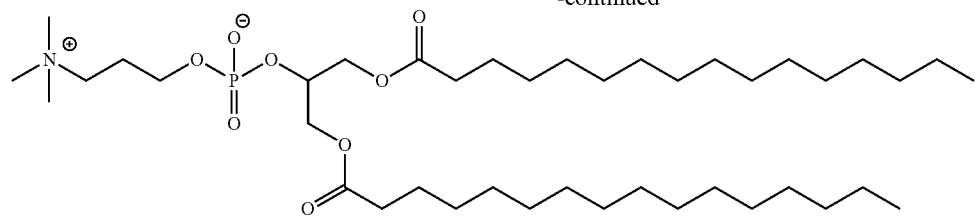
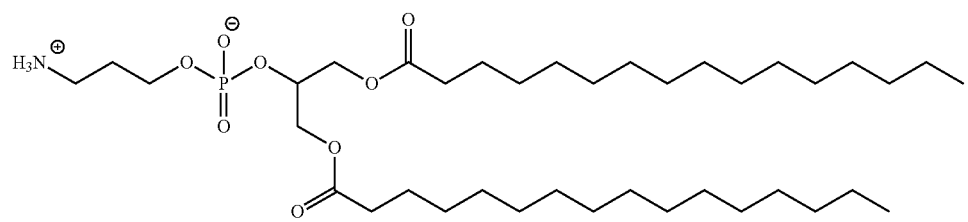
(Compound 411)
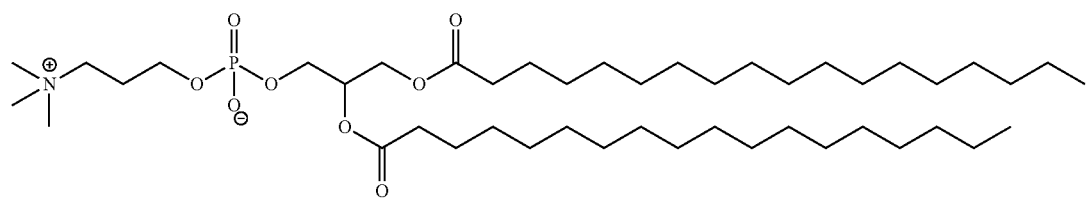
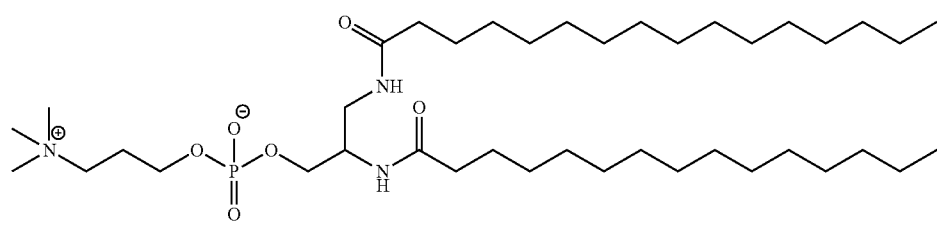
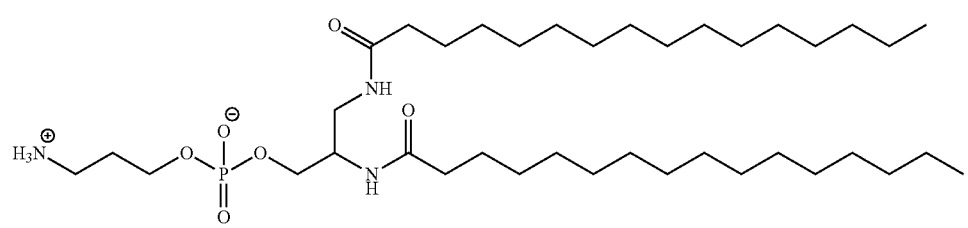
(Compound 412)
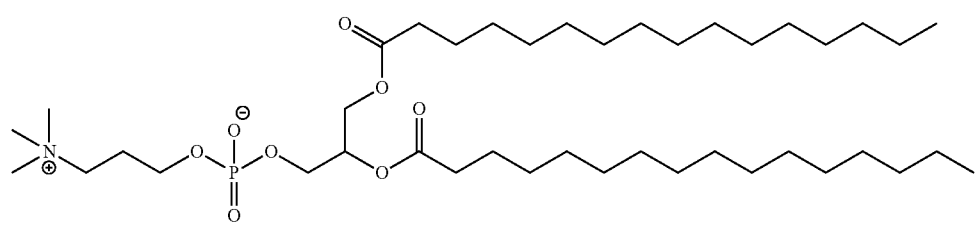
(Compound 413)
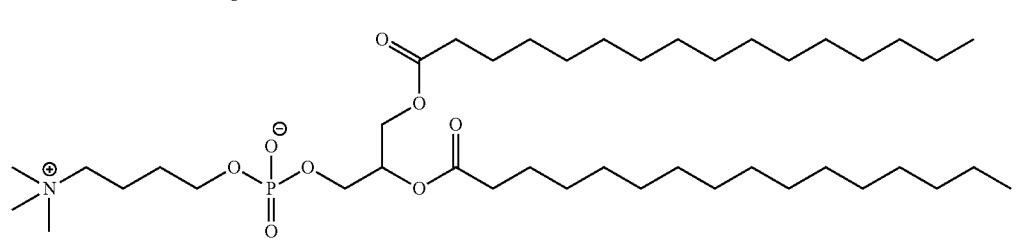

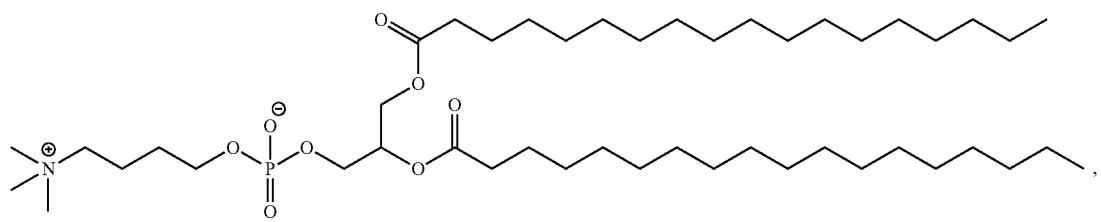
(Compound 414)
or salts thereof.
(ii) Alternative Lipids
In certain embodiments, an alternative lipid is used in place of a phospholipid of the invention. Non-limiting examples of such alternative lipids include the following:
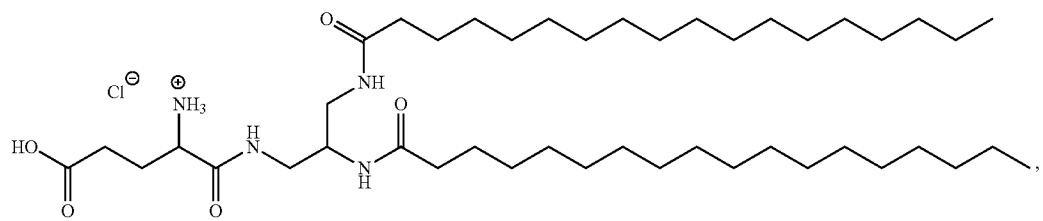
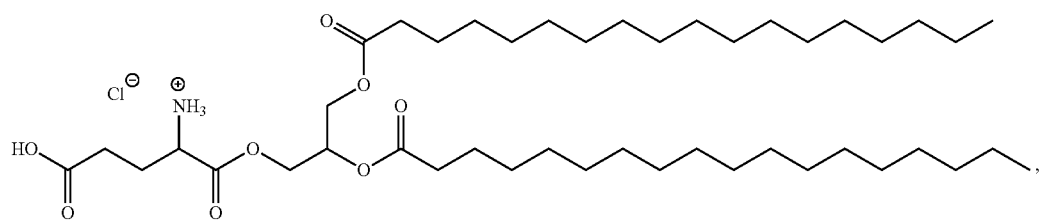
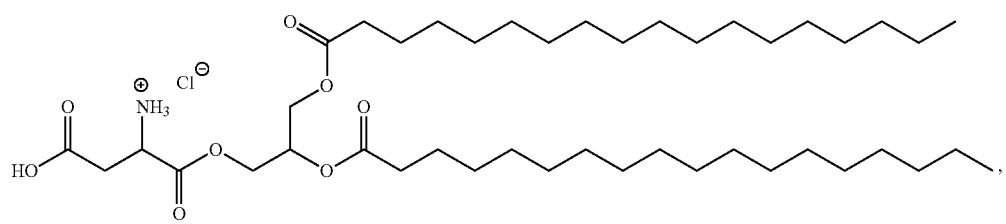
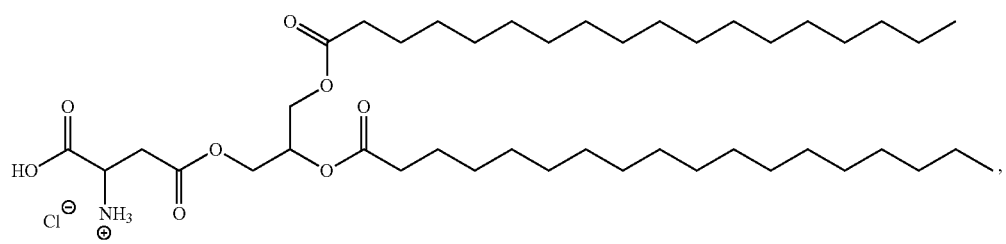
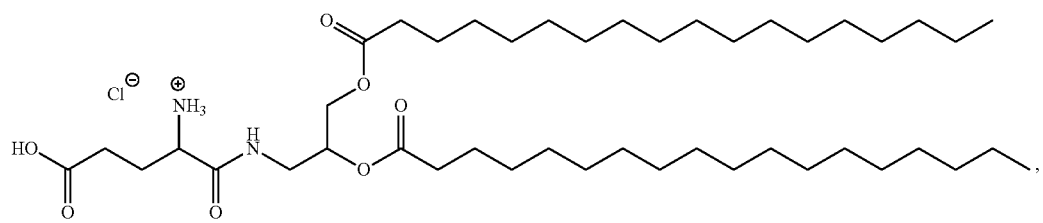

-continued

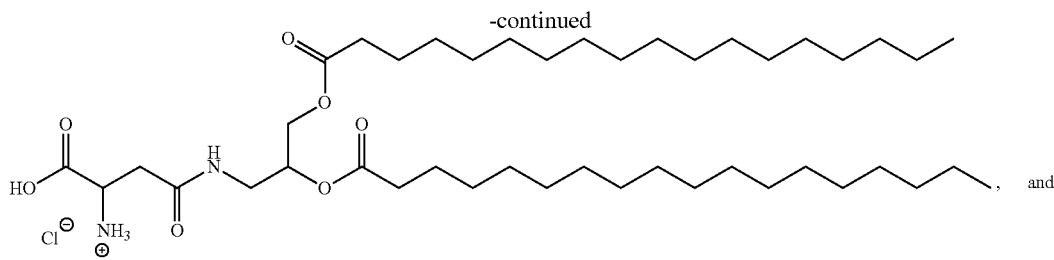
, and

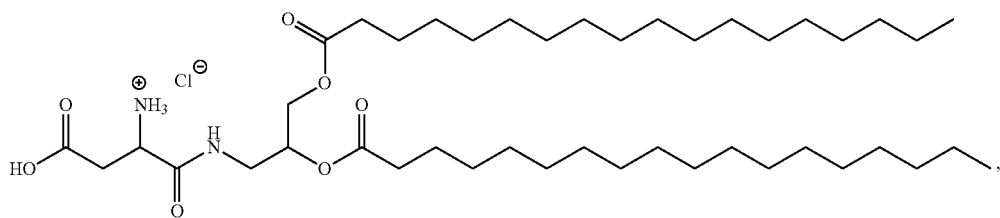
, (iii) Structural Lipids

The lipid composition of a pharmaceutical composition disclosed herein can comprise one or more structural lipids. As used herein, the term "structural lipid" refers to sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol. Examples of structural lipids include, but are not limited to, the following:

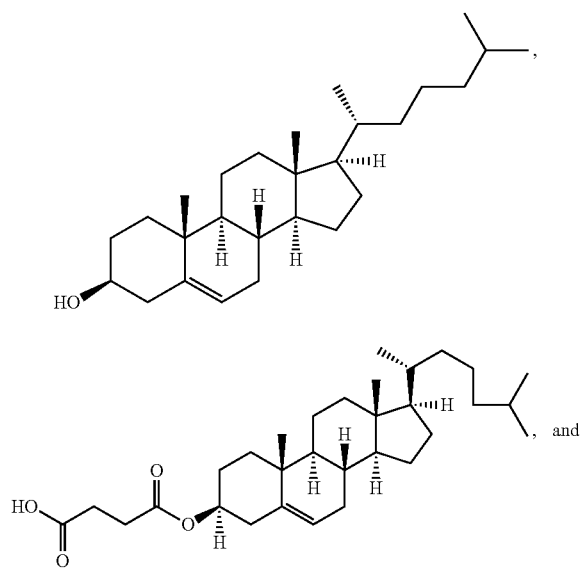
, and

-continued

In one embodiment, the amount of the structural lipid (e.g., an sterol such as cholesterol) in the lipid composition of a pharmaceutical composition disclosed herein ranges from about 20 mol % to about 60 mol %, from about 25 mol % to about 55 mol %, from about 30 mol % to about 50 mol %, or from about 35 mol % to about 45 mol %.

In one embodiment, the amount of the structural lipid (e.g., an sterol such as cholesterol) in the lipid composition disclosed herein ranges from about 25 mol % to about 30 mol %, from about 30 mol % to about 35 mol %, or from about 35 mol % to about 40 mol %.

In one embodiment, the amount of the structural lipid (e.g., a sterol such as cholesterol) in the lipid composition disclosed herein is about 24 mol %, about 29 mol %, about 34 mol %, or about 39 mol %.

In some embodiments, the amount of the structural lipid (e.g., an sterol such as cholesterol) in the lipid composition disclosed herein is at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mol %.

(iv) Polyethylene Glycol (PEG)-Lipids

The lipid composition of a pharmaceutical composition disclosed herein can comprise one or more a polyethylene glycol (PEG) lipid.

As used herein, the term "PEG-lipid" refers to polyethylene glycol (PEG)-modified lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, preferably from about $C_{14}$ to about $C_{16}$. In some embodiments, a PEG moiety, for example an mPEG-NH$_2$, has a size of about 1000, 2000, 5000, 10,000, 15,000 or 20,000 daltons. In one embodiment, the PEG-lipid is PEG$_{2k}$-DMG.

In one embodiment, the lipid nanoparticles described herein can comprise a PEG lipid which is a non-diffusible PEG. Non-limiting examples of non-diffusible PEGs include PEG-DSG and PEG-DSPE.

PEG-lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of Therapeutic Agents," which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

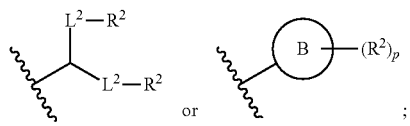

In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

In certain embodiments, a PEG lipid useful in the present invention is a compound of Formula (VII). Provided herein are compounds of Formula (VII):

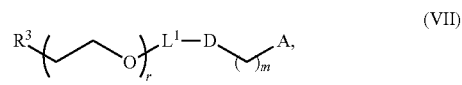

or salts thereof, wherein:

$R^3$ is —OR$^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, —O—, —N(R$^N$)—, —S—, —C(O)—, —C(O)N(R$^N$)—, —NR$^N$C(O)—, —C(O)O—, —OC(O)—, —OC(O)O—, —OC(O)N(R$^N$)—, —NR$^N$C(O)O—, or —NR$^N$C(O)N(R$^N$)—;

D is a moiety obtained by click chemistry or a moiety cleavable under physiological conditions;

m is 0, 1, 2, 3, 4, 5, 6, 7, 8, 9, or 10;

A is of the formula:

each instance of $L^2$ is independently a bond or optionally substituted $C_{1-6}$ alkylene, wherein one methylene unit of the optionally substituted $C_{1-6}$ alkylene is optionally replaced with —O—, —N(R$^N$)—, —S—, —C(O)—, —C(O)N(R$^N$)—, —NR$^N$C(O)—, —C(O)O—, —OC(O)—, —OC(O)O—, —OC(O)N(R$^N$)—, —NR$^N$C(O)O—, or —NR$^N$C(O)N(R$^N$)—;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Formula (VII) is a PEG-OH lipid (i.e., $R^3$ is —$OR^O$, and $R^O$ is hydrogen). In certain embodiments, the compound of Formula (VII) is of Formula (VII-OH):

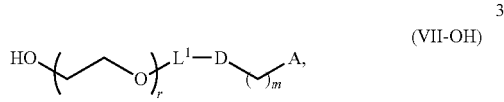
(VII-OH)

or a salt thereof.

In certain embodiments, D is a moiety obtained by click chemistry (e.g., triazole). In certain embodiments, the compound of Formula (VII) is of Formula (VII-a-1) or (VII-a-2):

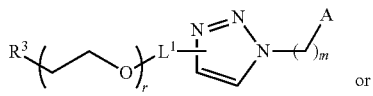
(VII-a-1)

or

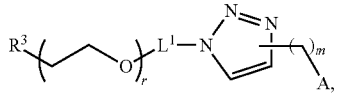
(VII-a-2)

or a salt thereof.

In certain embodiments, the compound of Formula (VII) is of one of the following formulae:

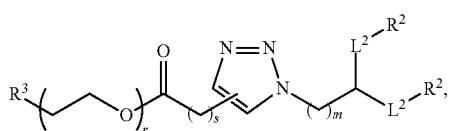

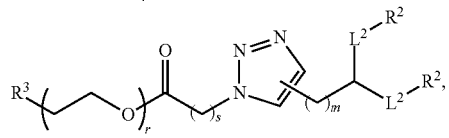

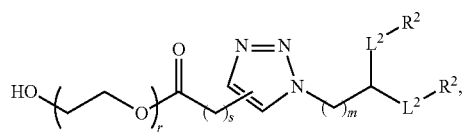

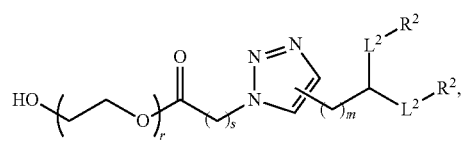

or a salt thereof, wherein s is 0, 1, 2, 3, 4, 5, 6, 7, 8, 9, or 10.

In certain embodiments, the compound of Formula (VII) is of one of the following formulae:

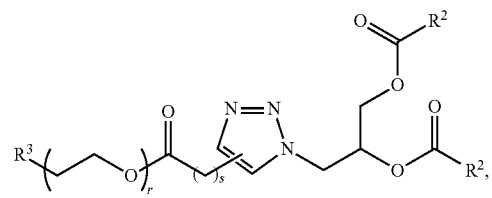

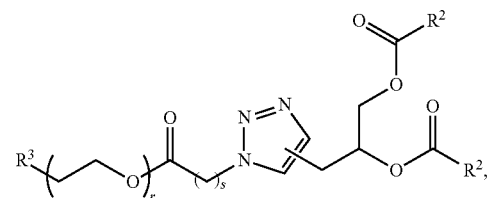

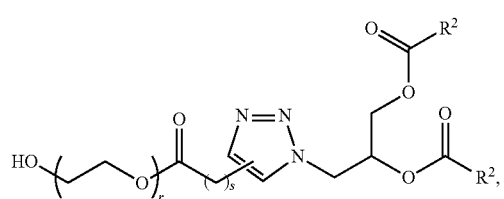

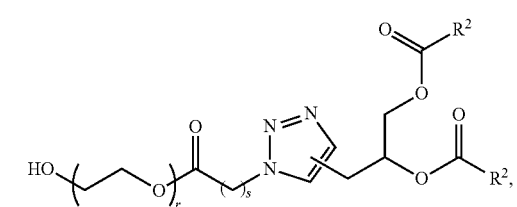

or a salt thereof.

In certain embodiments, a compound of Formula (VII) is of one of the following formulae:

323
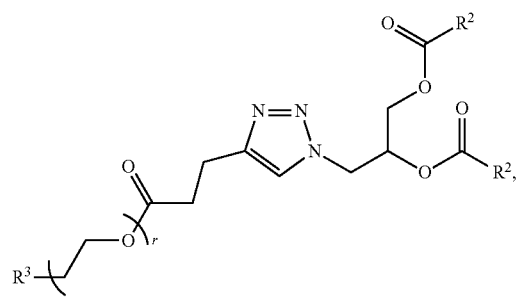
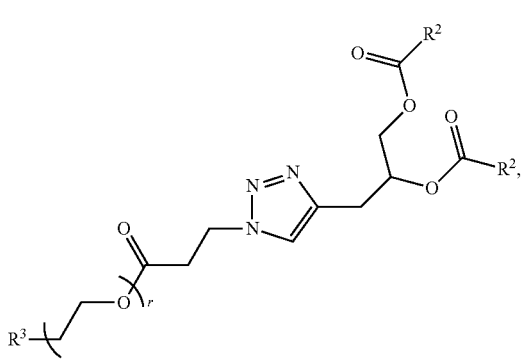
324
-continued
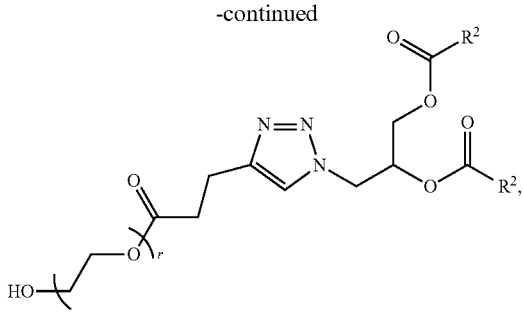
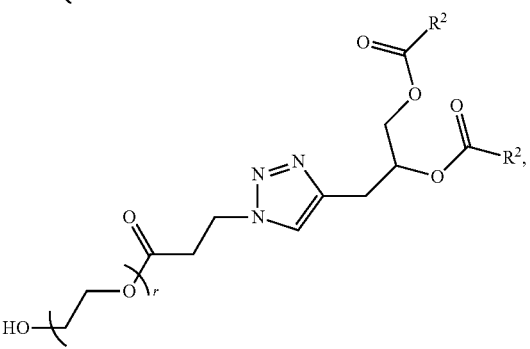
or a salt thereof.
In certain embodiments, a compound of Formula (VII) is of one of the following formulae:
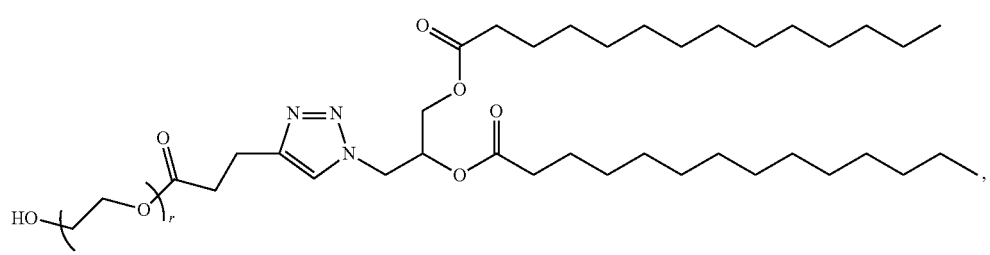
(Compound 415)
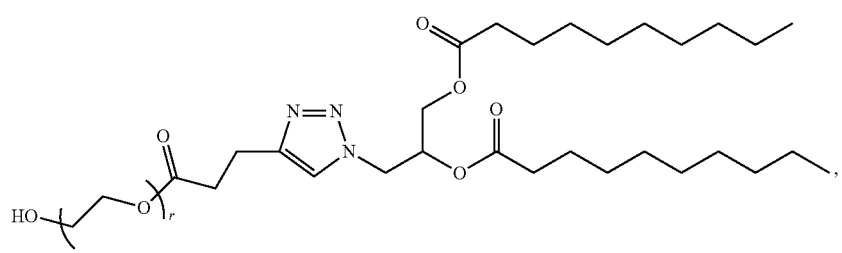
(Compound 416)
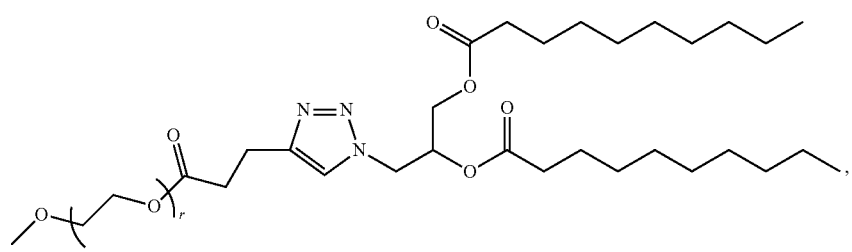
(Compound 417)

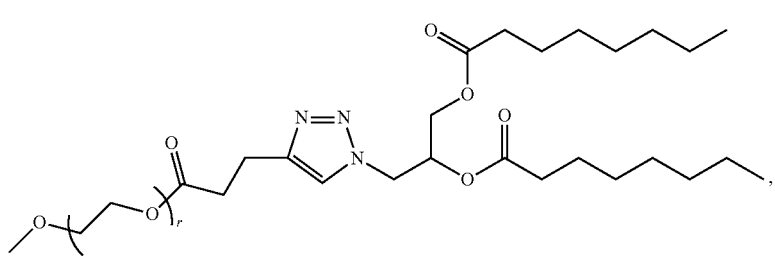

(Compound 418)

or a salt thereof.

In certain embodiments, D is a moiety cleavable under physiological conditions (e.g., ester, amide, carbonate, carbamate, urea). In certain embodiments, a compound of Formula (VII) is of Formula (VII-b-1) or (VII-b-2):

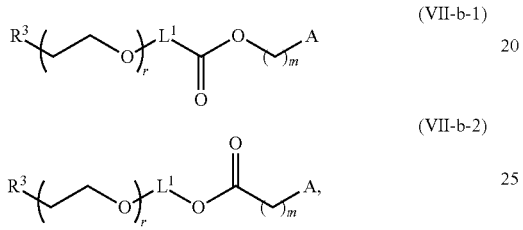

or a salt thereof.

In certain embodiments, a compound of Formula (VII) is of Formula (VII-b-1-OH) or (VII-b-2-OH):

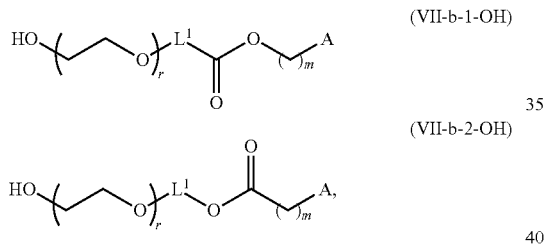

or a salt thereof.

In certain embodiments, the compound of Formula (VII) is of one of the following formulae:

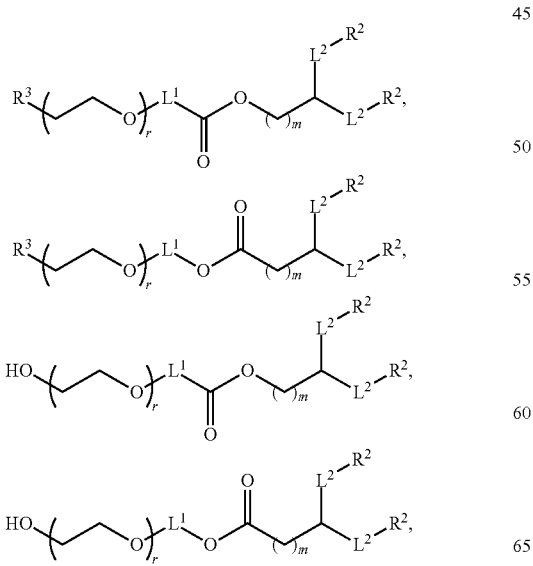

or a salt thereof.

In certain embodiments, a compound of Formula (VII) is of one of the following formulae:

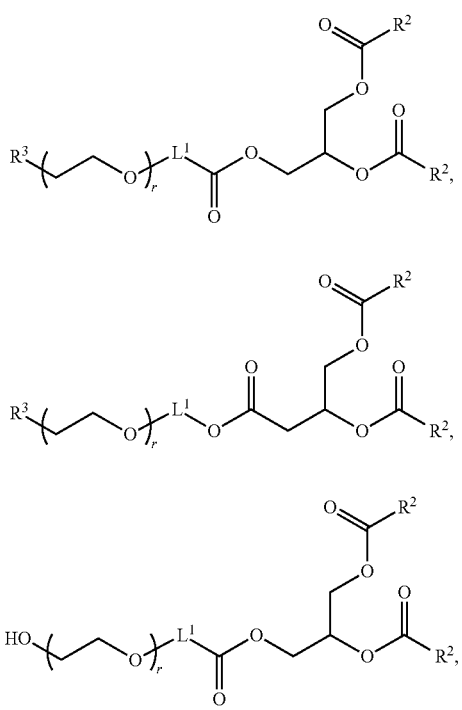

or a salt thereof.

In certain embodiments, a compound of Formula (VII) is of one of the following formulae:

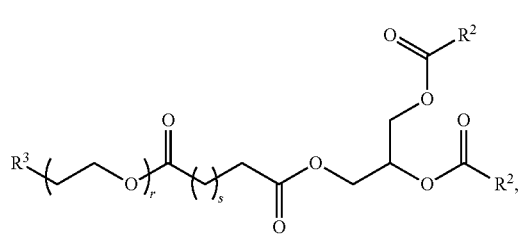

-continued

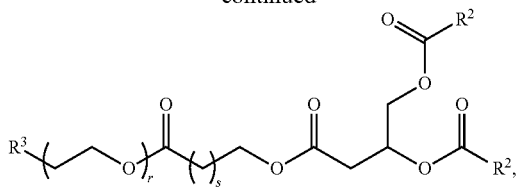

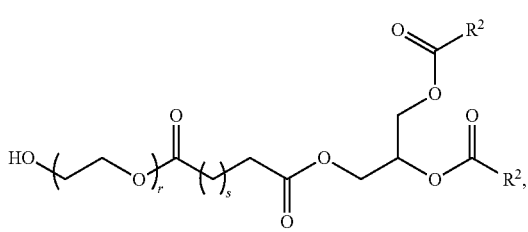

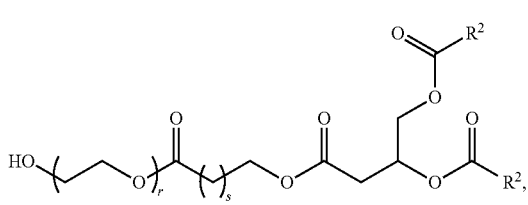

or a salt thereof.

In certain embodiments, a compound of Formula (VII) is of one of the following formulae:

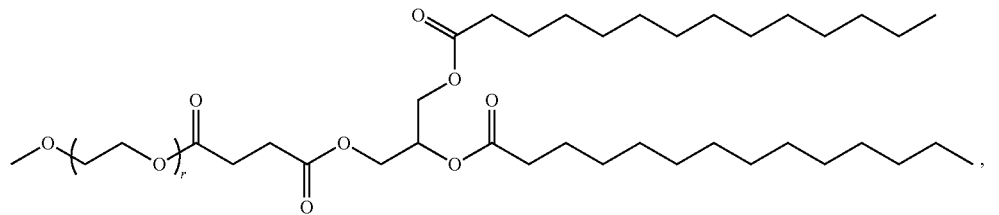

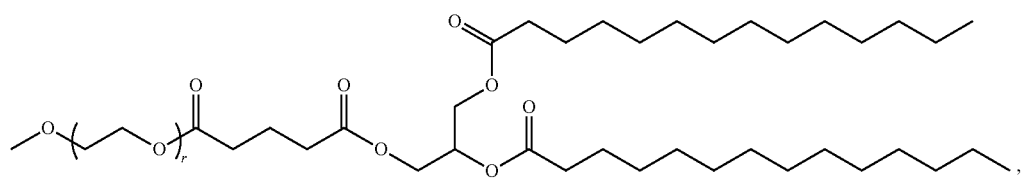

or salts thereof.

In certain embodiments, a PEG lipid useful in the present invention is a PEGylated fatty acid. In certain embodiments, a PEG lipid useful in the present invention is a compound of Formula (VIII). Provided herein are compounds of Formula (VIII):

(VIII)

$R^3 \{ \sim O \}_r \sim R^5$, or a salts thereof, wherein:

$R^3$ is —$OR^O$;

$R^O$ is hydrogen, optionally substituted alkyl or an oxygen protecting group;

r is an integer between 1 and 100, inclusive;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—; and each instance of $R^N$ is independently hydrogen, optionally substituted alkyl, or a nitrogen protecting group.

In certain embodiments, the compound of Formula (VIII) of Formula (VIII-OH):

(VIII-OH)

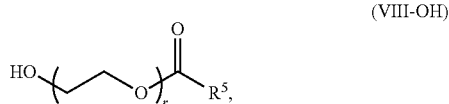

or a salt thereof. In some embodiments, r is 45.

In certain embodiments, a compound of Formula (VIII) is of one of the following formulae:

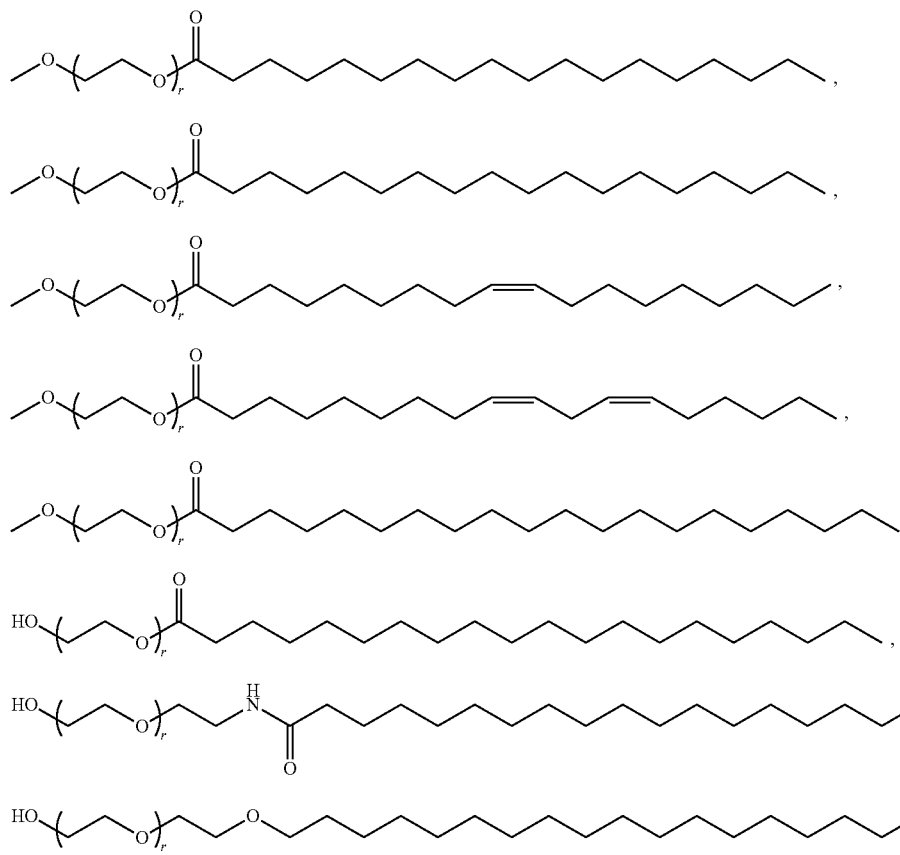

(Compound 419)
(Compound 420)
(Compound 421)
(Compound 422)
(Compound 423)
(Compound 424)
(Compound 425)
(Compound 426)

or a salt thereof. In some embodiments, r is 45.

In yet other embodiments the compound of Formula (VIII) is:

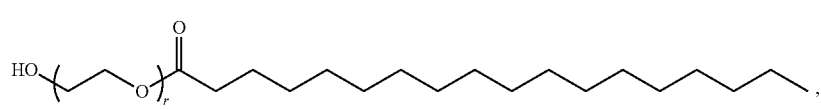

(Compound 427)

or a salt thereof.

In one embodiment, the compound of Formula (VIII)

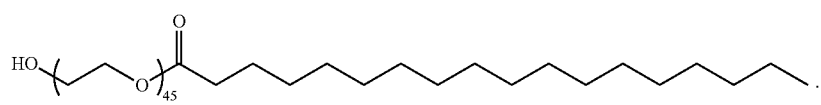

(Compound 428)

In one embodiment, the amount of PEG-lipid in the lipid composition of a pharmaceutical composition disclosed herein ranges from about 0.1 mol % to about 5 mol %, from about 0.5 mol % to about 5 mol %, from about 1 mol % to about 5 mol %, from about 1.5 mol % to about 5 mol %, from about 2 mol % to about 5 mol % mol %, from about 0.1 mol % to about 4 mol %, from about 0.5 mol % to about 4 mol %, from about 1 mol % to about 4 mol %, from about 1.5 mol % to about 4 mol %, from about 2 mol % to about 4 mol %, from about 0.1 mol % to about 3 mol %, from about 0.5 mol % to about 3 mol %, from about 1 mol % to about 3 mol %, from about 1.5 mol % to about 3 mol %, from about 2 mol % to about 3 mol %, from about 0.1 mol % to about 2 mol %, from about 0.5 mol % to about 2 mol %, from about 1 mol % to about 2 mol %, from about 1.5 mol % to about 2 mol %, from about 0.1 mol % to about 1.5 mol %, from about 0.5 mol % to about 1.5 mol %, or from about 1 mol % to about 1.5 mol %.

In one embodiment, the amount of PEG-lipid in the lipid composition disclosed herein is about 2 mol %.

In one embodiment, the amount of PEG-lipid in the lipid composition disclosed herein is at least about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 mol %.

In some aspects, the lipid composition of the pharmaceutical compositions disclosed herein does not comprise a PEG-lipid.

(v) Other Ionizable Amino Lipids

The lipid composition of the pharmaceutical composition disclosed herein can comprise one or more ionizable amino lipids in addition to a lipid according to Formula (I), (III), (IV), (V), or (VI).

Ionizable lipids can be selected from the non-limiting group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraazaoctatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)[1,3]-dioxolane (DLin-KC2-DMA), 1,2-dioleyloxy-N,N-dimethylaminopropane (DODMA), (13Z, 16SZ)—N,N-dimethyl-3-nonydocosa-13-16-dien-1-amine (L608), 2-({8-[(3β-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2 S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)). In addition to these, an ionizable amino lipid can also be a lipid including a cyclic amine group.

Ionizable lipids can also be the compounds disclosed in International Publication No. WO 2017/075531 A1, hereby incorporated by reference in its entirety. For example, the ionizable amino lipids include, but not limited to:

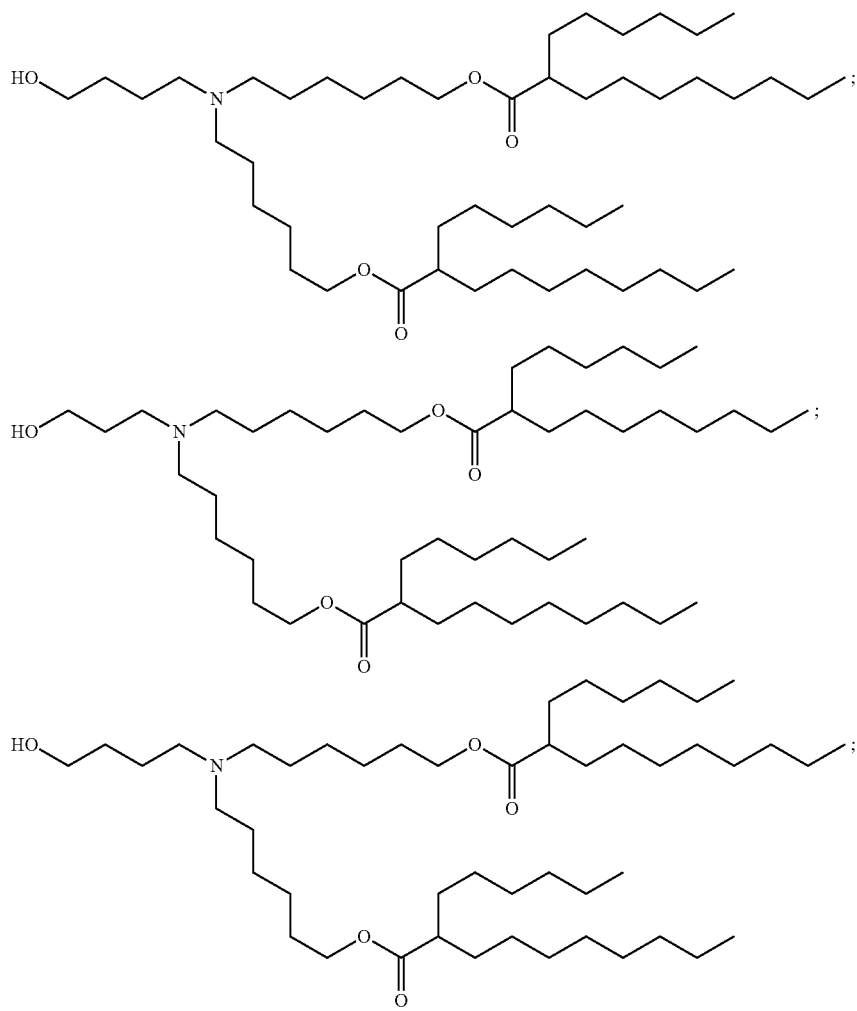

and any combination thereof.

Ionizable lipids can also be the compounds disclosed in International Publication No. WO 2015/199952 A1, hereby incorporated by reference in its entirety. For example, the ionizable amino lipids include, but not limited to:

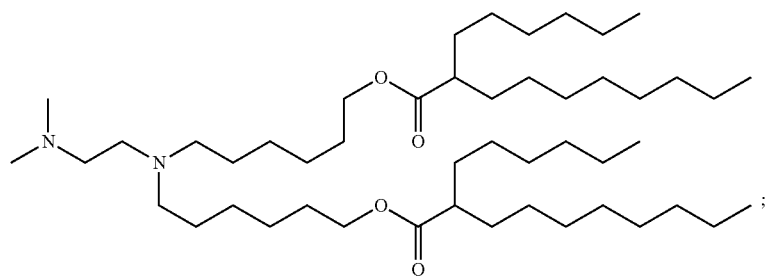
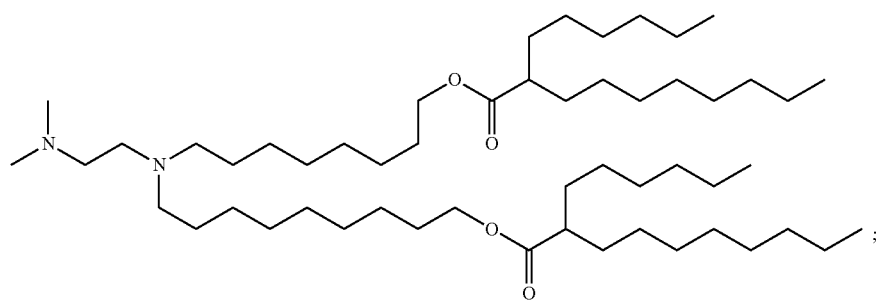
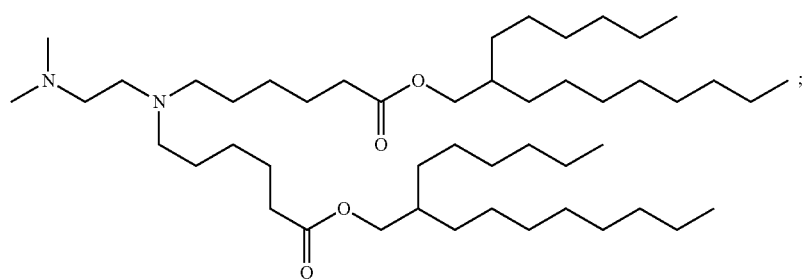
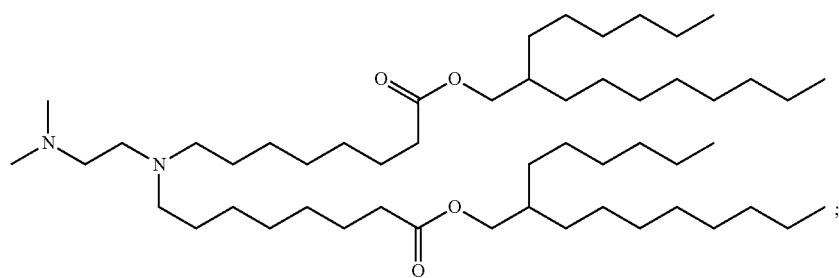
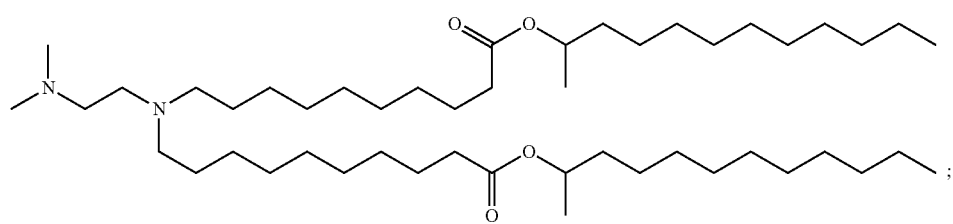
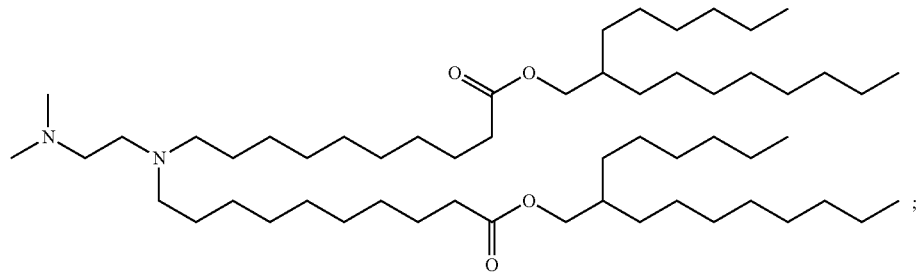

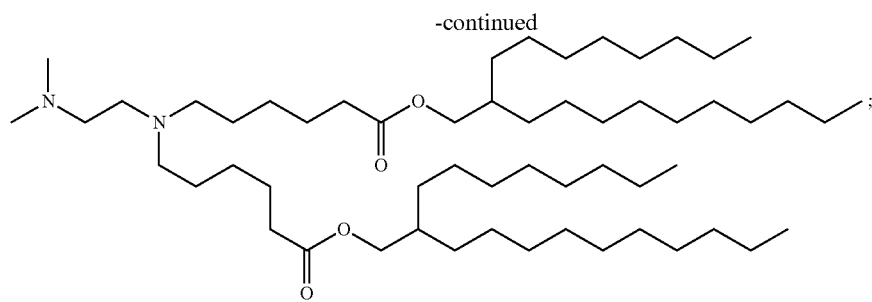
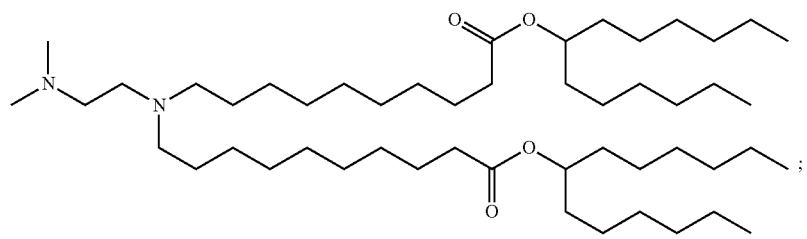
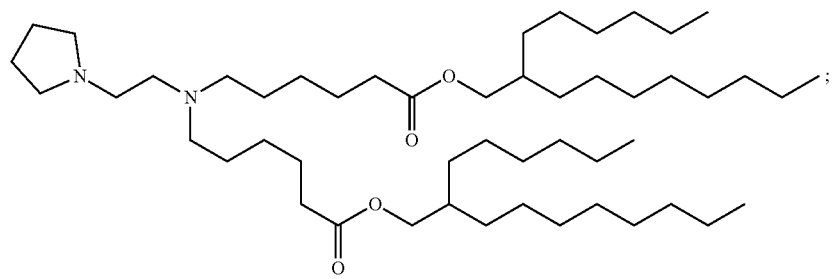
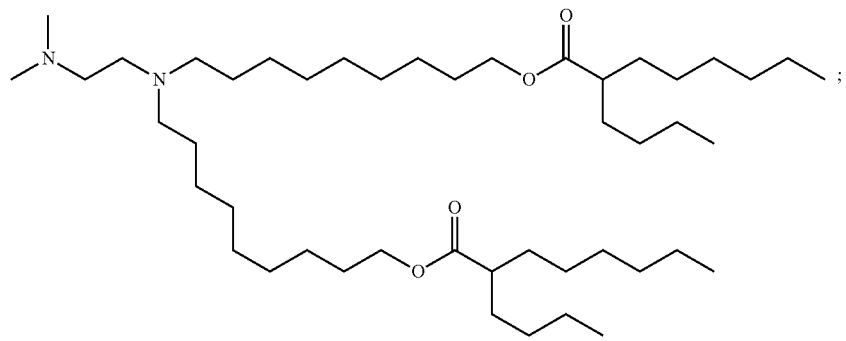
and any combination thereof.
Ionizable lipids can further include, but are not limited to:
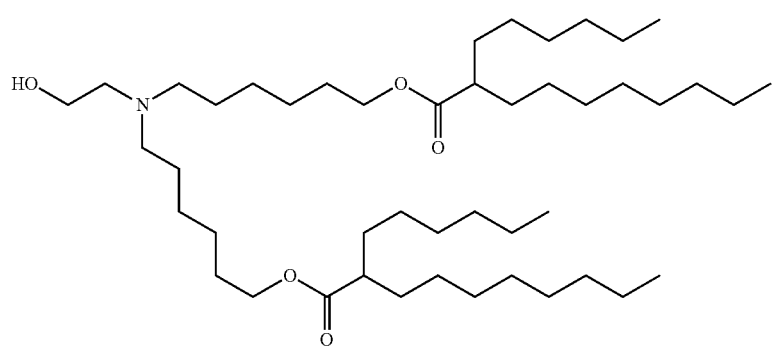

-continued

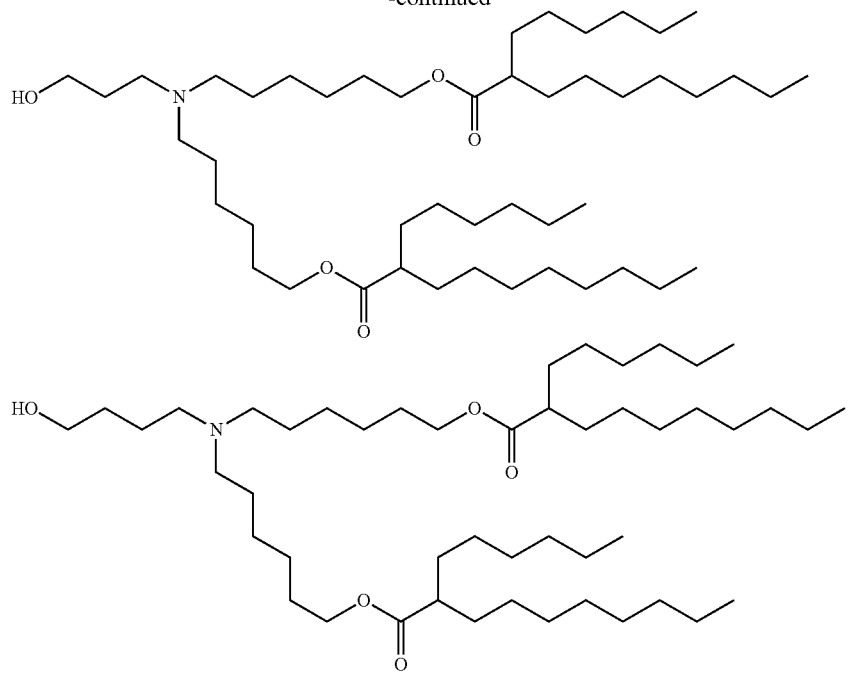

and any combination thereof.

(vi) Other Lipid Composition Components

The lipid composition of a pharmaceutical composition disclosed herein can include one or more components in addition to those described above. For example, the lipid composition can include one or more permeability enhancer molecules, carbohydrates, polymers, surface altering agents (e.g., surfactants), or other components. For example, a permeability enhancer molecule can be a molecule described by U.S. Patent Application Publication No. 2005/0222064. Carbohydrates can include simple sugars (e.g., glucose) and polysaccharides (e.g., glycogen and derivatives and analogs thereof).

A polymer can be included in and/or used to encapsulate or partially encapsulate a pharmaceutical composition disclosed herein (e.g., a pharmaceutical composition in lipid nanoparticle form). A polymer can be biodegradable and/or biocompatible. A polymer can be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates.

The ratio between the lipid composition and the polynucleotide range can be from about 10:1 to about 60:1 (wt/wt).

In some embodiments, the ratio between the lipid composition and the polynucleotide can be about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1 or 60:1 (wt/wt). In some embodiments, the wt/wt ratio of the lipid composition to the polynucleotide encoding a therapeutic agent is about 20:1 or about 15:1.

In some embodiments, the pharmaceutical composition disclosed herein can contain more than one polypeptides. For example, a pharmaceutical composition disclosed herein can contain two or more polynucleotides (e.g., RNA, e.g., mRNA).

In one embodiment, the lipid nanoparticles described herein can comprise polynucleotides (e.g., mRNA) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles described herein can comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

(vii) Nanoparticle Compositions

In some embodiments, the pharmaceutical compositions disclosed herein are formulated as lipid nanoparticles (LNP). Accordingly, the present disclosure also provides nanoparticle compositions comprising (i) a lipid composition comprising a delivery agent such as a compound of Formula (I) or (III) as described herein, and (ii) a polynucleotide encoding a GLA polypeptide. In such nanoparticle composition, the lipid composition disclosed herein can encapsulate the polynucleotide encoding a GLA polypeptide.

Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Nanoparticle compositions include, for example, lipid nanoparticles (LNPs), liposomes, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

In some embodiments, the nanoparticle compositions of the present disclosure comprise at least one compound according to Formula (I), (III), (IV), (V), or (VI). For example, the nanoparticle composition can include one or more of Compounds 1-147, or one or more of Compounds 1-342. Nanoparticle compositions can also include a variety of other components. For example, the nanoparticle composition may include one or more other lipids in addition to a lipid according to Formula (I), (III), (IV), (V), or (VI), such as (i) at least one phospholipid, (ii) at least one structural lipid, (iii) at least one PEG-lipid, or (iv) any combination thereof. Inclusion of structural lipid can be optional, for example when lipids according to Formula III are used in the lipid nanoparticle compositions of the invention.

In some embodiments, the nanoparticle composition comprises a compound of Formula (I), (e.g., Compounds 18, 25, 26 or 48). In some embodiments, the nanoparticle composition comprises a compound of Formula (I) (e.g., Compounds 18, 25, 26 or 48) and a phospholipid (e.g., DOPE or DSPC).

In some embodiments, the nanoparticle composition comprises a compound of Formula (III) (e.g., Compound 236). In some embodiments, the nanoparticle composition comprises a compound of Formula (III) (e.g., Compound 236) and a phospholipid (e.g., DOPE or DSPC).

In some embodiments, the nanoparticle composition comprises a lipid composition consisting or consisting essentially of compound of Formula (I) (e.g., Compounds 18, 25, 26 or 48). In some embodiments, the nanoparticle composition comprises a lipid composition consisting or consisting essentially of a compound of Formula (I) (e.g., Compounds 18, 25, 26 or 48) and a phospholipid (e.g., DSPC).

In some embodiments, the nanoparticle composition comprises a lipid composition consisting or consisting essentially of a compound of Formula (III) (e.g., Compound 236). In some embodiments, the nanoparticle composition comprises a lipid composition consisting or consisting essentially of a compound of Formula (III) (e.g., Compound 236) and a phospholipid (e.g., DSPC).

In one embodiment, a lipid nanoparticle comprises an ionizable lipid, a structural lipid, a phospholipid, and mRNA. In some embodiments, the LNP comprises an ionizable lipid, a PEG-modified lipid, a sterol and a structural lipid. In some embodiments, the LNP has a molar ratio of about 20-60% ionizable lipid:about 5-25% structural lipid: about 25-55% sterol; and about 0.5-15% PEG-modified lipid. In some embodiments, the LNP comprises a molar ratio of about 50% ionizable lipid, about 1.5% PEG-modified lipid, about 38.5% cholesterol and about 10% structural lipid. In some embodiments, the LNP comprises a molar ratio of about 55% ionizable lipid, about 2.5% PEG lipid, about 32.5% cholesterol and about 10% structural lipid. In some embodiments, the ionizable lipid is an ionizable amino lipid and the structural lipid is a neutral lipid, and the sterol is a cholesterol. In some embodiments, the LNP has a molar ratio of 50:38.5:10:1.5 of ionizable lipid: cholesterol: DSPC: PEG lipid. In some embodiments, the ionizable lipid is Compound 18 or Compound 236, and the PEG lipid is Compound 428.

In some embodiments, the LNP has a molar ratio of 50:38.5:10:1.5 of Compound 18:Cholesterol:Phospholipid: Compound 428. In some embodiments, the LNP has a molar ratio of 50:38.5:10:1.5 of Compound 18:Cholesterol:DSPC: Compound 428.

In some embodiments, the LNP has a molar ratio of 50:38.5:10:1.5 of Compound 236:Cholesterol:Phospholipid: Compound 428. In some embodiments, the LNP has a molar ratio of 50:38.5:10:1.5 of Compound 236:Cholesterol:DSPC:Compound 428.

In some embodiments, the LNP has a polydispersity value of less than 0.4. In some embodiments, the LNP has a net neutral charge at a neutral pH. In some embodiments, the LNP has a mean diameter of 50-150 nm. In some embodiments, the LNP has a mean diameter of 80-100 nm.

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

In some embodiments, a lipid nanoparticle (LNP) may comprise an ionizable lipid. As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, in which case it can be referred to as "cationic lipid". In certain embodiments, an ionizable lipid molecule may comprise an amine group, and can be referred to as an ionizable amino lipid. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidizolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid, sometimes referred to in the art as an "ionizable cationic lipid". In one embodiment, the ionizable amino lipid may have a positively charged hydrophilic head and a hydrophobic tail that are connected via a linker structure.

In addition to these, an ionizable lipid may also be a lipid including a cyclic amine group.

In one embodiment, the ionizable lipid may be selected from, but not limited to, an ionizable lipid described in International Publication Nos. WO2013086354 and WO2013116126; the contents of each of which are herein incorporated by reference in their entirety.

In yet another embodiment, the ionizable lipid may be selected from, but not limited to, Formula CLI-CLXXXXII of U.S. Pat. No. 7,404,969; each of which is herein incorporated by reference in their entirety.

In one embodiment, the lipid may be a cleavable lipid such as those described in International Publication No. WO2012170889, herein incorporated by reference in its entirety. In one embodiment, the lipid may be synthesized by methods known in the art and/or as described in International Publication Nos. WO2013086354; the contents of each of which are herein incorporated by reference in their entirety.

Nanoparticle compositions can be characterized by a variety of methods. For example, microscopy (e.g., transmission electron microscopy or scanning electron microscopy) can be used to examine the morphology and size distribution of a nanoparticle composition. Dynamic light scattering or potentiometry (e.g., potentiometric titrations) can be used to measure zeta potentials. Dynamic light scattering can also be utilized to determine particle sizes. Instruments such as the Zetasizer Nano ZS (Malvern Instruments Ltd, Malvern, Worcestershire, UK) can also be used to measure multiple characteristics of a nanoparticle composition, such as particle size, polydispersity index, and zeta potential.

The size of the nanoparticles can help counter biological reactions such as, but not limited to, inflammation, or can increase the biological effect of the polynucleotide.

As used herein, "size" or "mean size" in the context of nanoparticle compositions refers to the mean diameter of a nanoparticle composition.

In one embodiment, the polynucleotide encoding a GLA polypeptide are formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm. In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 µm or shorter (e.g., 1 µm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition can be relatively homogenous. A polydispersity index can be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition disclosed herein can be from about 0.10 to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition disclosed herein can be from about −10 mV to about +20 mV, from about −10 mV to about +15 mV, from about 10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the zeta potential of the lipid nanoparticles can be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about 30 mV, from about 0 mV to about 20 mV, from about 0 mV to about 10 mV, from about 10 mV to about 100 mV, from about 10 mV to about 90 mV, from about 10 mV to about 80 mV, from about 10 mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 20 mV to about 30 mV, from about 30 mV to about 100 mV, from about 30 mV to about 90 mV, from about 30 mV to about 80 mV, from about 30 mV to about 70 mV, from about 30 mV to about 60 mV, from about 30 mV to about 50 mV, from about 30 mV to about 40 mV, from about 40 mV to about 100 mV, from about 40 mV to about 90 mV, from about 40 mV to about 80 mV, from about 40 mV to about 70 mV, from about 40 mV to about 60 mV, and from about 40 mV to about 50 mV. In some embodiments, the zeta potential of the lipid nanoparticles can be from about 10 mV to about 50 mV, from about 15 mV to about 45 mV, from about 20 mV to about 40 mV, and from about 25 mV to about 35 mV. In some embodiments, the zeta potential of the lipid nanoparticles can be about 10 mV, about 20 mV, about 30 mV, about 40 mV, about 50 mV, about 60 mV, about 70 mV, about 80 mV, about 90 mV, and about 100 mV.

The term "encapsulation efficiency" of a polynucleotide describes the amount of the polynucleotide that is encapsulated by or otherwise associated with a nanoparticle composition after preparation, relative to the initial amount provided. As used herein, "encapsulation" can refer to complete, substantial, or partial enclosure, confinement, surrounding, or encasement.

Encapsulation efficiency is desirably high (e.g., close to 100%). The encapsulation efficiency can be measured, for example, by comparing the amount of the polynucleotide in a solution containing the nanoparticle composition before and after breaking up the nanoparticle composition with one or more organic solvents or detergents.

Fluorescence can be used to measure the amount of free polynucleotide in a solution. For the nanoparticle compositions described herein, the encapsulation efficiency of a polynucleotide can be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency can be at least 80%. In certain embodiments, the encapsulation efficiency can be at least 90%.

The amount of a polynucleotide present in a pharmaceutical composition disclosed herein can depend on multiple factors such as the size of the polynucleotide, desired target and/or application, or other properties of the nanoparticle composition as well as on the properties of the polynucleotide.

For example, the amount of an mRNA useful in a nanoparticle composition can depend on the size (expressed as length, or molecular mass), sequence, and other characteristics of the mRNA. The relative amounts of a polynucleotide in a nanoparticle composition can also vary.

The relative amounts of the lipid composition and the polynucleotide present in a lipid nanoparticle composition of the present disclosure can be optimized according to considerations of efficacy and tolerability. For compositions including an mRNA as a polynucleotide, the N:P ratio can serve as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition.

In general, a lower N:P ratio is preferred. The one or more RNA, lipids, and amounts thereof can be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio can be from about 2:1 to about 8:1. In other embodiments, the N:P ratio is from about 5:1 to about 8:1. In certain embodiments, the N:P ratio is between 5:1 and 6:1. In one specific aspect, the N:P ratio is about is about 5.67:1.

In addition to providing nanoparticle compositions, the present disclosure also provides methods of producing lipid nanoparticles comprising encapsulating a polynucleotide. Such method comprises using any of the pharmaceutical compositions disclosed herein and producing lipid nanoparticles in accordance with methods of production of lipid nanoparticles known in the art. See, e.g., Wang et al. (2015) "Delivery of oligonucleotides with lipid nanoparticles" Adv. Drug Deliv. Rev. 87:68-80; Silva et al. (2015) "Delivery Systems for Biopharmaceuticals. Part I: Nanoparticles and Microparticles" Curr. Pharm. Technol. 16: 940-954; Naseri et al. (2015) "Solid Lipid Nanoparticles and Nanostructured Lipid Carriers: Structure, Preparation and Application" Adv. Pharm. Bull. 5:305-13; Silva et al. (2015) "Lipid nanoparticles for the delivery of biopharmaceuticals" Curr. Pharm. Biotechnol. 16:291-302, and references cited therein.

23. Other Delivery Agents a. Liposomes, Lipoplexes, and Lipid Nanoparticles

In some embodiments, the compositions or formulations of the present disclosure comprise a delivery agent, e.g., a liposome, a lipoplex, a lipid nanoparticle, or any combination thereof. The polynucleotides described herein (e.g., a polynucleotide comprising a nucleotide sequence encoding a GLA polypeptide) can be formulated using one or more liposomes, lipoplexes, or lipid nanoparticles. Liposomes, lipoplexes, or lipid nanoparticles can be used to improve the efficacy of the polynucleotides directed protein production as these formulations can increase cell transfection by the polynucleotide; and/or increase the translation of encoded protein. The liposomes, lipoplexes, or lipid nanoparticles can also be used to increase the stability of the polynucleotides.

Liposomes are artificially-prepared vesicles that can primarily be composed of a lipid bilayer and can be used as a delivery vehicle for the administration of pharmaceutical formulations. Liposomes can be of different sizes. A multilamellar vesicle (MLV) can be hundreds of nanometers in diameter, and can contain a series of concentric bilayers separated by narrow aqueous compartments. A small unicellular vesicle (SUV) can be smaller than 50 nm in diameter, and a large unilamellar vesicle (LUV) can be between 50 and 500 nm in diameter. Liposome design can include, but is not limited to, opsonins or ligands to improve the attachment of liposomes to unhealthy tissue or to activate events such as, but not limited to, endocytosis. Liposomes can contain a low or a high pH value in order to improve the delivery of the pharmaceutical formulations.

The formation of liposomes can depend on the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimal size, polydispersity and the shelf-life of the vesicles for the intended application, and the batch-to-batch reproducibility and scale up production of safe and efficient liposomal products, etc.

As a non-limiting example, liposomes such as synthetic membrane vesicles can be prepared by the methods, apparatus and devices described in U.S. Pub. Nos. US20130177638, US20130177637, US20130177636, US20130177635, US20130177634, US20130177633, US20130183375, US20130183373, and US20130183372. In some embodiments, the polynucleotides described herein can be encapsulated by the liposome and/or it can be contained in an aqueous core that can then be encapsulated by the liposome as described in, e.g., Intl. Pub. Nos. WO2012031046, WO2012031043, WO2012030901, WO2012006378, and WO2013086526; and U.S. Pub. Nos. US20130189351, US20130195969 and US20130202684. Each of the references in herein incorporated by reference in its entirety.

In some embodiments, the polynucleotides described herein can be formulated in a cationic oil-in-water emulsion where the emulsion particle comprises an oil core and a cationic lipid that can interact with the polynucleotide anchoring the molecule to the emulsion particle. In some embodiments, the polynucleotides described herein can be formulated in a water-in-oil emulsion comprising a continuous hydrophobic phase in which the hydrophilic phase is dispersed. Exemplary emulsions can be made by the methods described in Intl. Pub. Nos. WO2012006380 and WO201087791, each of which is herein incorporated by reference in its entirety.

In some embodiments, the polynucleotides described herein can be formulated in a lipid-polycation complex. The formation of the lipid-polycation complex can be accomplished by methods as described in, e.g., U.S. Pub. No. US20120178702. As a non-limiting example, the polycation can include a cationic peptide or a polypeptide such as, but not limited to, polylysine, polyornithine and/or polyarginine and the cationic peptides described in Intl. Pub. No. WO2012013326 or U.S. Pub. No. US20130142818. Each of the references is herein incorporated by reference in its entirety.

In some embodiments, the polynucleotides described herein can be formulated in a lipid nanoparticle (LNP) such as those described in Intl. Pub. Nos. WO2013123523, WO2012170930, WO2011127255 and WO2008103276; and U.S. Pub. No. US20130171646, each of which is herein incorporated by reference in its entirety.

Lipid nanoparticle formulations typically comprise one or more lipids. In some embodiments, the lipid is an ionizable lipid (e.g., an ionizable amino lipid), sometimes referred to in the art as an "ionizable cationic lipid." In some embodiments, lipid nanoparticle formulations further comprise other components, including a phospholipid, a structural lipid, and a molecule capable of reducing particle aggregation, for example a PEG or PEG-modified lipid.

Exemplary ionizable lipids include, but not limited to, any one of Compounds 1-342 disclosed herein, DLin-MC3-DMA (MC3), DLin-DMA, DLenDMA, DLin-D-DMA, DLin-K-DMA, DLin-M-C2-DMA, DLin-K-DMA, DLin-KC2-DMA, DLin-KC3-DMA, DLin-KC4-DMA, DLin-C2K-DMA, DLin-MP-DMA, DODMA, 98N12-5, C12-200, DLin-C-DAP, DLin-DAC, DLinDAP, DLinAP, DLin-EG-DMA, DLin-2-DMAP, KL10, KL22, KL25, Octyl-CLinDMA, Octyl-CLinDMA (2R), Octyl-CLinDMA (2S), and any combination thereof. Other exemplary ionizable lipids include, (13Z,16Z)—N,N-dimethyl-3-nonyldocosa-13,16-dien-1-amine (L608), (20Z,23Z)—N,N-dimethyl-nonacosa-20,23-dien-10-amine, (17Z,20Z)—N,N-dimemyl-hexacosa-17,20-dien-9-amine, (16Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N, N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyleptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, N,N-dimethyl-1-[(1S,2R)-2-octylcyclopropyl]eptadecan-8-amine, 1-[(1S,2R)-2-hexyl cyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl]heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yl oxy]-3-(octyl oxy)propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-

[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z, 16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z, 12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl]oxy}-3-(octyloxy)propan-2-amine, and (11E,20Z,23Z)—N,N-dimethylnonacosa-11,20,2-trien-10-amine, and any combination thereof.

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin. In some embodiments, the phospholipids are DLPC, DMPC, DOPC, DPPC, DSPC, DUPC, 18:0 Diether PC, DLnPC, DAPC, DHAPC, DOPE, 4ME 16:0 PE, DSPE, DLPE, DLnPE, DAPE, DHAPE, DOPG, and any combination thereof. In some embodiments, the phospholipids are MPPC, MSPC, PMPC, PSPC, SMPC, SPPC, DHAPE, DOPG, and any combination thereof. In some embodiments, the amount of phospholipids (e.g., DSPC) in the lipid composition ranges from about 1 mol % to about 20 mol %.

The structural lipids include sterols and lipids containing sterol moieties. In some embodiments, the structural lipids include cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol. In some embodiments, the amount of the structural lipids (e.g., cholesterol) in the lipid composition ranges from about 20 mol % to about 60 mol %.

The PEG-modified lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG DMPE, PEG-DPPC, or a PEG-DSPE lipid. In some embodiments, the PEG-lipid are 1,2-dimyristoyl-sn-glycerol methoxypolyethylene glycol (PEG-DMG), 1,2-distearoyl-sn-glycero-3-phosphoethanolamine-N-[amino(polyethylene glycol)](PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidyletanolamine (PEG-DPPE), or PEG-1,2-dimyristyloxlpropyl-3-amine (PEG-c-DMA). In some embodiments, the PEG moiety has a size of about 1000, 2000, 5000, 10,000, 15,000 or 20,000 daltons. In some embodiments, the amount of PEG-lipid in the lipid composition ranges from about 0.1 mol % to about 5 mol %.

In some embodiments, the LNP formulations described herein can additionally comprise a permeability enhancer molecule. Non-limiting permeability enhancer molecules are described in U.S. Pub. No. US20050222064, herein incorporated by reference in its entirety.

The LNP formulations can further contain a phosphate conjugate. The phosphate conjugate can increase in vivo circulation times and/or increase the targeted delivery of the nanoparticle. Phosphate conjugates can be made by the methods described in, e.g., Intl. Pub. No. WO2013033438 or U.S. Pub. No. US20130196948. The LNP formulation can also contain a polymer conjugate (e.g., a water soluble conjugate) as described in, e.g., U.S. Pub. Nos. US20130059360, US20130196948, and US20130072709. Each of the references is herein incorporated by reference in its entirety.

The LNP formulations can comprise a conjugate to enhance the delivery of nanoparticles of the present invention in a subject. Further, the conjugate can inhibit phagocytic clearance of the nanoparticles in a subject. In some embodiments, the conjugate can be a "self" peptide designed from the human membrane protein CD47 (e.g., the "self" particles described by Rodriguez et al, Science 2013 339, 971-975, herein incorporated by reference in its entirety). As shown by Rodriguez et al. the self peptides delayed macrophage-mediated clearance of nanoparticles which enhanced delivery of the nanoparticles.

The LNP formulations can comprise a carbohydrate carrier. As a non-limiting example, the carbohydrate carrier can include, but is not limited to, an anhydride-modified phytoglycogen or glycogen-type material, phytoglycogen octenyl succinate, phytoglycogen beta-dextrin, anhydride-modified phytoglycogen beta-dextrin (e.g., Intl. Pub. No. WO2012109121, herein incorporated by reference in its entirety).

The LNP formulations can be coated with a surfactant or polymer to improve the delivery of the particle. In some embodiments, the LNP can be coated with a hydrophilic coating such as, but not limited to, PEG coatings and/or coatings that have a neutral surface charge as described in U.S. Pub. No. US20130183244, herein incorporated by reference in its entirety.

The LNP formulations can be engineered to alter the surface properties of particles so that the lipid nanoparticles can penetrate the mucosal barrier as described in U.S. Pat. No. 8,241,670 or Intl. Pub. No. WO2013110028, each of which is herein incorporated by reference in its entirety.

The LNP engineered to penetrate mucus can comprise a polymeric material (i.e., a polymeric core) and/or a polymer-vitamin conjugate and/or a tri-block co-polymer. The polymeric material can include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates.

LNP engineered to penetrate mucus can also include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4 dornase alfa, neltenexine, erdosteine) and various DNases including rhDNase.

In some embodiments, the mucus penetrating LNP can be a hypotonic formulation comprising a mucosal penetration enhancing coating. The formulation can be hypotonic for the epithelium to which it is being delivered. Non-limiting examples of hypotonic formulations can be found in, e.g., Intl. Pub. No. WO2013110028, herein incorporated by reference in its entirety.

In some embodiments, the polynucleotide described herein is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In some embodiments, the polynucleotides described herein are formulated as a solid lipid nanoparticle (SLN), which can be spherical with an average diameter between 10 to 1000 nm. SLN possess a solid lipid core matrix that can solubilize lipophilic molecules and can be stabilized with surfactants and/or emulsifiers. Exemplary SLN can be those as described in Intl. Pub. No. WO2013105101, herein incorporated by reference in its entirety.

In some embodiments, the polynucleotides described herein can be formulated for controlled release and/or targeted delivery. As used herein, "controlled release" refers to a pharmaceutical composition or compound release profile that conforms to a particular pattern of release to effect a therapeutic outcome. In one embodiment, the polynucleotides can be encapsulated into a delivery agent described herein and/or known in the art for controlled release and/or targeted delivery. As used herein, the term "encapsulate" means to enclose, surround or encase. As it relates to the formulation of the compounds of the invention, encapsulation can be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the invention can be enclosed, surrounded or encased within the delivery agent. "Partially encapsulation" means that less than 10, 10, 20, 30, 40 50 or less of the pharmaceutical composition or compound of the invention can be enclosed, surrounded or encased within the delivery agent.

Advantageously, encapsulation can be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the invention are encapsulated in the delivery agent.

In some embodiments, the polynucleotide controlled release formulation can include at least one controlled release coating (e.g., OPADRY®, EUDRAGIT RL®, EUDRAGIT RS® and cellulose derivatives such as ethylcellulose aqueous dispersions (AQUACOAT® and SURELEASE®)). In some embodiments, the polynucleotide controlled release formulation can comprise a polymer system as described in U.S. Pub. No. US20130130348, or a PEG and/or PEG related polymer derivative as described in U.S. Pat. No. 8,404,222, each of which is incorporated by reference in its entirety.

In some embodiments, the polynucleotides described herein can be encapsulated in a therapeutic nanoparticle, referred to herein as "therapeutic nanoparticle polynucleotides." Therapeutic nanoparticles can be formulated by methods described in, e.g., Intl. Pub. Nos. WO2010005740, WO2010030763, WO2010005721, WO2010005723, and WO2012054923; and U.S. Pub. Nos. US20110262491, US20100104645, US20100087337, US20100068285, US20110274759, US20100068286, US20120288541, US20120140790, US20130123351 and US20130230567; and U.S. Pat. Nos. 8,206,747, 8,293,276, 8,318,208 and 8,318,211, each of which is herein incorporated by reference in its entirety.

In some embodiments, the therapeutic nanoparticle polynucleotide can be formulated for sustained release. As used herein, "sustained release" refers to a pharmaceutical composition or compound that conforms to a release rate over a specific period of time. The period of time can include, but is not limited to, hours, days, weeks, months and years. As a non-limiting example, the sustained release nanoparticle of the polynucleotides described herein can be formulated as disclosed in Intl. Pub. No. WO2010075072 and U.S. Pub. Nos. US20100216804, US20110217377, US20120201859 and US20130150295, each of which is herein incorporated by reference in their entirety.

In some embodiments, the therapeutic nanoparticle polynucleotide can be formulated to be target specific, such as those described in Intl. Pub. Nos. WO2008121949, WO2010005726, WO2010005725, WO2011084521 and WO2011084518; and U.S. Pub. Nos. US20100069426, US20120004293 and US20100104655, each of which is herein incorporated by reference in its entirety.

The LNPs can be prepared using microfluidic mixers or micromixers. Exemplary microfluidic mixers can include, but are not limited to, a slit interdigitial micromixer including, but not limited to those manufactured by Microinnova (Allerheiligen bei Wildon, Austria) and/or a staggered herringbone micromixer (SHM) (see Zhigaltsev et al., "Bottom-up design and synthesis of limit size lipid nanoparticle systems with aqueous and triglyceride cores using millisecond microfluidic mixing," Langmuir 28:3633-40 (2012); Belliveau et al., "Microfluidic synthesis of highly potent limit-size lipid nanoparticles for in vivo delivery of siRNA," Molecular Therapy-Nucleic Acids. 1:e37 (2012); Chen et al., "Rapid discovery of potent siRNA-containing lipid nanoparticles enabled by controlled microfluidic formulation," J. Am. Chem. Soc. 134(16):6948-51 (2012); each of which is herein incorporated by reference in its entirety). Exemplary micromixers include Slit Interdigital Microstructured Mixer (SIMM-V2) or a Standard Slit Interdigital Micro Mixer (SSIMM) or Caterpillar (CPMM) or Impinging-jet (IJMM,) from the Institut für Mikrotechnik Mainz GmbH, Mainz Germany. In some embodiments, methods of making LNP using SHM further comprise mixing at least two input streams wherein mixing occurs by microstructure-induced chaotic advection (MICA). According to this method, fluid streams flow through channels present in a herringbone pattern causing rotational flow and folding the fluids around each other. This method can also comprise a surface for fluid mixing wherein the surface changes orientations during fluid cycling. Methods of generating LNPs using SHM include those disclosed in U.S. Pub. Nos.

US20040262223 and US20120276209, each of which is incorporated herein by reference in their entirety.

In some embodiments, the polynucleotides described herein can be formulated in lipid nanoparticles using microfluidic technology (see Whitesides, George M., "The Origins and the Future of Microfluidics," Nature 442: 368-373 (2006); and Abraham et al., "Chaotic Mixer for Microchannels," Science 295: 647-651 (2002); each of which is herein incorporated by reference in its entirety). In some embodiments, the polynucleotides can be formulated in lipid nanoparticles using a micromixer chip such as, but not limited to, those from Harvard Apparatus (Holliston, Mass.) or Dolomite Microfluidics (Royston, UK). A micromixer chip can be used for rapid mixing of two or more fluid streams with a split and recombine mechanism.

In some embodiments, the polynucleotides described herein can be formulated in lipid nanoparticles having a diameter from about 1 nm to about 100 nm such as, but not limited to, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles can have a diameter from about 10 to 500 nm. In one embodiment, the lipid nanoparticle can have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the polynucleotides can be delivered using smaller LNPs. Such particles can comprise a diameter from below 0.1 μm up to 100 nm such as, but not limited to, less than 0.1 μm, less than 1.0 μm, less than 5 μm, less than 10 μm, less than 15 μm, less than 20 μm, less than 25 μm, less than 30 μm, less than 35 μm, less than 40 μm, less than 50 μm, less than 55 μm, less than 60 μm, less than 65 μm, less than 70 μm, less than 75 μm, less than 80 μm, less than 85 μm, less than 90 μm, less than 95 μm, less than 100 μm, less than 125 μm, less than 150 μm, less than 175 μm, less than 200 μm, less than 225 μm, less than 250 μm, less than 275 μm, less than 300 μm, less than 325 μm, less than 350 μm, less than 375 μm, less than 400 μm, less than 425 μm, less than 450 μm, less than 475 μm, less than 500 μm, less than 525 μm, less than 550 μm, less than 575 μm, less than 600 μm, less than 625 μm, less than 650 μm, less than 675 μm, less than 700 μm, less than 725 μm, less than 750 μm, less than 775 μm, less than 800 μm, less than 825 μm, less than 850 μm, less than 875 μm, less than 900 μm, less than 925 μm, less than 950 μm, or less than 975 μm.

The nanoparticles and microparticles described herein can be geometrically engineered to modulate macrophage and/or the immune response. The geometrically engineered particles can have varied shapes, sizes and/or surface charges to incorporate the polynucleotides described herein for targeted delivery such as, but not limited to, pulmonary delivery (see, e.g., Intl. Pub. No. WO2013082111, herein incorporated by reference in its entirety). Other physical features the geometrically engineering particles can include, but are not limited to, fenestrations, angled arms, asymmetry and surface roughness, charge that can alter the interactions with cells and tissues.

In some embodiment, the nanoparticles described herein are stealth nanoparticles or target-specific stealth nanoparticles such as, but not limited to, those described in U.S. Pub. No. US20130172406, herein incorporated by reference in its entirety. The stealth or target-specific stealth nanoparticles can comprise a polymeric matrix, which can comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates, or combinations thereof.

b. Lipidoids

In some embodiments, the compositions or formulations of the present disclosure comprise a delivery agent, e.g., a lipidoid. The polynucleotides described herein (e.g., a polynucleotide comprising a nucleotide sequence encoding a GLA polypeptide) can be formulated with lipidoids. Complexes, micelles, liposomes or particles can be prepared containing these lipidoids and therefore to achieve an effective delivery of the polynucleotide, as judged by the production of an encoded protein, following the injection of a lipidoid formulation via localized and/or systemic routes of administration. Lipidoid complexes of polynucleotides can be administered by various means including, but not limited to, intravenous, intramuscular, or subcutaneous routes.

The synthesis of lipidoids is described in literature (see Mahon et al., Bioconjug. Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

Formulations with the different lipidoids, including, but not limited to penta[3-(1-laurylaminopropionyl)]-triethylenetetramine hydrochloride (TETA-5LAP; also known as 98N12-5, see Murugaiah et al., Analytical Biochemistry, 401:61 (2010)), C12-200 (including derivatives and variants), and MD1, can be tested for in vivo activity. The lipidoid "98N12-5" is disclosed by Akinc et al., Mol Ther.

2009 17:872-879. The lipidoid "C12-200" is disclosed by Love et al., Proc Natl Acad Sci USA. 2010 107:1864-1869 and Liu and Huang, Molecular Therapy. 2010 669-670. Each of the references is herein incorporated by reference in its entirety.

In one embodiment, the polynucleotides described herein can be formulated in an aminoalcohol lipidoid. Aminoalcohol lipidoids can be prepared by the methods described in U.S. Pat. No. 8,450,298 (herein incorporated by reference in its entirety).

The lipidoid formulations can include particles comprising either 3 or 4 or more components in addition to polynucleotides. Lipidoids and polynucleotide formulations comprising lipidoids are described in Intl. Pub. No. WO 2015051214 (herein incorporated by reference in its entirety.

c. Hyaluronidase

In some embodiments, the polynucleotides described herein (e.g., a polynucleotide comprising a nucleotide sequence encoding a GLA polypeptide) and hyaluronidase for injection (e.g., intramuscular or subcutaneous injection). Hyaluronidase catalyzes the hydrolysis of hyaluronan, which is a constituent of the interstitial barrier. Hyaluronidase lowers the viscosity of hyaluronan, thereby increases tissue permeability (Frost, Expert Opin. Drug Deliv. (2007) 4:427-440). Alternatively, the hyaluronidase can be used to increase the number of cells exposed to the polynucleotides administered intramuscularly or subcutaneously.

Nanoparticle Mimics

In some embodiments, the polynucleotides described herein (e.g., a polynucleotide comprising a nucleotide sequence encoding a GLA polypeptide) is encapsulated within and/or absorbed to a nanoparticle mimic. A nanoparticle mimic can mimic the delivery function organisms or particles such as, but not limited to, pathogens, viruses, bacteria, fungus, parasites, prions and cells. As a non-limiting example, the polynucleotides described herein can be encapsulated in a non-viron particle that can mimic the delivery function of a virus (see e.g., Intl. Pub. No. WO2012006376 and U.S. Pub. Nos. US20130171241 and US20130195968, each of which is herein incorporated by reference in its entirety).

e. Nanotubes

In some embodiments, the compositions or formulations of the present disclosure comprise the polynucleotides described herein (e.g., a polynucleotide comprising a nucleotide sequence encoding a GLA polypeptide) attached or otherwise bound to (e.g., through steric, ionic, covalent and/or other forces) at least one nanotube, such as, but not limited to, rosette nanotubes, rosette nanotubes having twin bases with a linker, carbon nanotubes and/or single-walled carbon nanotubes. Nanotubes and nanotube formulations comprising a polynucleotide are described in, e.g., Intl. Pub. No. WO2014152211, herein incorporated by reference in its entirety.

f. Self-Assembled Nanoparticles, or Self-Assembled Macromolecules

In some embodiments, the compositions or formulations of the present disclosure comprise the polynucleotides described herein (e.g., a polynucleotide comprising a nucleotide sequence encoding a GLA polypeptide) in self-assembled nanoparticles, or amphiphilic macromolecules (AMs) for delivery. AMs comprise biocompatible amphiphilic polymers that have an alkylated sugar backbone covalently linked to poly(ethylene glycol). In aqueous solution, the AMs self-assemble to form micelles. Nucleic acid self-assembled nanoparticles are described in Intl. Appl. No. PCT/US2014/027077, and AMs and methods of forming AMs are described in U.S. Pub. No. US20130217753, each of which is herein incorporated by reference in its entirety.

g. Inorganic Nanoparticles, Semi-Conductive and Metallic Nanoparticles

In some embodiments, the compositions or formulations of the present disclosure comprise the polynucleotides described herein (e.g., a polynucleotide comprising a nucleotide sequence encoding a GLA polypeptide) in inorganic nanoparticles, or water-dispersible nanoparticles comprising a semiconductive or metallic material. The inorganic nanoparticles can include, but are not limited to, clay substances that are water swellable. The water-dispersible nanoparticles can be hydrophobic or hydrophilic nanoparticles. As a non-limiting example, the inorganic, semiconductive and metallic nanoparticles are described in, e.g., U.S. Pat. Nos. 5,585,108 and 8,257,745; and U.S. Pub. Nos. US20120228565, US 20120265001 and US 20120283503, each of which is herein incorporated by reference in their entirety.

h. Surgical Sealants: Gels and Hydrogels

In some embodiments, the compositions or formulations of the present disclosure comprise the polynucleotides described herein (e.g., a polynucleotide comprising a nucleotide sequence encoding a GLA polypeptide) in a surgical sealant. Surgical sealants such as gels and hydrogels are described in Intl. Appl. No. PCT/US2014/027077, herein incorporated by reference in its entirety.

i. Suspension Formulations

In some embodiments, the compositions or formulations of the present disclosure comprise the polynucleotides described herein (e.g., a polynucleotide comprising a nucleotide sequence encoding a GLA polypeptide) in suspensions. In some embodiments, suspensions comprise a polynucleotide, water immiscible oil depots, surfactants and/or co-surfactants and/or co-solvents. Suspensions can be formed by first preparing an aqueous solution of a polynucleotide and an oil-based phase comprising one or more surfactants, and then mixing the two phases (aqueous and oil-based).

Exemplary oils for suspension formulations can include, but are not limited to, sesame oil and Miglyol (comprising esters of saturated coconut and palm kernel oil-derived caprylic and capric fatty acids and glycerin or propylene glycol), corn oil, soybean oil, peanut oil, beeswax and/or palm seed oil. Exemplary surfactants can include, but are not limited to Cremophor, polysorbate 20, polysorbate 80, polyethylene glycol, transcutol, Capmul®, labrasol, isopropyl myristate, and/or Span 80. In some embodiments, suspensions can comprise co-solvents including, but not limited to ethanol, glycerol and/or propylene glycol.

In some embodiments, suspensions can provide modulation of the release of the polynucleotides into the surrounding environment by diffusion from a water immiscible depot followed by resolubilization into a surrounding environment (e.g., an aqueous environment).

In some embodiments, the polynucleotides can be formulated such that upon injection, an emulsion forms spontaneously (e.g., when delivered to an aqueous phase), which can provide a high surface area to volume ratio for release of polynucleotides from an oil phase to an aqueous phase. In some embodiments, the polynucleotide is formulated in a nanoemulsion, which can comprise a liquid hydrophobic core surrounded by or coated with a lipid or surfactant layer. Exemplary nanoemulsions and their preparations are described in, e.g., U.S. Pat. No. 8,496,945, herein incorporated by reference in its entirety.

j. Cations and Anions

In some embodiments, the compositions or formulations of the present disclosure comprise the polynucleotides described herein (e.g., a polynucleotide comprising a nucleotide sequence encoding a GLA polypeptide) and a cation or anion, such as $Zn^{2+}$, $Ca^{2+}$, $Cu^{2+}$, $Mg^{2+}$ and combinations thereof. Exemplary formulations can include polymers and a polynucleotide complexed with a metal cation as described in, e.g., U.S. Pat. Nos. 6,265,389 and 6,555,525, each of which is herein incorporated by reference in its entirety. In some embodiments, cationic nanoparticles can contain a combination of divalent and monovalent cations. The delivery of polynucleotides in cationic nanoparticles or in one or more depot comprising cationic nanoparticles can improve polynucleotide bioavailability by acting as a long-acting depot and/or reducing the rate of degradation by nucleases.

k Molded Nanoparticles and Microparticles

In some embodiments, the compositions or formulations of the present disclosure comprise the polynucleotides described herein (e.g., a polynucleotide comprising a nucleotide sequence encoding a GLA polypeptide) in molded nanoparticles in various sizes, shapes and chemistry. For example, the nanoparticles and/or microparticles can be made using the PRINT® technology by LIQUIDA TECHNOLOGIES® (Morrisville, N.C.) (e.g., International Pub. No. WO2007024323, herein incorporated by reference in its entirety).

In some embodiments, the polynucleotides described herein (e.g., a polynucleotide comprising a nucleotide sequence encoding a GLA polypeptide) is formulated in microparticles. The microparticles can contain a core of the polynucleotide and a cortex of a biocompatible and/or biodegradable polymer, including but not limited to, poly (α-hydroxy acid), a polyhydroxy butyric acid, a polycaprolactone, a polyorthoester and a polyanhydride. The microparticle can have adsorbent surfaces to adsorb polynucleotides. The microparticles can have a diameter of from at least 1 micron to at least 100 microns (e.g., at least 1 micron, at least 10 micron, at least 20 micron, at least 30 micron, at least 50 micron, at least 75 micron, at least 95 micron, and at least 100 micron). In some embodiment, the compositions or formulations of the present disclosure are microemulsions comprising microparticles and polynucleotides. Exemplary microparticles, microemulsions and their preparations are described in, e.g., U.S. Pat. Nos. 8,460,709, 8,309,139 and 8,206,749; U.S. Pub. Nos. US20130129830, US2013195923 and US20130195898; and Intl. Pub. No. WO2013075068, each of which is herein incorporated by reference in its entirety.

l. NanoJackets and NanoLiposomes

In some embodiments, the compositions or formulations of the present disclosure comprise the polynucleotides described herein (e.g., a polynucleotide comprising a nucleotide sequence encoding a GLA polypeptide) in NanoJackets and NanoLiposomes by Keystone Nano (State College, Pa.). NanoJackets are made of materials that are naturally found in the body including calcium, phosphate and can also include a small amount of silicates. Nanojackets can have a size ranging from 5 to 50 nm.

NanoLiposomes are made of lipids such as, but not limited to, lipids that naturally occur in the body. NanoLiposomes can have a size ranging from 60-80 nm. In some embodiments, the polynucleotides disclosed herein are formulated in a NanoLiposome such as, but not limited to, Ceramide NanoLiposomes.

m. Cells or Minicells

In some embodiments, the compositions or formulations of the present disclosure comprise the polynucleotides described herein (e.g., a polynucleotide comprising a nucleotide sequence encoding a GLA polypeptide) that is transfected ex vivo into cells, which are subsequently transplanted into a subject. Cell-based formulations of the polynucleotide disclosed herein can be used to ensure cell transfection (e.g., in the cellular carrier), alter the biodistribution of the polynucleotide (e.g., by targeting the cell carrier to specific tissues or cell types), and/or increase the translation of encoded protein.

Exemplary cells include, but are not limited to, red blood cells, virosomes, and electroporated cells (see e.g., Godfrin et al., Expert Opin Biol Ther. 2012 12:127-133; Fang et al., Expert Opin Biol Ther. 2012 12:385-389; Hu et al., Proc Natl Acad Sci USA. 2011 108:10980-10985; Lund et al., Pharm Res. 2010 27:400-420; Huckriede et al., J Liposome Res. 2007; 17:39-47; Cusi, Hum Vaccin. 2006 2:1-7; de Jonge et al., Gene Ther. 2006 13:400-411; all of which are herein incorporated by reference in its entirety).

A variety of methods are known in the art and are suitable for introduction of nucleic acid into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion.

In some embodiments, the polynucleotides described herein can be delivered in synthetic virus-like particles (VLPs) synthesized by the methods as described in Intl. Pub Nos. WO2011085231 and WO2013116656; and U.S. Pub. No. 20110171248, each of which is herein incorporated by reference in its entirety.

The technique of sonoporation, or cellular sonication, is the use of sound (e.g., ultrasonic frequencies) for modifying the permeability of the cell plasma membrane. Sonoporation methods are known to deliver nucleic acids in vivo (Yoon and Park, Expert Opin Drug Deliv. 2010 7:321-330; Postema and Gilj a, Curr Pharm Biotechnol. 2007 8:355-361; Newman and Bettinger, Gene Ther. 2007 14:465-475; U.S. Pub. Nos. US20100196983 and US20100009424; all herein incorporated by reference in their entirety).

In some embodiments, the polynucleotides described herein can be delivered by electroporation. Electroporation techniques are known to deliver nucleic acids in vivo and clinically (Andre et al., Curr Gene Ther. 2010 10:267-280; Chiarella et al., Curr Gene Ther. 2010 10:281-286; Hojman, Curr Gene Ther. 2010 10:128-138; all herein incorporated by reference in their entirety). Electroporation devices are sold by many companies worldwide including, but not limited to BTX® Instruments (Holliston, Mass.) (e.g., the AgilePulse In Vivo System) and Inovio (Blue Bell, Pa.) (e.g., Inovio SP-5P intramuscular delivery device or the CELLECTRA® 3000 intradermal delivery device).

In some embodiments, the cells are selected from the group consisting of mammalian cells, bacterial cells, plant, microbial, algal and fungal cells. In some embodiments, the cells are mammalian cells, such as, but not limited to, human, mouse, rat, goat, horse, rabbit, hamster or cow cells. In a further embodiment, the cells can be from an established cell line, including, but not limited to, HeLa, NSO, SP2/0, KEK 293T, Vero, Caco, Caco-2, MDCK, COS-1, COS-7, K562, Jurkat, CHO-K1, DG44, CHOK1SV, CHO—S, Huvec, CV-1, Huh-7, NIH3T3, HEK293, 293, A549, HepG2, MCF-7, U-20S, Per.C$_6$, SF9, SF21 or Chinese Hamster Ovary (CHO) cells.

In certain embodiments, the cells are fungal cells, such as, but not limited to, *Chrysosporium* cells, *Aspergillus* cells, *Trichoderma* cells, *Dictyostelium* cells, *Candida* cells, *Saccharomyces* cells, *Schizosaccharomyces* cells, and *Penicillium* cells.

In certain embodiments, the cells are bacterial cells such as, but not limited to, *E. coli*, *B. subtilis*, or BL21 cells. Primary and secondary cells to be transfected by the methods of the invention can be obtained from a variety of tissues and include, but are not limited to, all cell types that can be maintained in culture. The primary and secondary cells include, but are not limited to, fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types. Primary cells can also be obtained from a donor of the same species or from another species (e.g., mouse, rat, rabbit, cat, dog, pig, cow, bird, sheep, goat, horse).

In some embodiments, the compositions or formulations of the present disclosure comprise the polynucleotides described herein in bacterial minicells. As a non-limiting example, bacterial minicells can be those described in Intl. Pub. No. WO2013088250 or U.S. Pub. No. US20130177499, each of which is herein incorporated by reference in its entirety.

n. Semi-Solid Compositions

In some embodiments, the compositions or formulations of the present disclosure comprise the polynucleotides described herein (e.g., a polynucleotide comprising a nucleotide sequence encoding a GLA polypeptide) in a hydrophobic matrix to form a semi-solid or paste-like composition. As a non-limiting example, the semi-solid or paste-like composition can be made by the methods described in Intl. Pub. No. WO201307604, herein incorporated by reference in its entirety.

o. Exosomes

In some embodiments, the compositions or formulations of the present disclosure comprise the polynucleotides described herein (e.g., a polynucleotide comprising a nucleotide sequence encoding a GLA polypeptide) in exosomes, which can be loaded with at least one polynucleotide and delivered to cells, tissues and/or organisms. As a non-limiting example, the polynucleotides can be loaded in the exosomes as described in Intl. Pub. No. WO2013084000, herein incorporated by reference in its entirety.

p. Silk-Based Delivery

In some embodiments, the compositions or formulations of the present disclosure comprise the polynucleotides described herein (e.g., a polynucleotide comprising a nucleotide sequence encoding a GLA polypeptide) that is formulated for silk-based delivery. The silk-based delivery system can be formed by contacting a silk fibroin solution with a polynucleotide described herein. As a non-limiting example, a sustained release silk-based delivery system and methods of making such system are described in U.S. Pub. No. US20130177611, herein incorporated by reference in its entirety.

q. Amino Acid Lipids

In some embodiments, the compositions or formulations of the present disclosure comprise the polynucleotides described herein (e.g., a polynucleotide comprising a nucleotide sequence encoding a GLA polypeptide) that is formulation with an amino acid lipid. Amino acid lipids are lipophilic compounds comprising an amino acid residue and one or more lipophilic tails. Non-limiting examples of amino acid lipids and methods of making amino acid lipids are described in U.S. Pat. No. 8,501,824. The amino acid lipid formulations can deliver a polynucleotide in releasable form that comprises an amino acid lipid that binds and releases the polynucleotides. As a non-limiting example, the release of the polynucleotides described herein can be provided by an acid-labile linker as described in, e.g., U.S. Pat. Nos. 7,098,032, 6,897,196, 6,426,086, 7,138,382, 5,563,250, and 5,505,931, each of which is herein incorporated by reference in its entirety.

r. Microvesicles

In some embodiments, the compositions or formulations of the present disclosure comprise the polynucleotides described herein (e.g., a polynucleotide comprising a nucleotide sequence encoding a GLA polypeptide) in a microvesicle formulation. Exemplary microvesicles include those described in U.S. Pub. No. US20130209544 (herein incorporated by reference in its entirety). In some embodiments, the microvesicle is an ARRDC1-mediated microvesicles (ARMMs) as described in Intl. Pub. No. WO2013119602 (herein incorporated by reference in its entirety).

s. Interpolyelectrolyte Complexes

In some embodiments, the compositions or formulations of the present disclosure comprise the polynucleotides described herein (e.g., a polynucleotide comprising a nucleotide sequence encoding a GLA polypeptide) in an interpolyelectrolyte complex. Interpolyelectrolyte complexes are formed when charge-dynamic polymers are complexed with one or more anionic molecules. Non-limiting examples of charge-dynamic polymers and interpolyelectrolyte complexes and methods of making interpolyelectrolyte complexes are described in U.S. Pat. No. 8,524,368, herein incorporated by reference in its entirety.

t. Crystalline Polymeric Systems

In some embodiments, the compositions or formulations of the present disclosure comprise the polynucleotides described herein (e.g., a polynucleotide comprising a nucleotide sequence encoding a GLA polypeptide) in crystalline polymeric systems. Crystalline polymeric systems are polymers with crystalline moieties and/or terminal units comprising crystalline moieties. Exemplary polymers are described in U.S. Pat. No. 8,524,259 (herein incorporated by reference in its entirety).

u. Polymers, Biodegradable Nanoparticles, and Core-Shell Nanoparticles

In some embodiments, the compositions or formulations of the present disclosure comprise the polynucleotides described herein (e.g., a polynucleotide comprising a nucleotide sequence encoding a GLA polypeptide) and a natural and/or synthetic polymer. The polymers include, but not limited to, polyethenes, polyethylene glycol (PEG), poly(1-lysine)(PLL), PEG grafted to PLL, cationic lipopolymer, biodegradable cationic lipopolymer, polyethyleneimine (PEI), cross-linked branched poly(alkylene imines), a polyamine derivative, a modified poloxamer, elastic biodegradable polymer, biodegradable copolymer, biodegradable polyester copolymer, biodegradable polyester copolymer, multiblock copolymers, poly[α-(4-aminobutyl)-L-glycolic acid) (PAGA), biodegradable cross-linked cationic multi-block copolymers, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyureas, polystyrenes, polyamines, polylysine, poly(ethylene imine), poly(serine ester), poly(L-lactide-co-L-lysine), poly(4-hydroxy-L-proline ester), amine-containing polymers, dextran polymers, dextran polymer derivatives or combinations thereof.

Exemplary polymers include, DYNAMIC POLYCONJUGATE® (Arrowhead Research Corp., Pasadena, Calif.) formulations from MIRUS® Bio (Madison, Wis.) and Roche Madison (Madison, Wis.), PHASERX™ polymer formulations such as, without limitation, SMARTT POLYMER TECHNOLOGY™ (PHASERX®, Seattle, Wash.), DMRI/DOPE, poloxamer, VAXFECTIN® adjuvant from Vical (San Diego, Calif.), chitosan, cyclodextrin from Calando Pharmaceuticals (Pasadena, Calif.), dendrimers and poly (lactic-co-glycolic acid) (PLGA) polymers. RONDEL™ (RNAi/Oligonucleotide Nanoparticle Delivery) polymers (Arrowhead Research Corporation, Pasadena, Calif.) and pH responsive co-block polymers such as PHASERX® (Seattle, Wash.).

The polymer formulations allow a sustained or delayed release of the polynucleotide (e.g., following intramuscular or subcutaneous injection). The altered release profile for the polynucleotide can result in, for example, translation of an encoded protein over an extended period of time. The polymer formulation can also be used to increase the stability of the polynucleotide. Sustained release formulations can include, but are not limited to, PLGA microspheres, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc. Deerfield, Ill.), PEG-based sealants, and COSEAL® (Baxter International, Inc. Deerfield, Ill.).

As a non-limiting example modified mRNA can be formulated in PLGA microspheres by preparing the PLGA microspheres with tunable release rates (e.g., days and weeks) and encapsulating the modified mRNA in the PLGA microspheres while maintaining the integrity of the modified mRNA during the encapsulation process. EVAc are non-biodegradable, biocompatible polymers that are used extensively in pre-clinical sustained release implant applications (e.g., extended release products Ocusert a pilocarpine ophthalmic insert for glaucoma or progestasert a sustained release progesterone intrauterine device; transdermal delivery systems Testoderm, Duragesic and Selegiline; catheters). Poloxamer F-407 NF is a hydrophilic, non-ionic surfactant triblock copolymer of polyoxyethylene-polyoxypropylene-polyoxyethylene having a low viscosity at temperatures less than 5° C. and forms a solid gel at temperatures greater than 15° C.

As a non-limiting example, the polynucleotides described herein can be formulated with the polymeric compound of PEG grafted with PLL as described in U.S. Pat. No. 6,177,274. As another non-limiting example, the polynucleotides described herein can be formulated with a block copolymer such as a PLGA-PEG block copolymer (see e.g., U.S. Pub. No. US20120004293 and U.S. Pat. Nos. 8,236,330 and 8,246,968), or a PLGA-PEG-PLGA block copolymer (see e.g., U.S. Pat. No. 6,004,573). Each of the references is herein incorporated by reference in its entirety.

In some embodiments, the polynucleotides described herein can be formulated with at least one amine-containing polymer such as, but not limited to polylysine, polyethylene imine, poly(amidoamine) dendrimers, poly(amine-co-esters) or combinations thereof. Exemplary polyamine polymers and their use as delivery agents are described in, e.g., U.S. Pat. Nos. 8,460,696, 8,236,280, each of which is herein incorporated by reference in its entirety.

In some embodiments, the polynucleotides described herein can be formulated in a biodegradable cationic lipopolymer, a biodegradable polymer, or a biodegradable copolymer, a biodegradable polyester copolymer, a biodegradable polyester polymer, a linear biodegradable copolymer, PAGA, a biodegradable cross-linked cationic multi-block copolymer or combinations thereof as described in, e.g., U.S. Pat. Nos. 6,696,038, 6,517,869, 6,267,987, 6,217,912, 6,652,886, 8,057,821, and 8,444,992; U.S. Pub. Nos. US20030073619, US20040142474, US20100004315, US2012009145 and US20130195920; and Intl Pub. Nos. WO2006063249 and WO2013086322, each of which is herein incorporated by reference in its entirety.

In some embodiments, the polynucleotides described herein can be formulated in or with at least one cyclodextrin polymer as described in U.S. Pub. No. US20130184453. In some embodiments, the polynucleotides described herein can be formulated in or with at least one crosslinked cation-binding polymers as described in Intl. Pub. Nos. WO2013106072, WO2013106073 and WO2013106086. In some embodiments, the polynucleotides described herein can be formulated in or with at least PEGylated albumin polymer as described in U.S. Pub. No. US20130231287. Each of the references is herein incorporated by reference in its entirety.

In some embodiments, the polynucleotides disclosed herein can be formulated as a nanoparticle using a combination of polymers, lipids, and/or other biodegradable agents, such as, but not limited to, calcium phosphate. Components can be combined in a core-shell, hybrid, and/or layer-by-layer architecture, to allow for fine-tuning of the nanoparticle for delivery (Wang et al., Nat Mater. 2006 5:791-796; Fuller et al., Biomaterials. 2008 29:1526-1532; DeKoker et al., Adv Drug Deliv Rev. 2011 63:748-761; Endres et al., Biomaterials. 2011 32:7721-7731; Su et al., Mol Pharm. 2011 Jun. 6; 8(3):774-87; herein incorporated by reference in their entireties). As a non-limiting example, the nanoparticle can comprise a plurality of polymers such as, but not limited to hydrophilic-hydrophobic polymers (e.g., PEG-PLGA), hydrophobic polymers (e.g., PEG) and/or hydrophilic polymers (Intl. Pub. No. WO20120225129, herein incorporated by reference in its entirety).

The use of core-shell nanoparticles has additionally focused on a high-throughput approach to synthesize cationic cross-linked nanogel cores and various shells (Siegwart et al., Proc Natl Acad Sci USA. 2011 108:12996-13001; herein incorporated by reference in its entirety). The complexation, delivery, and internalization of the polymeric nanoparticles can be precisely controlled by altering the chemical composition in both the core and shell components of the nanoparticle. For example, the core-shell nanoparticles can efficiently deliver siRNA to mouse hepatocytes after they covalently attach cholesterol to the nanoparticle.

In some embodiments, a hollow lipid core comprising a middle PLGA layer and an outer neutral lipid layer containing PEG can be used to delivery of the polynucleotides as described herein. In some embodiments, the lipid nanoparticles can comprise a core of the polynucleotides disclosed herein and a polymer shell, which is used to protect the polynucleotides in the core. The polymer shell can be any of the polymers described herein and are known in the art. The polymer shell can be used to protect the polynucleotides in the core.

Core-shell nanoparticles for use with the polynucleotides described herein are described in U.S. Pat. No. 8,313,777 or Intl. Pub. No. WO2013124867, each of which is herein incorporated by reference in their entirety.

v. Peptides and Proteins

In some embodiments, the compositions or formulations of the present disclosure comprise the polynucleotides described herein (e.g., a polynucleotide comprising a nucleotide sequence encoding a GLA polypeptide) that is formulated with peptides and/or proteins to increase transfection of cells by the polynucleotide, and/or to alter the biodistribution of the polynucleotide (e.g., by targeting specific tissues or cell types), and/or increase the translation of encoded protein (e.g., Intl. Pub. Nos. WO2012110636 and WO2013123298. In some embodiments, the peptides can be those described in U.S. Pub. Nos. US20130129726, US20130137644 and US20130164219. Each of the references is herein incorporated by reference in its entirety.

w. Conjugates

In some embodiments, the compositions or formulations of the present disclosure comprise the polynucleotides described herein (e.g., a polynucleotide comprising a nucleotide sequence encoding a GLA polypeptide) that is covalently linked to a carrier or targeting group, or including two encoding regions that together produce a fusion protein (e.g., bearing a targeting group and therapeutic protein or peptide) as a conjugate. The conjugate can be a peptide that selectively directs the nanoparticle to neurons in a tissue or organism, or assists in crossing the blood-brain barrier.

The conjugates include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand can also be a recombinant or synthetic molecule, such as a synthetic polymer, e.g., a synthetic polyamino acid, an oligonucleotide (e.g., an aptamer). Examples of polyamino acids include polyamino acid is a polylysine (PLL), poly L-aspartic acid, poly L-glutamic acid, styrene-maleic acid anhydride copolymer, poly (L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

In some embodiments, the conjugate can function as a carrier for the polynucleotide disclosed herein. The conjugate can comprise a cationic polymer such as, but not limited to, polyamine, polylysine, polyalkylenimine, and polyethylenimine that can be grafted to with poly(ethylene glycol). Exemplary conjugates and their preparations are described in U.S. Pat. No. 6,586,524 and U.S. Pub. No. US20130211249, each of which herein is incorporated by reference in its entirety.

The conjugates can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as an endothelial cell or bone cell. Targeting groups can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent frucose, or aptamers. The ligand can be, for example, a lipopolysaccharide, or an activator of p38 MAP kinase.

The targeting group can be any ligand that is capable of targeting a specific receptor. Examples include, without limitation, folate, GalNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein. As a non-limiting example, the targeting group can be a glutathione receptor (GR)-binding conjugate for targeted delivery across the blood-central nervous system barrier as described in, e.g., U.S. Pub. No. US2013021661012 (herein incorporated by reference in its entirety).

In some embodiments, the conjugate can be a synergistic biomolecule-polymer conjugate, which comprises a long-acting continuous-release system to provide a greater therapeutic efficacy. The synergistic biomolecule-polymer conjugate can be those described in U.S. Pub. No. US20130195799. In some embodiments, the conjugate can be an aptamer conjugate as described in Intl. Pat. Pub. No. WO2012040524. In some embodiments, the conjugate can be an amine containing polymer conjugate as described in U.S. Pat. No. 8,507,653. Each of the references is herein incorporated by reference in its entirety. In some embodiments, the polynucleotides can be conjugated to SMARTT POLYMER TECHNOLOGY® (PHASERX®, Inc. Seattle, Wash.).

In some embodiments, the polynucleotides described herein are covalently conjugated to a cell penetrating polypeptide, which can also include a signal sequence or a targeting sequence. The conjugates can be designed to have increased stability, and/or increased cell transfection; and/or altered the biodistribution (e.g., targeted to specific tissues or cell types).

In some embodiments, the polynucleotides described herein can be conjugated to an agent to enhance delivery. In some embodiments, the agent can be a monomer or polymer such as a targeting monomer or a polymer having targeting blocks as described in Intl. Pub. No. WO2011062965. In some embodiments, the agent can be a transport agent covalently coupled to a polynucleotide as described in, e.g., U.S. Pat. Nos. 6,835.393 and 7,374,778. In some embodiments, the agent can be a membrane barrier transport enhancing agent such as those described in U.S. Pat. Nos. 7,737,108 and 8,003,129. Each of the references is herein incorporated by reference in its entirety.

x. Micro-Organs

In some embodiments, the compositions or formulations of the present disclosure comprise the polynucleotides described herein (e.g., a polynucleotide comprising a nucleotide sequence encoding a GLA polypeptide) in a micro-organ that can then express an encoded polypeptide of interest in a long-lasting therapeutic formulation. Exemplary micro-organs and formulations are described in Intl. Pub. No. WO2014152211 (herein incorporated by reference in its entirety).

y. Pseudovirions

In some embodiments, the compositions or formulations of the present disclosure comprise the polynucleotides described herein (e.g., a polynucleotide comprising a nucleotide sequence encoding a GLA polypeptide) in pseudovirions (e.g., pseudovirions developed by Aura Biosciences, Cambridge, Mass.).

In some embodiments, the pseudovirion used for delivering the polynucleotides can be derived from viruses such as, but not limited to, herpes and papillomaviruses as described in, e.g., U.S. Pub. Nos. US20130012450, US20130012566, US21030012426 and US20120207840; and Intl. Pub. No. WO2013009717, each of which is herein incorporated by reference in its entirety.

The pseudovirion can be a virus-like particle (VLP) prepared by the methods described in U.S. Pub. Nos. US20120015899 and US20130177587, and Intl. Pub. Nos. WO2010047839, WO2013116656, WO2013106525 and WO2013122262. In one aspect, the VLP can be bacteriophages MS, Qfβ, R17, fr, GA, Sp, MI, I, MXI, NL95, AP205, f2, PP7, and the plant viruses Turnip crinkle virus (TCV), Tomato bushy stunt virus (TBSV), Southern bean mosaic virus (SBMV) and members of the genus Bromovirus including Broad bean mottle virus, Brome mosaic virus, Cassia yellow blotch virus, Cowpea chlorotic mottle virus (CCMV), Melandrium yellow fleck virus, and Spring beauty latent virus. In another aspect, the VLP can be derived from the influenza virus as described in U.S. Pub. No. US20130177587 and U.S. Pat. No. 8,506,967. In one aspect, the VLP can comprise a B7-1 and/or B7-2 molecule anchored to a lipid membrane or the exterior of the particle such as described in Intl. Pub. No. WO2013116656. In one aspect, the VLP can be derived from norovirus, rotavirus recombinant VP6 protein or double layered VP2/VP6 such as the VLP as described in Intl. Pub. No. WO2012049366. Each of the references is herein incorporated by reference in its entirety.

In some embodiments, the pseudovirion can be a human papilloma virus-like particle as described in Intl. Pub. No. WO2010120266 and U.S. Pub. No. US20120171290. In some embodiments, the virus-like particle (VLP) can be a self-assembled particle. In one aspect, the pseudovirions can be virion derived nanoparticles as described in U.S. Pub. Nos. US20130116408 and US20130115247; and Intl. Pub. No. WO2013119877. Each of the references is herein incorporated by reference in their entirety.

Non-limiting examples of formulations and methods for formulating the polynucleotides described herein are also provided in Intl. Pub. No WO2013090648 (incorporated herein by reference in their entirety).

24. Accelerated Blood Clearance

The invention provides compounds, compositions and methods of use thereof for reducing the effect of ABC on a repeatedly administered active agent such as a biologically active agent. As will be readily apparent, reducing or eliminating altogether the effect of ABC on an administered active agent effectively increases its half-life and thus its efficacy.

In some embodiments the term reducing ABC refers to any reduction in ABC in comparison to a positive reference control ABC inducing LNP such as an MC3 LNP. ABC inducing LNPs cause a reduction in circulating levels of an active agent upon a second or subsequent administration within a given time frame. Thus a reduction in ABC refers to less clearance of circulating agent upon a second or subsequent dose of agent, relative to a standard LNP. The reduction may be, for instance, at least 10%, 15%, 20%, 25%, 30%, 35%, 40%, 45%, 50%, 55%, 60%, 65%, 70%, 75%, 80%, 85%, 90%, 95%, 98%, or 100%. In some embodiments the reduction is 10-100%, 10-50%, 20-100%, 20-50%, 30-100%, 30-50%, 40%-100%, 40-80%, 50-90%, or 50-100%. Alternatively the reduction in ABC may be characterized as at least a detectable level of circulating agent following a second or subsequent administration or at least a 2 fold, 3 fold, 4 fold, 5 fold increase in circulating agent relative to circulating agent following administration of a standard LNP. In some embodiments the reduction is a 2-100 fold, 2-50 fold, 3-100 fold, 3-50 fold, 3-20 fold, 4-100 fold, 4-50 fold, 4-40 fold, 4-30 fold, 4-25 fold, 4-20 fold, 4-15 fold, 4-10 fold, 4-5 fold, 5-100 fold, 5-50 fold, 5-40 fold, 5-30 fold, 5-25 fold, 5-20 fold, 5-15 fold, 5-10 fold, 6-100 fold, 6-50 fold, 6-40 fold, 6-30 fold, 6-25 fold, 6-20 fold, 6-15 fold, 6-10 fold, 8-100 fold, 8-50 fold, 8-40 fold, 8-30 fold, 8-25 fold, 8-20 fold, 8-15 fold, 8-10 fold, 10-100 fold, 10-50 fold, 10-40 fold, 10-30 fold, 10-25 fold, 10-20 fold, 10-15 fold, 20-100 fold, 20-50 fold, 20-40 fold, 20-30 fold, or 20-25 fold.

The disclosure provides lipid-comprising compounds and compositions that are less susceptible to clearance and thus have a longer half-life in vivo. This is particularly the case where the compositions are intended for repeated including chronic administration, and even more particularly where such repeated administration occurs within days or weeks.

Significantly, these compositions are less susceptible or altogether circumvent the observed phenomenon of accelerated blood clearance (ABC). ABC is a phenomenon in which certain exogenously administered agents are rapidly cleared from the blood upon second and subsequent administrations. This phenomenon has been observed, in part, for a variety of lipid-containing compositions including but not limited to lipidated agents, liposomes or other lipid-based delivery vehicles, and lipid-encapsulated agents. Heretofore, the basis of ABC has been poorly understood and in some cases attributed to a humoral immune response and accordingly strategies for limiting its impact in vivo particularly in a clinical setting have remained elusive.

This disclosure provides compounds and compositions that are less susceptible, if at all susceptible, to ABC. In some important aspects, such compounds and compositions are lipid-comprising compounds or compositions. The lipid-containing compounds or compositions of this disclosure, surprisingly, do not experience ABC upon second and subsequent administration in vivo. This resistance to ABC renders these compounds and compositions particularly suitable for repeated use in vivo, including for repeated use within short periods of time, including days or 1-2 weeks. This enhanced stability and/or half-life is due, in part, to the inability of these compositions to activate B1a and/or B1b cells and/or conventional B cells, pDCs and/or platelets.

This disclosure therefore provides an elucidation of the mechanism underlying accelerated blood clearance (ABC). It has been found, in accordance with this disclosure and the inventions provided herein, that the ABC phenomenon at least as it relates to lipids and lipid nanoparticles is mediated, at least in part an innate immune response involving B1a and/or B1b cells, pDC and/or platelets. B1a cells are normally responsible for secreting natural antibody, in the form of circulating IgM. This IgM is poly-reactive, meaning that it is able to bind to a variety of antigens, albeit with a relatively low affinity for each.

It has been found in accordance with the invention that some lipidated agents or lipid-comprising formulations such as lipid nanoparticles administered in vivo trigger and are subject to ABC. It has now been found in accordance with the invention that upon administration of a first dose of the LNP, one or more cells involved in generating an innate immune response (referred to herein as sensors) bind such agent, are activated, and then initiate a cascade of immune factors (referred to herein as effectors) that promote ABC and toxicity. For instance, B1a and B1b cells may bind to LNP, become activated (alone or in the presence of other sensors such as pDC and/or effectors such as IL6) and secrete natural IgM that binds to the LNP. Pre-existing natural IgM in the subject may also recognize and bind to the LNP, thereby triggering complement fixation. After administration of the first dose, the production of natural IgM begins within 1-2 hours of administration of the LNP. Typically by about 2-3 weeks the natural IgM is cleared from the system due to the natural half-life of IgM. Natural IgG is produced beginning around 96 hours after administration of the LNP. The agent, when administered in a naïve setting, can exert its biological effects relatively unencumbered by the natural IgM produced post-activation of the B1a cells or B1b cells or natural IgG. The natural IgM and natural IgG are non-specific and thus are distinct from anti-PEG IgM and anti-PEG IgG.

Although Applicant is not bound by mechanism, it is proposed that LNPs trigger ABC and/or toxicity through the following mechanisms. It is believed that when an LNP is administered to a subject the LNP is rapidly transported through the blood to the spleen. The LNPs may encounter immune cells in the blood and/or the spleen. A rapid innate immune response is triggered in response to the presence of the LNP within the blood and/or spleen. Applicant has shown herein that within hours of administration of an LNP several immune sensors have reacted to the presence of the LNP. These sensors include but are not limited to immune cells involved in generating an immune response, such as B cells, pDC, and platelets. The sensors may be present in the spleen, such as in the marginal zone of the spleen and/or in the blood. The LNP may physically interact with one or more sensors, which may interact with other sensors. In such a case the LNP is directly or indirectly interacting with the sensors. The sensors may interact directly with one another in response to recognition of the LNP. For instance many sensors are located in the spleen and can easily interact with one another. Alternatively one or more of the sensors may interact with LNP in the blood and become activated. The activated sensor may then interact directly with other sensors or indirectly (e.g., through the stimulation or production of a messenger such as a cytokine e.g., IL6).

In some embodiments the LNP may interact directly with and activate each of the following sensors: pDC, B1a cells, B1b cells, and platelets. These cells may then interact directly or indirectly with one another to initiate the production of effectors which ultimately lead to the ABC and/or toxicity associated with repeated doses of LNP. For instance, Applicant has shown that LNP administration leads to pDC activation, platelet aggregation and activation and B cell activation. In response to LNP platelets also aggregate and are activated and aggregate with B cells. pDC cells are activated. LNP has been found to interact with the surface of platelets and B cells relatively quickly. Blocking the activation of any one or combination of these sensors in response to LNP is useful for dampening the immune response that would ordinarily occur. This dampening of the immune response results in the avoidance of ABC and/or toxicity.

The sensors once activated produce effectors. An effector, as used herein, is an immune molecule produced by an immune cell, such as a B cell. Effectors include but are not limited to immunoglobulin such as natural IgM and natural IgG and cytokines such as IL6. B1a and B1b cells stimulate the production of natural IgMs within 2-6 hours following administration of an LNP. Natural IgG can be detected within 96 hours. IL6 levels are increased within several hours. The natural IgM and IgG circulate in the body for several days to several weeks. During this time the circulating effectors can interact with newly administered LNPs, triggering those LNPs for clearance by the body. For instance, an effector may recognize and bind to an LNP. The Fc region of the effector may be recognized by and trigger uptake of the decorated LNP by macrophage. The macrophage are then transported to the spleen. The production of effectors by immune sensors is a transient response that correlates with the timing observed for ABC.

If the administered dose is the second or subsequent administered dose, and if such second or subsequent dose is administered before the previously induced natural IgM and/or IgG is cleared from the system (e.g., before the 2-3 window time period), then such second or subsequent dose is targeted by the circulating natural IgM and/or natural IgG or Fc which trigger alternative complement pathway activation and is itself rapidly cleared. When LNP are administered after the effectors have cleared from the body or are reduced in number, ABC is not observed.

Thus, it is useful according to aspects of the invention to inhibit the interaction between LNP and one or more sensors, to inhibit the activation of one or more sensors by LNP (direct or indirect), to inhibit the production of one or more effectors, and/or to inhibit the activity of one or more effectors. In some embodiments the LNP is designed to limit or block interaction of the LNP with a sensor. For instance the LNP may have an altered PC and/or PEG to prevent interactions with sensors. Alternatively or additionally an agent that inhibits immune responses induced by LNPs may be used to achieve any one or more of these effects.

It has also been determined that conventional B cells are also implicated in ABC. Specifically, upon first administration of an agent, conventional B cells, referred to herein as CD19(+), bind to and react against the agent. Unlike B1a and B1b cells though, conventional B cells are able to mount first an IgM response (beginning around 96 hours after administration of the LNPs) followed by an IgG response (beginning around 14 days after administration of the LNPs) concomitant with a memory response. Thus conventional B cells react against the administered agent and contribute to IgM (and eventually IgG) that mediates ABC. The IgM and IgG are typically anti-PEG IgM and anti-PEG IgG.

It is contemplated that in some instances, the majority of the ABC response is mediated through B1a cells and B1a-mediated immune responses. It is further contemplated that in some instances, the ABC response is mediated by both IgM and IgG, with both conventional B cells and B1a cells mediating such effects. In yet still other instances, the ABC response is mediated by natural IgM molecules, some of which are capable of binding to natural IgM, which may be produced by activated B1a cells. The natural IgMs may bind to one or more components of the LNPs, e.g., binding to a phospholipid component of the LNPs (such as binding to the PC moiety of the phospholipid) and/or binding to a PEG-lipid component of the LNPs (such as binding to PEG-DMG, in particular, binding to the PEG moiety of PEG-DMG). Since B1a expresses CD36, to which phosphatidylcholine is a ligand, it is contemplated that the CD36 receptor may mediate the activation of B1a cells and thus production of natural IgM. In yet still other instances, the ABC response is mediated primarily by conventional B cells.

It has been found in accordance with the invention that the ABC phenomenon can be reduced or abrogated, at least in part, through the use of compounds and compositions (such as agents, delivery vehicles, and formulations) that do not activate B1a cells. Compounds and compositions that do not activate B1a cells may be referred to herein as B1a inert compounds and compositions. It has been further found in accordance with the invention that the ABC phenomenon can be reduced or abrogated, at least in part, through the use of compounds and compositions that do not activate conventional B cells. Compounds and compositions that do not activate conventional B cells may in some embodiments be referred to herein as CD19-inert compounds and compositions. Thus, in some embodiments provided herein, the compounds and compositions do not activate B1a cells and they do not activate conventional B cells. Compounds and compositions that do not activate B1a cells and conventional B cells may in some embodiments be referred to herein as B1a/CD19-inert compounds and compositions.

These underlying mechanisms were not heretofore understood, and the role of B1a and B1b cells and their interplay with conventional B cells in this phenomenon was also not appreciated.

Accordingly, this disclosure provides compounds and compositions that do not promote ABC. These may be further characterized as not capable of activating B1a and/or B1b cells, platelets and/or pDC, and optionally conventional B cells also. These compounds (e.g., agents, including biologically active agents such as prophylactic agents, therapeutic agents and diagnostic agents, delivery vehicles, including liposomes, lipid nanoparticles, and other lipid-based encapsulating structures, etc.) and compositions (e.g., formulations, etc.) are particularly desirable for applications requiring repeated administration, and in particular repeated administrations that occur within with short periods of time (e.g., within 1-2 weeks). This is the case, for example, if the agent is a nucleic acid based therapeutic that is provided to a subject at regular, closely-spaced intervals. The findings provided herein may be applied to these and other agents that are similarly administered and/or that are subject to ABC.

Of particular interest are lipid-comprising compounds, lipid-comprising particles, and lipid-comprising compositions as these are known to be susceptible to ABC. Such lipid-comprising compounds particles, and compositions have been used extensively as biologically active agents or as delivery vehicles for such agents. Thus, the ability to improve their efficacy of such agents, whether by reducing the effect of ABC on the agent itself or on its delivery vehicle, is beneficial for a wide variety of active agents.

Also provided herein are compositions that do not stimulate or boost an acute phase response (ARP) associated with repeat dose administration of one or more biologically active agents.

The composition, in some instances, may not bind to IgM, including but not limited to natural IgM.

The composition, in some instances, may not bind to an acute phase protein such as but not limited to C-reactive protein.

The composition, in some instances, may not trigger a CD5(+) mediated immune response. As used herein, a CD5(+) mediated immune response is an immune response that is mediated by B1a and/or B1b cells. Such a response may include an ABC response, an acute phase response, induction of natural IgM and/or IgG, and the like.

The composition, in some instances, may not trigger a CD19(+) mediated immune response. As used herein, a CD19(+) mediated immune response is an immune response that is mediated by conventional CD19(+), CD5(−) B cells. Such a response may include induction of IgM, induction of IgG, induction of memory B cells, an ABC response, an anti-drug antibody (ADA) response including an anti-protein response where the protein may be encapsulated within an LNP, and the like.

B1a cells are a subset of B cells involved in innate immunity. These cells are the source of circulating IgM, referred to as natural antibody or natural serum antibody. Natural IgM antibodies are characterized as having weak affinity for a number of antigens, and therefore they are referred to as "poly-specific" or "poly-reactive", indicating their ability to bind to more than one antigen. B1a cells are not able to produce IgG. Additionally, they do not develop into memory cells and thus do not contribute to an adaptive immune response. However, they are able to secrete IgM upon activation. The secreted IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In humans, B1a cells are CD19(+), CD20(+), CD27(+), CD43(+), CD70(−) and CD5(+). In mice, B1a cells are CD19(+), CD5(+), and CD45 B cell isoform B220(+). It is the expression of CD5 which typically distinguishes B1a cells from other convention B cells. B1a cells may express high levels of CD5, and on this basis may be distinguished from other B-1 cells such as B-1b cells which express low or undetectable levels of CD5. CD5 is a pan-T cell surface glycoprotein. B1a cells also express CD36, also known as fatty acid translocase. CD36 is a member of the class B scavenger receptor family. CD36 can bind many ligands, including oxidized low density lipoproteins, native lipoproteins, oxidized phospholipids, and long-chain fatty acids.

B1b cells are another subset of B cells involved in innate immunity. These cells are another source of circulating natural IgM. Several antigens, including PS, are capable of inducing T cell independent immunity through B1b activation. CD27 is typically upregulated on B1b cells in response to antigen activation. Similar to B1a cells, the B1b cells are typically located in specific body locations such as the spleen and peritoneal cavity and are in very low abundance in the blood. The B1b secreted natural IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In some embodiments it is desirable to block B1a and/or B1b cell activation. One strategy for blocking B1a and/or B1b cell activation involves determining which components of a lipid nanoparticle promote B cell activation and neutralizing those components. It has been discovered herein that at least PEG and phosphatidylcholine (PC) contribute to B1a and B1b cell interaction with other cells and/or activation. PEG may play a role in promoting aggregation between B1 cells and platelets, which may lead to activation. PC (a helper lipid in LNPs) is also involved in activating the B1 cells, likely through interaction with the CD36 receptor on the B cell surface. Numerous particles have PEG-lipid alternatives, PEG-less, and/or PC replacement lipids (e.g. oleic acid or analogs thereof) have been designed and tested. Applicant has established that replacement of one or more of these components within an LNP that otherwise would promote ABC upon repeat administration, is useful in preventing ABC by reducing the production of natural IgM and/or B cell activation. Thus, the invention encompasses LNPs that have reduced ABC as a result of a design which eliminates the inclusion of B cell triggers.

Another strategy for blocking B1a and/or B1b cell activation involves using an agent that inhibits immune responses induced by LNPs. These types of agents are discussed in more detail below. In some embodiments these agents block the interaction between B1a/B1b cells and the LNP or platelets or pDC. For instance the agent may be an antibody or other binding agent that physically blocks the interaction. An example of this is an antibody that binds to CD36 or CD6. The agent may also be a compound that prevents or disables the B1a/B1b cell from signaling once activated or prior to activation. For instance, it is possible to block one or more components in the B1a/B1b signaling cascade the results from B cell interaction with LNP or other immune cells. In other embodiments the agent may act one or more effectors produced by the B1a/B1b cells following activation. These effectors include for instance, natural IgM and cytokines.

It has been demonstrated according to aspects of the invention that when activation of pDC cells is blocked, B cell activation in response to LNP is decreased. Thus, in order to avoid ABC and/or toxicity, it may be desirable to prevent pDC activation. Similar to the strategies discussed above, pDC cell activation may be blocked by agents that interfere with the interaction between pDC and LNP and/or B cells/platelets. Alternatively agents that act on the pDC to block its ability to get activated or on its effectors can be used together with the LNP to avoid ABC.

Platelets may also play an important role in ABC and toxicity. Very quickly after a first dose of LNP is administered to a subject platelets associate with the LNP, aggregate and are activated. In some embodiments it is desirable to block platelet aggregation and/or activation. One strategy for blocking platelet aggregation and/or activation involves determining which components of a lipid nanoparticle promote platelet aggregation and/or activation and neutralizing those components. It has been discovered herein that at least PEG contribute to platelet aggregation, activation and/or interaction with other cells. Numerous particles have PEG-lipid alternatives and PEG-less have been designed and tested. Applicant has established that replacement of one or more of these components within an LNP that otherwise would promote ABC upon repeat administration, is useful in preventing ABC by reducing the production of natural IgM and/or platelet aggregation. Thus, the invention encompasses LNPs that have reduced ABC as a result of a design which eliminates the inclusion of platelet triggers. Alternatively agents that act on the platelets to block its activity once it is activated or on its effectors can be used together with the LNP to avoid ABC.

(i) Measuring ABC Activity and Related Activities

Various compounds and compositions provided herein, including LNPs, do not promote ABC activity upon administration in vivo. These LNPs may be characterized and/or identified through any of a number of assays, such as but not limited to those described below, as well as any of the assays disclosed in the Examples section, include the methods subsection of the Examples.

In some embodiments the methods involve administering an LNP without producing an immune response that promotes ABC. An immune response that promotes ABC involves activation of one or more sensors, such as B1 cells, pDC, or platelets, and one or more effectors, such as natural IgM, natural IgG or cytokines such as IL6. Thus administration of an LNP without producing an immune response that promotes ABC, at a minimum involves administration of an LNP without significant activation of one or more sensors and significant production of one or more effectors. Significant used in this context refers to an amount that would lead to the physiological consequence of accelerated blood clearance of all or part of a second dose with respect to the level of blood clearance expected for a second dose of an ABC triggering LNP. For instance, the immune response should be dampened such that the ABC observed after the second dose is lower than would have been expected for an ABC triggering LNP.

(ii) B1a or B1b Activation Assay

Certain compositions provided in this disclosure do not activate B cells, such as B1a or B1b cells (CD19+CD5+) and/or conventional B cells (CD19+CD5−). Activation of B1a cells, B1b cells, or conventional B cells may be determined in a number of ways, some of which are provided below. B cell population may be provided as fractionated B cell populations or unfractionated populations of splenocytes or peripheral blood mononuclear cells (PBMC). If the latter, the cell population may be incubated with the LNP of choice for a period of time, and then harvested for further analysis. Alternatively, the supernatant may be harvested and analyzed.

(iii) Upregulation of Activation Marker Cell Surface Expression

Activation of B1a cells, B1b cells, or conventional B cells may be demonstrated as increased expression of B cell activation markers including late activation markers such as CD86. In an exemplary non-limiting assay, unfractionated B cells are provided as a splenocyte population or as a PBMC population, incubated with an LNP of choice for a particular period of time, and then stained for a standard B cell marker such as CD19 and for an activation marker such as CD86, and analyzed using for example flow cytometry. A suitable negative control involves incubating the same population with medium, and then performing the same staining and visualization steps. An increase in CD86 expression in the test population compared to the negative control indicates B cell activation.

(iv) Pro-Inflammatory Cytokine Release

B cell activation may also be assessed by cytokine release assay. For example, activation may be assessed through the production and/or secretion of cytokines such as IL-6 and/or TNF-alpha upon exposure with LNPs of interest.

Such assays may be performed using routine cytokine secretion assays well known in the art. An increase in cytokine secretion is indicative of B cell activation.

(v) LNP Binding/Association to and/or Uptake by B Cells

LNP association or binding to B cells may also be used to assess an LNP of interest and to further characterize such LNP. Association/binding and/or uptake/internalization may be assessed using a detectably labeled, such as fluorescently labeled, LNP and tracking the location of such LNP in or on B cells following various periods of incubation.

The invention further contemplates that the compositions provided herein may be capable of evading recognition or detection and optionally binding by downstream mediators of ABC such as circulating IgM and/or acute phase response mediators such as acute phase proteins (e.g., C-reactive protein (CRP).

(vi) Methods of Use for Reducing ABC

Also provided herein are methods for delivering LNPs, which may encapsulate an agent such as a therapeutic agent, to a subject without promoting ABC.

In some embodiments, the method comprises administering any of the LNPs described herein, which do not promote ABC, for example, do not induce production of natural IgM binding to the LNPs, do not activate B1a and/or B1b cells. As used herein, an LNP that "does not promote ABC" refers to an LNP that induces no immune responses that would lead to substantial ABC or a substantially low level of immune responses that is not sufficient to lead to substantial ABC. An LNP that does not induce the production of natural IgMs binding to the LNP refers to LNPs that induce either no natural IgM binding to the LNPs or a substantially low level of the natural IgM molecules, which is insufficient to lead to substantial ABC. An LNP that does not activate B1a and/or B1b cells refer to LNPs that induce no response of B1a and/or B1b cells to produce natural IgM binding to the LNPs or a substantially low level of B1a and/or B1b responses, which is insufficient to lead to substantial ABC.

In some embodiments the terms do not activate and do not induce production are a relative reduction to a reference value or condition. In some embodiments the reference value or condition is the amount of activation or induction of production of a molecule such as IgM by a standard LNP such as an MC3 LNP. In some embodiments the relative reduction is a reduction of at least 30%, for example at least 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%. In other embodiments the terms do not activate cells such as B cells and do not induce production of a protein such as IgM may refer to an undetectable amount of the active cells or the specific protein.

(vii) Platelet Effects and Toxicity

The invention is further premised in part on the elucidation of the mechanism underlying dose-limiting toxicity associated with LNP administration. Such toxicity may involve coagulopathy, disseminated intravascular coagulation (DIC, also referred to as consumptive coagulopathy), whether acute or chronic, and/or vascular thrombosis. In some instances, the dose-limiting toxicity associated with LNPs is acute phase response (APR) or complement activation-related pseudoallergy (CARPA).

As used herein, coagulopathy refers to increased coagulation (blood clotting) in vivo. The findings reported in this disclosure are consistent with such increased coagulation and significantly provide insight on the underlying mechanism. Coagulation is a process that involves a number of different factors and cell types, and heretofore the relationship between and interaction of LNPs and platelets has not been understood in this regard. This disclosure provides evidence of such interaction and also provides compounds and compositions that are modified to have reduced platelet effect, including reduced platelet association, reduced platelet aggregation, and/or reduced platelet aggregation. The ability to modulate, including preferably down-modulate, such platelet effects can reduce the incidence and/or severity of coagulopathy post-LNP administration. This in turn will reduce toxicity relating to such LNP, thereby allowing higher doses of LNPs and importantly their cargo to be administered to patients in need thereof.

CARPA is a class of acute immune toxicity manifested in hypersensitivity reactions (HSRs), which may be triggered by nanomedicines and biologicals. Unlike allergic reactions, CARPA typically does not involve IgE but arises as a consequence of activation of the complement system, which is part of the innate immune system that enhances the body's abilities to clear pathogens. One or more of the following pathways, the classical complement pathway (CP), the alternative pathway (AP), and the lectin pathway (LP), may be involved in CARPA. Szebeni, Molecular Immunology, 61:163-173 (2014).

The classical pathway is triggered by activation of the C1-complex, which contains. C1q, C1r, C1s, or C1qr2s2. Activation of the C1-complex occurs when C1q binds to IgM or IgG complexed with antigens, or when C1q binds directly to the surface of the pathogen. Such binding leads to conformational changes in the C1q molecule, which leads to the activation of C1r, which in turn, cleave C1s. The C1r2s2 component now splits C4 and then C2, producing C4a, C4b, C2a, and C2b. C4b and C2b bind to form the classical pathway C3-convertase (C4b2b complex), which promotes cleavage of C3 into C3a and C3b. C3b then binds the C3 convertase to from the C5 convertase (C4b2b3b complex). The alternative pathway is continuously activated as a result of spontaneous C3 hydrolysis. Factor P (properdin) is a positive regulator of the alternative pathway. Oligomerization of properdin stabilizes the C3 convertase, which can then cleave much more C3. The C3 molecules can bind to surfaces and recruit more B, D, and P activity, leading to amplification of the complement activation.

Acute phase response (APR) is a complex systemic innate immune responses for preventing infection and clearing potential pathogens. Numerous proteins are involved in APR and C-reactive protein is a well-characterized one.

It has been found, in accordance with the invention, that certain LNP are able to associate physically with platelets almost immediately after administration in vivo, while other LNP do not associate with platelets at all or only at background levels. Significantly, those LNPs that associate with platelets also apparently stabilize the platelet aggregates that are formed thereafter. Physical contact of the platelets with certain LNPs correlates with the ability of such platelets to remain aggregated or to form aggregates continuously for an extended period of time after administration. Such aggregates comprise activated platelets and also innate immune cells such as macrophages and B cells.

25. Methods of Use

The polynucleotides, pharmaceutical compositions and formulations described herein are used in the preparation, manufacture and therapeutic use to treat and/or prevent GLA-related diseases, disorders or conditions. In some embodiments, the polynucleotides, compositions and formulations of the invention are used to treat and/or prevent Fabry disease.

For instance, one aspect of the invention provides a method of alleviating the signs and symptoms of Fabry disease in a subject comprising the administration of a composition or formulation comprising a polynucleotide encoding GLA to that subject (e.g., an mRNA encoding a GLA polypeptide).

In some embodiments, the polynucleotides, pharmaceutical compositions and formulations of the invention are used to reduce the level of a metabolite associated with Fabry disease, the method comprising administering to the subject an effective amount of a polynucleotide encoding a GLA polypeptide.

In some embodiments, the administration of an effective amount of a polynucleotide, pharmaceutical composition or formulation of the invention reduces the levels of a biomarker of Fabry disease, e.g., Gb3 and/or lyso-Gb3. In some embodiments, the administration of the polynucleotide, pharmaceutical composition or formulation of the invention results in reduction in the level of one or more biomarkers of Fabry disease within a short period of time (e.g., within about 6 hours, within about 8 hours, within about 12 hours, within about 16 hours, within about 20 hours, or within about 24 hours) after administration of the polynucleotide, pharmaceutical composition or formulation of the invention.

Replacement therapy is a potential treatment for Fabry disease. Thus, in certain aspects of the invention, the polynucleotides, e.g., mRNA, disclosed herein comprise one or more sequences encoding a GLA polypeptide that is suitable for use in gene replacement therapy for Fabry disease. In some embodiments, the present disclosure treats a lack of GLA or GLA activity, or decreased or abnormal GLA activity in a subject by providing a polynucleotide, e.g., mRNA, that encodes a GLA polypeptide to the subject. In some embodiments, the polynucleotide is sequence-optimized. In some embodiments, the polynucleotide (e.g., an mRNA) comprises a nucleic acid sequence (e.g., an ORF) encoding a GLA polypeptide, wherein the nucleic acid is sequence-optimized, e.g., by modifying its G/C, uridine, or thymidine content, and/or the polynucleotide comprises at least one chemically modified nucleoside. In some embodiments, the polynucleotide comprises a miRNA binding site, e.g., a miRNA binding site that binds miRNA-142 and/or a miRNA binding site that binds miRNA-126.

In some embodiments, the administration of the polynucleotide, pharmaceutical composition or formulation of the invention results in expression of GLA protein in cells of the subject. In some embodiments, administering the polynucleotide, pharmaceutical composition or formulation of the invention results in an increase of GLA activity in the subject. For example, in some embodiments, the polynucleotides of the present invention are used in methods of administering a composition or formulation comprising an mRNA encoding a GLA polypeptide to a subject, wherein the method results in an increase of GLA activity in at least some cells of a subject.

In some embodiments, the administration of a composition or formulation comprising an mRNA encoding a GLA polypeptide to a subject results in an increase of GLA activity in cells subject to a level at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% or more of the activity level expected in a normal or reference subject, e.g., a human not suffering from Fabry disease.

In some embodiments, the expression of the encoded polypeptide is increased. In some embodiments, the polynucleotide increases GLA expression levels in cells when introduced into those cells, e.g., by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% with respect to the GLA expression level in the cells before the polypeptide is introduced in the cells.

In some embodiments, the method or use comprises administering a polynucleotide, e.g., mRNA, comprising a nucleotide sequence having sequence similarity to a polynucleotide selected from the group of SEQ ID NOs: 3 to 27, 79 to 80, and 141 to 159 (See TABLE 2) or a polynucleotide selected from the group of SEQ ID NOs: 119, 120, 122 to 140, and 160 (See TABLE 5), wherein the polynucleotide encodes an GLA polypeptide.

Other aspects of the present disclosure relate to transplantation of cells containing polynucleotides to a mammalian subject. Administration of cells to mammalian subjects is known to those of ordinary skill in the art, and includes, but is not limited to, local implantation (e.g., topical or subcutaneous administration), organ delivery or systemic injection (e.g., intravenous injection or inhalation), and the formulation of cells in pharmaceutically acceptable carriers.

The present disclosure also provides methods to increase GLA activity in a subject in need thereof, e.g., a subject with Fabry disease, comprising administering to the subject a therapeutically effective amount of a composition or formulation comprising mRNA encoding a GLA polypeptide disclosed herein, e.g., a human GLA polypeptide, a mutant thereof, or a fusion protein comprising a human GLA.

In some aspects, the GLA activity measured after administration to a subject in need thereof, e.g., a subject with Fabry disease, is at least the normal GLA activity level observed in healthy human subjects. In some aspects, the GLA activity measured after administration is at higher than the GLA activity level observed in Fabry disease patients, e.g., untreated Fabry disease patients. In some aspects, the increase in GLA activity in a subject in need thereof, e.g., a subject with Fabry disease, after administering to the subject a therapeutically effective amount of a composition or formulation comprising mRNA encoding a GLA polypeptide disclosed herein is at least about 5, 10, 15, 20, 25, 30, 35, 40, 45, 50, 55, 60, 65, 70, 75, 80, 85, 90, 95, 100, or greater than 100 percent of the normal GLA activity level observed in healthy human subjects. In some aspects, the increase in GLA activity above the GLA activity level observed in Fabry disease patients after administering to the subject a composition or formulation comprising an mRNA encoding a GLA polypeptide disclosed herein (e.g., after a single dose administration) is maintained for at least 1 day, 2 days, 3 days, 4 days, 5 days, 6 days, 7 days, 8 days, 9 days, 10 days, 12 days, 14 days, 21 days, 28 days, 35 days, or 42 days.

Gb3 and lyso-Gb3 levels can be measured in the plasma or tissues (e.g., liver, heart, kidney, or spleen tissue) using methods known in the art. The present disclosure also provides a method to decrease Gb3 and lyso-Gb3 levels in a subject in need thereof, e.g., untreated Fabry disease patients, comprising administering to the subject a therapeutically effective amount of a composition or formulation comprising mRNA encoding a GLA polypeptide disclosed herein.

The present disclosure also provides a method to treat, prevent, or ameliorate the symptoms of Fabry disease (e.g., pain, gastrointestinal disturbances, skin lesions such as angiokeratomata, renal impairment, cardiomyopathy, or stroke) in an Fabry disease patient comprising administering to the subject a therapeutically effective amount of a composition or formulation comprising mRNA encoding a GLA polypeptide disclosed herein. In some aspects, the administration of a therapeutically effective amount of a composition or formulation comprising mRNA encoding a GLA polypeptide disclosed herein to subject suffering from Fabry disease results in reducing the symptoms of Fabry disease.

In some aspects, the dose of mRNA encoding a GLA polypeptide disclosed herein is at least about 0.1 nmol/kg, at least about 0.2 nmol/kg, at least about 0.3 nmol/kg, at least about 0.4 nmol/kg, at least about 0.5 nmol/kg, at least about 0.6 nmol/kg, at least about 0.7 nmol/kg, at least about 0.8 nmol/kg, at least about 0.9 nmol/kg, at least about 1 nmol/kg, at least about 1.1 nmol/kg, at least about 1.2 nmol/kg, at least about 1.3 nmol/kg, at least about 1.4 nmol/kg, at least about 1.5 nmol/kg, at least about 1.6 nmol/kg, at least about 1.7 nmol/kg, at least about 1.8 nmol/kg, at least about 1.9 nmol/kg, at least about 2 nmol/kg, at least about 2.5 nmol/kg, at least about 3 nmol/kg, at least about 3.5 nmol/kg, at least about 4 nmol/kg, at least about 4.5 nmol/kg, or at least about 5 nmol/kg. In some aspects, the dose of mRNA encoding a GLA polypeptide disclosed herein is at least about 0.05 mg/kg, at least about 0.1 mg/kg, at least about 0.15 mg/kg, at least about 0.2 mg/kg, at least about 0.25 mg/kg, at least about 0.3 mg/kg, at least about 0.35 mg/kg, at least about 0.4 mg/kg, at least about 0.45 mg/kg, at least about 0.5 mg/kg, at least about 0.55 mg/kg, at least about 0.6 mg/kg, at least about 0.7 mg/kg, at least about 0.75 mg/kg, at least about 0.8 mg/kg, at least about 0.85 mg/kg, at least about 0.9 mg/kg, at least about 0.95 mg/kg, or at least about 1 mg/kg.

In some embodiments, the polynucleotides (e.g., mRNA), pharmaceutical compositions and formulations used in the methods of the invention comprise a uracil-modified sequence encoding a GLA polypeptide disclosed herein and a miRNA binding site disclosed herein, e.g., a miRNA binding site that binds to miR-142 and/or a miRNA binding site that binds to miR-126. In some embodiments, the uracil-modified sequence encoding a GLA polypeptide comprises at least one chemically modified nucleobase, e.g., 5-methoxyuracil. In some embodiments, at least 95% of a type of nucleobase (e.g., uracil) in a uracil-modified sequence encoding a GLA polypeptide of the invention are modified nucleobases. In some embodiments, at least 95% of uracil in a uracil-modified sequence encoding a GLA polypeptide is 5-methoxyuridine. In some embodiments, the polynucleotide comprising a nucleotide sequence encoding a GLA polypeptide disclosed herein and a miRNA binding site is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

The skilled artisan will appreciate that the therapeutic effectiveness of a drug or a treatment of the instant invention can be characterized or determined by measuring the level of expression of an encoded protein (e.g., enzyme) in a sample or in samples taken from a subject (e.g., from a preclinical test subject (rodent, primate, etc.) or from a clinical subject (human). Likewise, the therapeutic effectiveness of a drug or a treatment of the instant invention can be characterized or determined by measuring the level of activity of an encoded protein (e.g., enzyme) in a sample or in samples taken from a subject (e.g., from a preclinical test subject (rodent, primate, etc.) or from a clinical subject (human). Furthermore, the therapeutic effectiveness of a drug or a treatment of the instant invention can be characterized or determined by measuring the level of an appropriate biomarker in sample(s) taken from a subject. Levels of protein and/or biomarkers can be determined post-administration with a single dose of an mRNA therapeutic of the invention or can be determined and/or monitored at several time points following administration with a single dose or can be determined and/or monitored throughout a course of treatment, e.g., a multi-dose treatment.

(i) GLA Protein Expression Levels

Certain aspects of the invention feature measurement, determination and/or monitoring of the expression level or levels of α-galactosidase A (GLA) protein in a subject, for example, in an animal (e.g., rodents, primates, and the like) or in a human subject. Animals include normal, healthy or wild type animals, as well as animal models for use in understanding Fabry disease and treatments thereof. Exemplary animal models include rodent models, for example, GLA deficient mice also referred to as GLA-/- knockout mice.

GLA protein expression levels can be measured or determined by any art-recognized method for determining protein levels in biological samples, e.g., blood samples or needle tissue biopsy. The term "level" or "level of a protein" as used herein, preferably means the weight, mass or concentration of the protein within a sample or a subject. It will be understood by the skilled artisan that in certain embodiments the sample may be subjected, e.g., to any of the following: purification, precipitation, separation, e.g. centrifugation and/or HPLC, and subsequently subjected to determining the level of the protein, e.g., using mass and/or spectrometric analysis. In exemplary embodiments, enzyme-linked immunosorbent assay (ELISA) can be used to determine protein expression levels. In other exemplary embodiments, protein purification, separation and LC-MS can be used as a means for determining the level of a protein according to the invention. In some embodiments, an mRNA therapy of the invention (e.g., a single intravenous dose) results in increased GLA protein expression levels in the liver tissue of the subject (e.g., 2-fold, 3-fold, 4-fold, 5-fold, 6-fold, 7-fold, 8-fold, 9-fold, 10-fold, 20-fold, 30-fold, 40-fold, 50-fold increase and/or increased to at least 20%, at least 30%, at least 40%, at least 50%, at least 60%, at least 70%, at least 75%, 80%, at least 85%, at least 90%, at least 95%, or at least 100% of a reference level or normal level) for at least 6 hours, at least 12 hours, at least 24 hours, at least 36 hours, at least 48 hours, at least 60 hours, at least 72 hours, at least 84 hours, at least 96 hours, at least 108 hours, at least 122 hours, at least 144 hours, or at least 168 hours after administration of a single dose of the mRNA therapy.

(ii) GLA Protein Activity

In Fabry disease patients, GLA enzymatic activity is reduced, and Fabry disease patients typically have little to no GLA activity. Further aspects of the invention feature measurement, determination and/or monitoring of the activity level(s) (i.e., enzymatic activity level(s)) of GLA protein in a subject, for example, in an animal (e.g., rodent, primate, and the like) or in a human subject. Activity levels can be measured or determined by any art-recognized method for determining enzymatic activity levels in biological samples. The term "activity level" or "enzymatic activity level" as used herein, preferably means the activity of the enzyme per volume, mass or weight of sample or total protein within a sample. In exemplary embodiments, the "activity level" or "enzymatic activity level" is described in terms of units per milliliter of fluid (e.g., bodily fluid, e.g., serum, plasma, urine and the like) or is described in terms of units per weight of tissue or per weight of protein (e.g., total protein) within a sample. Units ("U") of enzyme activity can be described in terms of weight or mass of substrate hydrolyzed per unit time. Exemplary embodiments of the invention feature GLA activity described in terms of U/ml plasma or U/mg protein (tissue), where units ("U") are described in terms of nmol substrate hydrolyzed per hour (or nmol/hr). An exemplary GLA enzymatic assay measures the ability of GLA enzymatic activity to release the fluorescent indicator 4-Methylumbelliferone (4-MU) from the non-fluorescent 4MU-α-Gal substrate. GLA activity in the plasma and tissues (e.g., liver, heart, kidney, or spleen) can be quantitated, e.g., as the amount of 4-MU produced per mg of protein per hour.

In exemplary embodiments, an mRNA therapy of the invention features a pharmaceutical composition comprising a dose of mRNA effective to result in at least 5 U/mg, at least 10 U/mg, at least 20 U/mg, at least 30 U/mg, at least 40 U/mg, at least 50 U/mg, at least 60 U/mg, at least 70 U/mg, at least 80 U/mg, at least 90 U/mg, at least 100 U/mg, or at least 150 U/mg of GLA activity in plasma or tissue (e.g., liver, heart, kidney, or spleen) between 6 and 12 hours, or between 12 and 24 hours, between 24 and 48 hours, between 48 and 72 hours, more than 3 days, more than 4 days, more than 5 days, more than 6 days, more than 7 days, more than 1 week, more than 2 weeks, more than 3 weeks, more than 4 weeks, more than 5 weeks, or more than 6 weeks post administration.

In exemplary embodiments, the invention features a pharmaceutical composition comprising a dose of mRNA effective to result in an increase of plasma GLA activity level to a level at or above a reference GLA activity level or a normal physiologic level for at least 12 hours, at least 18 hours, at least 24 hours, at least 36 hours, at least 48 hours, or at least 72 hours. In some embodiments, the invention features a pharmaceutical composition comprising a dose of mRNA sufficient to maintain at least 50% of a reference plasma GLA activity level or normal physiologic plasma GLA activity level 24 hours, 48 hours, 72 hours, 96 hours, 120 hours, 144 hours, or 168 hours post-administration. In some embodiments, the invention features a pharmaceutical composition comprising a dose of mRNA effective to result in an increase of plasma GLA activity for at least 24 hours, for at least 48 hours, for at least 72 hours, for at least 96 hours, for at least 120 hours, for at least 144 hours, or for at least 168 hours post-administration, wherein the increased plasma GLA activity levels are at least 10%, at least 20%, at least 30%, at least 40%, at least 50%, at least 60%, at least 70%, at least 80%, at least 90%, or more than 100% of a corresponding reference plasma GLA activity level or normal physiological plasma GLA activity level.

In exemplary embodiments, the invention features a pharmaceutical composition comprising a dose of mRNA effective to result in an increase of tissue (e.g., liver, heart, kidney, or spleen) GLA activity level to a level at or above a reference tissue GLA activity level or a normal physiologic level for at least 12 hours, at least 18 hours, at least 24 hours, at least 36 hours, at least 48 hours, or at least 72 hours. In some embodiments the invention features a pharmaceutical composition comprising a dose of mRNA sufficient to maintain at least 50% of a reference tissue (e.g., liver, heart, kidney, or spleen) GLA activity level or normal physiologic tissue GLA activity 24 hours, 48 hours, 72 hours, 96 hours, 120 hours, 144 hours, or 168 hours post-administration. In some embodiments, the invention features a pharmaceutical composition comprising a dose of mRNA effective to result in an increase of tissue (e.g., liver, heart, kidney, or spleen) GLA activity level for at least 24 hours, for at least 48 hours, for at least 72 hours, for at least 96 hours, for at least 120 hours, for at least 144 hours, or for at least 168 hours post-administration, wherein the increased tissue GLA activity level is at least 10%, at least 20%, at least 30%, at least 40%, at least 50%, at least 60%, at least 70%, at least 80%, at least 90%, or more than 100% of a corresponding reference tissue GLA activity level or normal physiological tissue GLA activity level.

In exemplary embodiments, an mRNA therapy of the invention features a pharmaceutical composition comprising a single intravenous dose of mRNA that results in the above-described levels of activity. In another embodiment, an mRNA therapy of the invention features a pharmaceutical composition which can be administered in multiple single unit intravenous doses of mRNA that maintain the above-described levels of activity.

(iii) GLA Biomarkers

Further aspects of the invention feature determining the level (or levels) of a biomarker, e.g., Gb3 and/or lyso-Gb3, determined in a sample as compared to a level (e.g., a reference level) of the same or another biomarker in another sample, e.g., from the same patient, from another patient, from a control and/or from the same or different time points, and/or a physiologic level, and/or an elevated level, and/or a supraphysiologic level, and/or a level of a control. The skilled artisan will be familiar with physiologic levels of biomarkers, for example, levels in normal or wild type animals, normal or healthy subjects, and the like, in particular, the level or levels characteristic of subjects who are healthy and/or normal functioning. As used herein, the phrase "elevated level" means amounts greater than normally found in a normal or wild type preclinical animal or in a normal or healthy subject, e.g. a human subject. As used herein, the term "supraphysiologic" means amounts greater than normally found in a normal or wild type preclinical animal or in a normal or healthy subject, e.g. a human subject, optionally producing a significantly enhanced physiologic response. As used herein, the term "comparing" or "compared to" preferably means the mathematical comparison of the two or more values, e.g., of the levels of the biomarker(s). It will thus be readily apparent to the skilled artisan whether one of the values is higher, lower or identical to another value or group of values if at least two of such values are compared with each other. Comparing or comparison to can be in the context, for example, of comparing to a control value in said subject prior to administration (e.g., in a person suffering from Fabry disease) or in a normal or healthy subject. Comparing or comparison to can also be in the context, for example, of comparing to a control value, e.g., as compared to a reference level in said subject prior to administration (e.g., in a person suffering from Fabry disease) or in a normal or healthy subject.

As used herein, a "control" is preferably a sample from a subject wherein the Fabry disease status of said subject is known. In one embodiment, a control is a sample of a healthy patient. In another embodiment, the control is a sample from at least one subject having a known Fabry disease status, for example, a severe, mild, or healthy Fabry disease status, e.g. a control patient. In another embodiment, the control is a sample from a subject not being treated for Fabry disease. In a still further embodiment, the control is a sample from a single subject or a pool of samples from different subjects and/or samples taken from the subject(s) at different time points.

The term "level" or "level of a biomarker" as used herein, preferably means the mass, weight or concentration of a biomarker of the invention within a sample or a subject. Biomarkers of the invention include, for example, Gb3 and lyso-Gb3. It will be understood by the skilled artisan that in certain embodiments the sample may be subjected to, e.g., one or more of the following: substance purification, precipitation, separation, e.g. centrifugation and/or HPLC and subsequently subjected to determining the level of the biomarker, e.g. using an ELISA assay or mass spectrometric analysis. In exemplary embodiments, LC-MS can be used as a means for determining the level of a biomarker according to the invention.

Certain embodiments an mRNA of the invention can be used express a GLA polypeptide at a level sufficient to reduce the plasma or tissue levels of Gb3 and/or lyso-Gb3 in a Fabry disease patient to less than about 70, 60, 50, 45, 40, 35, 30, 25, 20, 15, or 10 percent of the a reference level in said subject for at least 24 hours, at least 48 hours, at least 72 hours, at least 96 hours, at least 120 hours, at least 144 hours, at least one week, at least two weeks, at least three weeks, at least four weeks, at least 5 weeks, at least 6 weeks, at least 7 weeks, at least eight weeks, at least 9 weeks, or at least 10 weeks post-administration.

The term "determining the level" of a biomarker as used herein can mean methods which include quantifying an amount of at least one substance in a sample from a subject, for example, in a bodily fluid from the subject (e.g., serum, plasma, urine, blood, lymph, fecal, etc.) or in a tissue of the subject (e.g., liver, heart, spleen kidney, etc.).

The term "reference level" as used herein can refer to levels (e.g., of a biomarker) in a subject prior to administration of an mRNA therapy of the invention (e.g., in a person suffering from Fabry disease) or in a normal or healthy subject.

As used herein, the term "normal subject" or "healthy subject" refers to a subject not suffering from symptoms associated with Fabry disease. Moreover, a subject will be considered to be normal (or healthy) if it has no mutation of the functional portions or domains of the GLA gene and/or no mutation of the GLA gene resulting in a reduction of or deficiency of the enzyme GLA or the activity thereof, resulting in symptoms associated with Fabry disease. Said mutations will be detected if a sample from the subject is subjected to a genetic testing for such GLA mutations. In exemplary embodiments of the present invention, a sample from a healthy subject is used as a control sample, or the known or standardized value for the level of biomarker from samples of healthy or normal subjects is used as a control.

In some embodiments, comparing the level of the biomarker in a sample from a subject in need of treatment for Fabry disease, a subject in need of prevention of Fabry disease, or a subject being treated for Fabry disease to a control level of the biomarker comprises comparing the level of the biomarker in the sample from the subject (in need of treatment or being treated for Fabry disease) to a baseline or reference level, wherein if a level of the biomarker in the sample from the subject (in need of treatment or being treated for Fabry disease) is elevated, increased or higher compared to the baseline or reference level, this is indicative that the subject is suffering from Fabry disease and/or is in need of treatment; and/or wherein if a level of the biomarker in the sample from the subject (in need of treatment or being treated for Fabry disease) is decreased or lower compared to the baseline level this is indicative that the subject is not suffering from, is successfully being treated for Fabry disease, or is not in need of treatment for Fabry disease. The stronger the reduction (e.g., at least 2-fold, at least 3-fold, at least 4-fold, at least 5-fold, at least 6-fold, at least 7-fold, at least 8-fold, at least 10-fold, at least 20-fold, at least-30 fold, at least 40-fold, at least 50-fold reduction and/or at least 10%, at least 20%, at least 30% at least 40%, at least 50%, at least 60%, at least 70%, at least 80%, at least 90%, or at least 100% reduction) of the level of a biomarker within a certain time period, e.g., within 6 hours, within 12 hours, 24 hours, 36 hours, 48 hours, 60 hours, or 72 hours, and/or for a certain duration of time, e.g., 48 hours, 72 hours, 96 hours, 120 hours, 144 hours, 1 week, 2 weeks, 3 weeks, 4 weeks, 1 month, 2 months, 3 months, 4 months, 5 months, 6 months, 7 months, 8 months, 9 months, 10 months, 11 months, 12 months, 18 months, 24 months, etc. the more successful is a therapy, such as for example an mRNA therapy of the invention (e.g., a single dose or a multiple regimen). In some embodiments, the Gb3 plasma level is reduced to less than 10 nmol/mL, less than 9 nmol/mL, less than 8 nmol/mL, less than 7 nmol/mL, less than 6 nmol/mL, less than 5 nmol/mL, less than 4 nmol/mL, less than 3 nmol/mL, or less than 2 nmol/mL in the subject.

A reduction of at least about 20%, at least about 30%, at least about 40%, at least about 50%, at least about 60%, at least about 70%, at least about 80%, at least about 90%, at least 100% or more of the level of biomarker, in particular, in bodily fluid (e.g., plasma) or in tissue(s) in a subject (e.g., liver, heart, spleen, or kidney), for example Gb3 and/or lyso-Gb3, within 1, 2, 3, 4, 5, 6 or more days following administration is indicative of a dose suitable for successful treatment Fabry disease, wherein reduction as used herein, preferably means that the level of biomarker determined at the end of a specified time period (e.g., post-administration, for example, of a single intravenous dose) is compared to the level of the same biomarker determined at the beginning of said time period (e.g., pre-administration of said dose). Exemplary time periods include 12, 24, 48, 72, 96, 120, 144, or 168 hours post administration, in particular 24, 48, 72 or 96 hours post administration.

A sustained reduction in substrate levels (e.g., biomarkers such as Gb3 and/or lyso-Gb3) is particularly indicative of mRNA therapeutic dosing and/or administration regimens successful for treatment of Fabry disease. Such sustained reduction can be referred to herein as "duration" of effect. In exemplary embodiments, a reduction of at least about 40%, at least about 50%, at least about 60%, at least about 65%, at least about 70%, at least about 75%, at least about 80%, at least about 85%, at least about 90%, at least about 95% at least about 96%, at least about 97%, at least about 98%, at least about 99%, or at least about 100% of the level of biomarker, in particular, in a bodily fluid (e.g., plasma) or in tissue(s) in a subject (e.g., liver, heart, spleen, or kidney) within 1, 2, 3, 4, 5, 6, 7, 8 or more days following administration is indicative of a successful therapeutic approach. In exemplary embodiments, sustained reduction in substrate (e.g., biomarker) levels in one or more samples (e.g., fluids and/or tissues) is preferred. For example, mRNA therapies resulting in sustained reduction in Gb3 and/or lyso-Gb3 (as defined herein), optionally in combination with sustained reduction of said biomarker in at least one tissue, preferably two, three, four, five or more tissues, is indicative of successful treatment.

In some embodiments, a single dose of an mRNA therapy of the invention is about 0.2 to about 0.8 mpk, about 0.3 to about 0.7 mpk, about 0.4 to about 0.8 mpk, or about 0.5 mpk.

In another embodiment, a single dose of an mRNA therapy of the invention is less than 1.5 mpk, less than 1.25 mpk, less than 1 mpk, less than 0.75 mpk, or less than 0.5 mpk.

26. Compositions and Formulations for Use

Certain aspects of the invention are directed to compositions or formulations comprising any of the polynucleotides disclosed above.

In some embodiments, the composition or formulation comprises:
(i) a polynucleotide (e.g., a RNA, e.g., an mRNA) comprising a sequence-optimized nucleotide sequence (e.g., an ORF) encoding a GLA polypeptide (e.g., the wild-type sequence, functional fragment, or variant thereof), wherein the polynucleotide comprises at least one chemically modified nucleobase, e.g., 5-methoxyuracil (e.g., wherein at least about 25%, at least about 30%, at least about 40%, at least about 50%, at least about 60%, at least about 70%, at least about 80%, at least about 90%, at least about 95%, at least about 99%, or 100% of the uracils are 5-methoxyuracils), and wherein the polynucleotide further comprises a miRNA binding site, e.g., a miRNA binding site that binds to miR-142 (e.g., a miR-142-3p or miR-142-5p binding site) and/or a miRNA binding site that binds to miR-126 (e.g., a miR-126-3p or miR-126-5p binding site); and
(ii) a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof.

In some embodiments, the uracil or thymine content of the ORF relative to the theoretical minimum uracil or thymine content of a nucleotide sequence encoding the GLA polypeptide (% $U_{TM}$ or % $T_{TM}$), is between about 100% and about 150%.

In some embodiments, the polynucleotides, compositions or formulations above are used to treat and/or prevent a GLA-related diseases, disorders or conditions, e.g., Fabry disease.

27. Forms of Administration

The polynucleotides, pharmaceutical compositions and formulations of the invention described above can be administered by any route that results in a therapeutically effective outcome. These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration that is then covered by a dressing that occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal. In specific embodiments, compositions can be administered in a way that allows them cross the blood-brain barrier, vascular barrier, or other epithelial barrier. In some embodiments, a formulation for a route of administration can include at least one inactive ingredient.

The polynucleotides of the present invention (e.g., a polynucleotide comprising a nucleotide sequence encoding a GLA polypeptide or a functional fragment or variant thereof) can be delivered to a cell naked. As used herein in, "naked" refers to delivering polynucleotides free from agents that promote transfection. The naked polynucleotides can be delivered to the cell using routes of administration known in the art and described herein.

The polynucleotides of the present invention (e.g., a polynucleotide comprising a nucleotide sequence encoding a GLA polypeptide or a functional fragment or variant thereof) can be formulated, using the methods described herein. The formulations can contain polynucleotides that can be modified and/or unmodified. The formulations can further include, but are not limited to, cell penetration agents, a pharmaceutically acceptable carrier, a delivery agent, a bioerodible or biocompatible polymer, a solvent, and a sustained-release delivery depot. The formulated polynucleotides can be delivered to the cell using routes of administration known in the art and described herein.

A pharmaceutical composition for parenteral administration can comprise at least one inactive ingredient. Any or none of the inactive ingredients used can have been approved by the US Food and Drug Administration (FDA). A non-exhaustive list of inactive ingredients for use in pharmaceutical compositions for parenteral administration includes hydrochloric acid, mannitol, nitrogen, sodium acetate, sodium chloride and sodium hydroxide.

Injectable preparations, for example, sterile injectable aqueous or oleaginous suspensions can be formulated according to the known art using suitable dispersing agents, wetting agents, and/or suspending agents. Sterile injectable preparations can be sterile injectable solutions, suspensions, and/or emulsions in nontoxic parenterally acceptable diluents and/or solvents, for example, as a solution in 1,3-butanediol. Among the acceptable vehicles and solvents that can be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables. The sterile formulation can also comprise adjuvants such as local anesthetics, preservatives and buffering agents.

Injectable formulations can be sterilized, for example, by filtration through a bacterial-retaining filter, and/or by incorporating sterilizing agents in the form of sterile solid compositions that can be dissolved or dispersed in sterile water or other sterile injectable medium prior to use.

Injectable formulations can be for direct injection into a region of a tissue, organ and/or subject. As a non-limiting example, a tissue, organ and/or subject can be directly injected a formulation by intramyocardial injection into the ischemic region. (See, e.g., Zangi et al. Nature Biotechnology 2013; the contents of which are herein incorporated by reference in its entirety).

In order to prolong the effect of an active ingredient, it is often desirable to slow the absorption of the active ingredient from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions that are compatible with body tissues.

28. Kits and Devices a. Kits

The invention provides a variety of kits for conveniently and/or effectively using the claimed nucleotides of the present invention. Typically kits will comprise sufficient amounts and/or numbers of components to allow a user to perform multiple treatments of a subject(s) and/or to perform multiple experiments.

In one aspect, the present invention provides kits comprising the molecules (polynucleotides) of the invention.

Said kits can be for protein production, comprising a first polynucleotides comprising a translatable region. The kit can further comprise packaging and instructions and/or a delivery agent to form a formulation composition. The delivery agent can comprise a saline, a buffered solution, a lipidoid or any delivery agent disclosed herein.

In some embodiments, the buffer solution can include sodium chloride, calcium chloride, phosphate and/or EDTA. In another embodiment, the buffer solution can include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See, e.g., U.S. Pub. No. 20120258046; herein incorporated by reference in its entirety). In a further embodiment, the buffer solutions can be precipitated or it can be lyophilized. The amount of each component can be varied to enable consistent, reproducible higher concentration saline or simple buffer formulations. The components can also be varied in order to increase the stability of modified RNA in the buffer solution over a period of time and/or under a variety of conditions. In one aspect, the present invention provides kits for protein production, comprising: a polynucleotide comprising a translatable region, provided in an amount effective to produce a desired amount of a protein encoded by the translatable region when introduced into a target cell; a second polynucleotide comprising an inhibitory nucleic acid, provided in an amount effective to substantially inhibit the innate immune response of the cell; and packaging and instructions.

In one aspect, the present invention provides kits for protein production, comprising a polynucleotide comprising a translatable region, wherein the polynucleotide exhibits reduced degradation by a cellular nuclease, and packaging and instructions.

In one aspect, the present invention provides kits for protein production, comprising a polynucleotide comprising a translatable region, wherein the polynucleotide exhibits reduced degradation by a cellular nuclease, and a mammalian cell suitable for translation of the translatable region of the first nucleic acid.

b. Devices

The present invention provides for devices that can incorporate polynucleotides that encode polypeptides of interest. These devices contain in a stable formulation the reagents to synthesize a polynucleotide in a formulation available to be immediately delivered to a subject in need thereof, such as a human patient Devices for administration can be employed to deliver the polynucleotides of the present invention according to single, multi- or split-dosing regimens taught herein. Such devices are taught in, for example, International Application Publ.

No. WO2013151666, the contents of which are incorporated herein by reference in their entirety.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

According to the present invention, these multi-administration devices can be utilized to deliver the single, multi- or split doses contemplated herein. Such devices are taught for example in, International Application Publ. No. WO2013151666, the contents of which are incorporated herein by reference in their entirety.

In some embodiments, the polynucleotide is administered subcutaneously or intramuscularly via at least 3 needles to three different, optionally adjacent, sites simultaneously, or within a 60 minutes period (e.g., administration to 4, 5, 6, 7, 8, 9, or 10 sites simultaneously or within a 60 minute period).

c. Methods and Devices Utilizing Catheters and/or Lumens

Methods and devices using catheters and lumens can be employed to administer the polynucleotides of the present invention on a single, multi- or split dosing schedule. Such methods and devices are described in International Application Publication No. WO2013151666, the contents of which are incorporated herein by reference in their entirety.

d. Methods and Devices Utilizing Electrical Current

Methods and devices utilizing electric current can be employed to deliver the polynucleotides of the present invention according to the single, multi- or split dosing regimens taught herein. Such methods and devices are described in International Application Publication No. WO2013151666, the contents of which are incorporated herein by reference in their entirety.

29. Definitions

In order that the present disclosure can be more readily understood, certain terms are first defined. As used in this application, except as otherwise expressly provided herein, each of the following terms shall have the meaning set forth below. Additional definitions are set forth throughout the application.

The invention includes embodiments in which exactly one member of the group is present in, employed in, or otherwise relevant to a given product or process. The invention includes embodiments in which more than one, or all of the group members are present in, employed in, or otherwise relevant to a given product or process.

In this specification and the appended claims, the singular forms "a", "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Wherever aspects are described herein with the language "comprising," otherwise analogous aspects described in terms of "consisting of" and/or "consisting essentially of" are also provided.

Units, prefixes, and symbols are denoted in their Systeme International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Nucleotides are referred to by their commonly accepted single-letter codes. Unless otherwise indicated, nucleic acids are written left to right in 5' to 3' orientation. Nucleobases are referred to herein by their commonly known one-letter symbols recommended by the IUPAC-IUB Biochemical Nomenclature Commission. Accordingly, A represents adenine, C represents cytosine, G represents guanine, T represents thymine, U represents uracil.

Amino acids are referred to herein by either their commonly known three letter symbols or by the one-letter symbols recommended by the IUPAC-IUB Biochemical Nomenclature Commission. Unless otherwise indicated, amino acid sequences are written left to right in amino to carboxy orientation.

About: The term "about" as used in connection with a numerical value throughout the specification and the claims denotes an interval of accuracy, familiar and acceptable to a person skilled in the art, such interval of accuracy is ±10%.

Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

Administered in combination: As used herein, the term "administered in combination" or "combined administration" means that two or more agents are administered to a subject at the same time or within an interval such that there can be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Amino acid substitution: The term "amino acid substitution" refers to replacing an amino acid residue present in a parent or reference sequence (e.g., a wild type GLA sequence) with another amino acid residue. An amino acid can be substituted in a parent or reference sequence (e.g., a wild type GLA polypeptide sequence), for example, via chemical peptide synthesis or through recombinant methods known in the art. Accordingly, a reference to a "substitution at position X" refers to the substitution of an amino acid present at position X with an alternative amino acid residue. In some aspects, substitution patterns can be described according to the schema AnY, wherein A is the single letter code corresponding to the amino acid naturally or originally present at position n, and Y is the substituting amino acid residue. In other aspects, substitution patterns can be described according to the schema An(YZ), wherein A is the single letter code corresponding to the amino acid residue substituting the amino acid naturally or originally present at position X, and Y and Z are alternative substituting amino acid residues.

In the context of the present disclosure, substitutions (even when they referred to as amino acid substitution) are conducted at the nucleic acid level, i.e., substituting an amino acid residue with an alternative amino acid residue is conducted by substituting the codon encoding the first amino acid with a codon encoding the second amino acid.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately," as applied to one or more values of interest, refers to a value that is similar to a stated reference value. In certain embodiments, the term "approximately" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein with respect to a disease, the term "associated with" means that the symptom, measurement, characteristic, or status in question is linked to the diagnosis, development, presence, or progression of that disease. As association can, but need not, be causatively linked to the disease. For example, signs and symptoms, sequelae, or any effects causing a decrease in the quality of life of a patient with Fabry disease are considered associated with Fabry disease and in some embodiments of the present invention can be treated, ameliorated, or prevented by administering the polynucleotides of the present invention to a subject in need thereof.

When used with respect to two or more moieties, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It can also suggest ionic or hydrogen bonding or a hybridization based connectivity sufficiently stable such that the "associated" entities remain physically associated.

Bifunctional: As used herein, the term "bifunctional" refers to any substance, molecule or moiety that is capable of or maintains at least two functions. The functions can affect the same outcome or a different outcome. The structure that produces the function can be the same or different. For example, bifunctional modified RNAs of the present invention can encode a GLA peptide (a first function) while those nucleosides that comprise the encoding RNA are, in and of themselves, capable of extending the half-life of the RNA (second function). In this example, delivery of the bifunctional modified RNA to a subject suffering from a protein deficiency would produce not only a peptide or protein molecule that can ameliorate or treat a disease or conditions, but would also maintain a population modified RNA present in the subject for a prolonged period of time. In other aspects, a bifunctional modified mRNA can be a chimeric or quimeric molecule comprising, for example, an RNA encoding a GLA peptide (a first function) and a second protein either fused to first protein or co-expressed with the first protein.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a polynucleotide of the present invention can be considered biologically active if even a portion of the polynucleotide is biologically active or mimics an activity considered biologically relevant.

Chimera: As used herein, "chimera" is an entity having two or more incongruous or heterogeneous parts or regions. For example, a chimeric molecule can comprise a first part comprising a GLA polypeptide, and a second part (e.g., genetically fused to the first part) comprising a second therapeutic protein (e.g., a protein with a distinct enzymatic activity, an antigen binding moiety, or a moiety capable of extending the plasma half life of GLA, for example, an Fc region of an antibody).

Sequence Optimization: The term "sequence optimization" refers to a process or series of processes by which nucleobases in a reference nucleic acid sequence are replaced with alternative nucleobases, resulting in a nucleic acid sequence with improved properties, e.g., improved protein expression or decreased immunogenicity.

In general, the goal in sequence optimization is to produce a synonymous nucleotide sequence than encodes the same polypeptide sequence encoded by the reference nucleotide sequence. Thus, there are no amino acid substitutions (as a result of codon optimization) in the polypeptide encoded by the codon optimized nucleotide sequence with respect to the polypeptide encoded by the reference nucleotide sequence.

Codon substitution: The terms "codon substitution" or "codon replacement" in the context of sequence optimization refer to replacing a codon present in a reference nucleic acid sequence with another codon. A codon can be substituted in a reference nucleic acid sequence, for example, via chemical peptide synthesis or through recombinant methods known in the art. Accordingly, references to a "substitution" or "replacement" at a certain location in a nucleic acid sequence (e.g., an mRNA) or within a certain region or subsequence of a nucleic acid sequence (e.g., an mRNA) refer to the substitution of a codon at such location or region with an alternative codon.

As used herein, the terms "coding region" and "region encoding" and grammatical variants thereof, refer to an Open Reading Frame (ORF) in a polynucleotide that upon expression yields a polypeptide or protein.

Compound: As used herein, the term "compound," is meant to include all stereoisomers and isotopes of the structure depicted. As used herein, the term "stereoisomer" means any geometric isomer (e.g., cis- and trans-isomer), enantiomer, or diastereomer of a compound. The present disclosure encompasses any and all stereoisomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

Contacting: As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal can be performed by varied routes of administration (e.g., intravenous, intramuscular, intradermal, and subcutaneous) and can involve varied amounts of nanoparticle compositions. Moreover, more than one mammalian cell can be contacted by a nanoparticle composition.

Conservative amino acid substitution: A "conservative amino acid substitution" is one in which the amino acid residue in a protein sequence is replaced with an amino acid residue having a similar side chain. Families of amino acid residues having similar side chains have been defined in the art, including basic side chains (e.g., lysine, arginine, or histidine), acidic side chains (e.g., aspartic acid or glutamic acid), uncharged polar side chains (e.g., glycine, asparagine, glutamine, serine, threonine, tyrosine, or cysteine), nonpolar side chains (e.g., alanine, valine, leucine, isoleucine, proline, phenylalanine, methionine, or tryptophan), beta-branched side chains (e.g., threonine, valine, isoleucine) and aromatic side chains (e.g., tyrosine, phenylalanine, tryptophan, or histidine). Thus, if an amino acid in a polypeptide is replaced with another amino acid from the same side chain family, the amino acid substitution is considered to be conservative. In another aspect, a string of amino acids can be conservatively replaced with a structurally similar string that differs in order and/or composition of side chain family members.

Non-conservative amino acid substitution: Non-conservative amino acid substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala or Ser) or no side chain (e.g., Gly).

Other amino acid substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence can apply to the entire length of a polynucleotide or polypeptide or can apply to a portion, region or feature thereof.

Controlled Release: As used herein, the term "controlled release" refers to a pharmaceutical composition or compound release profile that conforms to a particular pattern of release to effect a therapeutic outcome.

Cyclic or Cyclized: As used herein, the term "cyclic" refers to the presence of a continuous loop. Cyclic molecules need not be circular, only joined to form an unbroken chain of subunits. Cyclic molecules such as the engineered RNA or mRNA of the present invention can be single units or multimers or comprise one or more components of a complex or higher order structure.

Cytotoxic: As used herein, "cytotoxic" refers to killing or causing injurious, toxic, or deadly effect on a cell (e.g., a mammalian cell (e.g., a human cell)), *bacterium*, virus, fungus, protozoan, parasite, prion, or a combination thereof.

Delivering: As used herein, the term "delivering" means providing an entity to a destination. For example, delivering a polynucleotide to a subject can involve administering a nanoparticle composition including the polynucleotide to the subject (e.g., by an intravenous, intramuscular, intradermal, or subcutaneous route). Administration of a nanoparticle composition to a mammal or mammalian cell can involve contacting one or more cells with the nanoparticle composition.

Delivery Agent: As used herein, "delivery agent" refers to any substance that facilitates, at least in part, the in vivo, in vitro, or ex vivo delivery of a polynucleotide to targeted cells.

Destabilized: As used herein, the term "destable," "destabilize," or "destabilizing region" means a region or molecule that is less stable than a starting, wild-type or native form of the same region or molecule.

Diastereomer: As used herein, the term "diastereomer," means stereoisomers that are not mirror images of one another and are non-superimposable on one another.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Domain: As used herein, when referring to polypeptides, the term "domain" refers to a motif of a polypeptide having one or more identifiable structural or functional characteristics or properties (e.g., binding capacity, serving as a site for protein-protein interactions).

Dosing regimen: As used herein, a "dosing regimen" or a "dosing regimen" is a schedule of administration or physician determined regimen of treatment, prophylaxis, or palliative care.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats a protein deficiency (e.g., a GLA deficiency), an effective amount of an agent is, for example, an amount of mRNA expressing sufficient GLA to ameliorate, reduce, eliminate, or prevent the signs and symptoms associated with the GLA deficiency, as compared to the severity of the symptom observed without administration of the agent. The term "effective amount" can be used interchangeably with "effective dose," "therapeutically effective amount," or "therapeutically effective dose."

Enantiomer: As used herein, the term "enantiomer" means each individual optically active form of a compound of the invention, having an optical purity or enantiomeric excess (as determined by methods standard in the art) of at least 80% (i.e., at least 90% of one enantiomer and at most 10% of the other enantiomer), at least 90%, or at least 98%.

Encapsulate: As used herein, the term "encapsulate" means to enclose, surround or encase.

Encapsulation Efficiency: As used herein, "encapsulation efficiency" refers to the amount of a polynucleotide that becomes part of a nanoparticle composition, relative to the initial total amount of polynucleotide used in the preparation of a nanoparticle composition. For example, if 97 mg of polynucleotide are encapsulated in a nanoparticle composition out of a total 100 mg of polynucleotide initially provided to the composition, the encapsulation efficiency can be given as 97%. As used herein, "encapsulation" can refer to complete, substantial, or partial enclosure, confinement, surrounding, or encasement.

Encoded protein cleavage signal: As used herein, "encoded protein cleavage signal" refers to the nucleotide sequence that encodes a protein cleavage signal.

Engineered: As used herein, embodiments of the invention are "engineered" when they are designed to have a feature or property, whether structural or chemical, that varies from a starting point, wild type or native molecule.

Enhanced Delivery: As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to the level of delivery of a polynucleotide by a control nanoparticle to a target tissue of interest (e.g., MC3, KC2, or DLinDMA). The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. It will be understood that the enhanced delivery of a nanoparticle to a target tissue need not be determined in a subject being treated, it can be determined in a surrogate such as an animal model (e.g., a rat model).

Exosome: As used herein, "exosome" is a vesicle secreted by mammalian cells or a complex involved in RNA degradation.

Expression: As used herein, "expression" of a nucleic acid sequence refers to one or more of the following events: (1) production of an mRNA template from a DNA sequence (e.g., by transcription); (2) processing of an mRNA transcript (e.g., by splicing, editing, 5' cap formation, and/or 3' end processing); (3) translation of an mRNA into a polypeptide or protein; and (4) post-translational modification of a polypeptide or protein.

Ex Vivo: As used herein, the term "ex vivo" refers to events that occur outside of an organism (e.g., animal, plant, or microbe or cell or tissue thereof). Ex vivo events can take place in an environment minimally altered from a natural (e.g., in vivo) environment.

Feature: As used herein, a "feature" refers to a characteristic, a property, or a distinctive element. When referring to polypeptides, "features" are defined as distinct amino acid sequence-based components of a molecule. Features of the polypeptides encoded by the polynucleotides of the present invention include surface manifestations, local conformational shape, folds, loops, half-loops, domains, half-domains, sites, termini or any combination thereof.

Formulation: As used herein, a "formulation" includes at least a polynucleotide and one or more of a carrier, an excipient, and a delivery agent.

Fragment: A "fragment," as used herein, refers to a portion. For example, fragments of proteins can comprise polypeptides obtained by digesting full-length protein isolated from cultured cells. In some embodiments, a fragment is a subsequences of a full length protein (e.g., GLA) wherein N-terminal, and/or C-terminal, and/or internal subsequences have been deleted. In some preferred aspects of the present invention, the fragments of a protein of the present invention are functional fragments.

Functional: As used herein, a "functional" biological molecule is a biological molecule in a form in which it exhibits a property and/or activity by which it is characterized. Thus, a functional fragment of a polynucleotide of the present invention is a polynucleotide capable of expressing a functional GLA fragment. As used herein, a functional fragment of GLA refers to a fragment of wild type GLA (i.e., a fragment of any of its naturally occurring isoforms), or a mutant or variant thereof, wherein the fragment retains a least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the biological activity of the corresponding full length protein.

GLA Associated Disease: As use herein the terms "GLA-associated disease" or "GLA-associated disorder" refer to diseases or disorders, respectively, which result from aberrant GLA activity (e.g., decreased activity or increased activity). As a non-limiting example, Fabry disease is a GLA associated disease.

The terms "GLA activity," and "α-galactosidase A activity" are used interchangeably in the present disclosure and refer to GLA's α-galactosidase activity. Accordingly, a fragment or variant retaining or having GLA activity refers to a fragment or variant that has measurable α-galactosidase activity.

Helper Lipid: As used herein, the term "helper lipid" refers to a compound or molecule that includes a lipidic moiety (for insertion into a lipid layer, e.g., lipid bilayer) and a polar moiety (for interaction with physiologic solution at the surface of the lipid layer). Typically the helper lipid is a phospholipid. A function of the helper lipid is to "complement" the amino lipid and increase the fusogenicity of the bilayer and/or to help facilitate endosomal escape, e.g., of nucleic acid delivered to cells. Helper lipids are also believed to be a key structural component to the surface of the LNP.

Homology: As used herein, the term "homology" refers to the overall relatedness between polymeric molecules, e.g. between nucleic acid molecules (e.g. DNA molecules and/or RNA molecules) and/or between polypeptide molecules. Generally, the term "homology" implies an evolutionary relationship between two molecules. Thus, two molecules that are homologous will have a common evolutionary ancestor. In the context of the present invention, the term homology encompasses both to identity and similarity.

In some embodiments, polymeric molecules are considered to be "homologous" to one another if at least 25%, 30%, 35%, 40%, 45%, 50%, 55%, 60%, 65%, 70%, 75%, 80%, 85%, 90%, 95%, or 99% of the monomers in the molecule are identical (exactly the same monomer) or are similar (conservative substitutions). The term "homologous" necessarily refers to a comparison between at least two sequences (polynucleotide or polypeptide sequences).

Identity: As used herein, the term "identity" refers to the overall monomer conservation between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. When comparing DNA and RNA, thymine (T) and uracil (U) can be considered equivalent.

Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Sequence alignments can be conducted using methods known in the art such as MAFFT, Clustal (Clustal W, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity "% ID" of a first amino acid sequence (or nucleic acid sequence) to a second amino acid sequence (or nucleic acid sequence) is calculated as % ID=100×(Y/Z), where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

Immune response: The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues. In some cases, the administration of a nanoparticle comprising a lipid component and an encapsulated therapeutic agent can trigger an immune response, which can be caused by (i) the encapsulated therapeutic agent (e.g., an mRNA), (ii) the expression product of such encapsulated therapeutic agent (e.g., a polypeptide encoded by the mRNA), (iii) the lipid component of the nanoparticle, or (iv) a combination thereof.

Inflammatory response: "Inflammatory response" refers to immune responses involving specific and non-specific defense systems. A specific defense system reaction is a specific immune system reaction to an antigen. Examples of specific defense system reactions include antibody responses. A non-specific defense system reaction is an inflammatory response mediated by leukocytes generally incapable of immunological memory, e.g., macrophages, eosinophils and neutrophils. In some aspects, an immune response includes the secretion of inflammatory cytokines, resulting in elevated inflammatory cytokine levels.

Inflammatory cytokines: The term "inflammatory cytokine" refers to cytokines that are elevated in an inflammatory response. Examples of inflammatory cytokines include interleukin-6 (IL-6), CXCL1 (chemokine (C-X-C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL-12), interleukin-13 (I1-13), interferon α (IFN-α), etc.

In Vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In Vivo: As used herein, the term "in vivo" refers to events that occur within an organism (e.g., animal, plant, or microbe or cell or tissue thereof).

Insertional and deletional variants: "Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid. "Deletional variants" when referring to polypeptides are those with one or more amino acids in the native or starting amino acid sequence removed. Ordinarily, deletional variants will have one or more amino acids deleted in a particular region of the molecule.

Intact: As used herein, in the context of a polypeptide, the term "intact" means retaining an amino acid corresponding to the wild type protein, e.g., not mutating or substituting the wild type amino acid. Conversely, in the context of a nucleic acid, the term "intact" means retaining a nucleobase corresponding to the wild type nucleic acid, e.g., not mutating or substituting the wild type nucleobase.

Ionizable amino lipid: The term "ionizable amino lipid" includes those lipids having one, two, three, or more fatty acid or fatty alkyl chains and a pH-titratable amino head group (e.g., an alkylamino or dialkylamino head group). An ionizable amino lipid is typically protonated (i.e., positively charged) at a pH below the pKa of the amino head group and is substantially not charged at a pH above the pKa. Such ionizable amino lipids include, but are not limited to DLin-MC3-DMA (MC3) and (13Z,16Z)—N,N-dimethyl-3-nonydocosa-13-16-dien-1-amine (L608).

Isolated: As used herein, the term "isolated" refers to a substance or entity that has been separated from at least some of the components with which it was associated (whether in nature or in an experimental setting). Isolated substances (e.g., polynucleotides or polypeptides) can have varying levels of purity in reference to the substances from which they have been isolated. Isolated substances and/or entities can be separated from at least about 10%, about 20%, about 30%, about 40%, about 50%, about 60%, about 70%, about 80%, about 90%, or more of the other components with which they were initially associated. In some embodiments, isolated substances are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof.

A polynucleotide, vector, polypeptide, cell, or any composition disclosed herein which is "isolated" is a polynucleotide, vector, polypeptide, cell, or composition which is in a form not found in nature. Isolated polynucleotides, vectors, polypeptides, or compositions include those which have been purified to a degree that they are no longer in a form in which they are found in nature. In some aspects, a polynucleotide, vector, polypeptide, or composition which is isolated is substantially pure.

Isomer: As used herein, the term "isomer" means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

Linker: As used herein, a "linker" refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker can be of sufficient length as to not interfere with incorporation into a nucleic acid sequence. The linker can be used for any useful purpose, such as to form polynucleotide multimers (e.g., through linkage of two or more chimeric polynucleotides molecules or IVT polynucleotides) or polynucleotides conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof. Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Methods of Administration: As used herein, "methods of administration" can include intravenous, intramuscular, intradermal, subcutaneous, or other methods of delivering a composition to a subject. A method of administration can be selected to target delivery (e.g., to specifically deliver) to a specific region or system of a body.

Modified: As used herein "modified" refers to a changed state or structure of a molecule of the invention. Molecules can be modified in many ways including chemically, structurally, and functionally. In some embodiments, the mRNA molecules of the present invention are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Mucus: As used herein, "mucus" refers to the natural substance that is viscous and comprises mucin glycoproteins.

Nanoparticle Composition: As used herein, a "nanoparticle composition" is a composition comprising one or more lipids. Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Naturally occurring: As used herein, "naturally occurring" means existing in nature without artificial aid.

Non-human vertebrate: As used herein, a "non-human vertebrate" includes all vertebrates except Homo sapiens, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Nucleic acid sequence: The terms "nucleic acid sequence," "nucleotide sequence," or "polynucleotide sequence" are used interchangeably and refer to a contiguous nucleic acid sequence. The sequence can be either single stranded or double stranded DNA or RNA, e.g., an mRNA.

The term "nucleic acid," in its broadest sense, includes any compound and/or substance that comprises a polymer of nucleotides. These polymers are often referred to as polynucleotides. Exemplary nucleic acids or polynucleotides of the invention include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or hybrids or combinations thereof.

The phrase "nucleotide sequence encoding" refers to the nucleic acid (e.g., an mRNA or DNA molecule) coding sequence which encodes a polypeptide. The coding sequence can further include initiation and termination signals operably linked to regulatory elements including a promoter and polyadenylation signal capable of directing expression in the cells of an individual or mammal to which the nucleic acid is administered. The coding sequence can further include sequences that encode signal peptides.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g., alkyl) per se is optional.

Part: As used herein, a "part" or "region" of a polynucleotide is defined as any portion of the polynucleotide that is less than the entire length of the polynucleotide.

Patient: As used herein, "patient" refers to a subject who can seek or be in need of treatment, requires treatment, is receiving treatment, will receive treatment, or a subject who is under care by a trained professional for a particular disease or condition. In some embodiments, the treatment is needed, required, or received to prevent or decrease the risk of developing more severe forms of the disease, i.e., it is a prophylactic treatment.

Pharmaceutically acceptable: The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethyl amine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used. Lists of suitable salts are found in *Remington's Pharmaceutical Sciences*, 17$^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates can be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Polynucleotide: The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the term "polynucleotide" includes polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing non-nucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In particular aspects, the polynucleotide comprises an mRNA. In other aspect, the mRNA is a synthetic mRNA. In some aspects, the synthetic mRNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine). In some aspects, the polynucleotide (e.g., a synthetic RNA or a synthetic DNA) comprises only natural nucleobases, i.e., A (adenosine), G (guanosine), C (cytidine), and T (thymidine) in the case of a synthetic DNA, or A, C, G, and U (uridine) in the case of a synthetic RNA.

The skilled artisan will appreciate that the T bases in the codon maps disclosed herein are present in DNA, whereas the T bases would be replaced by U bases in corresponding RNAs. For example, a codon-nucleotide sequence disclosed herein in DNA form, e.g., a vector or an in-vitro translation (IVT) template, would have its T bases transcribed as U based in its corresponding transcribed mRNA. In this respect, both codon-optimized DNA sequences (comprising T) and their corresponding mRNA sequences (comprising U) are considered codon-optimized nucleotide sequence of the present invention. A skilled artisan would also understand that equivalent codon-maps can be generated by replaced one or more bases with non-natural bases. Thus, e.g., a TTC codon (DNA map) would correspond to a UUC codon (RNA map), which in turn would correspond to a ψψC codon (RNA map in which U has been replaced with pseudouridine).

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2 of cytidine and the C2-NH2, N'—H and C6-oxy, respectively, of guanosine. Thus, for example, guanosine (2-amino-6-oxy-9-β-D-ribofuranosyl-purine) can be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine can be prepared by the method described by Switzer et al. (1993) Biochemistry 32:10489-10496 and references cited therein; 2'-deoxy-5-methyl-isocytidine can be prepared by the method of Tor et al., 1993, J. Am. Chem. Soc. 115:4461-4467 and references cited therein; and isoguanine nucleotides can be prepared using the method described by Switzer et al., 1993, supra, and Mantsch et al., 1993, Biochem. 14:5593-5601, or by the method described in U.S. Pat. No. 5,780,610 to Collins et al. Other non-natural base pairs can be synthesized by the method described in Piccirilli et al., 1990, Nature 343:33-37, for the synthesis of 2,6-diaminopyrimidine and its complement (1-methylpyrazolo-[4,3]pyrimidine-5,7-(4H,6H)-dione. Other such modified nucleotide units which form unique base pairs are known, such as those described in Leach et al. (1992) J. Am. Chem. Soc. 114:3675-3683 and Switzer et al., supra.

Polypeptide: The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term, as used herein, refers to proteins, polypeptides, and peptides of any size, structure, or function. Polypeptides include encoded polynucleotide products, naturally occurring polypeptides, synthetic polypeptides, homologs, orthologs, paralogs, fragments and other equivalents, variants, and analogs of the foregoing. A polypeptide can be a monomer or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some embodiments, a "peptide" can be less than or equal to 50 amino acids long, e.g., about 5, 10, 15, 20, 25, 30, 35, 40, 45, or 50 amino acids long.

Polypeptide variant: As used herein, the term "polypeptide variant" refers to molecules that differ in their amino acid sequence from a native or reference sequence. The amino acid sequence variants can possess substitutions, deletions, and/or insertions at certain positions within the amino acid sequence, as compared to a native or reference sequence. Ordinarily, variants will possess at least about 50% identity, at least about 60% identity, at least about 70% identity, at least about 80% identity, at least about 90% identity, at least about 95% identity, at least about 99% identity to a native or reference sequence. In some embodiments, they will be at least about 80%, or at least about 90% identical to a native or reference sequence.

Polypeptide per unit drug (PUD): As used herein, a PUD or product per unit drug, is defined as a subdivided portion of total daily dose, usually 1 mg, pg, kg, etc., of a product (such as a polypeptide) as measured in body fluid or tissue, usually defined in concentration such as pmol/mL, mmol/mL, etc. divided by the measure in the body fluid.

Preventing: As used herein, the term "preventing" refers to partially or completely delaying onset of an infection, disease, disorder and/or condition; partially or completely delaying onset of one or more signs and symptoms, features, or clinical manifestations of a particular infection, disease, disorder, and/or condition; partially or completely delaying onset of one or more signs and symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease. An "immune prophylaxis" refers to a measure to produce active or passive immunity to prevent the spread of disease.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Pseudouridine: As used herein, pseudouridine ($\psi$) refers to the C-glycoside isomer of the nucleoside uridine. A "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methylpseudouridine ($m^1\psi$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thio-pseudouridine, N1-methyl-pseudouridine, 1-methyl-3-(3-amino-3-carboxypropyl)pseudouridine ($acp^3\psi$), and 2'-O-methyl-pseudouridine ($\psi m$).

Purified: As used herein, "purify," "purified," "purification" means to make substantially pure or clear from unwanted components, material defilement, admixture or imperfection.

Reference Nucleic Acid Sequence: The term "reference nucleic acid sequence" or "reference nucleic acid" or "reference nucleotide sequence" or "reference sequence" refers to a starting nucleic acid sequence (e.g., a RNA, e.g., an mRNA sequence) that can be sequence optimized. In some embodiments, the reference nucleic acid sequence is a wild type nucleic acid sequence, a fragment or a variant thereof. In some embodiments, the reference nucleic acid sequence is a previously sequence optimized nucleic acid sequence.

Salts: In some aspects, the pharmaceutical composition for delivery disclosed herein comprises salts of some of their lipid constituents. The term "salt" includes any anionic and cationic complex. Non-limiting examples of anions include inorganic and organic anions, e.g., fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof.

Sample: As used herein, the term "sample" or "biological sample" refers to a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). A sample further can include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, or organs. A sample further refers to a medium, such as a nutrient broth or gel, which can contain cellular components, such as proteins or nucleic acid molecule.

Signal Sequence: As used herein, the phrases "signal sequence," "signal peptide," and "transit peptide" are used interchangeably and refer to a sequence that can direct the transport or localization of a protein to a certain organelle, cell compartment, or extracellular export. The term encompasses both the signal sequence polypeptide and the nucleic acid sequence encoding the signal sequence. Thus, references to a signal sequence in the context of a nucleic acid refer in fact to the nucleic acid sequence encoding the signal sequence polypeptide.

Signal transduction pathway: A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Single unit dose: As used herein, a "single unit dose" is a dose of any therapeutic administered in one dose/at one time/single route/single point of contact, i.e., single administration event.

Split dose: As used herein, a "split dose" is the division of single unit dose or total daily dose into two or more doses.

Specific delivery: As used herein, the term "specific delivery," "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to an off-target tissue. The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. For example, for renovascular targeting, a polynucleotide is specifically provided to a mammalian kidney as compared to the liver and spleen if 1.5, 2-fold, 3-fold, 5-fold, 10-fold, 15 fold, or 20 fold more polynucleotide per 1 g of tissue is delivered to a kidney compared to that delivered to the liver or spleen following systemic administration of the polynucleotide. It will be understood that the ability of a nanoparticle to specifically deliver to a target tissue need not be determined in a subject being treated, it can be determined in a surrogate such as an animal model (e.g., a rat model).

Stable: As used herein "stable" refers to a compound that is sufficiently robust to survive isolation to a useful degree of purity from a reaction mixture, and in some cases capable of formulation into an efficacious therapeutic agent.

Stabilized: As used herein, the term "stabilize," "stabilized," "stabilized region" means to make or become stable.

Stereoisomer: As used herein, the term "stereoisomer" refers to all possible different isomeric as well as conformational forms that a compound can possess (e.g., a compound of any formula described herein), in particular all possible stereochemically and conformationally isomeric forms, all diastereomers, enantiomers and/or conformers of the basic molecular structure. Some compounds of the present invention can exist in different tautomeric forms, all of the latter being included within the scope of the present invention.

Subject: By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain embodiments, the mammal is a human subject. In other embodiments, a subject is a human patient. In a particular embodiment, a subject is a human patient in need of treatment.

Substantially: As used herein, the term "substantially" refers to the qualitative condition of exhibiting total or near-total extent or degree of a characteristic or property of interest. One of ordinary skill in the biological arts will understand that biological and chemical characteristics rarely, if ever, go to completion and/or proceed to completeness or achieve or avoid an absolute result. The term "substantially" is therefore used herein to capture the potential lack of completeness inherent in many biological and chemical characteristics.

Substantially equal: As used herein as it relates to time differences between doses, the term means plus/minus 2%.

Substantially simultaneous: As used herein and as it relates to plurality of doses, the term means within 2 seconds.

Suffering from: An individual who is "suffering from" a disease, disorder, and/or condition has been diagnosed with or displays one or more signs and symptoms of the disease, disorder, and/or condition.

Susceptible to: An individual who is "susceptible to" a disease, disorder, and/or condition has not been diagnosed with and/or can not exhibit signs and symptoms of the disease, disorder, and/or condition but harbors a propensity to develop a disease or its signs and symptoms. In some embodiments, an individual who is susceptible to a disease, disorder, and/or condition (for example, Fabry Disease) can be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or other molecules of the present invention can be chemical or enzymatic.

Targeted Cells: As used herein, "targeted cells" refers to any one or more cells of interest. The cells can be found in vitro, in vivo, in situ or in the tissue or organ of an organism. The organism can be an animal, for example a mammal, a human, a subject or a patient.

Target tissue: As used herein "target tissue" refers to any one or more tissue types of interest in which the delivery of a polynucleotide would result in a desired biological and/or pharmacological effect. Examples of target tissues of interest include specific tissues, organs, and systems or groups thereof. In particular applications, a target tissue can be a liver, a kidney, a lung, a spleen, or vascular endothelium in vessels (e.g., intra-coronary or intra-femoral). An "off-target tissue" refers to any one or more tissue types in which the expression of the encoded protein does not result in a desired biological and/or pharmacological effect.

The presence of a therapeutic agent in an off-target issue can be the result of: (i) leakage of a polynucleotide from the administration site to peripheral tissue or distant off-target tissue via diffusion or through the bloodstream (e.g., a polynucleotide intended to express a polypeptide in a certain tissue would reach the off-target tissue and the polypeptide would be expressed in the off-target tissue); or (ii) leakage of an polypeptide after administration of a polynucleotide encoding such polypeptide to peripheral tissue or distant off-target tissue via diffusion or through the bloodstream (e.g., a polynucleotide would expressed a polypeptide in the target tissue, and the polypeptide would diffuse to peripheral tissue).

Targeting sequence: As used herein, the phrase "targeting sequence" refers to a sequence that can direct the transport or localization of a protein or polypeptide.

Terminus: As used herein the terms "termini" or "terminus," when referring to polypeptides, refers to an extremity of a peptide or polypeptide. Such extremity is not limited only to the first or final site of the peptide or polypeptide but can include additional amino acids in the terminal regions. The polypeptide based molecules of the invention can be characterized as having both an N-terminus (terminated by an amino acid with a free amino group (NH2)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides can be modified such that they begin or end, as the case can be, with a non-polypeptide based moiety such as an organic conjugate.

Therapeutic Agent: The term "therapeutic agent" refers to an agent that, when administered to a subject, has a therapeutic, diagnostic, and/or prophylactic effect and/or elicits a desired biological and/or pharmacological effect. For example, in some embodiments, an mRNA encoding a GLA polypeptide can be a therapeutic agent.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve signs and symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve signs and symptoms of, diagnose, prevent, and/or delay the onset of the infection, disease, disorder, and/or condition.

Total daily dose: As used herein, a "total daily dose" is an amount given or prescribed in 24 hr. period. The total daily dose can be administered as a single unit dose or a split dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors can regulate transcription of a target gene alone or in a complex with other molecules.

Transcription: As used herein, the term "transcription" refers to methods to produce mRNA (e.g., an mRNA sequence or template) from DNA (e.g., a DNA template or sequence).

Transfection: As used herein, "transfection" refers to the introduction of a polynucleotide into a cell wherein a polypeptide (e.g., exogenous nucleic acids) encoded by the polynucleotide is expressed (e.g., mRNA) or the polypeptide modulates a cellular function (e.g., siRNA, miRNA). As used herein, "expression" of a nucleic acid sequence refers to translation of a polynucleotide (e.g., an mRNA) into a polypeptide or protein and/or post-translational modification of a polypeptide or protein. Methods of transfection include, but are not limited to, chemical methods, physical treatments and cationic lipids or mixtures.

Treating, treatment, therapy: As used herein, the term "treating" or "treatment" or "therapy" refers to partially or completely alleviating, ameliorating, improving, relieving, delaying onset of, inhibiting progression of, reducing severity of, and/or reducing incidence of one or more signs and symptoms or features of a disease, e.g., Fabry disease. For example, "treating" Fabry disease can refer to diminishing signs and symptoms associate with the disease, prolong the lifespan (increase the survival rate) of patients, reducing the severity of the disease, preventing or delaying the onset of the disease, etc. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in some way. Unmodified can, but does not always, refer to the wild type or native form of a biomolecule. Molecules can undergo a series of modifications whereby each modified molecule can serve as the "unmodified" starting molecule for a subsequent modification.

Uracil: Uracil is one of the four nucleobases in the nucleic acid of RNA, and it is represented by the letter U. Uracil can be attached to a ribose ring, or more specifically, a ribofuranose via a β-$N_1$-glycosidic bond to yield the nucleoside uridine. The nucleoside uridine is also commonly abbreviated according to the one letter code of its nucleobase, i.e., U. Thus, in the context of the present disclosure, when a monomer in a polynucleotide sequence is U, such U is designated interchangeably as a "uracil" or a "uridine."

Uridine Content: The terms "uridine content" or "uracil content" are interchangeable and refer to the amount of uracil or uridine present in a certain nucleic acid sequence. Uridine content or uracil content can be expressed as an absolute value (total number of uridine or uracil in the sequence) or relative (uridine or uracil percentage respect to the total number of nucleobases in the nucleic acid sequence).

Uridine Modified Sequence: The terms "uridine-modified sequence" refers to a sequence optimized nucleic acid (e.g., a synthetic mRNA sequence) with a different overall or local uridine content (higher or lower uridine content) or with different uridine patterns (e.g., gradient distribution or clustering) with respect to the uridine content and/or uridine patterns of a candidate nucleic acid sequence. In the content of the present disclosure, the terms "uridine-modified sequence" and "uracil-modified sequence" are considered equivalent and interchangeable.

A "high uridine codon" is defined as a codon comprising two or three uridines, a "low uridine codon" is defined as a codon comprising one uridine, and a "no uridine codon" is a codon without any uridines. In some embodiments, a uridine-modified sequence comprises substitutions of high uridine codons with low uridine codons, substitutions of high uridine codons with no uridine codons, substitutions of low uridine codons with high uridine codons, substitutions of low uridine codons with no uridine codons, substitution of no uridine codons with low uridine codons, substitutions of no uridine codons with high uridine codons, and combinations thereof. In some embodiments, a high uridine codon can be replaced with another high uridine codon. In some embodiments, a low uridine codon can be replaced with another low uridine codon. In some embodiments, a no uridine codon can be replaced with another no uridine codon. A uridine-modified sequence can be uridine enriched or uridine rarefied.

Uridine Enriched: As used herein, the terms "uridine enriched" and grammatical variants refer to the increase in uridine content (expressed in absolute value or as a percentage value) in an sequence optimized nucleic acid (e.g., a synthetic mRNA sequence) with respect to the uridine content of the corresponding candidate nucleic acid sequence. Uridine enrichment can be implemented by substituting codons in the candidate nucleic acid sequence with synonymous codons containing less uridine nucleobases. Uridine enrichment can be global (i.e., relative to the entire length of a candidate nucleic acid sequence) or local (i.e., relative to a subsequence or region of a candidate nucleic acid sequence).

Uridine Rarefied: As used herein, the terms "uridine rarefied" and grammatical variants refer to a decrease in uridine content (expressed in absolute value or as a percentage value) in an sequence optimized nucleic acid (e.g., a synthetic mRNA sequence) with respect to the uridine content of the corresponding candidate nucleic acid sequence. Uridine rarefication can be implemented by substituting codons in the candidate nucleic acid sequence with synonymous codons containing less uridine nucleobases. Uridine rarefication can be global (i.e., relative to the entire length of a candidate nucleic acid sequence) or local (i.e., relative to a subsequence or region of a candidate nucleic acid sequence).

Variant: The term variant as used in present disclosure refers to both natural variants (e.g., polymorphisms, isoforms, etc.) and artificial variants in which at least one amino acid residue in a native or starting sequence (e.g., a wild type sequence) has been removed and a different amino acid inserted in its place at the same position. These variants can be described as "substitutional variants." The substitutions can be single, where only one amino acid in the molecule has been substituted, or they can be multiple, where two or more amino acids have been substituted in the same molecule. If amino acids are inserted or deleted, the resulting variant would be an "insertional variant" or a "deletional variant" respectively.

30. Embodiments

Throughout this section, the term embodiment is abbreviated as 'E' followed by an ordinal. For example, E1 is equivalent to Embodiment 1.

E1. A polynucleotide comprising an open reading frame (ORF) encoding α-galactosidase A (GLA) polypeptide, wherein the uracil or thymine content of the ORF relative to the theoretical minimum uracil or thymine content of a nucleotide sequence encoding the GLA polypeptide (% $U_{TM}$ or % $T_{TM}$) is between about 100% and about 150%.

E2. The polynucleotide of E1, wherein the % $U_{TM}$ or % $T_{TM}$ is between about 110% and about 150%, about 115% and about 150%, about 120% and about 150%, about 110% and about 145%, about 115% and about 145%, about 120% and about 145%, about 110% and about 140%, about 115% and about 140%, or about 120% and about 140%.

E3. The polynucleotide of E2, wherein the % $U_{TM}$ or % $T_{TM}$ is between (i) 115%, 116%, 117%, 118%, 119%, 120%, 121%, 122%, or 123% and (ii) 138%, 139%, 140%, 141%, 142%, 143%, 144%, or 145%.

E4. The polynucleotide of any one of E1 to E3, wherein the uracil or thymine content of the ORF relative to the uracil or thymine content of the corresponding wild-type ORF (% $U_{WT}$ or % $T_{WT}$) is less than 100%.

E5. The polynucleotide of E4, wherein the % $U_{WT}$ or % $T_{WT}$ is less than about 95%, less than about 90%, less than about 85%, less than 80%, less than 75%, less than 74%, less than 73%, less than 72%, less than 71%, or less than 70%.

E6. The polynucleotide of E4, wherein the % $U_{WT}$ or % $T_{WT}$ is between 62% and 70%.

E7. The polynucleotide of any one of E1 to E6, wherein the uracil or thymine content in the ORF relative to the total nucleotide content in the ORF (% $U_{TL}$ or % $T_{TL}$) is less than about 50%, less than about 40%, less than about 30%, or less than about 20%.

E8. The polynucleotide of E7, wherein the % $U_{TL}$ or % $T_{TL}$, is less than about 20%.

E9. The polynucleotide of any one of E1 to E8, wherein the % $U_{TL}$ or % $T_{TL}$, is between about 16% and about 18%.

E10. The polynucleotide of any one of E1 to E9, wherein the guanine content of the ORF with respect to the theoretical maximum guanine content of a nucleotide sequence encoding the GLA polypeptide (% $G_{TMX}$) is at least 64%, at least 65%, at least 70%, at least 75%, at least 75%, at least about 80%, at least about 85%, at least about 90%, at least about 95%, or about 100%.

E11. The polynucleotide of E10, wherein the % $G_{TMX}$ is between about 70% and about 85%, between about 70% and about 80%, between about 71% and about 80%, or between about 72% and about 80%.

E12. The polynucleotide of any one of E1 to E11, wherein the cytosine content of the ORF relative to the theoretical maximum cytosine content of a nucleotide sequence encoding the GLA polypeptide (% $C_{TMX}$) is at least 54%, at least 55%, at least 60%, at least 65%, at least 70%, at least 75%, at least about 80%, at least about 85%, at least about 90%, at least about 95%, or about 100%.

E13. The polynucleotide of E12, wherein % $C_{TMX}$ is between about 60% and about 80%, between about 65% and about 80%, between about 70% and about 80%, or between about 70% and about 76%.

E14. The polynucleotide of any one of E1 to E13, wherein the guanine and cytosine content (G/C) of the ORF relative to the theoretical maximum G/C content in a nucleotide sequence encoding the GLA polypeptide (% $G/C_{TMX}$) is at least about 73%, at least about 75%, at least about 80%, at least about 85%, at least about 90%, at least about 95%, or about 100%.

E15. The polynucleotide of any one of E1 to E13, wherein % $G/C_{TMX}$ is between about 80% and about 100%, between about 85% and about 99%, between about 90% and about 97%, or between about 91% and about 95%.

E16. The polynucleotide of any one of E1 to E15, wherein the G/C content in the ORF relative to the G/C content in the corresponding wild-type ORF (% G/C$_{WT}$) is at least 102%, at least 103%, at least 104%, at least 105%, at least 106%, at least 107%, at least about 110%, at least about 115%, at least about 120%, or at least about 125%.

E17. The polynucleotide of any one of E1 to E15, wherein the average G/C content in the 3$^{rd}$ codon position in the ORF is at least 30%, at least 31%, at least 32%, at least 33%, at least 34%, at least 35%, at least 36%, at least 37%, at least 38%, at least 39%, or at least 40% higher than the average G/C content in the 3$^{rd}$ codon position in the corresponding wild-type ORF.

E18. The polynucleotide of any one of E1 to E17, wherein the ORF further comprises at least one low-frequency codon.

E19. The polynucleotide of any one of E1 to E18,
(i) wherein the ORF is at least 92%, at least 93%, at least 94%, at least 95%, at least 96%, at least 97%, at least 98%, at least 99%, or 100% identical to GLA-001, GLA-005, or GLA-0011,
(ii) wherein the ORF is at least 91%, at least 92%, at least 93%, at least 94%, at least 95%, at least 96%, at least 97%, at least 98%, at least 99%, or 100% identical to GLA-CO2, GLA-CO3, GLA-CO6, GLA-CO7, GLA-CO9, GLA-CO10, GLA-CO12, GLA-CO13, GLA-CO14, GLA-CO15, GLA-CO18, GLA-CO20, GLA-CO21, GLA-CO22, GLA-CO23, or GLA-CO24,
(iii) wherein the ORF is at least 90%, at least 91%, at least 92%, at least 93%, at least 94%, at least 95%, at least 96%, at least 97%, at least 98%, at least 99%, or 100% identical to GLA-CO8, GLA-CO16, GLA-CO17, GLA-CO19, or GLA-CO25, or
(iv) wherein the ORF is at least 89%, at least 90%, at least 91%, at least 91%, at least 92%, at least 93%, at least 94%, at least 95%, at least 96%, at least 97%, at least 98%, at least 99%, or 100% identical to GLA-004.

E20. A polynucleotide comprising an ORF,
(i) wherein the ORF is at least 92%, at least 93%, at least 94%, at least 95%, at least 96%, at least 97%, at least 98%, at least 99%, or 100% identical to GLA-CO1, GLA-CO5, or GLA-CO11,
(ii) wherein the ORF is at least 91%, at least 92%, at least 93%, at least 94%, at least 95%, at least 96%, at least 97%, at least 98%, at least 99%, or 100% identical to GLA-CO2, GLA-CO3, GLA-CO6, GLA-CO7, GLA-CO9, GLA-CO10, GLA-CO12, GLA-CO13, GLA-CO14, GLA-CO15, GLA-CO18, GLA-CO20, GLA-CO21, GLA-CO22, GLA-CO23, or GLA-CO24,
(iii) wherein the ORF is at least 90%, at least 91%, at least 92%, at least 93%, at least 94%, at least 95%, at least 96%, at least 97%, at least 98%, at least 99%, or 100% identical to GLA-CO8, GLA-CO16, GLA-CO17, GLA-CO19, or GLA-CO25, or
(iv) wherein the ORF is at least 89%, at least 90%, at least 91%, at least 91%, at least 92%, at least 93%, at least 94%, at least 95%, at least 96%, at least 97%, at least 98%, at least 99%, or 100% identical to GLA-CO4.

E21. The polynucleotide of any one of E1 to E20, wherein the ORF has at least 89%, at least 90%, at least 91%, at least 92%, at least 93%, at least 94%, at least 95%, at least 96%, at least 97%, at least 98%, at least 99%, or 100% sequence identity to a sequence selected from the group consisting of SEQ ID NOs: 3 to 27, 79 to 80, and 141 to 159.

E22. The polynucleotide of any one of E1 to E21, wherein the GLA polypeptide comprises an amino acid sequence at least about 95%, at least about 96%, at least about 97%, at least about 98%, at least about 99%, or about 100% identical to the polypeptide sequence of wild type GLA (SEQ ID NO: 1), and wherein the GLA polypeptide has α-galactosidase activity.

E23. The polynucleotide of E22, wherein the GLA polypeptide is a variant, derivative, or mutant having a α-galactosidase activity.

E24. The polynucleotide of any one of E1 to E23, wherein the polynucleotide sequence further comprises a nucleotide sequence encoding a transit peptide.

E25. The polynucleotide of any one of E1 to E24, wherein the polynucleotide is single stranded.

E26. The polynucleotide of any one of E1 to E24, wherein the polynucleotide is double stranded.

E27. The polynucleotide of any one of E1 to E26, wherein the polynucleotide is DNA.

E28. The polynucleotide of any one of E1 to E26, wherein the polynucleotide is RNA.

E29. The polynucleotide of E28, wherein the polynucleotide is mRNA.

E30. The polynucleotide of any one of E1 to E29, wherein the polynucleotide comprises at least one chemically modified nucleobase, sugar, backbone, or any combination thereof.

E31. The polynucleotide of E30, wherein the at least one chemically modified nucleobase is selected from the group consisting of pseudouracil (ψ), N1-methylpseudouracil (m1ψ), 2-thiouracil (s2U), 4'-thiouracil, 5-methyl cytosine, 5-methyluracil, and any combination thereof.

E32. The polynucleotide of E30, wherein the at least one chemically modified nucleobase is 5-methoxyuracil.

E33. The polynucleotide of E32, wherein at least about 25%, at least about 30%, at least about 40%, at least about 50%, at least about 60%, at least about 70%, at least about 80%, at least about 90%, at least about 95%, at least about 99%, or 100% of the uracils are 5-methoxyuracils.

E34. The polynucleotide of any one of E1 to E33, wherein the polynucleotide further comprises a miRNA binding site.

E35. The polynucleotide of E34, wherein the miRNA binding site comprises one or more nucleotide sequences selected from Table 3.

E36. The polynucleotide of E34, wherein the miRNA binding site binds to miR-142.

E37. The polynucleotide of E35 or E36, wherein the miRNA binding site binds to miR-142-3p or miR-142-5p.

E38. The polynucleotide of E36 or E37, wherein the miR-142 comprises SEQ ID NO: 28.

E39. The polynucleotide of any one of E1 to E38, wherein the polynucleotide further comprises a 5' UTR.

E40. The polynucleotide of E39, wherein the 5' UTR comprises a nucleic acid sequence at least 90%, at least about 95%, at least about 96%, at least about 97%, at least about 98%, at least about 99%, or about 100% identical to a 5' UTR sequence selected from the group consisting of SEQ ID NO: 33-50, 77, and 115-117, or any combination thereof.

E41. The polynucleotide of any one of E1 to E40, wherein the polynucleotide further comprises a 3' UTR.

E42. The polynucleotide of E41, wherein the 3' UTR comprises a nucleic acid sequence at least about 90%, at least about 95%, at least about 96%, at least about 97%, at least about 98%, at least about 99%, or about 100% identical to a 3' UTR sequence selected from the group consisting of SEQ ID NO: 51-75, 81-82, 88, 103, 106-113, 118, and 161-170, or any combination thereof.

E43. The polynucleotide of E41 or E42, wherein the miRNA binding site is located within the 3' UTR.

E44. The polynucleotide of any one of E1 to E43, wherein the polynucleotide further comprises a 5' terminal cap.

E45. The polynucleotide of E44, wherein the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

E46. The polynucleotide of any one of E1 to E45, wherein the polynucleotide further comprises a poly-A region.

E47. The polynucleotide of E46, wherein the poly-A region is at least about 10, at least about 20, at least about 30, at least about 40, at least about 50, at least about 60, at least about 70, at least about 80, or at least about 90 nucleotides in length.

E48. The polynucleotide of E47, wherein the poly-A region has about 10 to about 200, about 20 to about 180, about 50 to about 160, about 70 to about 140, or about 80 to about 120 nucleotides in length.

E49. The polynucleotide of any one of E1 to E48, wherein the polynucleotide encodes a GLA polypeptide that is fused to one or more heterologous polypeptides.

E50. The polynucleotide of E49, wherein the one or more heterologous polypeptides increase a pharmacokinetic property of the GLA polypeptide.

E51. The polynucleotide of any one of E1 to E50, wherein upon administration to a subject, the polynucleotide has:
 (i) a longer plasma half-life;
 (ii) increased expression of a GLA polypeptide encoded by the ORF;
 (iii) a lower frequency of arrested translation resulting in an expression fragment;
 (iv) greater structural stability; or
 (v) any combination thereof,
 relative to a corresponding polynucleotide comprising SEQ ID NO: 2.

E52. The polynucleotide of any one of E1 to E51, wherein the polynucleotide comprises:
 (i) a 5'-terminal cap;
 (ii) a 5'-UTR;
 (iii) an ORF encoding a GLA polypeptide;
 (iv) a 3'-UTR; and
 (v) a poly-A region.

E53. The polynucleotide of E52, wherein the 3'-UTR comprises a miRNA binding site.

E54. A method of producing the polynucleotide of any one of E1 to E53, the method comprising modifying an ORF encoding a GLA polypeptide by substituting at least one uracil nucleobase with an adenine, guanine, or cytosine nucleobase, or by substituting at least one adenine, guanine, or cytosine nucleobase with a uracil nucleobase, wherein all the substitutions are synonymous substitutions.

E55. The method of E54, wherein the method further comprises replacing at least about 90%, at least about 95%, at least about 99%, or about 100% of uracils with 5-methoxyuracils.

E56. A composition comprising
 (a) the polynucleotide of any one of E1 to E53; and
 (b) a delivery agent.

E57. The composition of E56, wherein the delivery agent comprises a lipidoid, a liposome, a lipoplex, a lipid nanoparticle, a polymeric compound, a peptide, a protein, a cell, a nanoparticle mimic, a nanotube, or a conjugate.

E58. The composition of E56, wherein the delivery agent comprises a lipid nanoparticle.

E59. The composition of E58, wherein the lipid nanoparticle comprises a lipid selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)[1,3]-dioxolane (DLin-KC2-DMA), 1,2-dioleyloxy-N,N-dimethylaminopropane (DODMA), (13Z,16Z)—N,N-dimethyl-3-nonydocosa-13-16-dien-1-amine (L608), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)), and any combination thereof.

E60. The composition of any one of E56 to E59, wherein the delivery agent comprises a compound having the Formula (I)

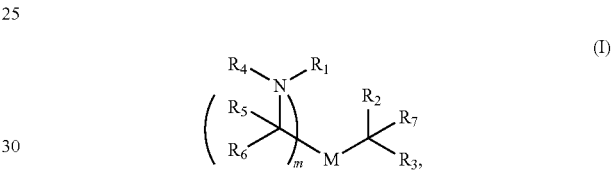

or a salt or stereoisomer thereof, wherein
$R_1$ is selected from the group consisting of $C_{5\text{-}30}$ alkyl, $C_{5\text{-}20}$ alkenyl, —R*YR", —YR", and —R"M'R';
$R_2$ and $R_3$ are independently selected from the group consisting of H, $C_{1\text{-}14}$ alkyl, $C_{2\text{-}14}$ alkenyl, —R*YR", —YR", and —R*OR", or $R_2$ and $R_3$, together with the atom to which they are attached, form a heterocycle or carbocycle;
$R_4$ is selected from the group consisting of a $C_{3\text{-}6}$ carbocycle, —$(CH_2)_nQ$, —$(CH_2)_n$CHQR, —CHQR, —CQ$(R)_2$, and unsubstituted $C_{1\text{-}6}$ alkyl, where Q is selected from a carbocycle, heterocycle, —OR, —O$(CH_2)_n$N$(R)_2$, —C(O)OR, —OC(O)R, —$CX_3$, —$CX_2$H, —$CXH_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, and —C(R)N(R)$_2$C(O)OR, and each n is independently selected from 1, 2, 3, 4, and 5;
each $R_5$ is independently selected from the group consisting of $C_{1\text{-}3}$ alkyl, $C_{2\text{-}3}$ alkenyl, and H;
each $R_6$ is independently selected from the group consisting of $C_{1\text{-}3}$ alkyl, $C_{2\text{-}3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;
$R_7$ is selected from the group consisting of $C_{1\text{-}3}$ alkyl, $C_{2\text{-}3}$ alkenyl, and H;
each R is independently selected from the group consisting of $C_{1\text{-}3}$ alkyl, $C_{2\text{-}3}$ alkenyl, and H;
each R' is independently selected from the group consisting of $C_{1\text{-}18}$ alkyl, $C_{2\text{-}18}$ alkenyl, —R*YR", —YR", and H;
each R" is independently selected from the group consisting of $C_{3\text{-}14}$ alkyl and $C_{3\text{-}14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is $—(CH_2)_nQ$, $—(CH_2)_nCHQR$, $—CHQR$, or $—CQ(R)_2$, then (i) Q is not $—N(R)_2$ when n is 1, 2, 3, 4 or 5, or (ii) Q is not 5, 6, or 7-membered heterocycloalkyl when n is 1 or 2.

E61. A composition comprising a nucleotide sequence encoding a GLA polypeptide and a delivery agent, wherein the delivery agent comprises a compound having the Formula (I)

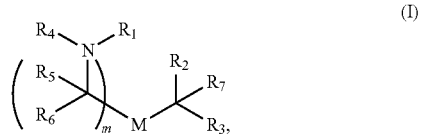

or a salt or stereoisomer thereof, wherein $R_1$ is selected from the group consisting of $C_{5-20}$ alkyl, $C_{5-20}$ alkenyl, $—R*YR''$, $—YR''$, and $—R''M'R'$;

$R_2$ and $R_3$ are independently selected from the group consisting of H, $C_{1-14}$ alkyl, $C_{2-14}$ alkenyl, $—R*YR''$, $—YR''$, and $—R*OR''$, or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, $—CHQR$, $—CQ(R)_2$, and unsubstituted $C_{1-6}$ alkyl, where Q is selected from a carbocycle, heterocycle, $—OR$, $—O(CH_2)_nN(R)_2$, $—C(O)OR$, $—OC(O)R$, $—CX_3$, $—CX_2H$, $—CXH_2$, $—CN$, $—N(R)_2$, $—C(O)N(R)_2$, $—N(R)C(O)R$, $—N(R)S(O)_2R$, $—N(R)C(O)N(R)_2$, $—N(R)C(S)N(R)_2$, and $—C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from $—C(O)O—$, $—OC(O)—$, $—C(O)N(R')—$, $—N(R')C(O)—$, $—C(O)—$, $—C(S)—$, $—C(S)S—$, $—SC(S)—$, $—CH(OH)—$, $—P(O)(OR')O—$, $—S(O)_2—$, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, $—R*YR''$, $—YR''$, and H;

each R'' is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is $—(CH_2)_nQ$, $—(CH_2)_nCHQR$, $—CHQR$, or $—CQ(R)_2$, then (i) Q is not $—N(R)_2$ when n is 1, 2, 3, 4 or 5, or (ii) Q is not 5, 6, or 7-membered heterocycloalkyl when n is 1 or 2.

E62. The composition of E60 or 61, wherein the compound is of Formula (IA):

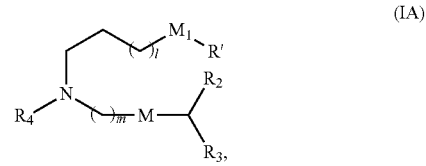

or a salt or stereoisomer thereof, wherein l is selected from 1, 2, 3, 4, and 5;

m is selected from 5, 6, 7, 8, and 9;

$M_1$ is a bond or M';

$R_4$ is unsubstituted $C_{1-3}$ alkyl, or $—(CH_2)_nQ$, in which n is 1, 2, 3, 4, or 5 and Q is OH, $—NHC(S)N(R)_2$, or $—NHC(O)N(R)_2$;

M and M' are independently selected from $—C(O)O—$, $—OC(O)—$, $—C(O)N(R')—$, $—P(O)(OR')O—$, an aryl group, and a heteroaryl group; and $R_2$ and $R_3$ are independently selected from the group consisting of H, $C_{1-14}$ alkyl, and $C_{2-14}$ alkenyl.

E63. The composition of any one of E60 to E62, wherein m is 5, 7, or 9.

E64. The composition of any one of E60 to E63, wherein the compound is of Formula (II):

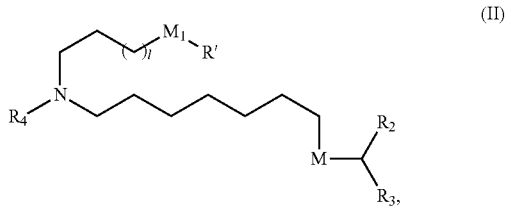

or a salt or stereoisomer thereof, wherein l is selected from 1, 2, 3, 4, and 5;

$M_1$ is a bond or M';

$R_4$ is unsubstituted $C_{1-3}$ alkyl, or $—(CH_2)_nQ$, in which n is 2, 3, or 4 and Q is OH, $—NHC(S)N(R)_2$, or $—NHC(O)N(R)_2$;

M and M' are independently selected from $—C(O)O—$, $—OC(O)—$, $—C(O)N(R')—$, $—P(O)(OR')O—$, an aryl group, and a heteroaryl group; and $R_2$ and $R_3$ are independently selected from the group consisting of H, $C_{1-14}$ alkyl, and $C_{2-14}$ alkenyl.

E65. The composition of any one of E62 to E64, wherein $M_1$ is M'.

E66. The composition of E65, wherein M and M' are independently $—C(O)O—$ or $—OC(O)—$.

E67. The composition of any one of E62 to E66, wherein l is 1, 3, or 5.

E68. The composition of E60 or E61, wherein the compound is selected from the group consisting of Compound 1 to Compound 147, salts and stereoisomers thereof, and any combination thereof.

E69. The composition of E60 or E61, wherein the compound is of the Formula (IIa), (IIa)

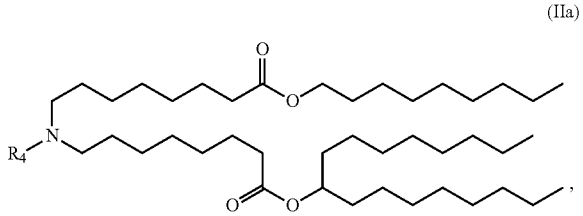

or a salt or stereoisomer thereof.

E70. The composition of E60 or E61, wherein the compound is of the Formula (IIb), (IIb)

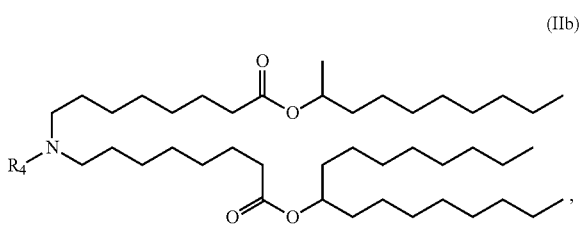

or a salt or stereoisomer thereof.

E71. The composition of E60 or E61, wherein the compound is of the Formula (IIc) or (IIe), (IIc)

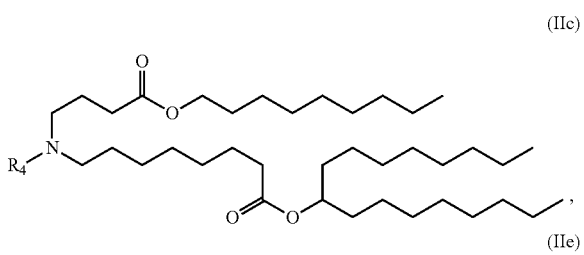

(IIe)

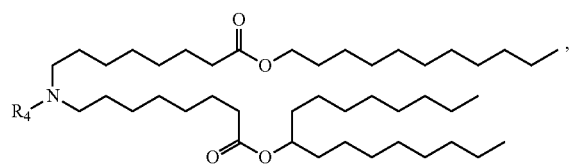

or a salt or stereoisomer thereof.

E72. The composition of any one of E69 to E71, wherein $R_4$ is selected from —$(CH_2)_nQ$ and —$(CH_2)_nCHQR$.

E73. The composition of E60 or E61, wherein the compound is of the Formula (IId), (IId)

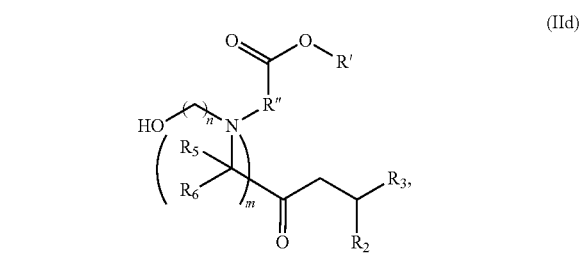

or a salt or stereoisomer thereof,
wherein $R_2$ and $R_3$ are independently selected from the group consisting of $C_{5-14}$ alkyl and $C_{5-14}$ alkenyl, n is selected from 2, 3, and 4, and R', R", $R_5$, $R_6$ and m are as defined in E60 or E61.

E74. The composition of E73, wherein $R_2$ is $C_8$ alkyl.

E75. The composition of E74, wherein $R_3$ is $C_5$ alkyl, $C_6$ alkyl, $C_7$ alkyl, $C_8$ alkyl, or $C_9$ alkyl.

E76. The composition of any one of E73 to E75, wherein m is 5, 7, or 9.

E77. The composition of any one of E73 to E76, wherein each $R_5$ is H.

E78. The composition of E77, wherein each $R_6$ is H.

E79. The composition of any one of E60 to E78, which is a nanoparticle composition.

E80. The composition of E79, wherein the delivery agent further comprises a phospholipid.

E81. The composition of E80, wherein the phospholipid is selected from the group consisting of 1,2-dilinoleoyl-sn-glycero-3-phosphocholine (DLPC), E82. 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16:0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and any mixtures thereof.

E83. The composition of any one of E60 to E81, wherein the delivery agent further comprises a structural lipid.

E84. The composition of E82, wherein the structural lipid is selected from the group consisting of cholesterol, fecosterol, sitosterol, ergosterol, campesterol, stigmasterol, brassicasterol, tomatidine, ursolic acid, alpha-tocopherol, and any mixtures thereof.

E85. The composition of any one of E60 to E83, wherein the delivery agent further comprises a PEG lipid.

E86. The composition of E84, wherein the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and any mixtures thereof.

E87. The composition of any one of E60 to E85, wherein the delivery agent further comprises an ionizable lipid selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl- CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)).

E88. The composition of any one of E60 to E86, wherein the delivery agent further comprises a phospholipid, a structural lipid, a PEG lipid, or any combination thereof.

E89. The composition of any one of E60 to E87, wherein the composition is formulated for in vivo delivery.

E90. The composition according any one of E60 to E88, which is formulated for intramuscular, subcutaneous, or intradermal delivery.

E91. A host cell comprising the polynucleotide of any one of E1 to E53.

E92. The host cell of E90, wherein the host cell is a eukaryotic cell.

E93. A vector comprising the polynucleotide of any one of E1 to E53.

E94. A method of making a polynucleotide comprising enzymatically or chemically synthesizing the polynucleotide of any one of E1 to E53.

E95. A polypeptide encoded by the polynucleotide of any one of E1 to E53, the composition of any one of E56 to E89, the host cell of E90 or E91, or the vector of E92 or produced by the method of E93.

E96. A method of expressing in vivo an active GLA polypeptide in a subject in need thereof comprising administering to the subject an effective amount of the polynucleotide of any one of E1 to E53, the composition of any one of E56 to E89, the host cell of E90 or E91, or the vector of E92.

E97. A method of treating or preventing Fabry disease in a subject in need thereof comprising administering to the subject a therapeutically effective amount of the polynucleotide of any one of E1 to E54, the composition of any one of E56 to E89, the host cell of E90 or E91, or the vector of E92, wherein the administration alleviates the signs or symptoms of Fabry disease in the subject.

E98. A method to prevent or delay the onset of Fabry disease signs or symptoms in a subject in need thereof comprising administering to the subject a prophylactically effective amount of the polynucleotide of any one of E1 to E53, the composition of any one of E56 to E89, the host cell of E90 or E91, or the vector of E92 before Fabry disease signs or symptoms manifest, wherein the administration prevents or delays the onset of Fabry disease signs or symptoms in the subject.

E99. A method to ameliorate the signs or symptoms of Fabry disease in a subject in need thereof comprising administering to the subject a therapeutically effective amount of the polynucleotide of any one of E1 to E53, the composition of any one of E56 to E89, the host cell of E90 or E91, or the vector of E92 before Fabry disease signs or symptoms manifest, wherein the administration ameliorates Fabry disease signs or symptoms in the subject.

31. Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" can mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art can be explicitly excluded from any one or more of the claims. Since such embodiments are deemed to be known to one of ordinary skill in the art, they can be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1: Chimeric Polynucleotide Synthesis

A. Triphosphate Route

Two regions or parts of a chimeric polynucleotide can be joined or ligated using triphosphate chemistry. According to this method, a first region or part of 100 nucleotides or less can be chemically synthesized with a 5' monophosphate and terminal 3'desOH or blocked OH. If the region is longer than 80 nucleotides, it can be synthesized as two strands for ligation.

If the first region or part is synthesized as a non-positionally modified region or part using in vitro transcription (IVT), conversion the 5'monophosphate with subsequent capping of the 3' terminus can follow. Monophosphate protecting groups can be selected from any of those known in the art.

The second region or part of the chimeric polynucleotide can be synthesized using either chemical synthesis or IVT methods. IVT methods can include an RNA polymerase that can utilize a primer with a modified cap. Alternatively, a cap of up to 80 nucleotides can be chemically synthesized and coupled to the IVT region or part.

It is noted that for ligation methods, ligation with DNA T4 ligase, followed by treatment with DNAse should readily avoid concatenation.

The entire chimeric polynucleotide need not be manufactured with a phosphate-sugar backbone. If one of the regions or parts encodes a polypeptide, then such region or part can comprise a phosphate-sugar backbone.

Ligation can then be performed using any known click chemistry, orthoclick chemistry, solulink, or other bioconjugate chemistries known to those in the art.

B. Synthetic Route

The chimeric polynucleotide can be made using a series of starting segments. Such segments include:
 (a) Capped and protected 5' segment comprising a normal 3'OH (SEG. 1)
 (b) 5' triphosphate segment which can include the coding region of a polypeptide and comprising a normal 3'OH (SEG. 2)
 (c) 5' monophosphate segment for the 3' end of the chimeric polynucleotide (e.g., the tail) comprising cordycepin or no 3'OH (SEG. 3)

After synthesis (chemical or IVT), segment 3 (SEG. 3) can be treated with cordycepin and then with pyrophosphatase to create the 5'monophosphate.

Segment 2 (SEG. 2) can then be ligated to SEG. 3 using RNA ligase. The ligated polynucleotide can then be purified and treated with pyrophosphatase to cleave the diphosphate. The treated SEG. 2-SEG. 3 construct is then purified and SEG. 1 is ligated to the 5' terminus. A further purification step of the chimeric polynucleotide can be performed.

Where the chimeric polynucleotide encodes a polypeptide, the ligated or joined segments can be represented as: 5'UTR (SEG. 1), open reading frame or ORF (SEG. 2) and 3'UTR+PolyA (SEG. 3).

The yields of each step can be as much as 90-95%.

Example 2: PCR for cDNA Production

PCR procedures for the preparation of cDNA can be performed using 2×KAPA HIFI™ HotStart ReadyMix by Kapa Biosystems (Woburn, Mass.). This system includes 2× KAPA ReadyMix12.5 µl; Forward Primer (10 µM) 0.75 µl; Reverse Primer (10 µM) 0.75 µl; Template cDNA—100 ng; and dH$_2$O diluted to 25.0 µl. The PCR reaction conditions can be: at 95° C. for 5 min. and 25 cycles of 98° C. for 20 sec, then 58° C. for 15 sec, then 72° C. for 45 sec, then 72° C. for 5 min. then 4° C. to termination.

The reverse primer of the instant invention can incorporate a poly-T$_{120}$ for a poly-A$_{120}$ in the mRNA. Other reverse primers with longer or shorter poly(T) tracts can be used to adjust the length of the poly(A) tail in the polynucleotide mRNA.

The reaction can be cleaned up using Invitrogen's PURELINK™ PCR Micro Kit (Carlsbad, Calif.) per manufacturer's instructions (up to 5 µg). Larger reactions will require a cleanup using a product with a larger capacity. Following the cleanup, the cDNA can be quantified using the NANODROP™ and analyzed by agarose gel electrophoresis to confirm the cDNA is the expected size. The cDNA can then be submitted for sequencing analysis before proceeding to the in vitro transcription reaction.

Example 3: In Vitro Transcription (IVT)

The in vitro transcription reactions can generate polynucleotides containing uniformly modified polynucleotides. Such uniformly modified polynucleotides can comprise a region or part of the polynucleotides of the invention. The input nucleotide triphosphate (NTP) mix can be made using natural and un-natural NTPs.

A typical in vitro transcription reaction can include the following:
 1 Template cDNA—1.0 µg
 2 10× transcription buffer (400 mM Tris-HCl pH 8.0, 190 mM MgCl$_2$, 50 mM DTT, 10 mM Spermidine)—2.0 µl
 3 Custom NTPs (25 mM each)—7.2 µl
 4 RNase Inhibitor—20 U
 5 T7 RNA polymerase—3000 U
 6 dH$_2$O—Up to 20.0 µl. and
 7 Incubation at 37° C. for 3 hr-5 hrs.

The crude IVT mix can be stored at 4° C. overnight for cleanup the next day. 1 U of RNase-free DNase can then be used to digest the original template. After 15 minutes of incubation at 37° C., the mRNA can be purified using Ambion's MEGACLEAR™ Kit (Austin, Tex.) following the manufacturer's instructions. This kit can purify up to 500 µs of RNA. Following the cleanup, the RNA can be quantified using the NanoDrop and analyzed by agarose gel electrophoresis to confirm the RNA is the proper size and that no degradation of the RNA has occurred.

Example 4: Enzymatic Capping

Capping of a polynucleotide can be performed with a mixture includes: IVT RNA 60 µg-180 µg and dH$_2$O up to 72 µl. The mixture can be incubated at 65° C. for 5 minutes to denature RNA, and then can be transferred immediately to ice.

The protocol can then involve the mixing of 10× Capping Buffer (0.5 M Tris-HCl (pH 8.0), 60 mM KCl, 12.5 mM MgCl$_2$) (10.0 µl); 20 mM GTP (5.0 µl); 20 mM S-Adenosyl Methionine (2.5 µl); RNase Inhibitor (100 U); 2'-O-Methyltransferase (400U); Vaccinia capping enzyme (Guanylyl transferase) (40 U); dH$_2$O (Up to 28 µl); and incubation at 37° C. for 30 minutes for 60 µg RNA or up to 2 hours for 180 µg of RNA.

The polynucleotide can then be purified using Ambion's MEGACLEAR™ Kit (Austin, Tex.) following the manufacturer's instructions. Following the cleanup, the RNA can be quantified using the NANODROP™ (ThermoFisher, Waltham, Mass.) and analyzed by agarose gel electrophoresis to confirm the RNA is the proper size and that no degradation of the RNA has occurred. The RNA product can also be sequenced by running a reverse-transcription-PCR to generate the cDNA for sequencing.

Example 5: PolyA Tailing Reaction

Without a poly-T in the cDNA, a poly-A tailing reaction must be performed before cleaning the final product. This can be done by mixing Capped IVT RNA (100 µl); RNase Inhibitor (20 U); 10× Tailing Buffer (0.5 M Tris-HCl (pH 8.0), 2.5 M NaCl, 100 mM MgCl$_2$)(12.0 µl); 20 mM ATP (6.0 µl); Poly-A Polymerase (20 U); dH$_2$O up to 123.5 µl and incubating at 37° C. for 30 min. If the poly-A tail is already in the transcript, then the tailing reaction can be skipped and proceed directly to cleanup with Ambion's MEGA-CLEAR™ kit (Austin, Tex.) (up to 500 µg). Poly-A Polymerase is, in some cases, a recombinant enzyme expressed in yeast.

It should be understood that the processivity or integrity of the polyA tailing reaction does not always result in an exact size polyA tail. Hence polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the invention.

Example 6: Natural 5' Caps and 5' Cap Analogues

5'-capping of polynucleotides can be completed concomitantly during the in vitro-transcription reaction using the following chemical RNA cap analogs to generate the 5'-guanosine cap structure according to manufacturer protocols: 3'-O-Me-m7G(5)ppp(5')G [the ARCA cap]; G(5')ppp(5')A; G(5')ppp(5')G; m7G(5')ppp(5')A; m7G(5')ppp(5')G (New England BioLabs, Ipswich, Mass.). 5'-capping of modified RNA can be completed post-transcriptionally using a Vaccinia Virus Capping Enzyme to generate the "Cap 0" structure: m7G(5')ppp(5')G (New England BioLabs, Ipswich, Mass.). Cap 1 structure can be generated using both Vaccinia Virus Capping Enzyme and a 2'-O methyl-transferase to generate: m7G(5')ppp(5')G-2'-O-methyl. Cap 2 structure can be generated from the Cap 1 structure followed by the 2'-O-methylation of the 5'-antepenultimate nucleotide using a 2'-O methyl-transferase. Cap 3 structure can be generated from the Cap 2 structure followed by the 2'-O-methylation of the 5'-preantepenultimate nucleotide using a 2'-0 methyl-transferase. Enzymes can be derived from a recombinant source.

When transfected into mammalian cells, the modified mRNAs can have a stability of between 12-18 hours or more than 18 hours, e.g., 24, 36, 48, 60, 72 or greater than 72 hours.

Example 7: Capping Assays

A. Protein Expression Assay

Polynucleotides encoding a polypeptide, containing any of the caps taught herein, can be transfected into cells at equal concentrations. After 6, 12, 24 and 36 hours post-transfection, the amount of protein secreted into the culture medium can be assayed by ELISA. Synthetic polynucleotides that secrete higher levels of protein into the medium would correspond to a synthetic polynucleotide with a higher translationally-competent Cap structure.

B. Purity Analysis Synthesis

Polynucleotides encoding a polypeptide, containing any of the caps taught herein, can be compared for purity using denaturing Agarose-Urea gel electrophoresis or HPLC analysis. Polynucleotides with a single, consolidated band by electrophoresis correspond to the higher purity product compared to polynucleotides with multiple bands or streaking bands. Synthetic polynucleotides with a single HPLC peak would also correspond to a higher purity product. The capping reaction with a higher efficiency would provide a more pure polynucleotide population.

C. Cytokine Analysis

Polynucleotides encoding a polypeptide, containing any of the caps taught herein, can be transfected into cells at multiple concentrations. After 6, 12, 24 and 36 hours post-transfection the amount of pro-inflammatory cytokines such as TNF-alpha and IFN-beta secreted into the culture medium can be assayed by ELISA. Polynucleotides resulting in the secretion of higher levels of pro-inflammatory cytokines into the medium would correspond to polynucleotides containing an immune-activating cap structure.

D. Capping Reaction Efficiency

Polynucleotides encoding a polypeptide, containing any of the caps taught herein, can be analyzed for capping reaction efficiency by LC-MS after nuclease treatment. Nuclease treatment of capped polynucleotides would yield a mixture of free nucleotides and the capped 5'-5-triphosphate cap structure detectable by LC-MS. The amount of capped product on the LC-MS spectra can be expressed as a percent of total polynucleotide from the reaction and would correspond to capping reaction efficiency. The cap structure with higher capping reaction efficiency would have a higher amount of capped product by LC-MS.

Example 8: Agarose Gel Electrophoresis of Modified RNA or RT PCR Products

Individual polynucleotides (200-400 ng in a 20 µl volume) or reverse transcribed PCR products (200-400 ng) can be loaded into a well on a non-denaturing 1.2% Agarose E-Gel (Invitrogen, Carlsbad, Calif.) and run for 12-15 minutes according to the manufacturer protocol.

Example 9: Nanodrop Modified RNA Quantification and UV Spectral Data

Modified polynucleotides in TE buffer (1 µl) can be used for Nanodrop UV absorbance readings to quantitate the yield of each polynucleotide from an chemical synthesis or in vitro transcription reaction.

Example 10: Formulation of Modified mRNA Using Lipidoids

Polynucleotides can be formulated for in vitro experiments by mixing the polynucleotides with the lipidoid at a set ratio prior to addition to cells. In vivo formulation can require the addition of extra ingredients to facilitate circulation throughout the body. To test the ability of these lipidoids to form particles suitable for in vivo work, a standard formulation process used for siRNA-lipidoid formulations can be used as a starting point. After formation of the particle, polynucleotide can be added and allowed to integrate with the complex. The encapsulation efficiency can be determined using a standard dye exclusion assays.

Example 11: Method of Screening for Protein Expression

A. Electrospray Ionization

A biological sample that can contain proteins encoded by a polynucleotide administered to the subject can be prepared and analyzed according to the manufacturer protocol for electrospray ionization (ESI) using 1, 2, 3 or 4 mass analyzers. A biologic sample can also be analyzed using a tandem ESI mass spectrometry system.

Patterns of protein fragments, or whole proteins, can be compared to known controls for a given protein and identity can be determined by comparison.

B. Matrix-Assisted Laser Desorption/Ionization

A biological sample that can contain proteins encoded by one or more polynucleotides administered to the subject can be prepared and analyzed according to the manufacturer protocol for matrix-assisted laser desorption/ionization (MALDI).

Patterns of protein fragments, or whole proteins, can be compared to known controls for a given protein and identity can be determined by comparison.

C. Liquid Chromatography-Mass Spectrometry-Mass Spectrometry

A biological sample, which can contain proteins encoded by one or more polynucleotides, can be treated with a trypsin enzyme to digest the proteins contained within. The resulting peptides can be analyzed by liquid chromatography-mass spectrometry-mass spectrometry (LC/MS/MS). The peptides can be fragmented in the mass spectrometer to yield diagnostic patterns that can be matched to protein sequence databases via computer algorithms. The digested sample can be diluted to achieve 1 ng or less starting material for a given protein. Biological samples containing a simple buffer background (e.g., water or volatile salts) are amenable to direct in-solution digest; more complex backgrounds (e.g., detergent, non-volatile salts, glycerol) require an additional clean-up step to facilitate the sample analysis.

Patterns of protein fragments, or whole proteins, can be compared to known controls for a given protein and identity can be determined by comparison.

Example 12: Synthesis of mRNA Encoding GLA

Sequence optimized polynucleotides encoding GLA polypeptides, e.g., SEQ ID NO: 1, are synthesized and characterized as described in Examples 1 to 11. mRNAs encoding human GLA are prepared for the Examples described below, and are synthesized and characterized as described in Examples 1 to 11.

An mRNA encoding human GLA is constructed, e.g., by using the ORF sequence provided in SEQ ID NO: 2. The mRNA sequence includes both 5' and 3' UTR regions (see, e.g., SEQ ID NOs: 33, 50, 75, and 81). In a construct, the 5'UTR and 3'UTR sequences are:

```
5' UTR
                               (SEQ ID NO: 50)
UCAAGCUUUUGGACCCUCGUACAGAAGCUAAUACGACUCACUAUAGGGAA

AUAAGAGAGAAAAGAAGAGUAAGAAGAAAUAUAAGAGCCACC

5' UTR
                               (SEQ ID NO: 33)
GGGAAAUAAGAGAGAAAAGAAGAGUAAGAAGAAAUAUAAGAGCCACC;
and 3' UTR
                               (SEQ ID NO: 75)
UGAUAAUAGGCUGGAGCCUCGGUGGCCAUGCUUCUUGCCCCUUGGGCCUC

CCCCCAGCCCCUCCUCCCCUUCCUGCACCCGUACCCCCGUGGUCUUUGAA

UAAAGUCUGAGUGGGCGGC
or

3' UTR
                               (SEQ ID NO: 81)
UGAUAAUAGUCCAUAAAGUAGGAAACACUACAGCUGGAGCCUCGGUGGCC

AUGCUUCUUGCCCCUUGGGCCUCCCCCCAGCCCCUCCUCCCCUUCCUGCA

CCCGUACCCCCCGCAUUAUUACUCACGGUACGAGUGGUCUUUGAAUAAAG

UCUGAGUGGGCGGC
```

The GLA mRNA sequence was prepared as modified mRNA. Specifically, during in vitro translation, modified mRNA can be generated using 5-methoxy-UTP to ensure that the mRNAs contain 100% 5-methoxy-uridine instead of uridine. Further, GLA mRNA can be synthesized with a primer that introduces a polyA-tail, and a Cap 1 structure is generated on both mRNAs using Vaccinia Virus Capping Enzyme and a 2'-O methyl-transferase to generate: m7G(5)ppp(5')G-2'-O-methyl.

Exemplary mRNAs encoding GLA are listed in Table 6 below. Table 6's modified mRNA constructs include optimized ORFS encoding human GLA. Each of constructs 1-23 comprises a Cap1 5' terminal cap and a 3' terminal polyA region

TABLE 6

Modified mRNA Constructs

| GLA mRNA construct | 5'UTR SEQ ID NO | GLA ORF Name | SEQ ID NO | 3'UTR SEQ ID NO |
|---|---|---|---|---|
| #1 (SEQ ID NO: 119) | 33 | GLA-CO26 | 79 | 81 |
| #2 (SEQ ID NO 120) | 33 | GLA-CO27 | 80 | 81 |
| #3 (SEQ ID NO: 121) | 33 | WT GLA | 2 | 81 |
| #4 (SEQ ID NO: 122) | 33 | GLA-CO28 | 141 | 81 |
| #5 (SEQ ID NO: 123) | 33 | GLA-CO29 | 142 | 81 |
| #6 (SEQ ID NO: 124) | 33 | GLA-CO30 | 143 | 81 |
| #7 (SEQ ID NO: 125) | 33 | GLA-CO31 | 144 | 81 |
| #8 (SEQ ID NO: 126) | 33 | GLA-CO32 | 145 | 81 |
| #9 (SEQ ID NO: 127) | 33 | GLA-CO33 | 146 | 81 |
| #10 (SEQ ID NO: 128) | 33 | GLA-CO34 | 147 | 81 |
| #11 (SEQ ID NO: 129) | 33 | GLA-CO35 | 148 | 81 |
| #12 (SEQ ID NO: 130) | 33 | GLA-CO36 | 149 | 81 |
| #13 (SEQ ID NO: 131) | 33 | GLA-CO37 | 150 | 81 |
| #14 (SEQ ID NO: 132) | 33 | GLA-CO38 | 151 | 81 |
| #15 (SEQ ID NO: 133) | 33 | GLA-CO39 | 152 | 81 |
| #16 (SEQ ID NO: 134) | 33 | GLA-CO40 | 153 | 81 |
| #17 (SEQ ID NO: 135) | 33 | GLA-CO41 | 154 | 81 |
| #18 (SEQ ID NO: 136) | 33 | GLA-CO42 | 155 | 81 |
| #19 (SEQ ID NO: 137) | 33 | GLA-CO43 | 156 | 81 |
| #20 (SEQ ID NO: 138) | 33 | GLA-CO44 | 157 | 81 |
| #21 (SEQ ID NO: 139) | 33 | GLA-CO45 | 158 | 81 |
| #22 (SEQ ID NO: 140) | 33 | GLA-CO46 | 159 | 81 |
| #23 (SEQ ID NO: 160) | 33 | GLA-CO26 | 79 | 103 |

Example 13: Detecting Endogenous GLA Expression In Vitro

GLA expression is characterized in a variety of cell lines derived from both mice and human sources. Cells are cultured in standard conditions and cell extracts are obtained by placing the cells in lysis buffer. For comparison purposes, appropriate controls are also prepared. To analyze GLA expression, lysate samples are prepared from the tested cells and mixed with lithium dodecyl sulfate sample loading buffer and subjected to standard Western blot analysis. For detection of GLA, the antibody used is a commercial anti-GLA antibody. For detection of a load control, the antibody used is anti-citrase synthase (rabbit polyclonal; PA5-22126;

Thermo-Fisher Scientific®). To examine the localization of endogenous GLA, immunofluorescence analysis is performed on cells. GLA expression is detected using a commercial anti-GLA. The location of specific organelles can be detected with existing commercial products. For example, mitochondria can be detected using Mitotracker, and the nucleus can be stained with DAPI. Image analysis is performed on a Zeiss ELYRA imaging system.

Endogenous GLA expression can be used as a base line to determine changes in GLA expression resulting from transfection with mRNAs comprising nucleic acids encoding GLA.

Example 14: In Vitro Expression of GLA in HeLa Cells

To measure in vitro expression of human GLA in HeLa cells, those cells are seeded on 12-well plates (BD Biosciences, San Jose, USA) one day prior to transfection. mRNA formulations comprising human GLA or a GFP control are transfected using 800 ng mRNA and 2 µL Lipofectamin 2000 in 60 µL OPTI-MEM per well and incubated.

After 24 hours, the cells in each well are lysed using a consistent amount of lysis buffer. Appropriate controls are used. Protein concentrations of each are determined using a BCA assay according to manufacturer's instructions. To analyze GLA expression, equal loads of each lysate (24 µg) are prepared in a loading buffer and subjected to standard Western blot analysis. For detection of GLA, a commercial anti-GLA antibody is used according to the manufacturer's instructions.

Example 15: In Vitro GLA Activity in HeLa Cells

An in vitro GLA activity assay is performed to determine whether GLA exogenously-expressed after introduction of mRNA comprising a GLA sequence is active.

A. Expression Assay

HeLa cells are transfected with mRNA formulations comprising human GLA or a GFP control. Cells are transfected with Lipofectamin 2000 and lysed as described in Example 14 above. Appropriate controls are also prepared.

B. Activity Assay

To assess whether exogenous GLA can function, an in vitro activity assay is performed using transfected HeLa cell lysates as the source of enzymatic activity. GLA activity was determined by mixing cell lysate samples with 2 mM 4-methylumbelliferyl-α-D-galactopyranoside (4MU-α-Gal) and 50 mM N-acetylgalactosamine inhibitor of α-galactosidase B at pH 4.6 in a plate-based assay. The assay mixtures were incubated at 37° C. for 30 min. The reactions were terminated by the addition of equal volume of 0.5 M ethylene-diamine (pH=10.4). 4-MU production was measured using a fluorescence plate reader with an excitation wavelength of 365 nm and an emission wavelength of 450 nm.

Example 16: Measuring In Vitro Expression of GLA in Cells

Cells from normal subjects and Fabry disease patients are examined for their capacity to express exogenous GLA. Cells are transfected with mRNA formulations comprising human GLA, mouse GLA, or a GFP control via electroporation using a standard protocol. Each construct is tested separately. After incubation, cells are lysed and protein concentration in each lysate is measured using a suitable assay, e.g., by BCA assay. To analyze GLA expression, equal loads of each lysate are prepared in a loading buffer and subjected to standard Western blot analysis. For detection of GLA, an anti-GLA is used. For detection of a load control, the antibody used is anti-citrase synthase (rabbit polyclonal; MA5-17625; Pierce®).

Example 17: Measuring In Vitro GLA Activity in Lysates

A. Expression

Cells from normal human subjects and Fabry disease patients are cultured. Cells are transfected with mRNA formulations comprising human GLA, mouse GLA, or a GFP control via electroporation using a standard protocol.

B. Activity Assay

To assess whether exogenous GLA function, an in vitro activity assay is performed using transfected cell lysates as the source of enzymatic activity. GLA activity was determined by mixing isolated protein samples with 2 mM 4-methylumbelliferyl-α-D-galactopyranoside (4MU-α-Gal) and 50 mM N-acetylgalactosamine inhibitor of α-galactosidase B at pH 4.6 in a plate-based assay. The assay mixtures were incubated at 37° C. for 30 min. The reactions were terminated by the addition of equal volume of 0.5 M ethylene-diamine (pH=10.4). 4-MU production was measured using a fluorescence plate reader with an excitation wavelength of 365 nm and an emission wavelength of 450 nm.

Example 18: In Vivo GLA Expression in Animal Models

To assess the ability of GLA-containing mRNAs to facilitate GLA expression in vivo, mRNA encoding human GLA is introduced into C57B/L6 mice. C57B/L6 mice are injected intravenously with either control mRNA (NT-FIX) or human GLA mRNA. The mRNA is formulated in lipid nanoparticles for delivery into the mice. Mice are sacrificed after 24 hrs. and GLA protein levels in liver lysates are determined by capillary electrophoresis (CE). Citrate synthase expression is examined for use as a load control. For control NT-FIX injections, 4 mice are tested for each time point. For human GLA mRNA injections, 4 mice are tested for each time point. Treatment with mRNA encoding GLA is expected to reliably induce expression of GLA.

Example 19: Human GLA Mutant and Chimeric Constructs

A polynucleotide of the present invention can comprise at least a first region of linked nucleosides encoding human GLA, which can be constructed, expressed, and characterized according to the examples above. Similarly, the polynucleotide sequence can contain one or more mutations that results in the expression of a GLA with increased or decreased activity. Furthermore, the polynucleotide sequence encoding GLA can be part of a construct encoding a chimeric fusion protein.

Example 20: Production of Nanoparticle Compositions

A. Production of Nanoparticle Compositions

Nanoparticles can be made with mixing processes such as microfluidics and T-junction mixing of two fluid streams, one of which contains the polynucleotide and the other has the lipid components.

Lipid compositions are prepared by combining a lipid according to Formula (I), such as Compound 18 or a lipid according to Formula (III) such as Compound 236, a phospholipid (such as DOPE or DSPC, obtainable from Avanti Polar Lipids, Alabaster, Ala.), a PEG lipid (such as 1,2-dimyristoyl-sn-glycerol methoxypolyethylene glycol, also known as PEG-DMG, obtainable from Avanti Polar Lipids, Alabaster, Ala. or Compound 428), and a structural lipid (such as cholesterol, obtainable from Sigma-Aldrich, Taufkirchen, Germany, or a corticosteroid (such as prednisolone, dexamethasone, prednisone, and hydrocortisone), or a combination thereof) at concentrations of about 50 mM in ethanol. Solutions should be refrigerated for storage at, for example, −20° C. Lipids are combined to yield desired molar ratios and diluted with water and ethanol to a final lipid concentration of between about 5.5 mM and about 25 mM.

Nanoparticle compositions including a polynucleotide and a lipid composition are prepared by combining the lipid solution with a solution including the a polynucleotide at lipid composition to polynucleotide wt:wt ratios between about 5:1 and about 50:1. The lipid solution is rapidly injected using a NanoAssemblr microfluidic based system at flow rates between about 10 ml/min and about 18 ml/min into the polynucleotide solution to produce a suspension with a water to ethanol ratio between about 1:1 and about 4:1.

For nanoparticle compositions including an RNA, solutions of the RNA at concentrations of 0.1 mg/ml in deionized water are diluted in 50 mM sodium citrate buffer at a pH between 3 and 4 to form a stock solution.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, Ill.) with a molecular weight cutoff of 10 kD. The first dialysis is carried out at room temperature for 3 hours. The formulations are then dialyzed overnight at 4° C. The resulting nanoparticle suspension is filtered through 0.2 μm sterile filters (Sarstedt, Numbrecht, Germany) into glass vials and sealed with crimp closures. Nanoparticle composition solutions of 0.01 mg/ml to 0.10 mg/ml are generally obtained.

The method described above induces nano-precipitation and particle formation. Alternative processes including, but not limited to, T-junction and direct injection, can be used to achieve the same nano-precipitation.

B. Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of a polynucleotide (e.g., RNA) in nanoparticle compositions. 100 μL of the diluted formulation in 1×PBS is added to 900 μL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, Calif.). The concentration of polynucleotide in the nanoparticle composition can be calculated based on the extinction coefficient of the polynucleotide used in the composition and on the difference between the absorbance at a wavelength of, for example, 260 nm and the baseline value at a wavelength of, for example, 330 nm.

For nanoparticle compositions including an RNA, a QUANT-IT™ RIBOGREEN® RNA assay (Invitrogen Corporation Carlsbad, Calif.) can be used to evaluate the encapsulation of an RNA by the nanoparticle composition. The samples are diluted to a concentration of approximately 5 μg/mL in a TE buffer solution (10 mM Tris-HCl, 1 mM EDTA, pH 7.5). 50 μL of the diluted samples are transferred to a polystyrene 96 well plate and either 50 μL of TE buffer or 50 μL of a 2% Triton X-100 solution is added to the wells. The plate is incubated at a temperature of 37° C. for 15 minutes. The RIBOGREEN® reagent is diluted 1:100 in TE buffer, and 100 μL of this solution is added to each well. The fluorescence intensity can be measured using a fluorescence plate reader (Wallac Victor 1420 Multilablel Counter; Perkin Elmer, Waltham, Mass.) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

Exemplary formulations of the nanoparticle compositions are presented in the TABLE 7 below. The term "Compound" refers to an ionizable lipid such as MC3, Compound 18, or Compound 236. "Phospholipid" can be DSPC or DOPE. "PEG-lipid" can be PEG-DMG or Compound 428.

TABLE 7

Exemplary Formulations of Nanoparticles

| Composition (mol %) | Components |
|---|---|
| 40:20:38.5:1.5 | Compound:Phospholipid:Chol:PEG-lipid |
| 45:15:38.5:1.5 | Compound:Phospholipid:Chol:PEG-lipid |
| 50:10:38.5:1.5 | Compound:Phospholipid:Chol:PEG-lipid |
| 55:5:38.5:1.5 | Compound:Phospholipid:Chol:PEG-lipid |
| 60:5:33.5:1.5 | Compound:Phospholipid:Chol:PEG-lipid |
| 45:20:33.5:1.5 | Compound:Phospholipid:Chol:PEG-lipid |
| 50:20:28.5:1.5 | Compound:Phospholipid:Chol:PEG-lipid |
| 55:20:23.5:1.5 | Compound:Phospholipid:Chol:PEG-lipid |
| 60:20:18.5:1.5 | Compound:Phospholipid:Chol:PEG-lipid |
| 40:15:43.5:1.5 | Compound:Phospholipid:Chol:PEG-lipid |
| 50:15:33.5:1.5 | Compound:Phospholipid:Chol:PEG-lipid |
| 55:15:28.5:1.5 | Compound:Phospholipid:Chol:PEG-lipid |
| 60:15:23.5:1.5 | Compound:Phospholipid:Chol:PEG-lipid |
| 40:10:48.5:1.5 | Compound:Phospholipid:Chol:PEG-lipid |
| 45:10:43.5:1.5 | Compound:Phospholipid:Chol:PEG-lipid |
| 55:10:33.5:1.5 | Compound:Phospholipid:Chol:PEG-lipid |
| 60:10:28.5:1.5 | Compound:Phospholipid:Chol:PEG-lipid |
| 40:5:53.5:1.5 | Compound:Phospholipid:Chol:PEG-lipid |
| 45:5:48.5:1.5 | Compound:Phospholipid:Chol:PEG-lipid |
| 50:5:43.5:1.5 | Compound:Phospholipid:Chol:PEG-lipid |
| 40:20:40:0 | Compound:Phospholipid:Chol:PEG-lipid |
| 45:20:35:0 | Compound:Phospholipid:Chol:PEG-lipid |
| 50:20:30:0 | Compound:Phospholipid:Chol:PEG-lipid |
| 55:20:25:0 | Compound:Phospholipid:Chol:PEG-lipid |
| 60:20:20:0 | Compound:Phospholipid:Chol:PEG-lipid |
| 40:15:45:0 | Compound:Phospholipid:Chol:PEG-lipid |
| 45:15:40:0 | Compound:Phospholipid:Chol:PEG-lipid |
| 50:15:35:0 | Compound:Phospholipid:Chol:PEG-lipid |
| 55:15:30:0 | Compound:Phospholipid:Chol:PEG-lipid |
| 60:15:25:0 | Compound:Phospholipid:Chol:PEG-lipid |
| 40:10:50:0 | Compound:Phospholipid:Chol:PEG-lipid |
| 45:10:45:0 | Compound:Phospholipid:Chol:PEG-lipid |
| 50:10:40:0 | Compound:Phospholipid:Chol:PEG-lipid |
| 55:10:35:0 | Compound:Phospholipid:Chol:PEG-lipid |
| 60:10:30:0 | Compound:Phospholipid:Chol:PEG-lipid |

Example 21: In Vivo GLA Activity in Wild-Type Mice Injected with GLA mRNA

A. Activity Assay

The GLA activity assay measures the ability of GLA enzymatic activity to release the fluorescent indicator 4-Methylumbelliferone (4-MU) from the non-fluorescent 4MU-α-Gal substrate. The assay was optimized for both wild-type and Fabry mice backgrounds. Standard curves of 4-MU for mouse plasma, kidney, heart, spleen, and liver were developed. One unit [U] of GLA activity was considered to be the amount capable of hydrolyzing 1 nmol of substrate per hour. This assay was adapted from Desnick et al., *J. Lab. Clin. Med.* 81(2):157-171 (1973); Ziegler et al., *Human Gene Therapy* 10:1667-1682 (Jul. 1, 1999); and Ioannou et al., *Am. J. Hum. Genet.* 68:14-25, 2001.

GLA activity was determined by mixing isolated protein samples with 2 mM 4-methylumbelliferyl-α-D-galactopyranoside (4MU-α-Gal) and 50 mM N-acetylgalactosamine inhibitor of α-galactosidase B at pH 4.6 in a plate-based assay. The assay mixtures were incubated at 37° C. for 30 min. The reactions were terminated by the addition of equal volume of 0.5 M ethylene-diamine (pH=10.4). 4-MU production was measured using a fluorescence plate reader with an excitation wavelength of 365 nm and an emission wavelength of 450 nm.

B. Comparison of Sequence Optimized mRNAs Encoding GLA

The ability of sequence optimized, chemically modified GLA-encoding mRNAs to facilitate GLA activity in vivo was tested. Wild-type CD1 mice (N=3 per group) were injected intravenously with (i) control mRNA (NT-FIX), (ii) wild-type mRNA without sequence engineering encoding human GLA (GLA-mRNA #3); (iii) sequence optimized, chemically modified mRNA (GLA-mRNA #s 1-2 and 4-22) encoding human GLA; or (iv) a PBS control solution. The sequence optimized, chemically modified GLA mRNAs included mir142/126 binding sites in the untranslated regions. The mRNAs were formulated in lipid nanoparticles (MC3) for delivery of 0.5 mg/kg mRNA into each mouse. Mice were sacrificed after 24 hours, and the mouse livers were harvested.

The GLA activity in the wild-type mouse livers 24 hours post-injection is shown in TABLE 8 below. Sequence optimized, chemically modified GLA mRNAs facilitated increased GLA activity in mouse livers compared to controls. Notably, two of the sequence optimized, chemically modified GLA mRNAs (GLA-mRNA #1 and GLA-mRNA #2) resulted in GLA activity approximately 10-fold higher than the endogenous mouse GLA activity. These two GLA mRNAs were used in the further studies described in Examples 22-25 below.

TABLE 8

| Sample ID | SEQ ID NO | GLA Activity (nmol/h/mg) | St. Dev. |
|---|---|---|---|
| Human Liver | | 15.78 | 7.70 |
| PBS | | 7.85 | 1.81 |
| NTFIX | | 10.92 | 2.02 |
| GLA-mRNA #22 | 140 | 15.76 | 4.32 |
| GLA mRNA #3 | 121 | 13.78 | 1.33 |
| GLA mRNA #4 | 122 | 28.62 | 5.37 |
| GLA mRNA #5 | 123 | 29.01 | 2.21 |
| GLA mRNA #6 | 124 | 52.83 | 12.78 |
| GLA mRNA #7 | 125 | 20.41 | 1.53 |
| GLA mRNA #8 | 126 | 33.29 | 8.39 |
| GLA mRNA #9 | 127 | 47.39 | 9.66 |
| GLA mRNA #10 | 128 | 50.02 | 7.92 |
| GLA mRNA #11 | 129 | 25.36 | 3.86 |
| GLA mRNA #12 | 130 | 57.65 | 15.49 |
| GLA mRNA #13 | 131 | 103.06 | 23.93 |
| GLA mRNA #14 | 132 | 56.06 | 19.53 |
| GLA mRNA #15 | 133 | 101.13 | 16.86 |
| GLA mRNA #16 | 134 | 41.35 | 6.57 |
| GLA mRNA #17 | 135 | 31.49 | 6.40 |
| GLA mRNA #1 | 119 | 137.91 | 24.17 |
| GLA mRNA #18 | 136 | 60.71 | 16.64 |

TABLE 8-continued

| Sample ID | SEQ ID NO | GLA Activity (nmol/h/mg) | St. Dev. |
|---|---|---|---|
| GLA mRNA #19 | 137 | 52.44 | 7.15 |
| GLA mRNA #2 | 120 | 132.40 | 34.30 |
| GLA mRNA #20 | 138 | 85.27 | 35.00 |
| GLA mRNA #21 | 139 | 71.45 | 26.75 |

Example 22: In Vivo GLA Protein Expression and Activity in Wild-type Mice Post-IV Injection with GLA mRNA GLA protein expression and GLA activity in wild-type mouse plasma and tissues were assessed after sequence optimized, chemically modified mRNA (GLA-mRNA #2) encoding human GLA or control mRNA encoding GFP was administered into wild-type CD1 mice. The GLA mRNA included mir142/126 binding sites. The mRNAs were formulated in lipid nanoparticles (MC3) for delivery, and were injected intravenously as a single dose of 0.5 mg/kg (N=3 per group). Mice were sacrificed 24 hours, 48 hours, 72 hours, 96 hours, or 7 days after dosing. After sacrifice, mice were perfused with PBS and tissues were collected (liver, spleen, kidney and heart). Plasma was also collected from the mice. The samples were analyzed as detailed below.

A. GLA Immunohistochemistry

GLA protein expression in the mouse livers 48 hours post-injection with GLA mRNA was analyzed by immunohistochemistry (IHC). Tissue sections were fixed, embedded, sectioned, and stained with an anti-GLA antibody (Abcam rabbit monoclonal ab168341) diluted 1:400 in Leica Diluent. Liver sections were counterstained with hematoxylin.

FIGS. 8 and 9 show representative tissue samples from three different mice stained with the anti-GLA antibody. FIG. 8 shows anti-GLA stained liver sections from mice treated with mRNA encoding GFP. Only low levels of anti-GLA staining were observed in these tissue sections. FIG. 9 shows anti-GLA stained liver sections from mice treated with mRNA encoding GLA. High levels of GLA expression were observed in both the hepatocytes and the sinusoids of the livers in GLA mRNA treated animals. In the GLA mRNA treated animals, uniform staining showed broad distribution in the livers and puncta expression that was indicative of GLA trafficking to the lysosome.

B. GLA Protein Activity Over Time in Plasma and Tissues of Wild-Type Mice Post-IV Injection of GLA mRNA GLA protein levels in plasma, liver, spleen, kidney, and heart from the control GFP mRNA and GLA mRNA injected wild-type CD1 mice were analyzed using the 4-MU fluorogenic GLA activity assay described in Example 21 above.

As a baseline, FIG. 10A shows GLA activity levels over time in spleen, liver, heart, kidney, and plasma of wild-type mice administered control GFP mRNA. FIG. 10B shows GLA activity levels over time in spleen, liver, heart, kidney, and plasma of wild-type mice treated with GLA mRNA. In both FIGS. 10A and 10B, the plasma GLA activity scale is shown on the right-hand Y axis and the tissue GLA activity scale is shown on the left-hand Y axis. FIGS. 10C, 10D, 10E, 10F, and 10G show the GLA activity for wild-type mice administered GFP mRNA compared to GLA mRNA in the heart, liver, kidney, spleen, and plasma, respectively. The approximate endogenous mouse GLA activities for the heart (FIG. 10C), liver (FIG. 10D), kidney (FIG. 10E), and plasma (FIG. 10G) are shown as a dotted line in each figure for reference.

These results show that after treatment with control GFP mRNA, GLA activity remained at low baseline endogenous levels in each tissue for the entire time course. After treatment with GLA mRNA, increased GLA activity levels were observed 24 hours after treatment in all tissues examined. At 24 hours post-injection, GLA activity in liver, spleen and plasma increased at least 8×; and GLA activity in heart and kidney increased at least 2-3×. GLA activity in the plasma and spleen began to decreased after 24 hours. GLA activity remained elevated above endogenous levels in plasma at least 144 hours after treatment and remained elevated above endogenous levels in spleen at least 72 hours after treatment. The increased GLA activity above endogenous levels in the heart, kidney, and liver decreased more slowly, and the increased activity in the heart and liver was sustained at least one week after a single dose single treatment with GLA mRNA.

When compared to published enzyme replacement therapy (ERT) results for liver and spleen, the AUC appears to be higher and ti/2 appears to be longer in tissues administered GLA mRNA compared to ERT (Ioannou et al., Am. J. Hum. Genet. 68:14-25, 2001). These results also suggest more uptake in the heart and kidney compared to reports with enzyme replacement therapy (ERT).

Example 23: GLA Expression, Activity and Lyso-Gb3 Levels in Fabry Mice Post-IV Injection with GLA mRNA GLA-/- knockout mice (SV129/C57B6 strain, males, 24-26 weeks old) were administered sequence optimized, chemically modified mRNA (GLA-mRNA #1) encoding GLA (N=5 per group) or control mRNA encoding GFP (N=3 per group). The GLA mRNAs were formulated in lipid nanoparticles (MC3) for delivery, and were injected intravenously as a single dose at 0.5 mg/kg, or 0.1 mg/kg, or 0.05 mg/kg of mRNA. Three mice were administered control mRNA encoding GFP formulated in lipid nanoparticles (MC3) and injected as a single dose at 0.5 mg/kg of mRNA. Three wild-type mice (CD1 strain, males, 24-26 weeks old) administered lipid nanoparticles (MC3) in PBS (no mRNA) were also included in the study for comparison. Blood was collected from each mouse at 0, 6 hours, 24 hours, and 72 hours. After 72 hours, the mice were sacrificed and the heart, kidney, liver and spleen were harvested. The samples were analyzed as detailed below.

A. mRNA-Mediated GLA Expression in Liver of GLA Knockout Mice

GLA protein levels in the GLA knockout mouse livers at 72 hours post-IV dosing were analyzed by capillary electrophoresis (CE). FIG. 11A shows a dose-response of GLA expression in the liver 72 hours after administration of mRNA encoding GLA. Significant GLA expression relative to GFP control was observed at each concentration of GLA mRNA administered, with the highest levels of GLA expression observed at the 0.5 mg/kg dose. No GLA expression was observed in livers of GLA knockout mice administered control GFP mRNA. Quantification of the protein expression at 72 hours is plotted in FIG. 11B. The mean GLA expression at the 0.5 mg/kg dose was 152.5 ng/mg.

B. GLA mRNA Dose-Response in Plasma of GLA Knockout Mice

Plasma was prepared from blood samples collected 0 hours, 6 hours, 24 hours, and 72 hours after administration. The 4-MU fluorogenic GLA activity assay described in Example 21 above was performed on each plasma sample.

FIG. 12A shows a logarithmic plot of GLA activity in plasma of GLA knockout mice over time for each dose of GLA mRNA compared to the GLA activity in plasma for mice administered control GFP mRNA. FIGS. 12B, 12C, and 12D show the GLA activity in plasma for each dose at 6 hours, 24 hours, and 72 hours after treatment, respectively. In FIG. 12D, 72 hour GLA activity data for the wild-type mice treated with lipid nanoparticle in PBS is included for comparison. The mice treated with mRNA encoding GLA showed increased GLA activity in a dose-dependent manner at each time point. The highest GLA activity level for each dose of GLA mRNA was observed 6 hours after treatment, and increased GLA activity compared to control was still observed 72 hours after treatment.

An ELISA assay was performed to quantitate GLA expression in plasma 6 hours post-administration. FIG. 13 shows that while no GLA protein was detected in the plasma of control GFP mice, significant levels of GLA protein were detected in the plasma of mice administered 0.1 mg/kg or 0.5 mg/kg GLA mRNA.

C. GLA mRNA Dose-Response in Tissues of GLA Knockout Mice

GLA activity was determined for heart, kidney, liver, and spleen tissues harvested from the GLA knockout mice 72 hours after administration of GLA mRNA. FIGS. 14A, 14B, 14C, and 14D show GLA activity levels in heart, kidney, liver, and spleen, respectively. In each tissue, the GLA activity was elevated for GLA mRNA treated mice in a dose dependent manner. GLA activity data for the control GFP mRNA and wild-type mice treated with lipid nanoparticle in PBS are included for comparison. At 72 hours after treatment with 0.5 mg/kg mRNA encoding GLA, the GLA activity level in the all of the tissues was increased compared to the controls. FIGS. 15A, 15B, and 15C shows the same tissue-specific GLA activity, but as a percentage relative to the GLA activity in wild-type mice injected with PBS. FIGS. 15A, 15B, and 15C show supraphysiologic (>100%) GLA activity in the liver, plasma, and heart with 0.5 mg/kg GLA mRNA administration, and at least 50% restoration of GLA activity in the kidney with 0.5 mg/kg GLA mRNA administration.

D. Lyso-Gb3 Levels in Fabry Mice Post-IV Injection with GLA mRNA

To determine whether mRNA encoding GLA can correct for the lack of endogenous GLA and combat the symptoms of Fabry disease, lyso-Gb3 was measured in GLA knockout mice after administration of GLA mRNA.

The level of lyso-Gb3 was determined in plasma and tissue samples from the GLA knockout mice administered GLA mRNA as well as controls. FIGS. 16A, 16B, and 16C show the lyso-Gb3 levels in plasma, kidney, and heart, respectively, 72 hours after administration of 0.5 mg/kg control GFP mRNA, 0.5 mg/kg GLA mRNA, 0.1 mg/kg GLA mRNA, or 0.05 mg/kg GLA mRNA. FIG. 16A shows plasma lyso-Gb3 levels pre-bleed (solid bar) compared to lyso-Gb3 levels 72 hours after mRNA administration (pattern bar) from the same mice. These results indicate a dose-dependent decrease in lyso-Gb3 levels in plasma 72 hours after administration of a single dose of GLA mRNA. FIGS. 16B and 16C show the lyso-Gb3 levels at 72 hours post-dose in kidney and heart, respectively, at the different GLA mRNA doses. Lyso-Gb3 levels decreased in a dose dependent manner in kidneys and hearts 72 hours after administration of a single dose of GLA mRNA.

FIGS. 16D and 16E show the dose-dependent reduction of lyso-Gb3 levels as a percent relative to the lyso-Gb3 levels in the plasma, heart, and kidney of untreated knockout mice. To obtain the percentage data, the lyso-Gb3 levels in each dosed group were normalized to the pre-bleed levels (for plasma) or to the GFP control group levels (for heart and kidney). FIG. 16D shows the percent reduction lyso-Gb3 data in chart form, while FIG. 16E shows the percent reduction lyso-Gb3 data in table form. At the 0.5 mg/kg dose of GLA mRNA, lyso-Gb3 was reduced by greater than 70% in plasma, and reduced by about 50% in heart and kidney.

FIGS. 16F and 16G show plots of GLA activity against measurements of GLA expression level in the plasma and liver, respectively. In both cases, there is a high degree of correlation (R squared>0.9). These results show that increased GLA expression correlates with increased GLA activity in both the blood and tissues of GLA knockout mice. FIG. 16H shows a plot of GLA activity against the levels of lyso-Gb3 in GLA knockout mice. This plot shows that the increased GLA activity in GLA knockout mice administered a single dose of GLA mRNA correlates with decreased levels of a Fabry Disease biomarker in vivo.

Example 24: In Vivo GLA Protein Activity in Fabry Mice Post-IV Injection with GLA mRNA GLA−/− knockout mice (SV129/C57B6 strain, males, 22-25 weeks old) were administered sequence optimized, chemically modified mRNA encoding GLA, specifically GLA-mRNA #1 or GLA-mRNA #23. The GLA mRNAs were formulated in lipid nanoparticles (Compound 18) for delivery, and were injected intravenously as a single dose of 0.5 mg/kg mRNA (N=3 per tested mRNA).

Blood was collected from each mouse just prior to injection, as well as 3 days, 7 days, 14 days, 21 days, 28 days, 35 days, and 42 days after administration. Mice injected with GLA-mRNA #1 were sacrificed 28 days after administration, while mice injected with GLA-mRNA #23 were sacrificed 42 days after administration. Upon sacrifice, the heart, kidney, liver, and spleen were harvested from each mouse.

The level of lyso-Gb3 was determined in plasma samples from the GLA knockout mice administered GLA mRNA as well as controls. FIGS. 17A and 17B show the reduction of lyso-Gb3 levels over time as a percent relative to the lyso-Gb3 levels in the plasma of untreated knockout mice. To obtain the percentage data, the lyso-Gb3 levels in each dosed group were normalized to the pre-bleed plasma levels. FIG. 17A shows the percent reduction lyso-Gb3 in mice treated with GLA-mRNA #1, while FIG. 17B shows the percent reduction lyso-Gb3 in mice treated with GLA-mRNA #23. In both cases, lyso-Gb3 was reduced by 80-90% in plasma by 3 days after treatment. Lyso-Gb3 levels remained at levels 70% below initial measurements for the entire 4 week time course for GLA-mRNA #1 (see FIG. 17A), and at levels 70% below initial measurements for the entire 6 week time course for GLA-mRNA #23 (see FIG. 17B).

FIG. 17C compares the results of an experiment testing the effects of administering mRNA to a previously reported experiment testing the effects of administering enzyme replacement therapy (ERT). As reported in Iannou et al., *Am. J. Hum. Genet.* 68:14-25 (2001), ERT therapy was administered intravenously to GLA−/− knockout mice as a single 3 mg/kg dose, an amount that is three times greater than the recommended clinical dose (N=3 per time point). GLA-mRNA #23 was also tested for comparison to this previously reported data (N=3). The GLA mRNAs were formulated in lipid nanoparticles (Compound 18) for delivery, and were injected intravenously as a single dose of 0.5 mg/kg mRNA (N=3 per tested mRNA). Blood was collected from each mRNA-injected mouse just prior to injection, as well as 3 days, 7 days, 14 days, 21 days, 28 days, 35 days, and 42 days after administration. Blood was collected from each mouse receiving ERT just prior to injection, as well as 3 days, 7 days, 11 days, 14 days, 18 days, and 21 days after administration. Groups of mice receiving ERT were sacrificed 1, 2, 3, and 4 weeks after administration. Upon sacrifice, the heart, liver, and spleen were harvested from each mouse. Gb3 levels were measured in each plasma or tissue sample using ELISA assay (for ERT-treated mice) or LCMSMS (for mRNA-treated mice). FIG. 17C shows that both ERT and mRNA therapy reduced Gb3 levels to approximately 20% of baseline levels. FIG. 17C shows a rebound in the level of plasma Gb3 in ERT-treated mice between two and three weeks after treatment. In contrast, FIG. 17C shows that the Gb3 plasma levels in mice treated with GLA-mRNA #23 remained at approximately 20% baseline levels for at least six weeks after treatment.

The level of lyso-Gb3 was also determined in heart, kidney, liver, and spleen samples from the GLA knockout mice administered GLA mRNA as well as controls. FIGS. 18A and 18B show the reduction of lyso-Gb3 levels four and six weeks after administration, respectively. The lyso-Gb3 levels are presented as a percent relative to the lyso-Gb3 levels in the tissues of untreated knockout mice. To obtain the percentage data, the lyso-Gb3 levels in each dosed group were normalized to the untreated tissue levels. FIG. 18A shows the percent reduction lyso-Gb3 in the tissues of mice four weeks after treatment with a single dose of GLA-mRNA #1. FIG. 18A shows that the heart and kidney of treated mice had only 30-40% of the lyso-Gb3 observed in untreated knockout mice, and that the liver and spleen of treated mice had only 10-20% of the lyso-Gb3 observed in untreated knockout mice. FIG. 18B shows the percent reduction lyso-Gb3 in the tissues of mice six weeks after treatment with a single dose of GLA-mRNA #23. FIG. 18B shows that the heart and kidney of treated mice had only 40-45% of the lyso-Gb3 observed in untreated knockout mice, and that the liver and spleen of treated mice had approximately 20% of the lyso-Gb3 observed in untreated knockout mice.

Example 25: In Vivo GLA Activity in Non-Human Primates Injected with GLA mRNA

A. Activity Assay

The GLA activity assay measures the ability of GLA enzymatic activity to release the fluorescent indicator 4-Methylumbelliferone (4-MU) from the non-fluorescent 4MU-α-Gal substrate. The assay was optimized for both wild-type and Fabry mice backgrounds. A standard curves of 4-MU for the plasma of cynomolgus monkeys was developed. One unit [U] of GLA activity was considered to be the amount capable of hydrolyzing 1 nmol of substrate per hour. This assay was adapted from Desnick et al., *J. Lab. Clin. Med.* 81(2):157-171 (1973); Ziegler et al., *Human Gene Therapy* 10:1667-1682 (Jul. 1, 1999); and Ioannou et al., *Am. J. Hum. Genet.* 68:14-25, 2001.

GLA activity was determined by mixing isolated protein samples with 2 mM 4-methylumbelliferyl-α-D-galactopyranoside (4MU-α-Gal) and 50 mM N-acetylgalactosamine inhibitor of α-galactosidase B at pH 4.6 in a plate-based assay. The assay mixtures were incubated at 37° C. for 30 min. The reactions were terminated by the addition of equal volume of 0.5 M ethylene-diamine (pH=10.4). 4-MU production was measured using a fluorescence plate reader with an excitation wavelength of 365 nm and an emission wavelength of 450 nm.

A. GLA Protein Activity Over Time in Plasma of Cynomolgus Monkeys Post-IV Injection of GLA mRNA The ability of sequence optimized, chemically modified GLA-encoding mRNAs to facilitate GLA activity in vivo was tested. Cynomolgus monkeys (N=4 per group) were injected intravenously with (i) 0.2 mg/kg GLA-mRNA #23 formulated in in lipid nanoparticles (Compound 18), (ii) 0.5 mg/kg GLA-mRNA #23 formulated in in lipid nanoparticles (Compound 18), or (iii) 0.5 mg/kg GLA-mRNA #23 formulated in in lipid nanoparticles (Compound 18 and Compound 428).

Blood was collected from each monkey just prior to injection, as well as 1 hour, 3 hours, 6 hours, 12 hours, 24 hours, 48 hours, 72 hours, 120 hours, and 168 hours after administration. GLA protein activity levels in each plasma sample were analyzed using the 4-MU fluorogenic GLA activity assay described in Part A above. FIG. 19 shows the GLA activity level in the plasma of untreated monkeys and monkeys treated with GLA-mRNA in each treatment group. The dotted line in FIG. 19 shows the average GLA activity level in wild type cynomolgus monkeys (9.11 U/mL; N=15). FIG. 19 shows that GLA activity peaked around 6-12 hours after treatment with GLA-mRNA.

B. GLA Protein Activity in Plasma of Cynomolgus Monkeys After Multiple Doses of GLA mRNA The ability of sequence optimized, chemically modified GLA-encoding mRNAs to facilitate GLA activity in vivo after administration of multiple doses was tested. Cynomolgus monkeys (N=4) were injected intravenously with 0.5 mg/kg GLA-mRNA #23 formulated in in lipid nanoparticles (Compound 18) on day 1 and on day 14.

Blood was collected from each monkey just prior to injection, as well as 1 hour, 3 hours, 6 hours, 12 hours, 24 hours, 48 hours, 72 hours, 120 hours, and 168 hours after each administration. GLA protein activity levels in each plasma sample were analyzed using the 4-MU fluorogenic GLA activity assay described in Part A above. FIG. 20 shows the GLA activity level in the plasma of untreated monkeys and monkeys after each GLA-mRNA treatment. The dotted line in FIG. 20 shows the average GLA activity level in wild type cynomolgus monkeys (9.11 U/mL; N=15). FIG. 20 shows that GLA activity peaked around 6-12 hours after each treatment with GLA-mRNA. Further, the GLA activity levels were higher at each time point after the second treatment with GLA-mRNA, relative to the equivalent time point after the first treatment with GLA-mRNA.

It is to be appreciated that the Detailed Description section, and not the Summary and Abstract sections, is intended to be used to interpret the claims. The Summary and Abstract sections can set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All publications, patent applications, patents, and other references mentioned herein are incorporated by reference in their entirety. In case of conflict, the present specification, including definitions, will control.

What is claimed is:

1. A messenger RNA (mRNA) comprising:
an open reading frame (ORF) encoding a human α-galactosidase A (GLA) polypeptide of SEQ ID NO: 1, wherein the ORF comprises a nucleotide sequence 95% identical to the nucleotide sequence of SEQ ID NO: 79.

2. An mRNA comprising an ORF encoding a human GLA polypeptide of SEQ ID NO: 1, wherein the ORF comprises a nucleotide sequence 96% identical to the nucleotide sequence of SEQ ID NO: 79.

3. An mRNA comprising an ORF encoding a human GLA polypeptide of SEQ ID NO: 1, wherein the ORF comprises a nucleotide sequence 97% identical to the nucleotide sequence of SEQ ID NO: 79.

4. An mRNA comprising an ORF encoding a human GLA polypeptide of SEQ ID NO: 1, wherein the ORF comprises a nucleotide sequence 100% identical to the nucleotide sequence of SEQ ID NO: 79.

5. The mRNA of claim 1, wherein the mRNA comprises a 5' terminal cap comprising a guanine cap nucleotide containing an N7 methylation and the 5'-terminal nucleotide of the mRNA contains a 2'-O-methyl.

6. The mRNA of claim 1, wherein the mRNA comprises a poly-A tail about 100 residues in length.

7. The mRNA of claim 1, wherein at least 95% of uridines in the ORF are 5-methoxyuridines.

8. The mRNA of claim 1, wherein at least 99% of uridines in the ORF are 5-methoxyuridines.

9. The mRNA of claim 1, wherein 100% of uridines in the ORF are 5-methoxyuridines.

10. The mRNA of claim 4, wherein the mRNA comprises a 5' terminal cap comprising a guanine cap nucleotide containing an N7 methylation and the 5'-terminal nucleotide of the mRNA contains a 2'-O-methyl.

11. The mRNA of claim 4, wherein the mRNA comprises a poly-A tail about 100 residues in length.

12. The mRNA of claim 4, wherein at least 95% of uridines in the ORF are 5-methoxyuridines.

13. The mRNA of claim 4, wherein at least 99% of uridines in the ORF are 5-methoxyuridines.

14. The mRNA of claim 4, wherein 100% of uridines in the ORF are 5-methoxyuridines.

15. A lipid nanoparticle comprising the mRNA of claim 1.

16. A lipid nanoparticle comprising the mRNA of claim 4.

17. A lipid nanoparticle comprising the mRNA of claim 2.

18. A lipid nanoparticle comprising the mRNA of claim 3.

19. A lipid nanoparticle comprising the mRNA of claim 9.

20. A lipid nanoparticle comprising the mRNA of claim 14.

21. The mRNA of claim 2, wherein 100% of uridines in the ORF are 5-methoxyuridines.

22. The mRNA of claim 3, wherein 100% of uridines in the ORF are 5-methoxyuridines.

23. A lipid nanoparticle comprising the mRNA of claim 21.

24. A lipid nanoparticle comprising the mRNA of claim 22.

25. A pharmaceutical composition comprising the mRNA of claim 1 and a pharmaceutically acceptable excipient.

26. A pharmaceutical composition comprising the mRNA of claim 2 and a pharmaceutically acceptable excipient.

27. A pharmaceutical composition comprising the mRNA of claim 3 and a pharmaceutically acceptable excipient.

28. A pharmaceutical composition comprising the mRNA of claim 4 and a pharmaceutically acceptable excipient.

29. A pharmaceutical composition comprising the lipid nanoparticle of claim 20 and a pharmaceutically acceptable excipient.

* * * * *